US006204293B1

(12) United States Patent
Sebti et al.

(10) Patent No.: US 6,204,293 B1
(45) Date of Patent: Mar. 20, 2001

(54) INHIBITORS OF PROTEIN ISOPRENYL TRANSFERASES

(75) Inventors: Said M. Sebti, Tampa, FL (US); Andrew D. Hamilton, Guilford, CT (US); David J. Augeri, Kenosha, WI (US); Kenneth J. Barr, Chicago, IL (US); Stephen A. Fakhoury, Mundelein, IL (US); David A. Janowick, Beach Park, IL (US); Douglas M. Kalvin, Buffalo Grove, IL (US); Stephen J. O'Connor, Wilmette, IL (US); Saul H. Rosenberg, Grayslake, IL (US); Wang Shen, Gurnee, IL (US); Rolf E. Swenson, Grayslake, IL (US); Bryan K. Sorensen, Waukegan, IL (US); Gerard M. Sullivan, Round Lake Beach, IL (US); Andrew S. Tasker, Simi Valley, CA (US); James T. Wasicak, Waterford, WI (US); Lissa T. J. Nelson, Highland Park, IL (US); Kenneth J. Henry, Fishers, IN (US); Le Wang, Mundelein, IL (US); Gang Liu, Gurnee, IL (US); Indrani W. Gunawardana, Libertyville, IL (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/073,807

(22) Filed: May 7, 1998

Related U.S. Application Data

(63) Continuation-in-part of application No. 08/852,858, filed on May 7, 1997, now abandoned, which is a continuation-in-part of application No. 08/740,909, filed on Nov. 5, 1996, now abandoned

(60) Provisional application No. 60/007,247, filed on Nov. 6, 1995.

(51) Int. Cl.[7] ...................... C07C 263/02; C07C 303/00; A61K 31/38

(52) U.S. Cl. ............................................ 514/570; 562/426

(58) Field of Search .............................. 514/570; 562/426

(56) References Cited

U.S. PATENT DOCUMENTS

| 5,043,268 | 8/1991 | Stock ................................ 435/15 |
| 5,141,851 | 8/1992 | Brown et al. ....................... 435/15 |
| 5,238,922 | 8/1993 | Graham et al. ..................... 514/18 |
| 5,534,537 | 7/1996 | Ciccarone et al. ................. 514/397 |
| 5,578,629 | 11/1996 | Ciccarone et al. ................. 514/397 |
| 5,631,280 | 5/1997 | Ciccarone et al. ................. 514/416 |

FOREIGN PATENT DOCUMENTS 2072033   6/1992   (CA) .

(List continued on next page.)

OTHER PUBLICATIONS

Hancock et al, "A polybasic Domain or Palmitoylation is Required in Addition to the CAAX Motif to Localize p21[ras] to the Plasma Membrane", Cell, vol. 63, Oct. 5, 1990, pp. 133–139.

(List continued on next page.)

Primary Examiner—Mukund J. Shah
Assistant Examiner—Deepak R. Rao
(74) Attorney, Agent, or Firm—Pillsbury Madison & Sutro, LLP

(57) ABSTRACT

Compounds having the formula

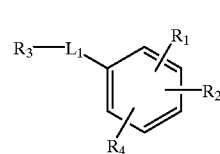

or a pharmaceutically acceptable salt thereof wherein $R_1$ is (a) hydrogen, (b) loweralkyl, (c) alkenyl, (d) alkoxy, (e) thioalkoxy, (f) halo, (g) haloalkyl, (h) aryl-$L_2$—, and (i) heterocyclic-$L_2$—; $R_2$ is selected from

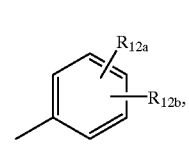

(b) —C(O)NH—CH($R_{14}$)—C(O)O$R_{15}$,

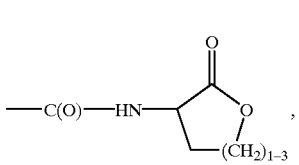

(d) —C(O)NH—CH($R_{14}$)—C(O)NHSO$_2R_{16}$, (e) —C(O)NH—CH($R_{14}$)-tetrazolyl, (f) —C(O)NH-heterocyclic, and (g) —C(O)NH—CH($R_{14}$)—C(O)N$R_{17}R_{18}$; $R_3$ is heterocyclic, aryl, substituted or unsubstituted cycloalkyl; $R_4$ is hydrogen, lower alkyl, haloalkyl, halogen, aryl, arylakyl, heterocyclic, or (heterocyclic)alkyl; $L_1$ is absent or is selected from (a) —$L_4$—N($R_5$)—$L_5$—, (b) —$L_4$—O—$L_5$—, (c) —$L_4$—S(O)$_n$—$L_5$— (d) —$L_4$—$L_6$—C(W)—N($R_5$)—$L_5$—, (e) —$L_4$—$L_6$—S(O)m—N($R_5$)—$L_5$ —, (f) —$L_4$—N($R_5$)—C(W)—$L_7$—$L_5$ —, (g) —$L_4$—N($R_5$)—S(O)$_p$—$L_7$—$L_5$—, (h) optionally substituted alkylene, (i) optionally substituted alkenylene, and (j) optionally substituted alkynylene are inhibitors of protein isoprenyl transferases. Also disclosed are protein isoprenyl transferase inhibiting compositions and a method of inhibiting protein isoprenyl transferases.

15 Claims, No Drawings

FOREIGN PATENT DOCUMENTS

| | | | |
|---|---|---|---|
| 0203587 | 12/1986 | (EP) . | |
| 0456180 | 11/1991 | (EP) . | |
| 0461869 | 12/1991 | (EP) . | |
| 0512865 | 11/1992 | (EP) . | |
| 0520823 | 12/1992 | (EP) . | |
| 0523873 | 1/1993 | (EP) . | |
| 0528486 | 2/1993 | (EP) | C07K/5/10 |
| 0534546 | 3/1993 | (EP) | C07F/9/38 |
| 0535730 | 4/1993 | (EP) | C07K/5/08 |
| WO9116340 | 10/1991 | (WO) . | |
| WO9218465 | 10/1992 | (WO) . | |
| WO9409766 | 5/1994 | (WO) . | |
| WO9525086 | 9/1995 | (WO) . | |
| WO9630014 | 10/1996 | (WO) . | |
| WO9630015 | 10/1996 | (WO) . | |
| WO9706138 | 2/1997 | (WO) . | |
| WO9807692 | 2/1998 | (WO) . | |
| WO9838162 | 9/1998 | (WO) . | |

OTHER PUBLICATIONS

Reiss et al, "Inhibition of Purified p21$^{ras}$ Farnesyl:Protein Transferase by Cys–AAX Tetrapeptides", Cell, vol. 62, Jul. 13, 1990, pp. 81–88.

Willumsen et al.,"The p21 *ras* c–terminus is required for transformation and membrane association," Nature, vol. 310, Aug. 16, 1984, pp. 583–586.

Gibbs, J.B., Ras C–Terminal Processing Enzymes–New Drug Targets, Cell, 65:1–4 (1991).

Gibbs et al., Farnesyltransferase Inhibitors: Ras Research Yields a Potential Cancer Terapeutic, Cell, 77:175–178 (1994).

Brown et al., Tetrapeptide inhibitors of protein farnesyltransferase: Amino–terminal substitution in phenylalanine–containing tetrapeptides restores farnesylation, Proc. Natl. Acad. Sci. U.S.A., 89:8313–8316 (1992).

Kohl et al., Selective Inhibition of ras–Dependent Transformation by a Farnesyltransferase Inhibitor, Science, 260:1934–1937 (1993).

Graham et al., Pseudopeptide Inhibitors of Ras Farnesyl–Protein Transferase, J. Med. Chem., 37:725–732 (1994).

Garcia et al., Peptidomimetic Inhibitors of Ras Farnesylation and Function in Whole Cells, J. Biol. Chem., 268:18415–18418 (1993).

Qian et al., Design and Structural Requirements of Potent Peptidomimetic Inhibitors of p21$^{ras}$ Farnesyltransferase, J. Biol. Chem., 269:12410–12413 (1994).

Qian et al., Peptidomimetic Inhibitors of P21RAS Farnesyltransferase: Hydrophobic Functionalization Leads to Disruption of P21RAS Membrane Association in Whole Cells, Bioorg. Med. Chem. Lett., 4:2579–2584 (1994).

Goldstein et al., Benzodiazepine Peptidomimetics: Potent Inhibitors of Ras Farnesylation in Animal Cells, Science, 260:1937–1942 (1993).

Reiss et al., Inhibition of Purified p21$^{ras}$ Farnesyl:Protein Transferase by Cys–AAX Tetrapeptides, Cell, 62:81–88 (1990).

Vogt et al., A Non–peptide Mimetic of Ras–CAAX:Selective Inhibition of Farnesyltransferase and Ras Processing, (1995) J. Biol. Chem. 270:660–664.

Kohl et al., Protein farnesyltransferase inhibitors block the growth of ras–dependent tumors in nude mice, (1994) Proc. Natl. Acad. Sci. USA 91:9141–9145.

Cox et al., The CAAX Peptidomimetic Compound B581 Specifically Blocks Farnesylated, but Not Geranylgeranylated or Myristylated, Oncogenic Ras Signaling and Transformation, (1994) J. Biol. Chem. 269:19203–19206.

Lerner et al., Ras CAAX Peptidomimetic FTI–277 Selectively Blocks Oncogenic Ras Signaling by Inducing Cytoplasmic Accumulation of Inactive Ras–Raf Complexes (1995) J. Biol. Chem. 270:26802–26806.

Sun et al., Ras CAAX Peptidomimetic FTI 276 Selectively Blocks Tumor Growth in Nude Mice of a Human Lung Carcinoma with K–Ras Mutation and p53 Deletion, (1995) Cancer Research 55, 4243–4247.

Database HCAPLUS on STN, 1997:247953, Boyle, F. T. et al., 'Preparation of 2–aminomethyl–4–mercaptopyrrolidines and analogs as farnesyl transferase inhibitors', Feb. 20, 1997, PCT Int. Appl. pp. 189.

Naylor–Olsen et al., Chem. Abstract 128:243953, 1998.*

Hashizume et al., Chem. Abstract 126:157280, 1997.*

Tanaka et al., USPATFULL Abstract 1999:99789, 1995.*

Shaw et al., USPATFULL Abstract 97:112626, 1993.*

Miyake et al., USPATFULL Abstract 96:29567, 1994.*

Yamada et al., USPATFULL Abstract 94:73416, 1994*

Kampe et al., USPATFULL Abstract 94:22010, 1994.*

Million et al., Chem. Abstract 125:48353, 1996.*

Omenn, Cancer Prevention, Cecil Textbook of Medicine, 20th Edition, vol. 1, pp. 1006–10, 1996.*

\* cited by examiner

INHIBITORS OF PROTEIN ISOPRENYL TRANSFERASES

CROSS REFERENCE TO RELATED APPLICATIONS

This application is a continuation-in-part of U.S. Ser. No. 08/852,858, filed May 7, 1997, now abandoned, which is a continuation-in-part of U.S. Ser. No. 08/740,909, filed Nov. 5, 1996, now abandoned, which claims the benefit of U.S. Provisional Application Ser. No. 60/007,247, filed Nov. 6, 1995.

TECHNICAL FIELD

The present invention relates to novel compounds which are useful in inhibiting protein isoprenyl transferases (for example, protein farnesyltransferase and protein geranylgeranyltransferase) and the farnesylation or geranylgeranylation of the oncogene protein Ras and other related small g-proteins, compositions containing such compounds and methods of using such compounds.

BACKGROUND OF THE INVENTION

Ras oncogenes are the most frequently identified activated oncogenes in human tumors. Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase, and thereby farnesylation of the Ras protein, blocks the ability of transformed cells to proliferate. Inhibition of protein geranylgeranyltransferase and, thereby, of geranylgeranylation of Ras proteins, also results in down regulation of Ras protein function.

Activation of Ras and other related small g-proteins that are farnesylated and/or geranylated also partially mediates smooth muscle cell proliferation (Circulation, I-3: 88 (1993), which is hereby incorporated herein by reference). Inhibition of protein isoprenyl transferases, and thereby farnesylation or geranylgeranylation of the Ras protein, also aids in the prevention of intimal hyperplasia associated with restenosis and atherosclerosis, a condition which compromises the success of angioplasty and surgical bypass for obstructive vascular lesions.

There is therefore a need for compounds which are inhibitors of protein farnesyltransferase and protein geranylgeranyltransferase.

SUMMARY OF THE INVENTION

In its principle embodiment, the invention provides a compound having the formula:

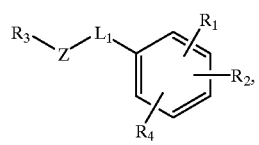

I or a pharmaceutically acceptable salt thereof, wherein
$R_1$ is selected from the group consisting of
(1) hydrogen,
(2) alkenyl,
(3) alkynyl,
(4) alkoxy,
(5) haloalkyl,
(6) halogen,
(7) loweralkyl,
(8) thioalkoxy,
(9) aryl-$L_2$— wherein aryl is selected from the group consisting of
  (a) phenyl,
  (b) naphthyl,
  (c) dihydronaphthyl,
  (d) tetrahydronaphthyl,
  (e) indanyl, and
  (f) indenyl
  wherein (a)–(f) are unsubstituted or substituted with at least one of X, Y, or Z wherein X, Y, and Z are independently selected from the group consisting of
    alkenyl,
    alkynyl,
    alkoxy,
    aryl,
    carboxy,
    cyano,
    halogen,
    haloalkyl,
    hydroxy,
    hydroxyalkyl,
    loweralkyl,
    nitro,
    N-protected amino, and
    —NRR' wherein R and and R' are independently selected from the group consisting of hydrogen and loweralkyl,
    oxo (=O), and
    thioalkoxy and
  $L_2$ is absent or is selected from the group consisting of
    —CH$_2$—,
    —CH$_2$CH$_2$—,
    —CH(CH$_3$)—,
    —O—,
    —C(O)—,
    —S(O)$_q$ wherein q is 0, 1 or 2, and
    —N(R)—, and
(10) heterocycle-$L_2$— wherein $L_2$ is as defined above and the heterocycle is unsubstituted or substituted with 1, 2, 3 or 4 substituents independently selected from the group consisting of
  (a) loweralkyl,
  (b) hydroxy,
  (c) hydroxyalkyl,
  (d) halogen
  (e) cyano,
  (f) nitro,
  (g) oxo (=O),
  (h) —NRR',
  (i) N-protected amino,
  (j) alkoxy,
  (k) thioalkoxy,
  (l) haloalkyl,
  (m) carboxy, and
  (n) aryl;

$R_2$ is selected from the group consisting of

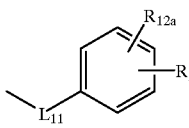 wherein $L_{11}$ is selected from the group wherein $L_{11}$ is selected from the group consisting of
(a) a covalent bond,
(b) —C(W)N(R)— wherein R is defined previously and W is selected from the group consisting of O and S,
(c) —C(O)—,
(d) —N(R)C(W)—,
(e) —CH$_2$O—,
(f) —C(O)O—, and
(g) —CH$_2$N(R)—,
$R_{12a}$ is selected from the group consisting of
(a) hydrogen,
(b) loweralkyl, and
(c) —C(O)OR$_{13}$ wherein $R_{13}$ is selected from the group consisting of
hydrogen and
a carboxy-protecting group, and
$R_{12b}$ is selected from the group consisting of
(a) hydrogen and
(b) loweralkyl,
with the proviso that $R_{12a}$ and $R_{12b}$ are not both hydrogen,
(2) —L$_{11}$—C(R$_{14}$)(R$_v$)—C(O)OR$_{15}$ wherein $L_{11}$ is defined previously,
$R_v$ is selected from the group consisting of
(a) hydrogen and
(b) loweralkyl,
$R_{15}$ is selected from the group consisting of
(a) hydrogen,
(b) alkanoyloxyalkyl,
(c) loweralkyl, and
(b) a carboxy-protecting group, and
$R_{14}$ is selected from the group consisting of
(a) alkoxyalkyl,
(b) alkoxyarylalkyl,
(c) alkoxycarbonylalkyl,
(d) alkylsulfinyalkyl,
(e) alkylsulfonylalkyl,
(f) alkynyl,
(g) aminoalkyl,
(h) aminocarbonylalkyl,
(i) aminothiocarbonylalkyl,
(j) aryl,
(k) arylalkyl,
(l) carboxyalkyl,
(m) cyanoalkyl,
(n) cycloalkyl,
(o) cycloalkylalkoxyalkyl,
(p) cycloalkylalkyl,
(q) (heterocyclic)alkyl,
(r) hydroxyalkyl,
(s) hydroxyarylalkyl,
(t) loweralkyl,
(u) sulfhydrylalkyl,
(v) thioalkoxyalkyl wherein the thioalkoxyalkyl is unsubstituted or substituted with 1, 2, 3, or 4 substituents selected from the group consisting of halogen,
(w) thioalkoxyalkylamino, and
(x) thiocycloalkyloxyalkyl,

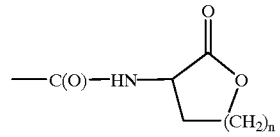

wherein n is 1–3,
(4) —C(O)NH—CH(R$_{14}$)—C(O)NHSO$_2$R$_{16}$ wherein $R_{14}$ is defined previously and $R_{16}$ is selected from the group consisting of
(a) loweralkyl,
(b) haloalkyl,
(c) aryl wherein the aryl is unsubstituted or substituted with 1, 2, 3, 4, or 5 substituents independently selected from the group consisting of
loweralkyl,
hydroxy,
hydroxyalkyl,
halogen,
cyano,
nitro,
oxo (=O),
—NRR'
N-protected amino,
alkoxy,
thioalkoxy,
haloalkyl,
carboxy, and
aryl, and
(d) heterocycle wherein the heterocycle is unsubstituted or substituted with substituents independently selected from the group consisting of
loweralkyl,
hydroxy,
hydroxyalkyl,
halogen,
cyano,
nitro,
oxo (=O),
—NRR',
N-protected amino,
alkoxy,
thioalkoxy,
haloalkyl,
carboxy, and
aryl;
(5) —C(O)NH—CH(R$_{14}$)-tetrazolyl wherein the tetrazole ring is unsubstituted or substituted with loweralkyl or haloalkyl,
(6) —L$_{11}$-heterocycle,
(7) —C(O)NH—CH(R$_{14}$)—C(O)NR$_{17}$R$_{18}$ wherein $R_{14}$ is defined previously and $R_{17}$ and $R_{18}$ are independently selected from the group consisting of
(a) hydrogen,
(b) loweralkyl,
(c) arylalkyl, (d) hydroxy, and
(e) dialkylaminoalkyl,
(8) —C(O)OR$_{15}$, and
(9) —C(O)NH—CH(R$_{14}$)-heterocycle wherein R$_{14}$ is as previously defined and the heterocycle is unsubstituted or substituted with loweralkyl or haloalkyl;

L$_1$ is absent or is selected from the group consisting of
(1) —L$_4$—N(R$_5$)—L$_5$— wherein L$_4$ is absent or selected from the group consisting of
(a) C$_1$-to-C$_{10}$-alkylene and
(b) C$_2$-to-C$_{16}$-alkenylene,
wherein the alkylene and alkenylene groups are unsubstituted or substituted with 1, 2, 3 or 4 substituents independently selected from the group consisting of
alkenyl,
alkenyloxy,
alkenyloxyalkyl,
alkenyl[S(O)$_q$]alkyl,
alkoxy,
alkoxyalkyl wherein the alkoxyalkyl is unsubstituted or substituted with 1 or 2 hydroxyl substituents,
with the proviso that no two hydroxyls are attached to the same carbon,
alkoxycarbonyl wherein the alkoxycarbonyl is unsubstituted or substituted with 1, 2, or 3 substituents independently selected from the group consisting of
halogen and
cycloalkyl,
alkylsilyloxy,
alkyl[S(O)$_q$],
alkyl[S(O)$_q$]alkyl,
aryl wherein the aryl is unsubstituted or substituted with 1, 2, 3, 4, or 5 substituents independently selected from the group consisting of
alkoxy wherein the alkoxy is unsubstituted or substituted with substituents selected from the group consisting of cycloalkyl,
aryl,
arylalkyl,
aryloxy wherein the aryloxy is unsubstituted or substituted with 1, 2, 3, 4, or 5 substituents independently selected from the group consisting of,
halogen,
nitro, and
—NRR',
cycloalkyl,
halogen,
loweralkyl,
hydroxyl,
nitro,
—NRR', and
—SO$_2$NRR',
arylalkoxy wherein the arylalkoxy is unsubstituted or substituted with substituents selected from the group consisting of alkoxy,
arylalkyl,
arylalkyl[S(O)$_q$]alkyl,
aryl[S(O)$_q$],
aryl[S(O)$_q$]alkyl wherein the aryl[S(O)$_q$]alkyl is unsubstituted or substituted with 1, 2, 3, 4, or 5 substituents independently selected from
alkoxy and
loweralkyl,
arylalkoxyalkyl wherein the arylalkoxyalkyl is unsubstituted or substituted with substituents selected from the group consisting of
alkoxy, and
halogen,
aryloxy,
aryloxyalkyl wherein the aryloxyalkyl is unsubstituted or substituted with substituents selected from the group consisting of halogen,
carboxyl,
—C(O)NR$_C$R$_D$ wherein R$_C$ and R$_D$ are independently selected from the group consisting of
hydrogen,
loweralkyl, and
alkoxycarbonyl or
R$_C$ and R$_D$ together with the nitrogen to which they are attached form a ring selected from the group consisting of
morpholine,
piperidine,
pyrrolidine
thiomorpholine,
thiomorpholine sulfone, and
thiomorpholine sulfoxide,
wherein the ring formed by R$_C$ and R$_D$ together is unsubstituted or substituted with 1 or 2 substituents independently selected from the group consisting of alkoxy and alkoxyalkyl,
cycloalkenyl wherein the cycloalkenyl is unsubstituted or substituted with 1 or 2 substituents selected from the group consisting of alkenyl,
cyclolalkoxy,
cycloalkoxycarbonyl,
cyclolalkoxyalkyl,
cyclolalkyl wherein the cycloalkyl is unsubstituted or substituted with 1, 2, 3, 4, or 5 substituents independently selected from the group consisting
of aryl,
loweralkyl, and
alkanoyl,
cycloalkylalkoxy,
cycloalkylalkoxycarbonyl,
cycloalkylalkoxyalkyl,
cycloalkylalkyl,
cyclolalkyl[S(O)$_q$]alkyl,
cycloalkylalkyl[S(O)$_q$]alkyl,
fluorenyl,
heterocycle wherein the heterocycle is unsubstituted or substituted with 1, 2, 3, or 4 substituents independently selected from the group consisting of
alkoxy wherein the alkoxy is unsubstituted or substituted with 1 or 2 substituents independently selected from the group consisting of aryl and cycloalkyl,
alkoxyalkyl wherein the alkoxyalkyl is unsubstituted or substituted with 1 or 2 substituents independently selected from the group consisting of
aryl and
cycloalkyl,
alkoxycarbonyl wherein the alkoxycarbonyl is unsubstituted or substituted with 1 or 2 substituents independently selected from the group consisting of
aryl and
cycloalkyl,
aryl wherein the aryl is unsubstituted or substituted with 1, 2, 3, 4, or 5 substituents independently selected from the group consisting of
alkanoyl,
alkoxy, carboxaldehyde,
haloalkyl,
halogen,
loweralkyl,
nitro,
—NRR', and
thioalkoxy,
arylalkyl,
aryloxy,
cycloalkoxyalkyl,
cycloalkyl,
cycloalkylalkyl,
halogen,
heterocycle,
hydroxyl,
loweralkyl wherein the loweralkyl is unsubstituted or substituted with 1, 2, or 3 substituents independently selected from the group consisting of
    heterocycle,
    hydroxyl,
    with the proviso that no two hydroxyls are attached to the same carbon, and
—NR$^{R3R3'}$ wherein R$^{R3}$ and R$^{R3'}$ are independently selected from the group consisting of
    hydrogen
    aryl,
    loweralkyl,
    aryl,
    arylalkyl,
    heterocycle,
    (heterocyclic)alkyl,
    cycloalkyl, and
    cycloalkylalkyl, and
    sulfhydryl,
(heterocyclic)alkoxy,
(heterocyclic)alkyl,
(heterocyclic)alkyl[S(O)$_q$]alkyl,
(heterocyclic)oxy,
(heterocyclic)alkoxyalkyl,
(heterocyclic)oxyalkyl,
heterocycle[S(O)$_q$]alkyl,
hydroxyl,
hydroxyalkyl,
imino,
N-protected amino,
=N—O-aryl, and
=N—OH,
=N—O-heterocycle wherein the heterocycle is unsubstituted or substituted with 1, 2, 3, or 4 substituents independently selected from the group consisting of
    loweralkyl,
    hydroxy,
    hydroxyalkyl,
    halogen,
    cyano,
    nitro,
    oxo (=O),
    —NRR'
    N-protected amino,
    alkoxy,
    thioalkoxy,
    haloalkyl,
    carboxy, and
    aryl,
=N—O-loweralkyl,
—NR$^{R3}$R$^{R3'}$, —NHNR$_C$R$_D$,
—OG wherein G is a hydroxyl protecting group,
—O—NH—R,

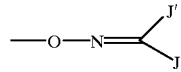

wherein J and J' are independently selected from the group consisting of
    loweralkyl and
    arylalkyl,
oxo,
oxyamino(alkyl)carbonylalkyl,
oxyamino(arylalkyl)carbonylalkyl,
oxyaminocarbonylalkyl,
—SO$_2$—A wherein A is selected from the group consisting of
    loweralkyl,
    aryl, and
    heterocycle
    wherein the loweralkyl, aryl, and heterocycle are unsubstituted or substituted with 1, 2, 3, 4, or 5 substituents independently selected from the group consisting of
        alkoxy,
        halogen,
        haloalkyl,
        loweralkyl, and
        nitro,
sulfhydryl,
thioxo, and
thioalkoxy,
L$_5$ is absent or selected from the group consisting of
    (a) C$_1$-to-C$_{10}$-alkylene and
    (b) C$_2$-to-C$_{16}$-alkenylene
    wherein (a) and (b) are unsubstituted or substituted as defined previously, and
R$_5$ is selected from the group consisting of
    hydrogen,
    alkanoyl wherein the alkanoyl is unsubstituted or substituted with substituents selected from the group consisting of aryl,
    alkoxy,
    alkoxyalkyl,
    alkoxycarbonyl wherein the alkoxycarbonyl is unsubstituted or substituted with 1, 2 or 3 substituents independently selected from the group consisting of
        aryl and
        halogen,
    alkylaminocarbonylalkyl wherein the alkylaminocarbonylalkyl is unsubstituted or substituted with 1 or 2 substituents independently selected from the group consisting of aryl,
    (anthracenyl)alkyl,
    aryl,
    arylalkoxy,
    arylalkyl wherein the arylalkyl is unsubstituted or substituted with 1, 2, 3, 4, or 5 substituents independently selected from the group consisting of
        alkoxy,
        aryl,
        carboxyl,
        cyano,
        halogen,
        haloalkoxy,
        haloalkyl, nitro,
oxo, and
—$L_{11}$—C($R_{14}$)($R_y$)—C(O)O$R_{15}$,
(aryl)oyl wherein the (aryl)oyl is unsubstituted or substituted with substituents selected from the group consisting of halogen,
aryloxycarbonyl,
carboxaldehyde,
—C(O)NRR',
cycloalkoxycarbonyl,
cycloalkylaminocarbonyl,
cycloalkylaminothiocarbonyl,
cyanoalkyl,
cyclolalkyl,
cycloalkylalkyl wherein the cycloalkylalkyl is unsubstituted or substituted with 1 or 2 hydroxyl substituents,
with the proviso that no two hydroxyls are attached to the same carbon,
(cyclolalkyl)oyl,
(9,10-dihydroanthracenyl)alkyl wherein the (9,10-dihydroanthracenyl)alkyl is unsubstituted or substituted with 1 or 2 oxo substituents,
haloalkyl,
heterocycle,
(heterocyclic)alkyl wherein the (heterocyclic)alkyl is unsubstituted or substituted with 1, 2, 3, 4, or 5 substituents selected from the group consisting of loweralkyl,
(heterocyclic)oyl,
loweralkyl, wherein the loweralkyl is unsubstituted or substituted with substituents selected from the group consisting of —NRR',
—$SO_2$—A, and
thioalkoxyalkyl;
(3) —$L_4$—S(O)$_m$—$L_5$— wherein $L_4$ and $L_5$ are defined previously and m is 0, 1, or 2,
(4) —$L_4$—$L_6$—C(W)—N($R_6$)—$L_5$— wherein $L_4$, W, and $L_5$ are defined previously, $R_6$ is selected from the group consisting of
(a) hydrogen,
(b) loweralkyl,
(c) aryl,
(d) arylalkyl,
(e) heterocycle,
(f) (heterocyclic)alkyl,
(g) cyclolakyl, and
(h) cycloalkylalkyl, and
$L_6$ is absent or is selected from the group consisting of
(a) —O—,
(b) —S—, and
(c) —N($R_{6'}$)— wherein $R_{6'}$ is selected from the group consisting of
hydrogen,
loweralkyl,
aryl,
arylalkyl,
heterocycle,
(heterocyclic)alkyl,
cyclolakyl, and
cycloalkylalkyl,
(5) —$L_4$—$L_6$—S(O)$_m$—N($R_5$)—$L_5$—,
(6) —$L_4$—$L_6$—N($R_5$)—S(O)$_m$—$L_5$—,
(7) —$L_4$—N($R_5$)—C(W)—$L_7$—$L_5$— wherein $L_4$, $R_5$, W, and $L_5$ are defined previously and $L_7$ is absent or is selected from the group consisting of —O— and —S—, (8) $C_1$–$C_{10}$-alkylene wherein the alkylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(9) $C_2$-to-$C_{10}$-alkenylene wherein the alkenylene group is unsubstituted or substituted with 1 or 2 substituents independently selected from the group consisting of
(a) aryl,
(b) arylalkyl,
(c) (aryl)oxyalkyl wherein the (aryl)oxyalkyl is unsubstituted or substituted with 1, 2, 3, 4, or 5 substituents selected from the group consisting of halogen,
(d) heterocycle,
(e) (hererocycle)alkyl,
(f) hydroxyalkyl,
(g) cyclolakyl,
(h) cycloalkylalkyl,
(i) alkylthioalkyl, and
(j) hydroxy,
(10) $C_2$-to-$C_{10}$-alkynylene wherein the alkynylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(11) —$L_4$-heterocycle-$L_5$—,
(12) a covalent bond, wherein B is selected from the group consisting of
loweralkyl and
arylalkyl, and (14)

Z is selected from the group consisting of
(1) a covalent bond,
(2) —O—,
(3) —S(O)$_q$—, and (4) —NR$_z$— wherein R$_z$ is selected from the group consisting of
  (a) hydrogen
  (b) loweralkyl,
  (c) aryl,
  (d) arylalkyl,
  (e) heterocycle,
  (f) (heterocyclic)alkyl,
  (g) cyclolakyl, and
  (h) cycloalkylalkyl;
R$_3$ is selected from the group consisting of
(1) hydrogen,
(2) aryl,
(3) fluorenyl,
(4) heterocycle,
  wherein (2)–(4) are unsubstituted or substituted with 1, 2, 3, 4, or 5 substituents independently selected from the group consisting of
  (a) alkanoyl,
  (b) alkoxy wherein the alkoxy is unsubstituted or substituted with 1, 2, 3, 4, or 5 substituents independently selected from the group consisting of
    halogen,
    aryl, and
    cycloalkyl,
  (c) alkoxyalkyl wherein the alkoxyalkyl is unsubstituted or substituted with 1 or 2, 3, 4 or 5 substituents independently selected from the group consisting of
    aryl and
    cycloalkyl,
  (d) alkoxycarbonyl wherein the alkoxycarbonyl is unsubstituted or substituted with 1, 2, 3, 4 or 5 substituents independently selected from the group consisting of
    aryl, and
    cycloalkyl,
  (e) alkylsilyloxyalkyl,
  (f) arylalkyl,
  (g) aryl wherein the aryl is unsubstituted or substituted with 1, 2, 3, 4, or 5 substituents independently selected from the group consisting of
    alkanoyl,
    alkoxy wherein the alkoxy is unsubstituted or substituted with 1 or 2 substituents selected from the group consisting of cycloalkyl,
    carboxaldehyde,
    haloalkyl,
    halogen,
    loweralkyl,
    nitro,
    —NRR', and
    thioalkoxy,
  (h) arylalkyl,
  (i) aryloxy wherein the aryloxy is unsubstituted or substituted with 1, 2, 3, 4, or 5 substituents independently selected from the group consisting of,
    halogen,
    nitro, and
    —NRR',
  (j) (aryl)oyl,
  (k) carboxaldehyde,
  (l) carboxy,
  (m) carboxyalkyl,
  (n) —C(O)NRR" wherein R is defined previously and R" is selected from the group consisting of
    hydrogen,
    loweralkyl, and
    carboxyalkyl,
  (o) cyano,
  (p) cyanoalkyl,
  (q) cycloalkyl,
  (r) cycloalkylalkyl,
  (s) cycloalkoxyalkyl,
  (t) halogen,
  (u) haloalkyl wherein the haloalkyl is unsubstituted or substituted with 1, 2, 3, 4, or 5 hydroxyl substituents, with the proviso that no two hydroxyls are attached to the same carbon,
  (v) heterocycle,
  (w) hydroxyl,
  (x) hydroxyalkyl wherein the hydroxyalkyl is unsubstituted or substituted with substitutients selected from the group consisting of aryl,
  (y) loweralkyl wherein the loweralkyl is unsubstituted or substituted with substituents selected from the group consisting of
    heterocycle,
    hydroxyl,
    with the proviso that no two hydroxyls are attached to the same carbon,
    —NR$^{R3}$R$^{R3'}$, and
    —P(O)(OR)(OR'),
  (z) nitro,
  (aa) —NRR',
  (bb) oxo,
  (cc) —SO$_2$NR$_{A'}$R$_{B'}$ wherein R$_{A'}$ and R$_{B'}$ are independently selected from the group consisting of
    hydrogen,
    (aryl)oyl,
    loweralkyl, and
    heterocycle wherein the heterocycle is unsubstituted or substituted with 1, 2, or 3 substituents independently selected from the group consisting of loweralkyl,
  (dd) sulfhydryl, and
  (ee) thioalkoxy,
(5) cycloalkyl wherein the cycloalkyl is unsubstituted or substituted with 1, 2, 3, 4 or 5 substituents selected from the group consisting of
  (a) alkoxy,
  (b) aryl,
  (c) arylalkoxy
  (d) aryloxy wherein the aryloxy is unsubstituted or substituted with 1, 2, 3, 4, or 5 substituents selected from the group consisting of halogen,
  (e) loweralkyl,
  (f) halogen,
  (g) NR$^{R3}$R$^{R3'}$,
  (h) oxo, and
  (i)

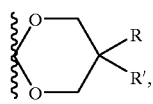

(6) cycloalkenyl wherein the cycloalkenyl is unsubstituted or substituted with 1, 2, 3 or 4 substituents independently selected from the group consisting of (a) loweralkyl,
(b) alkoxy,
(c) halogen,
(d) aryl,
(e) aryloxy,
(f) alkanoyl, and
(g) NR$^{R3}$R$^{R3'}$,

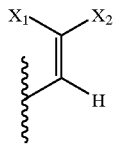

wherein $X_1$ and $X_2$ together are cycloalkyl wherein the cycloalkyl is unsubstituted or substituted with 1 or 2 substituents selected from the group consisting of aryl, and (8) —P(W)R$^{R3}$R$^{R3'}$; and $R_4$ is selected from the group consisting of
(1) hydrogen,
(2) loweralkyl,
(3) haloalkyl
(4) halogen,
(5) aryl,
(6) arylalkyl,
(7) heterocycle,
(8) (heterocyclic)alkyl
(9) alkoxy, and
(10) —NRR'; or $L_1$, Z, and $R_3$ together are selected from the group consisting of
(1) aminoalkyl,
(1) haloalkyl,
(2) halogen,
(3) carboxaldehyde, and
(4) (carboxaldehyde)alkyl, and
(5) hydroxyalkyl, with the proviso that when $L_1$, Z, and $R_3$ together are (1)–(5), $R_1$ is other than hydrogen.

In a further aspect of the present invention are disclosed pharmaceutical compositions which comprise a compound of formula I in combination with a pharmaceutically acceptable carrier.

In yet another aspect of the present invention are disclosed pharmaceutical compositions which comprise a compound of formula I in combination with another chemotherapeutic agent and a pharmaceutically acceptable carrier.

In yet another aspect of the present invention is disclosed a method for inhibiting protein isoprenyl transferases (i.e., protein farnesyltransferase and/or geranylgeranyltransferase) in a human or lower mammal, comprising administering to the patient a therapeutically effective amount of a compound compound of formula I.

In yet another aspect of the present invention is disclosed a method for inhibiting post-translational modification of the oncogenic Ras protein by protein farnesyltransferase, protein geranylgeranyltransferase or both.

In yet another aspect of the present invention is disclosed a method for treatment of conditions mediated by farnesylated or geranylgeranylated proteins, for example, treatment of Ras associated tumors in humans and other mammals.

In yet another aspect of the present invention is disclosed a method for inhibiting or treating cancer in a human or lower mammal comprising administering to the patient a therapeutically effective amount of a compound of the invention alone or in combination with another chemotherapeutic agent In yet another aspect of the present invention is disclosed a method for treating or preventing intimal hyperplasia associated with restenosis and atherosclerosis in a mammal comprising administering to the mammal a therapeutically effective amount of a compound of claim 1.

The compounds of the invention can comprise asymmetrically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30, which is hereby incorporated herein by reference.

DETAILED DESCRIPTION

Definitions of Terms

As used herein the terms "Cys," "Glu," "Leu," "Lys," "Met," "nor-Leu," "nor-Val," "Phe," "Ser" and "Val" refer to cysteine, glutamine, leucine, lysine, methionine, norleucine, norvaline, phenylalanine, serine and valine in their L-, D- or DL forms. As used herein these amino acids are in their naturally occuring L- form.

As used herein, the term "carboxy protecting group" refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo (for example by enzymatic hydrolysis) to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields (as described in U.S. Pat. Nos. 3,840,556 and 3,719,667, the disclosures of which are hereby incorporated herein by reference). Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy) ethyl, 2-(5-indanyloxycarbonyloxy)ethyl and the like; alkoxyalkylcarbonyloxyalkyl, such as 2-(1-methoxy-2-methylpropan-2-oyloxy)ethyl and like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl) alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups In Organic Synthesis," (John Wiley & Sons, New York (1981)), which is hereby incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, a,a-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to $R_{29}C(O)$— wherein $R_{29}$ is a loweralkyl group. The alkanoyl groups of this invention can be optionally substituted.

The term "alkanoylaminoalkyl" as used herein refers to a loweralkyl radical to which is appended $R_{71}$—NH— wherein $R_{71}$ is an alkanoyl group. The alkanoylaminoalkyl groups of this invention can be optionally substituted.

The term "alkanoyloxy" as used herein refers to $R_{29}C(O)$—O— wherein $R_{29}$ is a loweralkyl group. The alkanoyloxy groups of this invention can be optionally substituted.

The term "alkanoyloxyalkyl" as used herein refers to a loweralkyl radical to which is appended an alkanoyloxy group. The alkanoyloxyalkyl groups of this invention can be optionally substituted.

The term "alkenyl" as used herein refers to a straight or branched chain hydrocarbon containing from 2 to 10 carbon atoms and also containing at least one carbon-carbon double bond. Examples of alkenyl include —CH=CH$_2$, —CH$_2$CH=CH$_2$, —C(CH$_3$)=CH$_2$, —CH$_2$CH=CHCH$_3$, and the like. The alkenyl groups of this invention can be optionally substituted.

The term "alkenylene" as used herein refers to a divalent group derived from a straight or branched chain hydrocarbon containing from 2 to 20 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like. The alkenylene groups of this invention can be optionally substituted.

The term "alkenyloxy" as used herein refers to an alkenyl group attached to the parent molecular group through an oxygen atom. The alkenyloxy groups of this invention can be optionally substituted.

The term "alkenyloxyalkyl" as used herein refers to a loweralkyl group to which is attached an alkenyloxy group. The alkenyloxyalkyl groups of this invention can be optionally substituted.

The term "alkoxy" as used herein refers to $R_{30}$O— wherein $R_{30}$ is loweralkyl as defined above. Representative examples of alkoxy groups include methoxy, ethoxy, t-butoxy and the like. The alkoxy groups of this invention can be optionally substituted.

The term "alkoxyalkyl" as used herein refers to a loweralkyl group to which is attached an alkoxy group. The alkoxyalkyl groups of this invention can be optionally substituted.

The term "alkoxyalkoxy" as used herein refers to $R_{31}$O—$R_{32}$O— wherein $R_{31}$ is loweralkyl as defined above and $R_{32}$ is an alkylene radical. Representative examples of alkoxyalkoxy groups include methoxymethoxy, ethoxymethoxy, t-butoxymethoxy and the like. The alkoxyalkoxy groups of this invention can be optionally substituted.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like. The alkoxyalkyl groups of this invention can be optionally substituted.

The term "alkoxyalkylcarbonyloxyalkyl" as used herein refers to a loweralkyl radical to which is appended $R_{66}$—C(O)—O— wherein $R_{66}$ is an alkoxyalkyl group.

The term "alkoxyarylalkyl" as used herein refers to a an arylalkyl group to which is attached an alkoxy group. The alkoxyarylalkyl groups of this invention can be optionally substituted.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like. The alkoxycarbonyl groups of this invention can be optionally substituted. The alkoxycarbonyl groups of this invention can be optionally substituted.

The term "alkoxycarbonylalkyl" as used herein refers to an alkoxylcarbonyl group as previously defined appended to a loweralkyl radical. Examples of alkoxycarbonylalkyl include methoxycarbonylmethyl, 2-ethoxycarbonylethyl and the like. The alkoxycarbonylalkyl groups of this invention can be optionally substituted.

The term "alkoxycarbonylaminoalkyl" as used herein refers to a loweralkyl radical to which is appended $R_{69}$—NH— wherein $R_{69}$ is an alkoxycarbonyl group. The alkoxycarbonylaminoalkyl groups of this invention can be optionally substituted.

The term "alkoxycarbonyloxyalkyl" as used herein refers to a loweralkyl radical to which is appended $R_{63}$—O— wherein $R_{63}$ is an alkoxycarbonyl group. The alkoxycarbonyloxyalkyl groups of this invention can be optionally substituted.

The term "alkylamino" as used herein refers to $R_{35}$NH— wherein $R_{35}$ is a loweralkyl group, for example, methylamino, ethylamino, butylamino, and the like. The alkylamino groups of this invention can be optionally substituted.

The term "alkylaminoalkyl" as used herein refers a loweralkyl radical to which is appended an alkylamino group. The alkylaminoalkyl groups of this invention can be optionally substituted.

The term "alkylaminocarbonylaminoalkyl" as used herein refers to a loweralkyl radical to which is appended $R_{70}$—C(O)—NH— wherein $R_{70}$ is an alkylamino group. The alkylaminocarbonylaminoalkyl groups of this invention can be optionally substituted.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted.

The term "alkylsilyloxy" as used herein refers to a loweralkyl group to which is attached —OSiR$_W$R$_X$R$_Y$ wherein R$_W$, R$_X$, and R$_Y$ are selected from the group consisting of loweralkyl.

The term "alkylsulfinyl" as used herein refers to $R_{33}$S(O)— wherein $R_{33}$ is a loweralkyl group. The alkylsulfinyl groups of this invention can be optionally substituted.

The term "alkylsulfinylalkyl" as used herein refers to an alkyl group to which is attached a alkylsulfinyl group. The alkylsulfinylalkyl groups of this invention can be optionally substituted.

The term "alkylsulfonyl" as used herein refers to $R_{34}$S(O)$_2$— wherein $R_{34}$ is a loweralkyl group. The alkylsulfonyl groups of this invention can be optionally substituted.

The term "alkylsulfonylalkyl" as used herein refers to a loweralkyl radical to which is appended an alkylsulfonyl group. The alkylsulfonylalkyl groups of this invention can be optionally substituted.

The term alkylthioalkyl as used herein refers to a lower alkyl group as defined herein attached to the parent molecular moiety through a sulfur atom and an alkylene group. The alkylthioalkyl groups of this invention can be optionally substituted.

The term "alkynyl" as used herein refers to a straight or branched chain hydrocarbon containing from 2 to 10 carbon atoms and also containing at least one carbon-carbon triple bond. Examples of alkynyl include —C≡CH, —CH$_2$C≡CH, —CH$_2$C≡CCH$_3$, and the like. The alkynyl groups of this invention can be optionally substituted.

The term "alkynylene" as used herein refers to a divalent group derived from a straight or branched chain hydrocarbon containing from 2 to 10 carbon atoms and also containing at least one carbon-carbon triple bond. Examples of alkynylene include —C≡C—, —CH$_2$C≡C—, —CH$_2$C≡CCH$_2$—, and the like. The alkynylene groups of this invention can be optionally substituted.

The term "amino" as used herein refers to —NH$_2$.

The term "aminocarbonyl" as used herein refers to an amino group attached to the parent molecular group through a carbonyl group. The aminocarbonyl groups of this invention can be optionally substituted.

The term "aminocarbonylalkyl" as used herein refers to an alkyl group to which is attached an aminocarbonyl group. The aminocarbonylalkyl groups of this invention can be optionally substituted.

The term "aminoalkyl" as used herein refers to a loweralkyl radical to which is appended an amino group. The aminoalkyl groups of this invention can be optionally substituted.

The term "aminothiocarbonyl" as used herein refers to an amino group attached to the parent molecular group through a thiocarbonylcarbonyl (C=S) group. The aminothiocarbonyl groups of this invention can be optionally substituted.

The term "aroyloxyalkyl" as used herein refers to a loweralkyl radical to which is appended an aroyloxy group (i.e., $R_{61}$—C(O)O— wherein $R_{61}$ is an aryl group). The aroyloxyalkyl groups of this invention can be optionally substituted.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, sulfhydryl, nitro, cyano, carboxaldehyde, carboxy, alkoxycarbonyl, haloalkyl-C(O)—NH—, haloalkenyl-C(O)—NH— and carboxamide. In addition, substituted aryl groups include tetrafluorophenyl and pentafluorophenyl.

The term "arylalkenyl" as used herein refers to an alkenyl radical to which is appended an aryl group. The arylalkenyl groups of this invention can be optionally substituted.

The term "arylalkenyloxycarbonyloxyalkyl" as used herein refers to a loweralkyl radical to which is appended $R_{68}$—O—C(O)—O— wherein $R_{68}$ is an arylalkenyl group. The arylalkenyloxycarbonyloxyalkyl groups of this invention can be optionally substituted.

The term "arylalkoxy" as used herein refers to an alkoxy group to which is attached an aryl group. The arylalkoxy groups of this invention can be optionally substituted.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like. The arylalkyl groups of this invention can be optionally substituted.

The term "arylalkylcarbonyloxyalkyl" as used herein refers to a loweralkyl radical to which is appended an arylalkylcarbonyloxy group (i.e., $R_{62}$C(O)O— wherein $R_{62}$ is an arylalkyl group). The arylalkylcarbonyloxyalkyl groups of this invention can be optionally substituted.

The term "aryloxy" as used herein refers to an aryl group attached to the parent molecular group through an oxygen atom. The aryloxy groups of this invention can be optionally substituted.

The term "aryloxycarbonyl" as used herein refers to an aryloxy group attached to the parent molecular group through a carbonyl group. The aryloxycarbonyl groups of this invention can be optionally substituted.

The term "aryloyl" as used herein refers to an aryl group attached to the parent molecular group through a carbonyl group. The aryloyl groups of this invention can be optionally substituted.

The term "arylalkyloxycarbonyloxyalkyl" as used herein refers to a loweralkyl radical to which is appended $R_{67}$—O—C(O)—O— wherein $R_{67}$ is an arylalkyl group. The arylalkyloxycarbonyloxyalkyl groups of this invention can be optionally substituted.

The term "aryloxyalkyl" as used herein refers to a loweralkyl radical to which is appended $R_{65}$—O— wherein $R_{65}$ is an aryl group. The aryloxyalkyl groups of this invention can be optionally substituted.

The term "arylalkoxy" as used herein refers to an alkoxy radical to which is appended $R_{65}$—O— wherein $R_{65}$ is an aryl group. The arylalkoxy groups of this invention can be optionally substituted.

The term "arylalkyloxyalkyl" as used herein refers to a loweralkyl radical to which is appended an arylalkoxy group. The arylalkyloxyalkyl groups of this invention can be optionally substituted.

The term "aryloxy" as used herein refers to $R_{65}$—O— wherein $R_{65}$ is an aryl group. The aryloxy groups of this invention can be optionally substituted. The aryloxy groups of this invention can be optionally substituted.

The term "(aryl)oyl" as used herein refers to an aryl group attached to the parent molecular group through a carbonyl group. The (aryl)oyl groups of this invention can be optionally substituted.

The term "aryloxythioalkoxyalkyl" as used herein refers to a loweralkyl radical to which is appended $R_{75}$—S— wherein $R_{75}$ is an aryloxyalkyl group. The aryloxythioalkoxyalkyl groups of this invention can be optionally substituted.

The term "aryloxycarbonyloxyalkyl" as used herein refers to a loweralkyl radical to which is appended $R_{65}$—O—C(O)—O— wherein $R_{65}$ is an aryl group. The aryloxycarbonyloxyalkyl groups of this invention can be optionally substituted.

The term "arylsulfonyl" as used herein refers to $R_{36}$S(O)$_2$— wherein $R_{36}$ is an aryl group. The arylsulfonyl groups of this invention can be optionally substituted.

The term "arylsulfonyloxy" as used herein refers to $R_{37}$S(O)$_2$O— wherein $R_{37}$ is an aryl group. The arylsulfonyloxy groups of this invention can be optionally substituted.

The term "carboxy" as used herein refers to —COOH.

The term "carboxyalkyl" as used herein refers to a loweralkyl radical to which is appended a carboxy (—COOH) group. The carboxyalkyl groups of this invention can be optionally substituted.

The term "cyanoalkyl" as used herein used herein refers to a loweralkyl radical to which is appended a cyano (—CN) group. The cyanoalkyl groups of this invention can be optionally substituted.

The term "carboxaldehyde" as used herein used herein refers to —CHO.

The term "(carboxaldehyde)alkyl" as used herein used herein refers to a carboxaldehyde group attached to a loweralkyl group. The (carboxaldehyde)alkyl groups of this invention can be optionally substituted.

The terms "cycloalkanoyl" and "(cycloalkyl)oyl" refer to a cycloalkyl group attached to the parent molecular group through a carbonyl group. The cycloalkanoyl and (cycloalkyl)oyl groups of this invention can be optionally substituted.

The term "cycloalkanoylalkyl" as used herein refers to a loweralkyl radical to which is appended a cycloalkanoyl group (i.e., $R_{60}$—C(O)— wherein $R_{60}$ is a cycloalkyl group). The cycloalkanoylalkyl groups of this invention can be optionally substituted.

The term "cycloalkylalkoxyalkyl" as used herein refers to an alkoxyalkyl group to which is attached a cycloalkyl group. The cycloalkylalkoxyalkyl groups of this invention can be optionally substituted.

The term "cycloalkenyl" as used herein refers to an alicyclic group comprising from 3 to 10 carbon atoms and containing a carbon-carbon double bond including, but not limited to, cyclopentenyl, cyclohexenyl and the like. The cycloalkenyl groups of this invention can be optionally substituted.

The term "cycloalkoxy" as used herein refers to a cycloalkyl group attached to the parent molecular group through an oxygen atom. The cycloalkoxy groups of this invention can be optionally substituted.

The term "cycloalkoxyalkyl" as used herein refers to a loweralkyl group to which is attached a cycloalkoxy group. The cycloalkoxyalkyl groups of this invention can be optionally substituted.

The term "cycloalkoxycarbonyl" as used herein refers to a cycloalkoxy group attached to the parent molecular group through a carbonyl group. The cycloalkoxycarbonyl groups of this invention can be optionally substituted.

The term "cycloalkyl" as used herein refers to an alicyclic group comprising from 3 to 10 carbon atoms including, but not limited to, cyclopropyl, cyclobutyl, cyclopentyl, cyclohexyl, norbornyl, adamantyl and the like. The cycloalkyl groups of this invention can be optionally substituted. The cycloalkyl groups of this invention can be optionally substituted.

The term "cycloalkylaminocarbonyl" as used herein refers to NHR$_{60'}$C(O)— wherein R$_{60'}$ is a cycloalkyl group. The cycloalkylaminocarbonyl groups of this invention can be optionally substituted.

The term "cycloalkylaminothiocarbonyl" as used herein refers to $NHR_{60'}C(S)$— wherein $R_{60'}$ is defined above. The cycloalkylaminothiocarbonyl groups of this invention can be optionally substituted.

The term "cycloalkylalkoxy" as used herein refers to an alkoxy radical to which is appended a cycloalkyl group. The cycloalkylalkoxy groups of this invention can be optionally substituted.

The term "cycloalkylalkoxyalkyl" as used herein refers to an alkyl radical to which is appended a cycloalkylalkoxy group. The cycloalkylalkoxyalkyl groups of this invention can be optionally substituted.

The term "cycloalkylalkoxycarbonyl" as used herein refers to a cycloalkylalkoxy radical attached to the parent molecular group through a carbonyl group. The cycloalkylalkoxycarbonyl groups of this invention can be optionally substituted.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl, adamantylmethyl and the like. The cycloalkylalkyl groups of this invention can be optionally substituted.

The term "cycloalkyloxycarbonyloxyalkyl" as used herein refers to a loweralkyl radical to which is appended $R_{64}$—O—C(O)—O— wherein $R_{64}$ is a cycloalkyl group. The cycloalkyloxycarbonyloxyalkyl groups of this invention can be optionally substituted.

The term "dialkoxyalkyl" as used herein refers to a loweralkyl radical to which is appended two alkoxy groups. The dialkoxyalkyl groups of this invention can be optionally substituted.

The term "dialkylamino" as used herein refers to $R_{38}R_{39}N$— wherein $R_{38}$ and $R_{39}$ are independently selected from loweralkyl, for example dimethylamino, diethylamino, methyl propylamino, and the like. The dialkylamino groups of this invention can be optionally substituted.

The term "dialkylaminoalkyl" as used herein refers to a loweralkyl radical to which is appended a dialkylamino group. The dialkylaminoalkyl groups of this invention can be optionally substituted.

The term "dialkyaminocarbonylalkyl" as used herein refers to a loweralkyl radical to which is appended $R_{73}$—C(O)— wherein $R_{73}$ is a dialkylamino group. The dialkyaminocarbonylalkyl groups of this invention can be optionally substituted.

The term "dioxoalkyl" as used herein refers to a loweralkyl radical which is substituted with two oxo (=O) groups. The dioxoalkyl groups of this invention can be optionally substituted.

The term "dithioalkoxyalkyl" as used herein refers to a loweralkyl radical to which is appended two thioalkoxy groups. The dithioalkoxyalkyl groups of this invention can be optionally substituted.

The term "halogen" or "halo" as used herein refers to I, Br, Cl or F.

The term "haloalkenyl" as used herein refers to an alkenyl radical, as defined above, bearing at least one halogen substituent. The haloalkenyl groups of this invention can be optionally substituted.

The term "haloalkyl" as used herein refers to a lower alkyl radical, as defined above, bearing at least one halogen substituent, for example, chloromethyl, fluoroethyl or trifluoromethyl and the like. Haloalkyl can also include perfluoroalkyl wherein all hydrogens of a loweralkyl group are replaced with fluorides.

The term "heterocyclic ring" or "heterocyclic" or "heterocycle" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The term "heterocyclic" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring (for example, indolyl, quinolyl, isoquinolyl, tetrahydroquinolyl, benzofuryl or benzothienyl and the like). Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl and benzothienyl. Heterocyclics also include bridged bicyclic groups wherein a monocyclic heterocyclic group is bridged by an alkylene group, for example,

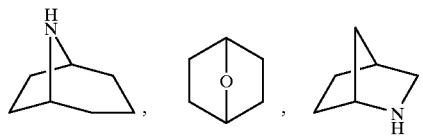

and the like.

Heterocyclics also include compounds of the formula

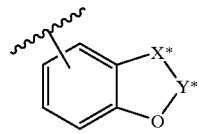

wherein X* is —CH$_2$—, —CH$_2$O— or —O— and Y* is —C(O)— or —(C(R')$_2$)$_v$— wherein R" is hydrogen or C$_1$–C$_4$-alkyl and v is 1, 2 or 3 such as 1,3-benzodioxolyl, 1,4-benzodioxanyl and the like.

Heterocyclics can be unsubstituted or substituted with one, two, three, four or five substituents independently selected from the group consisting of a) hydroxy, b) —SH, c) halo, d) oxo (=O), e) thioxo (=S), f) amino, g) —NHOH, h) alkylamino, i) dialkylamino, j) alkoxy, k) alkoxyalkoxy, l) haloalkyl, m) hydroxyalkyl, n) alkoxyalkyl, o) cycloalkyl which is unsubstituted or substituted with one, two, three or four loweralkyl groups, p) cycloalkenyl which is unsubstituted or substituted with one, two, three or four loweralkyl groups, q) alkenyl, r) alkynyl, s) aryl, t) arylalkyl, u) —COOH, v) —SO$_3$H, w) loweralkyl, x) alkoxycarbonyl, y) —C(O)NH$_2$, z) —C(S)NH$_2$, aa) —C(=N—OH)NH$_2$, bb) aryl-L$_{16}$—C(O)— wherein L$_{16}$ is an alkenylene radical, cc) —S—L$_{17}$—C(O)OR$_{40}$ wherein L$_{17}$ is an alkylene radical which is unsubstituted or substituted with one or two substitutents independently selected from the group consisting of alkanoyl, oxo (=O) or methinylamino (=CHNR$_{41}$R$_{42}$ wherein R$_{41}$ is hydrogen or loweralkyl and R$_{42}$ is loweralkyl) and R$_{40}$ is hydrogen or a carboxy-protecting group, dd) —S—L$_{18}$—C(O)NR$_{43}$R$_{44}$ wherein L$_{18}$ is an alkylene radical which is unsubstituted or substituted with one or two substitutents independently selected from the group consisting of alkanoyl, oxo (=O) or methinylamino (=CHNR$_{41}$R$_{42}$ wherein R$_{41}$ is hydrogen or loweralkyl and R$_{43}$ and R$_{44}$ are independently selected from the group consisting of hydrogen, loweralkyl and aryl, ee) —S—L$_{19}$— CN wherein L$_{19}$ is an alkylene radical, ff) —S—L$_{20}$—R$_{45}$ wherein L$_{20}$ is absent or is an alkylene radical or an alkenylene radical or an alkynylene radical wherein the alkylene, alkenylene or alkynylene radical is unsubstituted or substituted with oxo (=O) and R$_{45}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, gg) —O—L$_{21}$—R$_{46}$ wherein L$_{21}$ is absent or is an alkylene radical or an alkenylene radical or an alkynylene radical wherein the alkylene, alkenylene or alkynylene radical is unsubstituted or substituted with one or two substitutents independently selected from the group consisting of alkanoyl, oxo (=O) or methinylamino (=CHNR$_{41}$R$_{42}$ wherein R$_{41}$ is hydrogen or loweralkyl and R$_{46}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, hh) —O—S(O)$_2$—R$_{47}$ wherein R$_{47}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, ii) —S(O)$_2$—NH—R$_{48}$ wherein R$_{48}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, jj) alkylsulfinyl, kk) alkylsulfonyl, ll) arylsulfonyl, mm) arylsulfonyloxy, nn) —C(=NOR$_{49}$)C(O)OR$_{50}$ wherein R$_{49}$ is hydrogen or loweralkyl and R$_{50}$ is hydrogen or a carboxy-protecting group, oo) alkoxycarbonylalkyl, pp) carboxyalkyl, qq) cyanoalkyl, rr) alkylaminoalkyl, ss) N-protected alkylaminoalkyl, tt) dialkylaminoalkyl, uu) dioxoalkyl, vv) loweralkyl-C(O)—, ww) loweralkyl-C(S)—, xx) aryl- C(O)—, yy) aryl-C(S)—, zz) loweralkyl-C(O)—O—, aaa) loweralkyl-S—C(S)— bbb) N-protected amino, ccc) aminoalkyl—C(O)—, ddd) N-protected aminoalkyl—C(O)— eee) aminoalkyl-C(S)—, fff) N-protected aminoalkyl-C(S)—, ggg) aminoalkyl, hhh) N-protected aminoalkyl, iii) formyl, jjj) cyano, kkk) nitro, lll) spiroalkyl, mmm) oxoalkyloxy, nnn) R$_{53}$—L$_{22}$—, wherein L$_{22}$ is alkenylene or alkynylene and R$_{53}$ is aryl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, ooo) aryl-NH—C (O)—, ppp) R$_{54}$—N=N— wherein R$_{54}$ is aryl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, qqq) =N—R$_{55}$ wherein R$_{55}$ is hydrogen, aryl, heterocyclic, —S(O)$_2$-aryl or —S(O)$_2$-heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, rrr) diarylalkyl-N=N—, sss) aryl-N(R$_{56}$)— or arylalkyl-N(R$_{56}$)— wherein R$_{56}$ is hydrogen or an N-protecting group, ttt) aryl-sulfonylalkyl, uuu) heterocyclicsulfonylalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, vvv) =C(CN)(C(O)NH$_2$), www) =C(CN)(C(O)O-loweralkyl), xxx) heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, yyy) hydroxythioalkoxy, zzz) aryloxyalkyl, aaaa) aryloxyalkylthioalkoxy, bbbb) dialkoxyalkyl, cccc) dithioalkoxyalkyl, dddd) arylalkyl-NH—L$_{23}$— wherein L$_{23}$ is an alkylene group, eeee) heterocyclicalkyl-NH—L$_{24}$— wherein L$_{24}$ is an alkylene group, ffff) aryl-S(O)$_2$—NH— L$_{25}$— wherein L$_{25}$ is an alkylene group, gggg) heterocyclic-S(O)$_2$—NH—L$_{26}$— wherein L$_{26}$ is an alkylene group, hhhh) aryl-C(O)—NH—L$_{27}$— wherein L$_{27}$ is an alkylene group and iiii) heterocyclic-C(O)—NH—L$_{28}$— wherein L$_{28}$ is an alkylene group, jjjj) R$_{yy}$(CH$_2$)$_n$—X—Y—Z—(CH$_2$)$_m$ wherein Ryy is cycloalkyl, aryl and loweralkyl, n amd m are independently 0–2, Z is O or absent, Y is absent, CH$_2$, CHOH or C(O), with the proviso that when X is O, Z is absent and with the proviso that when Z is O, X is absent and with the proviso that when Y is CHOH, X and Z are absent.

The term "(heterocyclic)alkoxy" as used herein refers to an alkoxy group to which is attached a heterocycle. The (heterocyclic)alkoxy groups of this invention can be optionally substituted.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like. The (heterocyclic)alkyl groups of this invention can be optionally substituted.

The term "(heterocyclic)oxy" as used herein refers to a heterocycle connected to the parent molecular group through an oxygen atom. The (heterocyclic)oxy groups of this invention can be optionally substituted.

The term "(heterocyclic)oxyalkyl" as used herein refers to a loweralkyl group to which is attached a (heterocyclic)oxy group. The (heterocyclic)oxyalkyl groups of this invention can be optionally substituted.

The term "(heterocyclic)alkoxyalkyl" as used herein refers to an alkoxyalkyl group to which is attached a heterocycle. The (heterocyclic)alkoxyalkyl groups of this invention can be optionally substituted.

The term "heterocycliccarbonyloxyalkyl" as used herein refers to a loweralkyl radical to which is appended $R_{72}$—C(O)—O— wherein $R_{72}$ is a heterocyclic group. The heterocycliccarbonyloxyalkyl groups of this invention can be optionally substituted.

The term "hydroxy" as used herein refers to —OH.

The term "hydroxyalkyl" as used herein refers to a loweralkyl radical to which is appended an hydroxy group. The hydroxyalkyl groups of this invention can be optionally substituted.

The term "hydroxyarylalkyl" as used herein refers to a arylalkyl group to which is appended a hydroxy group. The hydroxyarylalkyl groups of this invention can be optionally substituted.

The term "hydroxythioalkoxy" as used herein refers to $R_{51}S$— wherein $R_{51}$ is a hydroxyalkyl group. The hydroxythioalkoxy groups of this invention can be optionally substituted.

The term "loweralkyl" as used herein refers to branched or straight chain alkyl groups comprising one to ten carbon atoms, including methyl, ethyl, propyl, isopropyl, n-butyl, t-butyl, neopentyl and the like. The loweralkyl groups of this invention can be optionally substituted.

The term "N-protected alkylaminoalkyl" as used herein refers to an alkylaminoalkyl group wherein the nitrogen is N-protected. The N-protected alkylaminoalkyl groups of this invention can be optionally substituted.

The term "nitro" as used herein refers to —$NO_2$.

The term "oxo" as used herein refers to (=O).

The term "oxoalkyloxy" as used herein refers to an alkoxy radical wherein the loweralkyl moiety is substituted with an oxo (=O) group. The oxoalkyloxy groups of this invention can be optionally substituted.

The term "oxyamino(alkyl)carbonylalkyl" as used herein refers to a —O—NR—C(O)—R' group wherein R and R' are loweralkyl.

The term "oxyamino(arylalkyl)carbonylalkyl" as used herein refers to a —O—$NR^{R}3$—C(O)—R group wherein $R^{R}3$ is arylalkyl and R is loweralkyl.

The term "oxyaminocarbonylalkyl" as used herein refers to —O—NH—C(O)—R group wherein R is loweralkyl.

The term "spiroalkyl" as used herein refers to an alkylene diradical, both ends of which are bonded to the same carbon atom of the parent group to form a spirocyclic group. The spiroalkyl groups of this invention can be optionally substituted.

The term "sulfhydryl" as used herein refers to —SH.

The term "sulfhydrylalkyl" as used herein refers to a loweralkyl group to which is attached a sulfhydryl group. The sulfhydrylalkyl groups of this invention can be optionally substituted.

The term "thioalkoxy" as used herein refers to $R_{52}S$— wherein $R_{52}$ is loweralkyl. Examples of thioalkoxy include, but are not limited to, methylthio, ethylthio and the like. The thioalkoxy groups of this invention can be optionally substituted.

The term "thioalkoxyalkyl" as used herein refers to a thioalkoxy group as previously defined appended to a loweralkyl group as previously defined. Examples of thioalkoxyalkyl include thiomethoxymethyl, 2-thiomethoxyethyl and the like. The thioalkoxyalkyl groups of this invention can be optionally substituted.

The term "thiocycloalkoxy" as used herein refers to a cycloalkyl group attached to the parent molecular group through a sulfur atom. The thiocycloalkoxy groups of this invention can be optionally substituted.

The term "thiocycloalkoxyalkyl" as used herein refers to a loweralkyl group to which is attached a thiocycloalkoxy group. The thiocycloalkoxyalkyl groups of this invention can be optionally substituted.

Preferred Embodiments

Preferred compounds of the invention are compounds of formula I wherein $R_1$ is unsubstituted or substituted phenyl and $R_2$ is —C(O)NH—CH($R_{14}$)—C(O)$OR_{15}$ or —C(O)NH—CH($R_{14}$)—C(O)$NHSO_2R_{16}$ wherein $L_2$, $R_{14}$ $R_{15}$ and $R_{16}$ are defined above.

More preferred compounds of the invention are compounds of formula I wherein $R_1$ is unsubstituted or substituted phenyl and $R_2$ is

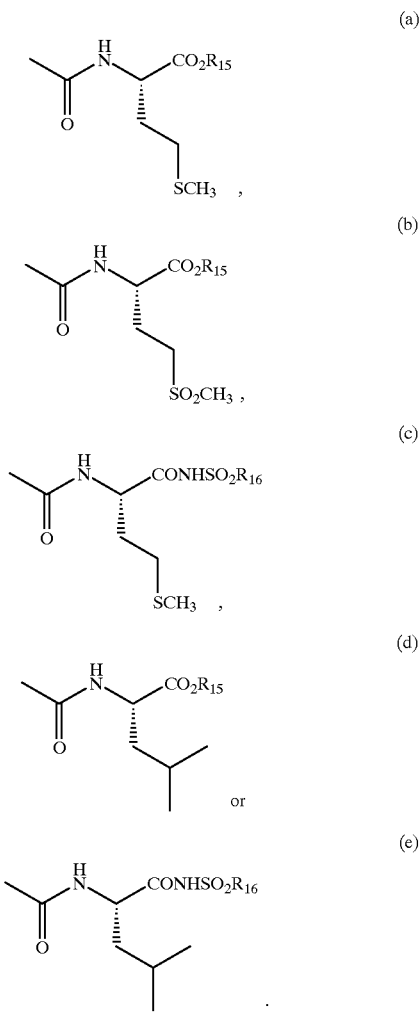

Still more preferred compounds have formula I wherein $R_3$ is selected from the group consisting of (a) pyridyl, (b) imidazolyl, and (c) furyl wherein the pyridyl, imidazolyl, or furyl group may be substituted with 1, 2 or 3 substituents selected from the group consisting of aryl, loweralkyl, halo, nitro, haloalkyl, hydroxy, hydroxyalkyl, amino, N-protected amino, alkoxy, and thioalkoxy.

Still more preferred compounds of the invention have the structure defined immediately above wherein $R_1$ is unsubstituted or substituted phenyl and $R_2$ is (a) 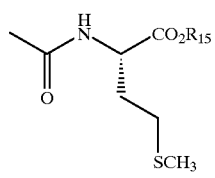

(b) 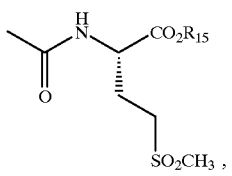

(c) 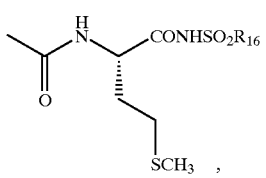

(d) 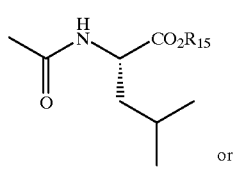

or (e) 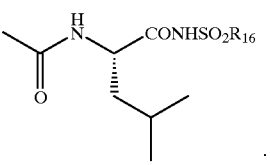

The most preferred compounds have the structure defined immediately above wherein $R_3$ is unsubstituted or substituted pyridyl or imidazolyl.

Protein Farnesyltransferase Inhibition

The ability of the compounds of the invention to inhibit protein farnesyltransferase or protein geranylgeranyltransferase can be measured according to the method of Moores, et al., J. Biol. Chem. 266: 14603 (1991) or the method of Vogt, et al., J. Biol. Chem. 270:660–664 (1995). In addition, procedures for determination of the inhibition of farnesylation of the oncogene protein Ras are described by Goldstein, et al., J. Biol. Chem., 266:15575–15578 (1991) and by Singh in U.S. Pat. No. 5,245,061.

In addition, in vitro inhibition of protein farnesyltransferase may be measured by the following procedure. Rat brain protein farnesyltransferase activity is measured using an Amersham Life Science commercial scintillation proximity assay kit and substituting a biotin-K Ras B fragment (biotin-Lys-Lys-Ser-Lys-Thr-Lys-Cys-Val-Ile-Met-$CO_2H$), 0.1 mM final concentration, for the biotin-lamin substrate provided by Amersham. The enzyme is purified according to Reiss, Y., et al., Cell, 62: 81–88 (1990), utilizing steps one through three. The specific activity of the enzyme is approximately 10 nmol substrate farnesylated/mg enzyme/hour. The percent inhibition of the farnesylation caused by the compounds of the invention (at $10 \times 10^{-6}$ M) compared to an uninhibited control sample is evaluated in the same Amersham test system.

The % inhibition of protein farnesyltransferase was determined for representative compounds of the invention. The results are summarized in Table 1.

Tables 1–5

In Vitro Potencies of Representative Compounds

TABLE 1

Inhibition of farnesyltransferase

| Example | % inhibition at $1 \times 10^{-5}$M |
|---|---|
| 200 | 93 |
| 350 | 53 |
| 351 | 82 |
| 352 | 52 |
| 353 | 62 |
| 354 | 47 |
| 355 | 43 |
| 356 | 58 |
| 357 | 56 |
| 358 | 45 |
| 359 | 36 |
| 360 | 88 |
| 361 | 97 |
| 362 | 83 |
| 363 | 96 |
| 364 | 69 |
| 365 | 97 |
| 366 | 83 |
| 367 | 81 |
| 368 | 71 |
| 369 | 87 |
| 370 | 86 |
| 371 | 66 |
| 372 | 69 |
| 373 | 76 |
| 374 | 61 |
| 375 | 68 |
| 376 | 80 |
| 377 | 71 |
| 378 | 54 |
| 380 | 45 |
| 381 | 79 |
| 382 | >50 |
| 383 | >50 |
| 387 | >50 |
| 388 | >50 |
| 390 | >50 |
| 639 | 44 |
| 659 | 55 |
| 663 | 43 |
| 664 | 75 |
| 669 | 52 |
| 670 | 78 |
| 672 | 48 |
| 674 | 40 |
| 676 | 76 |
| 678 | 73 |
| 680 | 58 |
| 683 | 57 |
| 684 | 48 |
| 685 | 55 |
| 686 | 48 |
| 687 | 78 |
| 688 | 71 |
| 689 | 73 |
| 690 | 61 |
| 692 | 74 |
| 699 | 74 |
| 700 | 68 |
| 701 | 64 |
| 702 | 79 |

TABLE 1-continued

Inhibition of farnesyltransferase

| Example | % inhibition at $1 \times 10^{-5}$M |
|---|---|
| 704 | 67 |
| 705 | 72 |
| 706 | 53 |
| 707 | 66 |
| 708 | 76 |
| 709 | 55 |
| 710 | 45 |
| 711 | 46 |
| 712 | 69 |
| 713 | 40 |
| 714 | 56 |
| 715 | 67 |
| 717 | 75 |
| 718 | 40 |
| 750 | 44 |
| 752 | 58 |
| 753 | 55 |
| 754 | 40 |
| 755 | 44 |
| 756 | 47 |
| 757 | 58 |
| 758 | 46 |
| 759 | 49 |
| 952 | >50 |
| 955 | 50 |
| 974 | >50 |

TABLE 2

Inhibition of farnesyltransferase

| Example | % inhibition at $1 \times 10^{-6}$M |
|---|---|
| 157 | 92 |
| 158 | 2 |
| 159 | 84 |
| 160 | 30 |
| 161 | 54 |
| 162 | 12 |
| 163 | 18 |
| 164 | 92 |
| 165 | 74 |
| 166 | 97 |
| 167 | 98 |
| 168 | 92 |
| 183 | 98 |
| 184 | 36 |
| 185 | 93 |
| 186 | 86 |
| 187 | 68 |
| 188 | 40 |
| 189 | 88 |
| 190 | 4 |
| 191 | 28 |
| 192 | 95 |
| 193 | 4 |
| 196 | 43 |
| 197 | 1 |
| 201 | 63 |
| 202 | 31 |
| 203 | 76 |
| 204 | 98 |
| 205 | 98 |
| 206 | 67 |
| 207 | 98 |
| 208 | 98 |
| 209 | 74 |
| 210 | 5 |
| 211 | 98 |
| 212 | 12 |

TABLE 2-continued

Inhibition of farnesyltransferase

| Example | % inhibition at $1 \times 10^{-6}$M |
|---|---|
| 213 | 98 |
| 214 | 97 |
| 215 | 82 |
| 216 | 67 |
| 217 | 99 |
| 218 | 89 |
| 219 | 56 |
| 220 | 92 |
| 221 | 55 |
| 222 | 41 |
| 223 | 63 |
| 224 | 41 |
| 225 | 93 |
| 226 | 23 |
| 227 | 94 |
| 228 | 39 |
| 231 | 50 |
| 233 | 65 |
| 234 | 4 |
| 235 | 95 |
| 237 | 98 |
| 238 | 22 |
| 239 | 97 |
| 240 | 98 |
| 241 | 41 |
| 242 | 99 |
| 243 | 23 |
| 244 | 21 |
| 245 | 50 |
| 248 | 79 |
| 249 | 77 |
| 250 | 96 |
| 252 | 98 |
| 253 | 99 |
| 254 | 96 |
| 255 | 98 |
| 256 | 98 |
| 257 | 98 |
| 258 | 98 |
| 259 | 98 |
| 260 | 98 |
| 261 | 98 |
| 262 | 98 |
| 263 | 99 |
| 264 | 98 |
| 265 | 98 |
| 266 | 97 |
| 267 | 96 |
| 268 | 98 |
| 269 | 98 |
| 270 | 98 |
| 271 | 84 |
| 272 | 96 |
| 273 | 96 |
| 274 | 94 |
| 276 | 98 |
| 277 | 98 |
| 278 | 99 |
| 279 | 99 |
| 280 | 98 |
| 281 | 98 |
| 282 | 76 |
| 283 | 98 |
| 284 | 83 |
| 286 | 84 |
| 287 | 24 |
| 288 | 22 |
| 289 | 23 |
| 290 | 74 |
| 291 | 23 |
| 292 | 36 |
| 294 | 98 |
| 295 | 94 |
| 296 | 89 |

TABLE 2-continued

Inhibition of farnesyltransferase

| Example | % inhibition at $1 \times 10^{-6}$M |
|---|---|
| 297 | 65 |
| 298 | 43 |
| 299 | 94 |
| 300 | 22 |
| 301 | 98 |
| 302 | 31 |
| 304 | 99 |
| 305 | 99 |
| 306 | 99 |
| 307 | 82 |
| 308 | 62 |
| 309 | 98 |
| 310 | 98 |
| 311 | 97 |
| 313 | 94 |
| 314 | 97 |
| 315 | 93 |
| 316 | 63 |
| 317 | 54 |
| 318 | 98 |
| 319 | 98 |
| 320 | 93 |
| 321 | 90 |
| 322 | 98 |
| 323 | 98 |
| 324 | 98 |
| 325 | 99 |
| 326 | 91 |
| 327 | 97 |
| 328 | 96 |
| 329 | 98 |
| 330 | 98 |
| 331 | 98 |
| 332 | 26 |
| 333 | 99 |
| 334 | 93 |
| 343 | 72 |
| 344 | 95 |
| 345 | 91 |
| 346 | 98 |
| 347 | 95 |
| 348 | 66 |
| 349 | 99 |
| 379 | 21 |
| 541 | 37 |
| 542 | 67 |
| 544 | 35 |
| 545 | 88 |
| 546 | 97 |
| 547 | 91 |
| 550 | 96 |
| 728 | 78 |
| 552 | 88 |
| 553 | 92 |
| 554 | 96 |
| 555 | 85 |
| 556 | 99 |
| 557 | 93 |
| 560 | 91 |
| 561 | 91 |
| 564 | 98 |
| 565 | 94 |
| 566 | 98 |
| 568 | 93 |
| 569 | 91 |
| 572 | 91 |
| 575 | 70 |
| 576 | 88 |
| 577 | 94 |
| 582 | 99 |
| 583 | 98 |
| 587 | 97 |
| 595 | 97 |
| 607 | 96 |
| 610 | 94 |
| 613 | 97 |
| 617 | 99 |
| 620 | 98 |
| 626 | 61 |
| 627 | 85 |
| 632 | 43 |
| 633 | 32 |
| 636 | 72 |
| 641 | 34 |
| 642 | 48 |
| 644 | 54 |
| 386 | >50 |
| 399 | >50 |
| 403 | 99 |
| 404 | 98 |
| 405 | 98 |
| 406 | 95 |
| 407 | 98 |
| 435 | 96 |
| 451 | 85 |
| 452 | 96 |
| 453 | 90 |
| 456 | 81 |
| 457 | 92 |
| 460 | 88 |
| 463 | 91 |
| 465 | 92 |
| 466 | 93 |
| 467 | 97 |
| 468 | 96 |
| 469 | 92 |
| 470 | 95 |
| 471 | 94 |
| 472 | 97 |
| 473 | 96 |
| 474 | 92 |
| 475 | 21 |
| 476 | 91 |
| 477 | 98 |
| 478 | 98 |
| 479 | 95 |
| 480 | 87 |
| 481 | 95 |
| 488 | 41 |
| 494 | 96 |
| 495 | 95 |
| 496 | 93 |
| 497 | 94 |
| 498 | 98 |
| 499 | 98 |
| 500 | 98 |
| 501 | 84 |
| 502 | 24 |
| 503 | 57 |
| 504 | 90 |
| 505 | 72 |
| 507 | 95 |
| 507 | 96 |
| 508 | 95 |
| 509 | 77 |
| 510 | 84 |
| 512 | 94 |
| 513 | 96 |
| 514 | 94 |
| 515 | 72 |
| 516 | 95 |
| 525 | 99 |
| 528 | 99 |
| 529 | 99 |
| 530 | 94 |
| 537 | 97 |
| 540 | 40 |
| 645 | 37 |

TABLE 2-continued

Inhibition of farnesyltransferase

| Example | % inhibition at $1 \times 10^{-6}$M |
|---|---|
| 646 | 58 |
| 649 | 86 |
| 650 | 68 |
| 651 | 33 |
| 652 | 41 |
| 653 | 62 |
| 655 | 35 |
| 657 | 32 |
| 658 | 73 |
| 661 | 45 |
| 662 | 68 |
| 665 | 55 |
| 666 | 82 |
| 667 | 83 |
| 671 | 36 |
| 673 | 59 |
| 677 | 37 |
| 682 | 31 |
| 691 | 34 |
| 693 | 53 |
| 694 | 45 |
| 696 | 57 |
| 697 | 39 |
| 703 | 40 |
| 716 | 69 |
| 719 | 90 |
| 720 | 70 |
| 721 | 83 |
| 722 | 96 |
| 723 | 87 |
| 724 | 87 |
| 725 | 78 |
| 726 | 81 |
| 727 | 95 |
| 744 | 84 |
| 749 | 84 |
| 751 | 32 |
| 764 | 88 |
| 765 | 76 |
| 768 | 67 |
| 771 | 72 |
| 772 | 79 |
| 773 | 41 |
| 774 | 48 |
| 775 | 32 |
| 776 | 36 |
| 777 | 83 |
| 782 | 96 |
| 786 | 34 |
| 787 | 70 |
| 788 | 44 |
| 789 | 86 |
| 790 | 88 |
| 791 | 53 |
| 792 | 88 |
| 793 | 94 |
| 794 | 92 |
| 796 | 35 |
| 797 | 35 |
| 806 | 72 |
| 807 | 90 |
| 808 | 88 |
| 809 | 78 |
| 810 | 89 |
| 812 | 94 |
| 813 | 95 |
| 816 | 87 |
| 824 | 90 |
| 831 | 92 |
| 832 | 80 |
| 834 | 55 |
| 835 | 96 |
| 844 | 92 |
| 846 | 85 |

TABLE 2-continued

Inhibition of farnesyltransferase

| Example | % inhibition at $1 \times 10^{-6}$M |
|---|---|
| 850 | 90 |
| 862 | 95 |
| 866 | 62 |
| 867 | 71 |
| 868 | 89 |
| 872 | 74 |
| 878 | 95 |
| 879 | 95 |
| 886 | 35 |
| 889 | 95 |
| 902 | 85 |
| 903 | 78 |
| 908 | 88 |
| 910 | 42 |
| 911 | 65 |
| 918 | 97 |
| 923 | 78 |
| 924 | 77 |
| 925 | 87 |
| 926 | 69 |
| 936 | 69 |
| 937 | 95 |
| 962 | >50 |
| 964 | >50 |
| 979 | 26 |
| 982 | 64 |
| 987 | 93 |
| 988 | 92 |
| 989 | 88 |

TABLE 3

Inhibition of farnesyltransferase

| Example | % inhibition at $1 \times 10^{-7}$M |
|---|---|
| 434 | 93 |
| 436 | 89 |
| 437 | 89 |
| 438 | 90 |
| 439 | 80 |
| 440 | 92 |
| 441 | 91 |
| 442 | 88 |
| 443 | 97 |
| 444 | 95 |
| 445 | 94 |
| 446 | 91 |
| 447 | 91 |
| 448 | 92 |
| 449 | 91 |
| 450 | 96 |
| 455 | 83 |
| 458 | 87 |
| 459 | 92 |
| 461 | 93 |
| 462 | 91 |
| 464 | 86 |
| 482 | 96 |
| 483 | 95 |
| 484 | 97 |
| 485 | 96 |
| 486 | 97 |
| 487 | 81 |
| 489 | 86 |
| 490 | 70 |
| 491 | 94 |
| 492 | 95 |
| 493 | 51 |
| 511 | 82 |

TABLE 3-continued

Inhibition of farnesyltransferase

| Example | % inhibition at $1 \times 10^{-7}$M |
|---|---|
| 519 | 89 |
| 520 | 97 |
| 521 | 94 |
| 522 | 93 |
| 523 | 97 |
| 524 | 99 |
| 526 | 96 |
| 527 | 97 |
| 531 | 74 |
| 532 | 88 |
| 533 | 91 |
| 534 | 84 |
| 535 | 89 |
| 536 | 79 |
| 539 | 89 |
| 548 | 86 |
| 549 | 98 |
| 551 | 93 |
| 558 | 87 |
| 559 | 96 |
| 562 | 95 |
| 563 | 95 |
| 570 | 92 |
| 571 | 88 |
| 573 | 72 |
| 574 | 81 |
| 578 | 90 |
| 579 | 92 |
| 580 | 90 |
| 581 | 96 |
| 584 | 96 |
| 585 | 96 |
| 589 | 91 |
| 590 | 95 |
| 592 | 93 |
| 593 | 86 |
| 594 | 95 |
| 597 | 75 |
| 600 | 93 |
| 601 | 92 |
| 602 | 97 |
| 604 | 86 |
| 609 | 95 |
| 611 | 95 |
| 615 | 94 |
| 616 | 95 |
| 618 | 89 |
| 621 | 98 |
| 622 | 95 |
| 623 | 96 |
| 729 | 73 |
| 730 | 96 |
| 731 | 65 |
| 732 | 84 |
| 733 | 60 |
| 734 | 49 |
| 735 | 96 |
| 736 | 96 |
| 737 | 95 |
| 738 | 54 |
| 739 | 83 |
| 740 | 94 |
| 741 | 89 |
| 742 | 87 |
| 743 | 51 |
| 745 | 93 |
| 746 | 84 |
| 747 | 68 |
| 748 | 56 |
| 769 | 90 |
| 770 | 91 |
| 781 | 91 |
| 785 | 96 |
| 795 | 87 |

TABLE 3-continued

Inhibition of farnesyltransferase

| Example | % inhibition at $1 \times 10^{-7}$M |
|---|---|
| 798 | 95 |
| 799 | 96 |
| 800 | 74 |
| 801 | 87 |
| 802 | 88 |
| 811 | 85 |
| 814 | 81 |
| 815 | 71 |
| 817 | 60 |
| 818 | 78 |
| 822 | 93 |
| 823 | 75 |
| 825 | 79 |
| 839 | 63 |
| 849 | 66 |
| 854 | 78 |
| 855 | 92 |
| 856 | 97 |
| 857 | 92 |
| 859 | 86 |
| 861 | 65 |
| 863 | 72 |
| 864 | 84 |
| 865 | 95 |
| 869 | 92 |
| 874 | 90 |
| 875 | 92 |
| 876 | 92 |
| 891 | 94 |
| 893 | 87 |
| 894 | 89 |
| 895 | 92 |
| 896 | 96 |
| 900 | 95 |
| 906 | 88 |
| 912 | 85 |
| 913 | 89 |
| 914 | 91 |
| 917 | 78 |
| 919 | 91 |
| 921 | 82 |
| 929 | 81 |
| 931 | 98 |
| 933 | 91 |
| 935 | 72 |
| 940 | 92 |
| 941 | 90 |
| 945 | 80 |
| 947 | 79 |
| 948 | 75 |
| 949 | 57 |
| 950 | 71 |
| 951 | 71 |
| 959 | >50 |
| 983 | 66 |
| 984 | 86 |
| 990 | 84 |
| 993 | 90 |

TABLE 4

Inhibition of farnesyltransferase

| Example | % inhibition at $1 \times 10^{-8}$M |
|---|---|
| 384 | 91 |
| 397 | 50 |
| 398 | >50 |
| 400 | 98 |
| 401 | 66 |

TABLE 4-continued

Inhibition of farnesyltransferase

| Example | % inhibition at $1 \times 10^{-8}$M |
|---|---|
| 408 | >95 |
| 409 | 84 |
| 410 | 94 |
| 517 | 92 |
| 518 | 90 |
| 567 | 69 |
| 586 | 90 |
| 588 | 68 |
| 591 | 82 |
| 599 | 86 |
| 603 | 94 |
| 605 | 68 |
| 606 | 93 |
| 608 | 91 |
| 612 | 96 |
| 614 | 92 |
| 619 | 95 |
| 760 | 95 |
| 762 | 84 |
| 763 | 92 |
| 766 | 95 |
| 767 | 97 |
| 779 | 70 |
| 780 | 71 |
| 803 | 95 |
| 804 | 95 |
| 805 | 96 |
| 819 | 76 |
| 820 | 66 |
| 821 | 75 |
| 826 | 92 |
| 827 | 77 |
| 828 | 87 |
| 829 | 92 |
| 833 | 78 |
| 836 | 95 |
| 837 | 91 |
| 838 | 92 |
| 840 | 73 |
| 841 | 93 |
| 842 | 88 |
| 843 | 96 |
| 845 | 85 |
| 847 | 85 |
| 848 | 87 |
| 851 | 82 |
| 852 | 79 |
| 853 | 85 |
| 858 | 60 |
| 860 | 85 |
| 870 | 91 |
| 871 | 94 |
| 873 | 97 |
| 877 | 68 |
| 880 | 95 |
| 881 | 69 |
| 882 | 79 |
| 883 | 91 |
| 884 | 94 |
| 885 | 95 |
| 887 | 92 |
| 888 | 86 |
| 892 | 59 |
| 897 | 76 |
| 898 | 82 |
| 899 | 88 |
| 901 | 84 |
| 904 | 85 |
| 905 | 86 |
| 907 | 79 |
| 909 | 79 |
| 916 | 96 |
| 920 | 96 |
| 922 | 96 |

TABLE 4-continued

Inhibition of farnesyltransferase

| Example | % inhibition at $1 \times 10^{-8}$M |
|---|---|
| 927 | 74 |
| 928 | 84 |
| 930 | 66 |
| 932 | 60 |
| 934 | 71 |
| 938 | 61 |
| 939 | 72 |
| 942 | 58 |
| 943 | 79 |
| 944 | 88 |
| 946 | 52 |
| 954 | >50 |
| 958 | >50 |
| 960 | >50 |
| 985 | 89 |
| 986 | 95 |
| 991 | 69 |
| 992 | 93 |
| 994 | 83 |
| 995 | 92 |
| 996 | 80 |

TABLE 5

Inhibition of geranylgeranyltransferase I.

| Example | Activity |
|---|---|
| 387 | >50% inhibition at $1 \times 10^{-6}$M |
| 388 | >50% inhibition at $1 \times 10^{-7}$M |
| 389 | >50% inhibition at $1 \times 10^{-6}$M |
| 390 | >50% inhibition at $1 \times 10^{-5}$M |
| 392 | >50% inhibition at $1 \times 10^{-5}$M |
| 399 | >50% inhibition at $1 \times 10^{-6}$M |
| 953 | >50% inhibition at $1 \times 10^{-6}$M |
| 955 | >50% inhibition at $1 \times 10^{-7}$M |
| 962 | >50% inhibition at $1 \times 10^{-7}$M |
| 964 | >50% inhibition at $1 \times 10^{-6}$M |
| 966 | >50% inhibition at $1 \times 10^{-6}$M |
| 967 | >50% inhibition at $1 \times 10^{-6}$M |
| 969 | >50% inhibition at $1 \times 10^{-5}$M |
| 974 | >50% inhibition at $1 \times 10^{-5}$M |

TABLE 6

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 997 | | 91** |
| 998 | | 79** |
| 999 | | 90 |
| 1000 | | 82* |
| 1001 | | 92** |
| 1002 | | 82** |
| 1003 | | 92* |
| 1004 | | 92** |
| 1005 | | 95** |
| 1006 | | 95** |
| 1007 | | 85** |
| 1008 | | 95** |
| 1009 | | 86** |
| 1010 | | 90* |
| 1011 | | 92** |
| 1012 | | 88* |
| 1013 | | 80* |
| 1014 | | 91 |

TABLE 6-continued

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 1015 | | 59* |
| 1016 | | 92* |
| 1017 | | 51* |
| 1018 | | 97 |
| 1019 | | 70 |
| 1020 | | 39 |
| 1021 | | 93* |
| 1022 | | 91** |
| 1023 | | 89** |
| 1024 | | 89** |
| 1025 | | 91** |
| 1026 | | 74** |
| 1027 | | 81** |
| 1028 | | 92** |
| 1029 | | 82** |
| 1030 | | 92** |
| 1031 | | 90** |
| 1032 | | 93** |
| 1033 | | 76** |
| 1034 | | 77 |
| 1035 | | 76 |
| 1036 | | 79 |
| 1037 | | 88 |
| 1038 | | 57 |
| 1039 | | 89** |
| 1040 | | 90** |
| 1041 | | 48 |
| 1042 | | 88 |
| 1043 | | 90* |
| 1044 | | 76* |
| 1045 | | 86* |
| 1046 | | 93 |
| 1047 | | 95 |
| 1048 | | 78** |
| 1049 | | 93** |
| 1050 | | 62** |
| 1051 | | 79** |
| 1052 | | 91** |
| 1053 | | 60** |
| 1054 | | 89** |
| 1055 | | 85** |
| 1056 | | 75** |
| 1057 | | 82* |
| 1058 | | 89 |
| 1059 | | 92* |
| 1060 | | 42 |
| 1061 | | 88* |
| 1062 | | 93 |
| 1063 | | 92** |
| 1064 | | 95** |
| 1065 | | 78* |
| 1066 | | 73** |
| 1067 | | 93* |
| 1068 | | 79** |
| 1069 | | 74* |
| 1070 | | 93** |
| 1071 | | 95* |
| 1072 | | 82* |
| 1073 | | 93** |
| 1074 | | 82 |
| 1075 | | 90** |
| 1076 | | 69** |
| 1077 | | 93** |
| 1078 | | 86* |
| 1079 | | 90 |
| 1080 | | 87 |
| 1081 | | 61 |
| 1082 | | 84* |
| 1083 | | 88 |
| 1084 | | 76** |
| 1085 | | 93* |
| 1086 | | 87* |
| 1087 | | 76* |
| 1088 | | 73* |
| 1089 | | 86* |
| 1090 | | 81** |
| 1091 | | 87* |
| 1092 | | 74** |
| 1093 | | 95** |
| 1094 | | 96** |
| 1095 | | 76* |
| 1096 | | 86* |
| 1097 | | 80** |
| 1098 | | 60* |
| 1099 | | 87** |
| 1100 | | 82** |
| 1101 | | 86* |
| 1102 | | 84** |
| 1103 | | 92* |
| 1104 | | 89** |
| 1105 | | 91** |
| 1106 | | 67** |
| 1107 | | 88** |
| 1108 | | 95** |
| 1109 | | 74** |
| 1110 | | |
| 1111 | | 63** |
| 1112 | | 62 |
| 1113 | | 55 |
| 1114 | | 83** |
| 1115 | | 94* |
| 1116 | | 91** |
| 1117 | | 92* |
| 1118 | | 86* |
| 1119 | | 84** |
| 1120 | | 93 |
| 1121 | | 72* |
| 1122 | | 92** |
| 1123 | | 90* |
| 1124 | | 90* |
| 1125 | | 92* |
| 1126 | | 87 |
| 1127 | | 90* |
| 1128 | | 86* |
| 1129 | | 92** |
| 1130 | | 88** |
| 1131 | | 96** |
| 1132 | | 97* |
| 1133 | | 75* |
| 1134 | | 95** |
| 1135 | | 88* |
| 1136 | | 91 |
| 1137 | | 83** |
| 1138 | | 65* |
| 1139 | | 92* |
| 1140 | | 77** |
| 1141 | | 80* |
| 1142 | | 84** |
| 1143 | | 92* |
| 1144 | | 76* |
| 1145 | | 83* |
| 1146 | | 61** |
| 1147 | | 93* |
| 1148 | | 79** |
| 1149 | | 94* |
| 1150 | | 92* |
| 1151 | | 91* |
| 1152 | | 96* |
| 1153 | | 89* |
| 1154 | | 93* |
| 1155 | | 91* |
| 1156 | | 87 |
| 1157 | | 66** |
| 1158 | 75 | |
| 1159 | | 72* |
| 1160 | | 83* |

TABLE 6-continued

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 1161 | | 87* |
| 1162 | | 84* |
| 1163 | | 73** |
| 1164 | | 94 |
| 1165 | | 84* |
| 1166 | | 74** |
| 1167 | | 91* |
| 1168 | | 88* |
| 1169 | | 77 |
| 1170 | | 74* |
| 1171 | | 74** |
| 1172 | | 38* |
| 1173 | | 89** |
| 1174 | | 79** |
| 1175 | | 96 |
| 1176 | | 97* |
| 1177 | | 19 |
| 1178 | | 88** |
| 1179 | | 85* |
| 1180 | | 93* |
| 1181 | | 82* |
| 1182 | | 92** |
| 1183 | | 79** |
| 1184 | | 84** |
| 1185 | | 85** |
| 1186 | | 93** |
| 1187 | | 93** |
| 1188 | | 93** |
| 1189 | | 74** |
| 1190 | | 95** |
| 1191 | | 85** |
| 1192 | | 91* |
| 1193 | | 95** |
| 1194 | | 78** |
| 1195 | | 94* |
| 1196 | | 87* |
| 1197 | | 85* |
| 1198 | | 86* |
| 1199 | | 71 |
| 1200 | | 97* |
| 1201 | | 73* |
| 1202 | | 96** |
| 1203 | | 84* |
| 1204 | | 93* |
| 1205 | | 55** |
| 1206 | | 63** |
| 1207 | | 91* |
| 1208 | | 89* |
| 1209 | | 87* |
| 1210 | | 64** |
| 1211 | | 94 |
| 1212 | | 86* |
| 1213 | | 79** |
| 1214 | | 92** |
| 1215 | | 17 |
| 1216 | | 88** |
| 1217 | | 87* |
| 1218 | | 54** |
| 1219 | | 85** |
| 1220 | | |
| 1221 | | 82** |
| 1222 | | 89* |
| 1223 | | 91** |
| 1224 | | 88* |
| 1225 | | 92** |
| 1226 | | 69** |
| 1227 | | 91 |
| 1228 | | 88* |
| 1229 | | 66** |
| 1230 | | 77** |
| 1231 | | 93* |
| 1232 | | 68** |
| 1233 | | 77** |
| 1234 | | 71** |
| 1235 | | 86** |
| 1236 | | 83** |
| 1237 | | 89** |
| 1238 | | 91** |
| 1239 | | 85* |
| 1240 | | 64** |
| 1241 | | 74* |
| 1242 | | 75* |
| 1243 | | 95* |
| 1244 | | 84 |
| 1245 | | 92 |
| 1246 | | 82 |
| 1247 | | 95* |
| 1248 | | 88 |
| 1249 | | 89 |
| 1250 | | 79** |
| 1251 | | 91** |
| 1252 | | 84* |
| 1253 | | 76* |
| 1254 | | 67 |
| 1255 | | 82* |
| 1256 | | 95* |
| 1257 | | 93** |
| 1258 | | 97** |
| 1259 | | 89** |
| 1260 | | 90** |
| 1261 | | 94 |
| 1262 | | 95 |
| 1263 | | 85* |
| 1264 | | 83** |
| 1265 | | 90 |
| 1266 | | 85* |
| 1267 | | 96 |
| 1268 | | 95* |
| 1269 | | 84** |
| 1270 | | 91** |
| 1271 | | 78** |
| 1272 | | 73** |
| 1273 | | 94* |
| 1274 | | 89* |
| 1275 | | 86** |
| 1276 | | 88** |
| 1277 | | 90** |
| 1278 | | 68 |
| 1279 | | 87** |
| 1280 | | 78** |
| 1281 | | 81* |
| 1282 | | 69* |
| 1283 | | 74* |
| 1284 | | 86 |
| 1285 | | 94 |
| 1286 | | 85** |
| 1287 | | 95** |
| 1288 | | 69* |
| 1289 | | 93 |
| 1290 | | 80 |
| 1291 | | |
| 1292 | | |
| 1293 | | |
| 1294 | | |
| 1295 | | |
| 1296 | | |
| 1297 | | |
| 1298 | | 97** |
| 1299 | | 96** |
| 1300 | | 97* |
| 1301 | | 97* |
| 1302 | | 93** |
| 1303 | | 91** |
| 1304 | | 90** |
| 1305 | | 91** |
| 1306 | | 85** |

TABLE 6-continued

Inhibition of farnesyltransferase at concentrations of 10 mM and 1 mM unless specified as *(0.1 mM) or **(0.01 mM)

| Example | % inhibition 10 mM | % inhibition 1 mM |
|---|---|---|
| 1307 | | 85** |
| 1308 | | 91** |
| 1309 | | 96* |
| 1310 | | 90** |
| 1311 | | 95** |
| 1312 | | 91** |
| 1313 | | 91** |
| 1314 | | 96* |
| 1315 | | 86* |
| 1316 | | 78* |
| 1317 | 99 | 96 |
| 1318 | | |
| 1319 | | 79** |
| 1320 | | 79 |
| 1321 | | |
| 1322 | | |
| 1323 | | |
| 1324 | | |
| 1325 | | |
| 1326 | | |
| 1327 | | |
| 1328 | | |
| 1329 | | |
| 1330 | | |
| 1331 | | |
| 1332 | | 92** |
| 1333 | | 95* |
| 1334 | | 72** |
| 1335 | | 90* |
| 1336 | | 74 |
| 1337 | | 83** |
| 1338 | | 65* |
| 1339 | | |
| 1340 | | 77* |
| 1341 | | 89 |
| 1342 | | |
| 1343 | | 88 |
| 1344 | | 93** |
| 1345 | | 94** |
| 1346 | | 94* |
| 1347 | | 81** |
| 1348 | | 78** |
| 1349 | | 92** |
| 1350 | | |
| 1351 | | |
| 1352 | | |
| 1353 | | |
| 1354 | | 38 |
| 1355 | | 46 |
| 1356 | | 80 |
| 1357 | | 78 |
| 1358 | | |
| 1359 | | |
| 1360 | | 98** |
| 1361 | | 96* |
| 1362 | | 83** |
| 1363 | | 88** |
| 1364 | | |
| 1365 | | |
| 1366 | | 79* |
| 1367 | | 93* |
| 1368 | | 92** |
| 1369 | | 94* |
| 1370 | | 86** |
| 1371 | | 94* |
| 1372 | | 95** |
| 1373 | | 95** |
| 1374 | | 93** |
| 1375 | | 80** |
| 1376 | | 86** |
| 1377 | | 95* |
| 1378 | | 68 |
| 1379 | | 41 |
| 1380 | | 87** |
| 1381 | | 65** |
| 1382 | | 86** |
| 1383 | | 88* |
| 1384 | | 69** |
| 1385 | | 93* |
| 1386 | | 88* |
| 1387 | | 82** |
| 1392 | | 93* |
| 1397 | | 87** |
| 1398 | | 81* |
| 1399 | | 94 |
| 1400 | | 95 |

*% inhibition at 0.1 μM
**% inhibition at 0.01 μM

Additional methods for the measurement of in vitro inhibition of protein prenylation (i.e., inhibition of farnesyltransferase or geranygeranyltransferase) are described below.

Assays are performed using the glass fiber filter binding assay procedure with either rabbit reticulocyte lysate or FTase or GGTase I fractions isolated from bovine brains using a combination of hydrophobic and DEAE column chromatography procedures. Protein substrates are purchased from Panvera Corporation (H-ras for FTase, H-ras-CVLL for GGTase I). Tritium labeled prenyl lipid substrates (FPP or GGPP) are obtained from Amersham Life Science.

FTase $^3$H-Farnesyldiphosphate (final concentration 0.6 μM), H-Ras (final concentration 50 μM) and the test compound (various final concentrations from a stock solution in 50% DMSO/water; final concentration DMSO<2%) were mixed in buffer (50 mM HEPES (pH 7.5), 30 mM $MgCl_2$, 20 mM KCl, 10 μM $ZnCl_2$, 5 mM DTT, 0.01% Triton X-100) to give a final volume of 50 μL. The mixture was brought to 37° C., enzyme was added, and the reaction is incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial and 5 mL of scintillation fluid was added. The radioisotope retained on the glass fiber filter was counted to reflect the activity of the enzymes. The $IC_{50}$ value was calculated by measuring the activity of the enzyme over a suitable range of inhibitor concentrations.

GGTase I $^3$H-geranylgeranyldiphosphate (final concentration 0.5 μM), H-Ras-CVLL (final concentration 5.0 μM) and the test compound (various final concentrations from a stock solution in 1:1 DMSO/water; final concentration DMSO<2%) were mixed in buffer (50 mM Tris-HCl (pH 7.2), 30 mM $MgCl_2$, 20 mM KCl, 10 μM $ZnCl_2$, 5 mM DTT, 0.01% Triton X-100) to give a final volume of 50 μL. The mixture was brought to 37° C., treated with enzyme, andincubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial, and 5 mL scintillation fluid was added. The radioisotope retained on the glass fiber filter was counted to reflect the activity of the enzymes. The $IC_{50}$ value was calculated by measuring the activity of the enzyme over a suitable range of inhibitor concentrations.

Additionally, the ability of the compounds of the invention to inhibit prenylation in whole cells, inhibit anchorage-independent tumor cell growth and inhibit human tumor xenograft in mice could be demonstrated according to the methods described in PCT Patent Application No. WO95/25086, published Sep. 21, 1995, which is hereby incorporated herein by reference.

Pharmaceutical Compositions

The compounds of the present invention can be used in the form of pharmaceutically acceptable salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I)–(XII) or separately by reacting the carboxylic acid function with a suitable base such as the hydroxide, carbonate or bicarbonate of a pharmaceutically acceptable metal cation or with ammonia or an organic primary, secondary or tertiary amine. Such pharmaceutically acceptable salts include, but are not limited to, cations based on the alkali and alkaline earth metals such as sodium, lithium, potassium, calcium, magnesium, aluminum salts and the like as well as nontoxic ammonium, quaternary ammonium, and amine cations including, but not limited to, ammonium, tetraethylammonium, tetraethylammonium, methylamine, dimethylamine, trimethylamine, triethylamine, ethylamine and the like. Other representative organic amines useful for the formation of base addition salts include diethylamine, ethylenediamine, ethanolamine, diethanolamine, piperazine and the like.

The compounds of the invention are useful (in humans and other mammals) for inhibiting protein isoprenyltransferases (i.e, protein farnesyltransferase and/or protein geranylgeranyltransferase) and the isoprenylation (i.e., farnesylation and/or geranylgeranylation) of Ras. These inhibitors of protein isoprenyltransferases are also useful for inhibiting or treating cancer in humans and other mammals. Examples of cancers which may be treated with the compounds of the invention include, but are not limited to, carcinomas such as lung, colorectal, bladder, breast, kidney, ovarian, liver, exocrine pancreatic, cervical, esophageal, stomach and small intestinal; sarcomas such as oesteroma, osteosarcoma, lepoma, liposarcoma, hemanioma and hemangiosarcoma; melanomas such as amelanotic and melanotic; mixed types of cancers such as carcinosarcoma, lymphoid tissue type, follicular reticulum, cell sarcoma and Hodgkins disease and leukemias, such as myeloid, acute lymphoblastic, chronic lymphocytic, acute myloblastic and chronic mylocytic.

The ability of the compounds of the invention to inhibit or treat cancer can be demonstrated according to the methods of Mazerska Z., Woynarowska B., Stefanska B., Borowski S., Drugs Exptl. Clin. Res. 13(6), 345–351 (1987) Bissery, M. C., Guenard F., Guerritte-Voegelein F., Lavelle F., Cancer Res. 51, 4845–4852 (1991) and Rygaard J., and Povlsen C., Acta Pathol. Microbiol. Scand. 77, 758 (1969), which are hereby incorporated herein by reference.

These inhibitors of protein isoprenyltransferases are also useful for treating or preventing restenosis in humans and other mammals. The ability of the compounds of the invention to treat or prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993), which are hereby incorporated herein by reference.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

For treatment or prevention of restenosis, the total daily dose administered to a host in single or divided doses may be in amounts, for example, from 0.001 to 1000 mg/kg body weight daily and more preferred from 1.0 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, sublingually, by inhalation spray, rectally or topically in dosage unit formulations containing conventional nontoxic pharmaceutically acceptable carriers, adjuvants, and vehicles. Topical administration may also involve the use of transdermal administration such as transdermal patches or iontophoresis devices. The term parenteral as used herein includes subcutaneous injections, intravenous, intramuscular, intrasternal injection or infusion techniques.

Injectable preparations, for example sterile injectable aqueous or oleagenous suspensions, may be formulated according to the known art using suitable dispersing or wetting and suspending agents. The sterile injectable preparation may also be a sterile injectable solution or suspension in a nontoxic parenterally acceptable diluent or solvent (as in a solution in 1,3-propanediol, for example). Among the acceptable vehicles and solvents that may be employed are water, Ringer's solution and isotonic sodium chloride solution. Additionally, sterile, fixed oils are conventionally employed as a solvent or suspending medium. For this purpose, any bland fixed oil may be employed including synthetic mono- or diglycerides. Fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose, lactose or starch. These dosage forms may also comprise additional substances other than inert diluents such as lubricating agents like magnesium stearate. With capsules, tablets and pills, the dosage forms may also comprise buffering agents. Tablets and pills mayalso be prepared with enteric coatings.

Liquid dosage forms for oral administration may include pharmaceutically acceptable emulsions, solutions, suspensions, syrups and elixirs containing inert diluents commonly used in the art such as water. Such compositions may also comprise adjuvants such as wetting agents, emulsifying and suspending agents and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals dispersed in an aqueous medium. Any non-toxic, physiologically aceptable and metabolizable lipid capable of forming liposomes can be used. The present compositions in liposome form can contain, in addition to a compound of the present invention, stabilizers, preservatives, excipients and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq., which is hereby incorporated herein by reference.

While the compounds of the invention can be administered as the sole active pharmaceutical agent for the treatment of cancer, they can also be used in combination with one or more other chemotherapeutic agents.

Representative examples of chemotherapeutic agents are described in Holleb, et al., *Clinical Oncology*, American Cancer Society, United States (1991) p 56 et seq., which is hereby incorporated herein by reference. These agents include alkylating agents such as the nitrogen mustards (mechloethamine, melphalan, chorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine and vinblastine) and etoposide (VP-16); hormones and hormone antagonists (tamoxifen and corticosteroids); and miscellaneous agents (cisplatin, taxol and brequinar).

The above compounds to be employed in combination with the isoprenyl protein transferase inhibitor of the invention will be used in therapeutic amounts as indicated in the Physicians' Desk Reference (PDR) 47th Edition (1993), which is incorporated herein by reference or by such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied to obtain a desired therapeutic response depending on the route of administration, severity of the disease and the response of the patient.

When administered as a combination, the therapeutic agents can be formulated as separate compositions which are given at the same time or different times, or the therapeutic agents can be given as a single composition.

Preparation of the Compounds of the Invention

In general, the compounds of the invention can be prepared by the processes illustrated in the following Schemes 1–16. In these general schemes compounds of the formula I are used to exemplify the methods, but the methods are intended to be applicable to all of the compounds of the invention.

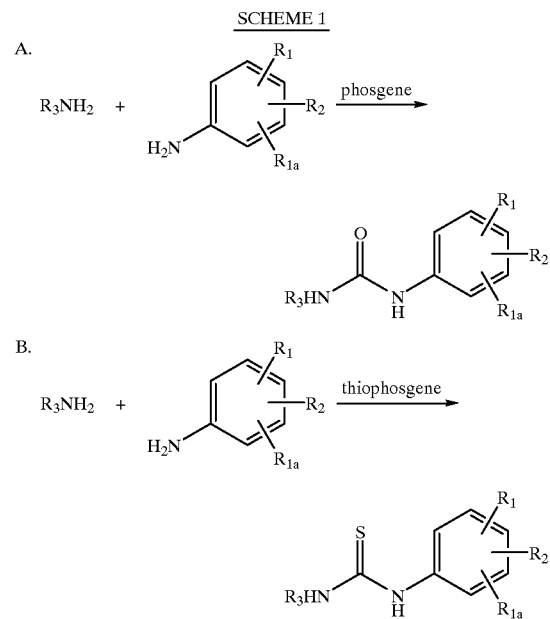

C.
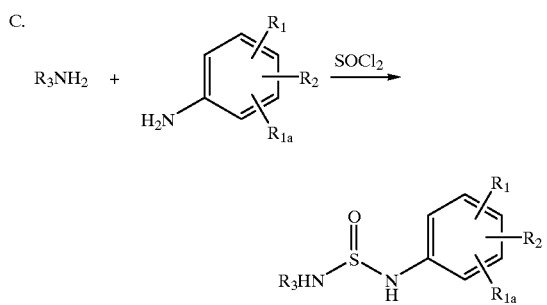
D.
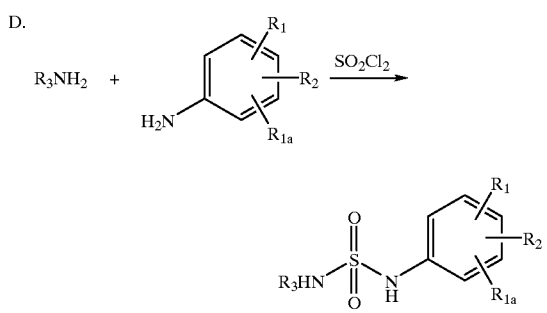
SCHEME 2
A.
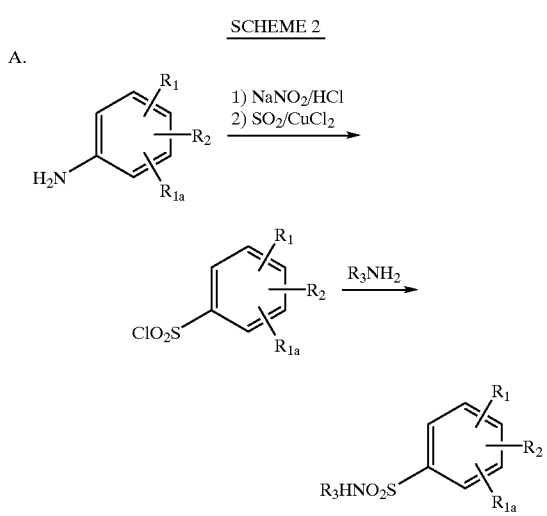
B.
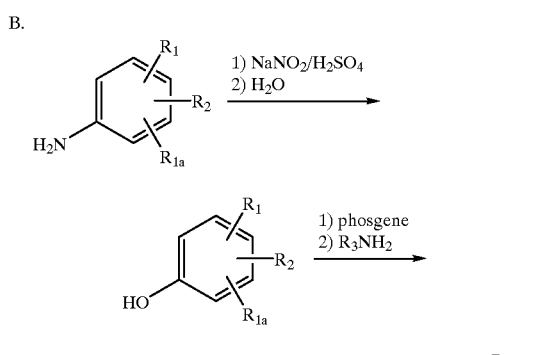
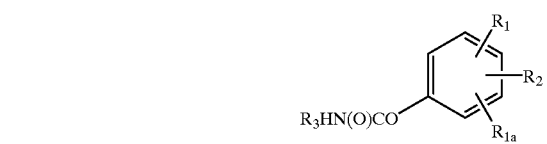
C.
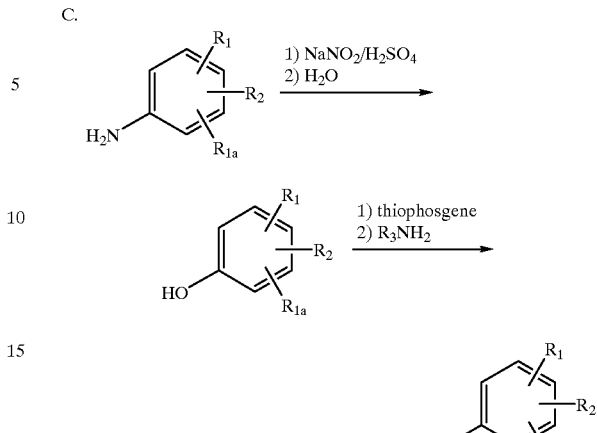
D.
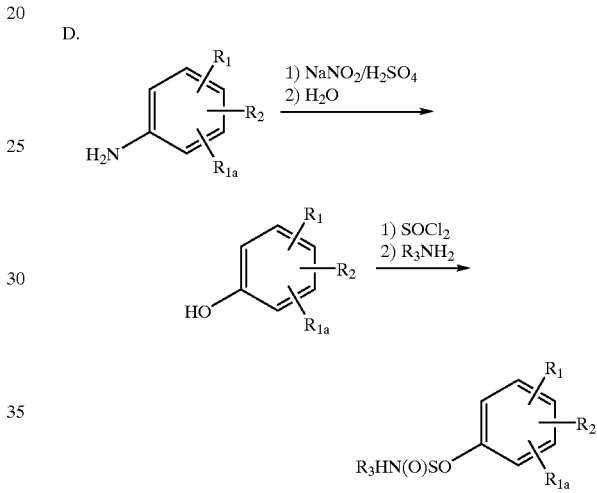
E.
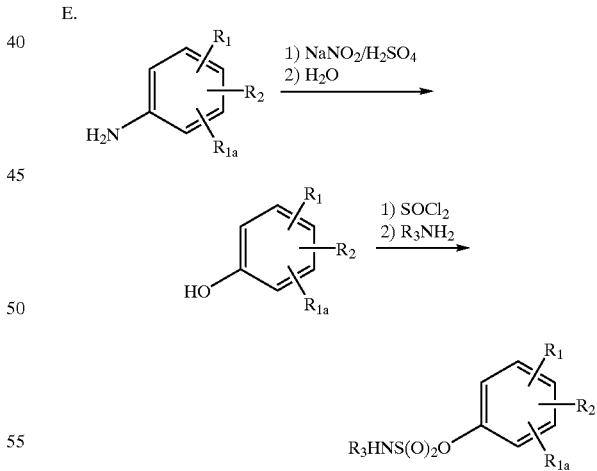
SCHEME 3
A.
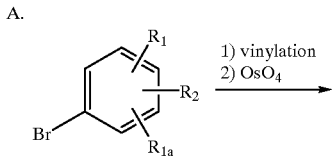

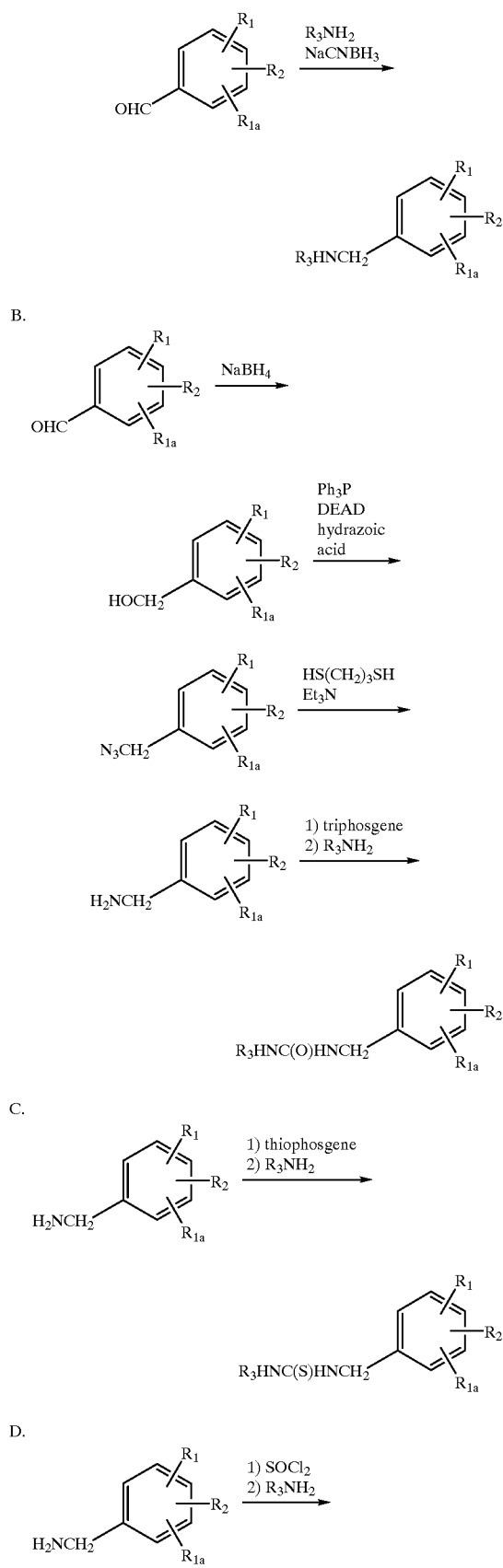
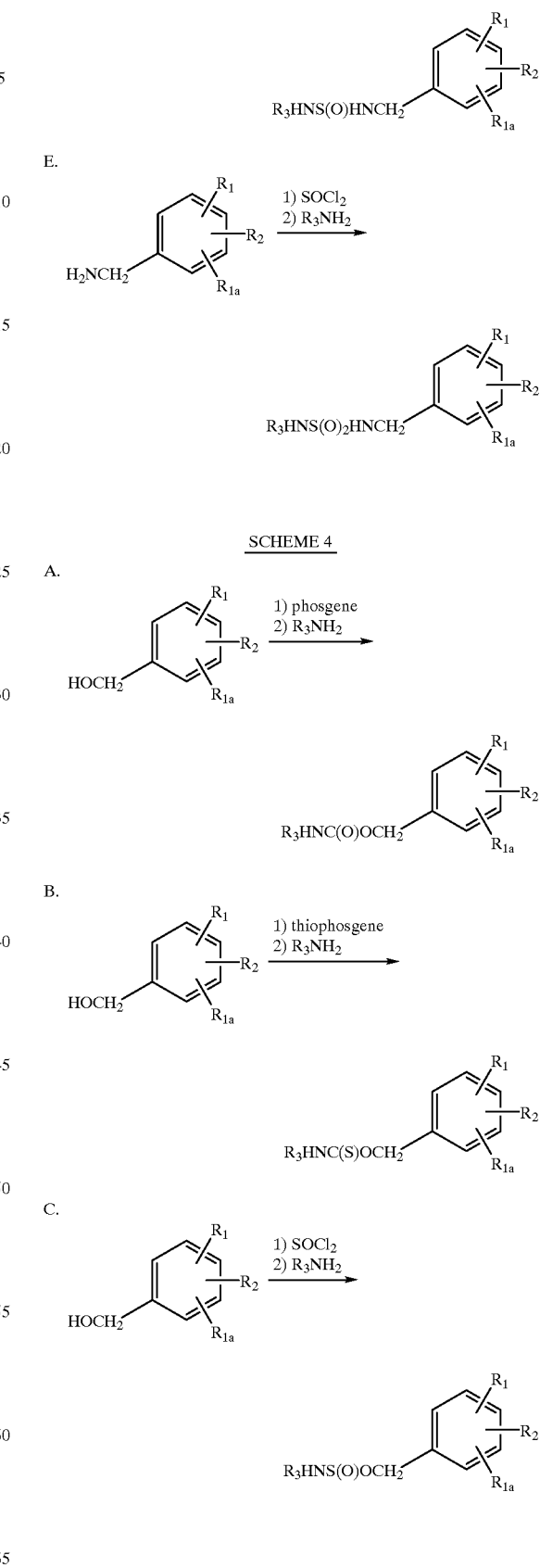
SCHEME 4

D.
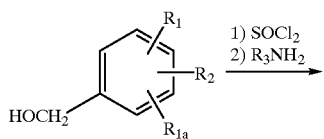
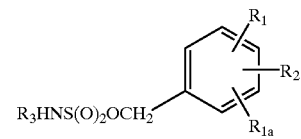
SCHEME 5
A.
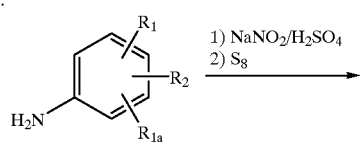
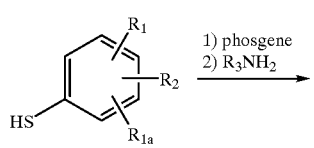
B.
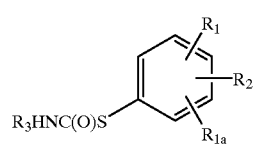
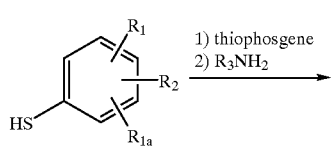
C.
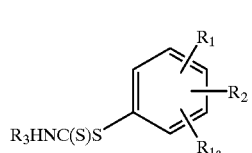
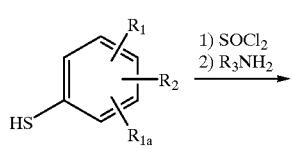
D.
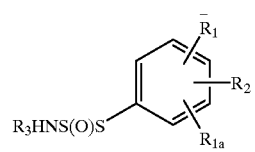
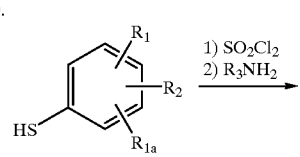
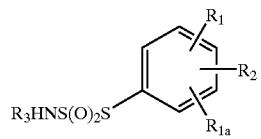
SCHEME 6
A.
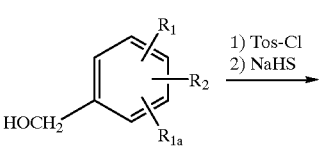
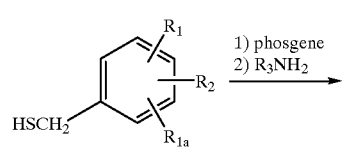
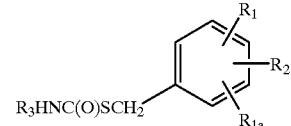
B.
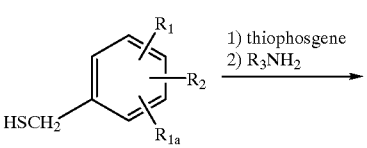
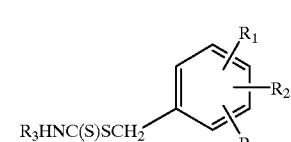
C.
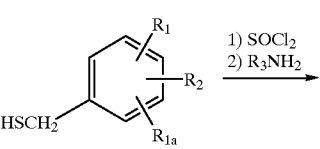
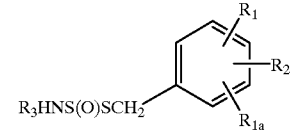
D.
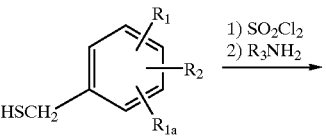
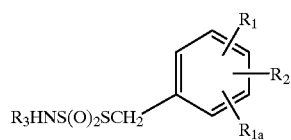

SCHEME 7
A.
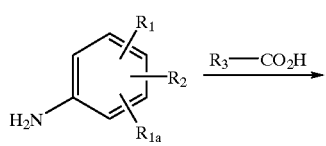
B.
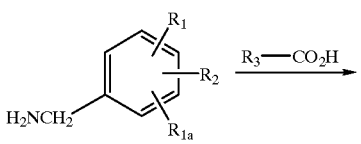
C.
D.
E.
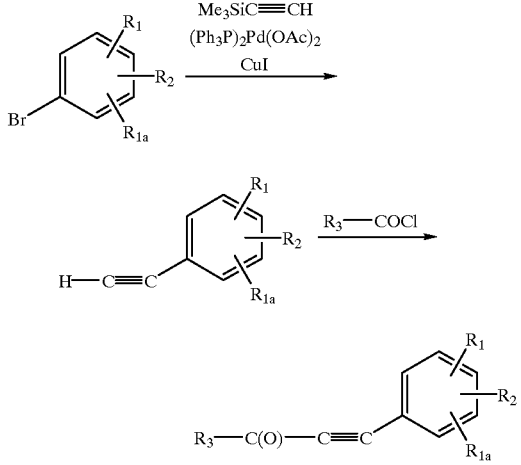
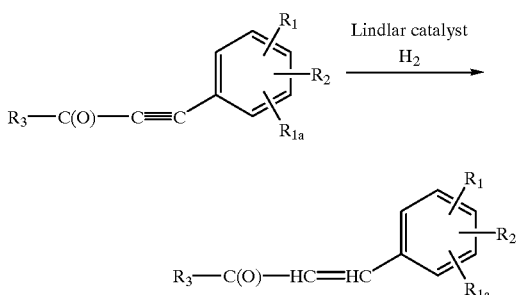
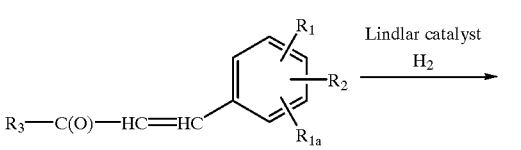
SCHEME 8
A.
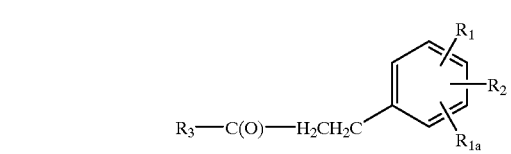
B.
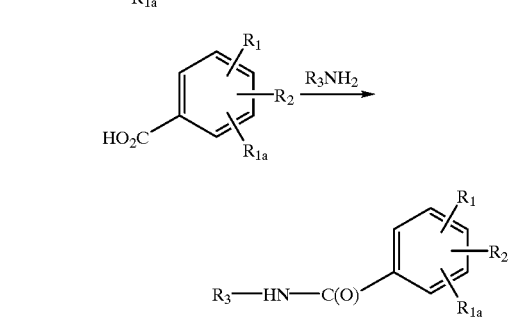
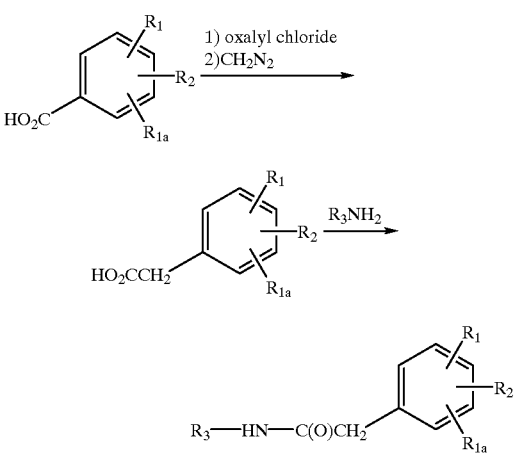
C.
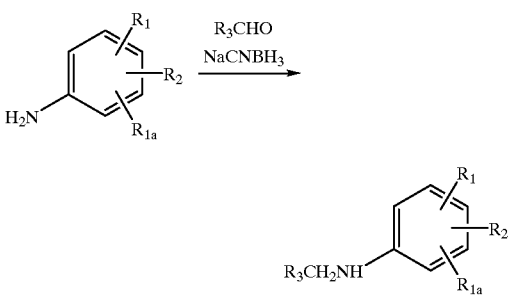
D.
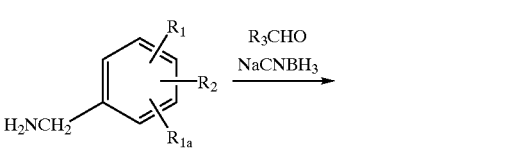

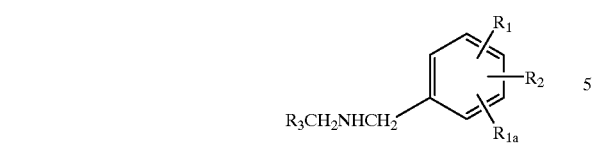
SCHEME 9
A.
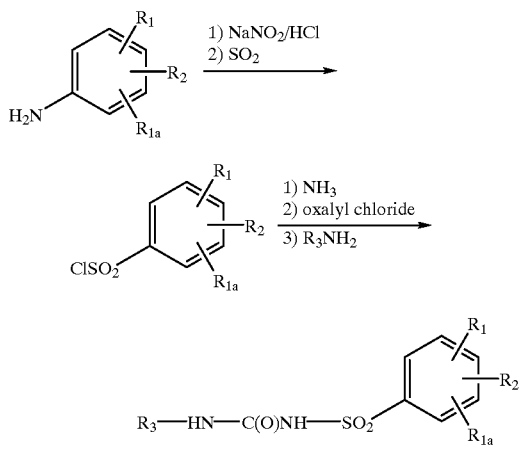
B.
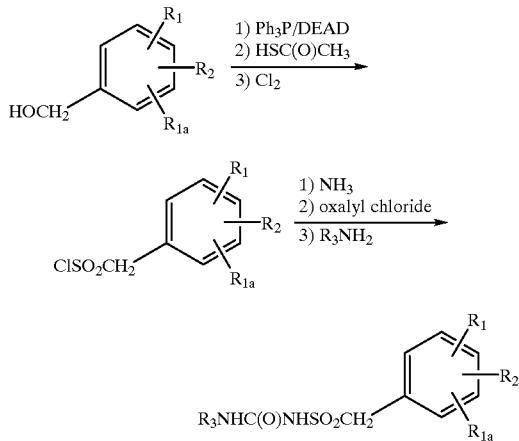
C.
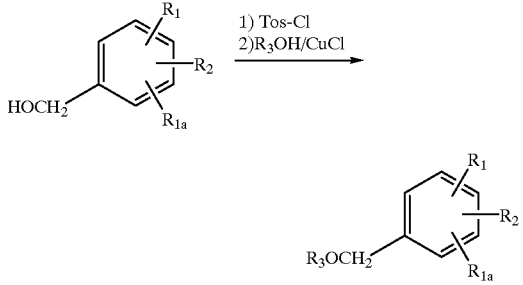
D.
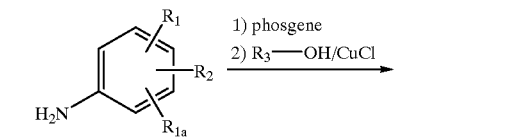
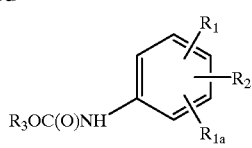
E.
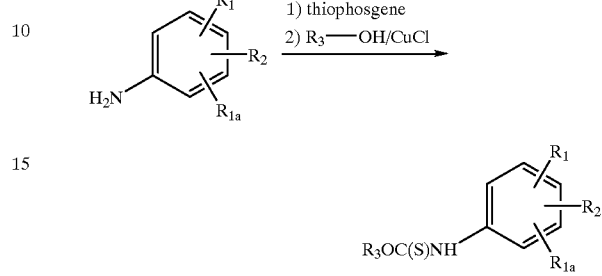
F.
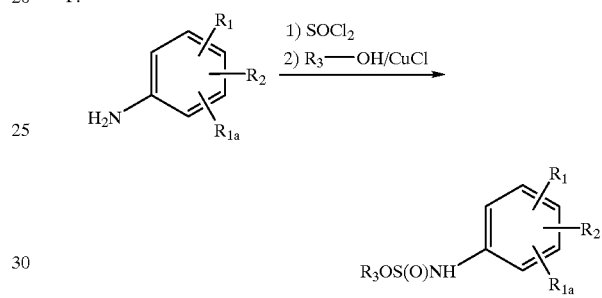
G.

SCHEME 10
A.
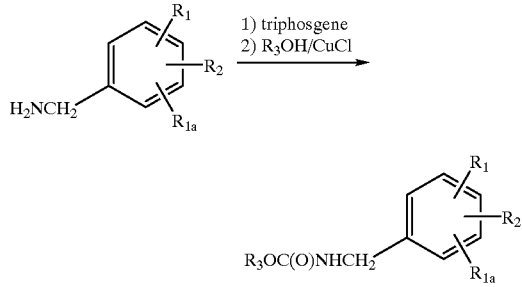
B.
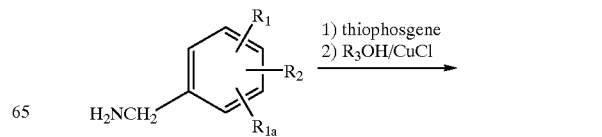

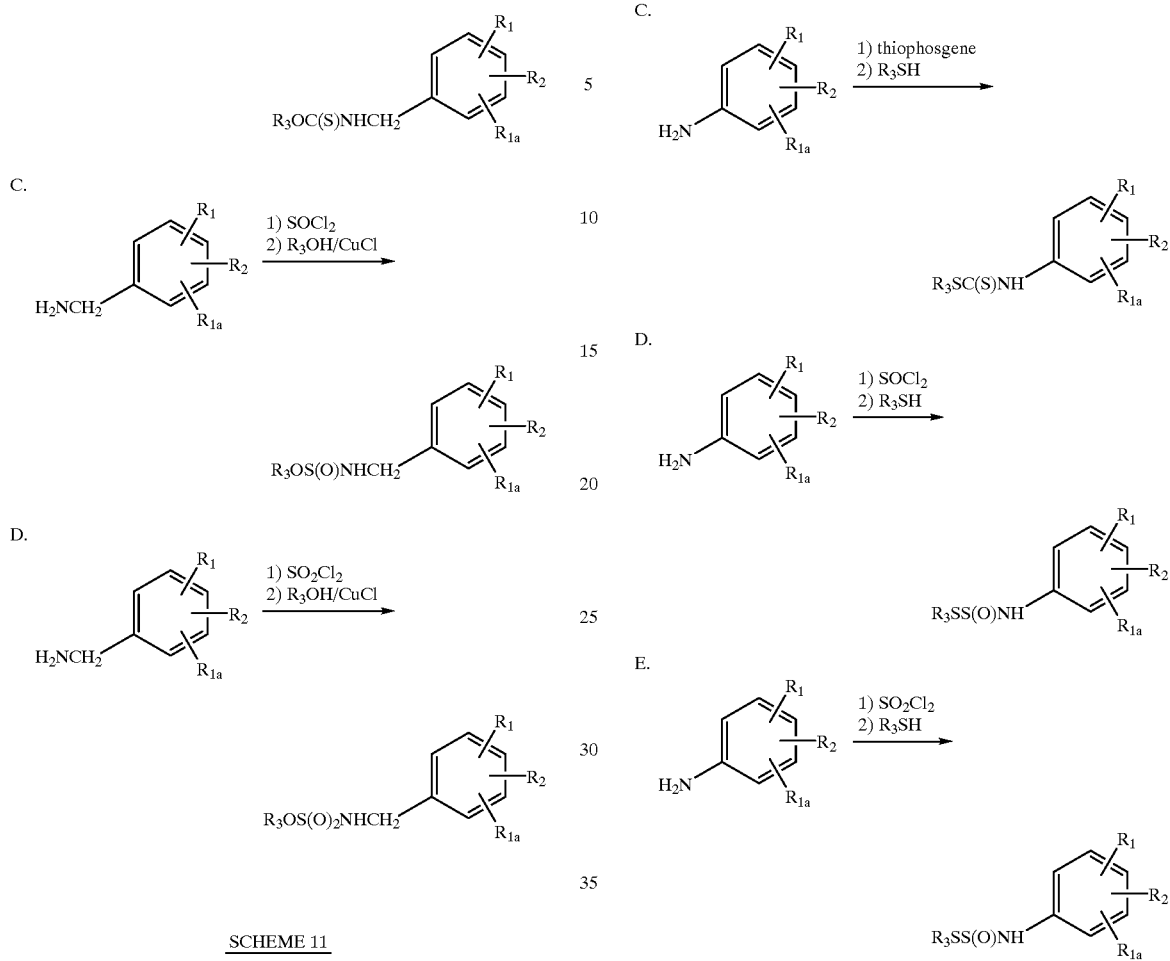
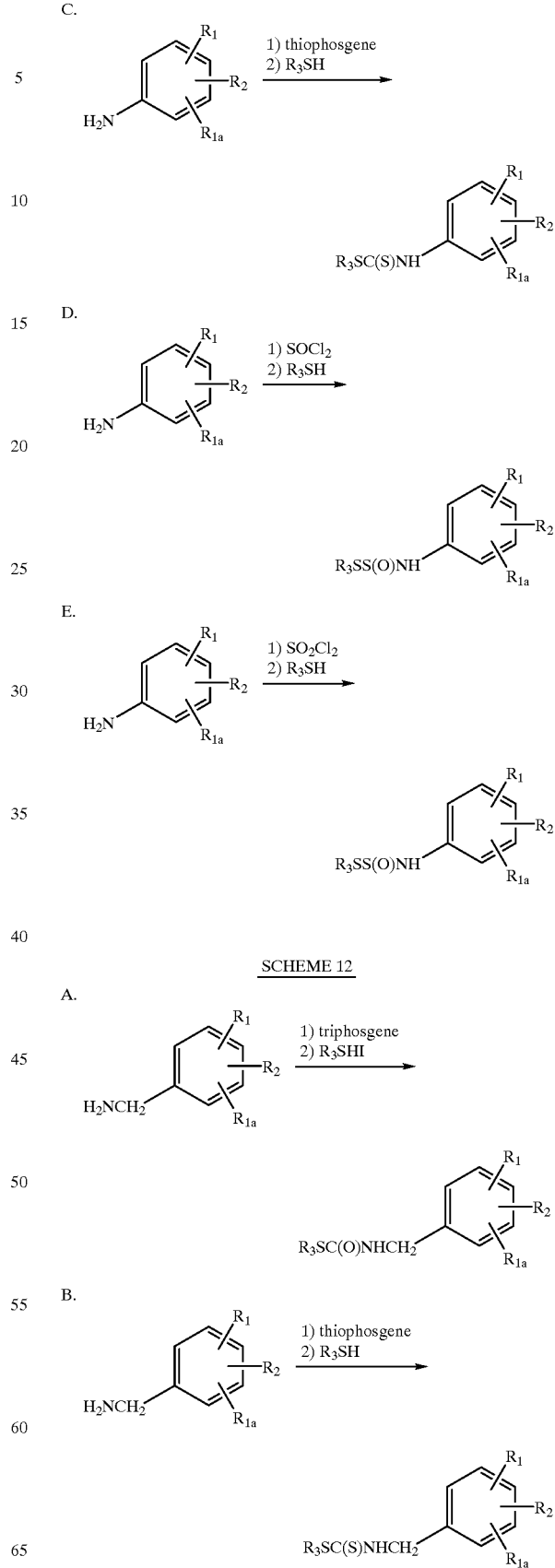

-continued
C.
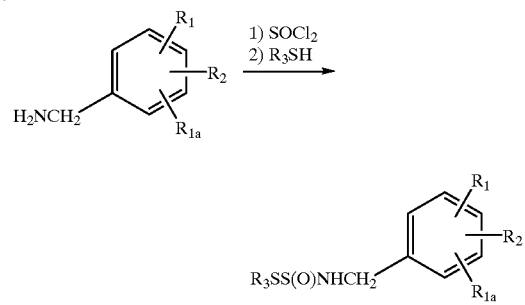
D.
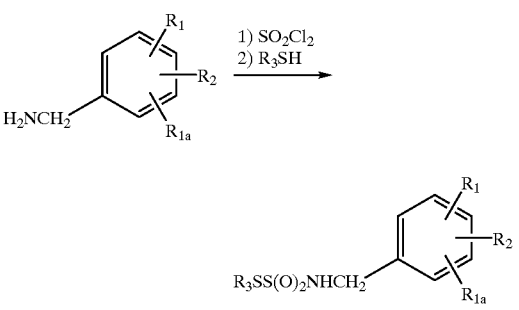
SCHEME 13
A.
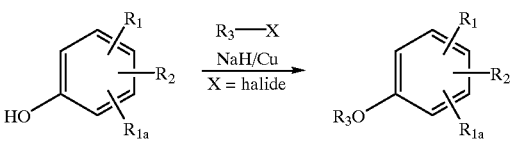
B.
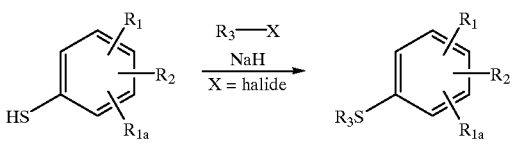
C.
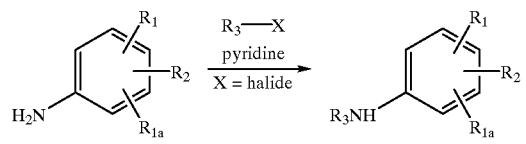
D.
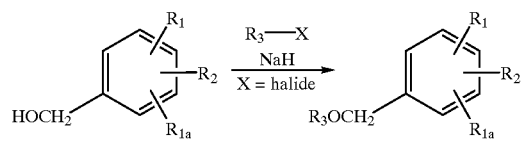
E.
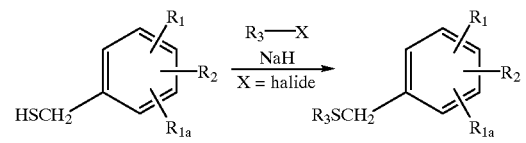
SCHEME 14
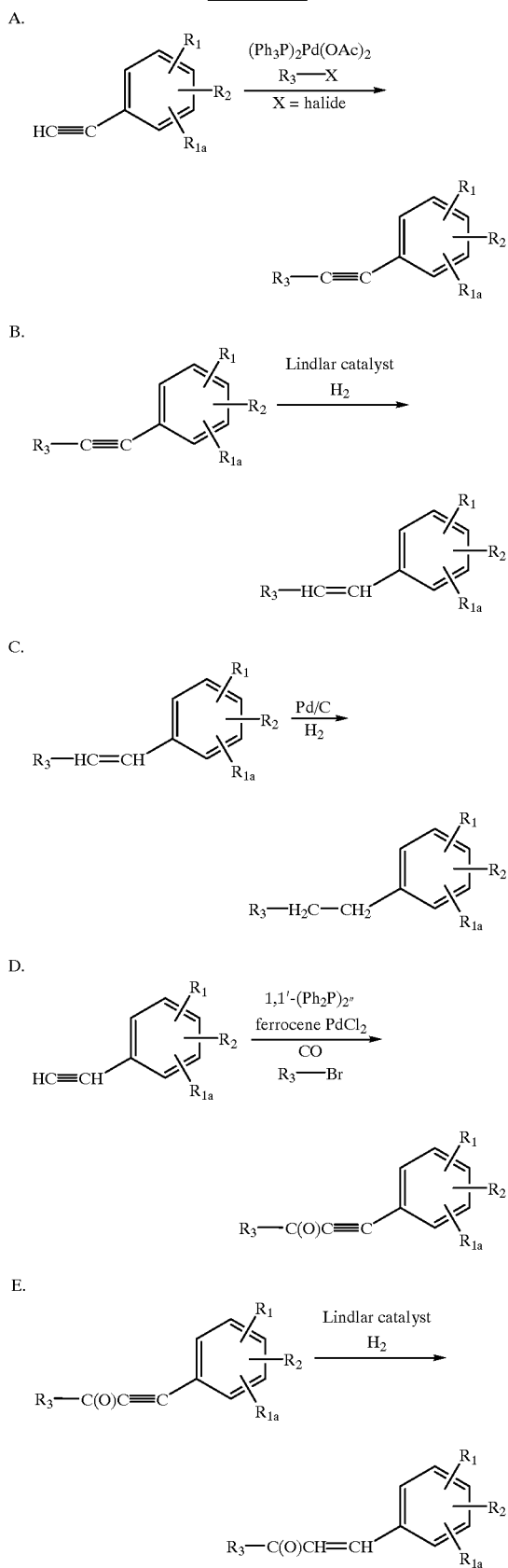

F. 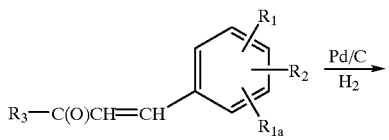
E. 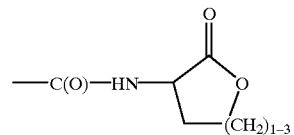
Scheme 16 illustrates an alternative method for preparing compounds wherein $R_2$ is —C(O)NH—CH($R_{14}$)—C(O)O$R_{15}$ or
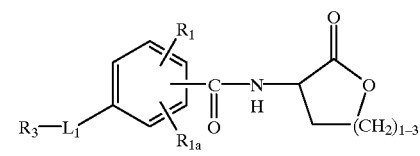
as defined above.
SCHEME 15
A. 
B. 
C. 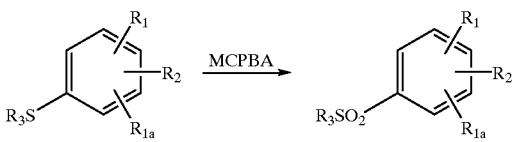
SCHEME 16
A. 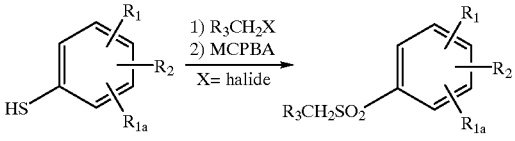
B. 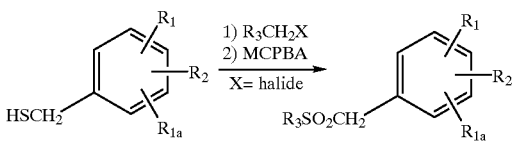
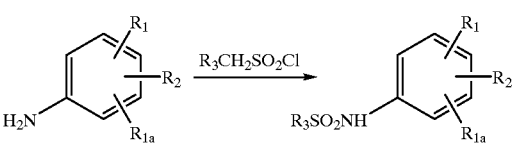
D. 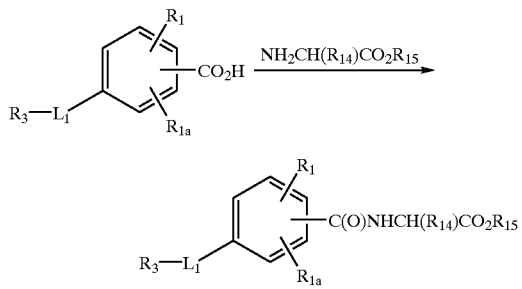

TABLE 6
Amines of the Type A(B)N-L₁
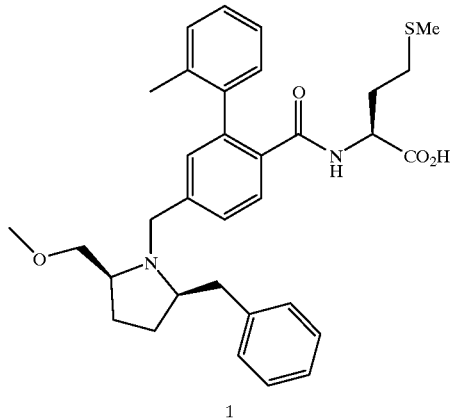
1
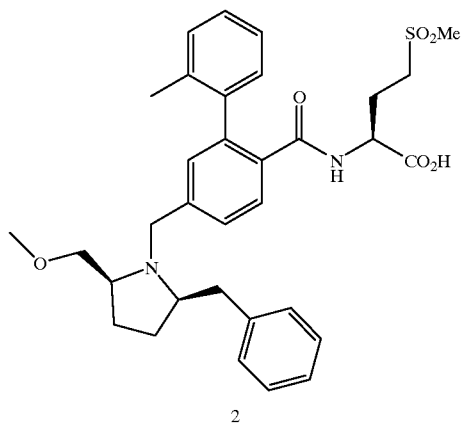
2
3
TABLE 6-continued
Amines of the Type A(B)N-L₁
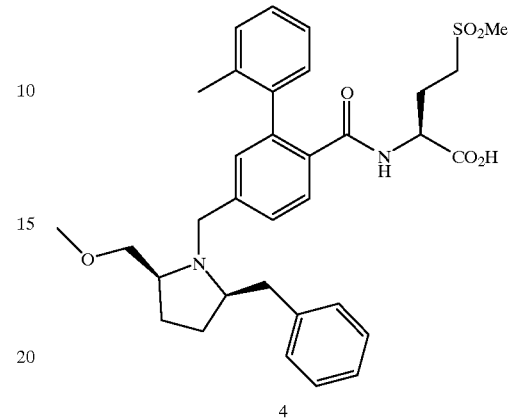
4
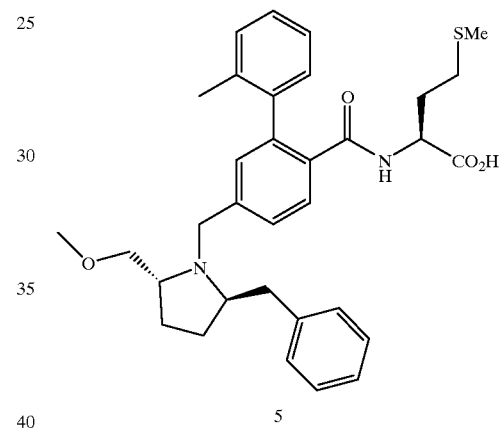
5
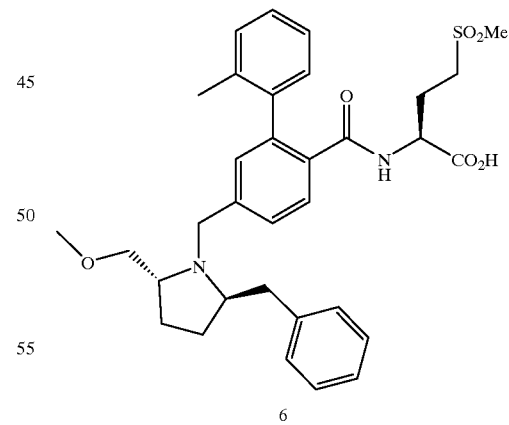
6

TABLE 6-continued
Amines of the Type A(B)N-L₁
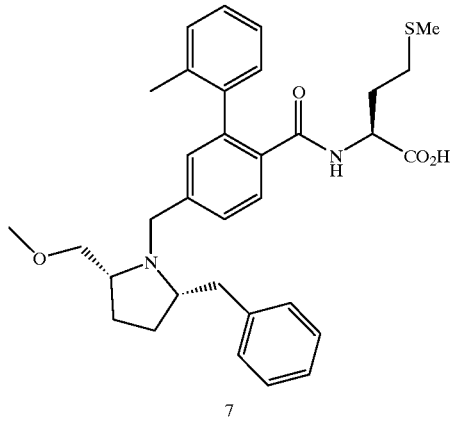
7
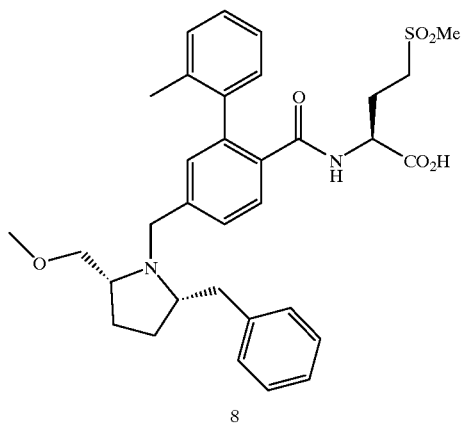
8
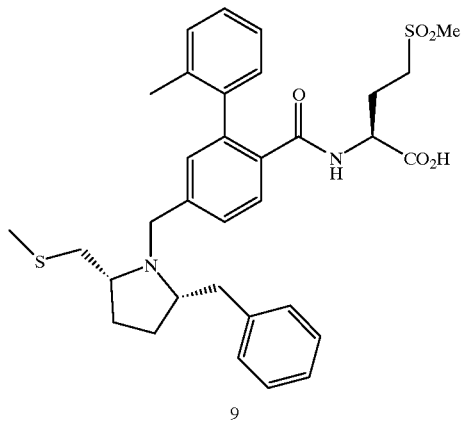
9
TABLE 6-continued
Amines of the Type A(B)N-L₁
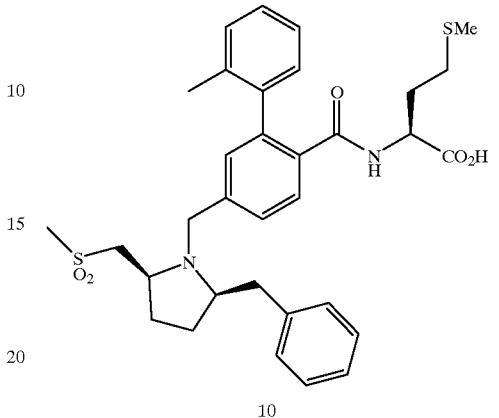
10
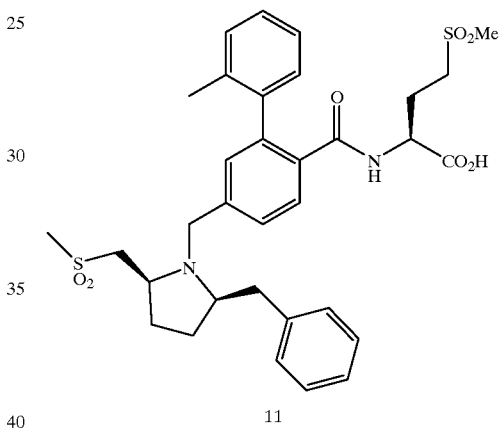
11
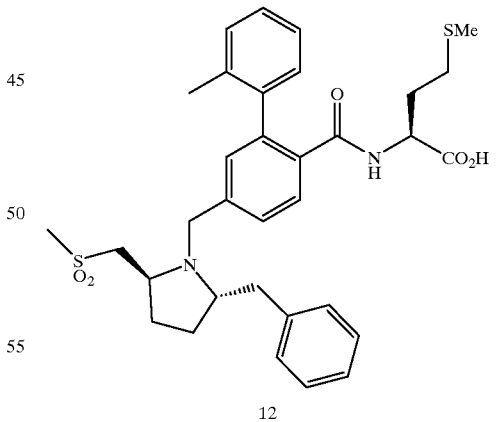
12

TABLE 6-continued
Amines of the Type A(B)N-L₁
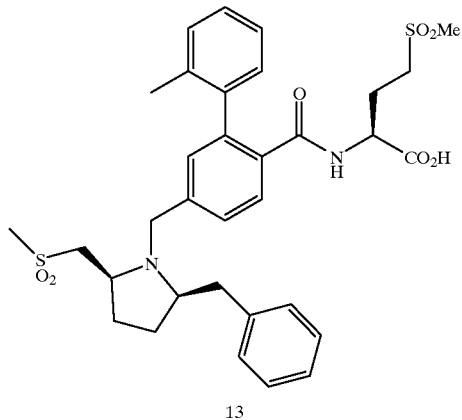
13
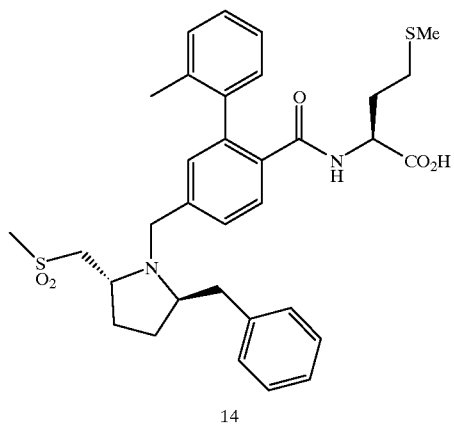
14
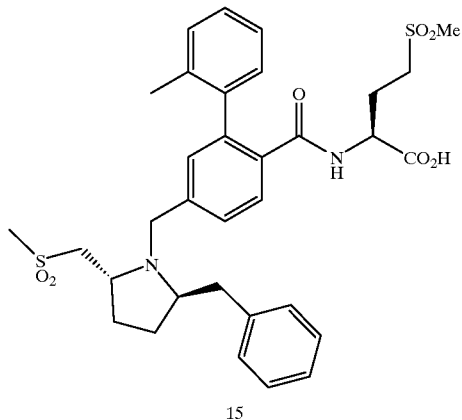
15
TABLE 6-continued
Amines of the Type A(B)N-L₁
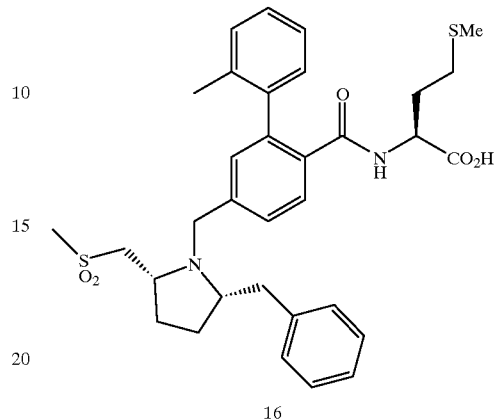
16
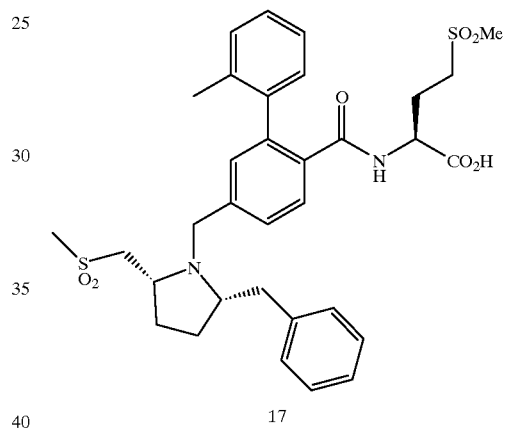
17
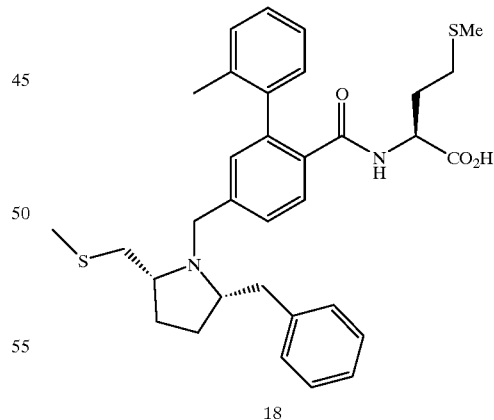
18

TABLE 6-continued
Amines of the Type A(B)N-L₁
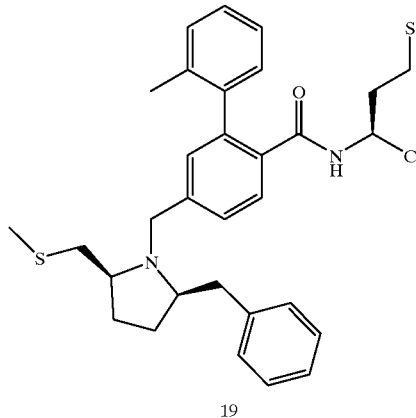
19
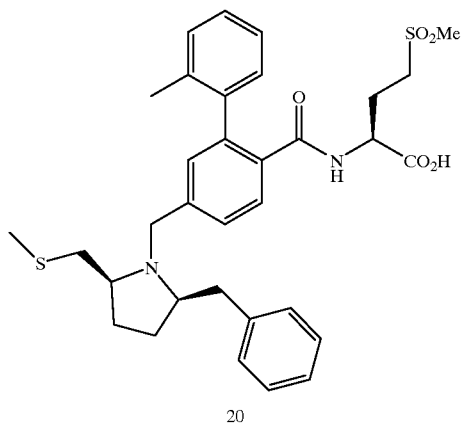
20
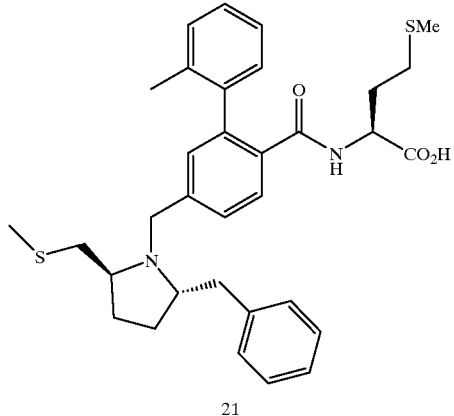
21
TABLE 6-continued
Amines of the Type A(B)N-L₁
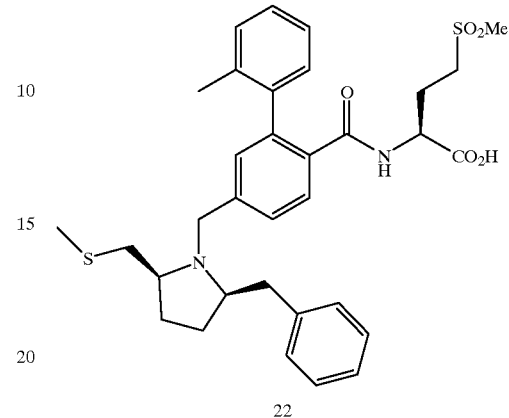
22
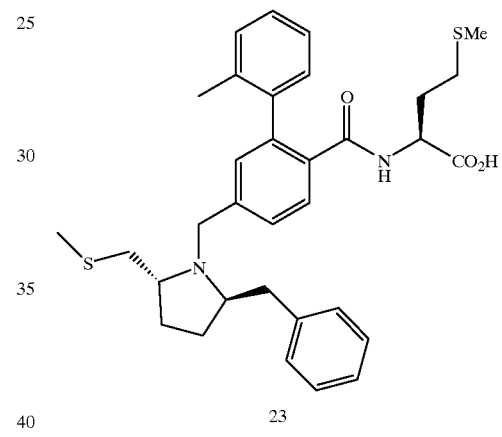
23
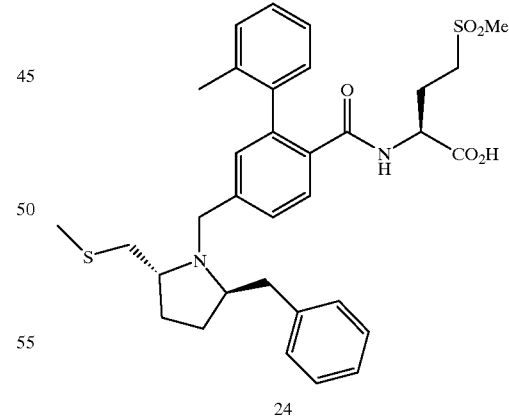
24

TABLE 6-continued
Amines of the Type A(B)N-L₁
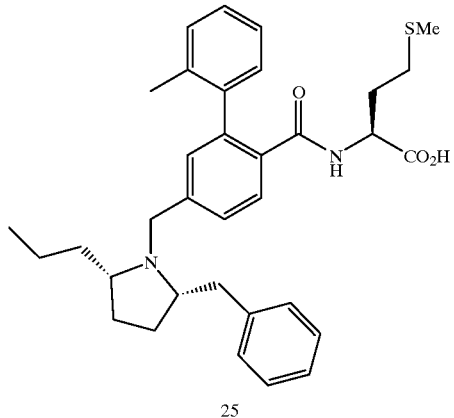
25
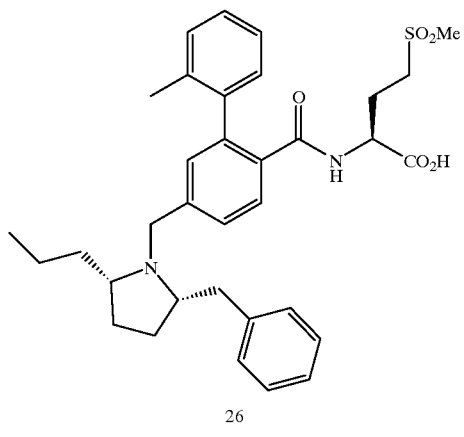
26
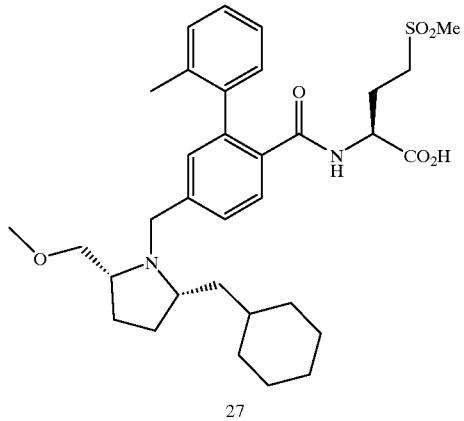
27
TABLE 6-continued
Amines of the Type A(B)N-L₁
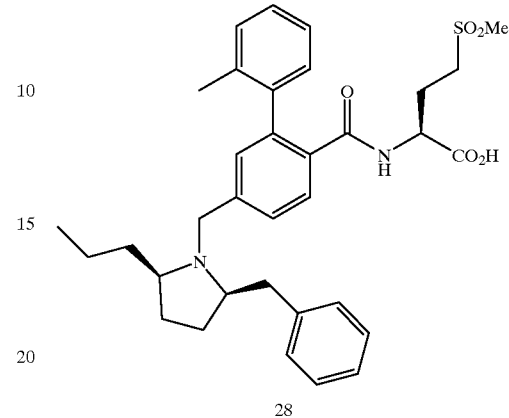
28
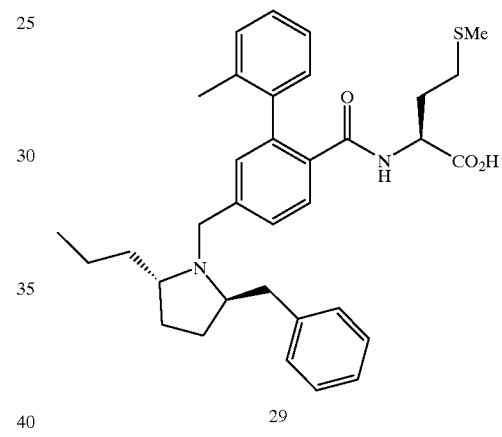
29
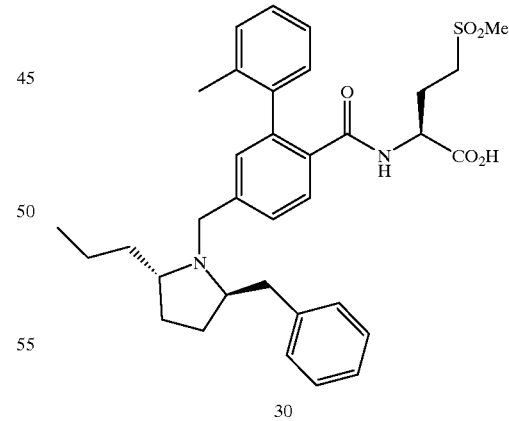
30

TABLE 6-continued
Amines of the Type A(B)N-L₁
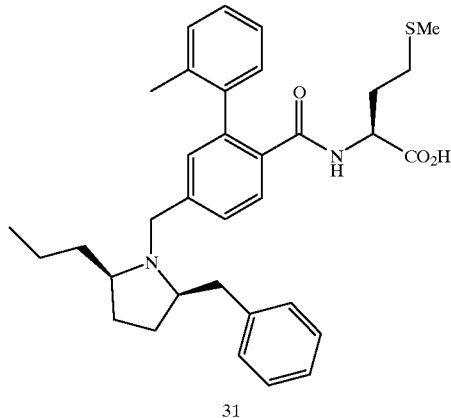
31
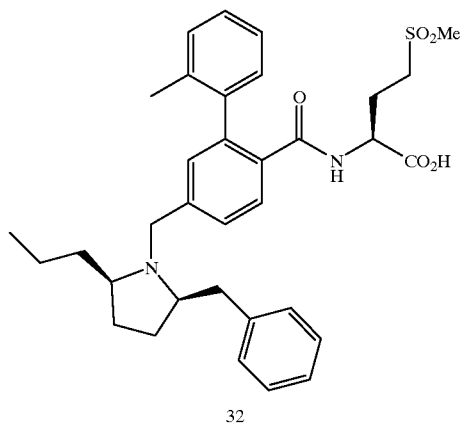
32
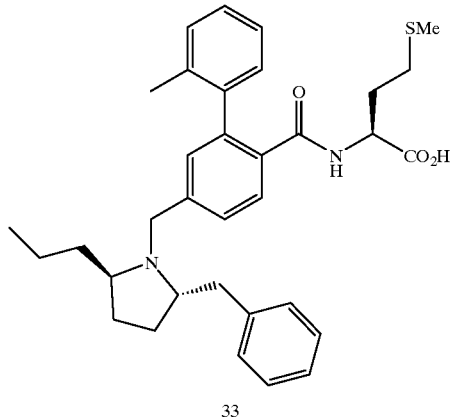
33
TABLE 6-continued
Amines of the Type A(B)N-L₁
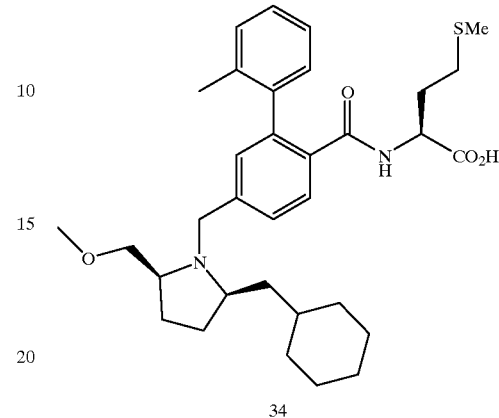
34
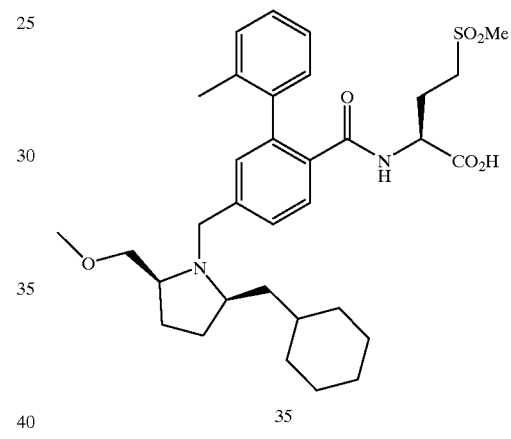
35
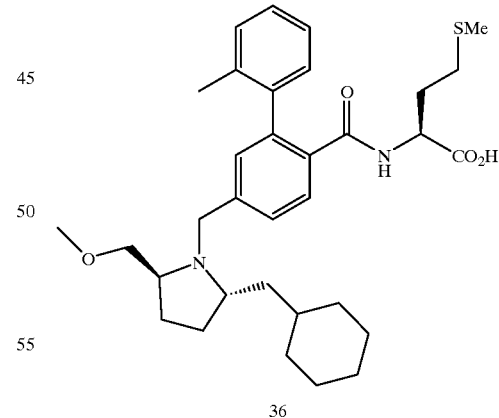
36

TABLE 6-continued
Amines of the Type A(B)N-L₁
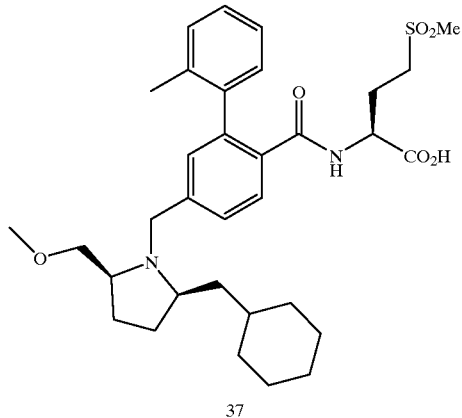
37
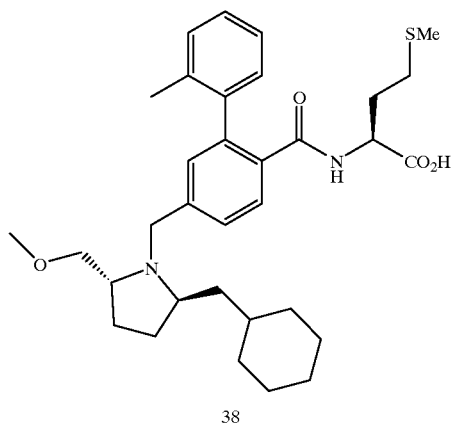
38
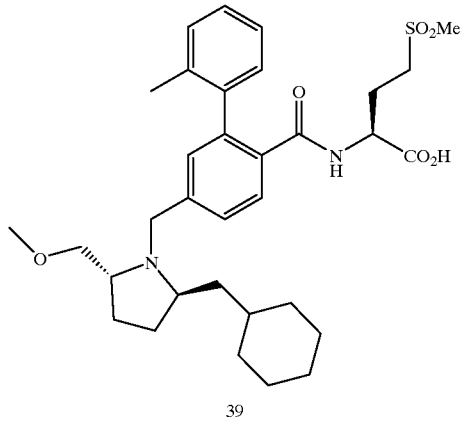
39
TABLE 6-continued
Amines of the Type A(B)N-L₁
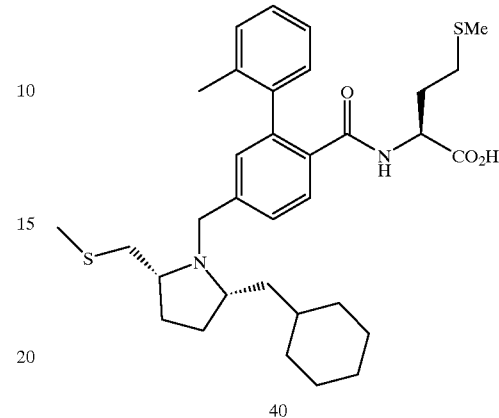
40
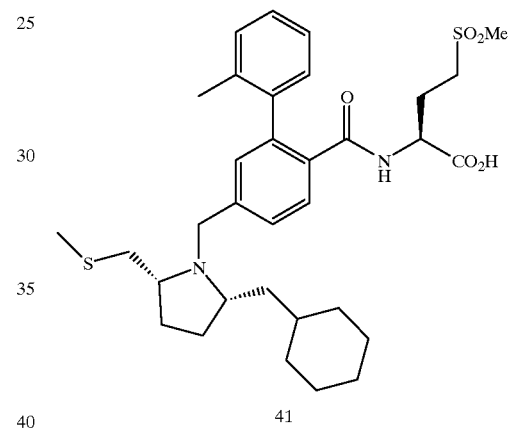
41
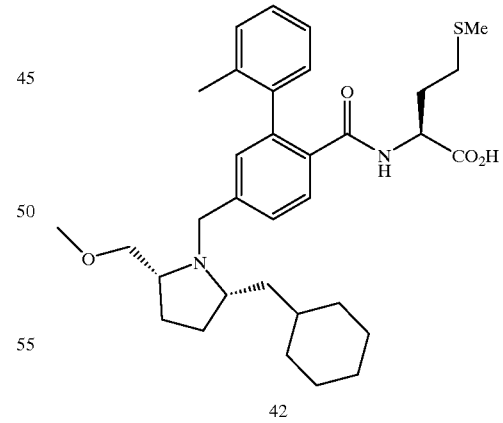
42

TABLE 6-continued
Amines of the Type A(B)N-L₁
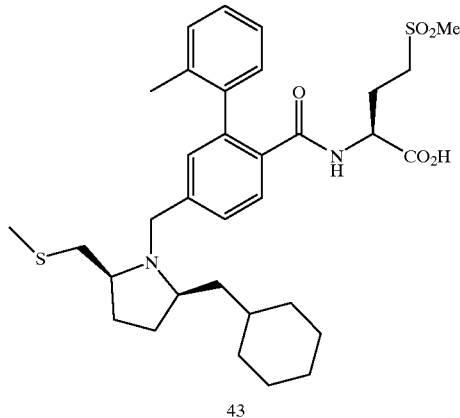
43
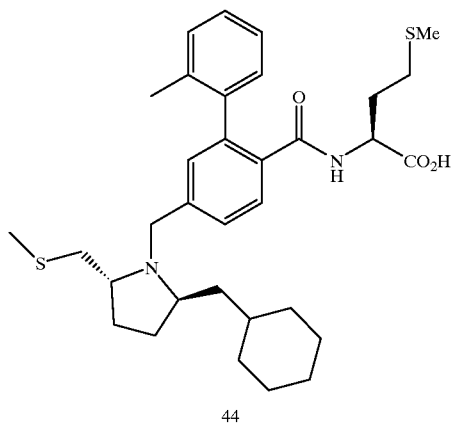
44
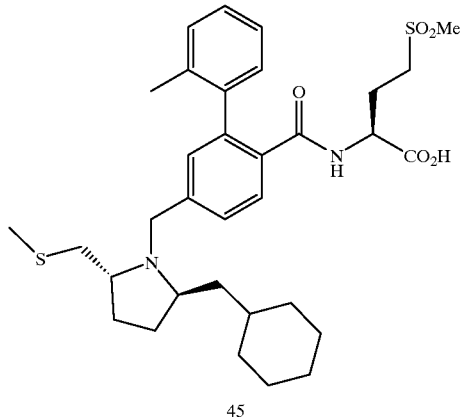
45
TABLE 6-continued
Amines of the Type A(B)N-L₁
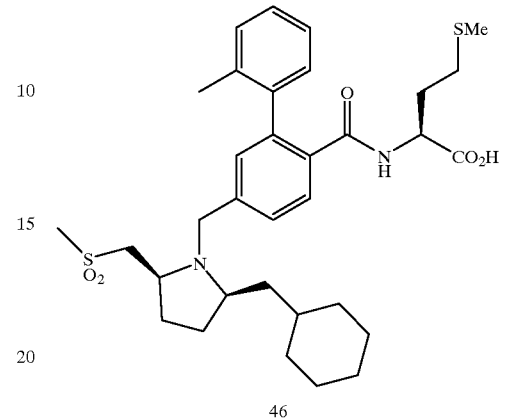
46
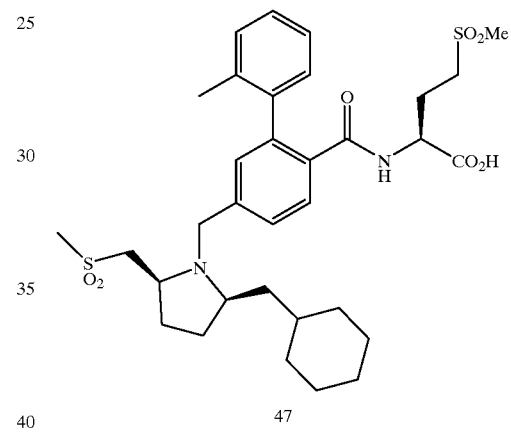
47
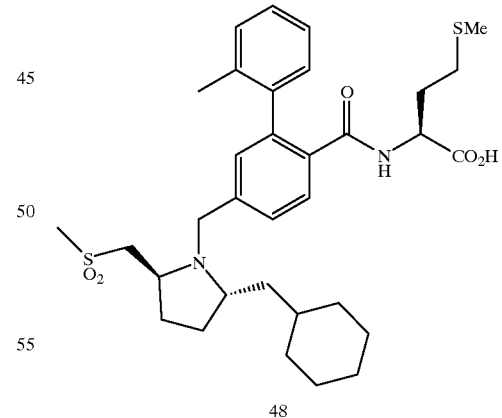
48

TABLE 6-continued
Amines of the Type A(B)N-L₁
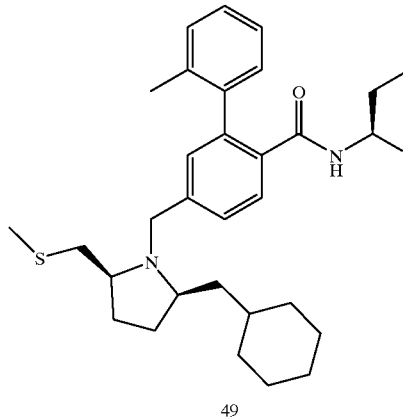
49
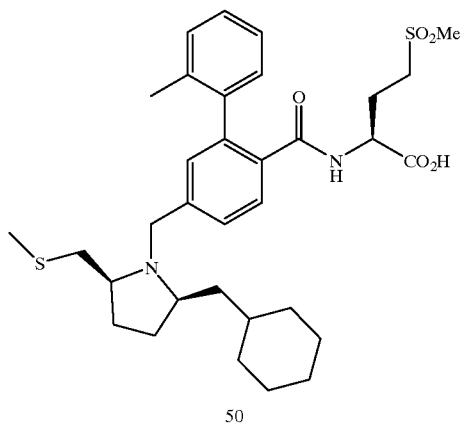
50
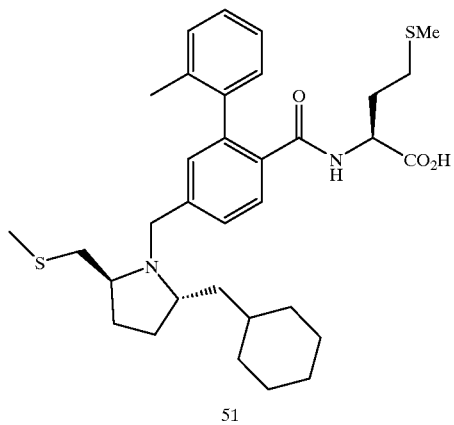
51
TABLE 6-continued
Amines of the Type A(B)N-L₁
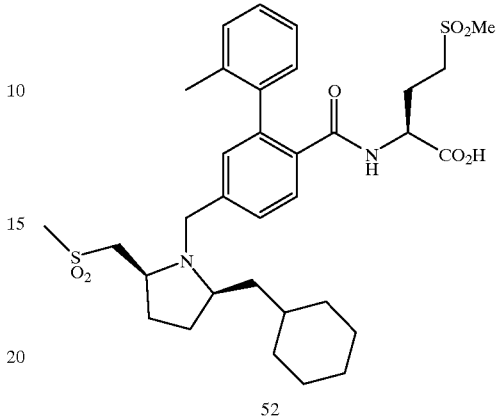
52
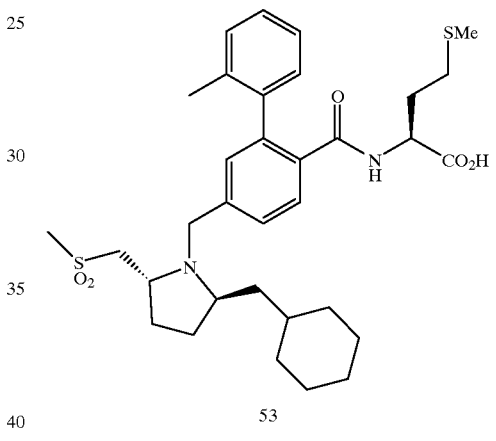
53
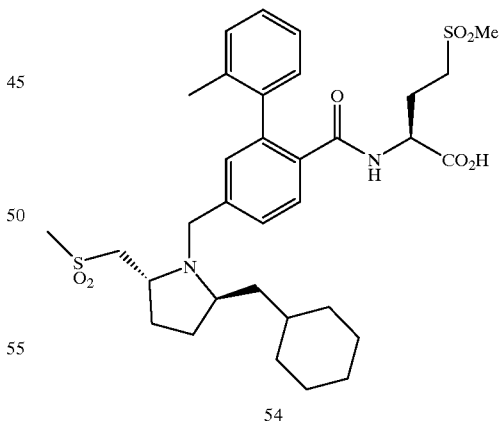
54

TABLE 6-continued
Amines of the Type A(B)N-L₁
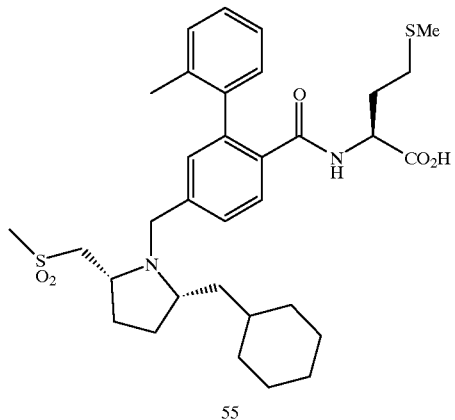
55
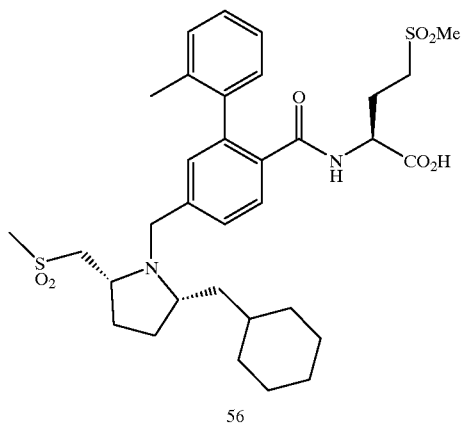
56
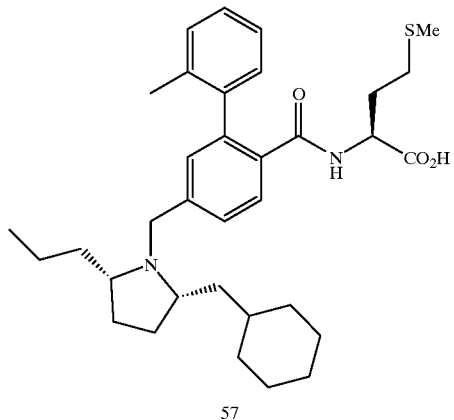
57
TABLE 6-continued
Amines of the Type A(B)N-L₁
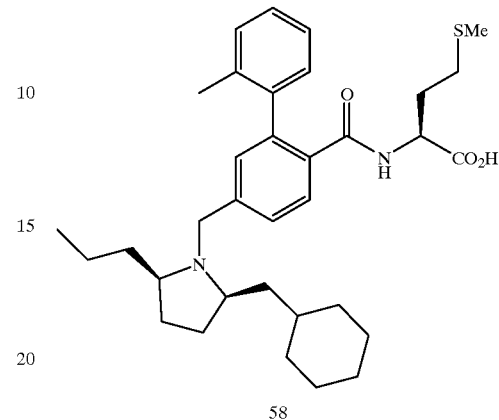
58
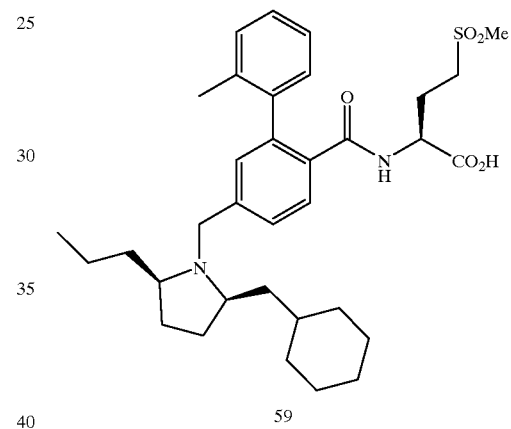
59
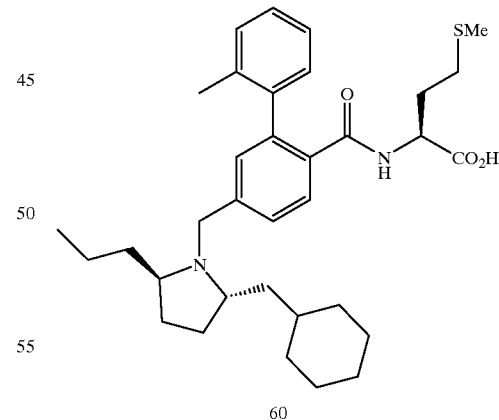
60

TABLE 6-continued
Amines of the Type A(B)N-L$_1$
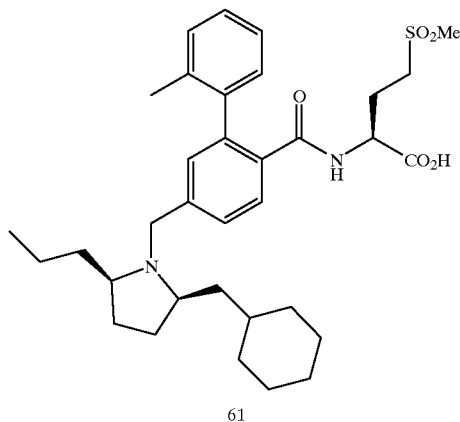
61
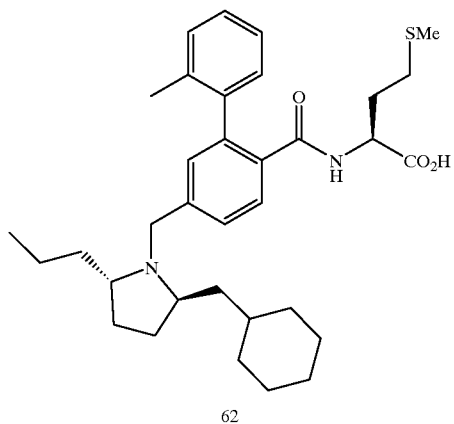
62
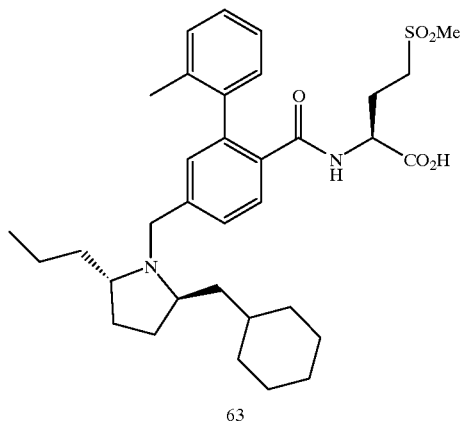
63
TABLE 6-continued
Amines of the Type A(B)N-L$_1$
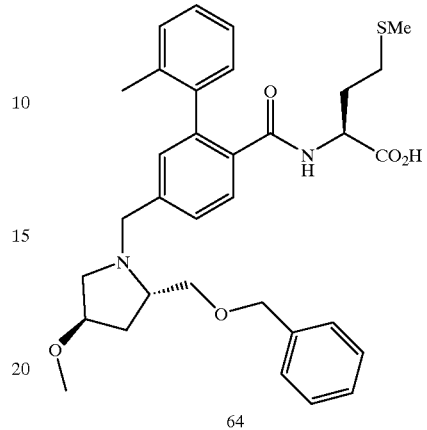
64
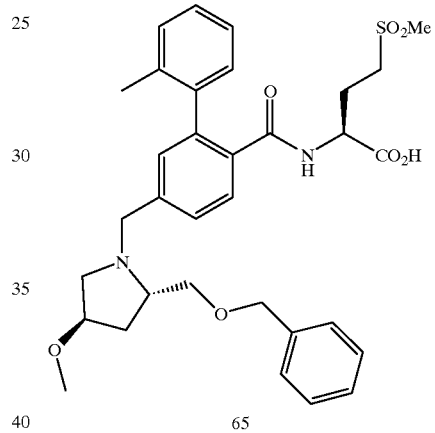
65
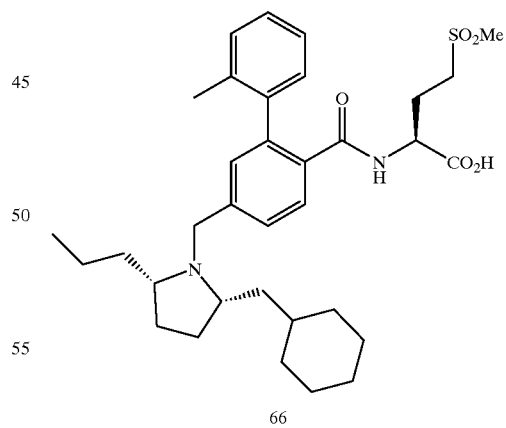
66

TABLE 6-continued
Amines of the Type A(B)N-L₁
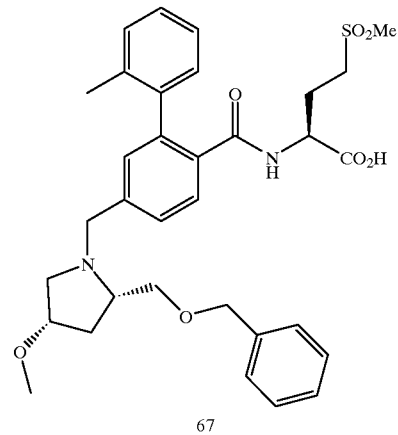
67
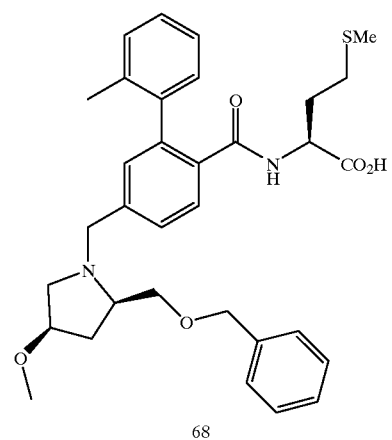
68
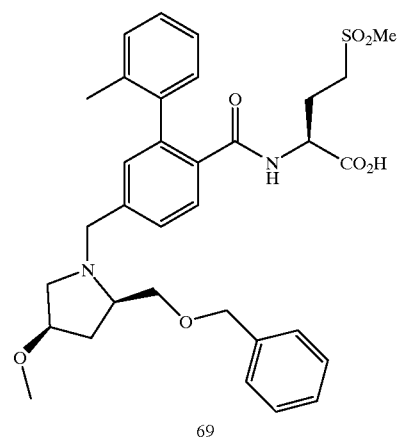
69
TABLE 6-continued
Amines of the Type A(B)N-L₁
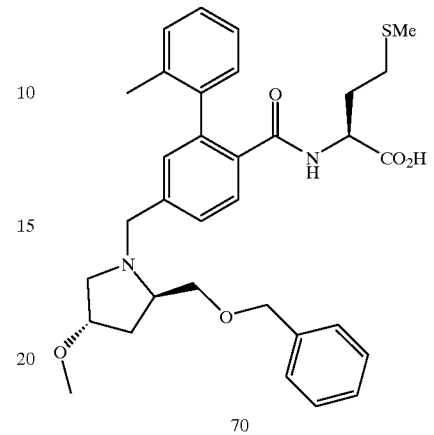
70
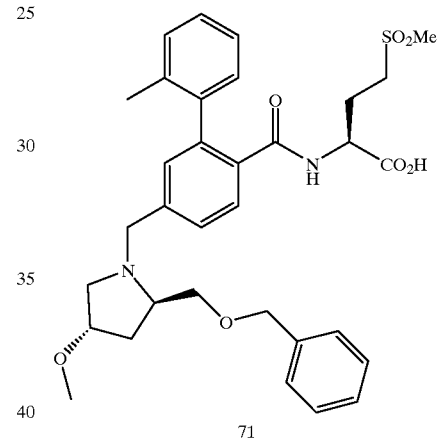
71
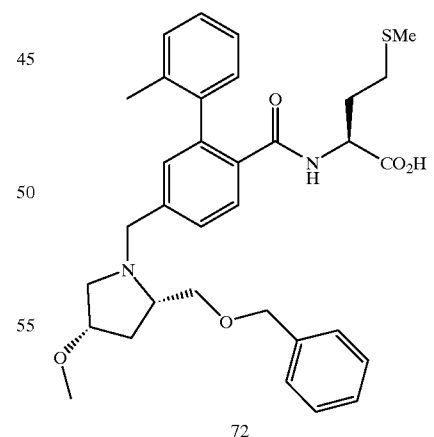
72

TABLE 6-continued
Amines of the Type A(B)N-L$_1$
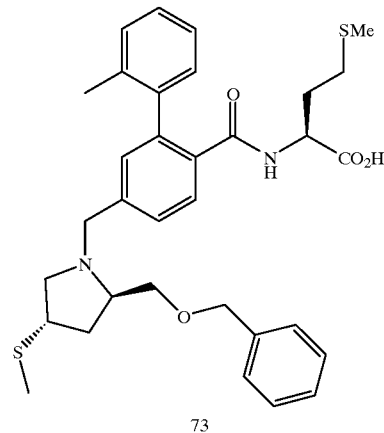
73
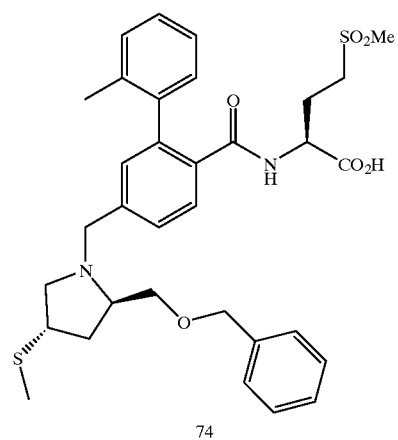
74
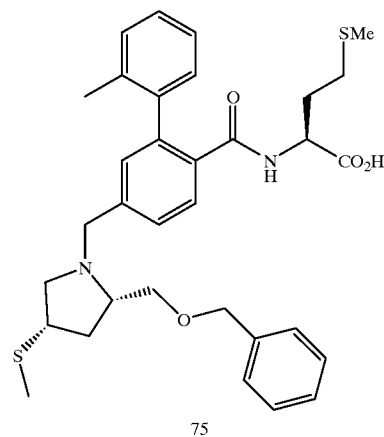
75
TABLE 6-continued
Amines of the Type A(B)N-L$_1$
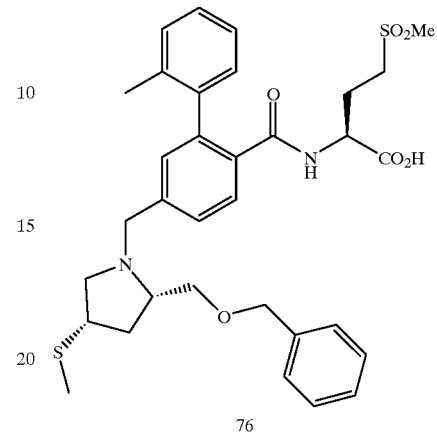
76
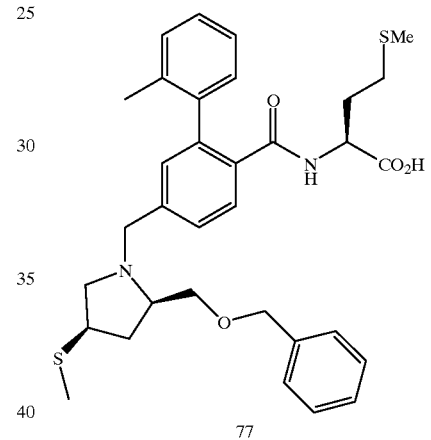
77
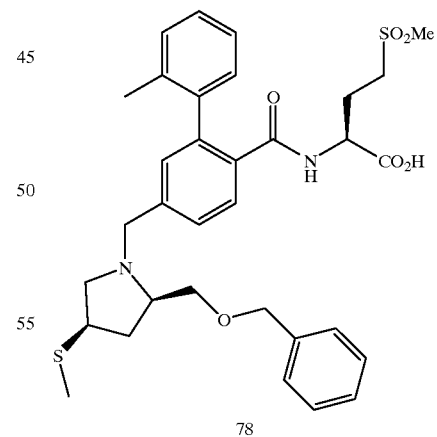
78

TABLE 6-continued
Amines of the Type A(B)N-L₁
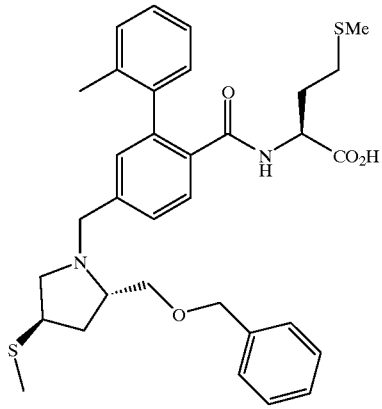
79
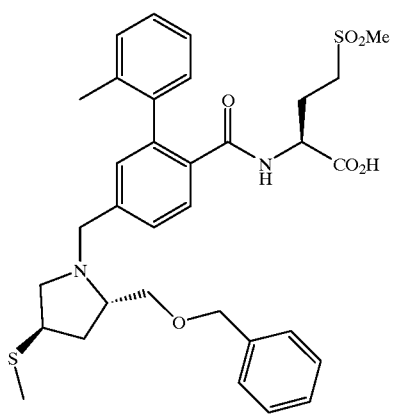
80
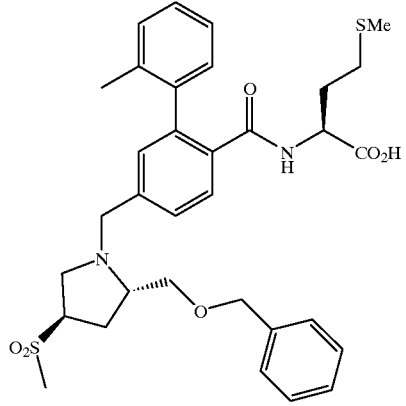
81
TABLE 6-continued
Amines of the Type A(B)N-L₁
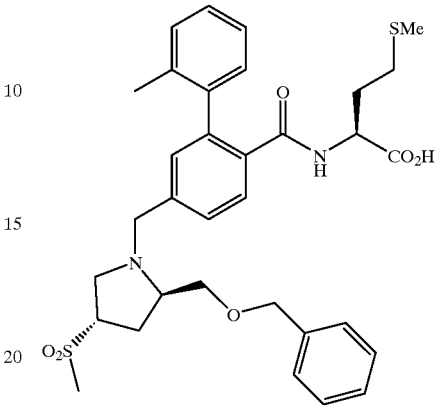
82
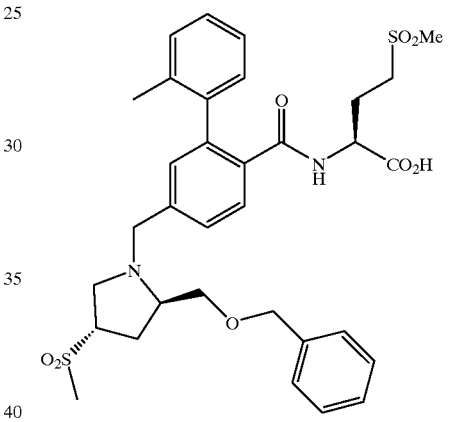
83
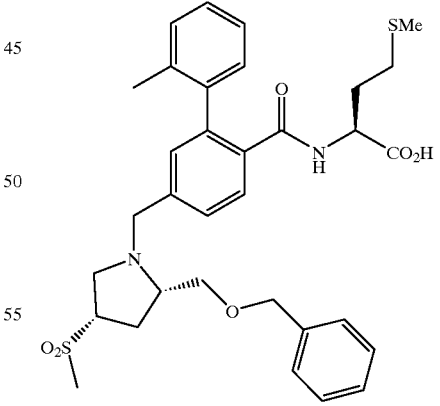
84

TABLE 6-continued
Amines of the Type A(B)N-L₁
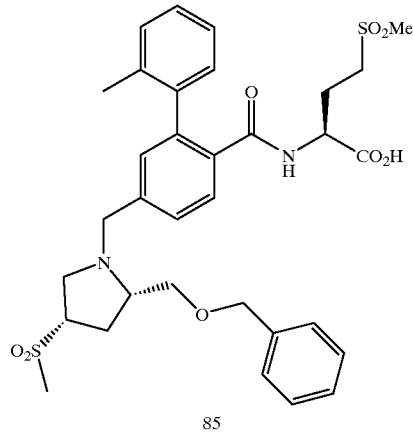
85
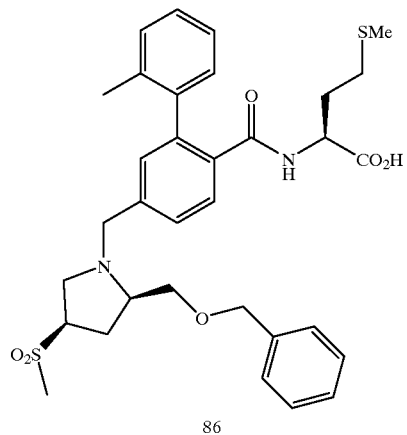
86
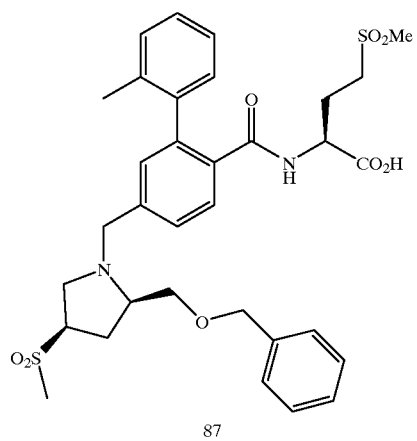
87
TABLE 6-continued
Amines of the Type A(B)N-L₁
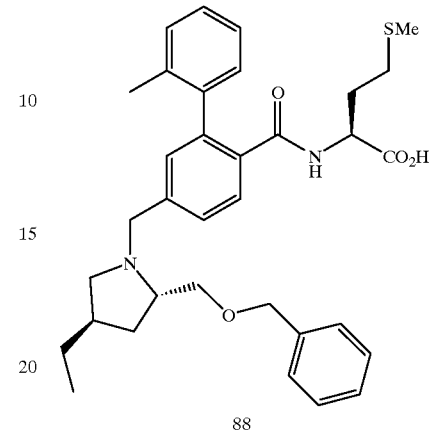
88
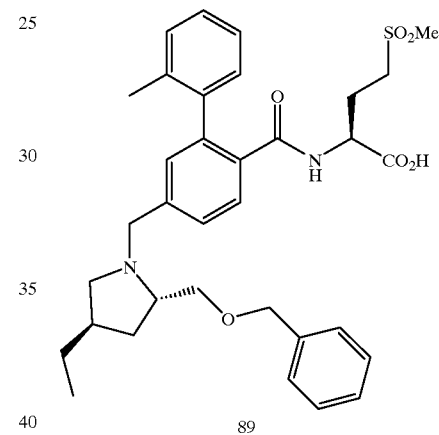
89
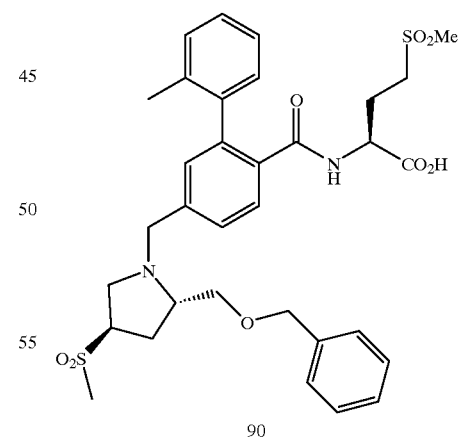
90

TABLE 6-continued
Amines of the Type A(B)N-L₁
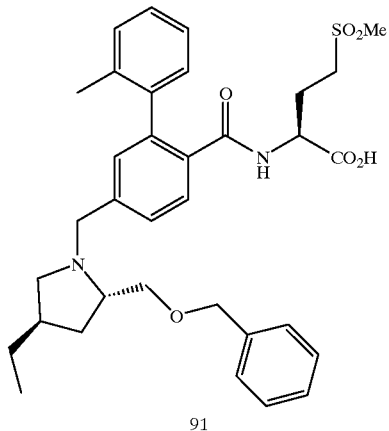
91
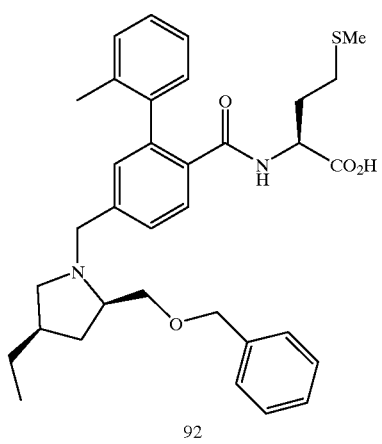
92
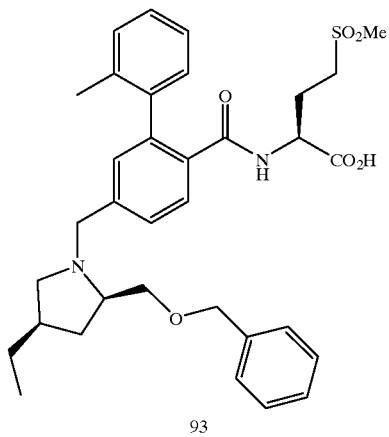
93
TABLE 6-continued
Amines of the Type A(B)N-L₁
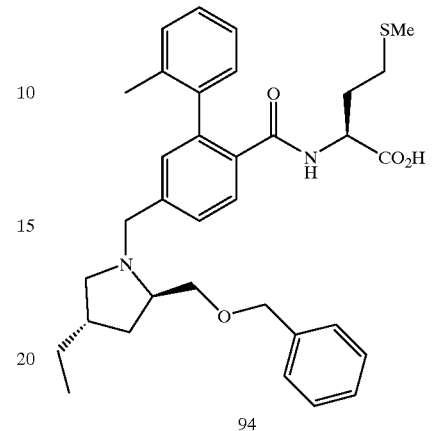
94
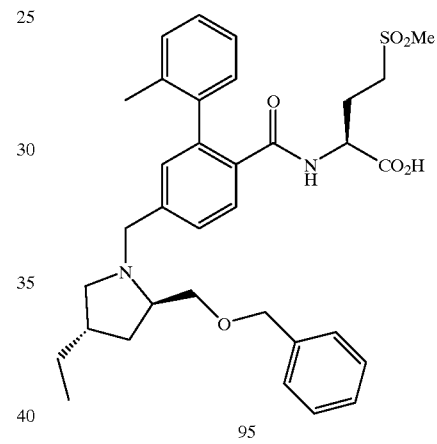
95
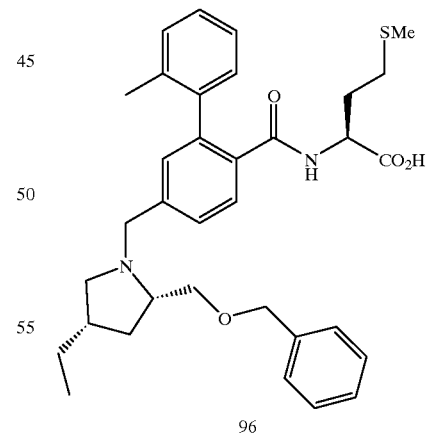
96

TABLE 6-continued
Amines of the Type A(B)N-L$_1$
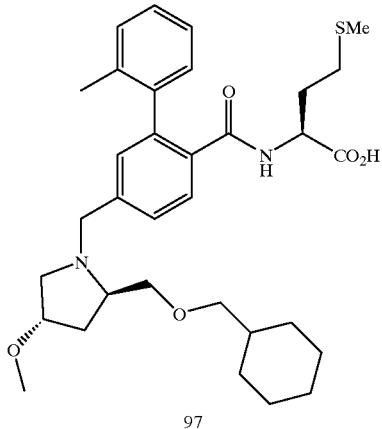
97
98
99
TABLE 6-continued
Amines of the Type A(B)N-L$_1$
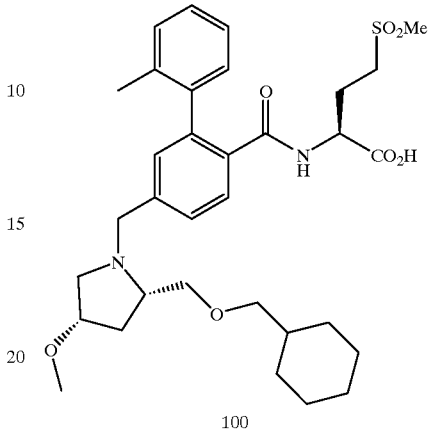
100
101
102

TABLE 6-continued
Amines of the Type A(B)N-L₁
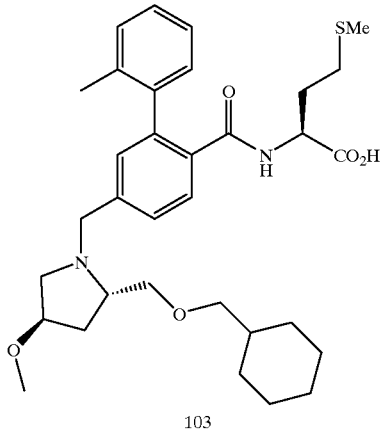
103
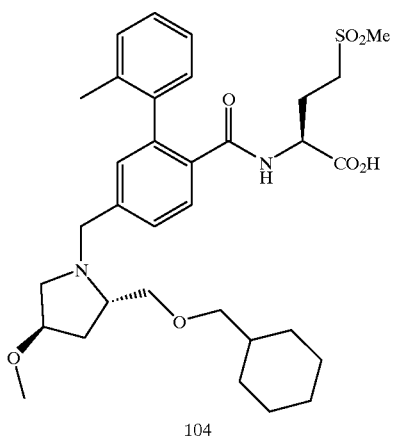
104
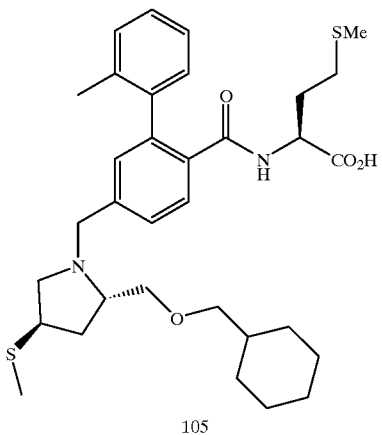
105
TABLE 6-continued
Amines of the Type A(B)N-L₁
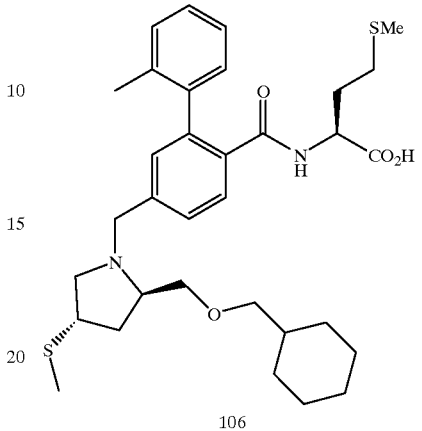
106
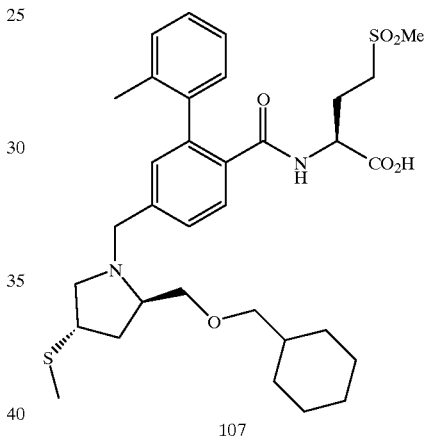
107
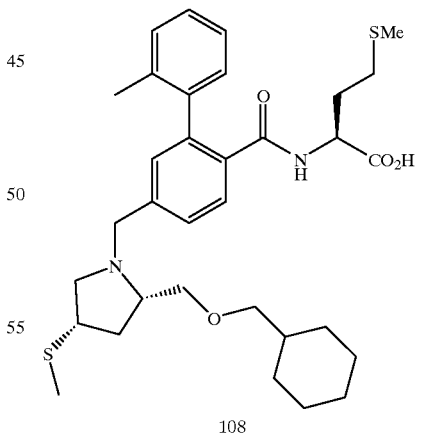
108

TABLE 6-continued
Amines of the Type A(B)N-L$_1$
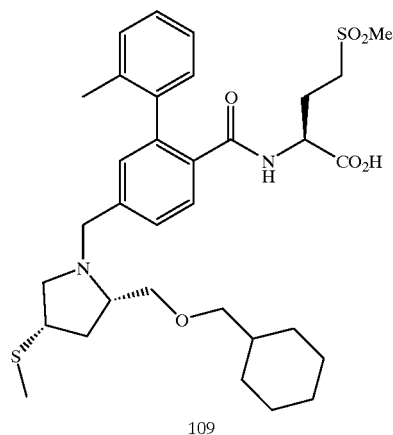
109
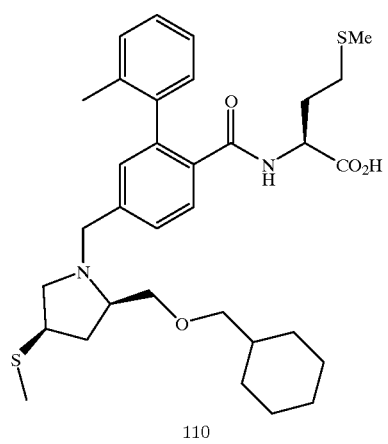
110
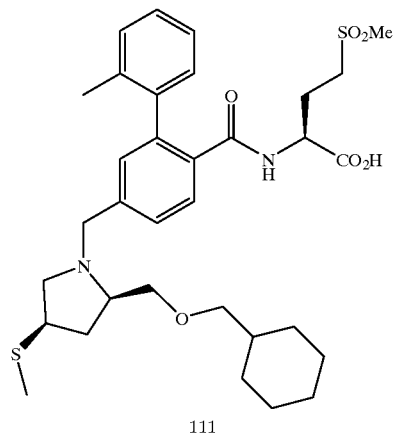
111
TABLE 6-continued
Amines of the Type A(B)N-L$_1$
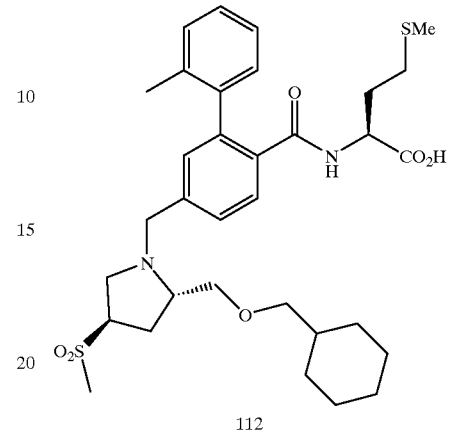
112
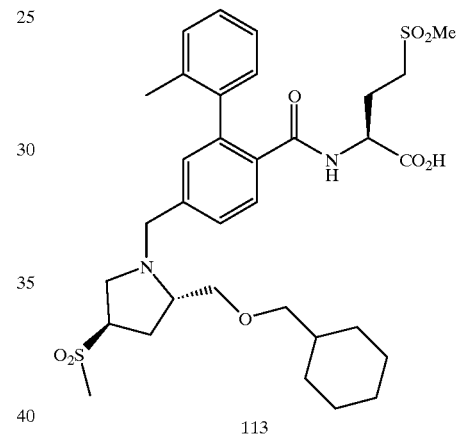
113
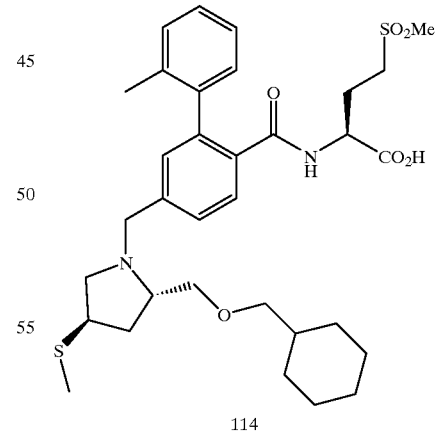
114

TABLE 6-continued
Amines of the Type A(B)N-L₁
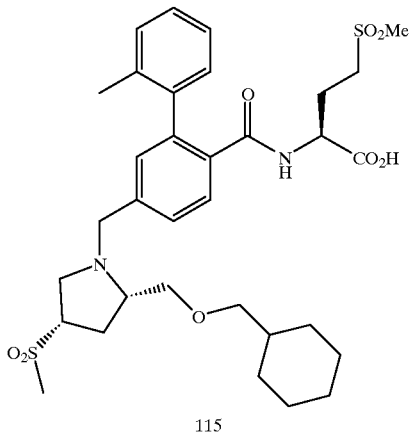
115
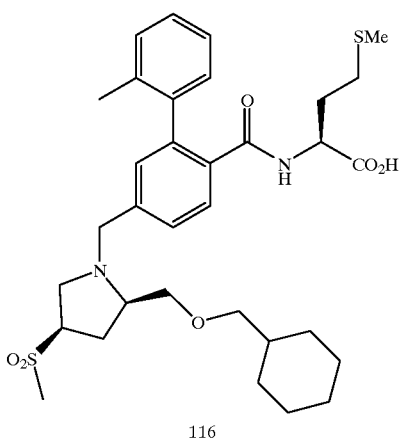
116
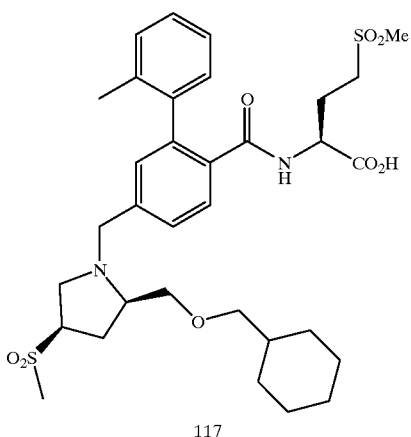
117
TABLE 6-continued
Amines of the Type A(B)N-L₁
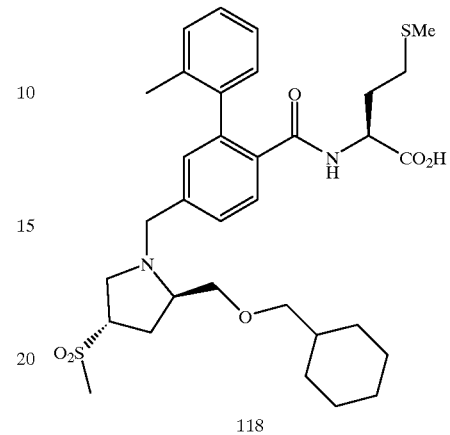
118
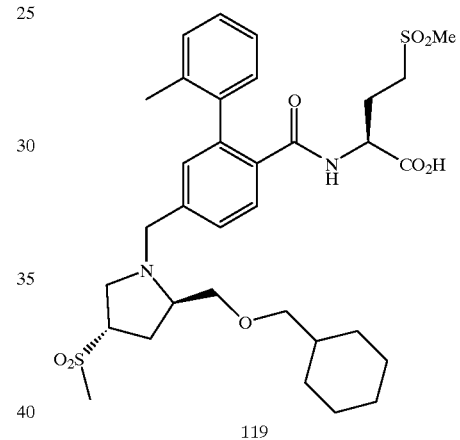
119
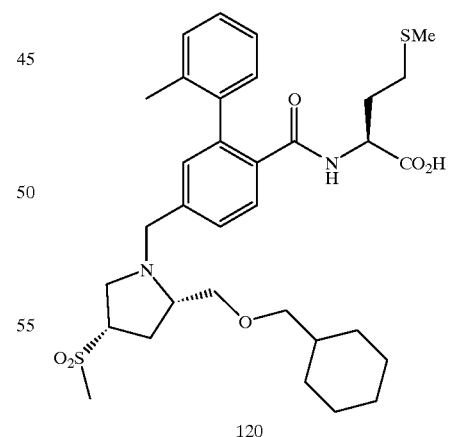
120

TABLE 6-continued
Amines of the Type A(B)N-L₁
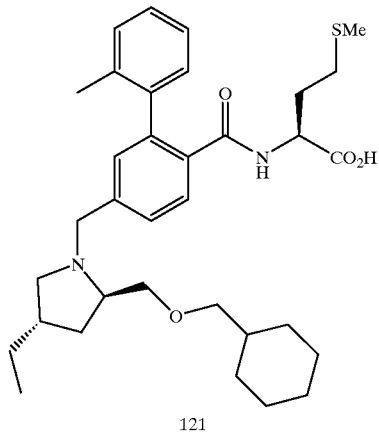
121
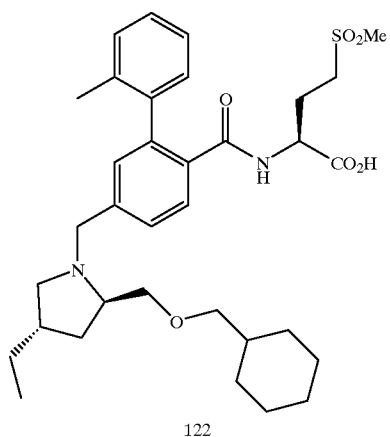
122
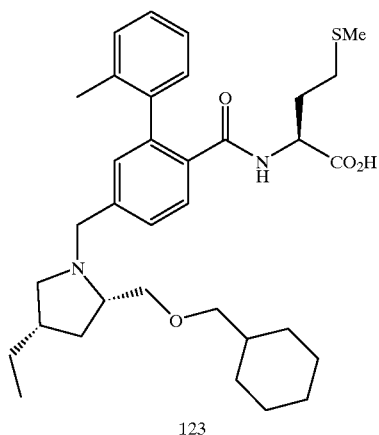
123
TABLE 6-continued
Amines of the Type A(B)N-L₁
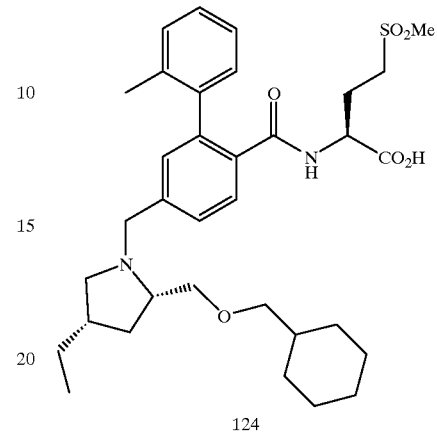
124
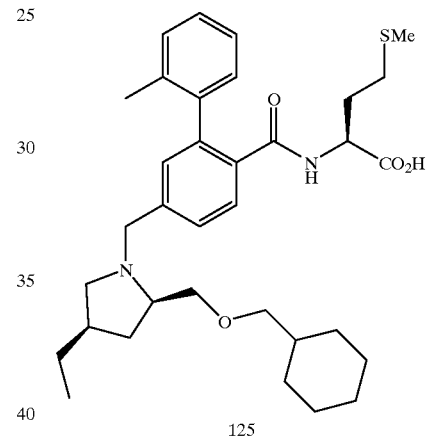
125
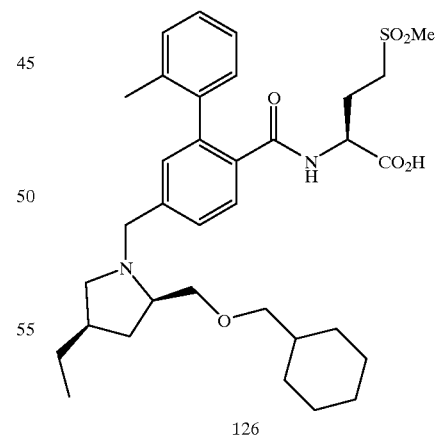
126

TABLE 6-continued
Amines of the Type A(B)N-L₁
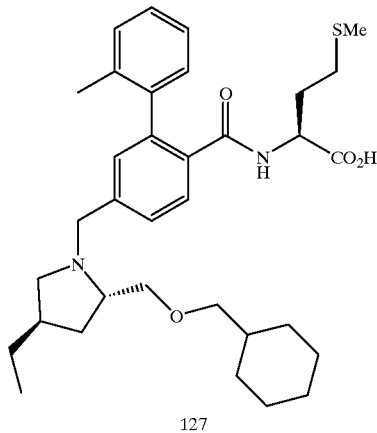
127
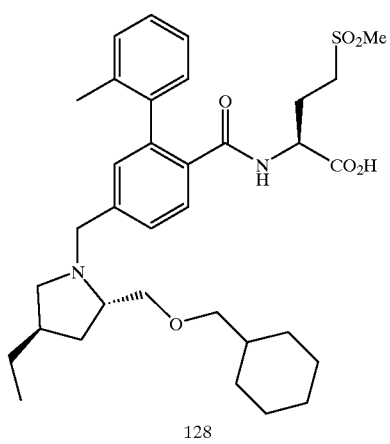
128
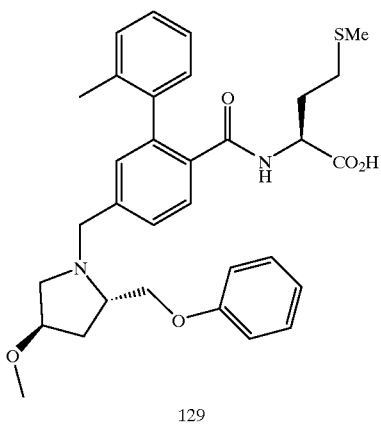
129
TABLE 6-continued
Amines of the Type A(B)N-L₁
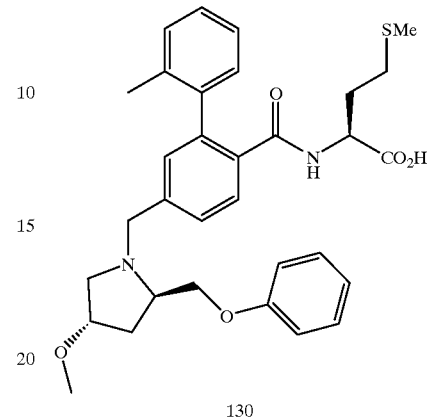
130
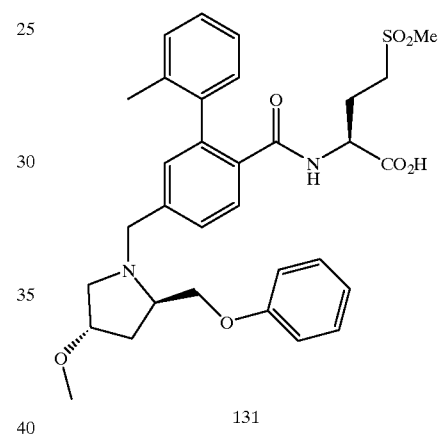
131
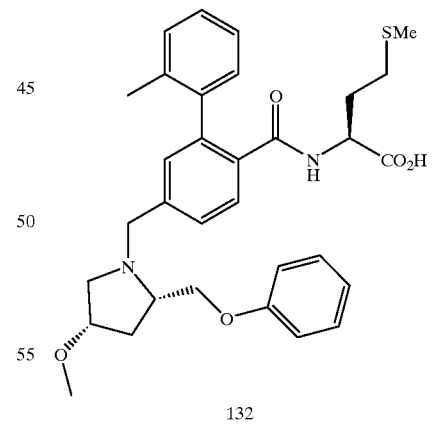
132

TABLE 6-continued
Amines of the Type A(B)N-L₁
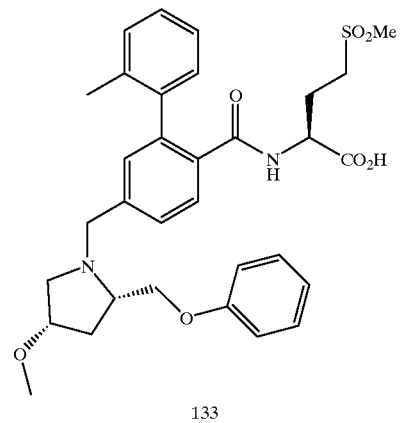
133
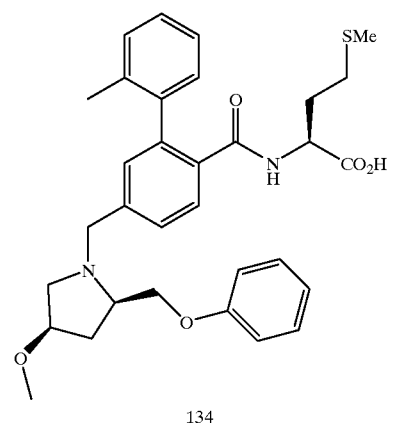
134
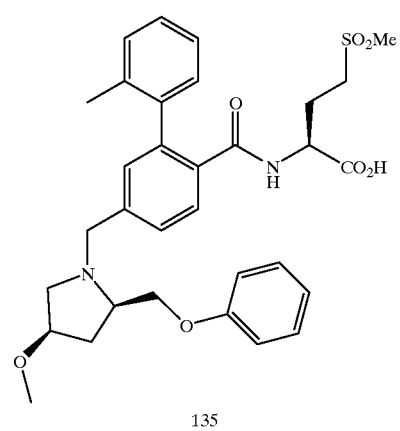
135
TABLE 6-continued
Amines of the Type A(B)N-L₁
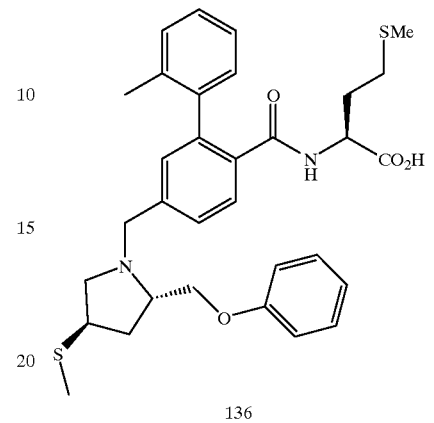
136
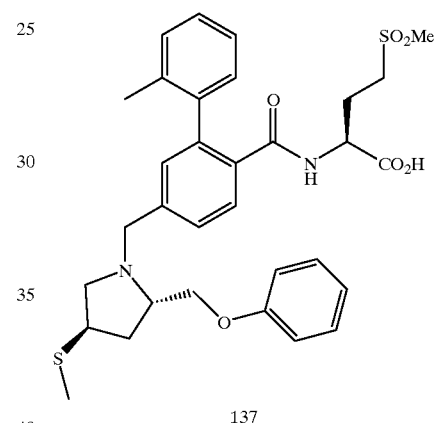
137

138

TABLE 6-continued
Amines of the Type A(B)N-L₁
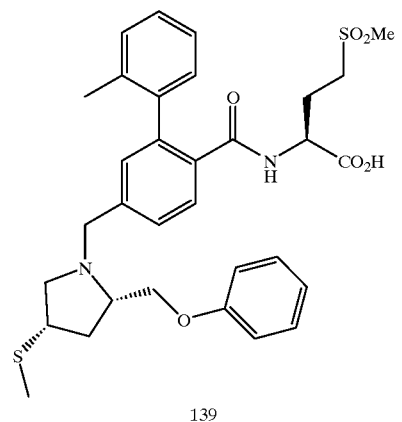
139
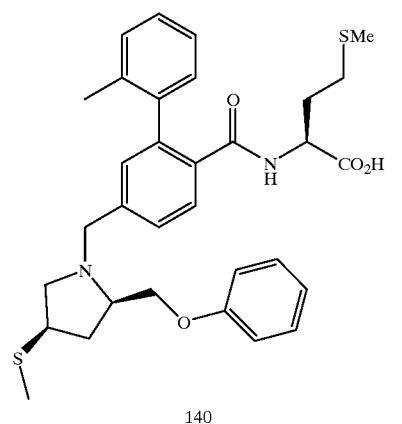
140
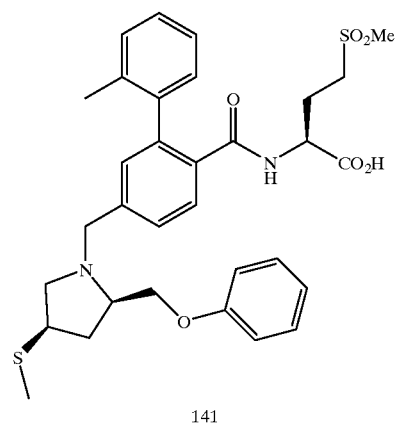
141
TABLE 6-continued
Amines of the Type A(B)N-L₁
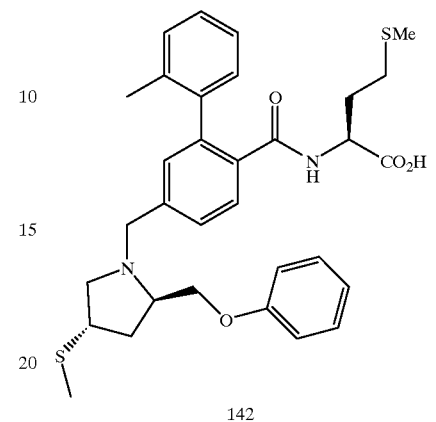
142
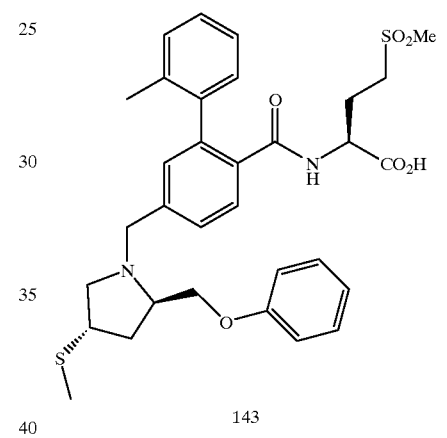
143
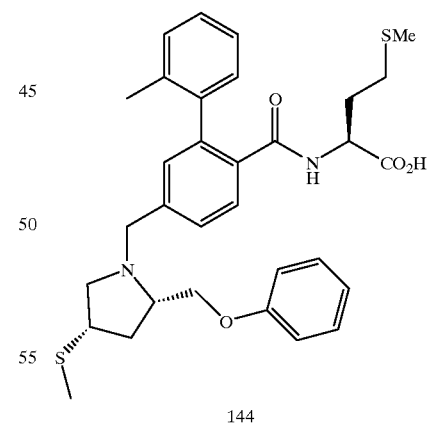
144

TABLE 6-continued
Amines of the Type A(B)N-L$_1$
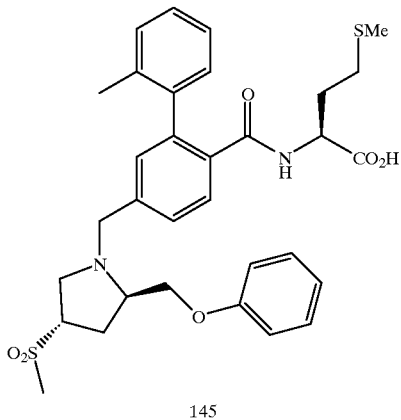
145
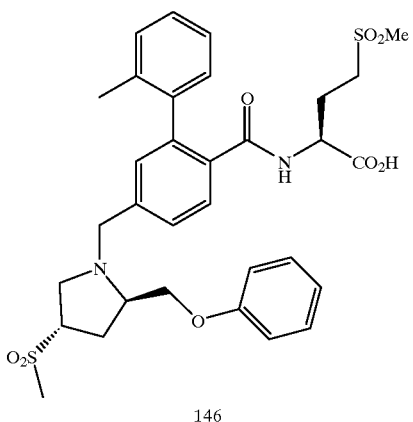
146
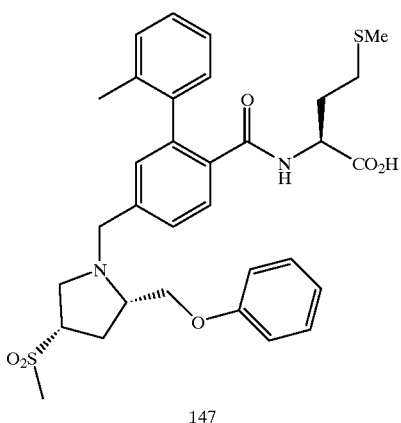
147
TABLE 6-continued
Amines of the Type A(B)N-L$_1$
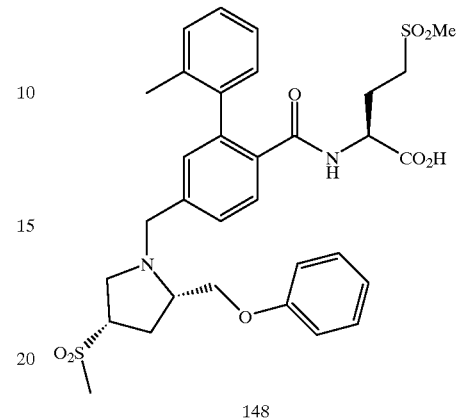
148
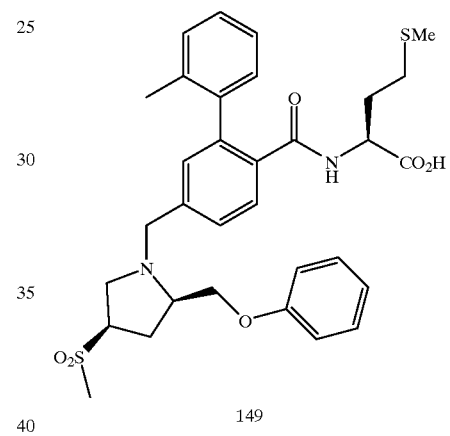
149
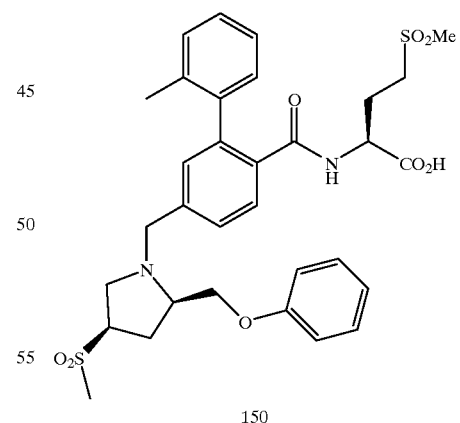
150

TABLE 6-continued
Amines of the Type A(B)N-L₁
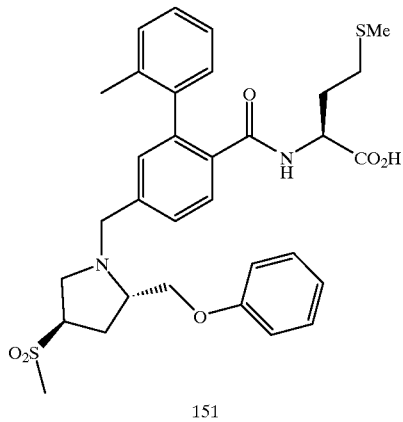
151
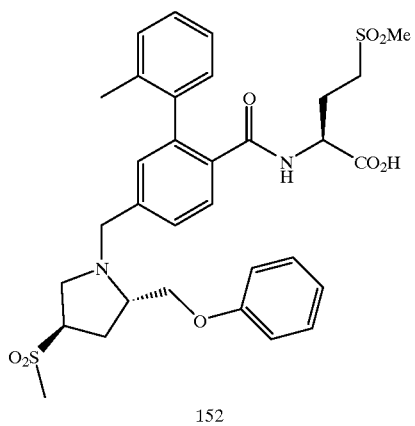
152
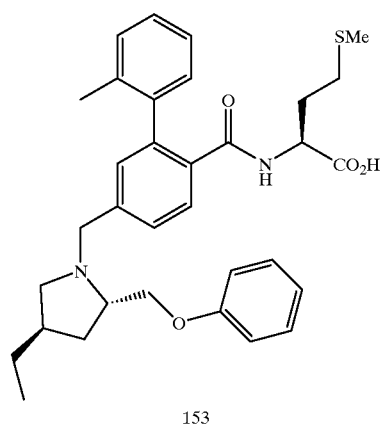
153
TABLE 6-continued
Amines of the Type A(B)N-L₁
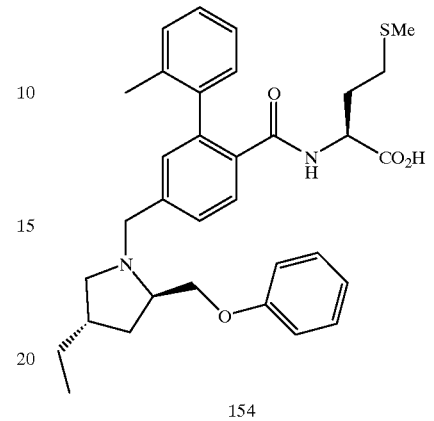
154
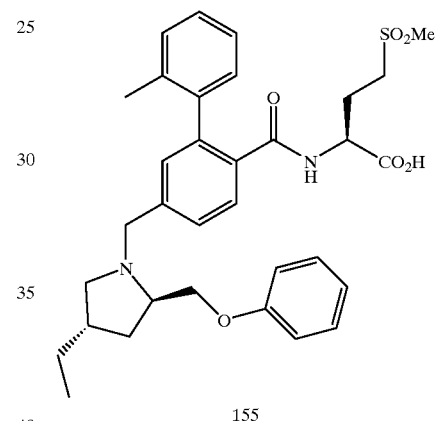
155
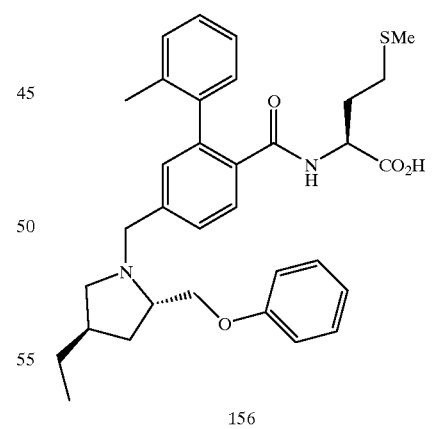
156

TABLE 6-continued
Amines of the Type A(B)N-L₁
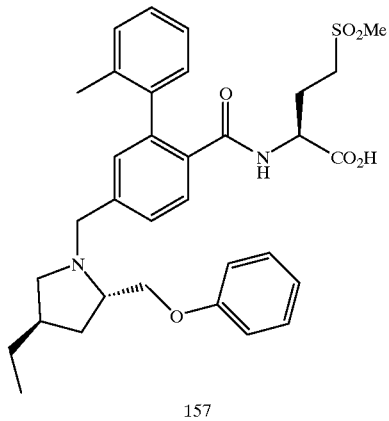
157
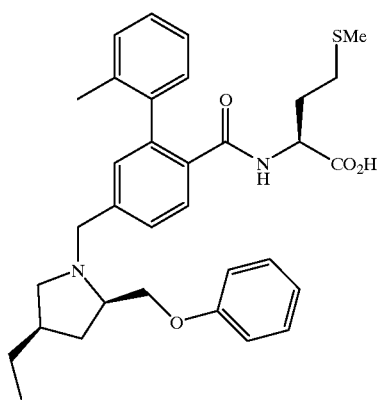
158
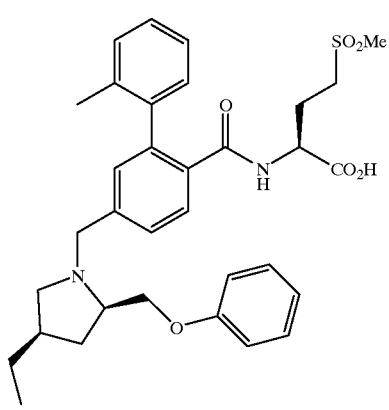
159
TABLE 6-continued
Amines of the Type A(B)N-L₁
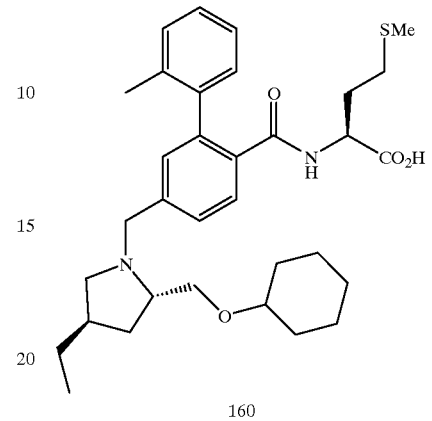
160
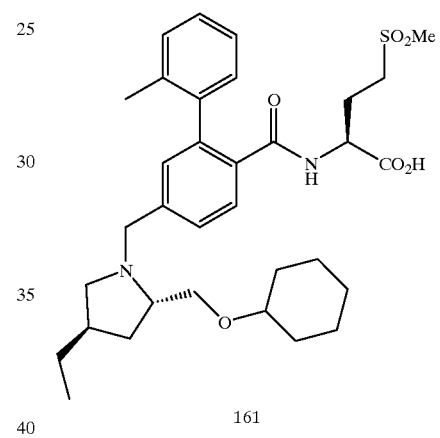
161
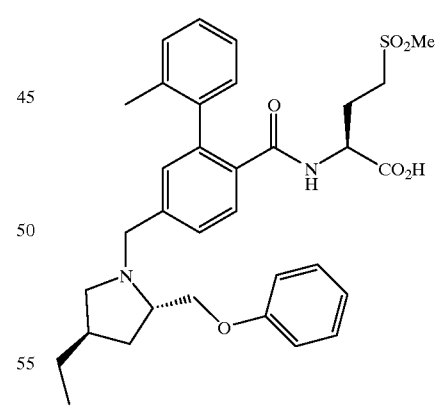
162

TABLE 6-continued
Amines of the Type A(B)N-L₁
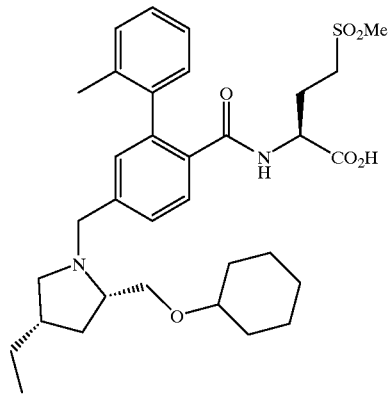
163
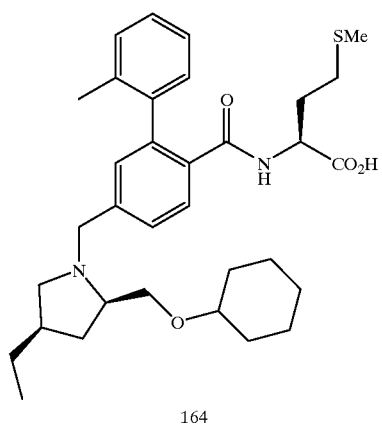
164
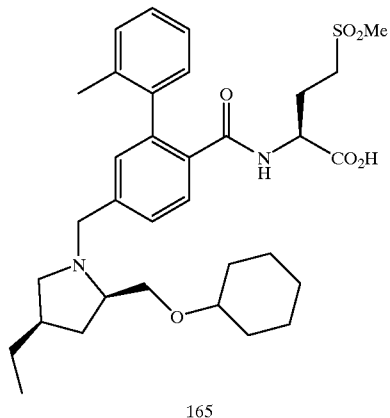
165
TABLE 6-continued
Amines of the Type A(B)N-L₁
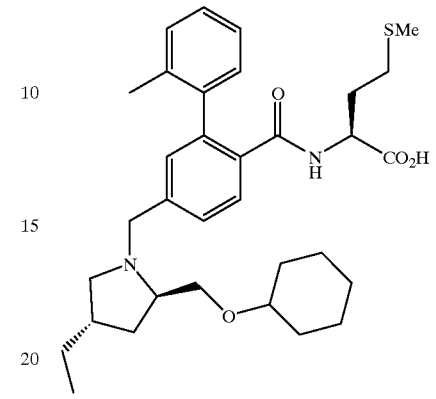
166
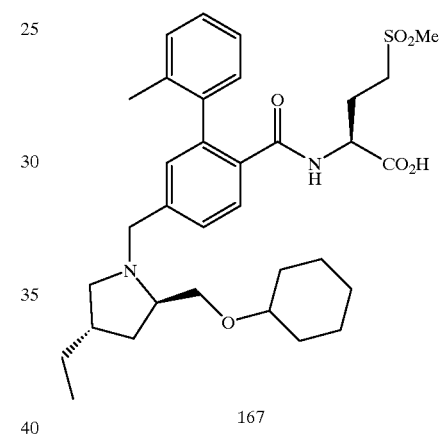
167
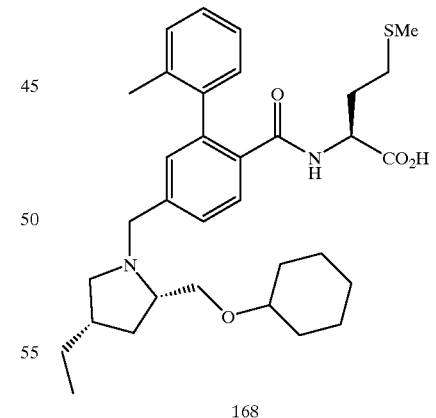
168

TABLE 6-continued
Amines of the Type A(B)N-L₁
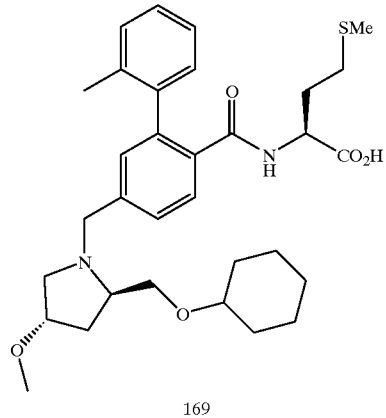
169
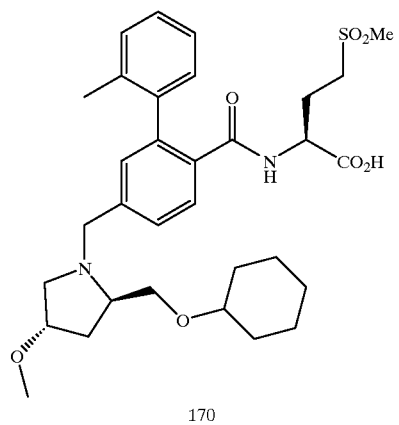
170
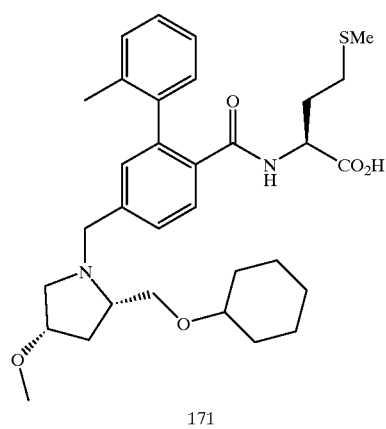
171
TABLE 6-continued
Amines of the Type A(B)N-L₁
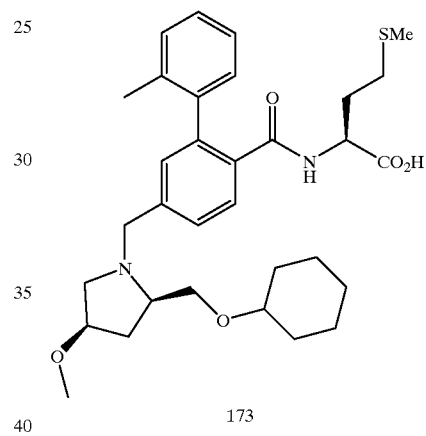
172
173
174

TABLE 6-continued
Amines of the Type A(B)N-L₁
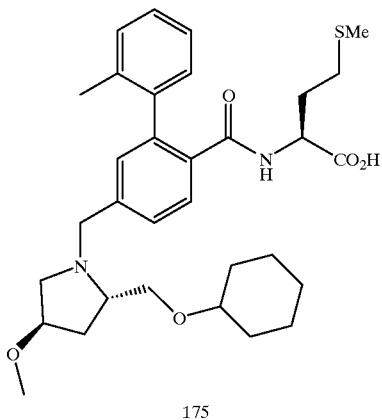
175
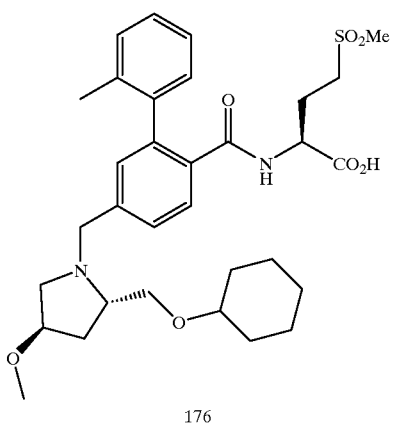
176
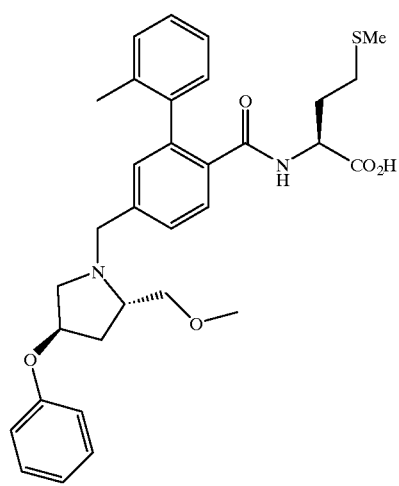
177
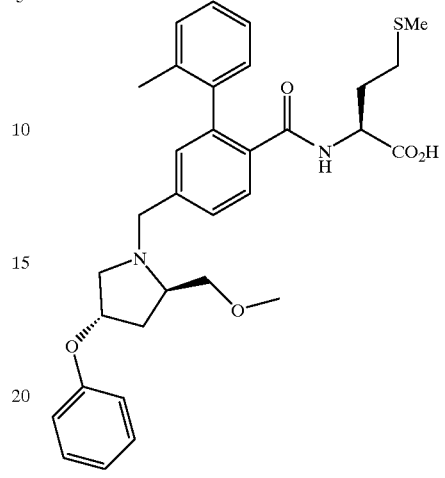
178
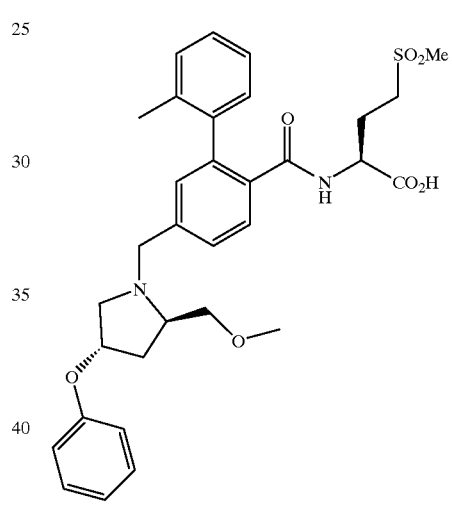
179
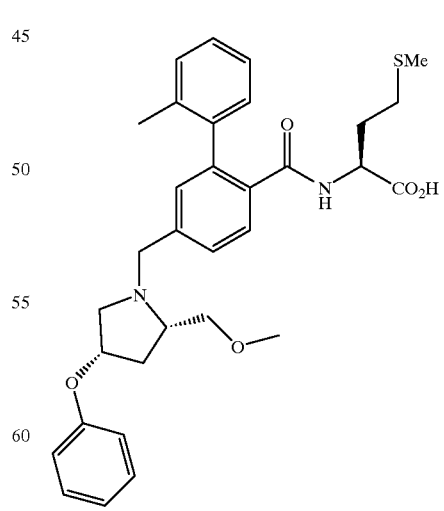
180

TABLE 6-continued
Amines of the Type A(B)N-L₁
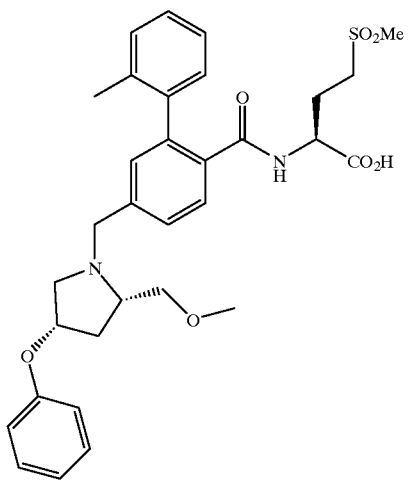
181
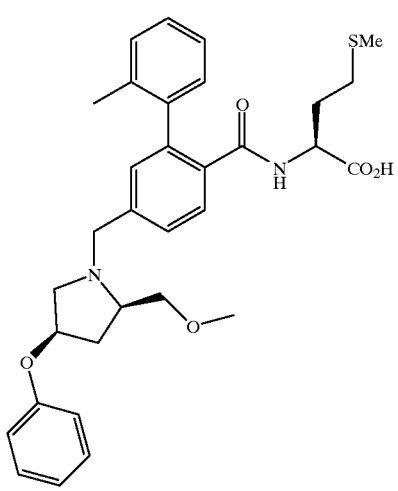
182
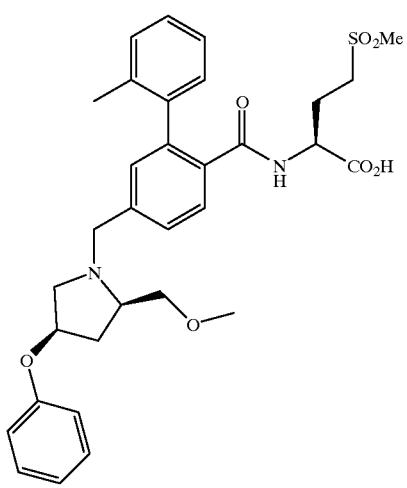
183
TABLE 6-continued
Amines of the Type A(B)N-L₁
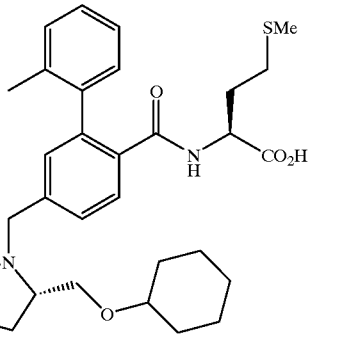
184
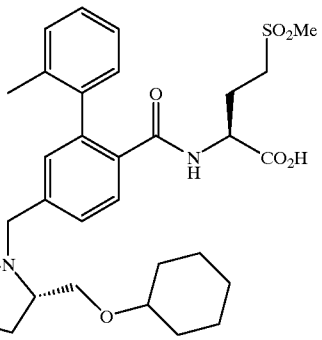
185
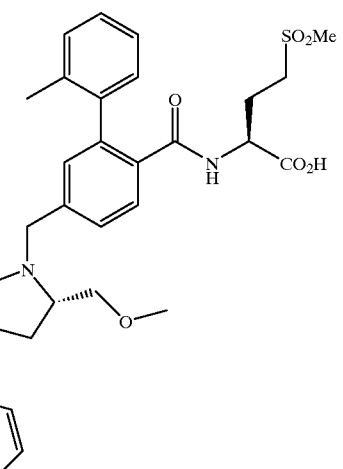
186

TABLE 6-continued
Amines of the Type A(B)N-L₁
187
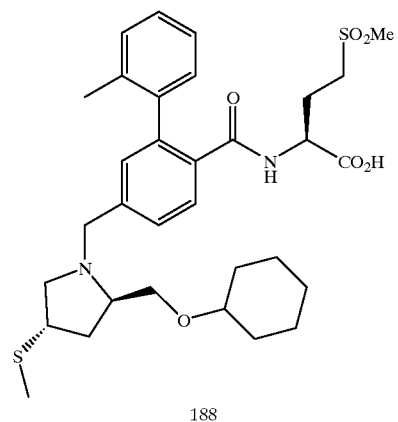
188
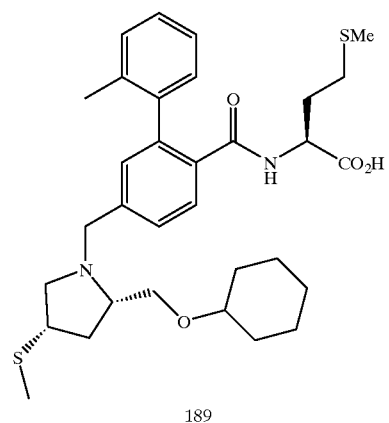
189
TABLE 6-continued
Amines of the Type A(B)N-L₁
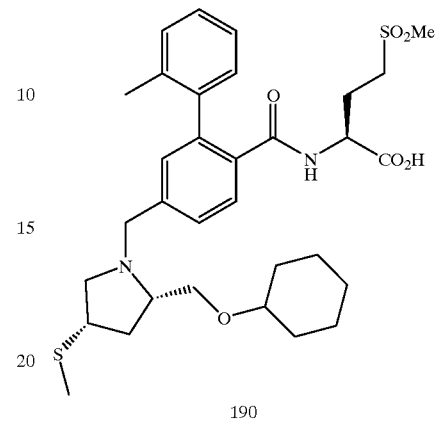
190
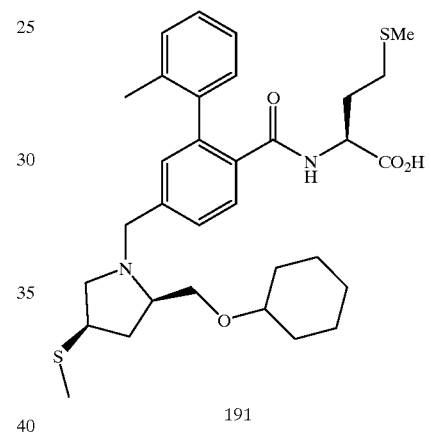
191
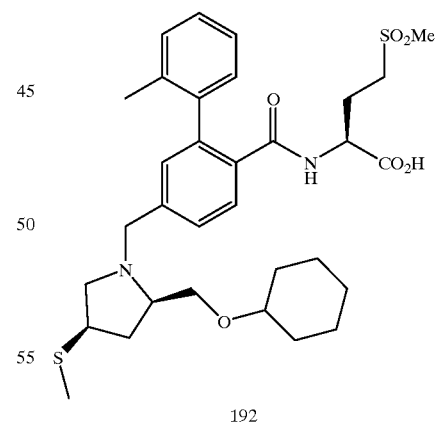
192

TABLE 6-continued
Amines of the Type A(B)N-L₁
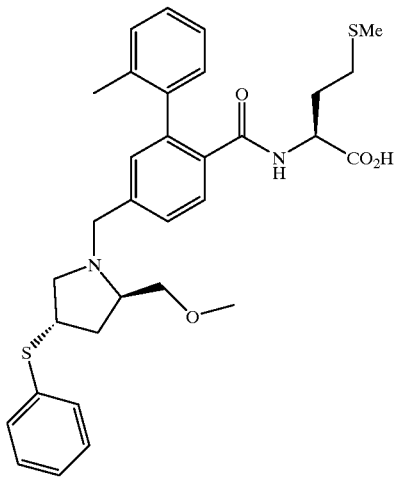
193
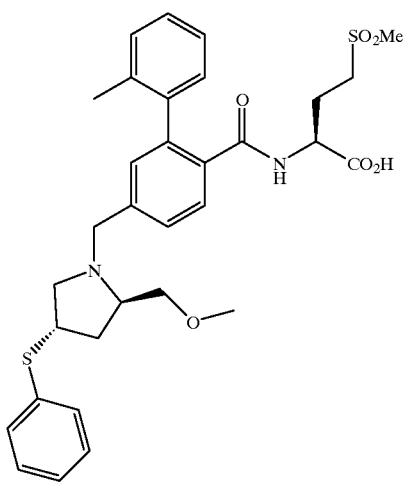
194
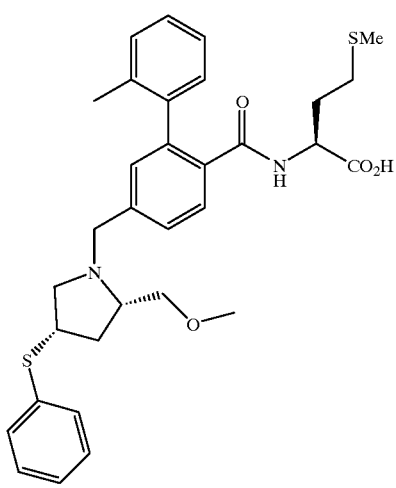
195
TABLE 6-continued
Amines of the Type A(B)N-L₁
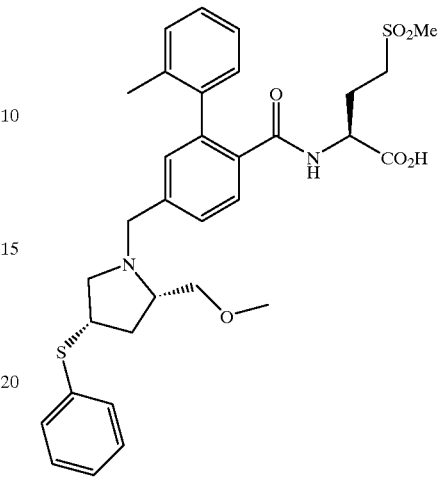
196
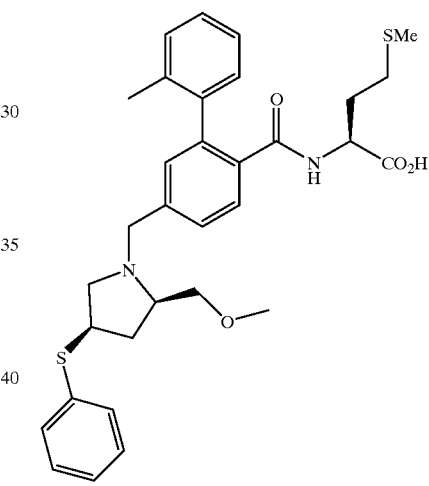
197
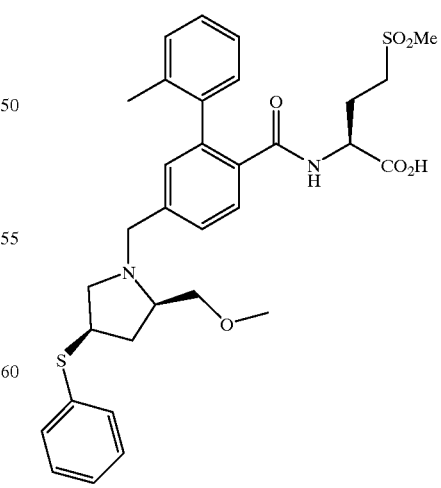
198

TABLE 6-continued
Amines of the Type A(B)N-L$_1$
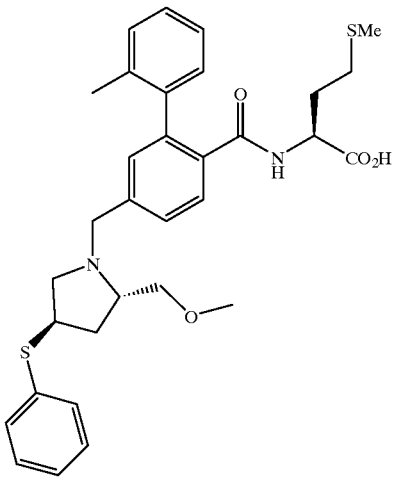
199
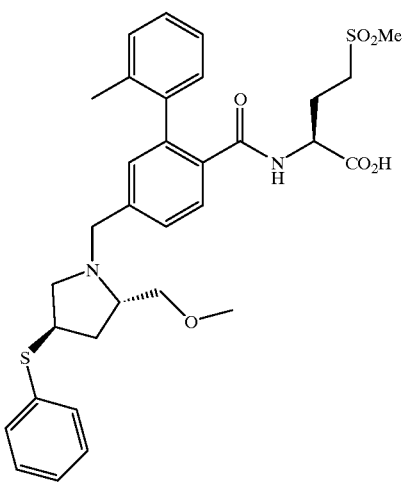
200
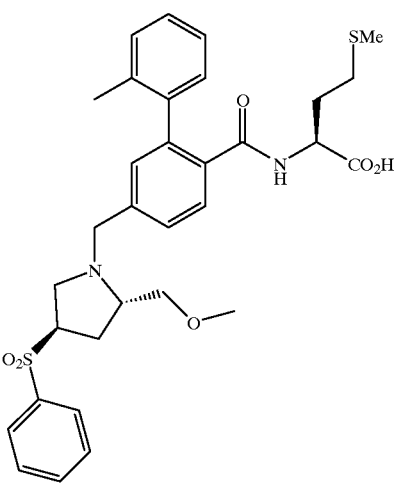
201
TABLE 6-continued
Amines of the Type A(B)N-L$_1$
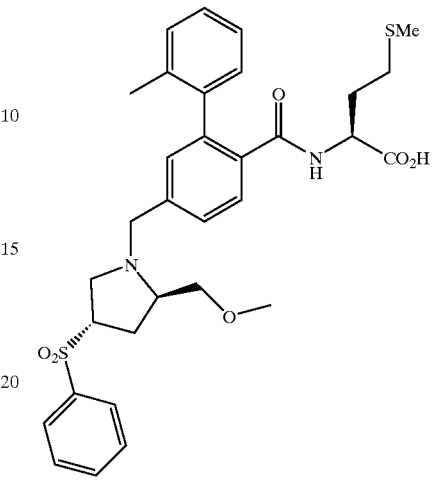
202
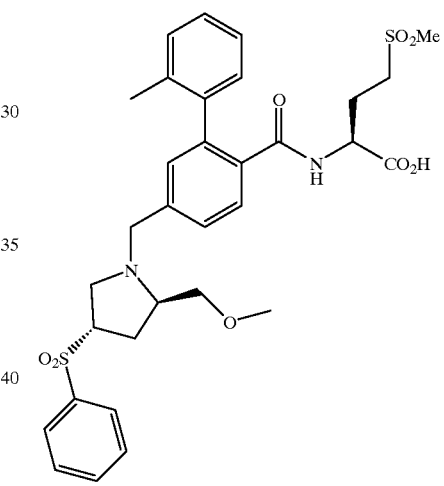
203
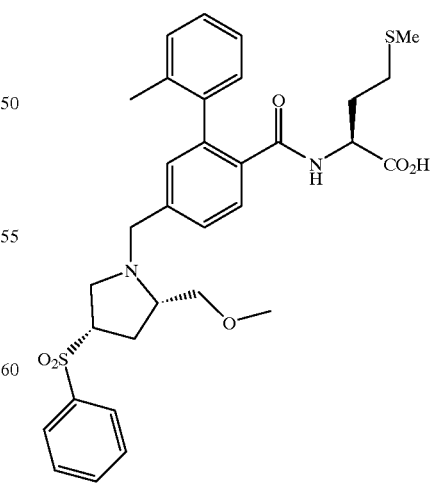
204

TABLE 6-continued
Amines of the Type A(B)N-L₁
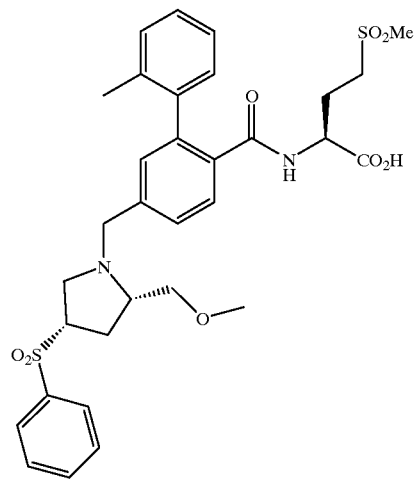
205
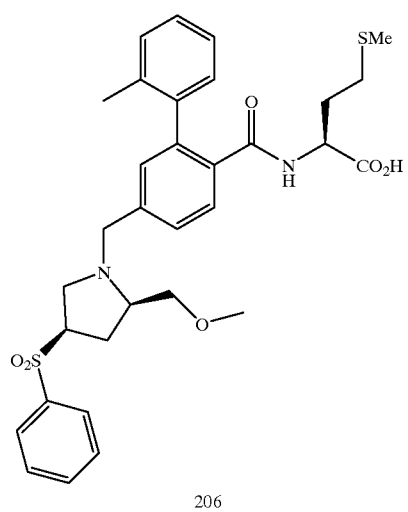
206
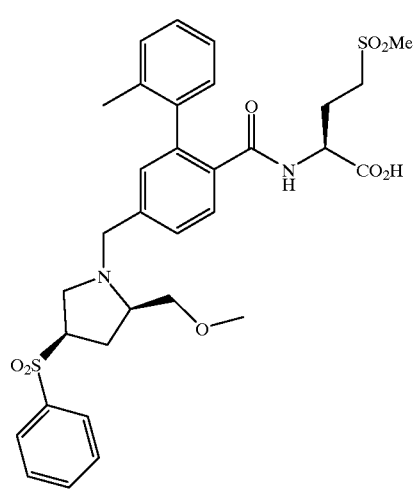
207
TABLE 6-continued
Amines of the Type A(B)N-L₁
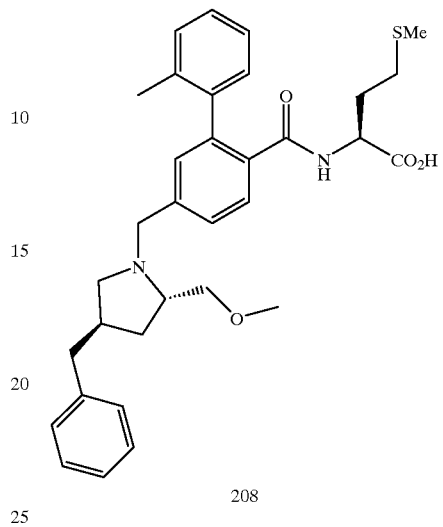
208
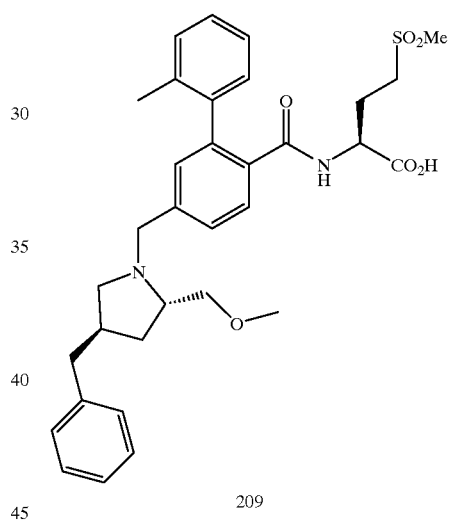
209
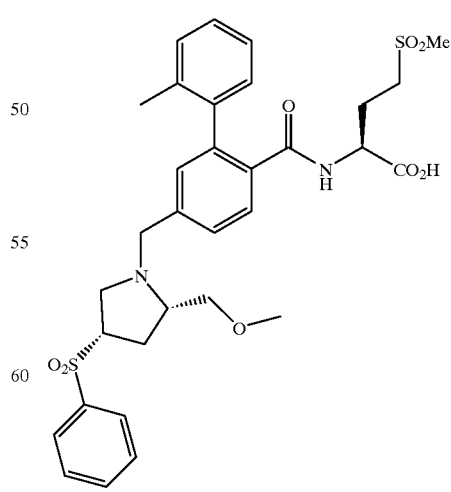
210

TABLE 6-continued
Amines of the Type A(B)N-L₁
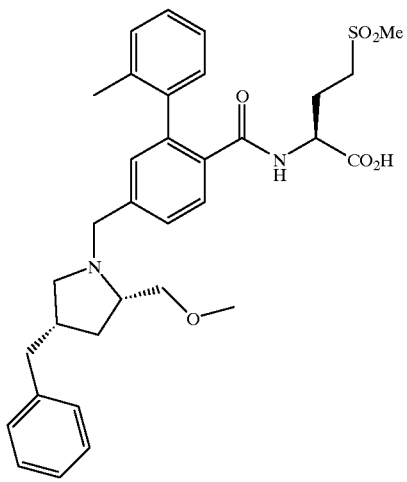
211
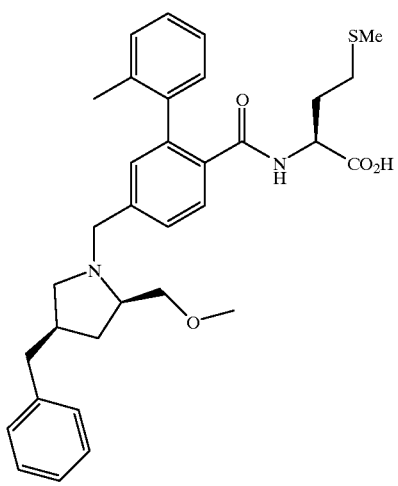
212
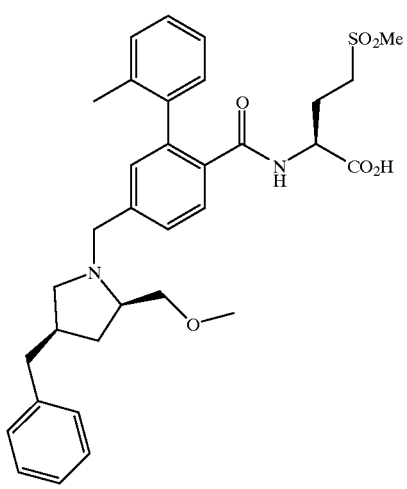
213
TABLE 6-continued
Amines of the Type A(B)N-L₁
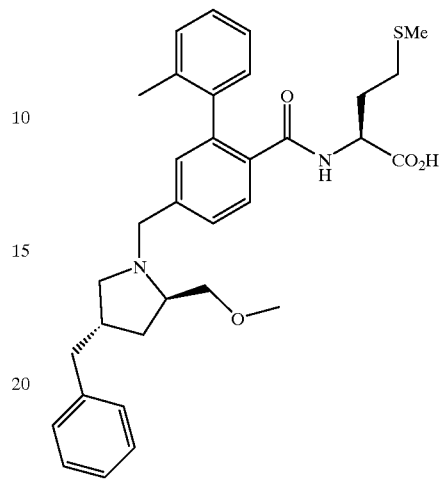
214
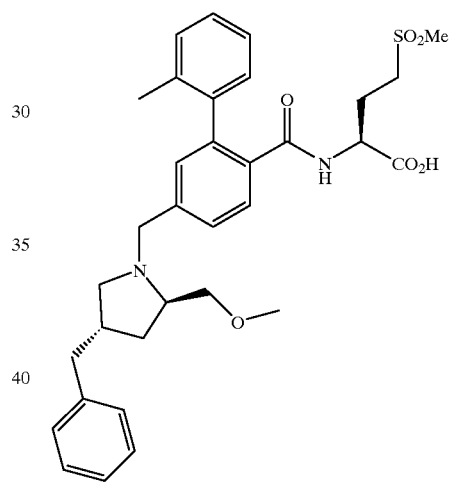
215
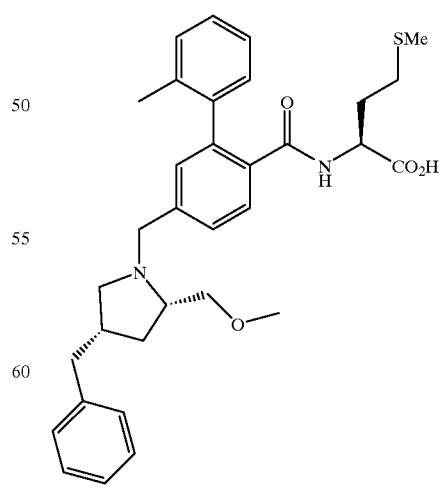
216

TABLE 6-continued
Amines of the Type A(B)N-L₁
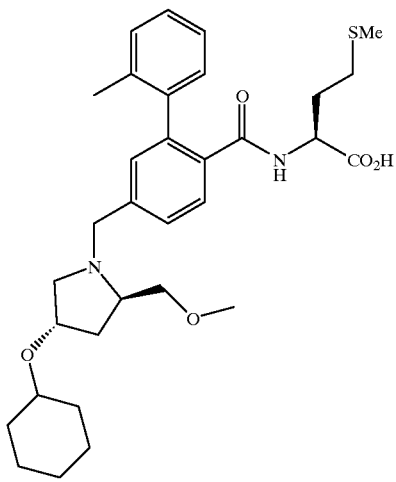
217
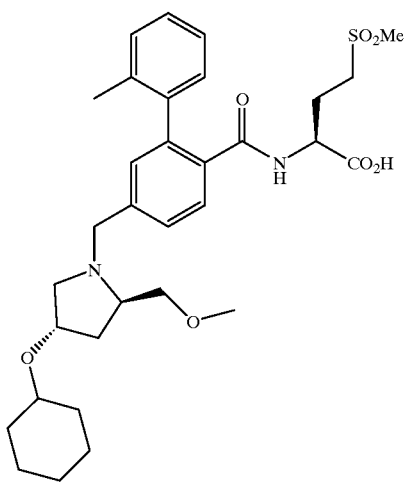
218
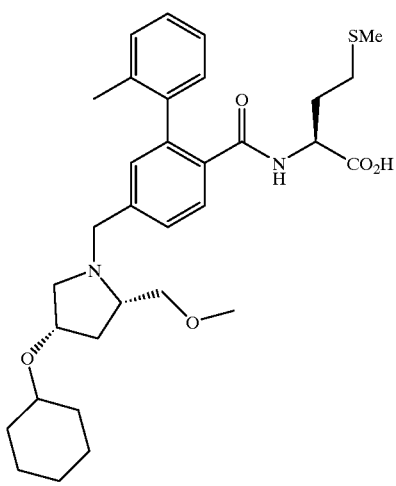
219
TABLE 6-continued
Amines of the Type A(B)N-L₁
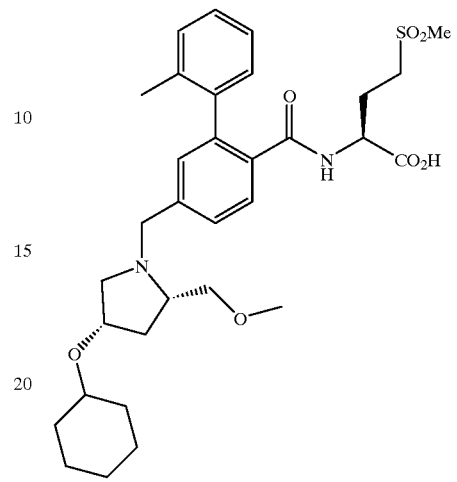
220
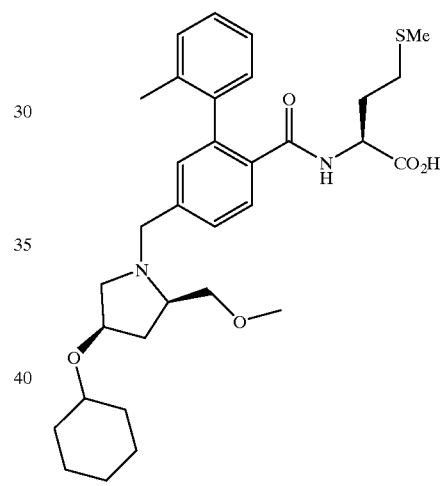
221
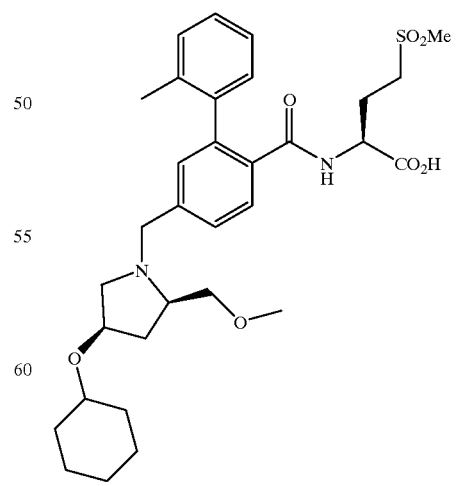
222

TABLE 6-continued
Amines of the Type A(B)N-L₁
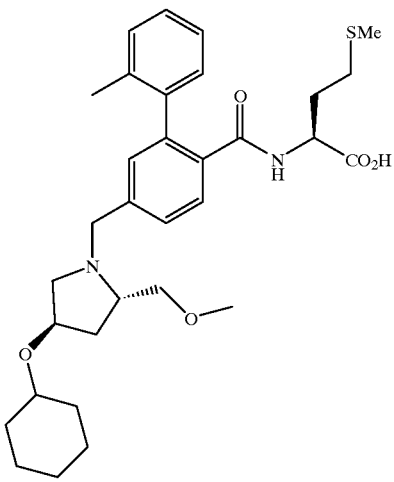
223
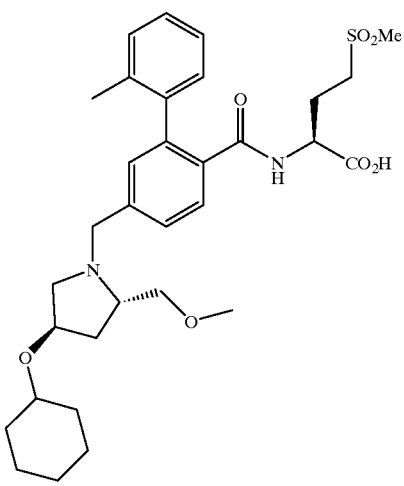
224
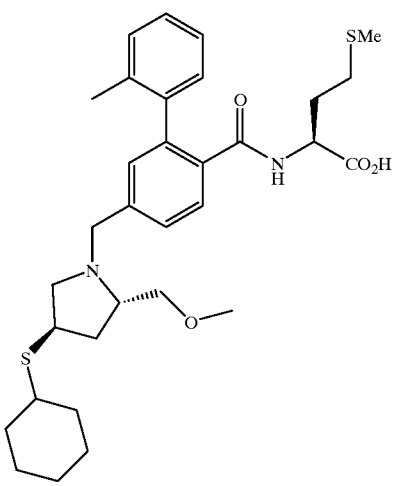
225
TABLE 6-continued
Amines of the Type A(B)N-L₁
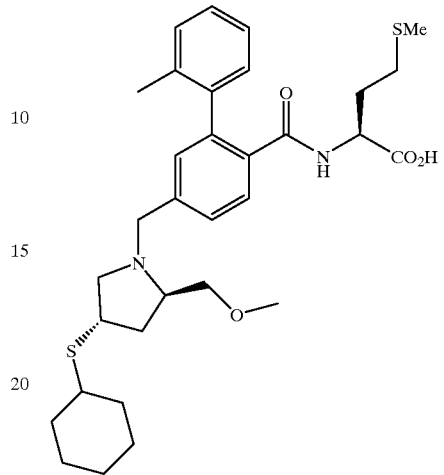
226
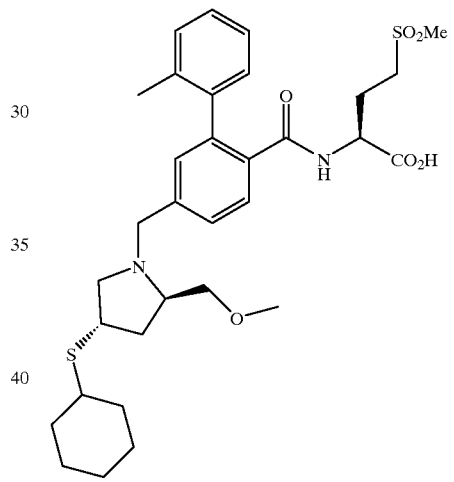
227
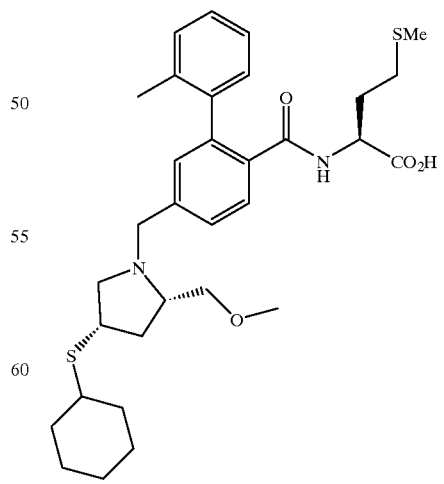
228

TABLE 6-continued
Amines of the Type A(B)N-L₁
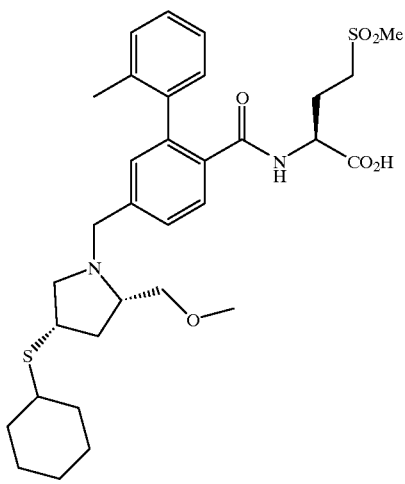
229
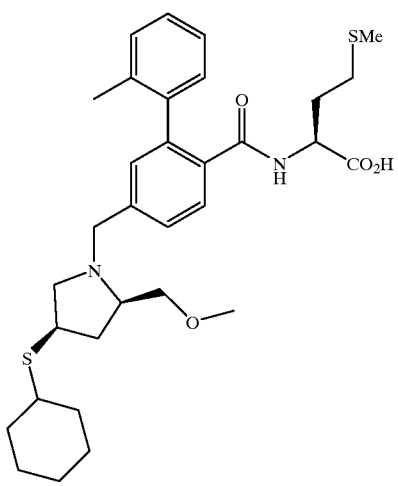
230
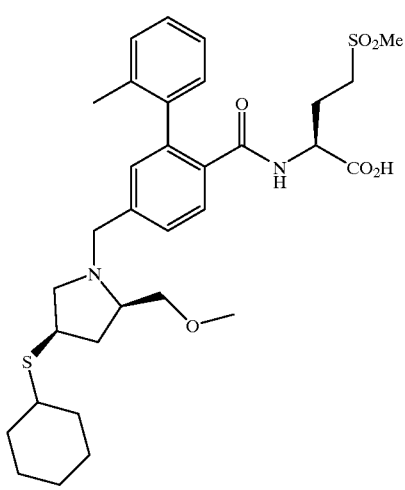
231
TABLE 6-continued
Amines of the Type A(B)N-L₁
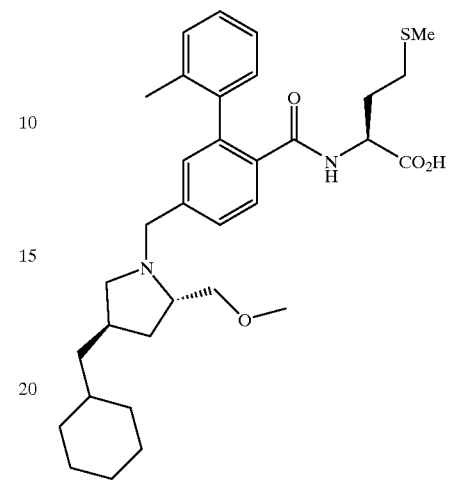
232
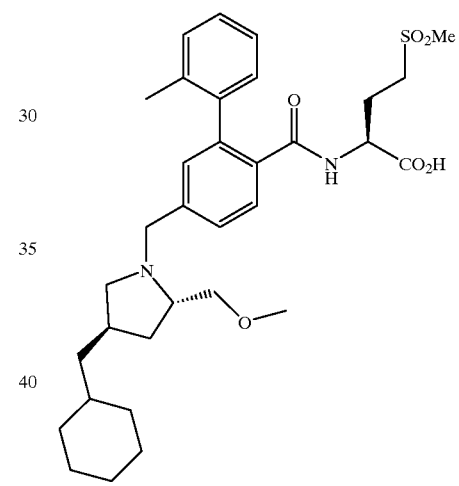
233

234

TABLE 6-continued
Amines of the Type A(B)N-L₁
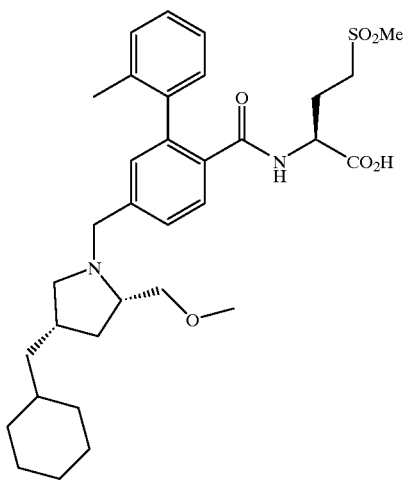
235
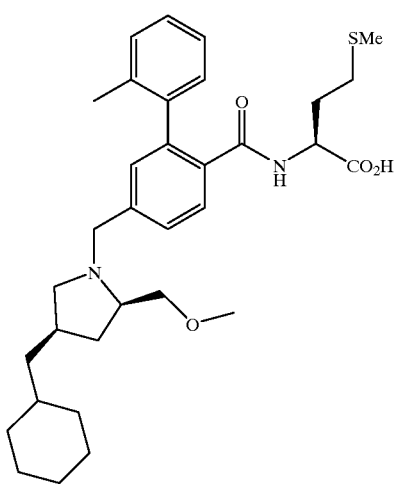
236
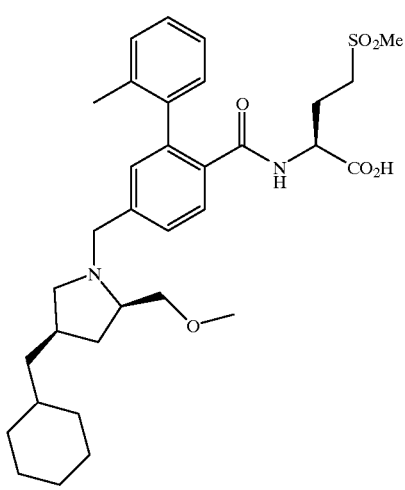
237
TABLE 6-continued
Amines of the Type A(B)N-L₁
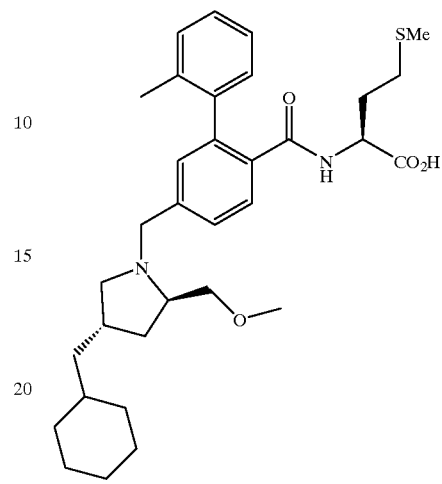
238
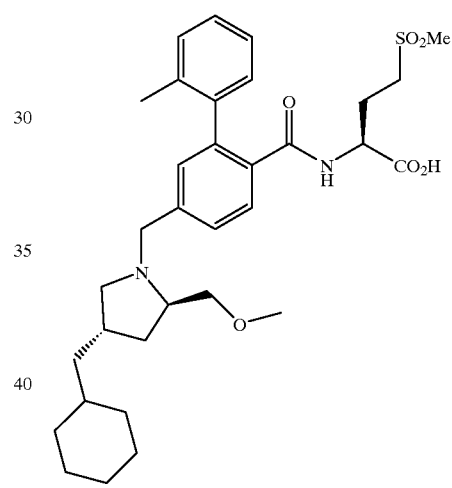
239
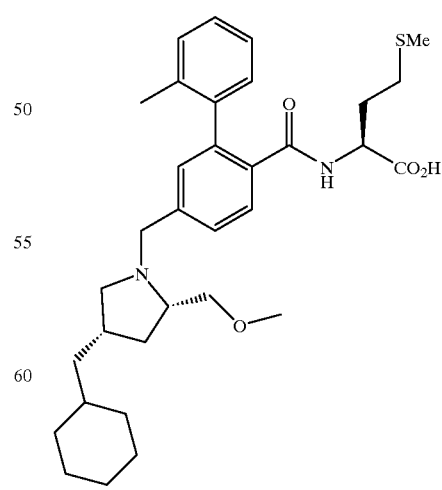
240

TABLE 6-continued
Amines of the Type A(B)N-L₁
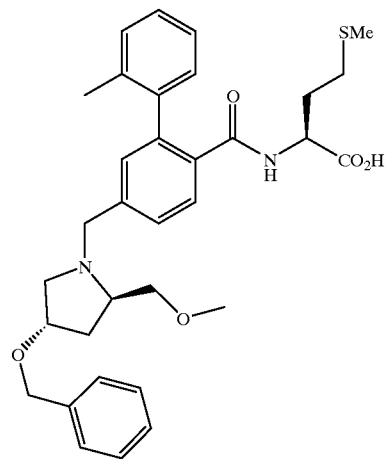
241
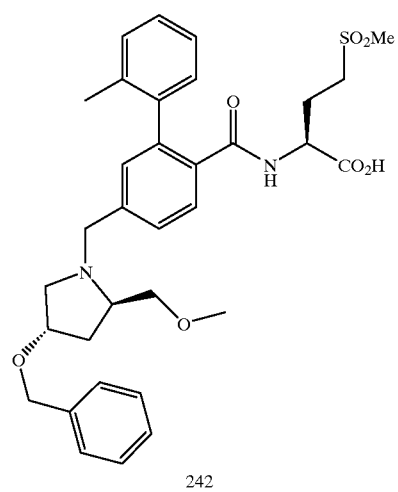
242
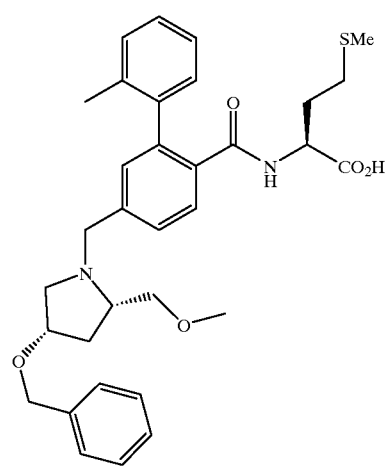
243
TABLE 6-continued
Amines of the Type A(B)N-L₁
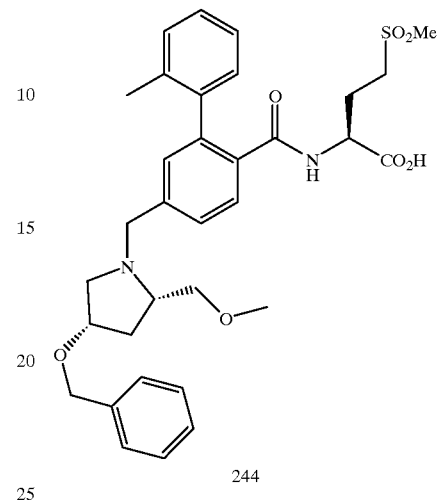
244
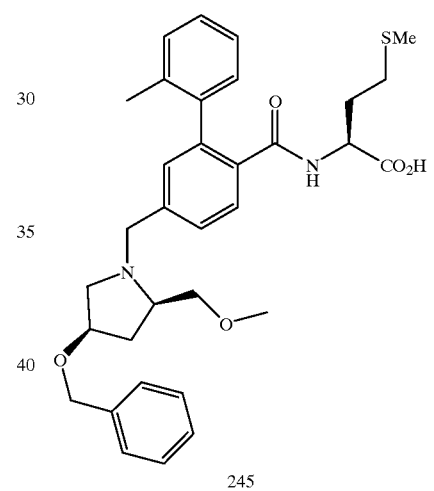
245
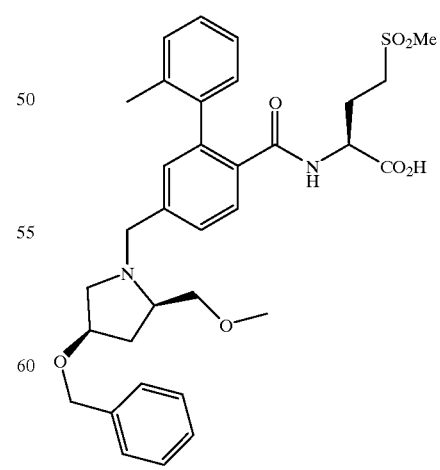
246

TABLE 6-continued
Amines of the Type A(B)N-L₁
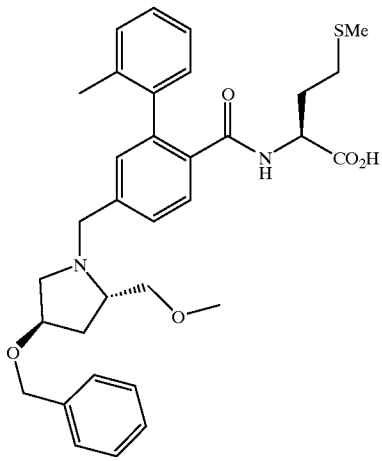
247
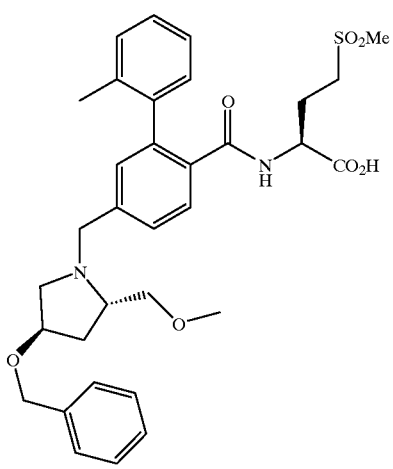
248
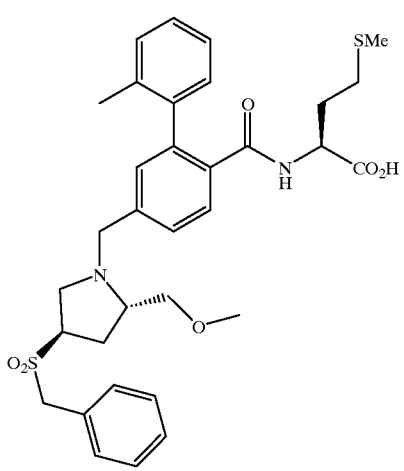
249
TABLE 6-continued
Amines of the Type A(B)N-L₁
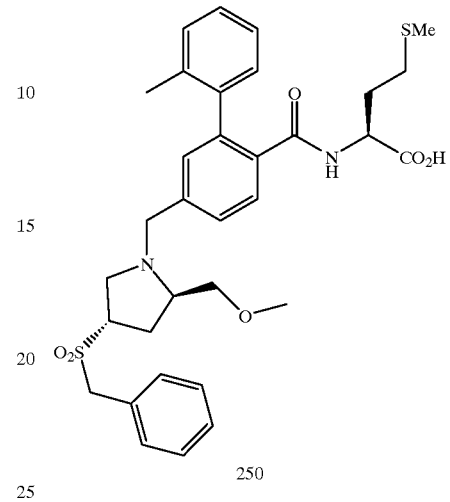
250
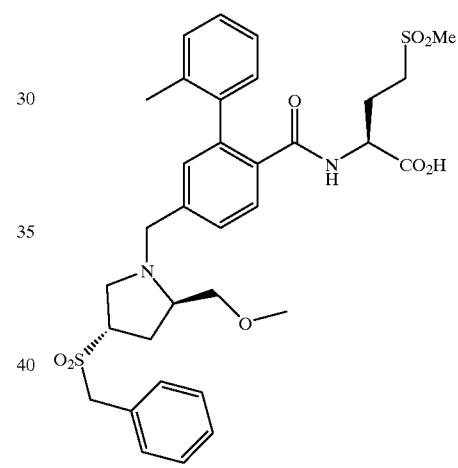
251
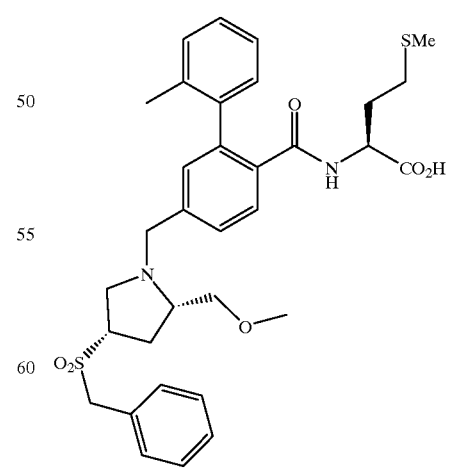
252

TABLE 6-continued
Amines of the Type A(B)N-L₁
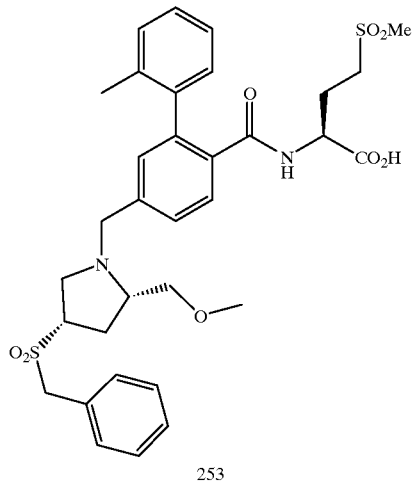
253
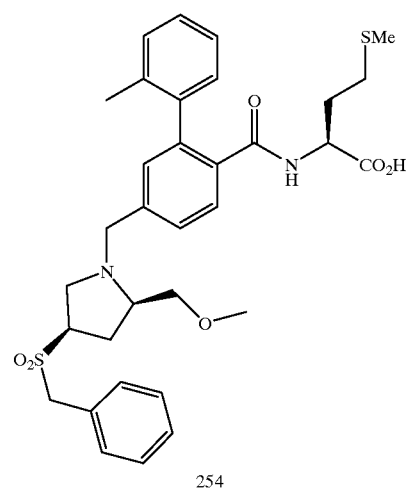
254
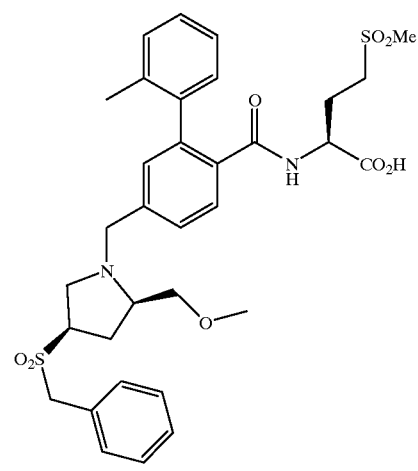
255
TABLE 6-continued
Amines of the Type A(B)N-L₁
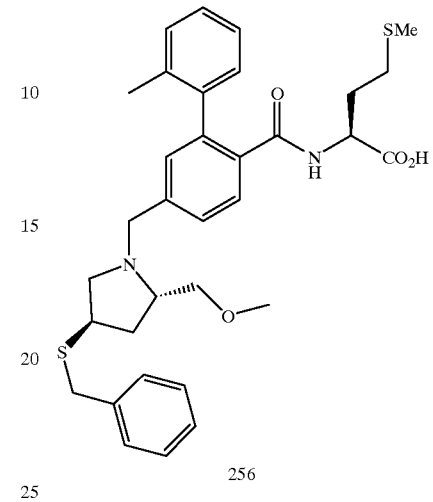
256
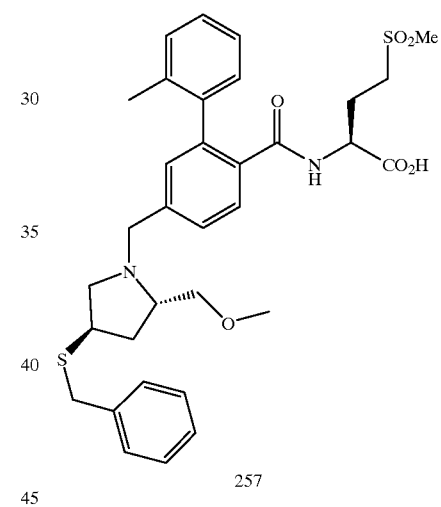
257
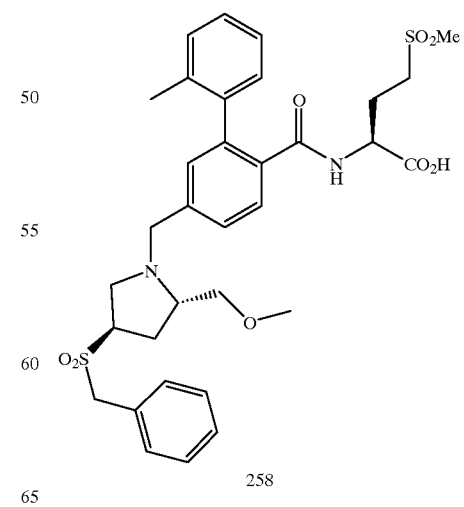
258

TABLE 6-continued
Amines of the Type A(B)N-L₁
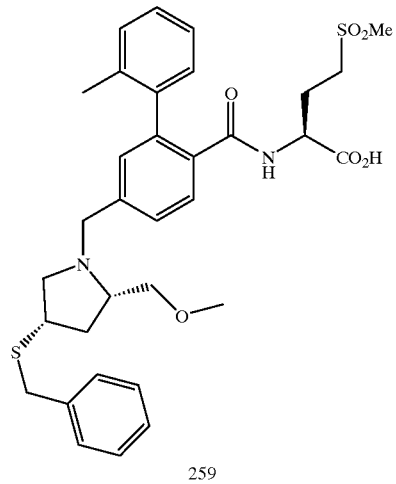
259
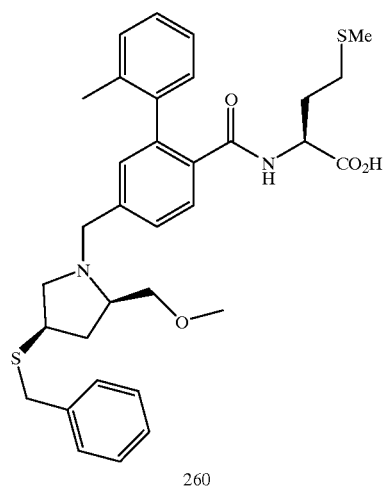
260
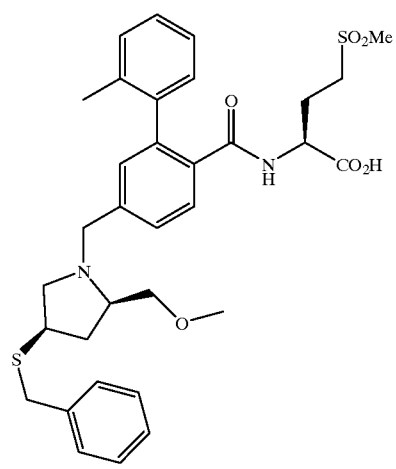
261
TABLE 6-continued
Amines of the Type A(B)N-L₁
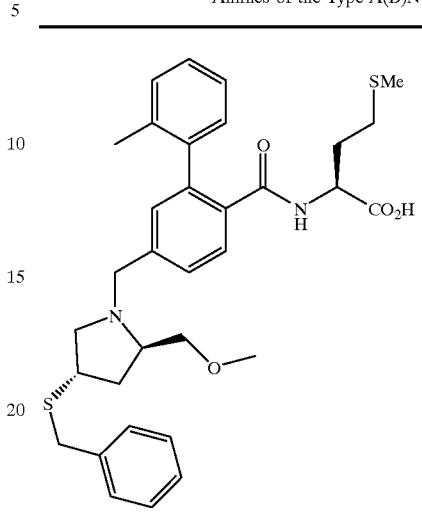
262
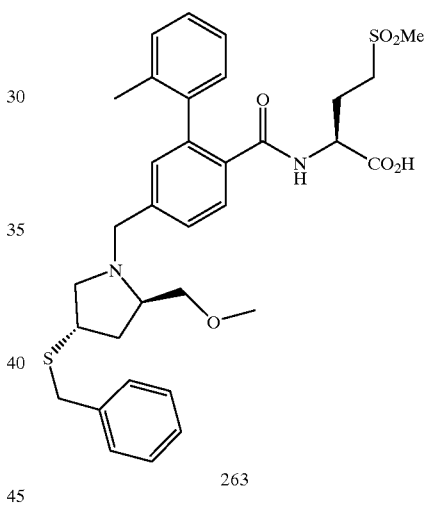
263
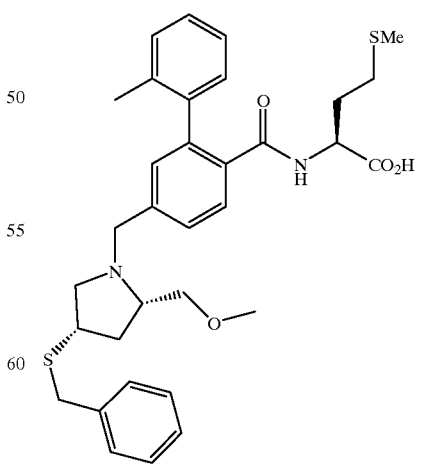
264

TABLE 6-continued
Amines of the Type A(B)N-L₁
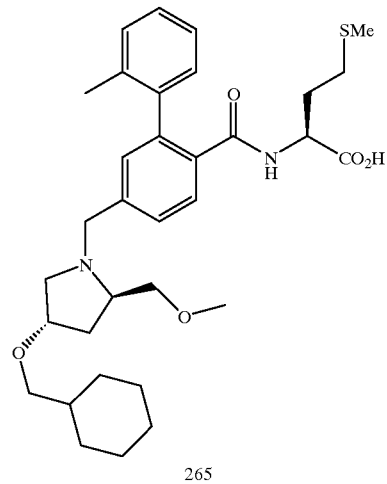
265
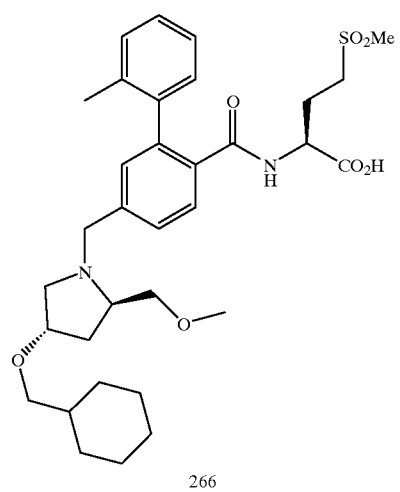
266
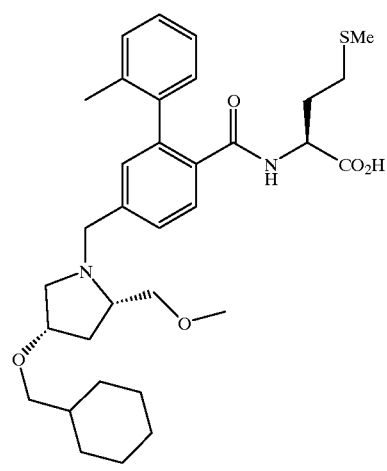
267
TABLE 6-continued
Amines of the Type A(B)N-L₁
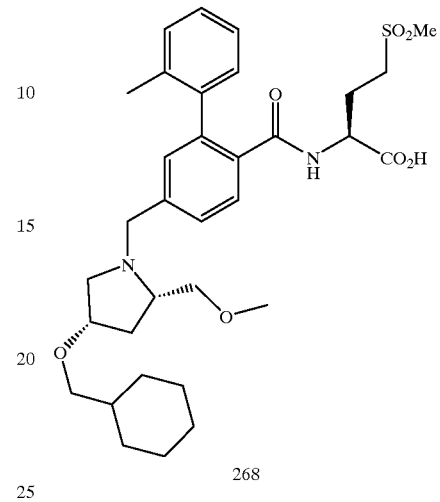
268
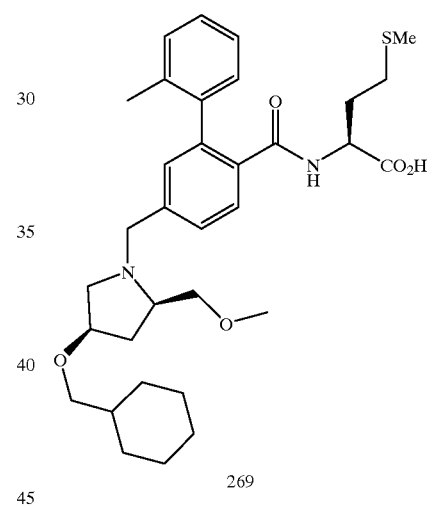
269
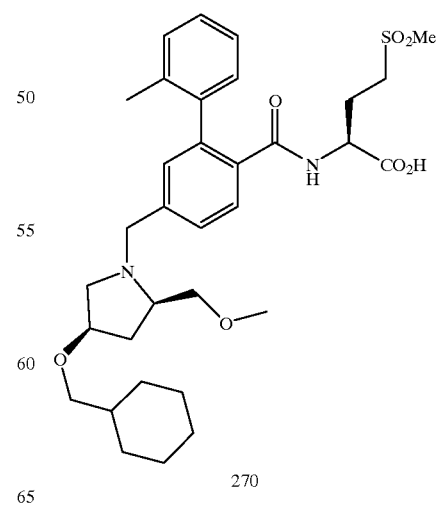
270

TABLE 6-continued
Amines of the Type A(B)N-L₁
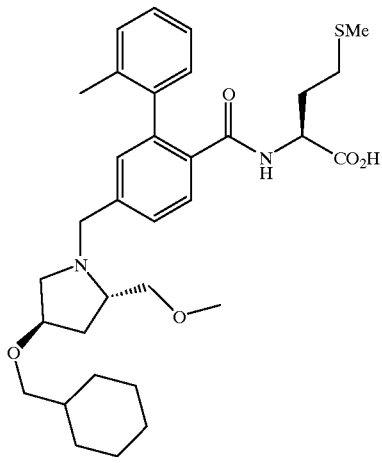
271
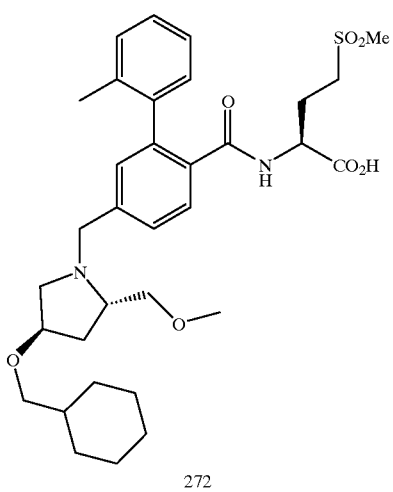
272
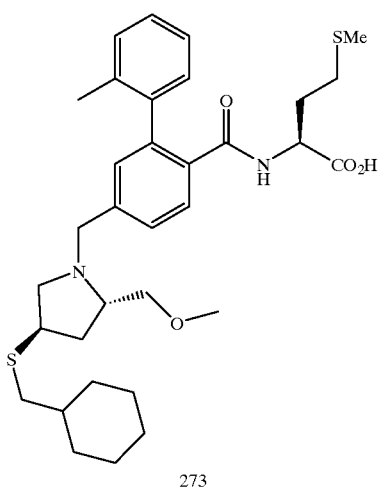
273
TABLE 6-continued
Amines of the Type A(B)N-L₁
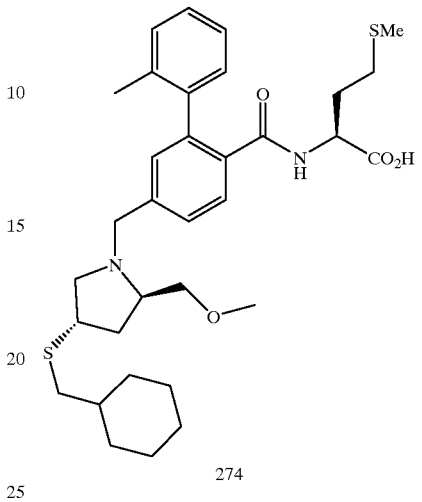
274
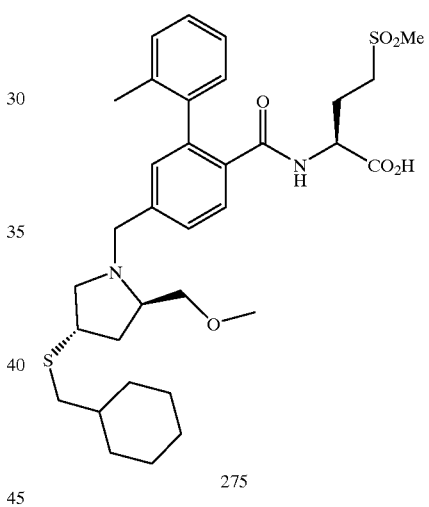
275
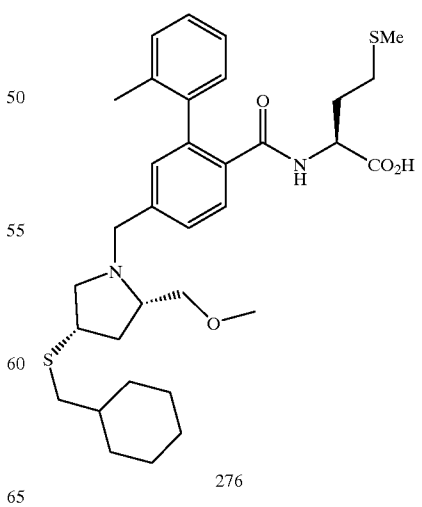
276

TABLE 6-continued
Amines of the Type A(B)N-L₁
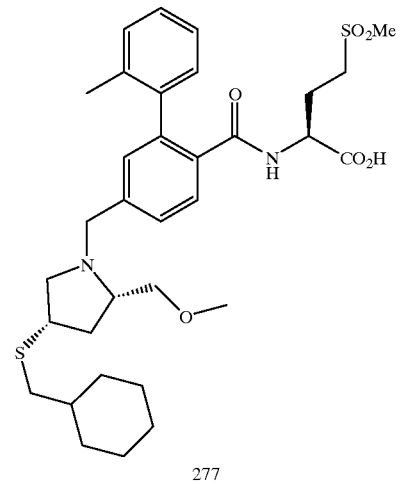
277
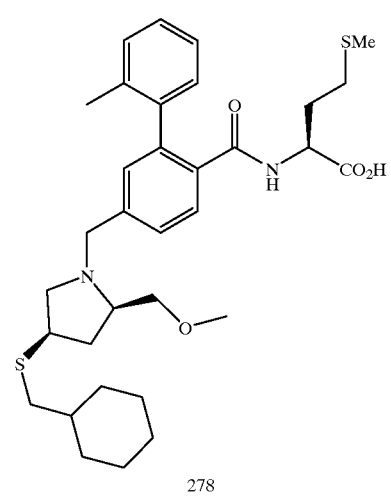
278
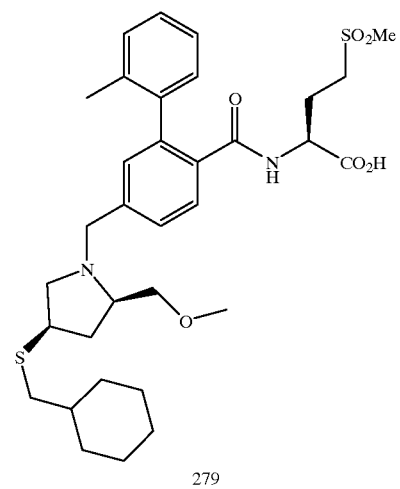
279
TABLE 6-continued
Amines of the Type A(B)N-L₁
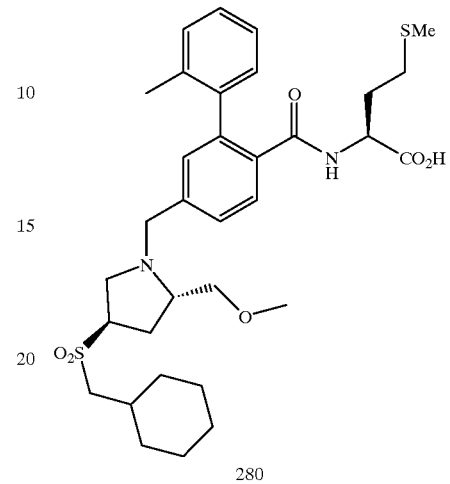
280
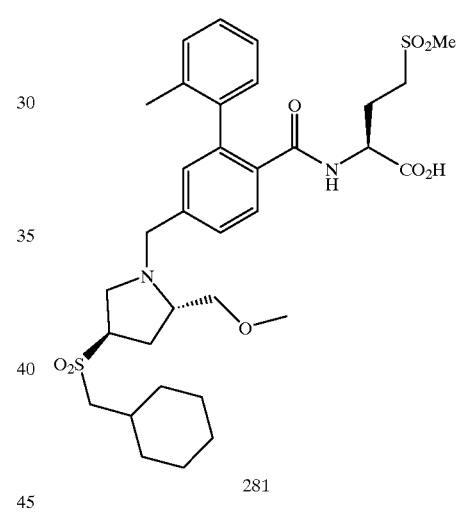
281
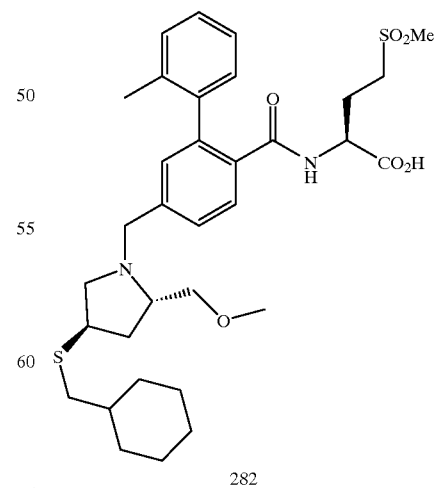
282

TABLE 6-continued
Amines of the Type A(B)N-L₁
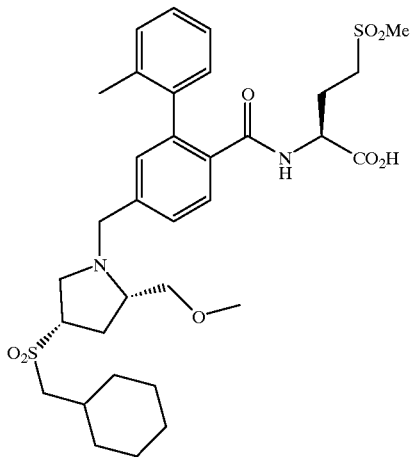
283
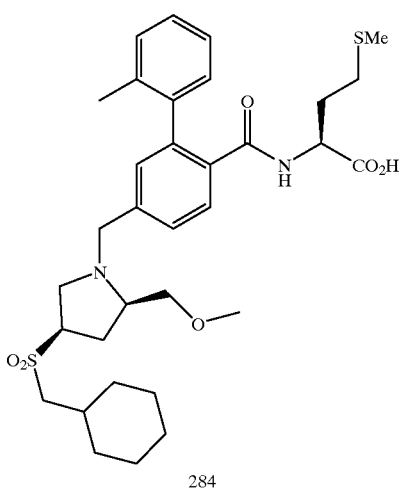
284
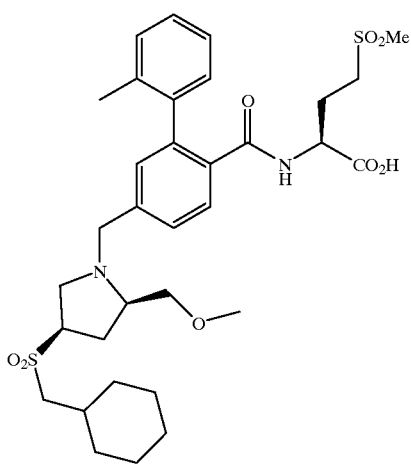
285
TABLE 6-continued
Amines of the Type A(B)N-L₁
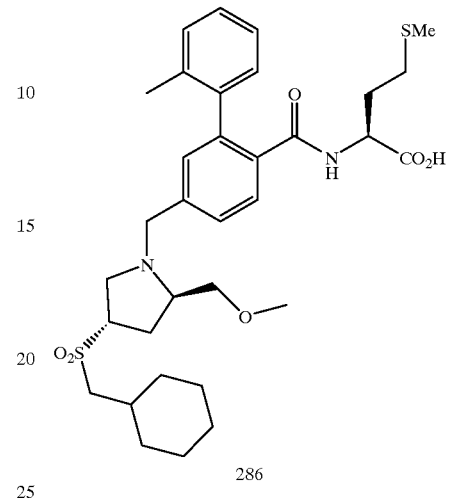
286
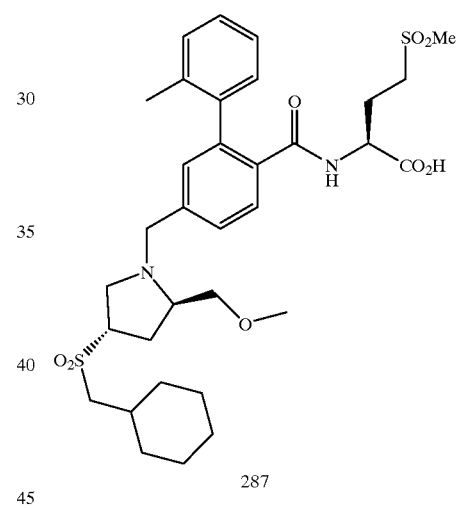
287
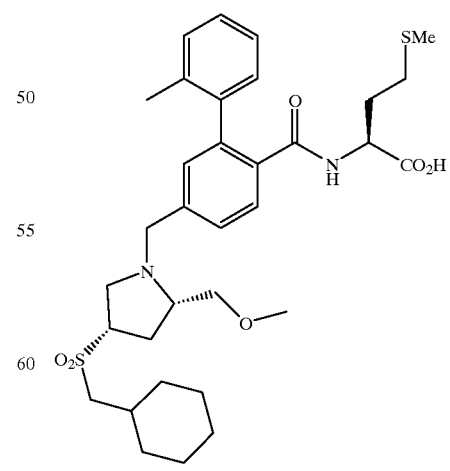
288

TABLE 6-continued
Amines of the Type A(B)N-L₁
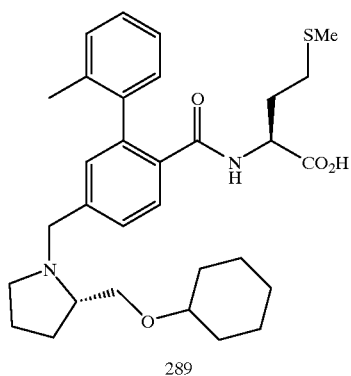
289
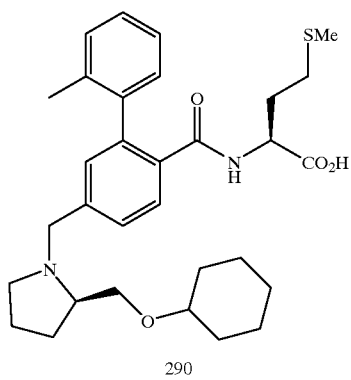
290
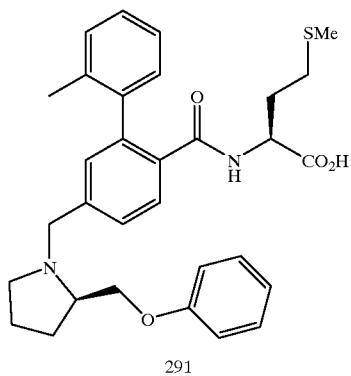
291
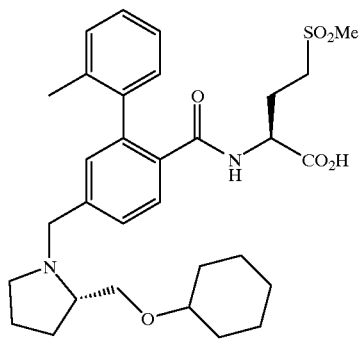
292
TABLE 6-continued
Amines of the Type A(B)N-L₁

293

294
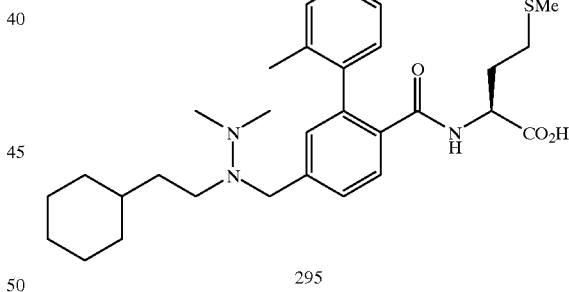
295
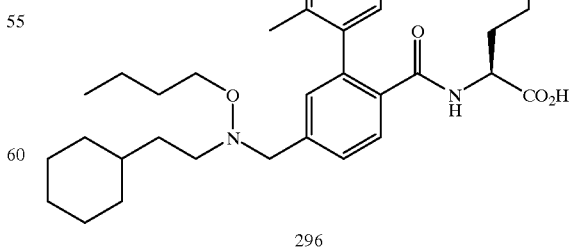
296

TABLE 6-continued
Amines of the Type A(B)N-L₁
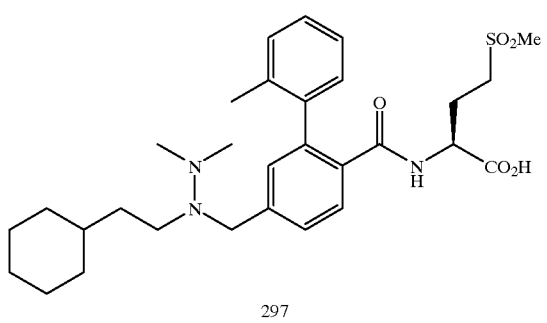
297
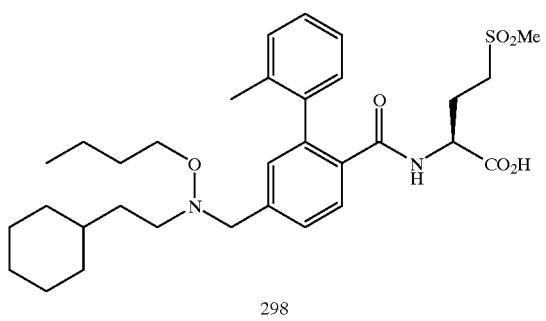
298
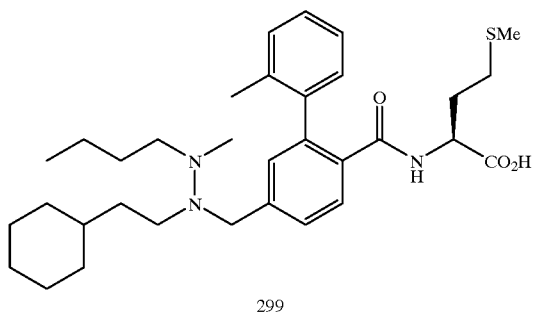
299
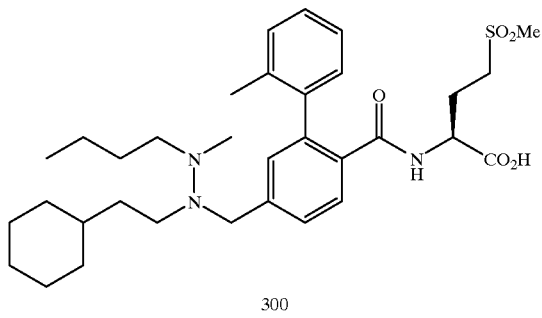
300
TABLE 6-continued
Amines of the Type A(B)N-L₁
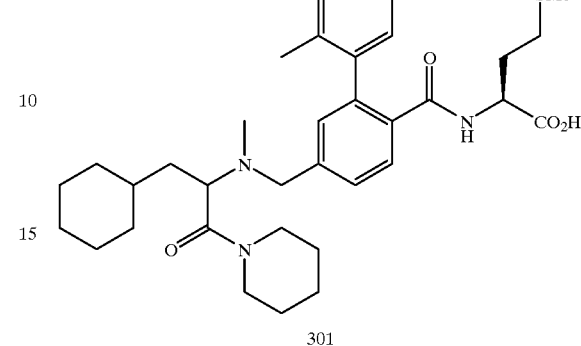
301
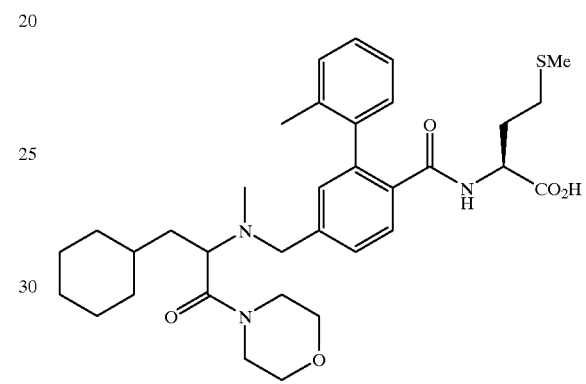
302
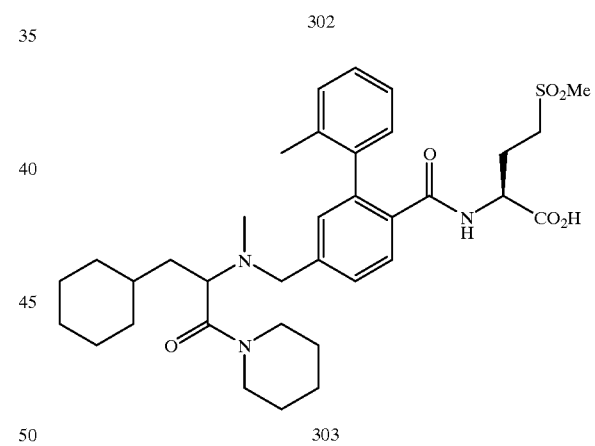
303
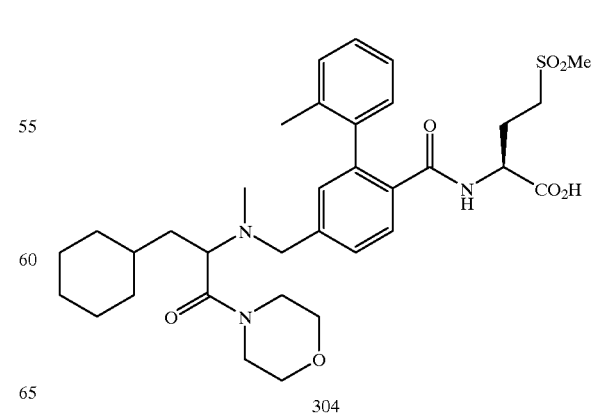
304

TABLE 6-continued
Amines of the Type A(B)N-L₁
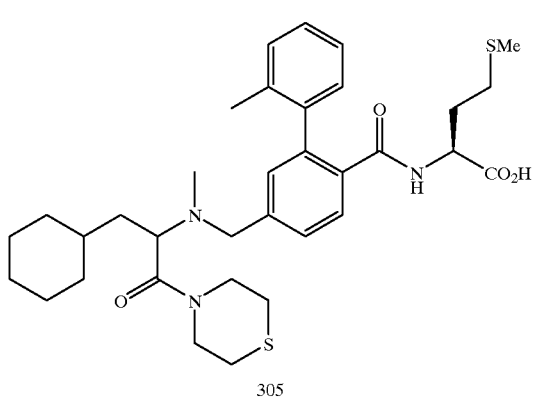
305
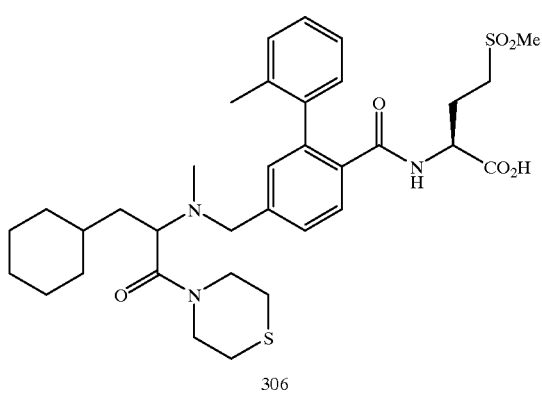
306
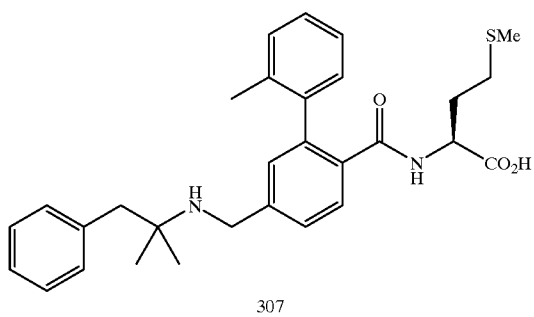
307
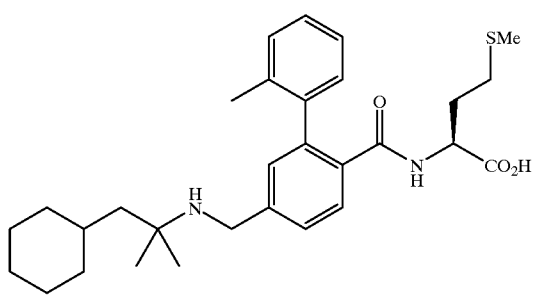
308
TABLE 6-continued
Amines of the Type A(B)N-L₁
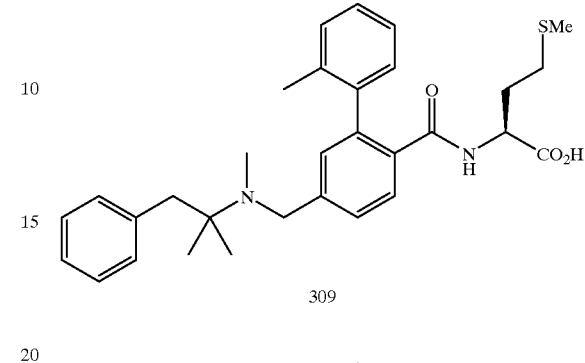
309
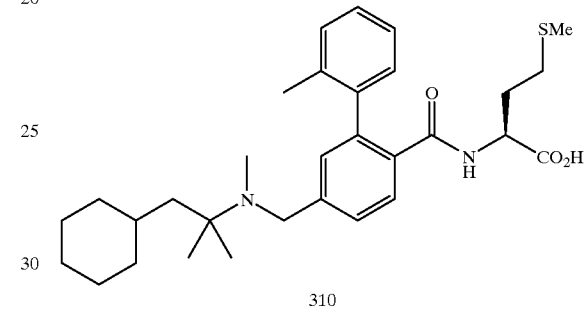
310
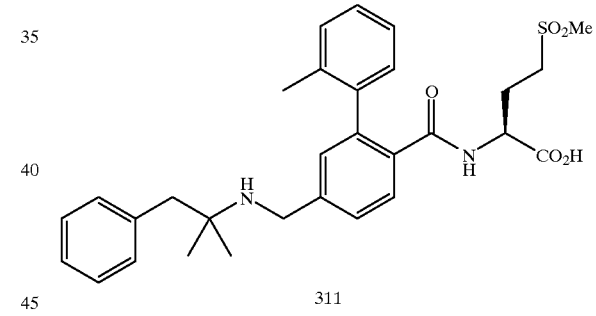
311
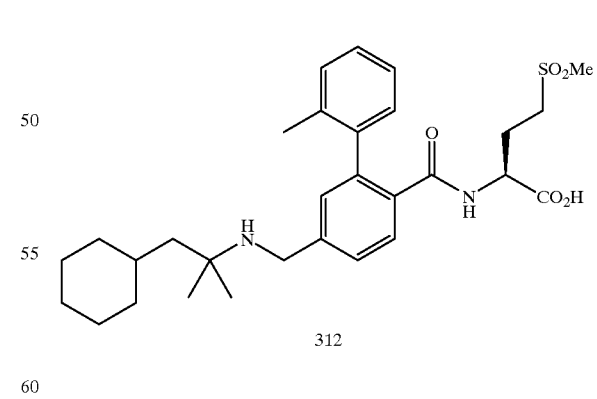
312

TABLE 6-continued
Amines of the Type A(B)N-L₁
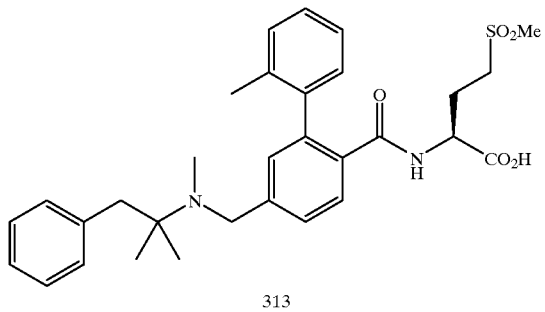
313
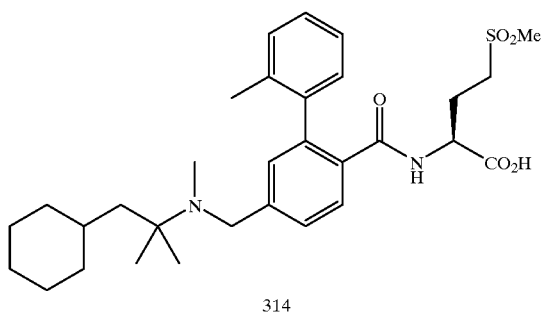
314
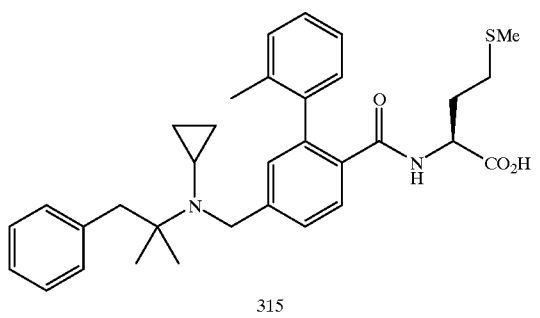
315
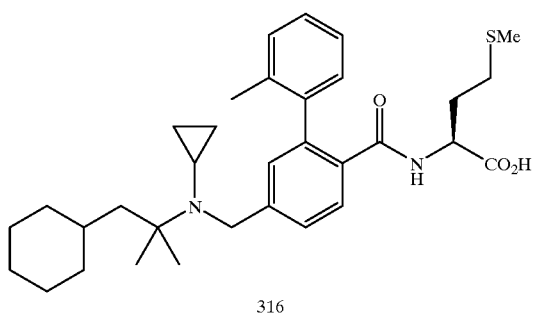
316
TABLE 6-continued
Amines of the Type A(B)N-L₁
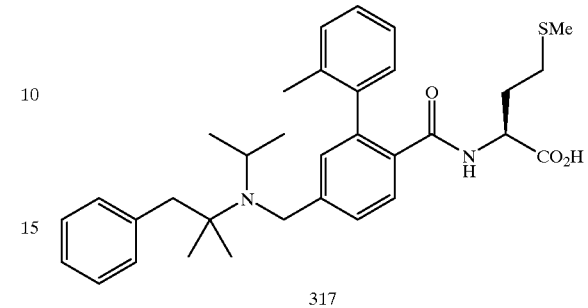
317
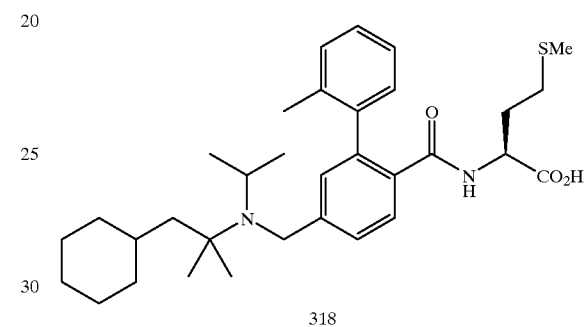
318
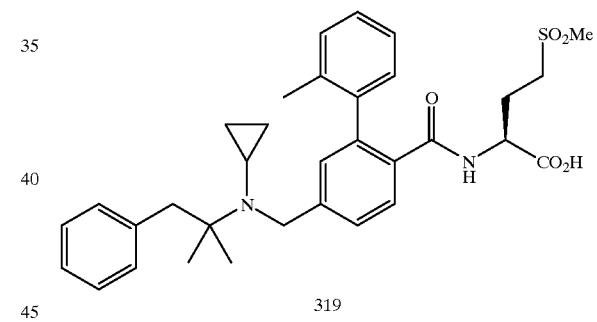
319
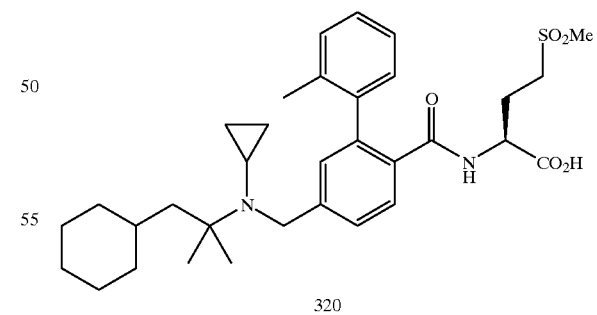
320

TABLE 6-continued

Amines of the Type A(B)N-L₁

321

322

323

324

325

326

327

328

TABLE 6-continued
Amines of the Type A(B)N-L₁
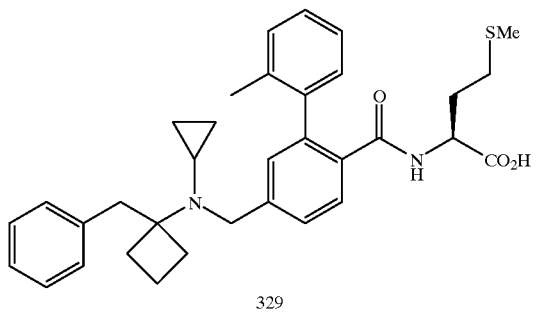
329
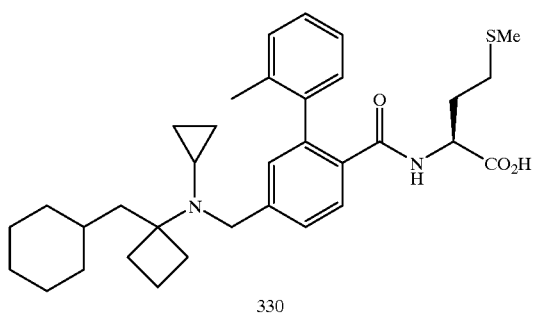
330
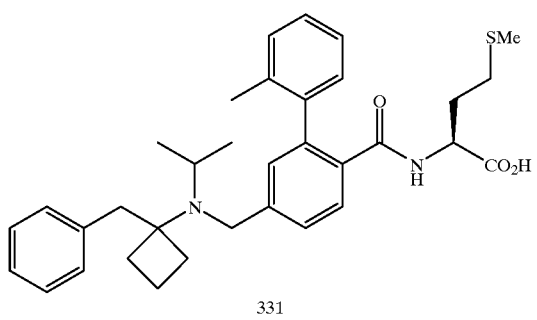
331
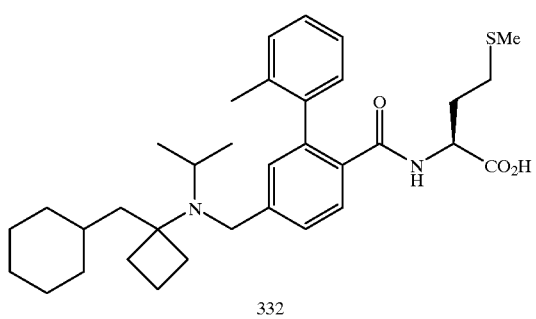
332
TABLE 6-continued
Amines of the Type A(B)N-L₁
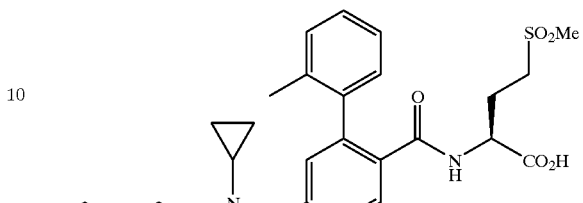
333
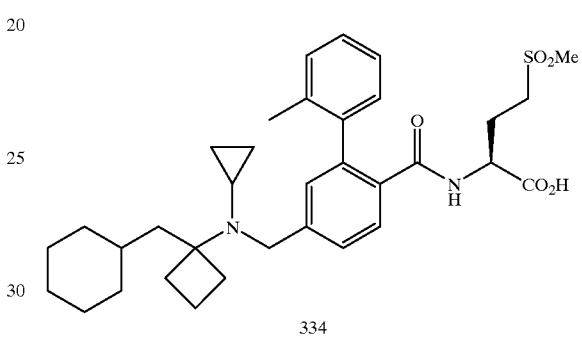
334
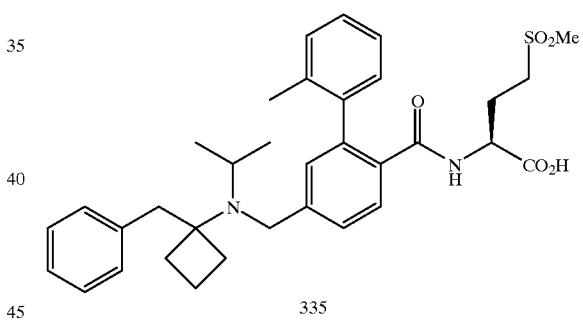
335
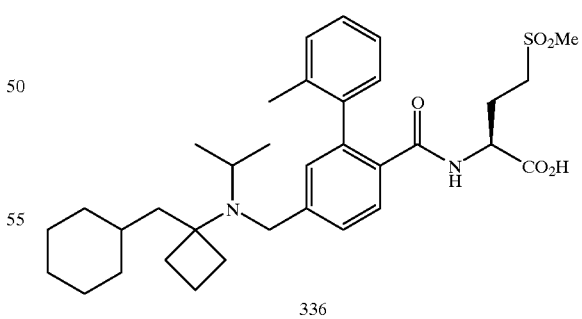
336

TABLE 6-continued
Amines of the Type A(B)N-L$_1$
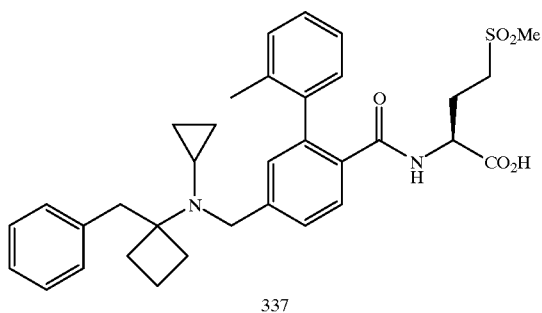
337
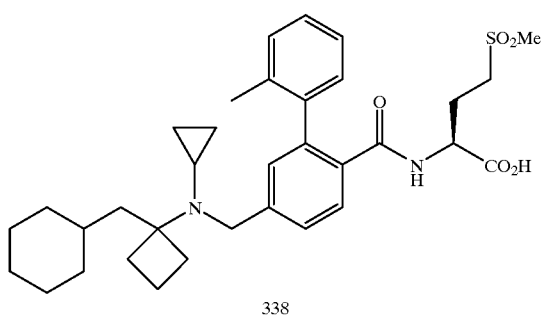
338
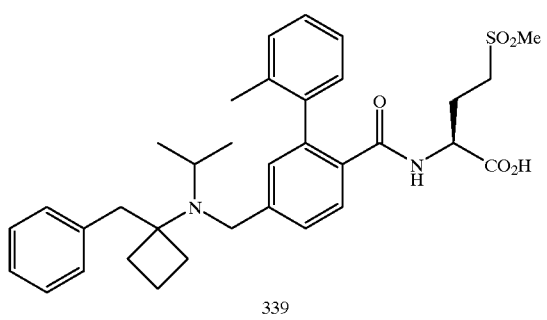
339
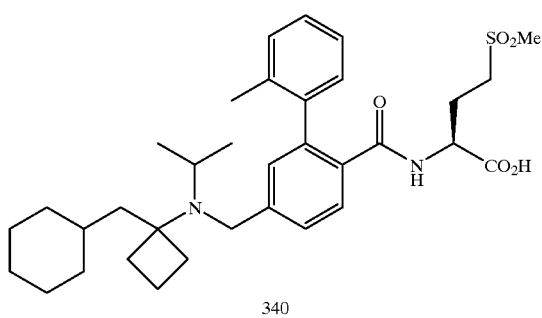
340
TABLE 6-continued
Amines of the Type A(B)N-L$_1$
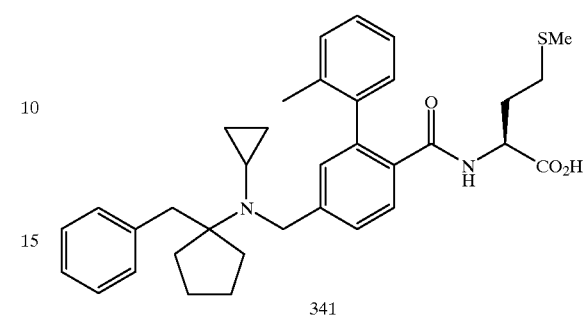
341
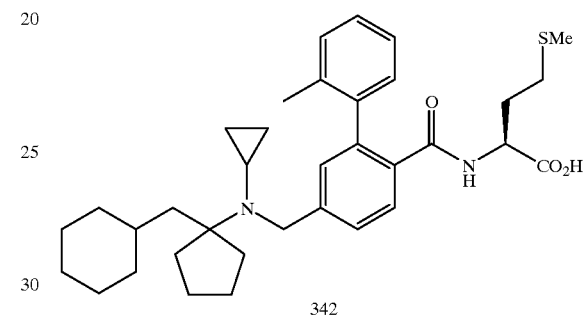
342

343
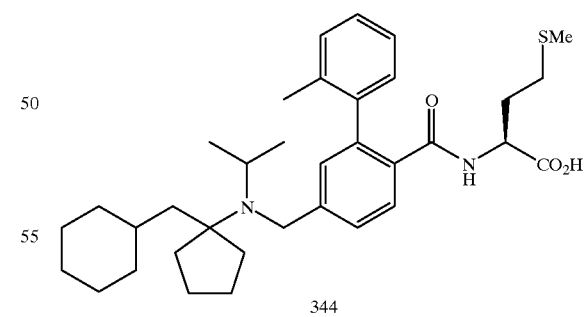
344

TABLE 6-continued
Amines of the Type A(B)N-L₁
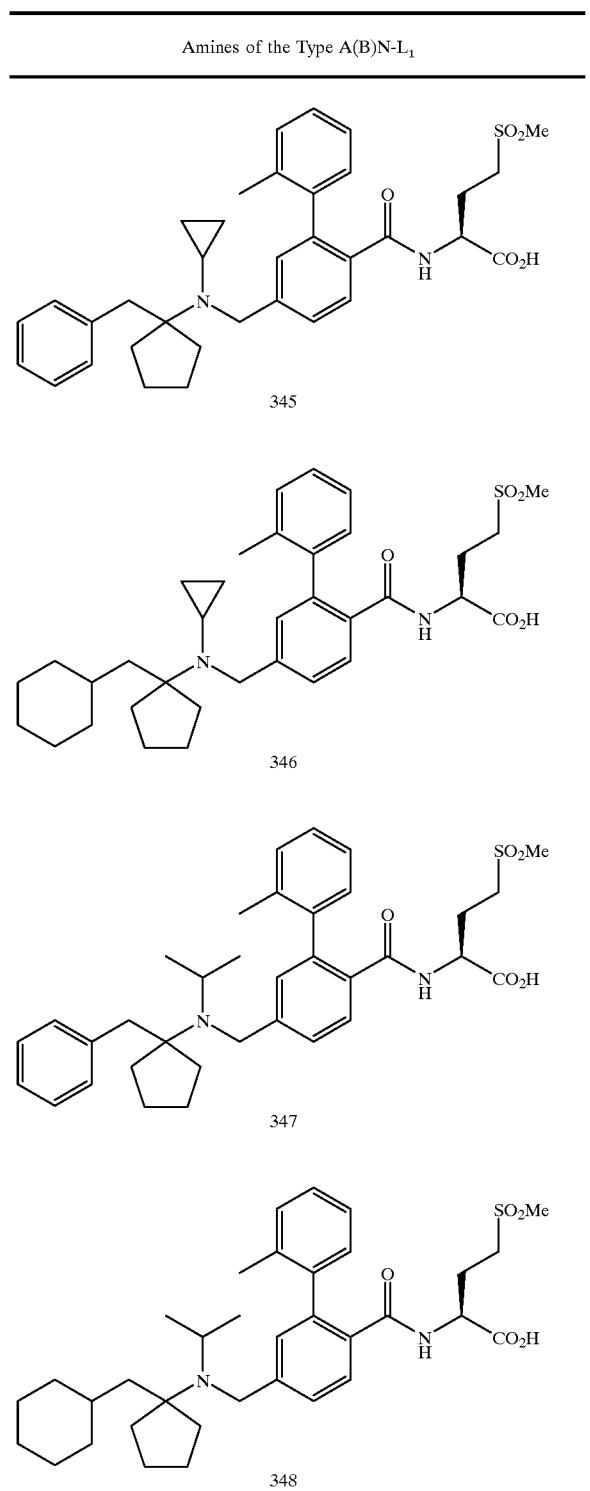
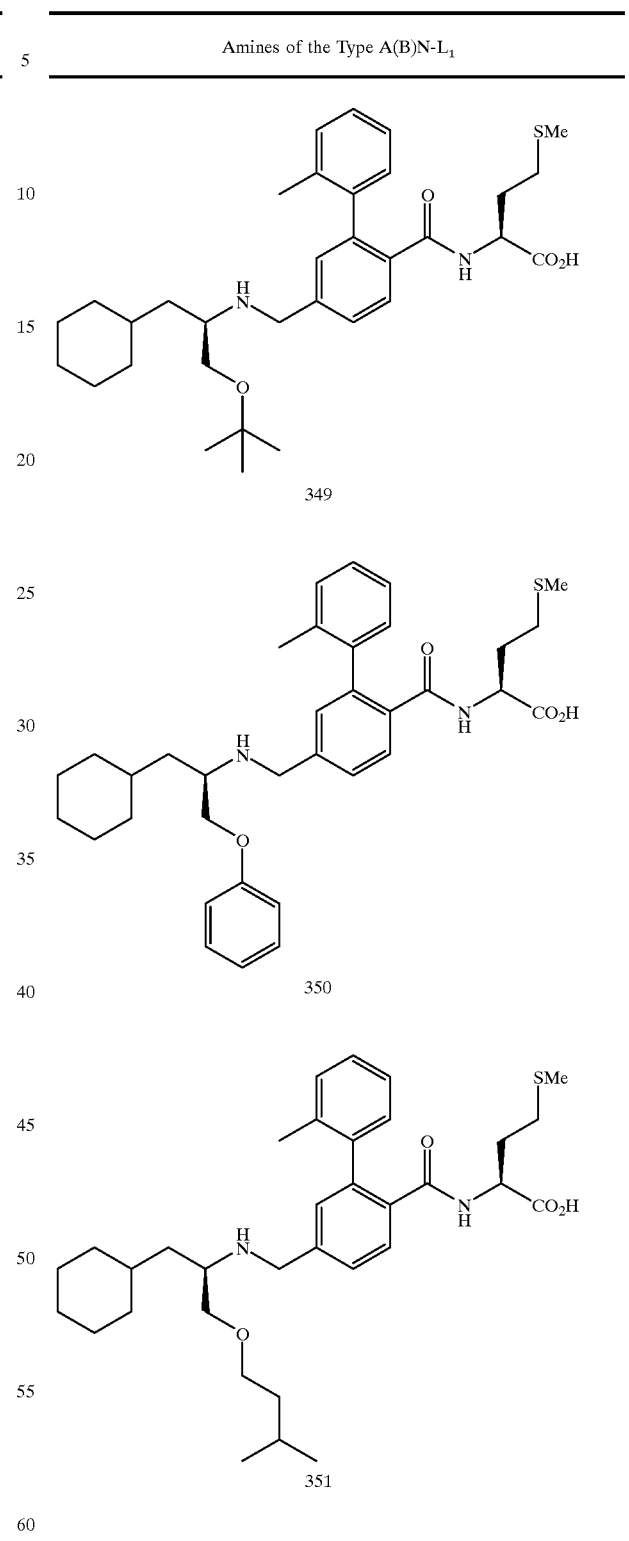

TABLE 6-continued
Amines of the Type A(B)N-L₁
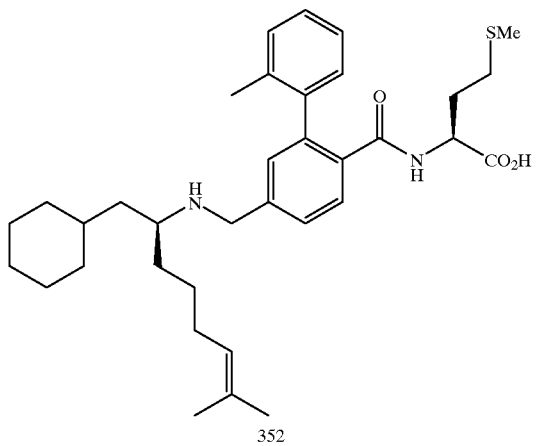
352
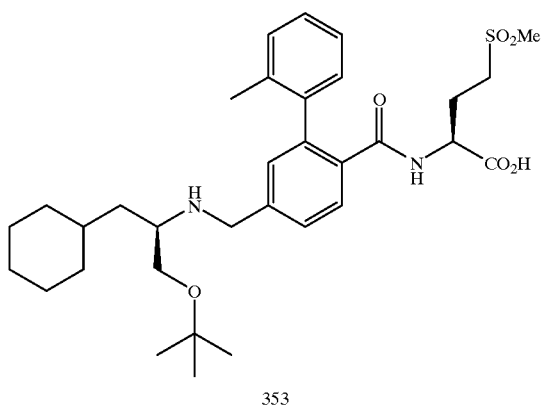
353
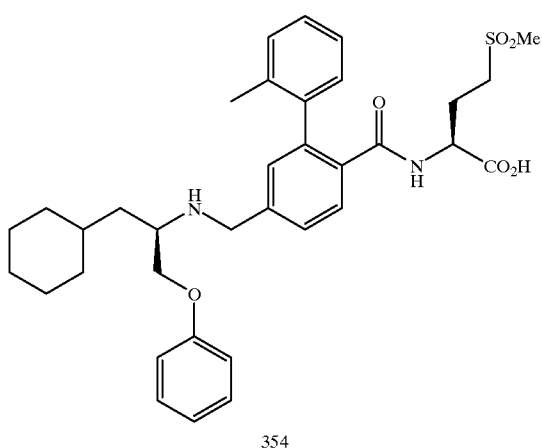
354
TABLE 6-continued
Amines of the Type A(B)N-L₁
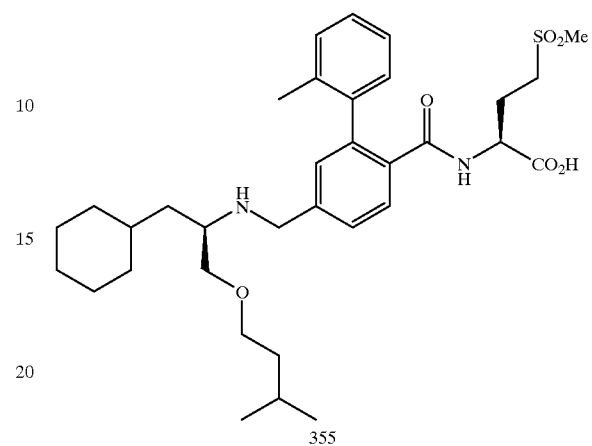
355
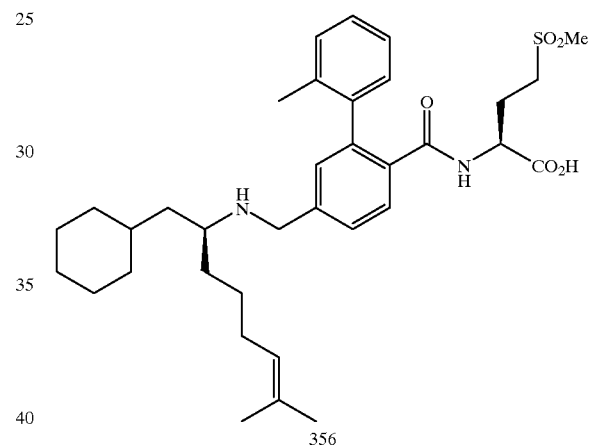
356
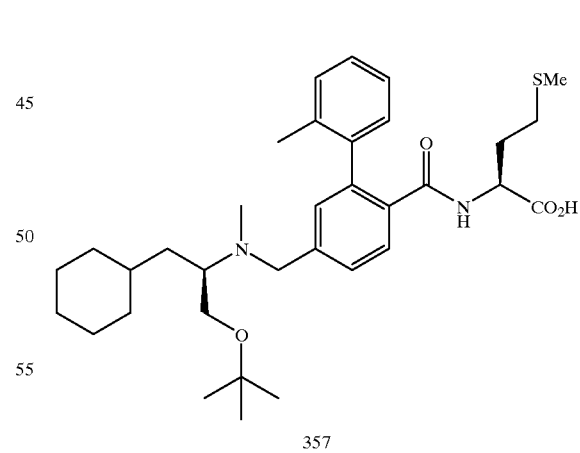
357

TABLE 6-continued
Amines of the Type A(B)N-L₁
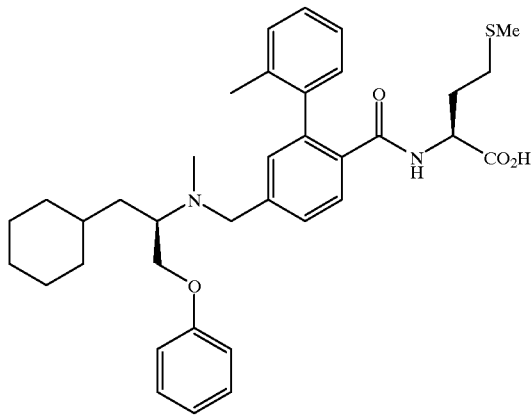
358
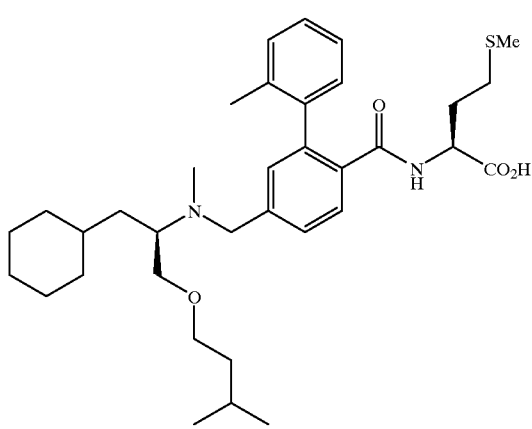
359
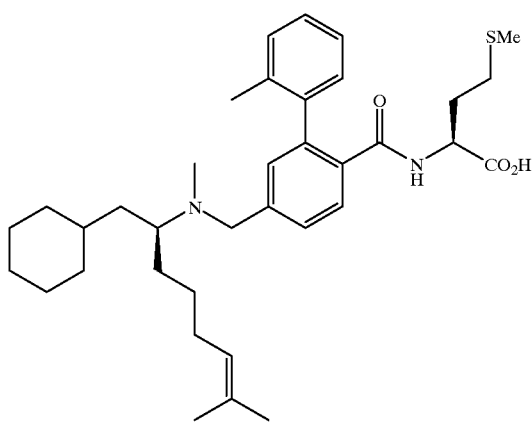
360
TABLE 6-continued
Amines of the Type A(B)N-L₁
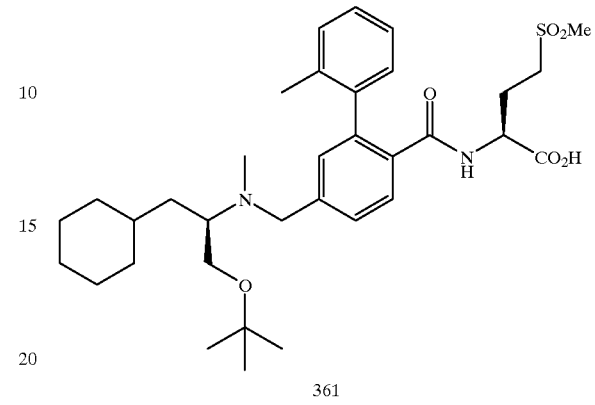
361
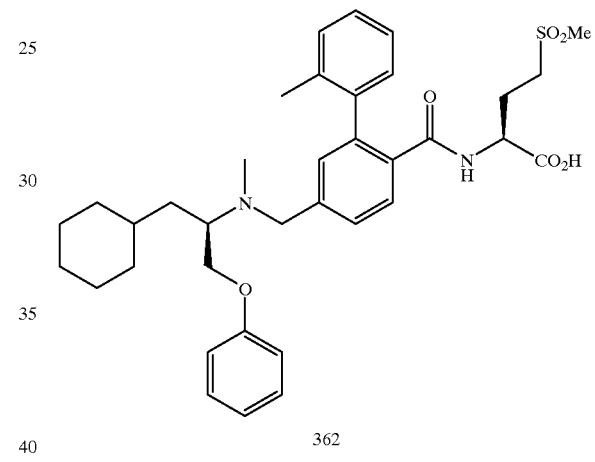
362
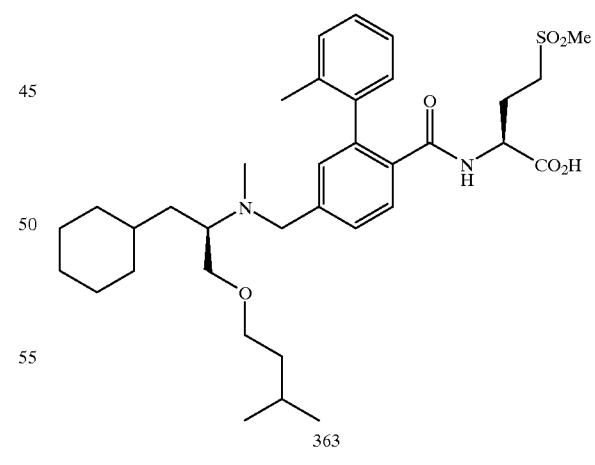
363

TABLE 6-continued
Amines of the Type A(B)N-L₁
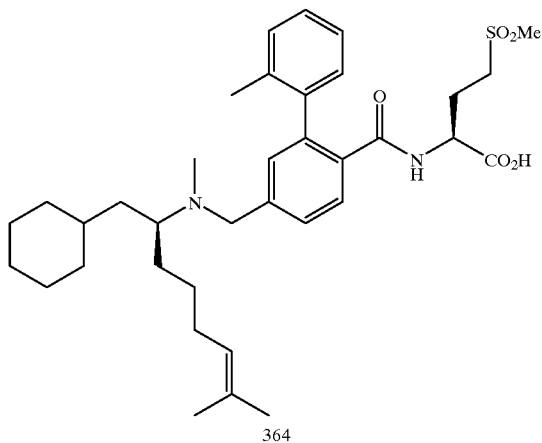
364
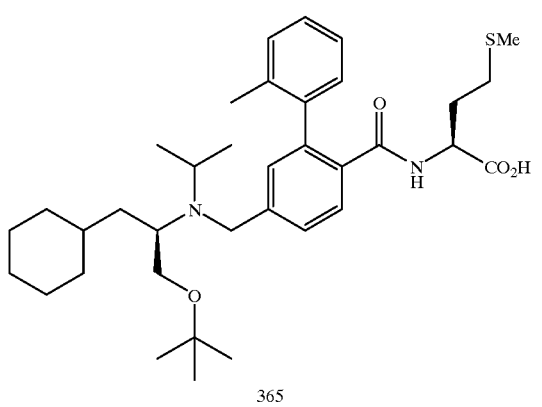
365
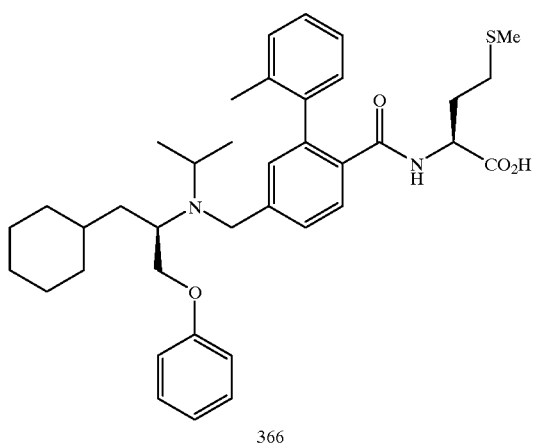
366
TABLE 6-continued
Amines of the Type A(B)N-L₁
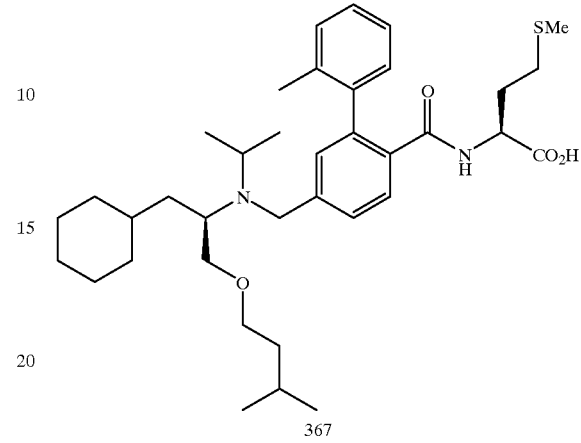
367
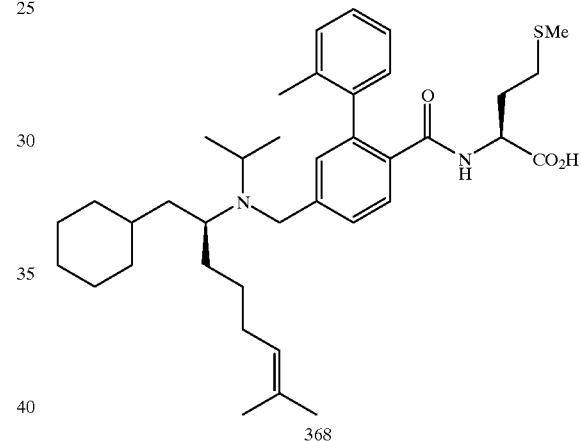
368
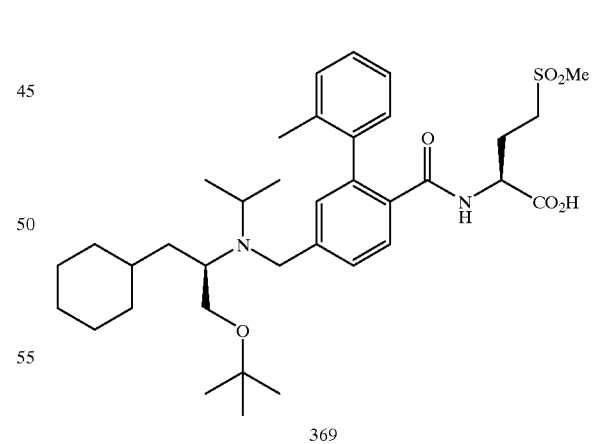
369

TABLE 6-continued
Amines of the Type A(B)N-L₁
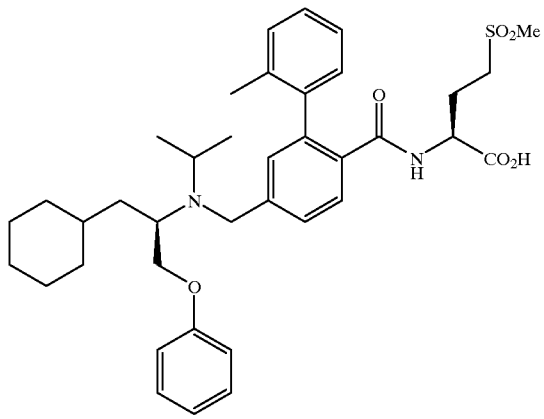
370
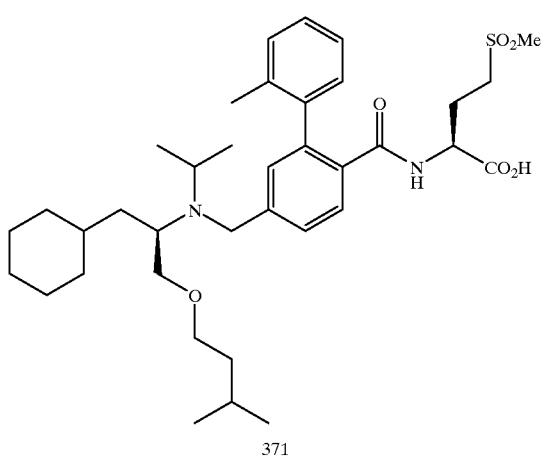
371
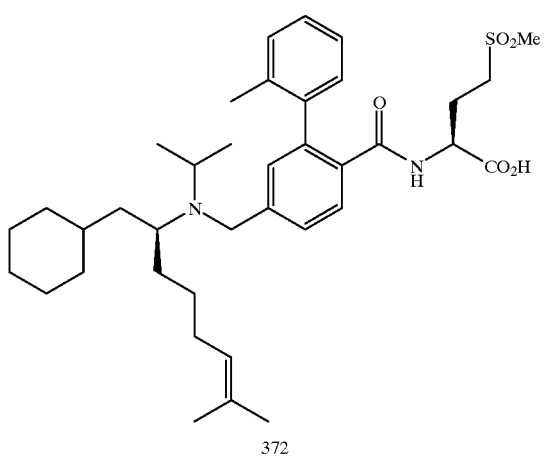
372
TABLE 6-continued
Amines of the Type A(B)N-L₁
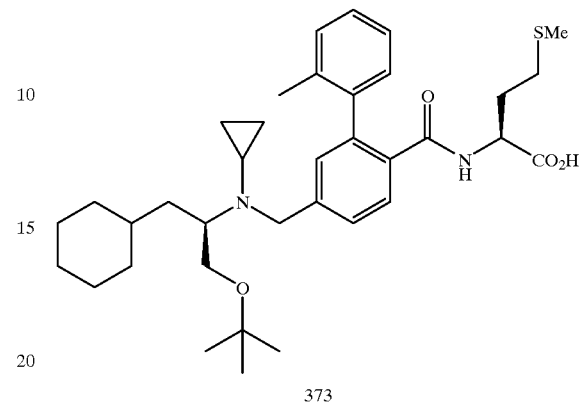
373
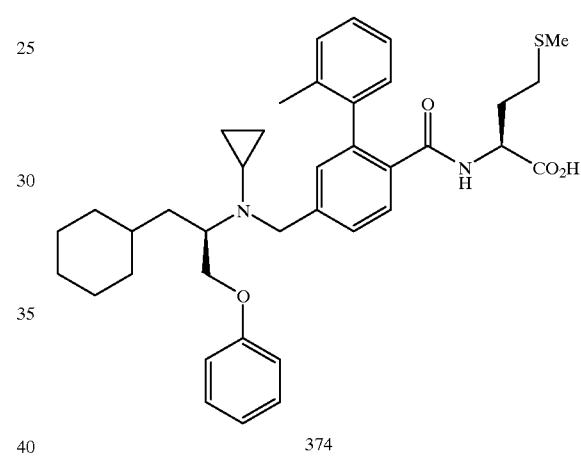
374
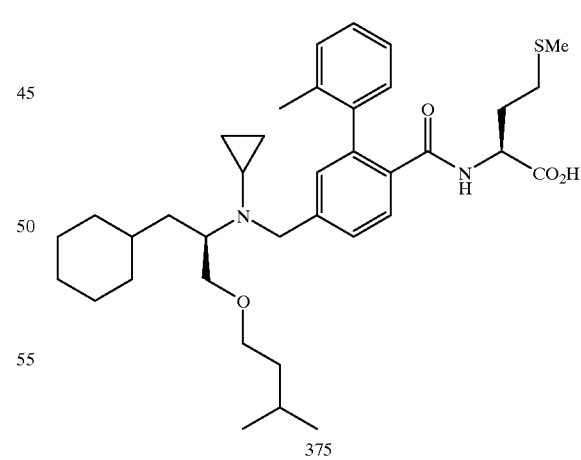
375

TABLE 6-continued
Amines of the Type A(B)N-L₁
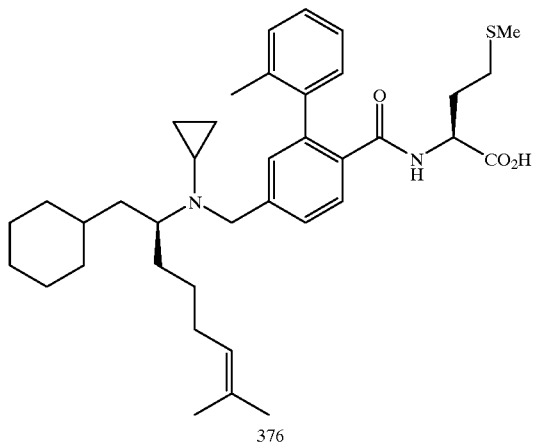
376
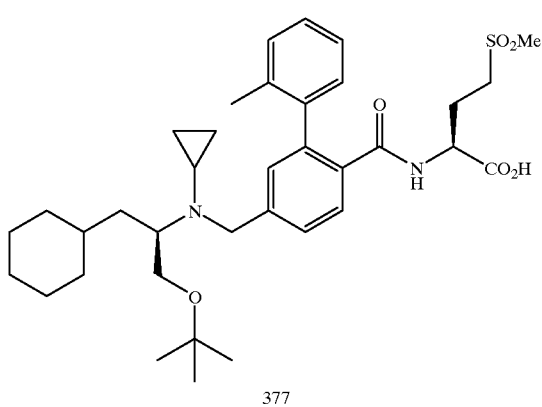
377
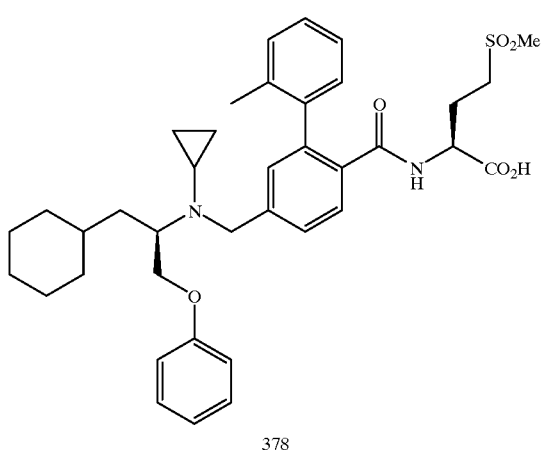
378
TABLE 6-continued
Amines of the Type A(B)N-L₁
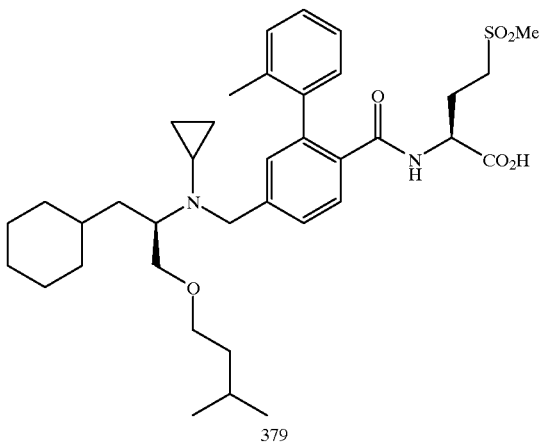
379
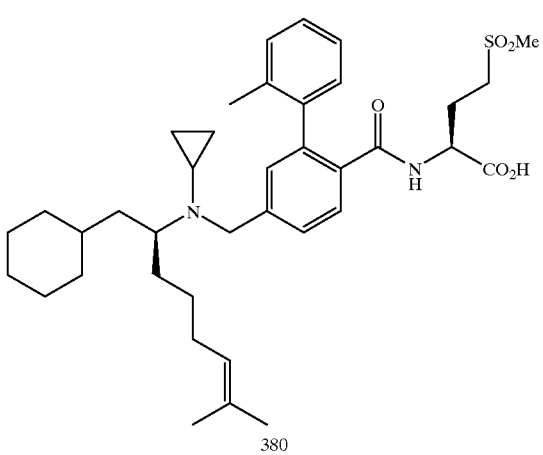
380
TABLE 7
Ethers of the Type A-OL₁
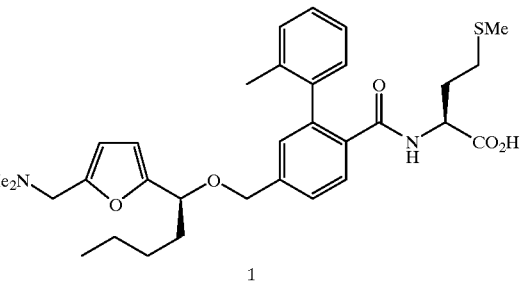
1

TABLE 7-continued

Ethers of the Type A-OL₁

TABLE 7-continued
Ethers of the Type A-OL₁
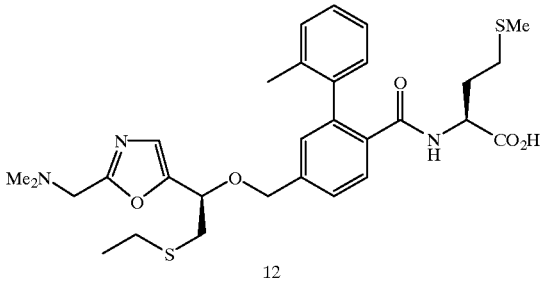
12
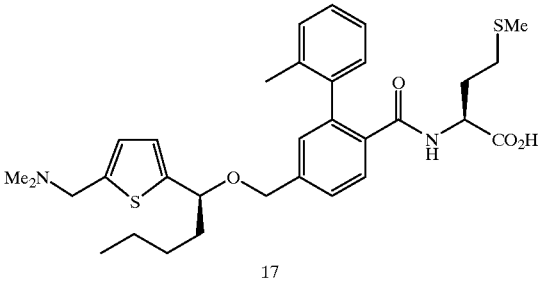
13
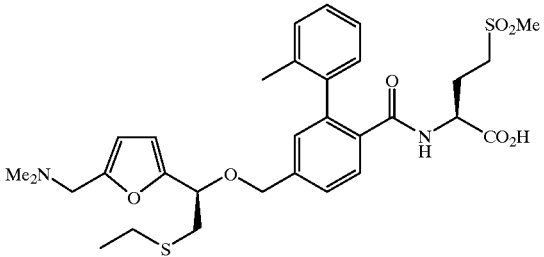
14
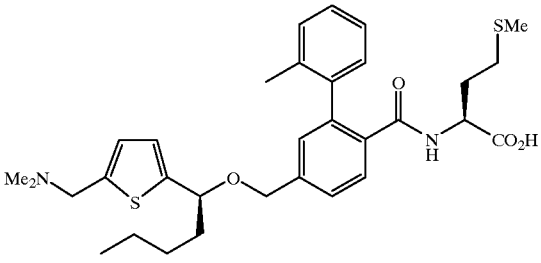
15
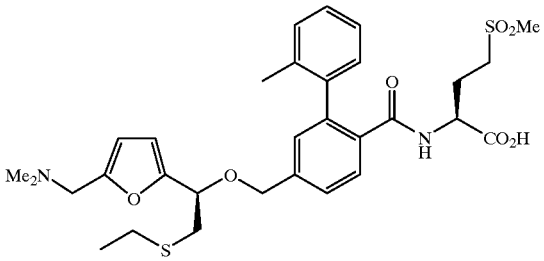
16
TABLE 7-continued
Ethers of the Type A-OL₁
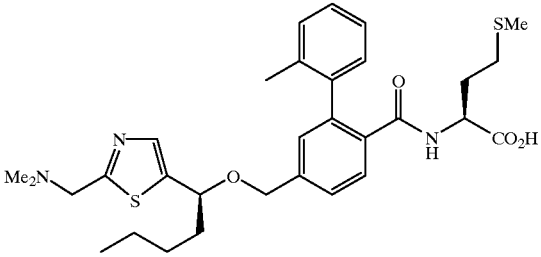
17
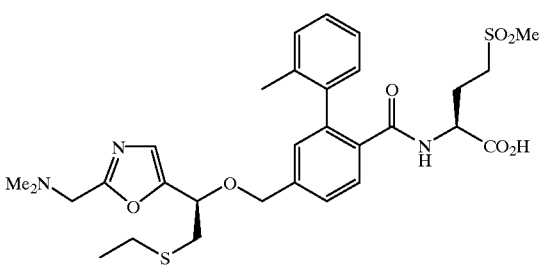
18
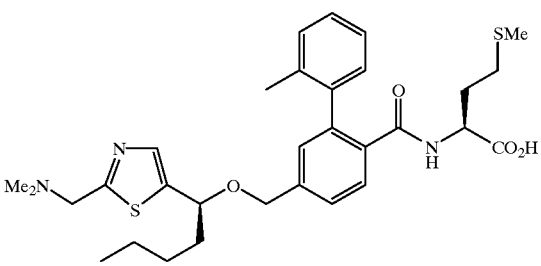
19
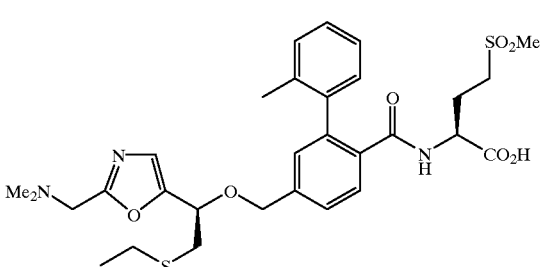
20
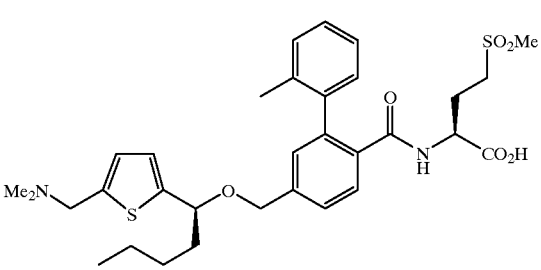
21

TABLE 7-continued
Ethers of the Type A-OL₁
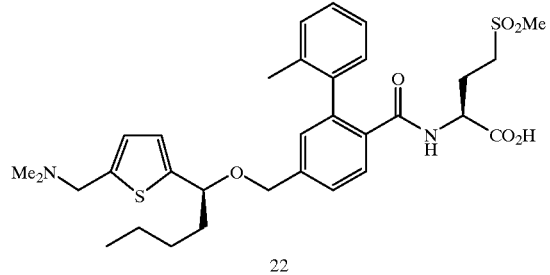
22
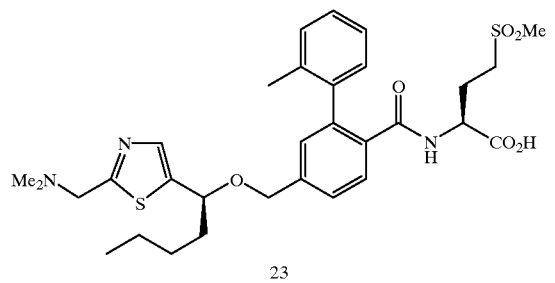
23
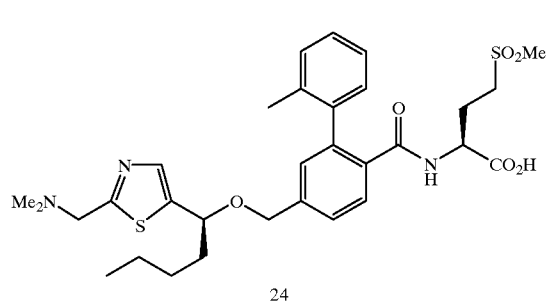
24
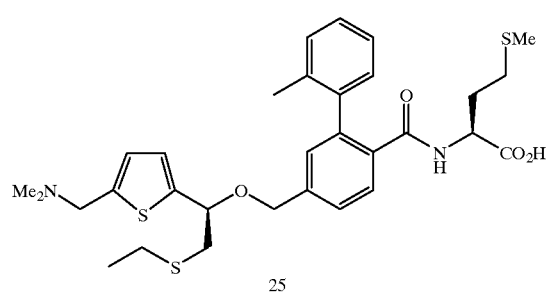
25
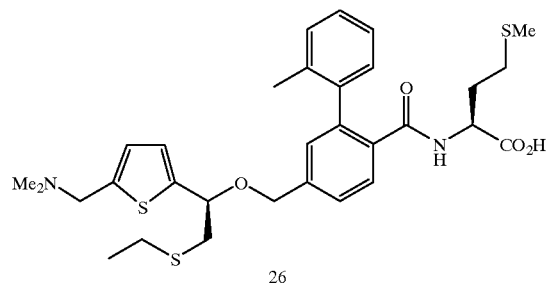
26
TABLE 7-continued
Ethers of the Type A-OL₁
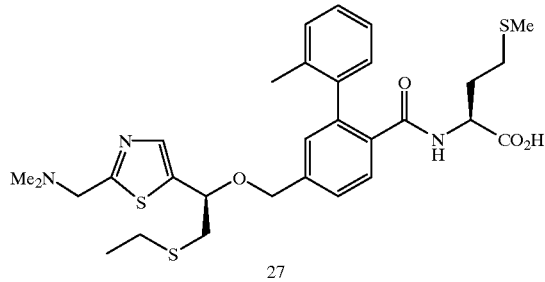
27
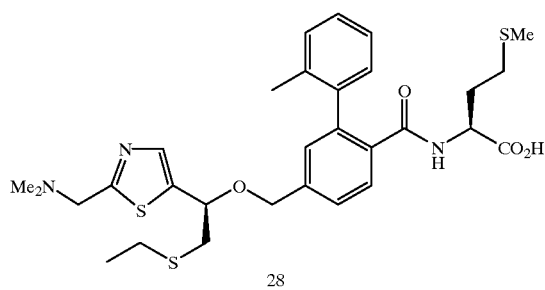
28
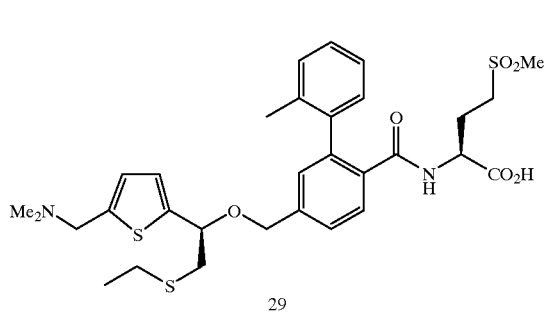
29
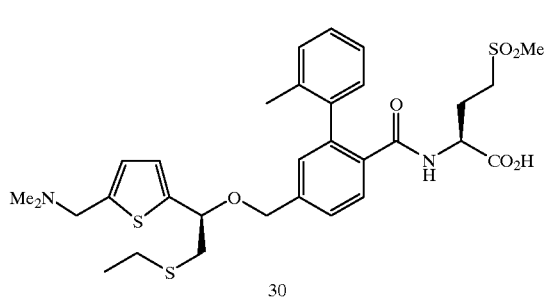
30
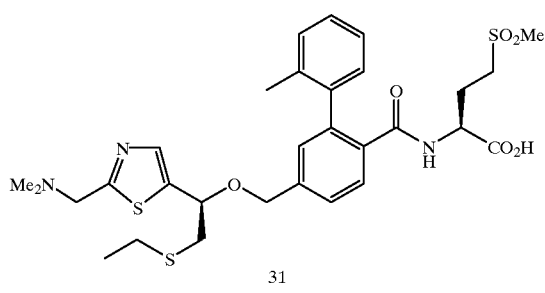
31

TABLE 7-continued
Ethers of the Type A-OL₁
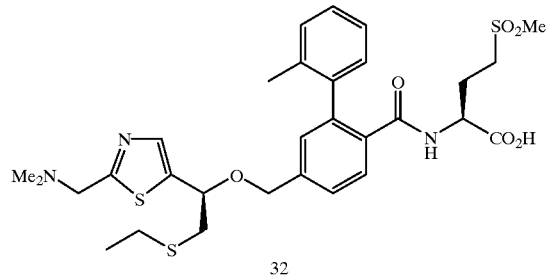
32
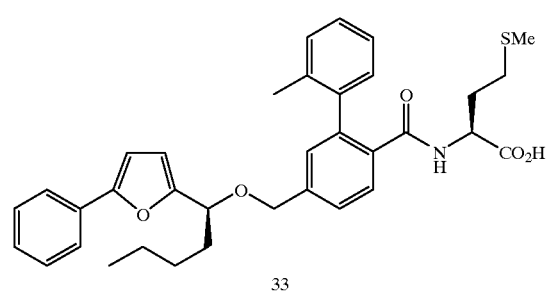
33
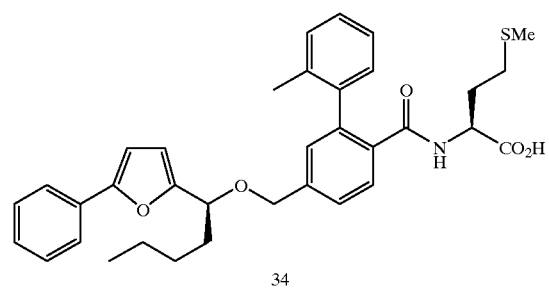
34
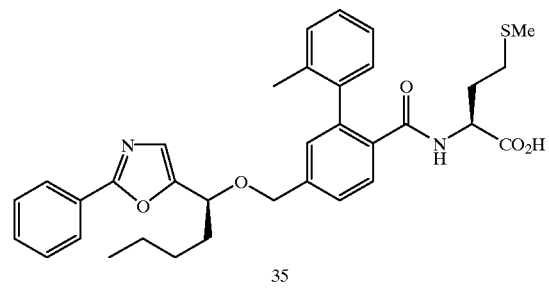
35
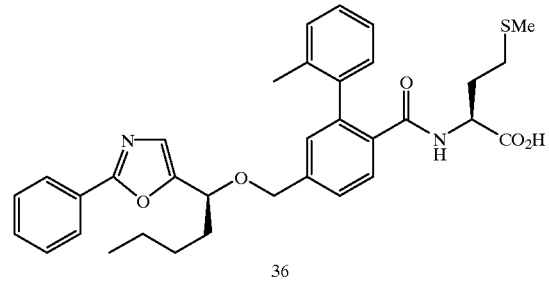
36
TABLE 7-continued
Ethers of the Type A-OL₁
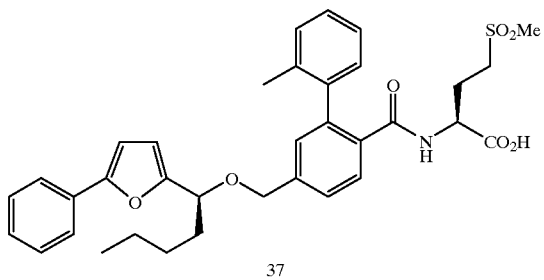
37
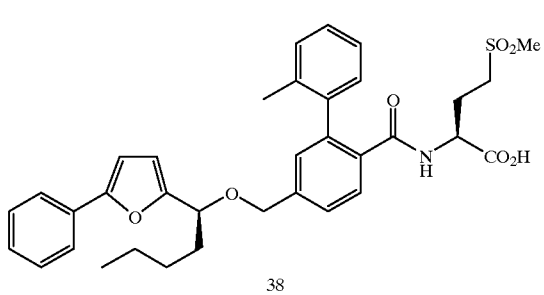
38
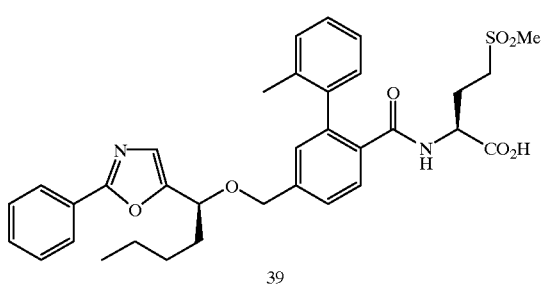
39
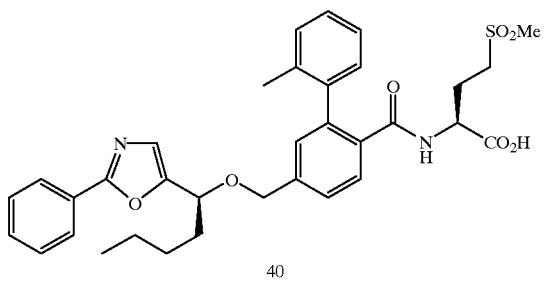
40
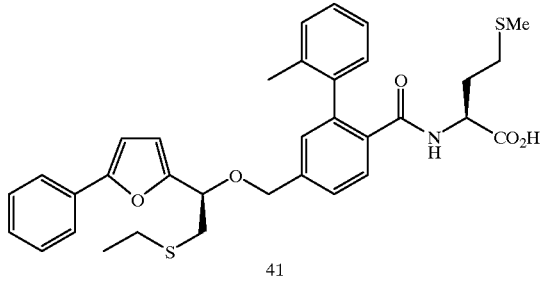
41

TABLE 7-continued

Ethers of the Type A-OL₁

TABLE 7-continued
Ethers of the Type A-OL₁
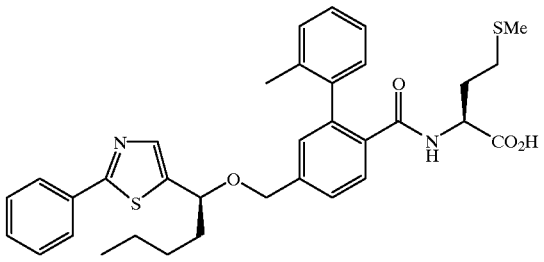
52

53
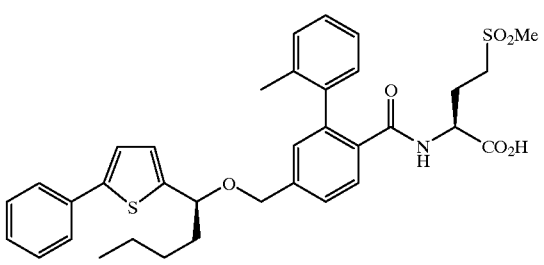
54

55

56
TABLE 7-continued
Ethers of the Type A-OL₁

57
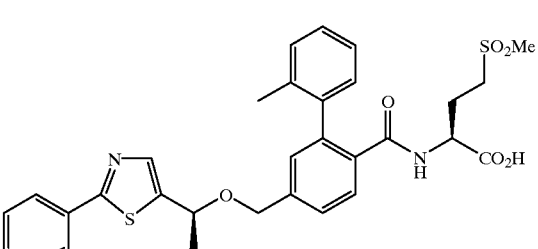
58
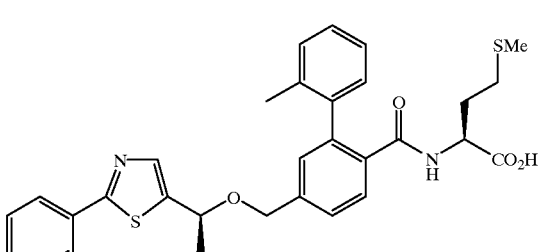
59
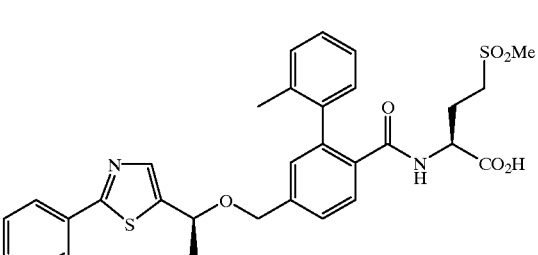
60
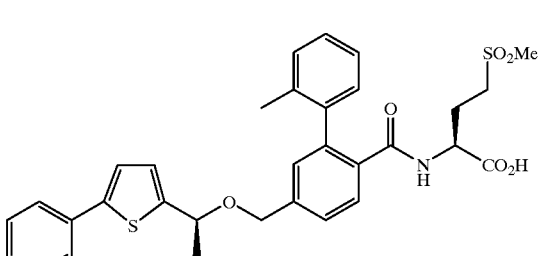
61

TABLE 7-continued
Ethers of the Type A-OL₁
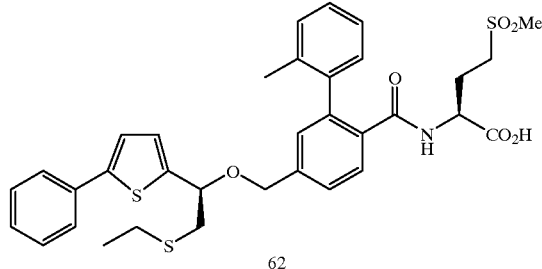
62
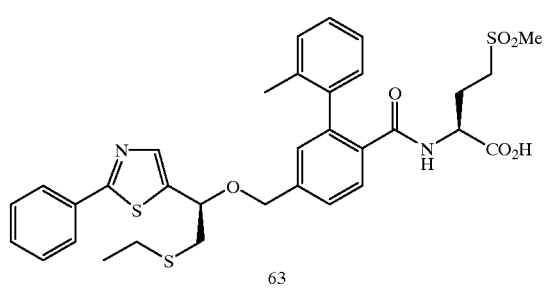
63
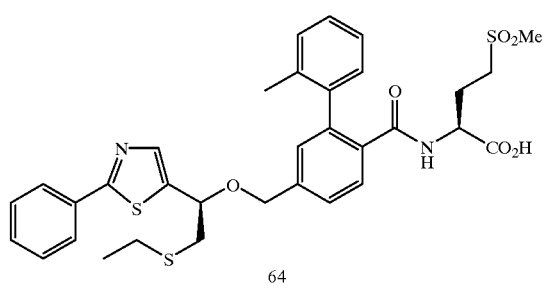
64
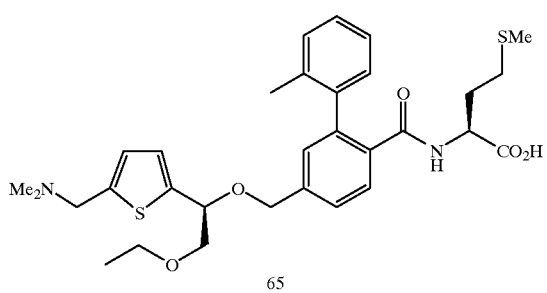
65
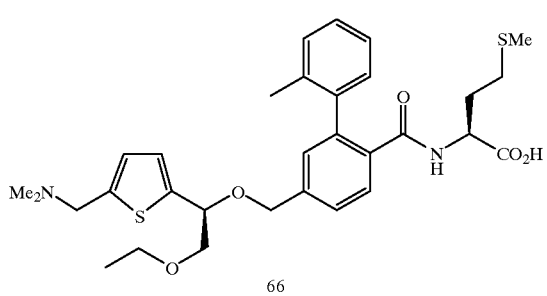
66
TABLE 7-continued
Ethers of the Type A-OL₁
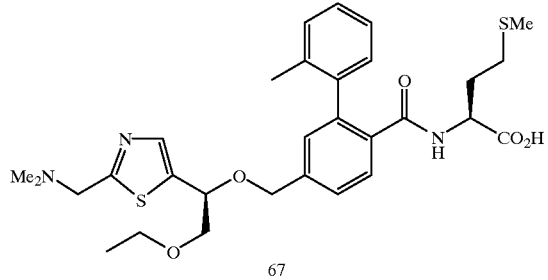
67
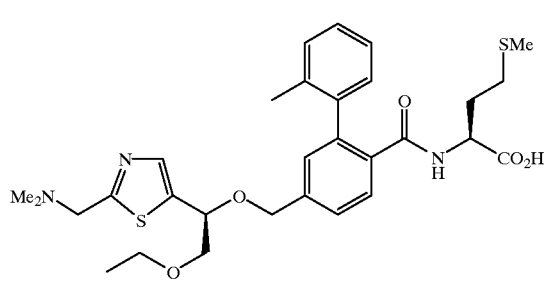
68
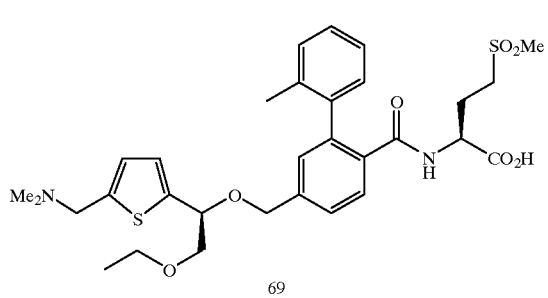
69
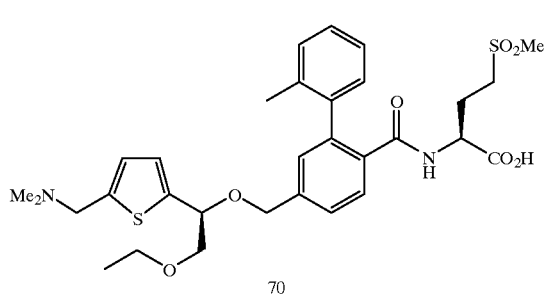
70
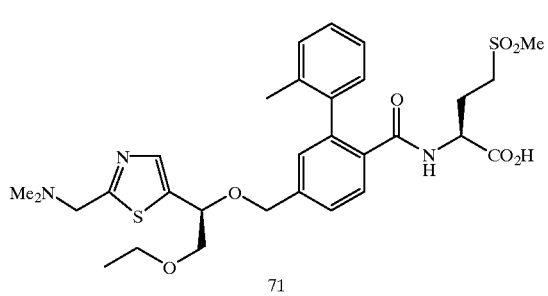
71

TABLE 7-continued
Ethers of the Type A-OL₁
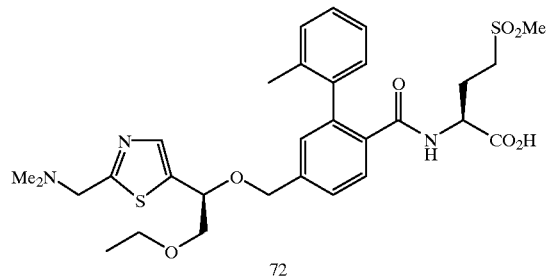
72
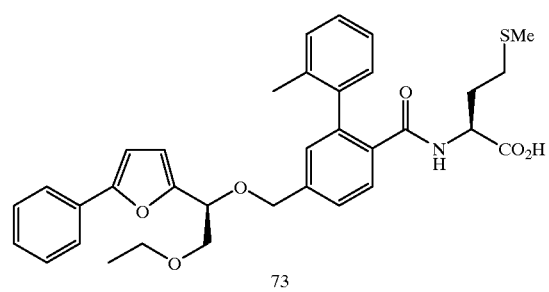
73
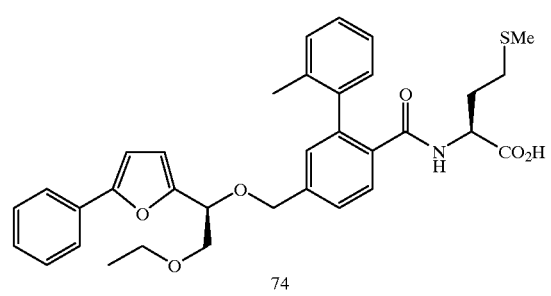
74
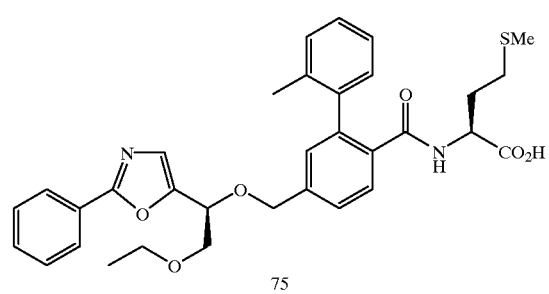
75
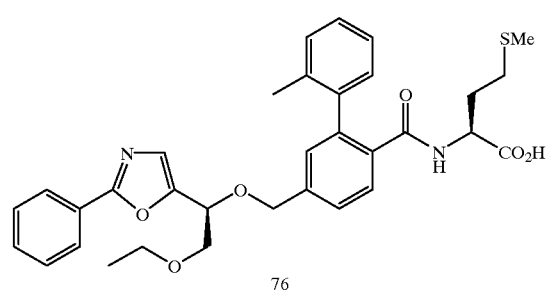
76
TABLE 7-continued
Ethers of the Type A-OL₁
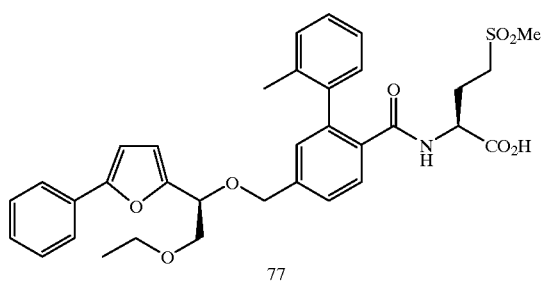
77
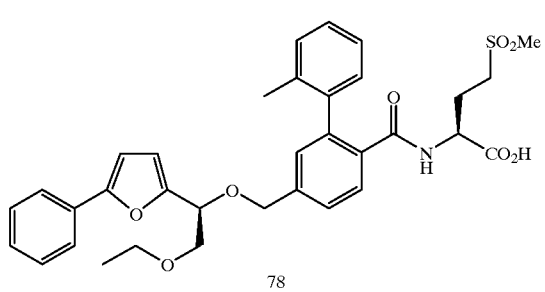
78
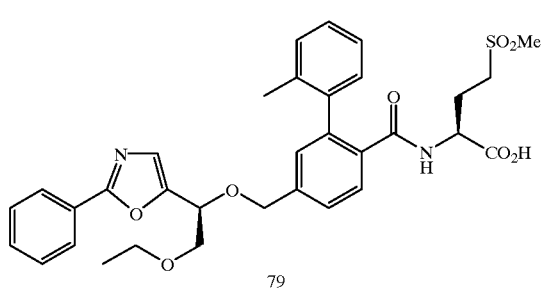
79
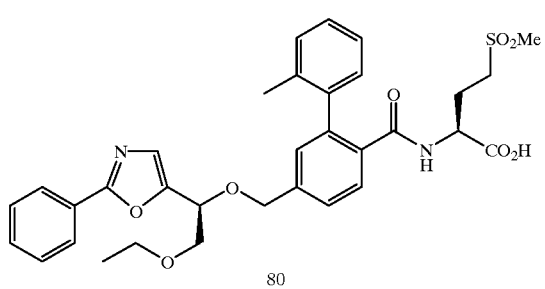
80
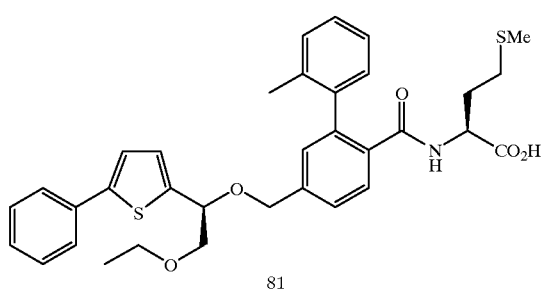
81

TABLE 7-continued
Ethers of the Type A-OL₁
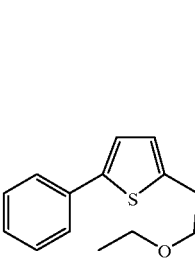
82
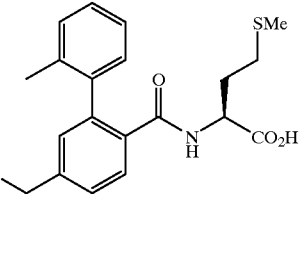
83
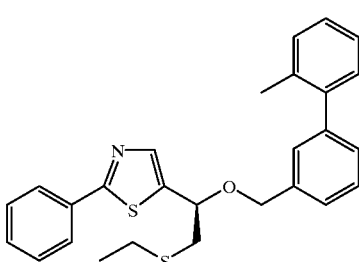
84
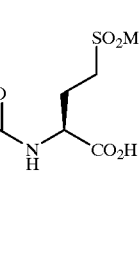
85
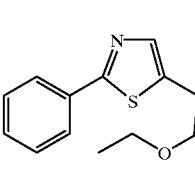
86
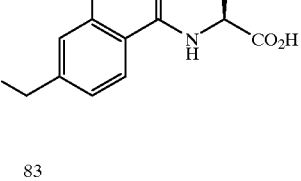
87
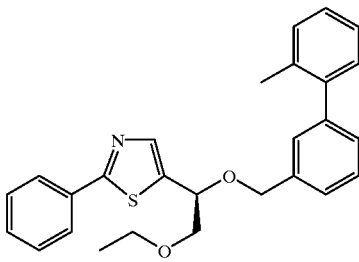
88
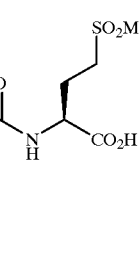
89
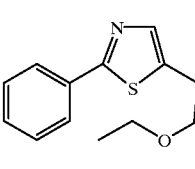
90
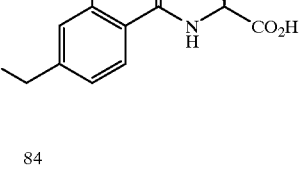
91

TABLE 7-continued
Ethers of the Type A-OL₁
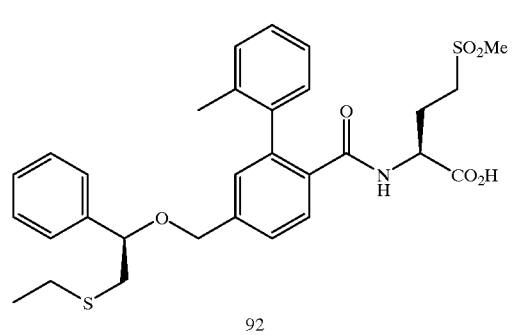
92
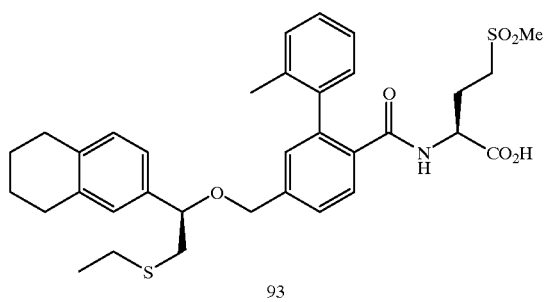
93
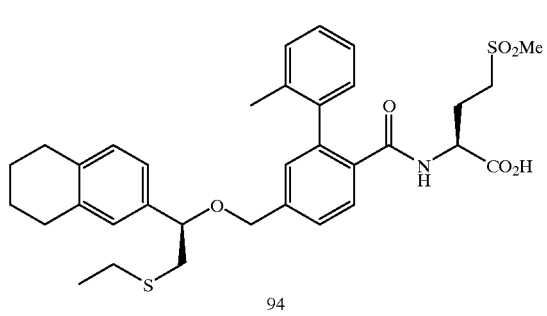
94
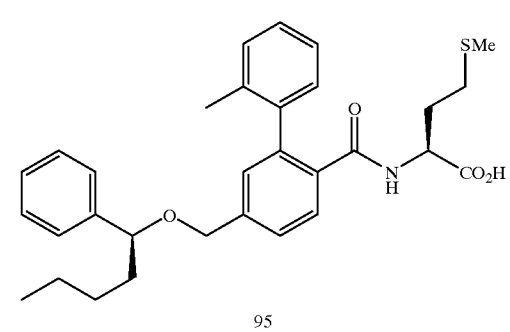
95
TABLE 7-continued
Ethers of the Type A-OL₁
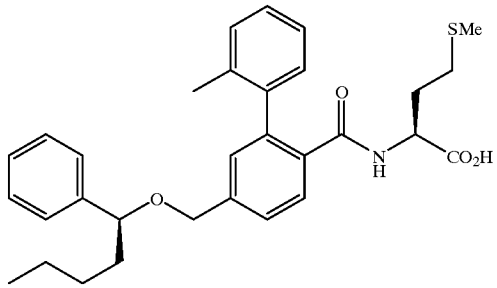
96
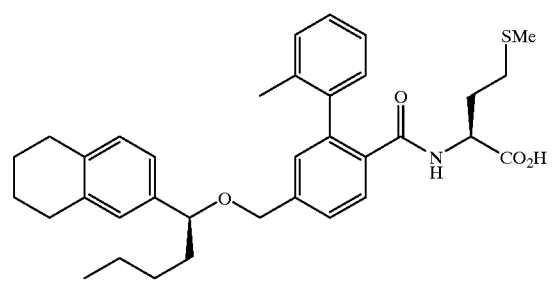
97
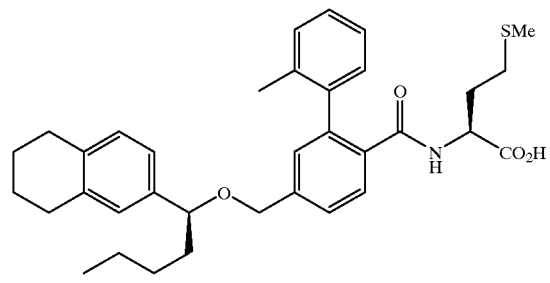
98
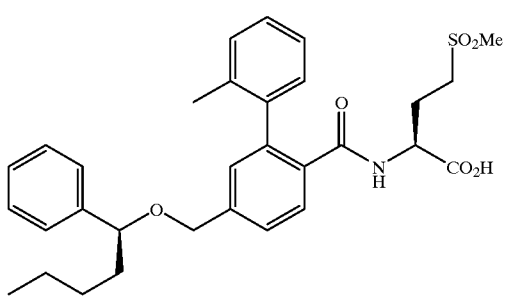
99

TABLE 7-continued
Ethers of the Type A-OL₁
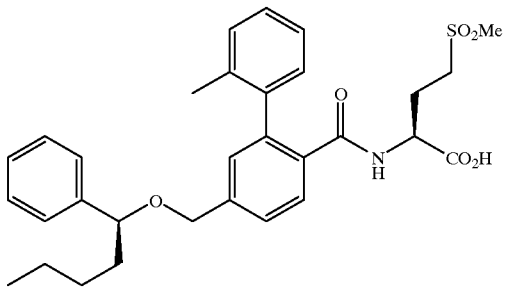
100
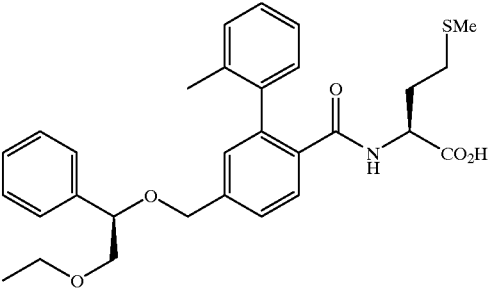
101
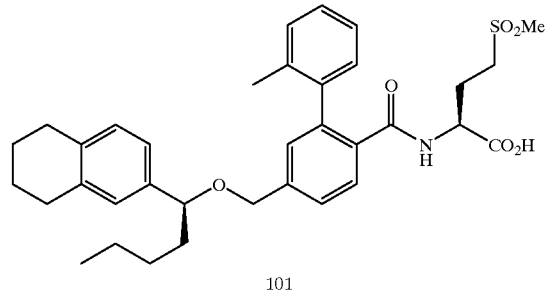
102
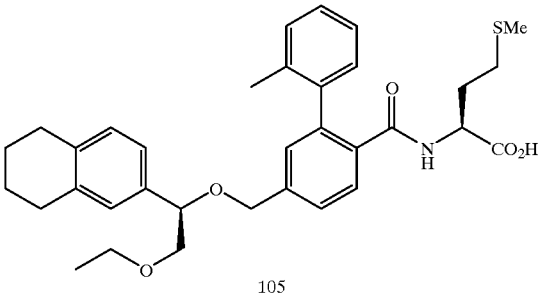
103
TABLE 7-continued
Ethers of the Type A-OL₁
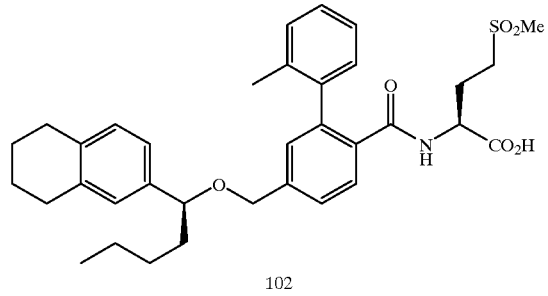
104
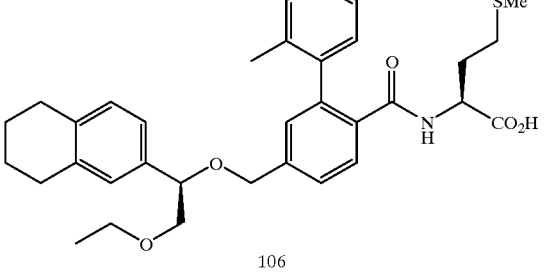
105
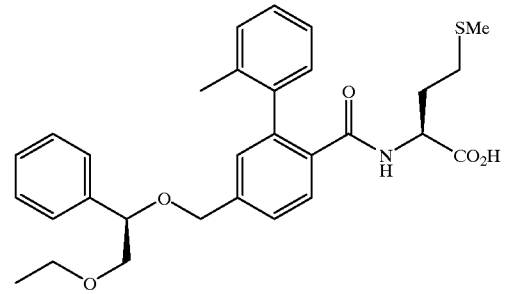
106
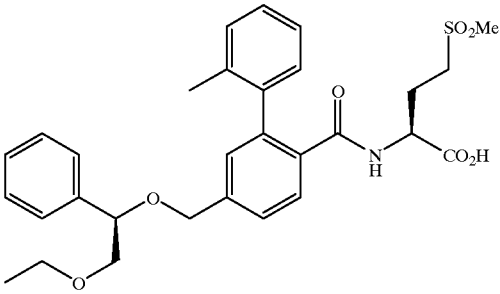
107

TABLE 7-continued
Ethers of the Type A-OL₁
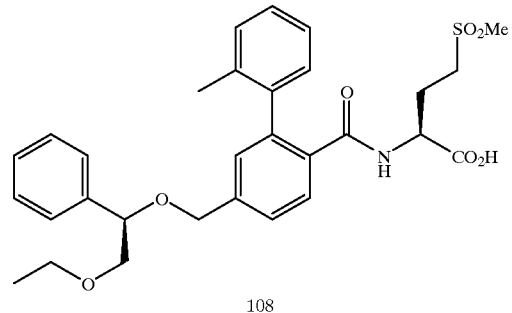
108
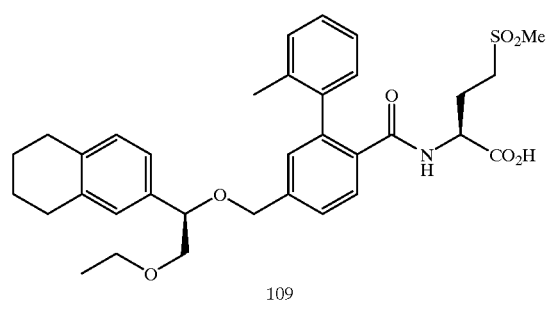
109
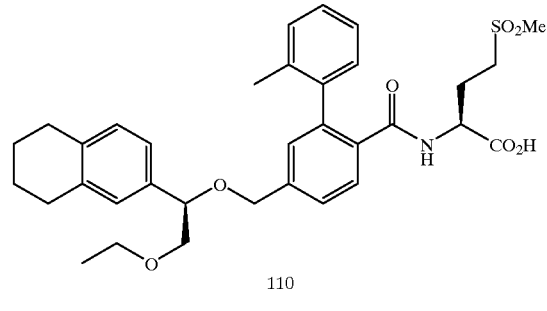
110
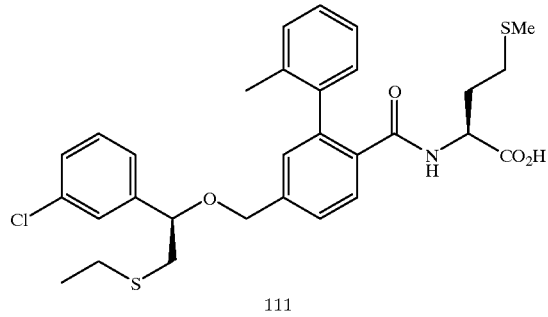
111
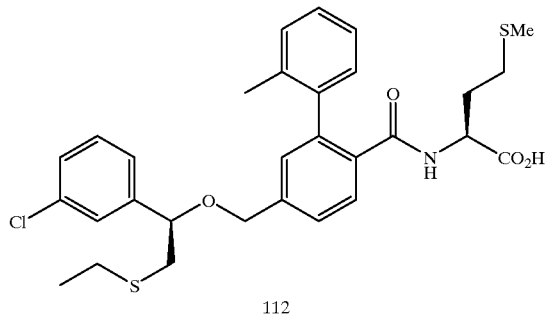
112
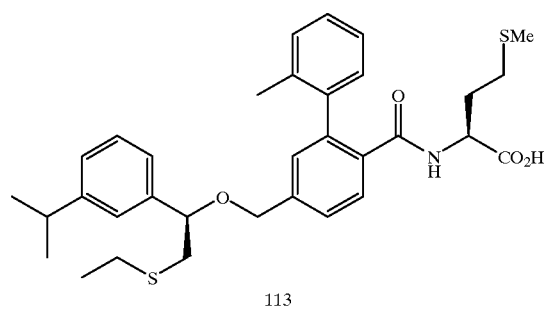
113
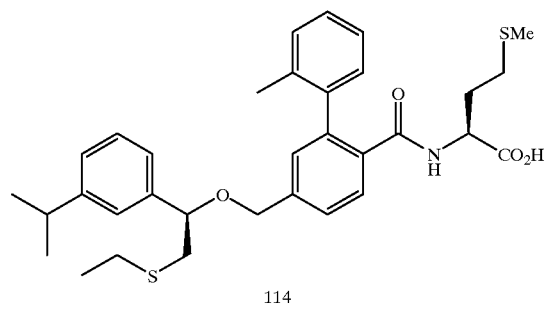
114
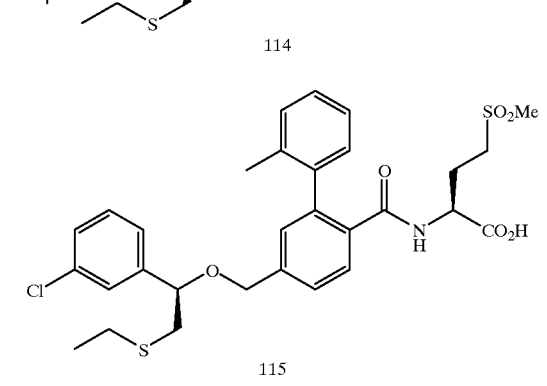
115
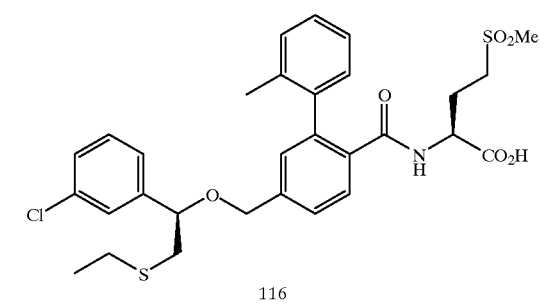
116

TABLE 7-continued
Ethers of the Type A-OL₁
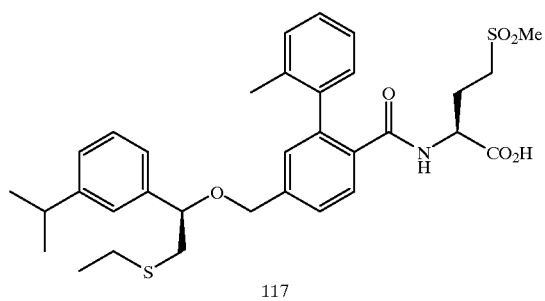
117
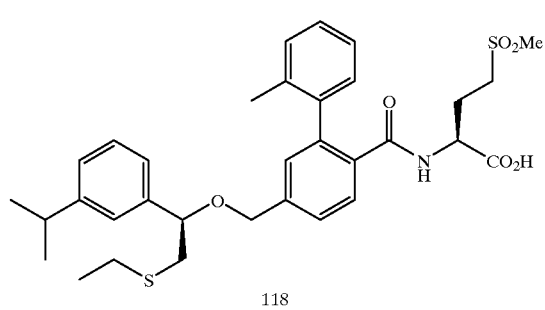
118
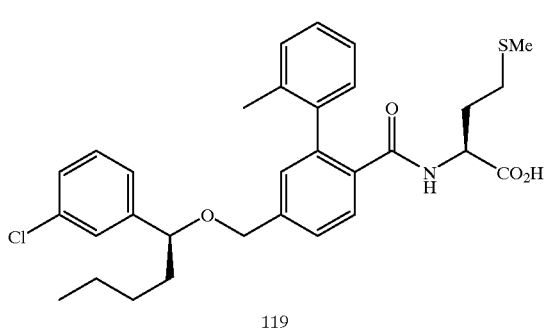
119
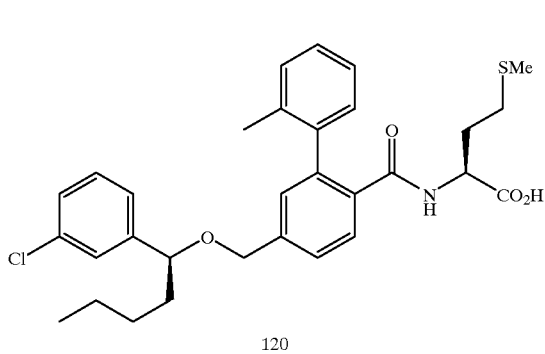
120
TABLE 7-continued
Ethers of the Type A-OL₁
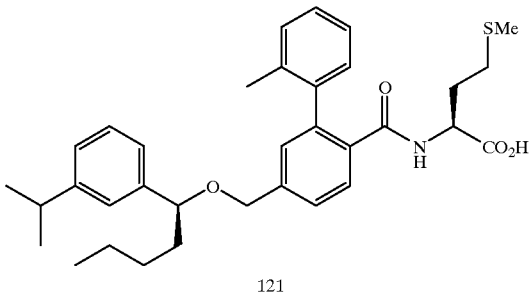
121
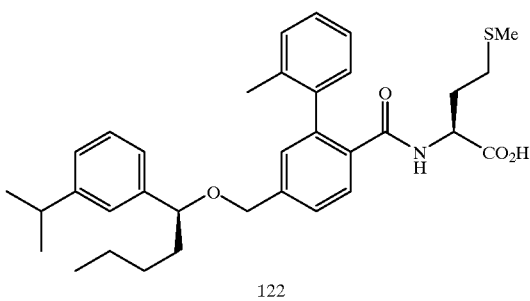
122
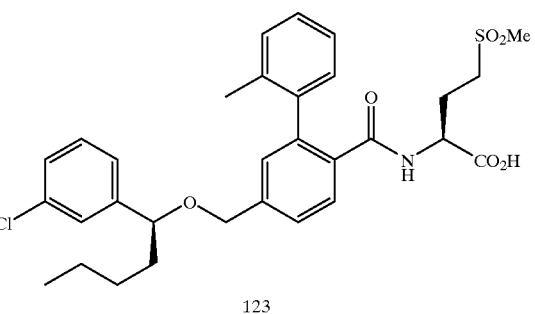
123
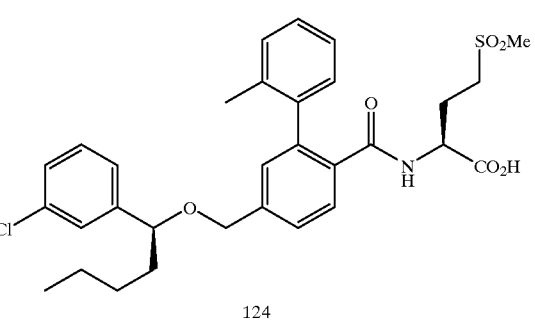
124
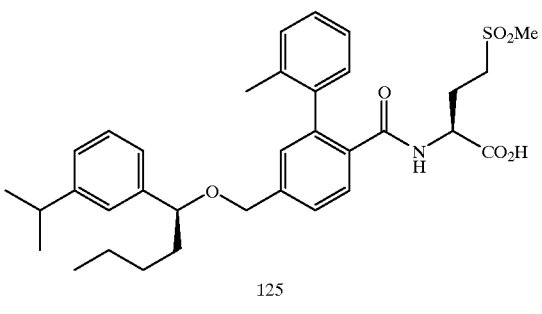
125

TABLE 7-continued
Ethers of the Type A-OL₁
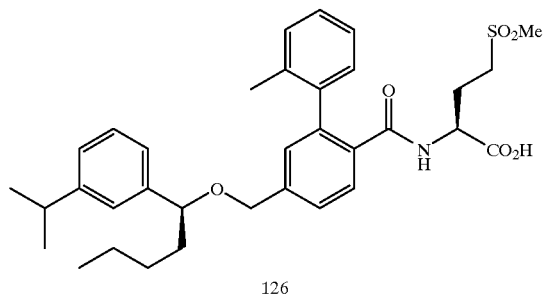
126
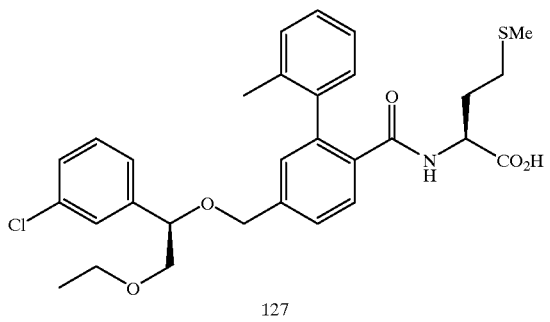
127
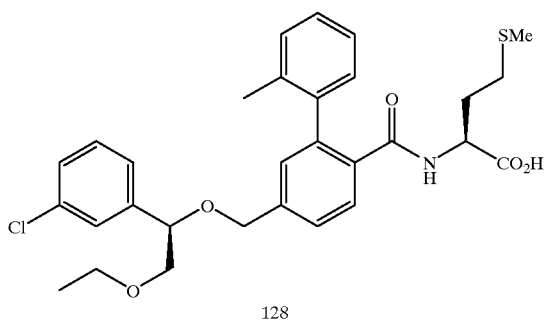
128
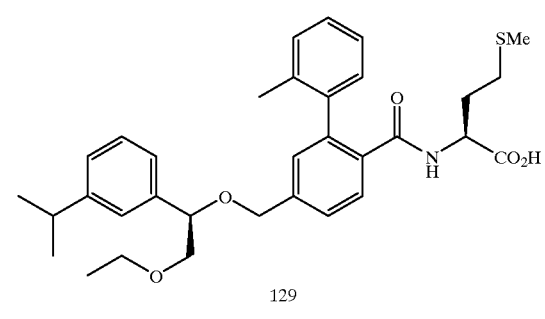
129
TABLE 7-continued
Ethers of the Type A-OL₁
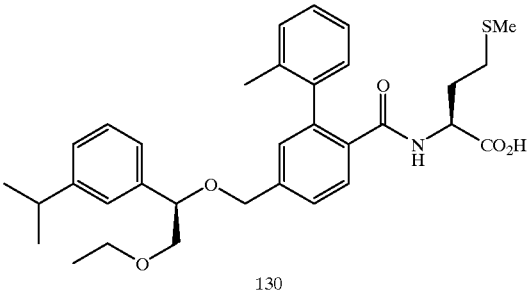
130
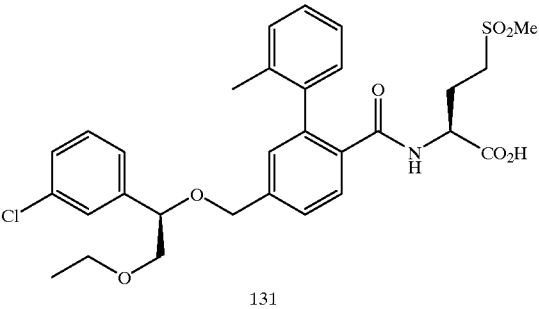
131
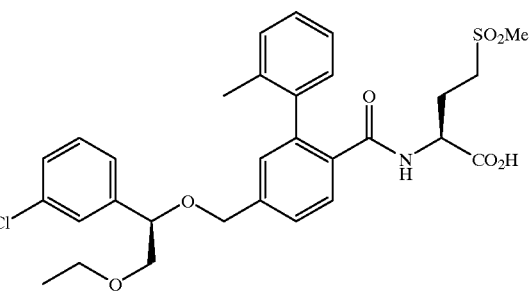
132
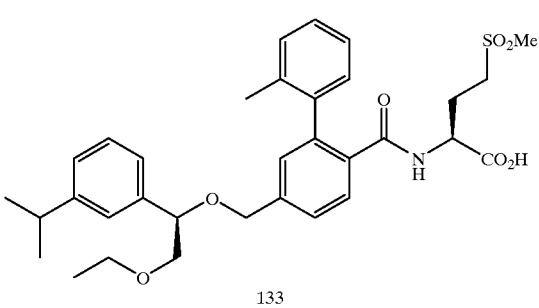
133

134

TABLE 7-continued
Ethers of the Type A-OL₁
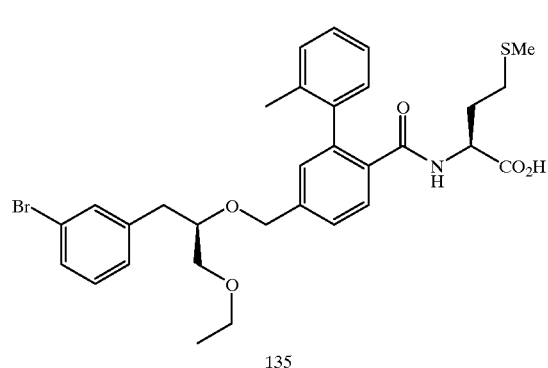
135
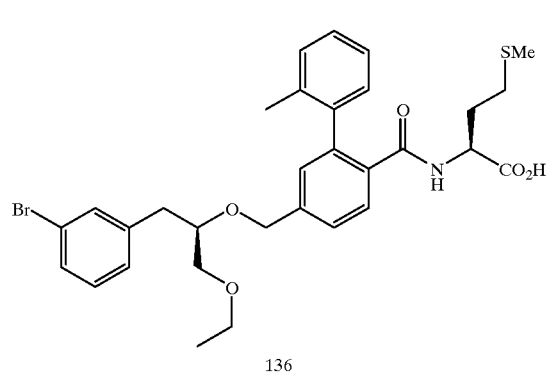
136
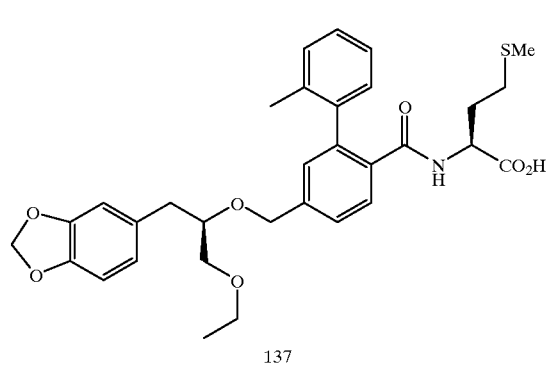
137
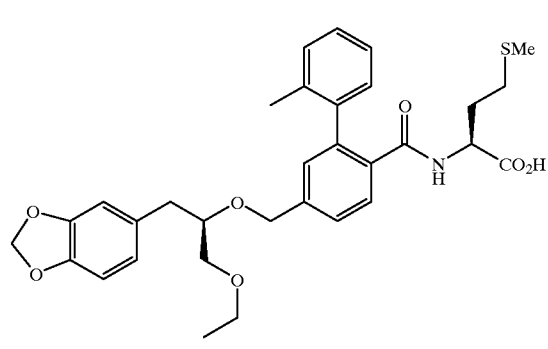
138
TABLE 7-continued
Ethers of the Type A-OL₁
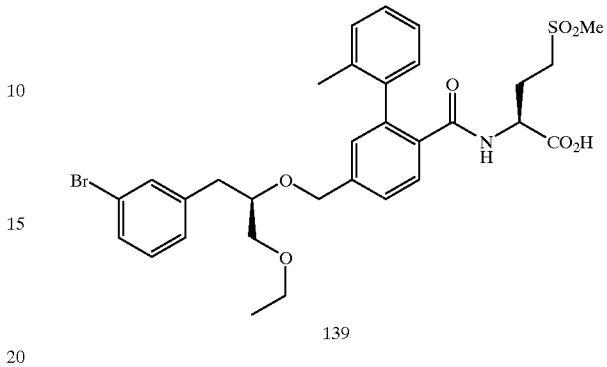
139
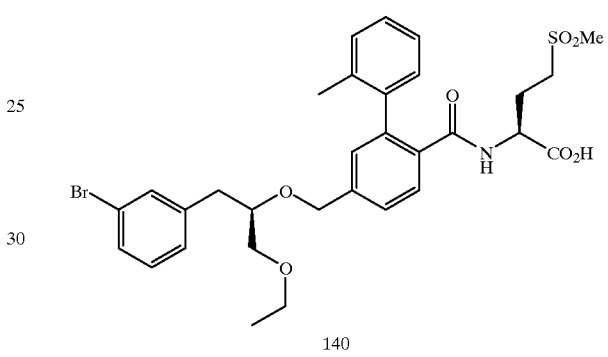
140
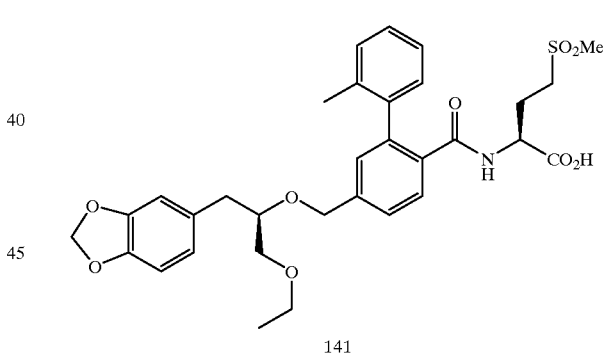
141
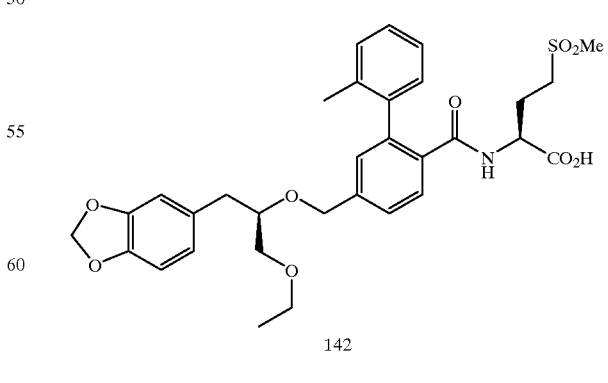
142

TABLE 7-continued
Ethers of the Type A-OL₁
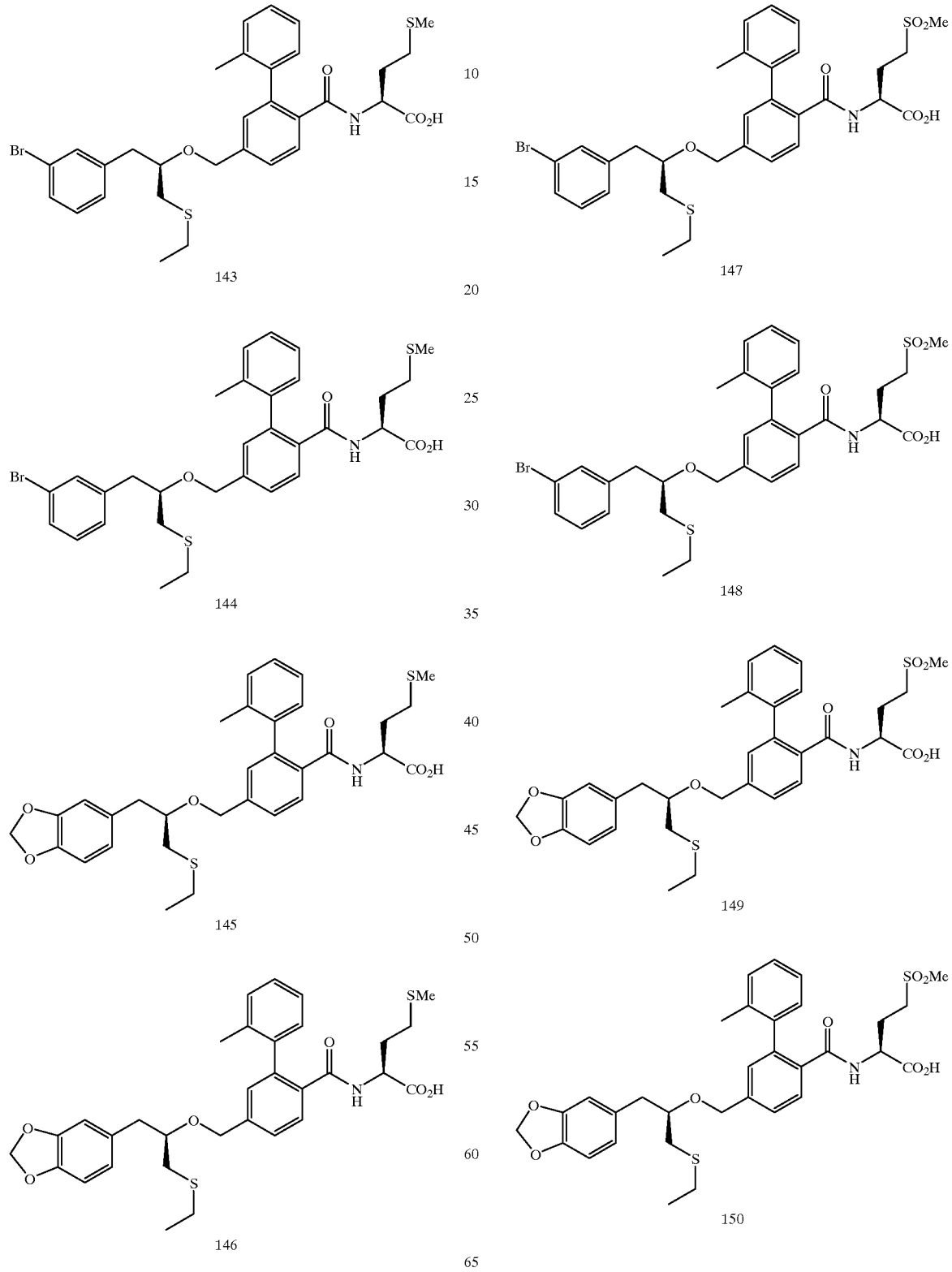

TABLE 7-continued
Ethers of the Type A-OL₁
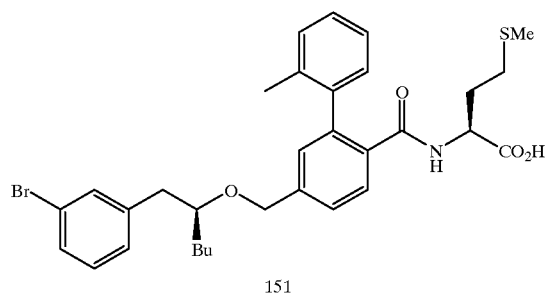
151
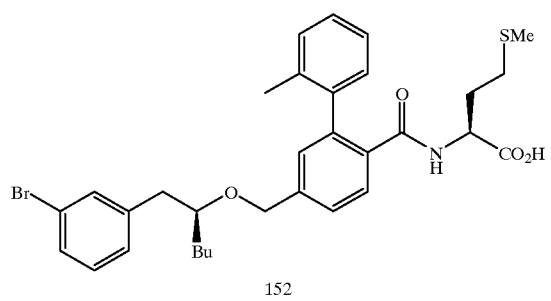
152
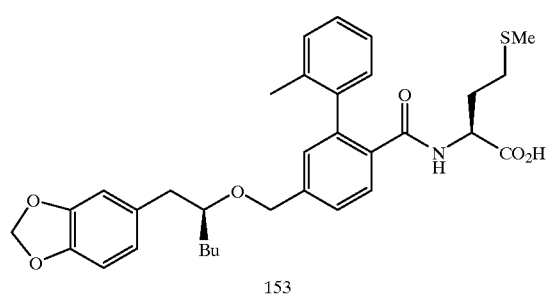
153
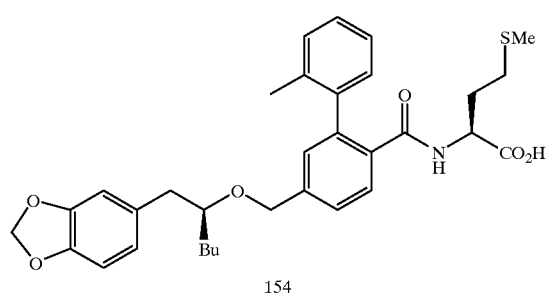
154
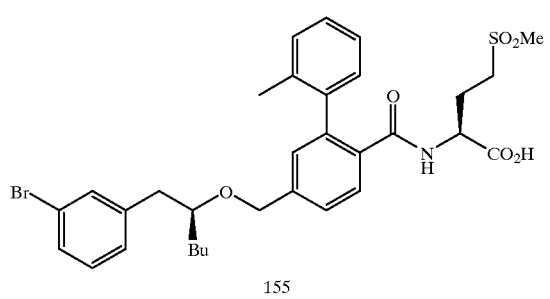
155
TABLE 7-continued
Ethers of the Type A-OL₁
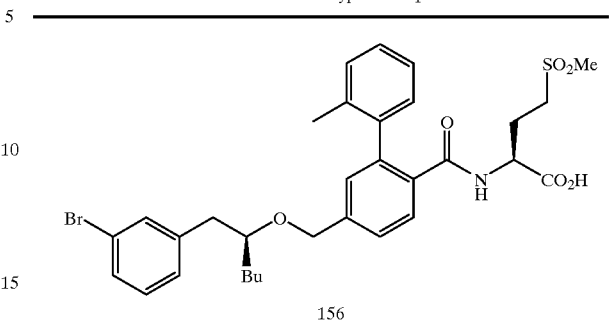
156
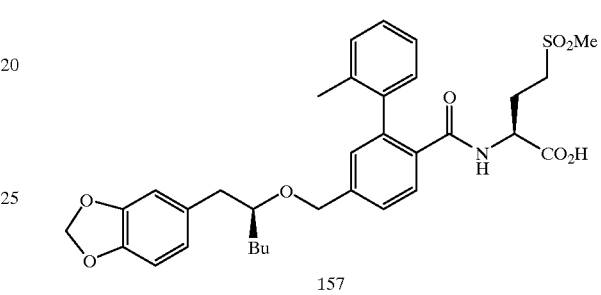
157

158
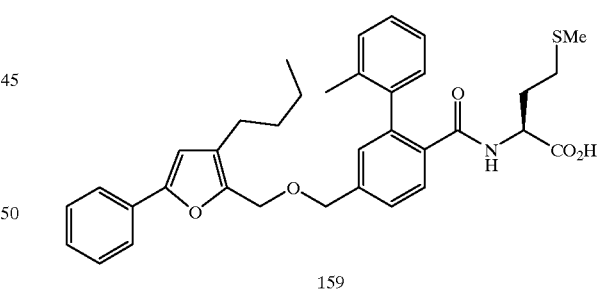
159
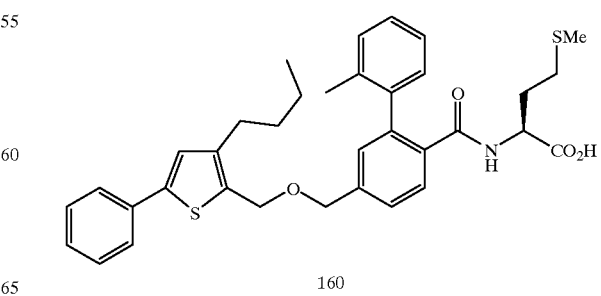
160

TABLE 7-continued
Ethers of the Type A-OL₁
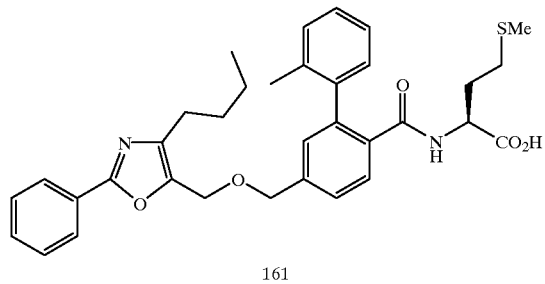
161
162
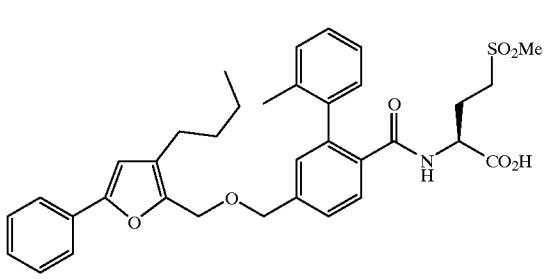
163
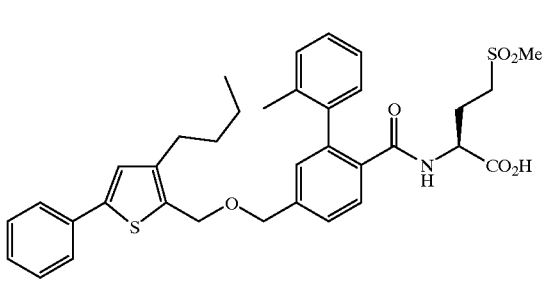
164
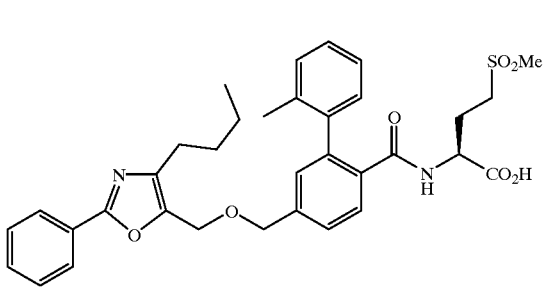
165
TABLE 7-continued
Ethers of the Type A-OL₁
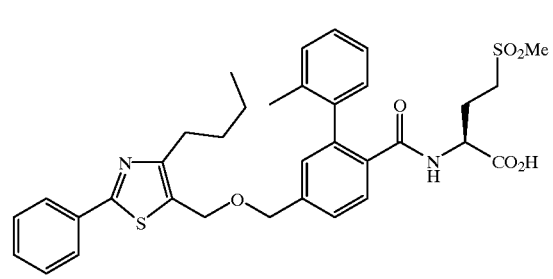
166
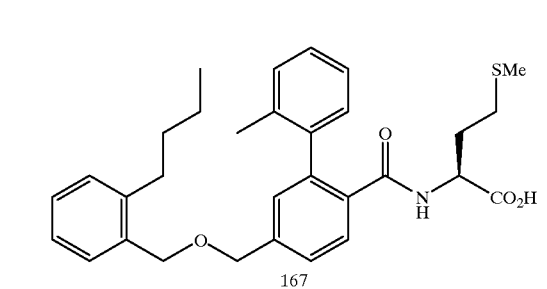
167
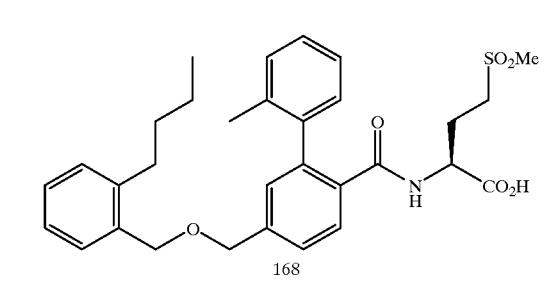
168
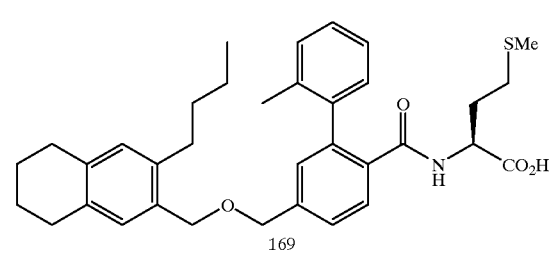
169
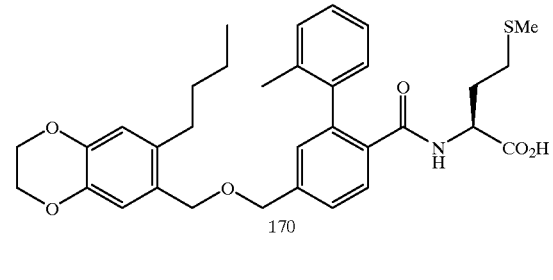
170

TABLE 7-continued
Ethers of the Type A-OL₁
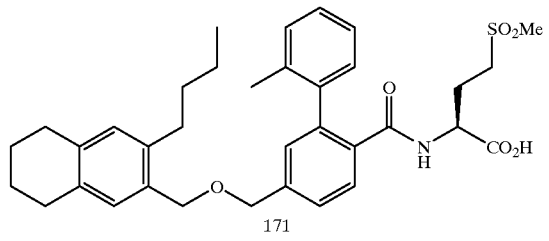
171
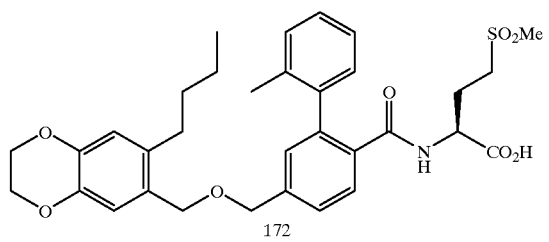
172
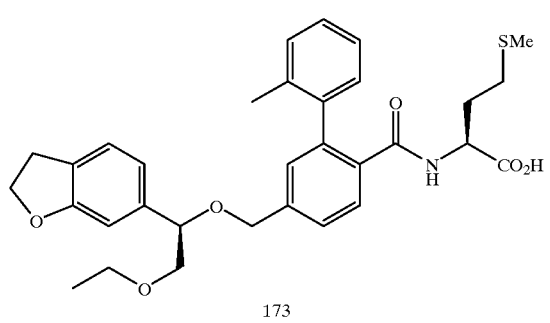
173
174
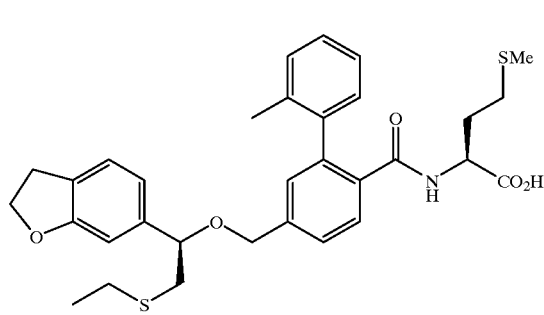
175
TABLE 7-continued
Ethers of the Type A-OL₁
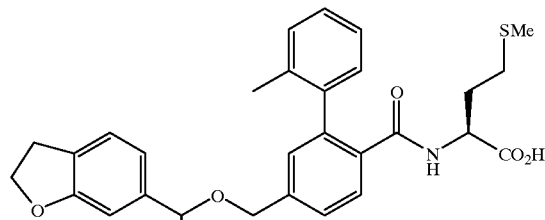
176
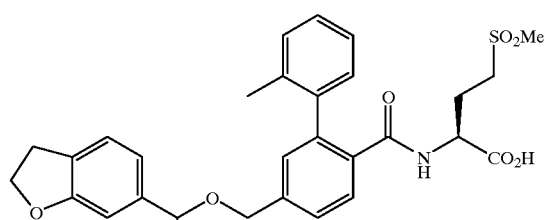
177
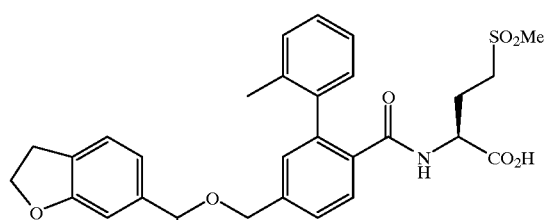
178
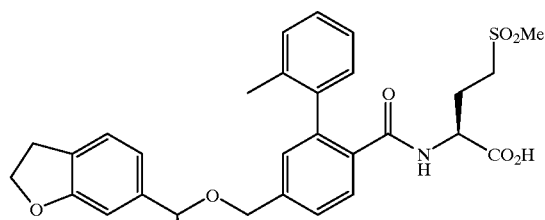
179

TABLE 7-continued
Ethers of the Type A-OL₁
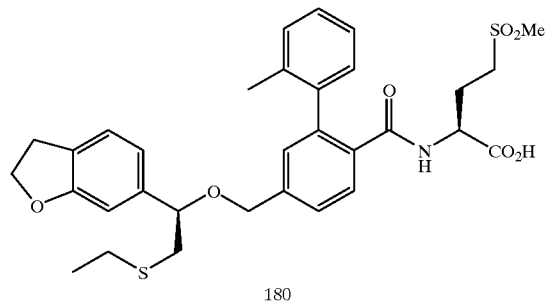
180
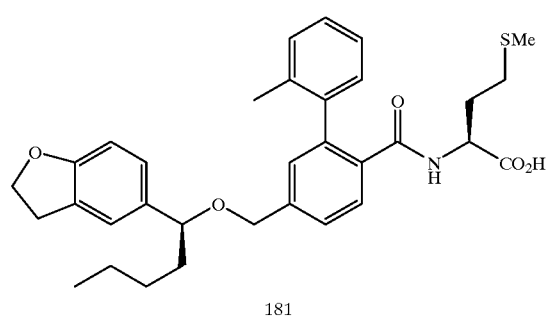
181
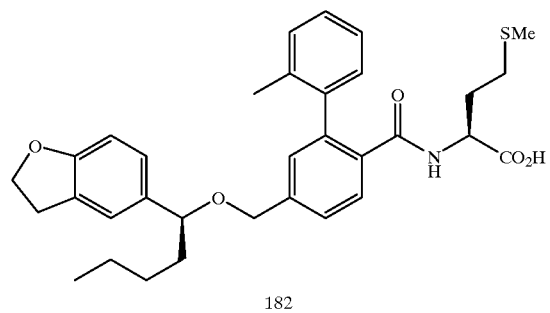
182
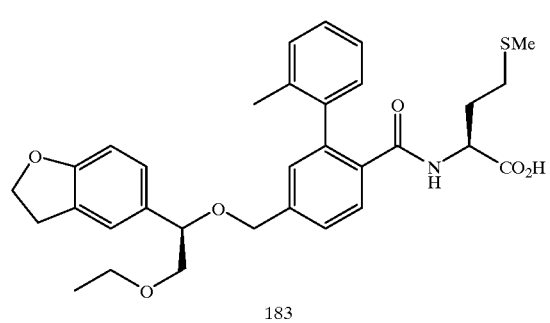
183
TABLE 7-continued
Ethers of the Type A-OL₁
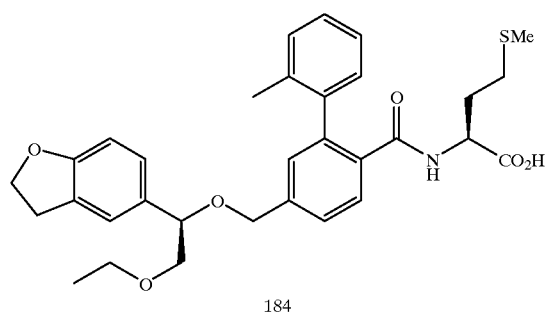
184
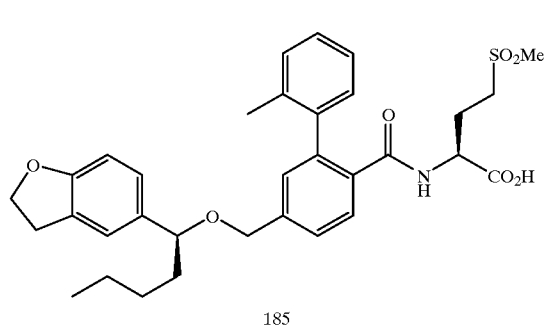
185
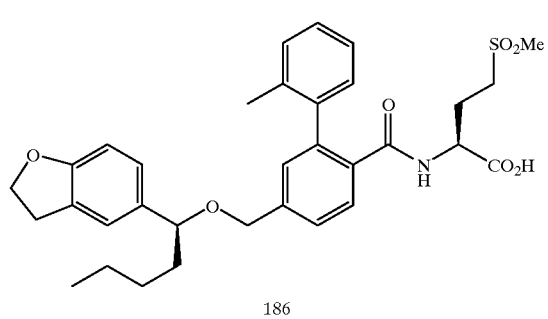
186
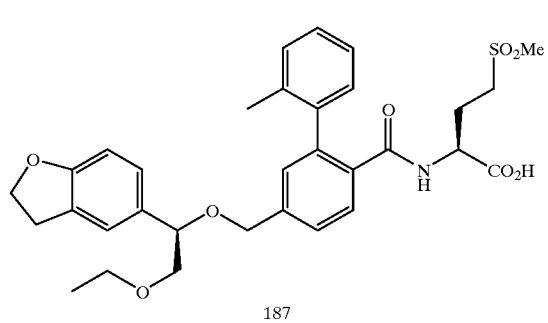
187

TABLE 7-continued
Ethers of the Type A-OL₁
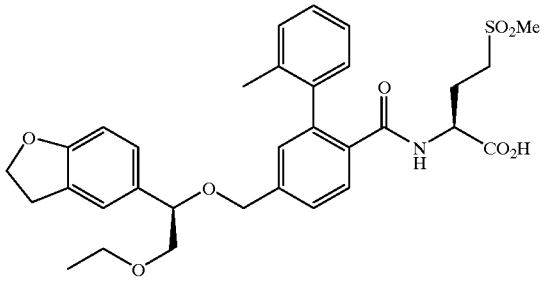
188
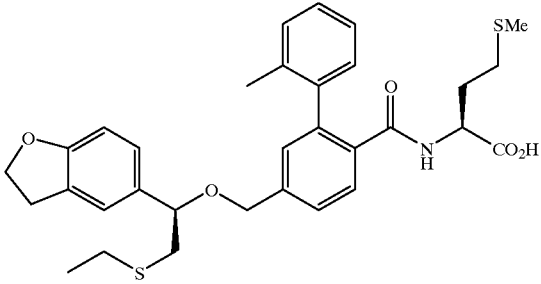
189
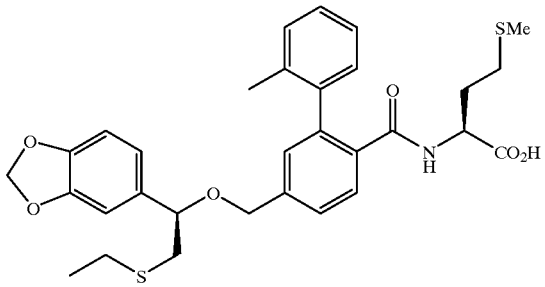
190
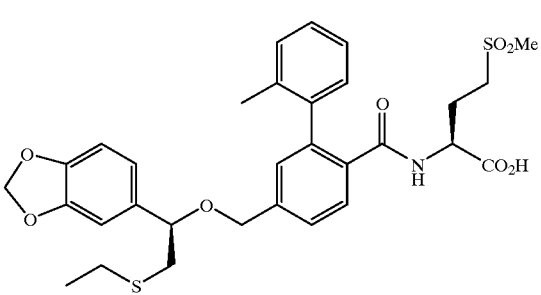
191
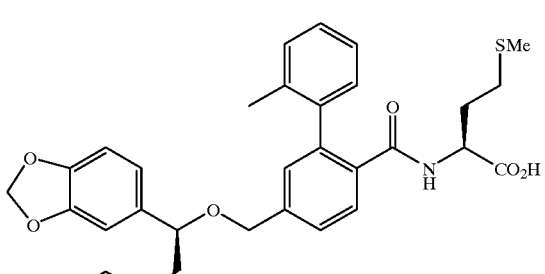
192
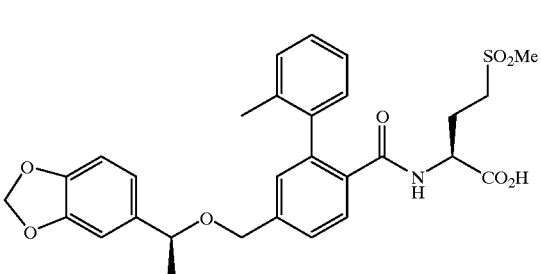
193
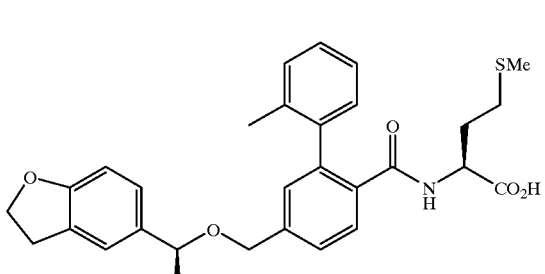
194
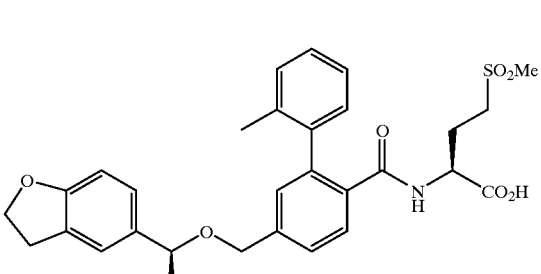
195

TABLE 7-continued
Ethers of the Type A-OL₁
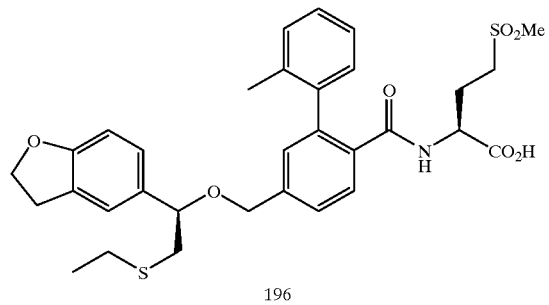
196
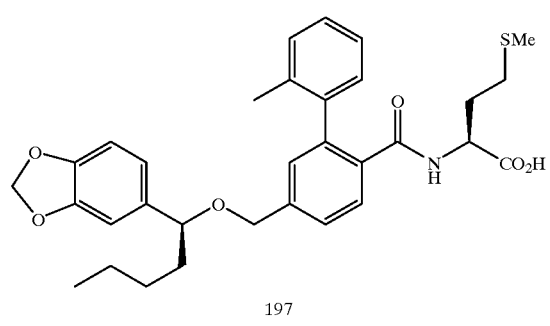
197
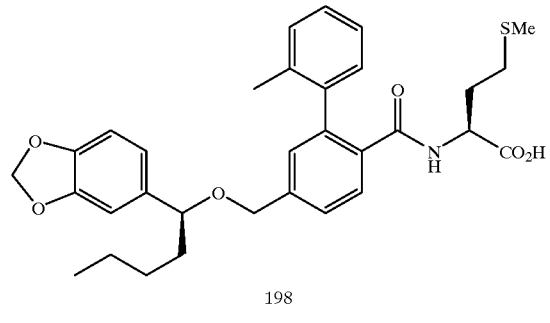
198
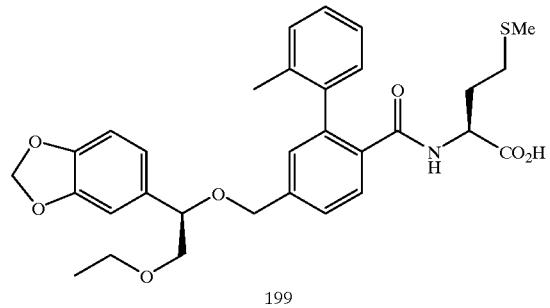
199
TABLE 7-continued
Ethers of the Type A-OL₁
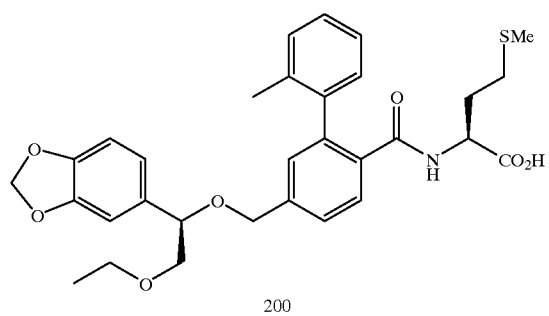
200
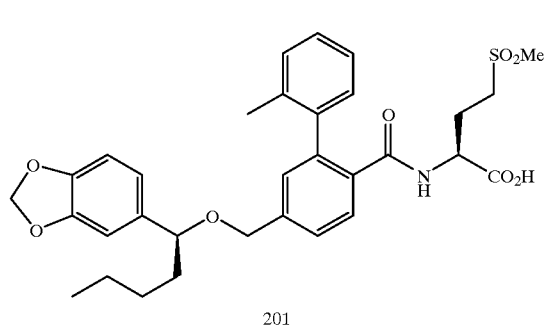
201
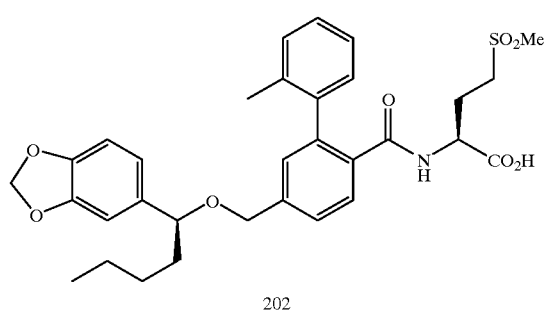
202
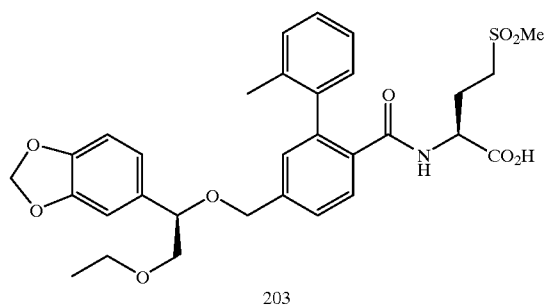
203

TABLE 7-continued
Ethers of the Type A-OL₁
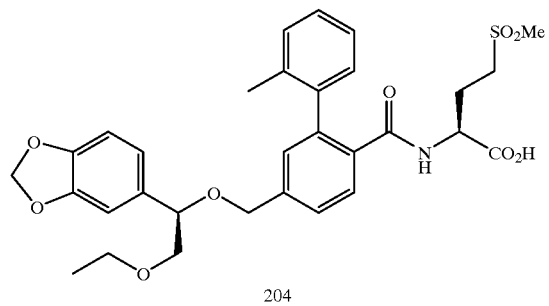
204
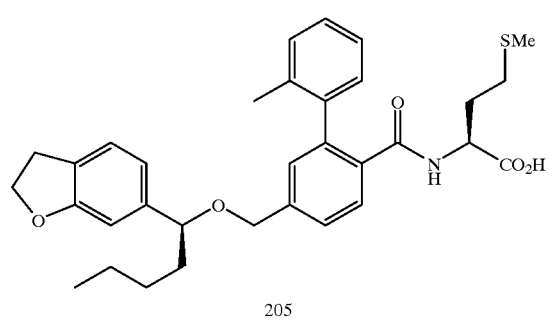
205
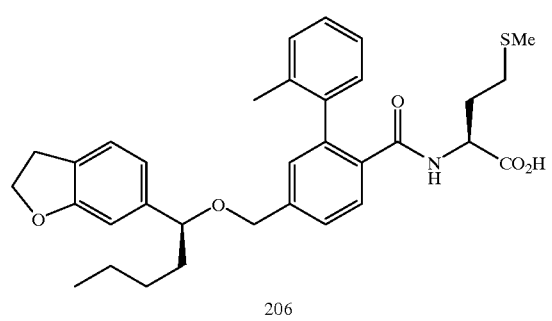
206
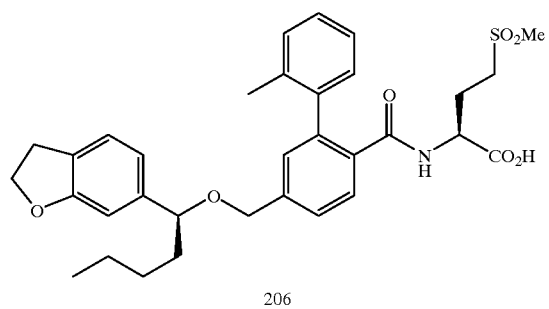
206
TABLE 7-continued
Ethers of the Type A-OL₁
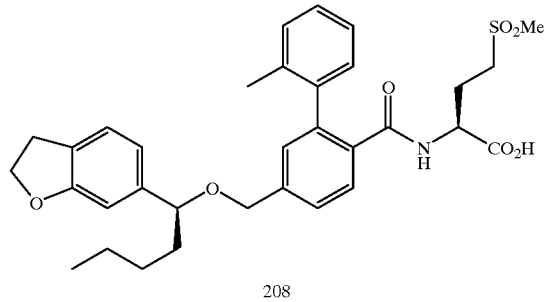
208
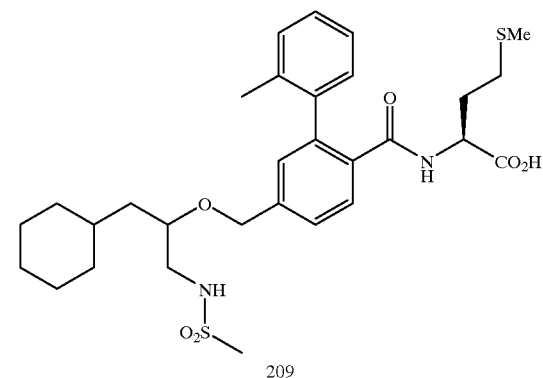
209
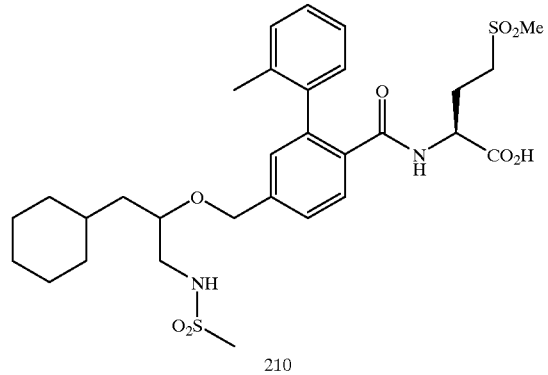
210
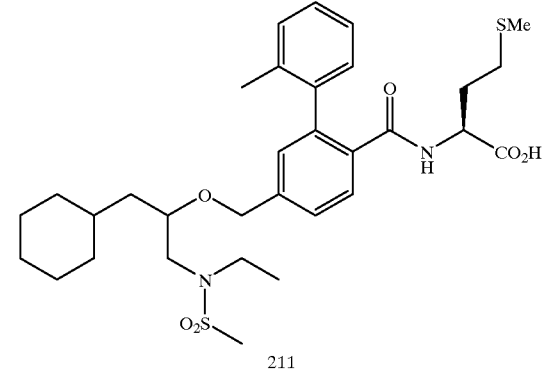
211

TABLE 7-continued
Ethers of the Type A-OL₁
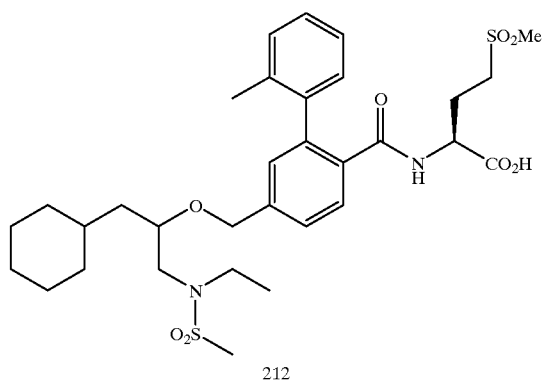
212
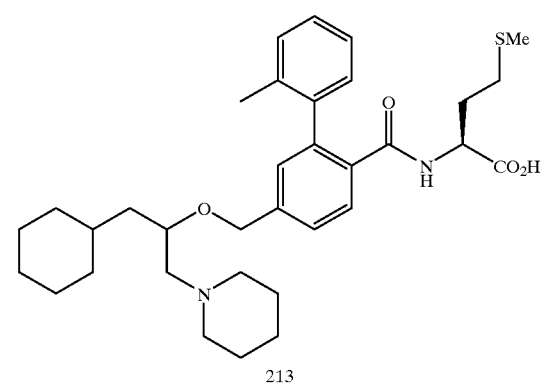
213
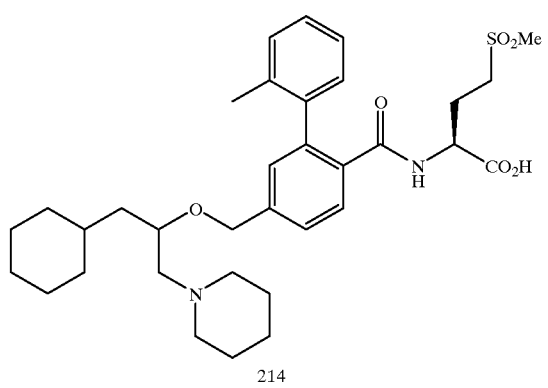
214
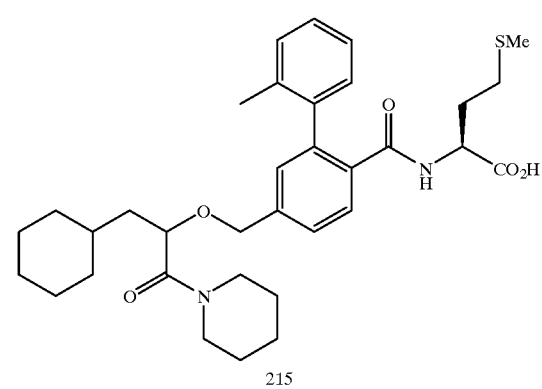
215
TABLE 7-continued
Ethers of the Type A-OL₁
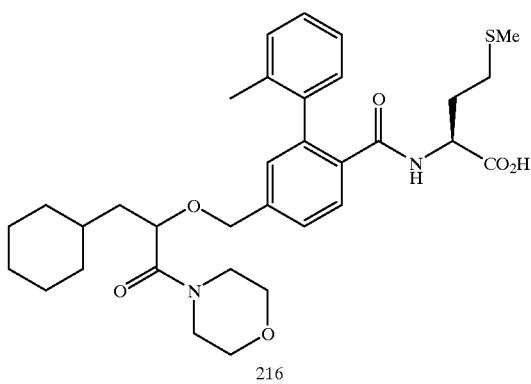
216
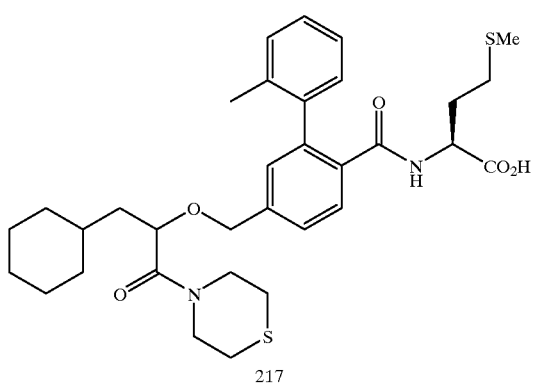
217
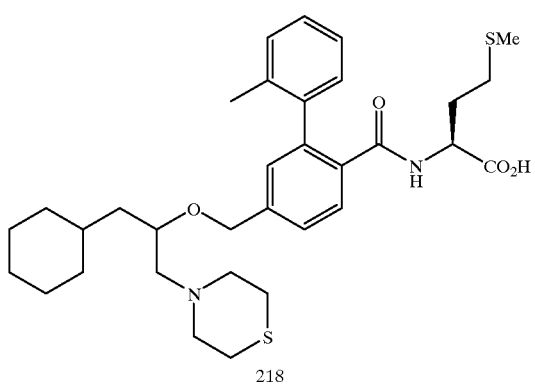
218
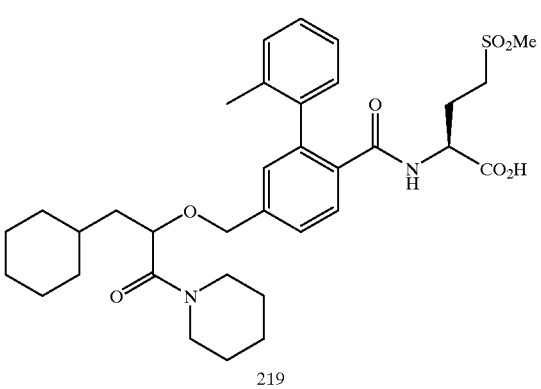
219

TABLE 7-continued
Ethers of the Type A-OL₁
220
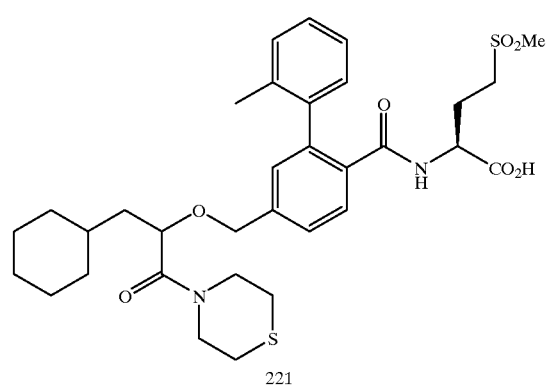
221
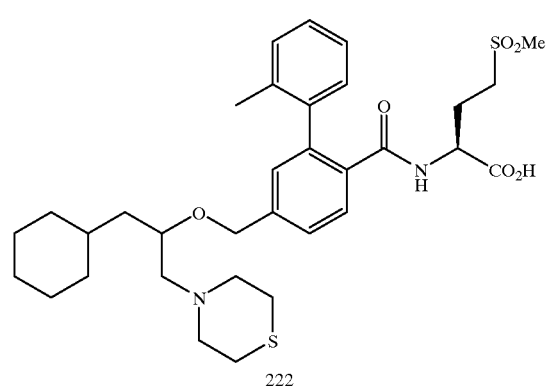
222
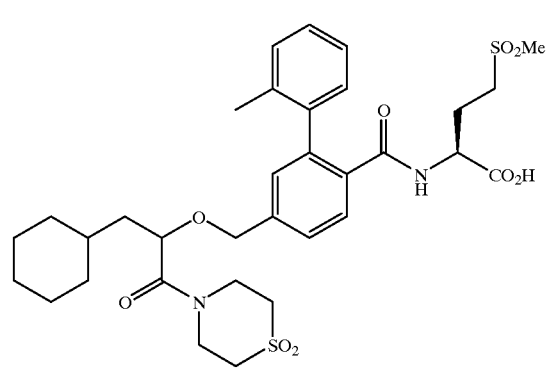
223
TABLE 7-continued
Ethers of the Type A-OL₁
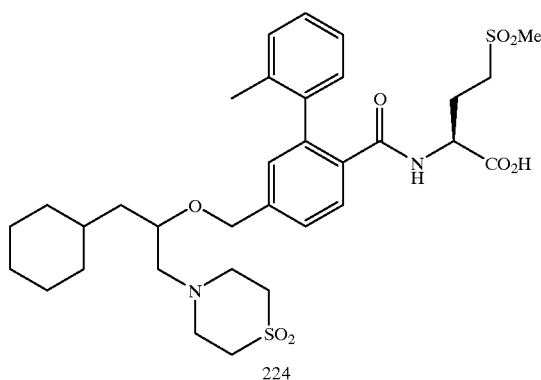
224
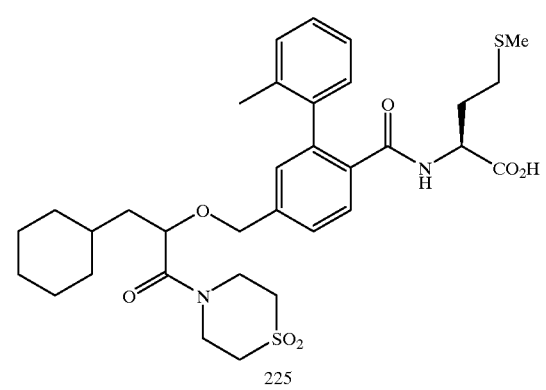
225
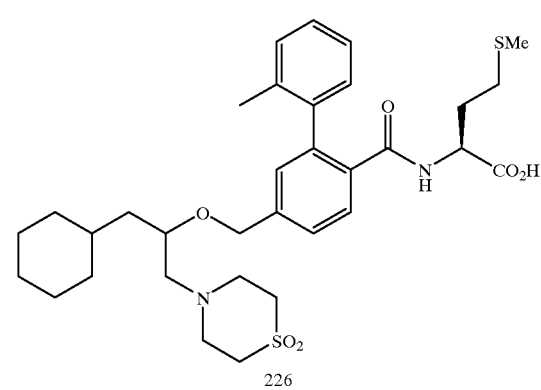
226
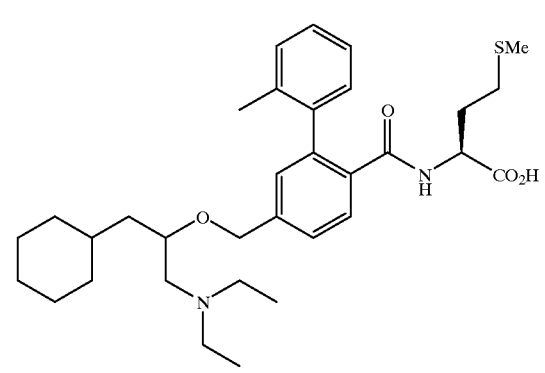
227

TABLE 7-continued

Ethers of the Type A-OL₁

228

TABLE 8

Sulfonamides of the Type ASO₂(B)N-L₁

1
2
3
4
5
6

TABLE 8-continued
Sulfonamides of the Type ASO$_2$(B)N-L$_1$
7
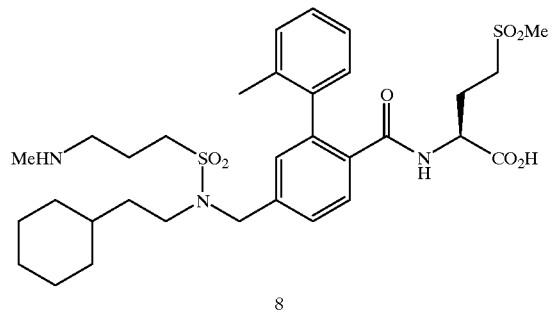
8
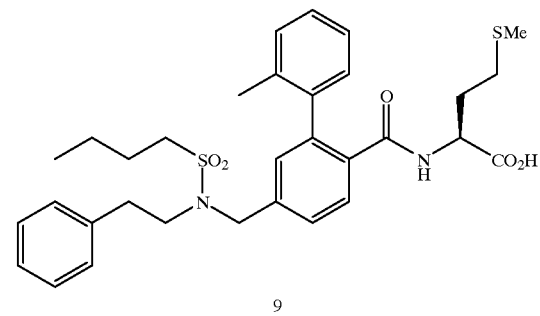
9
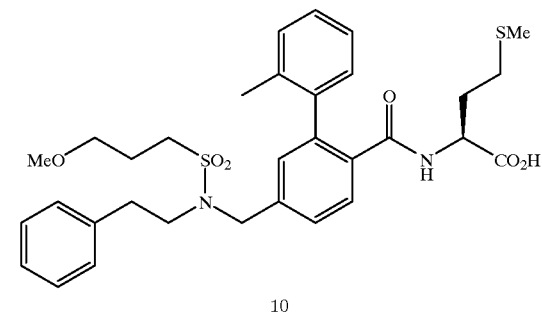
10
11
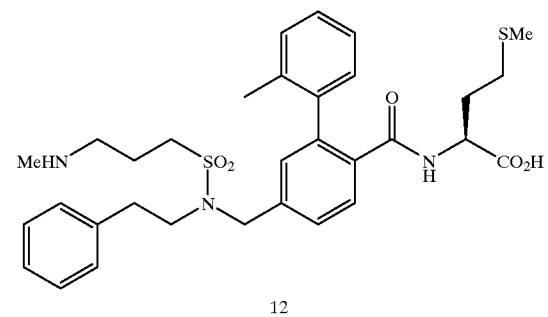
12
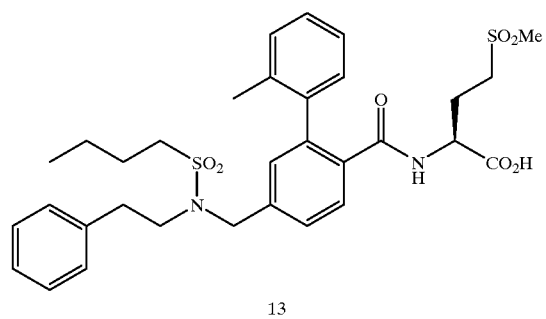
13
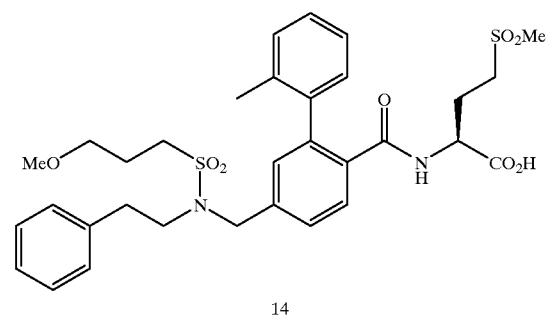
14

TABLE 8-continued
Sulfonamides of the Type $ASO_2(B)N-L_1$
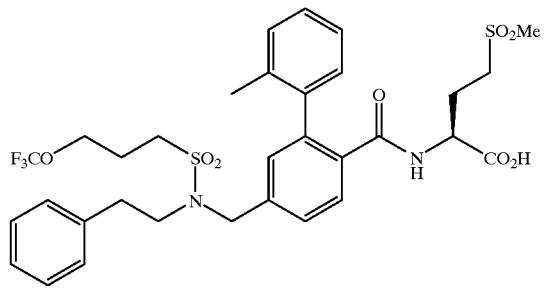
15
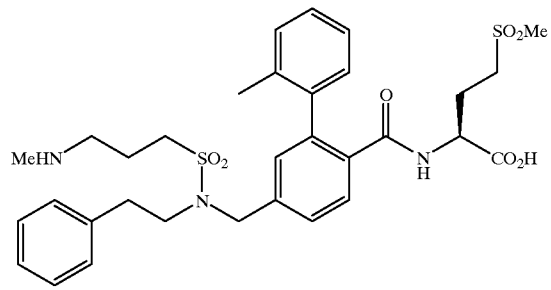
16
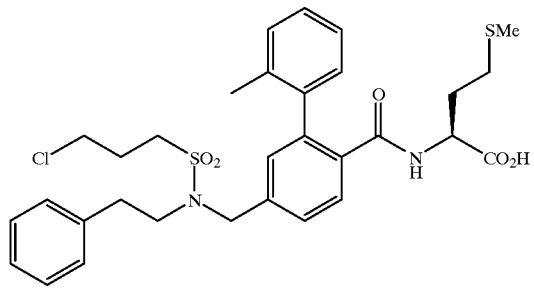
17
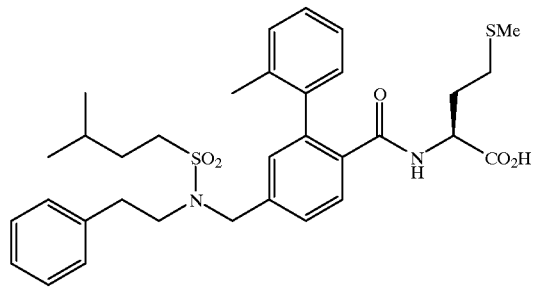
18
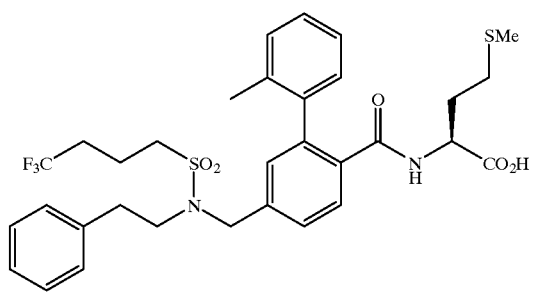
19
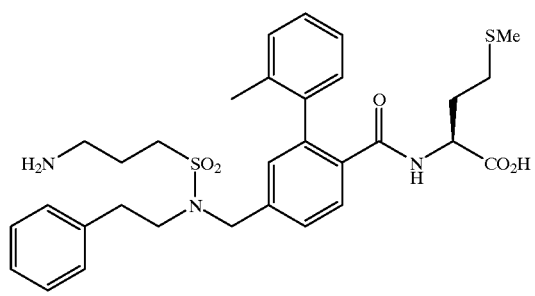
20
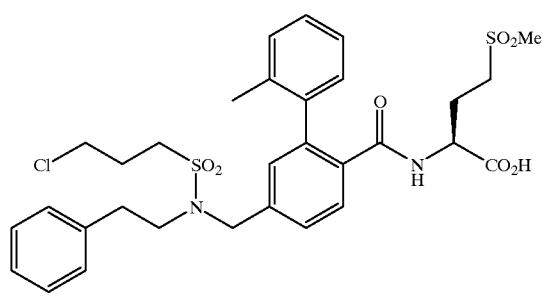
21
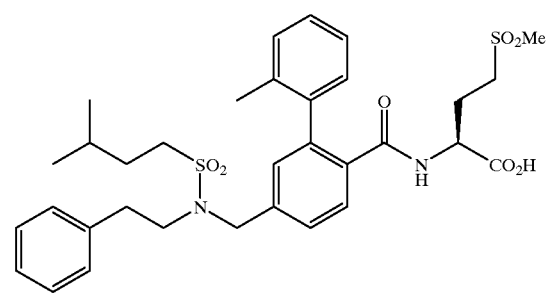
22

TABLE 8-continued
Sulfonamides of the Type $ASO_2(B)N-L_1$
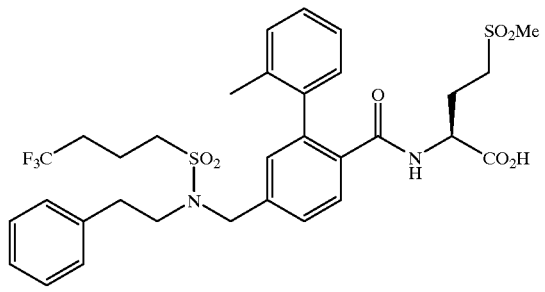
23
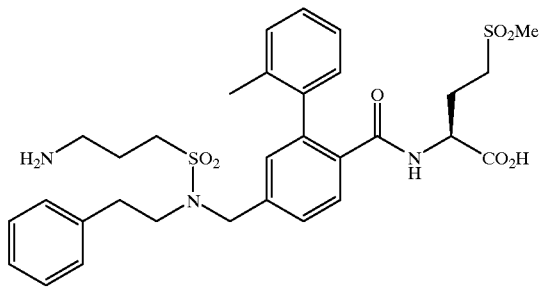
24
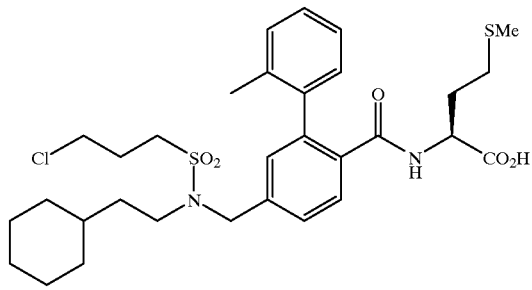
25
26
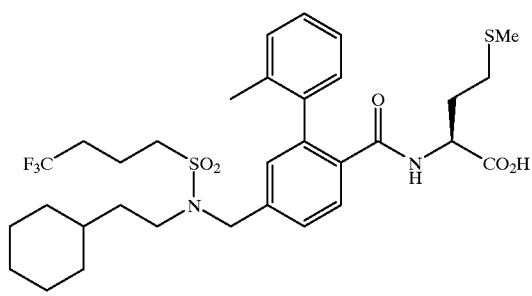
27
28
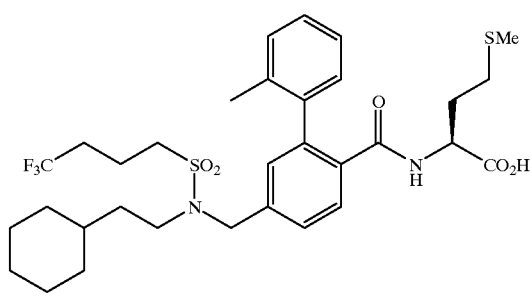
29
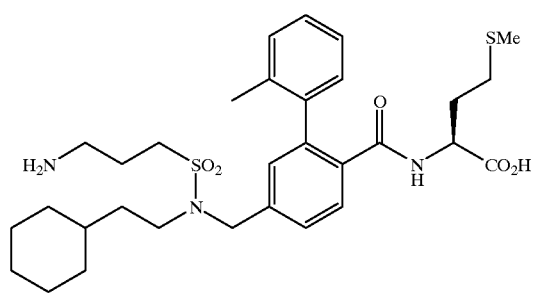
30

TABLE 8-continued
Sulfonamides of the Type ASO$_2$(B)N-L$_1$
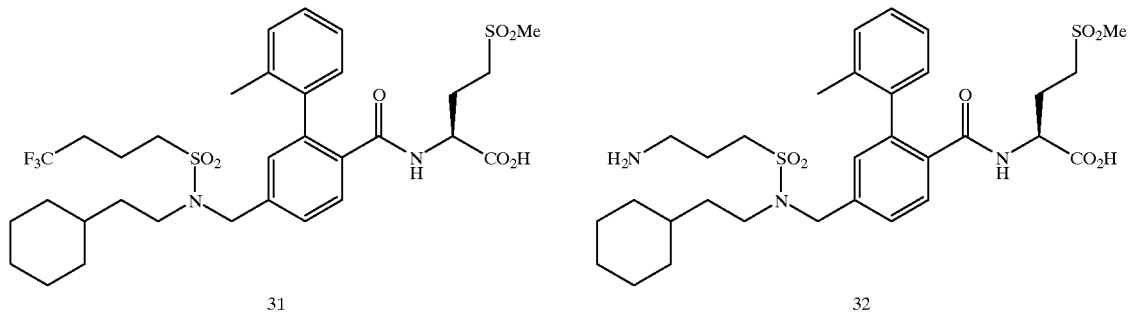
TABLE 9
Hydrocarbons of the Type A(B)CH$_2$-L$_1$
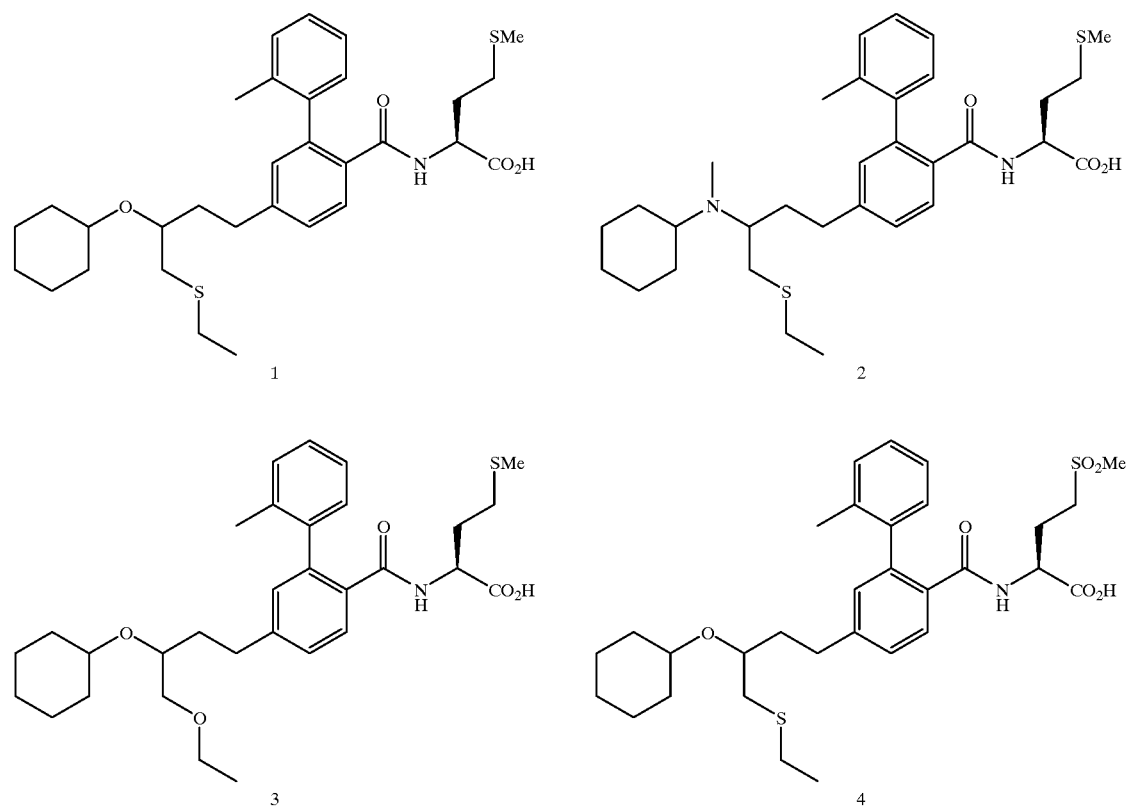

TABLE 9-continued
Hydrocarbons of the Type A(B)CH$_2$-L$_1$
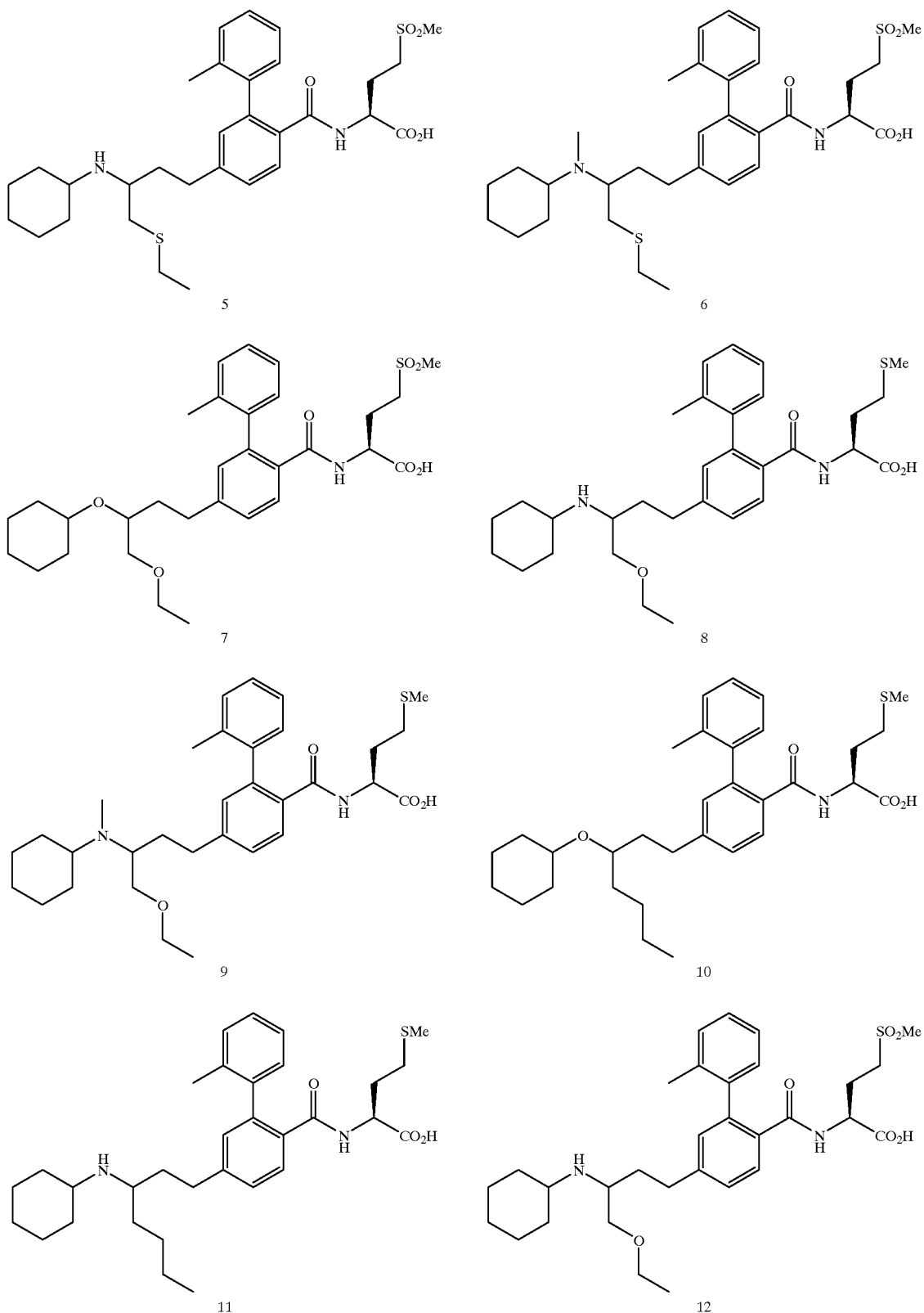

TABLE 9-continued
Hydrocarbons of the Type A(B)CH$_2$-L$_1$
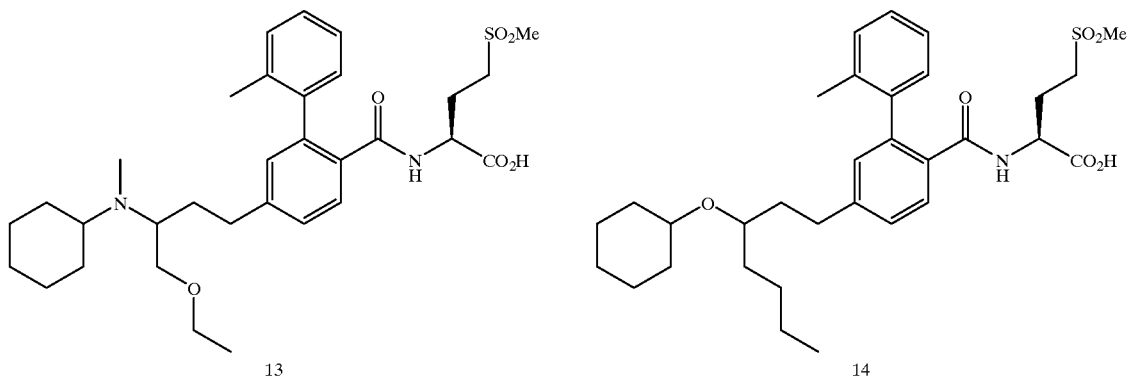
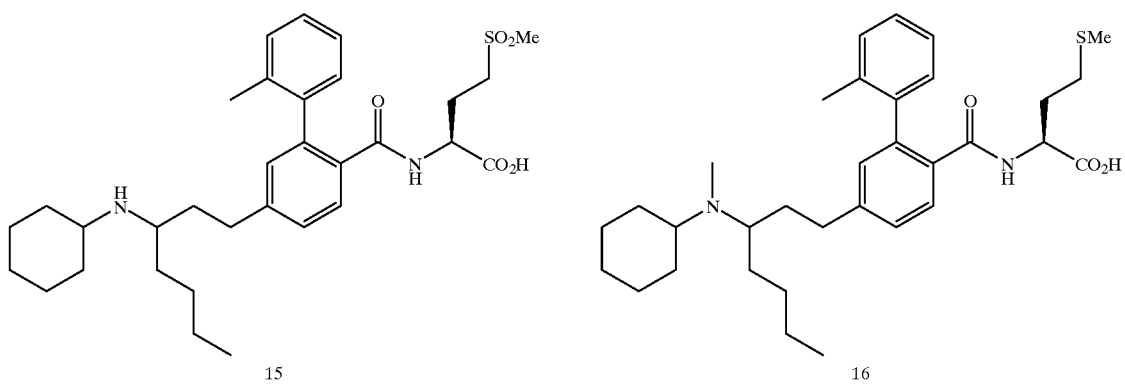
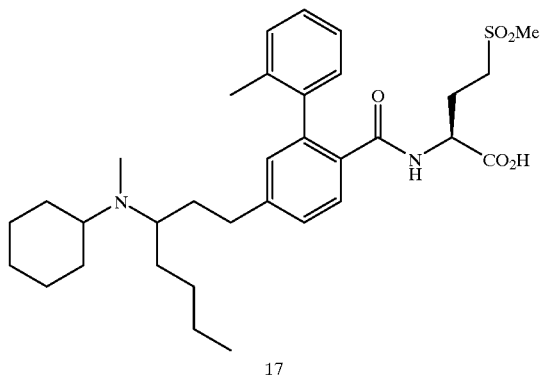
TABLE 10
Amines of the type B—NH$_2$
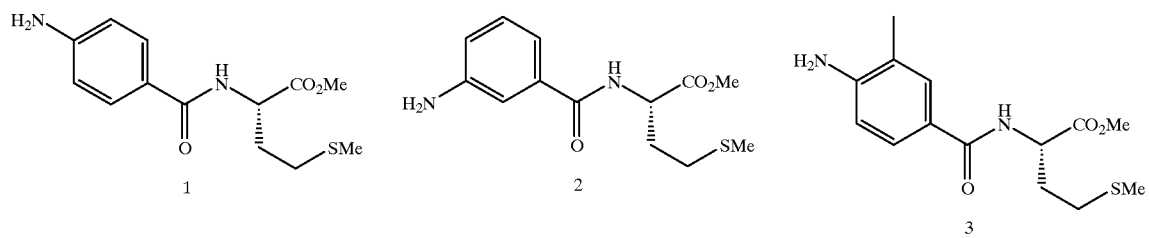

TABLE 10-continued
Amines of the type B—NH$_2$
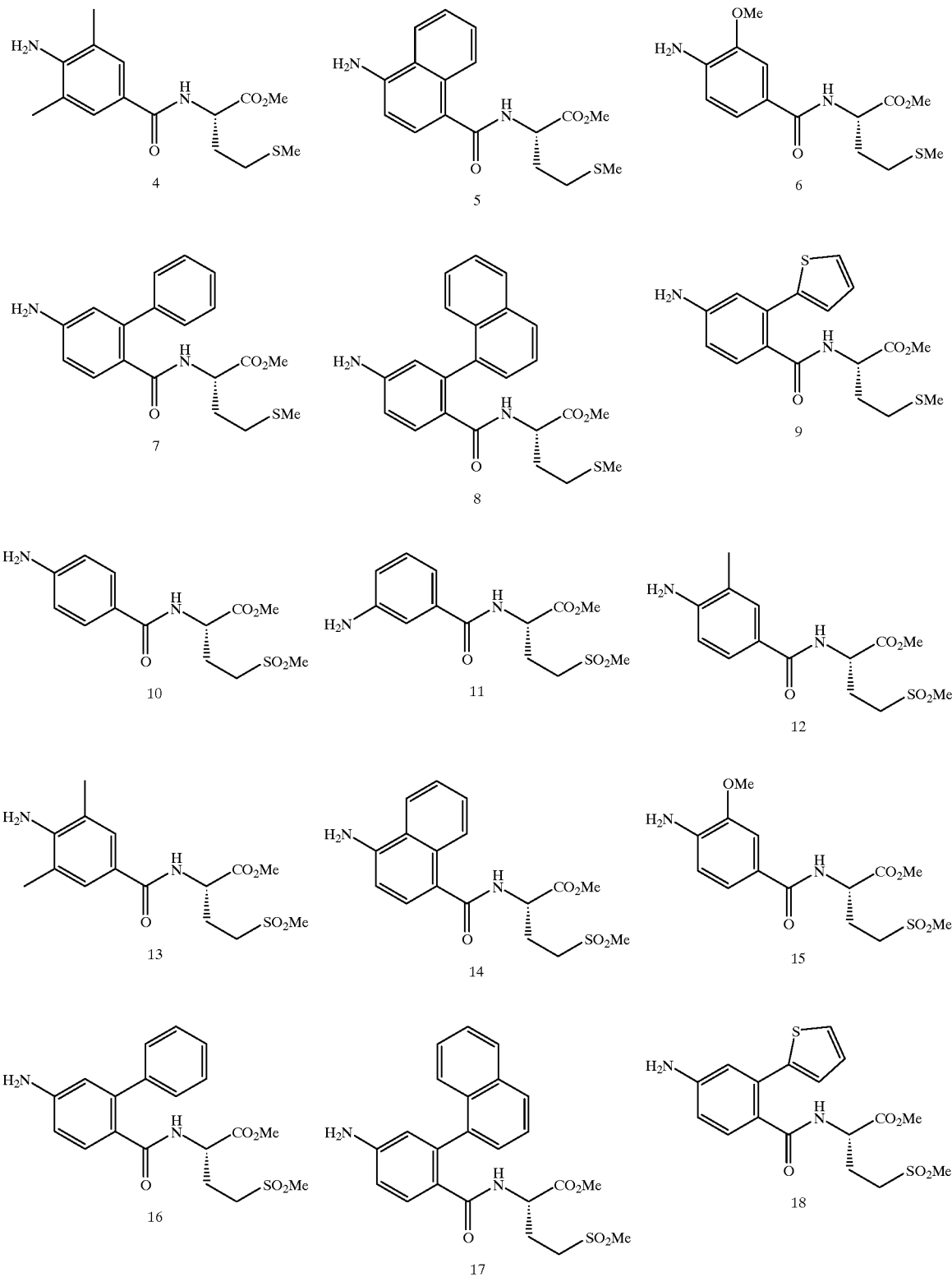

TABLE 10-continued
Amines of the type B—NH₂
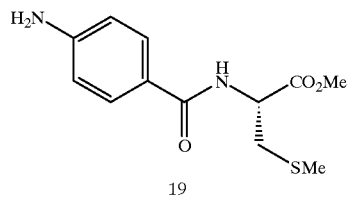
19
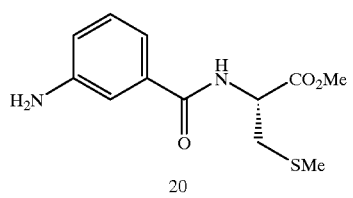
20
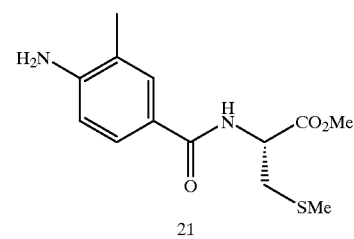
21
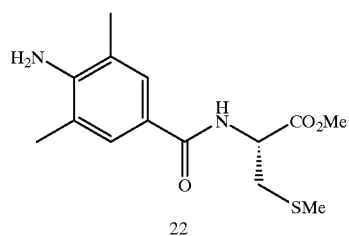
22
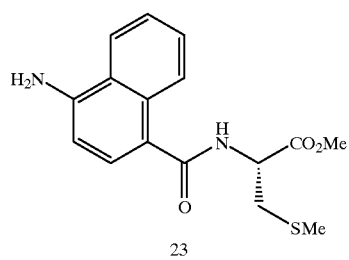
23
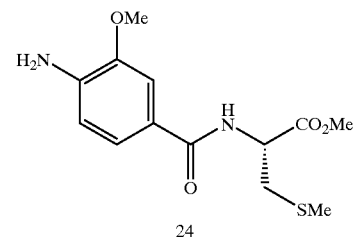
24
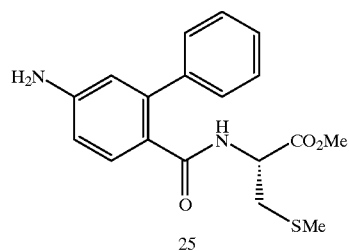
25
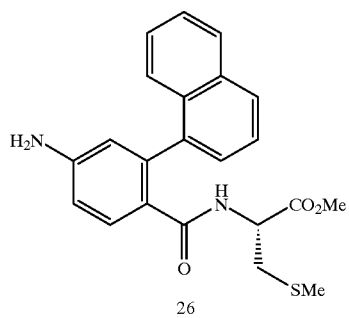
26
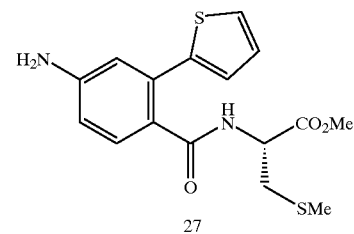
27
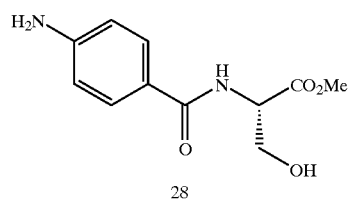
28
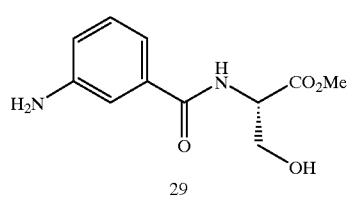
29
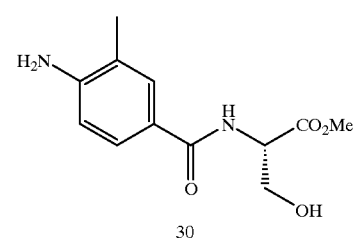
30
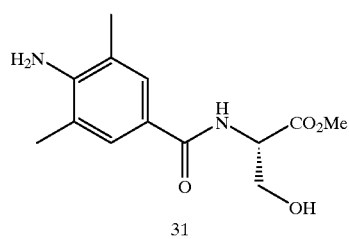
31
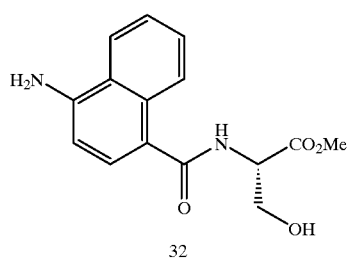
32
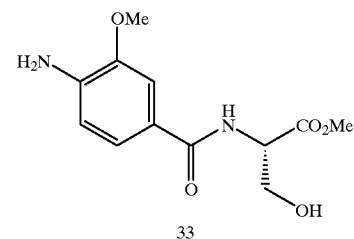
33

TABLE 10-continued
Amines of the type B—NH$_2$
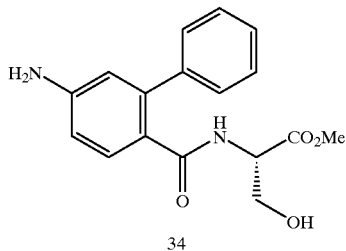
34
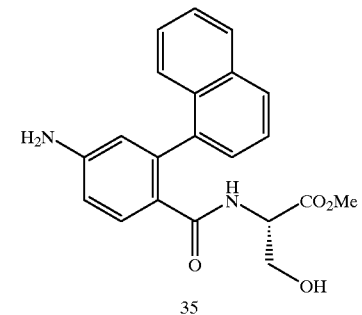
35
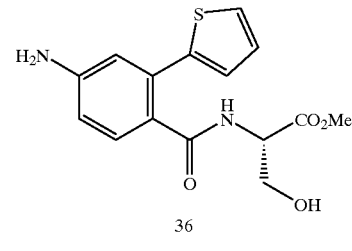
36
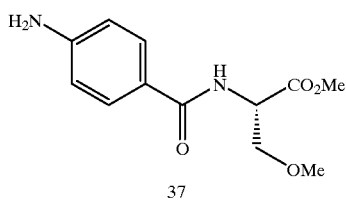
37
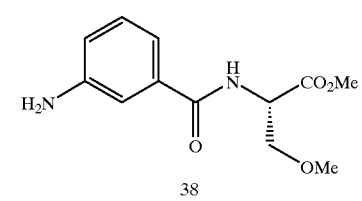
38
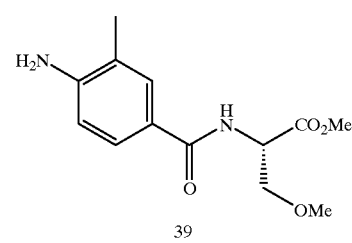
39
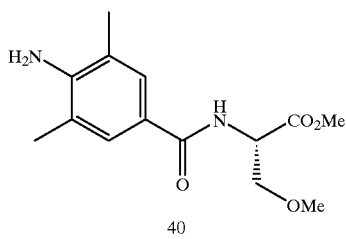
40
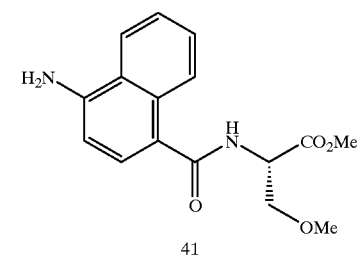
41
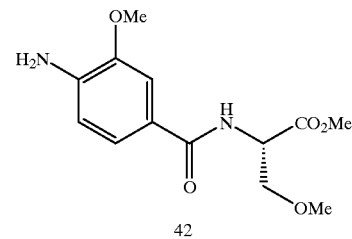
42
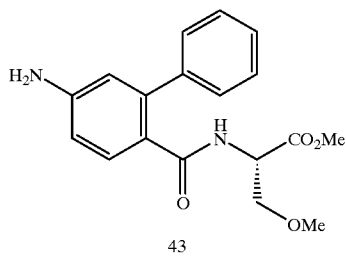
43
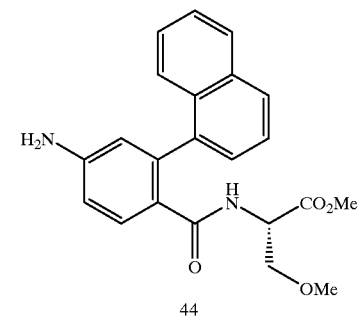
44
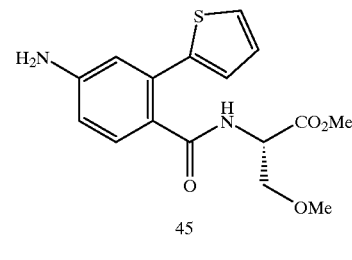
45
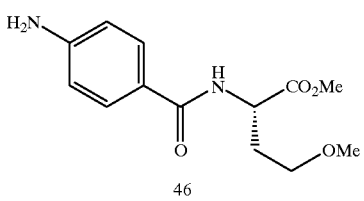
46
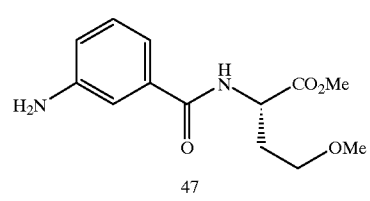
47
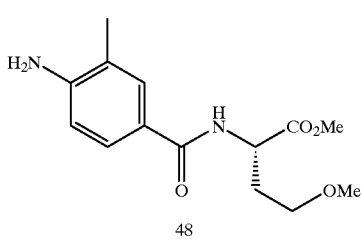
48

TABLE 10-continued
Amines of the type B—NH$_2$
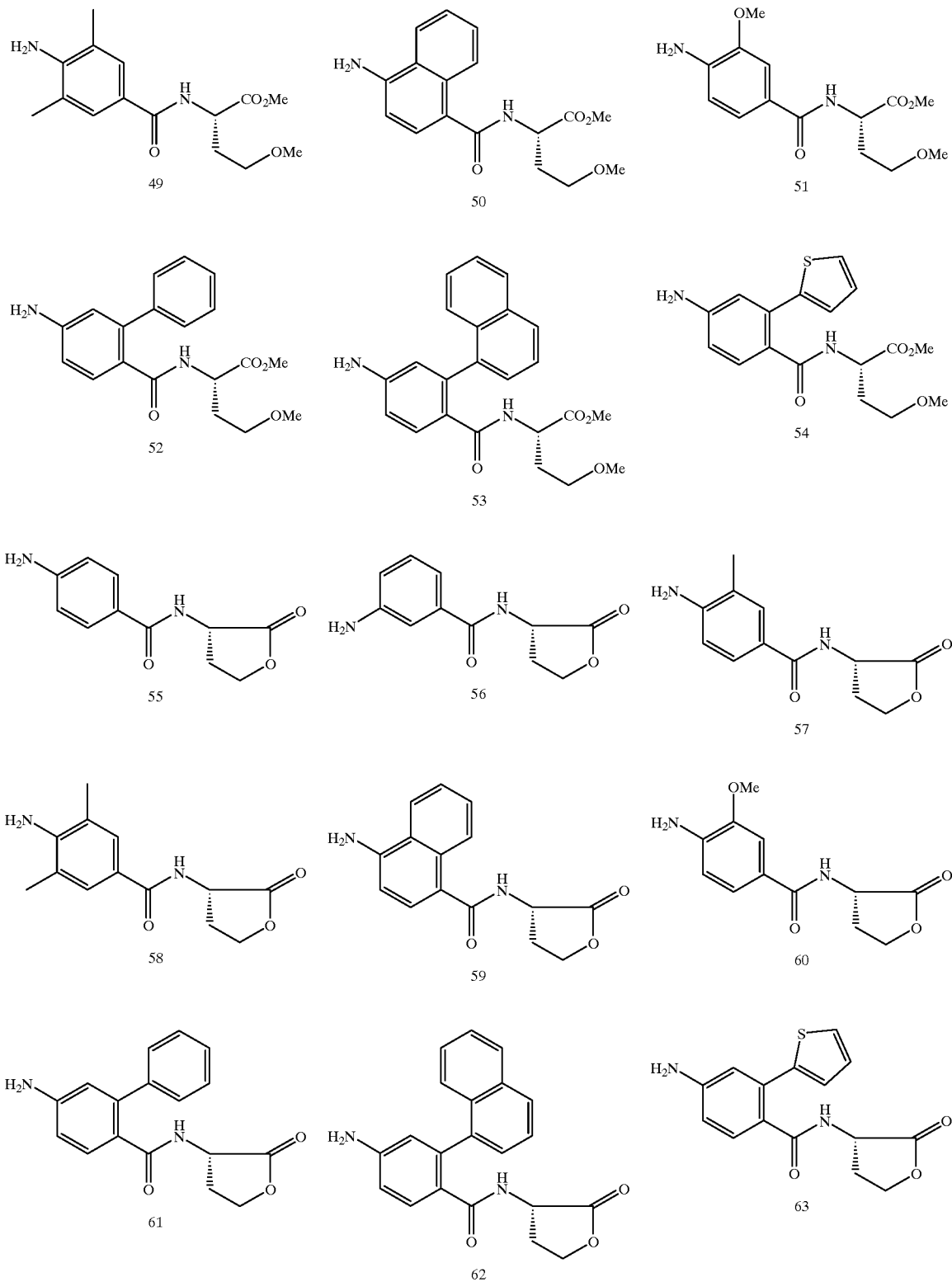

TABLE 10-continued
Amines of the type B—NH₂
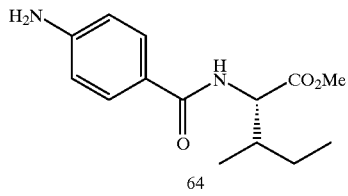
64
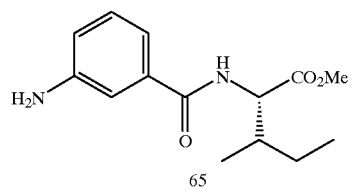
65
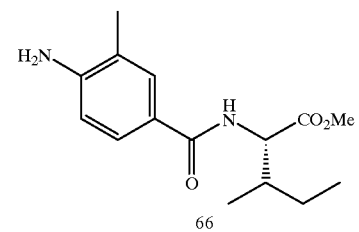
66
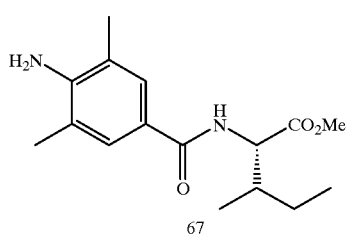
67
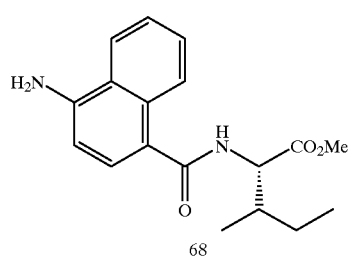
68
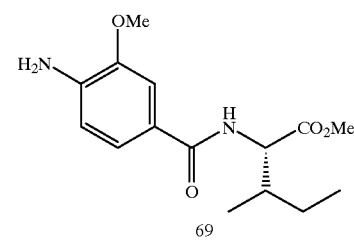
69
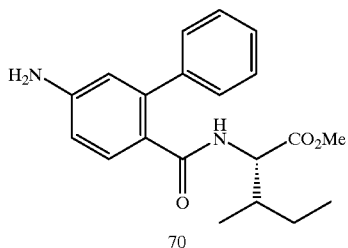
70
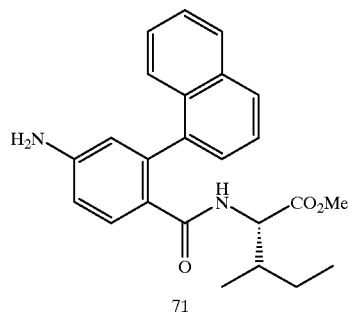
71
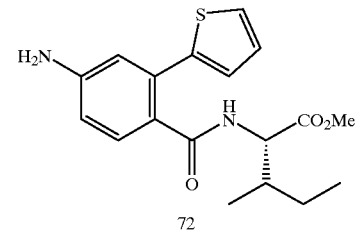
72
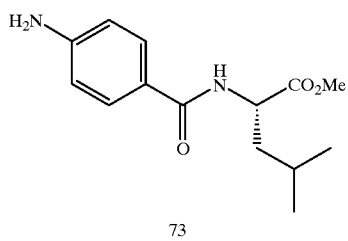
73
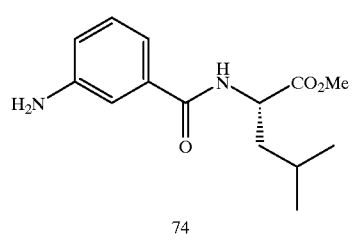
74
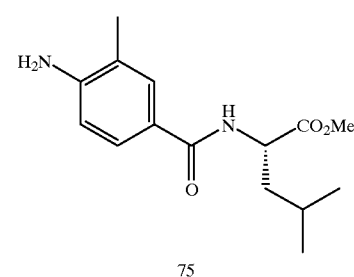
75
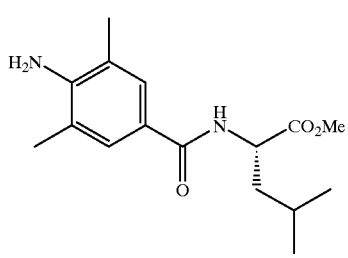
76
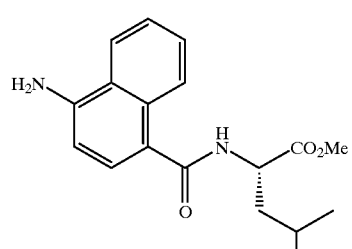
77
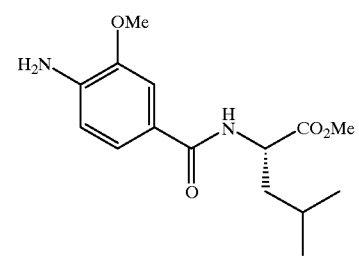
78

TABLE 10-continued
Amines of the type B—NH$_2$
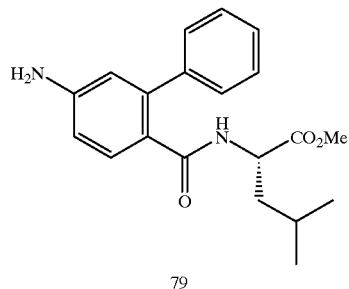
79
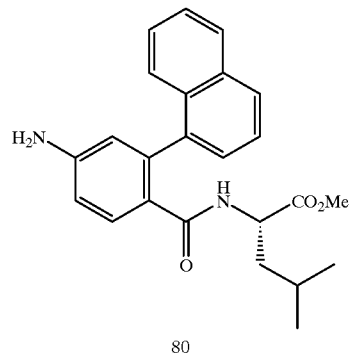
80
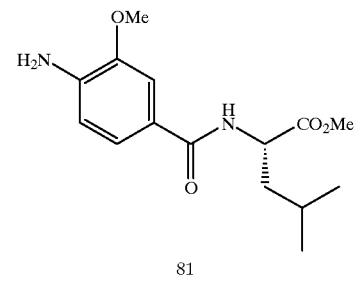
81
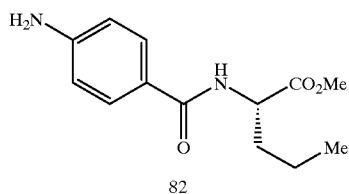
82
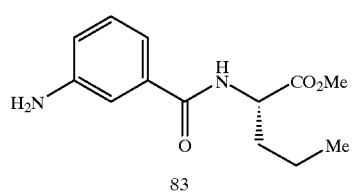
83
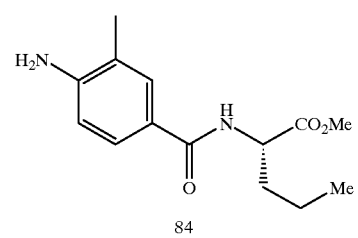
84
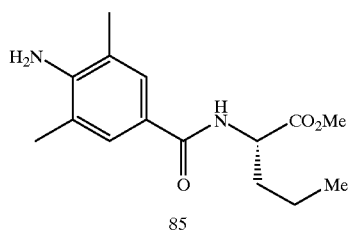
85
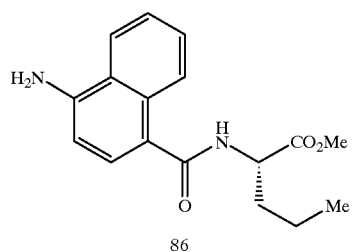
86
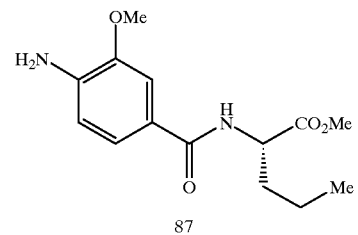
87
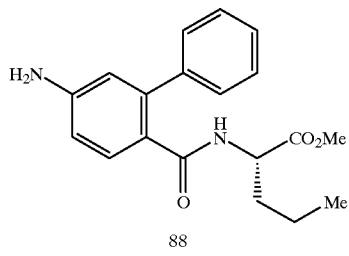
88
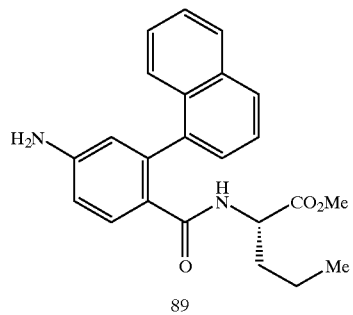
89
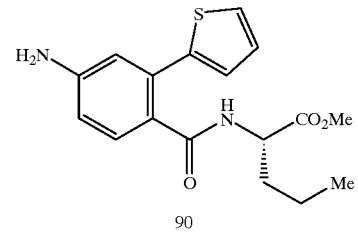
90
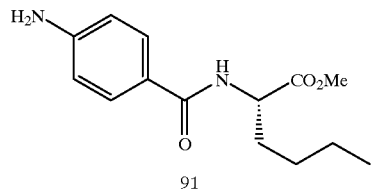
91
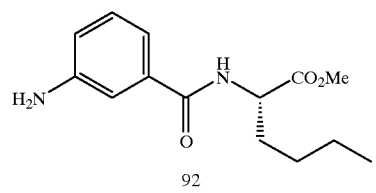
92
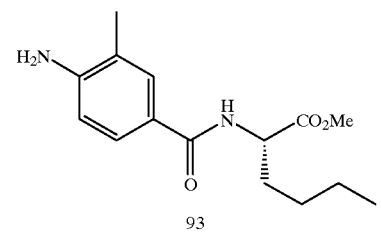
93

TABLE 10-continued
Amines of the type B—NH$_2$
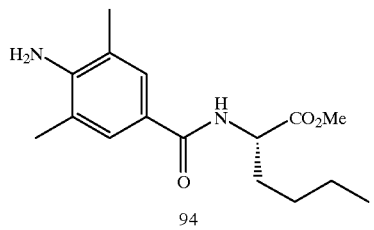
94
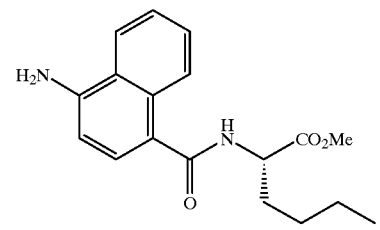
95
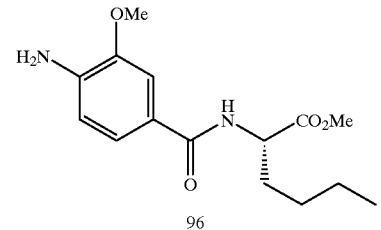
96
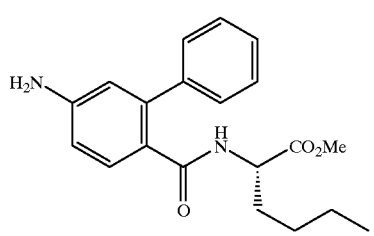
97
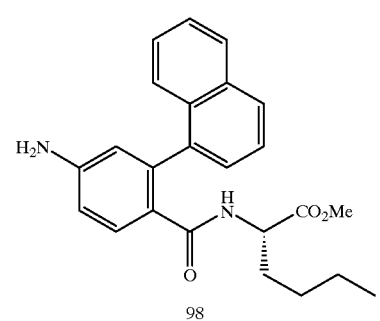
98
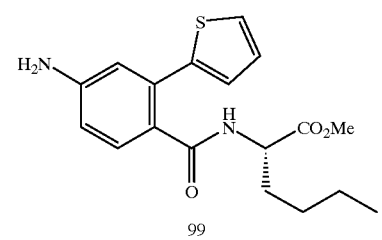
99
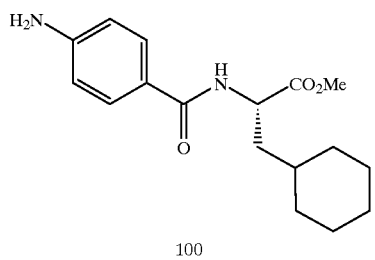
100
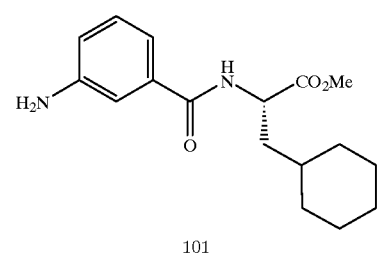
101
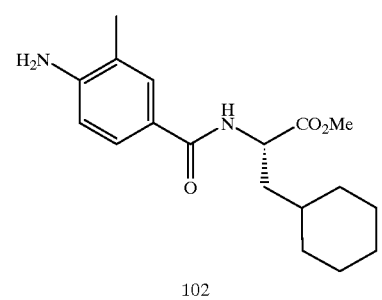
102
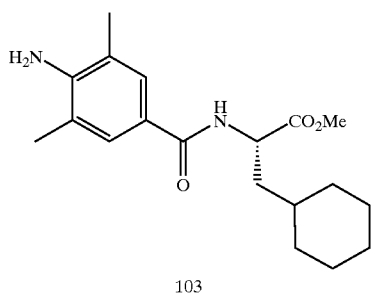
103
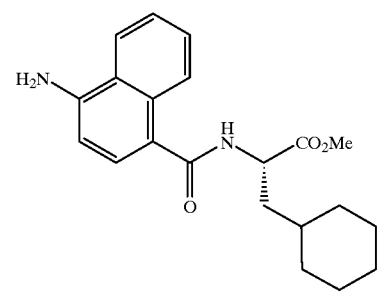
104
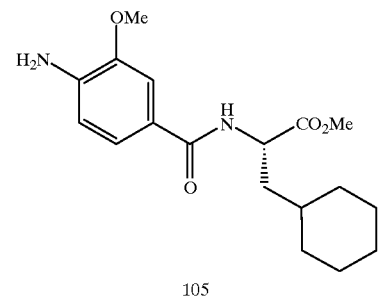
105

TABLE 10-continued
Amines of the type B—NH$_2$
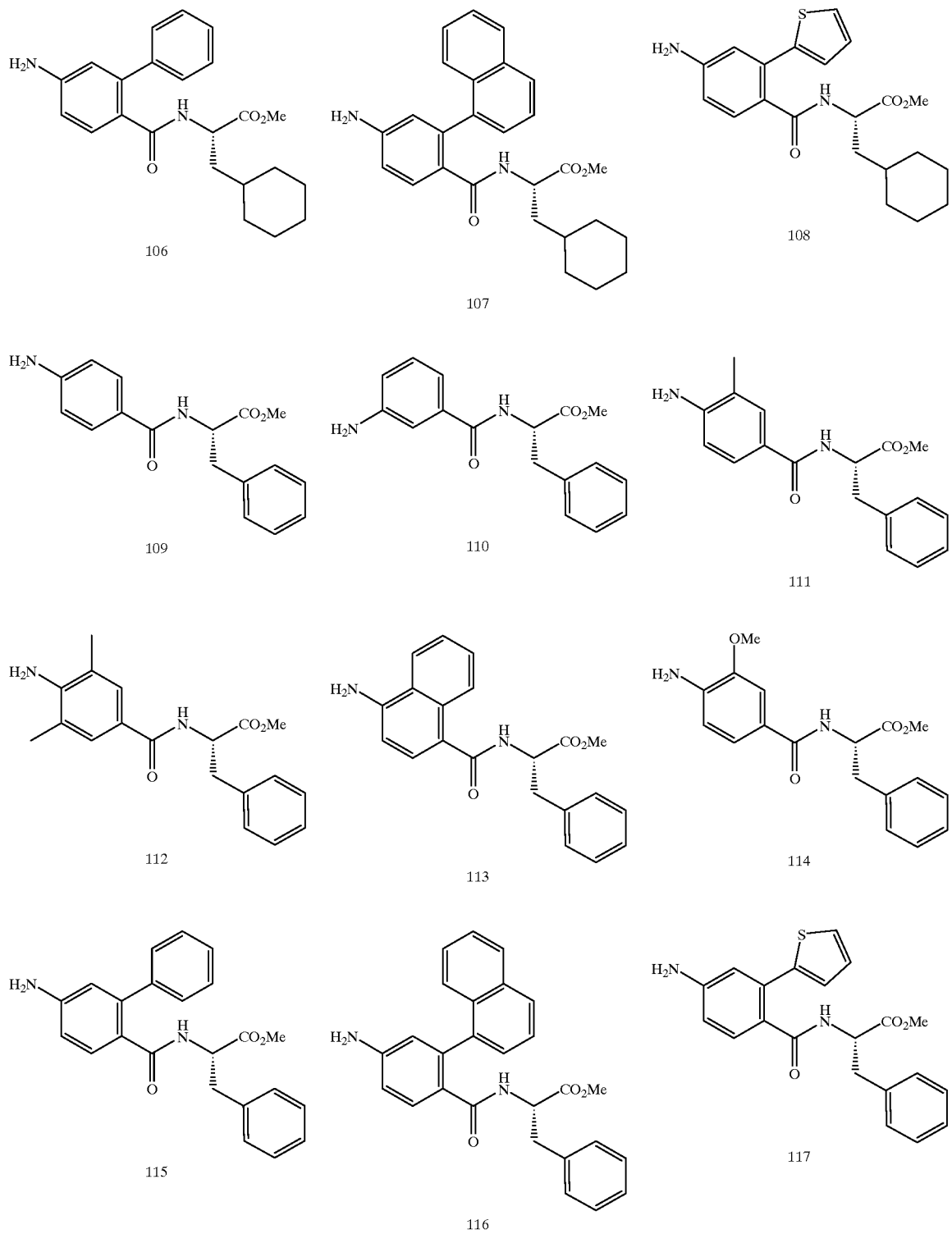

TABLE 10-continued
Amines of the type B—NH$_2$
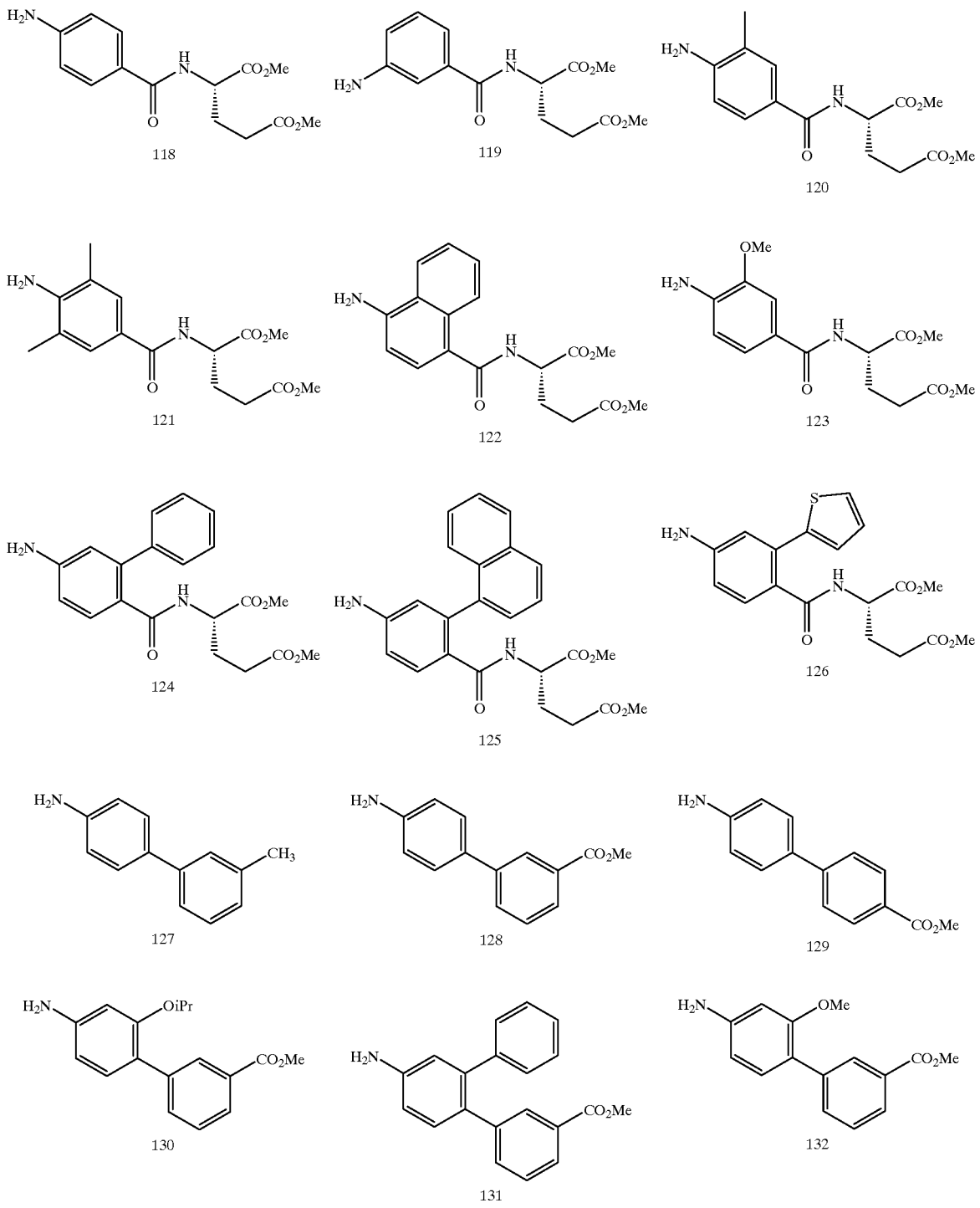

TABLE 11
Bromides of the type B—Br
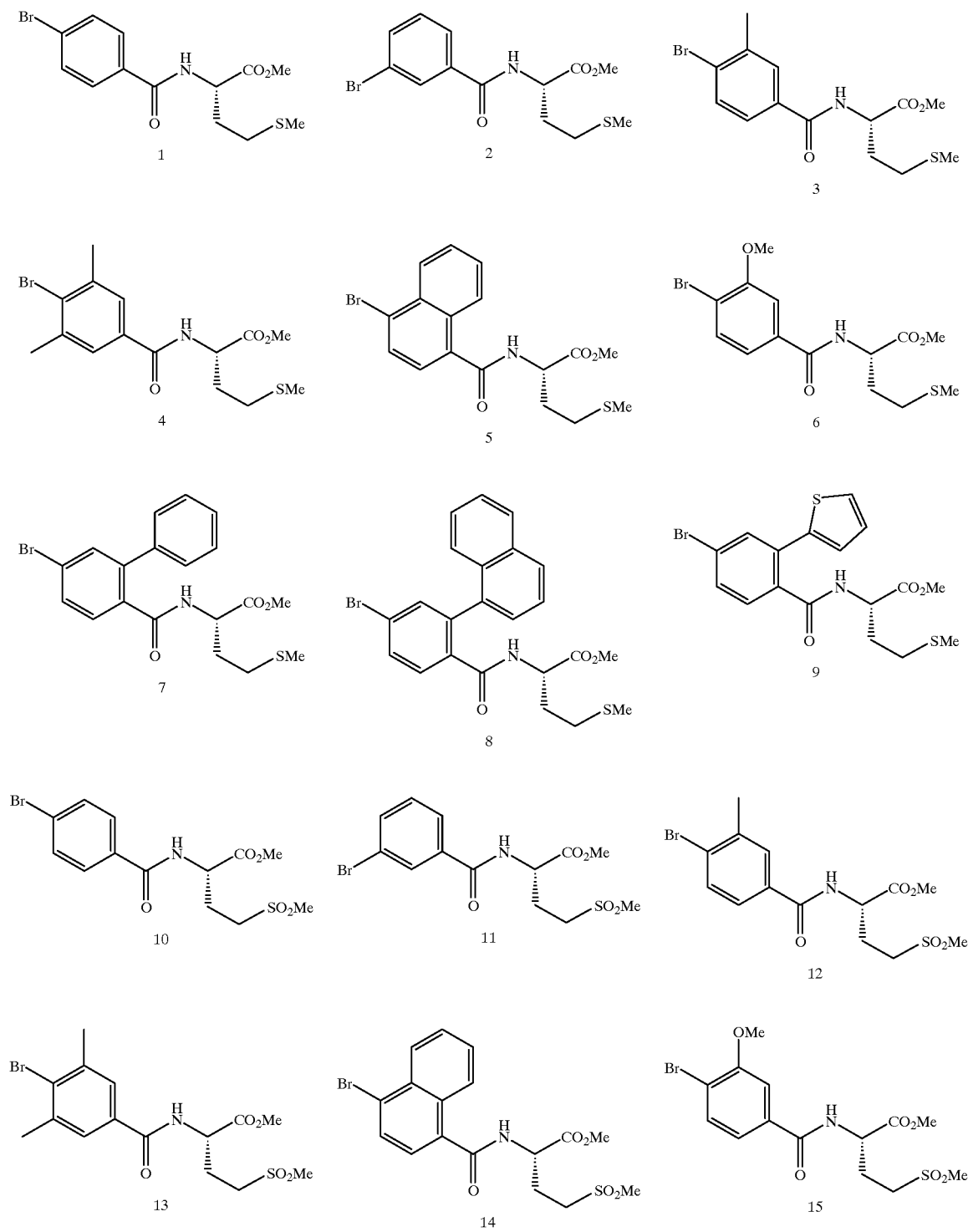

TABLE 11-continued
Bromides of the type B—Br
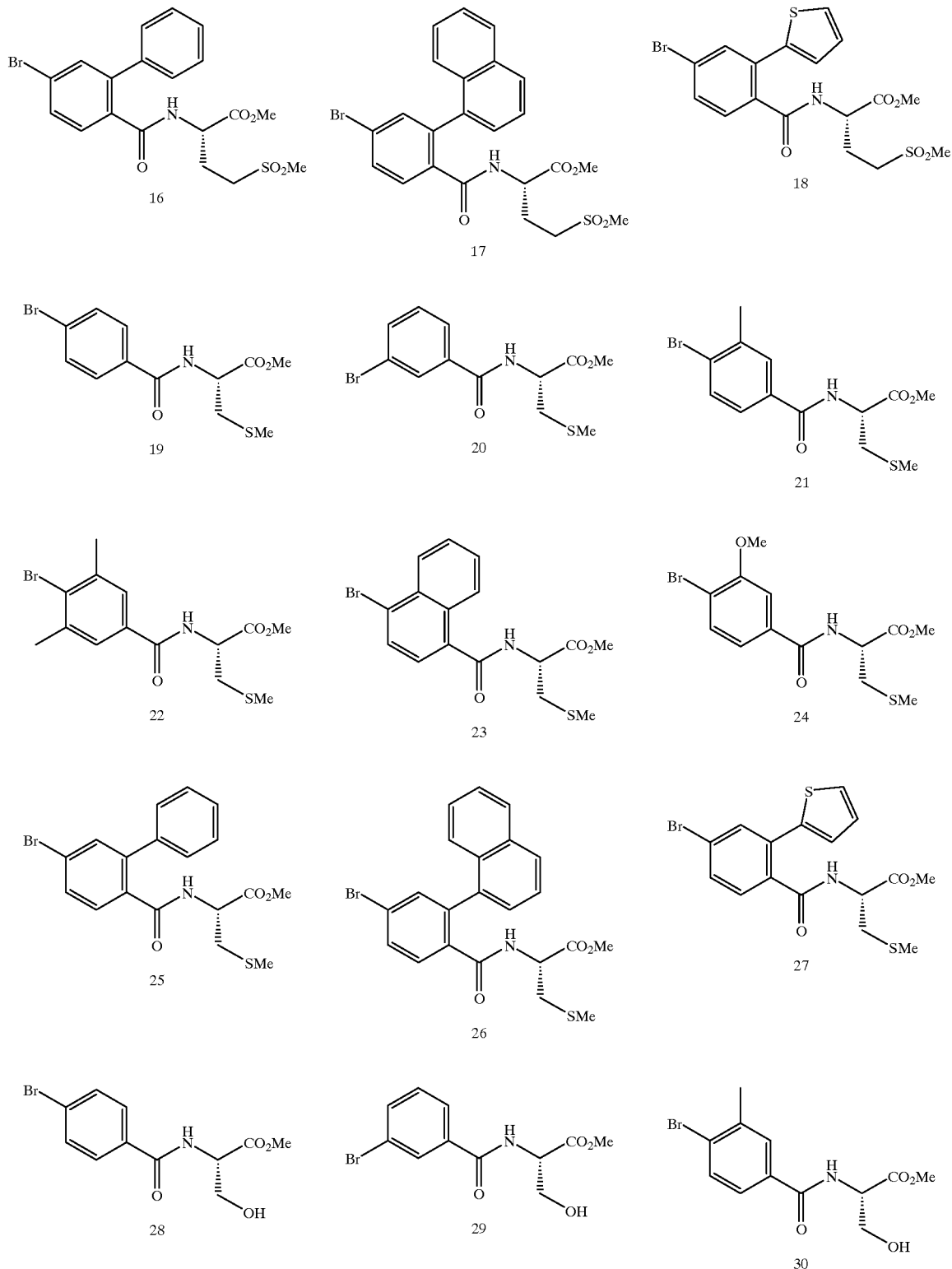

TABLE 11-continued
Bromides of the type B—Br
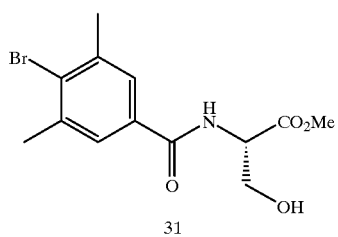
31
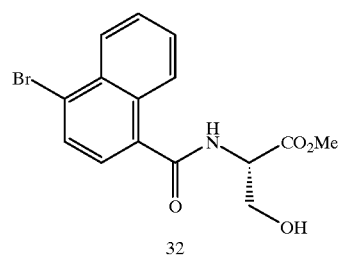
32
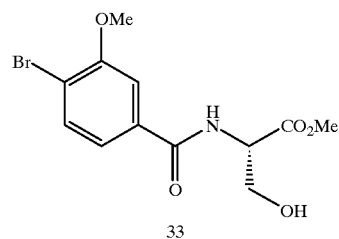
33
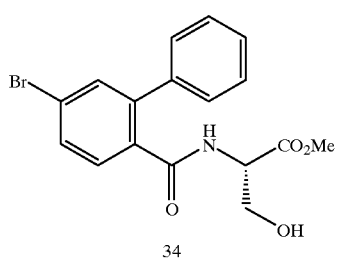
34
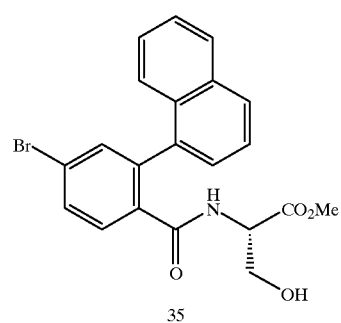
35
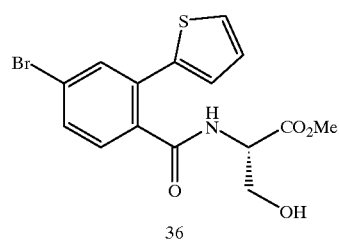
36
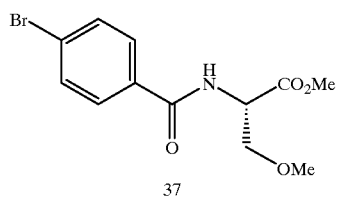
37
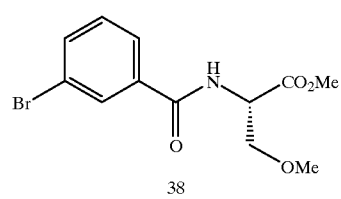
38
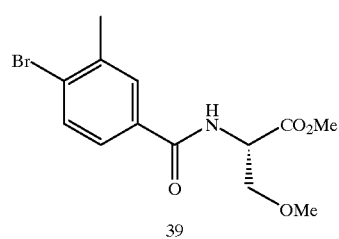
39
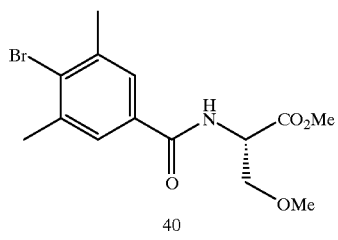
40
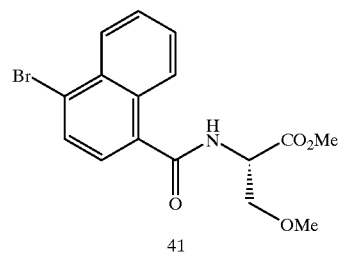
41
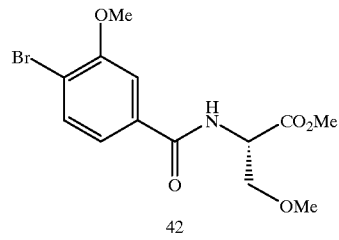
42
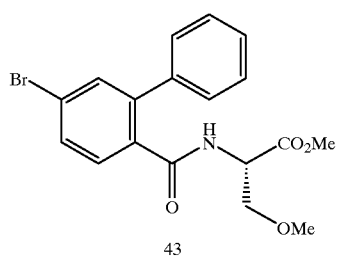
43
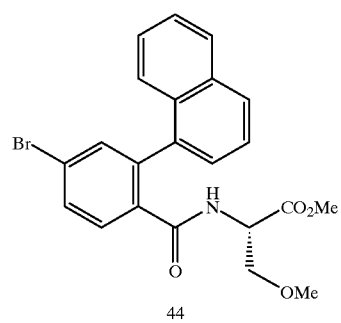
44
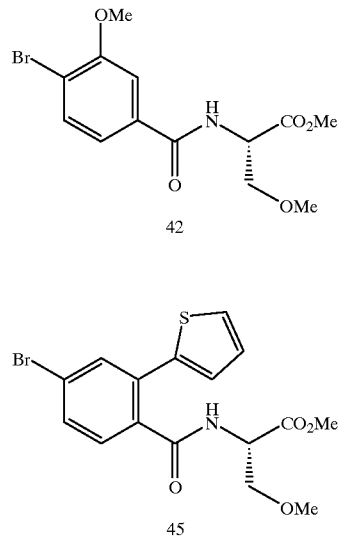
45

TABLE 11-continued
Bromides of the type B—Br
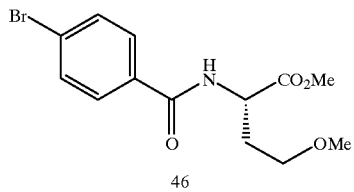
46
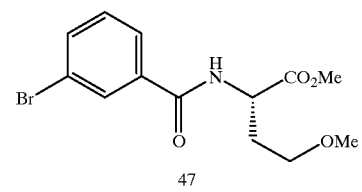
47
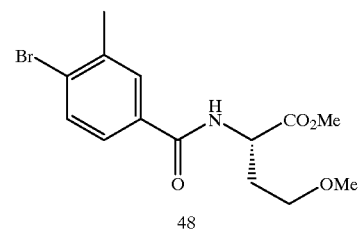
48
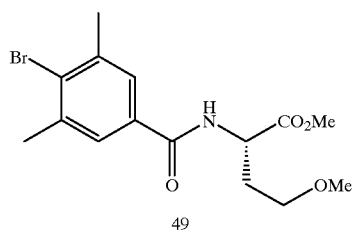
49
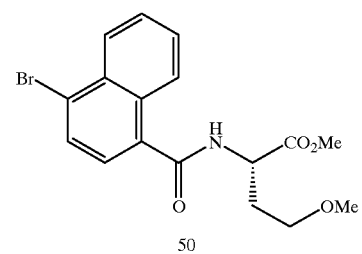
50
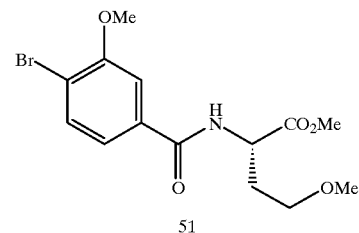
51
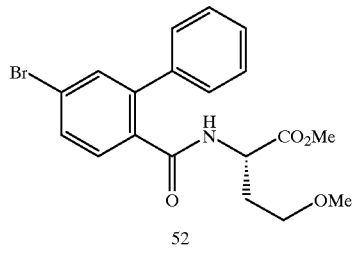
52
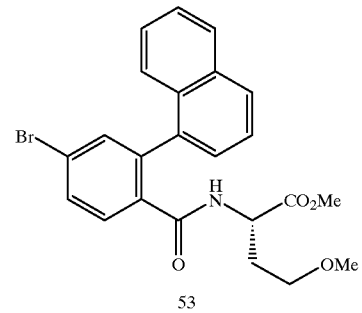
53
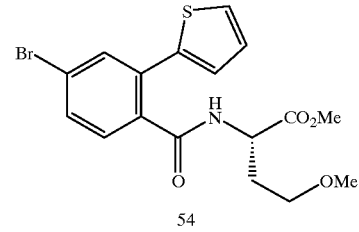
54
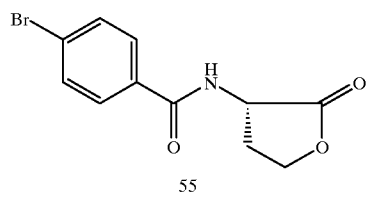
55
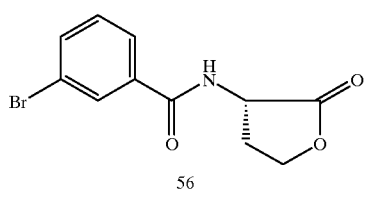
56
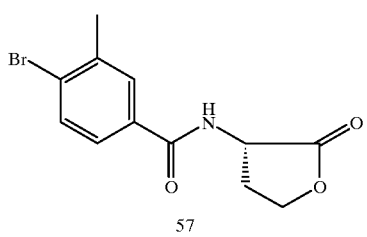
57
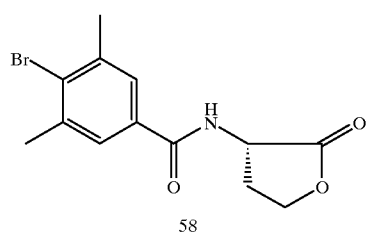
58
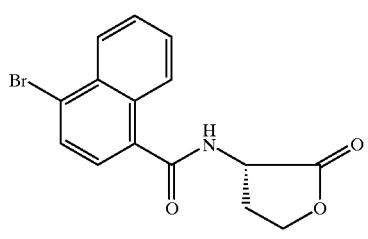
59
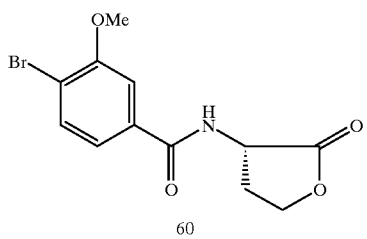
60

TABLE 11-continued
Bromides of the type B—Br
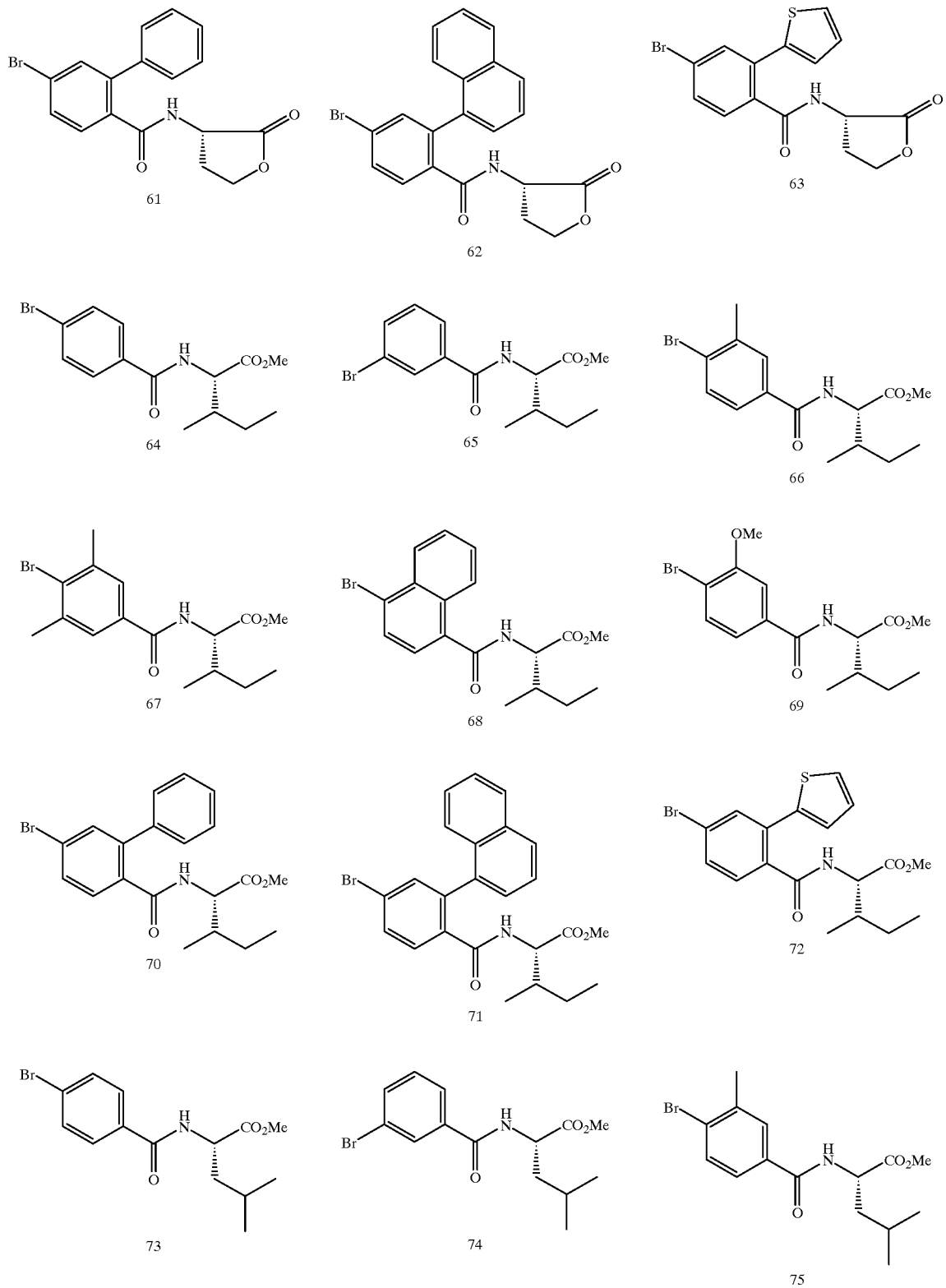

TABLE 11-continued
Bromides of the type B—Br
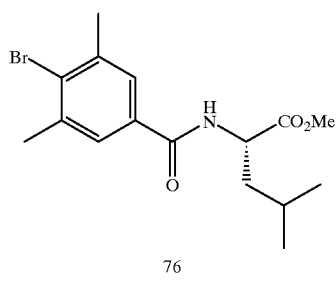
76
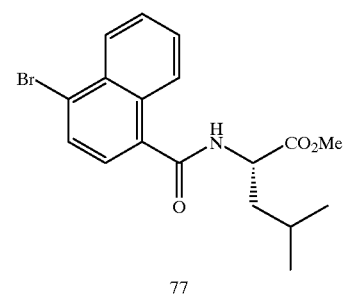
77
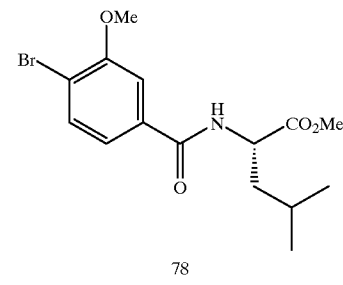
78
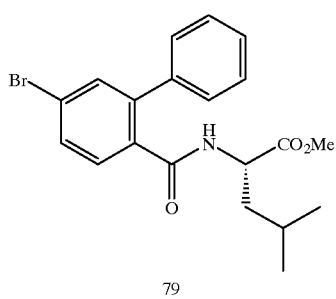
79
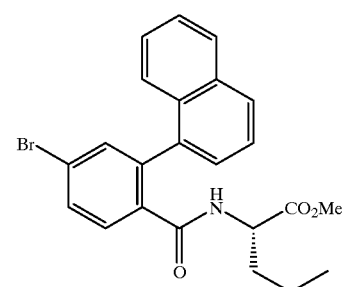
80
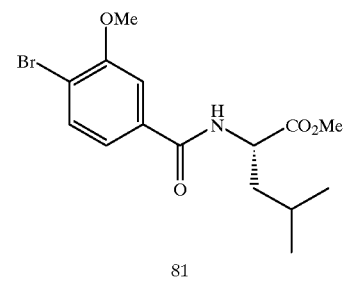
81
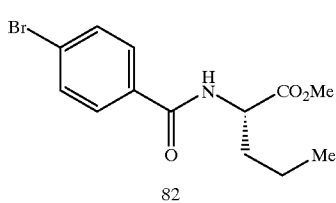
82
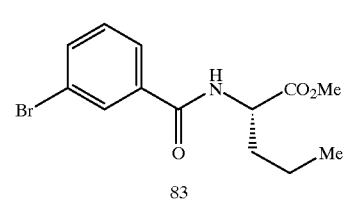
83
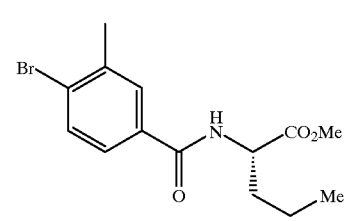
84
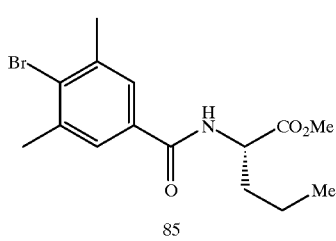
85
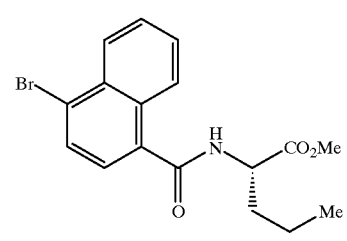
86
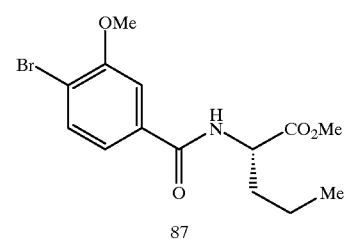
87
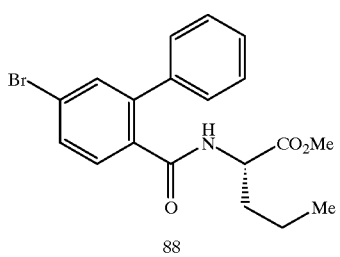
88
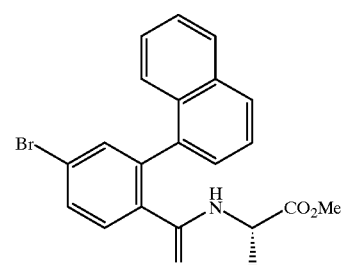
89
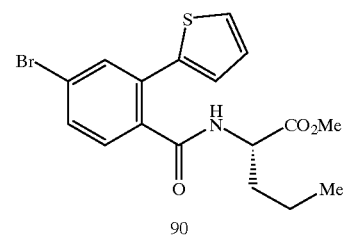
90

TABLE 11-continued
Bromides of the type B—Br
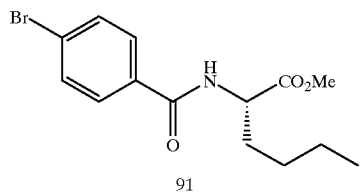
91
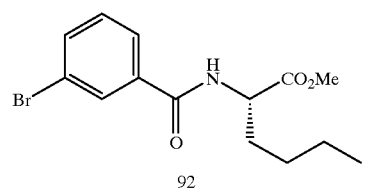
92
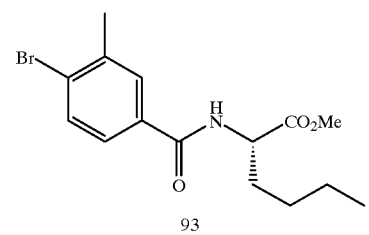
93
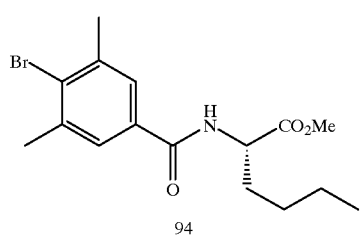
94
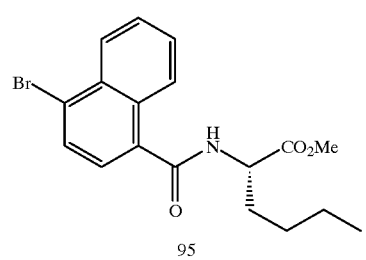
95
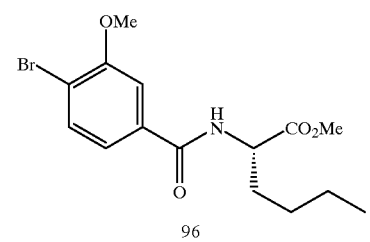
96
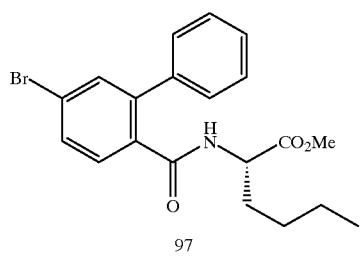
97
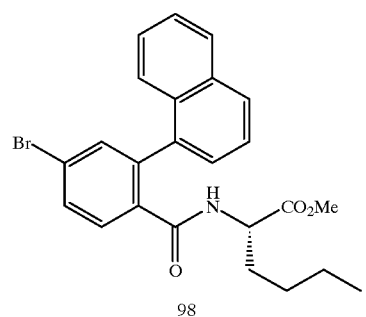
98
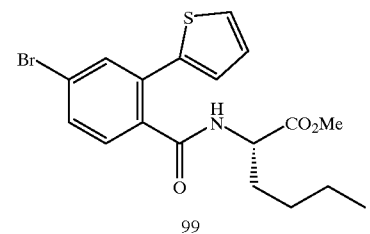
99
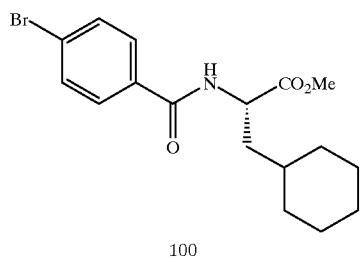
100
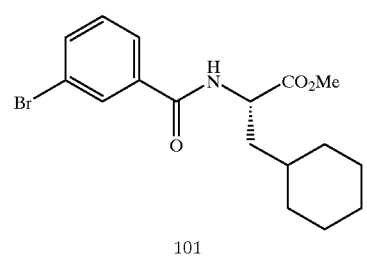
101
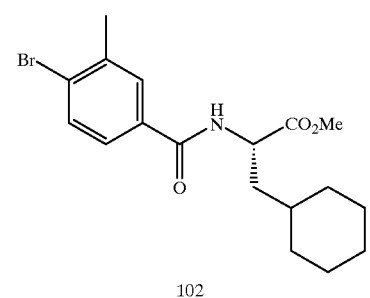
102
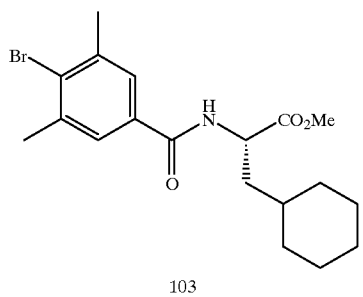
103
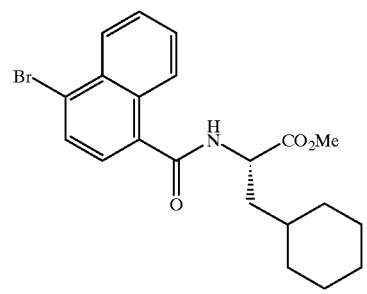
104
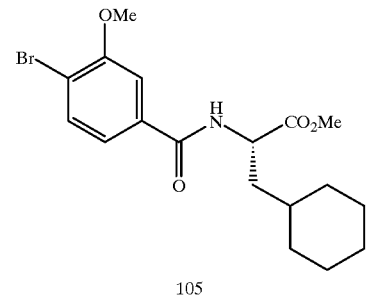
105

TABLE 11-continued
Bromides of the type B—Br
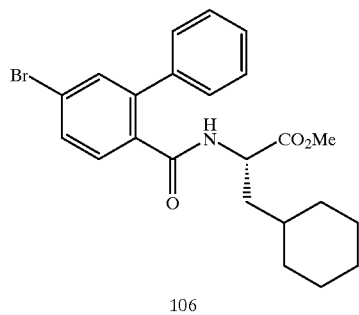
106
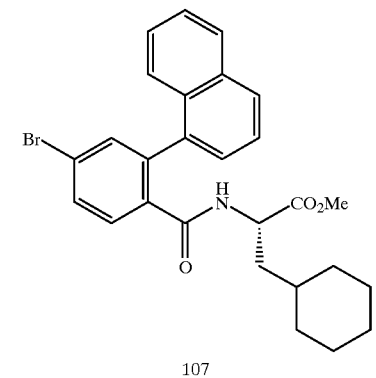
107
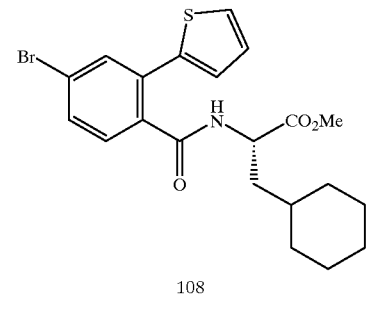
108
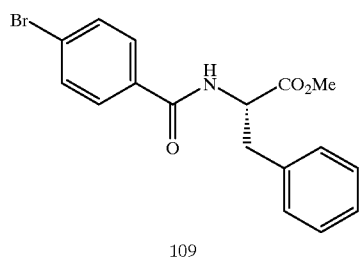
109
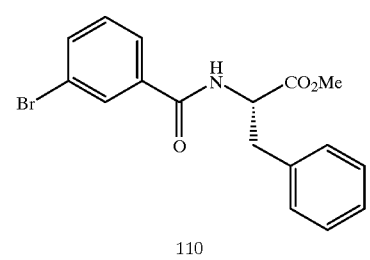
110
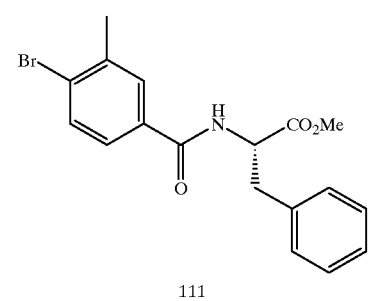
111
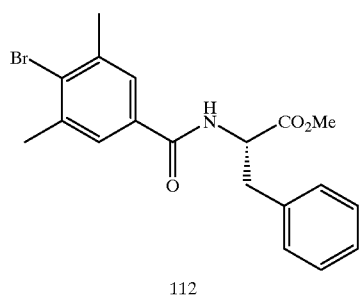
112
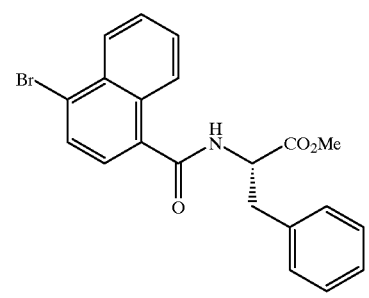
113
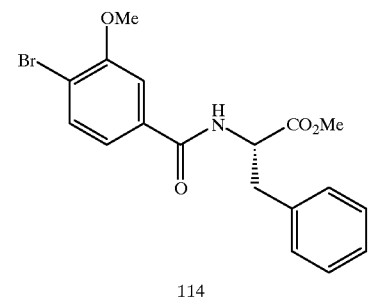
114
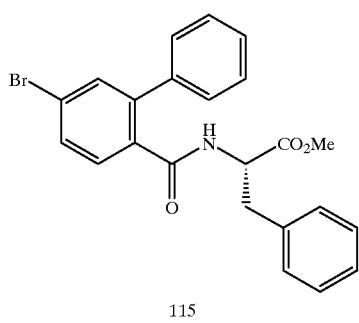
115
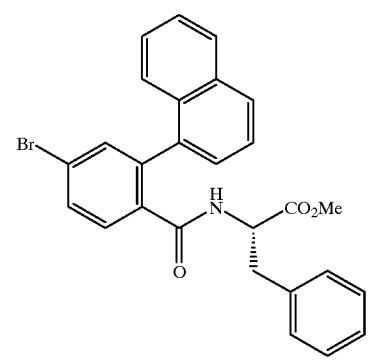
116
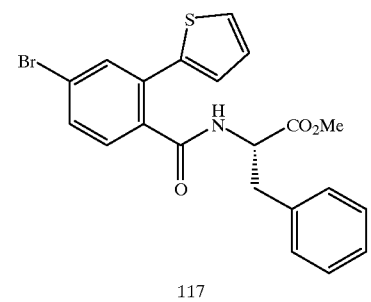
117

TABLE 11-continued
Bromides of the type B—Br
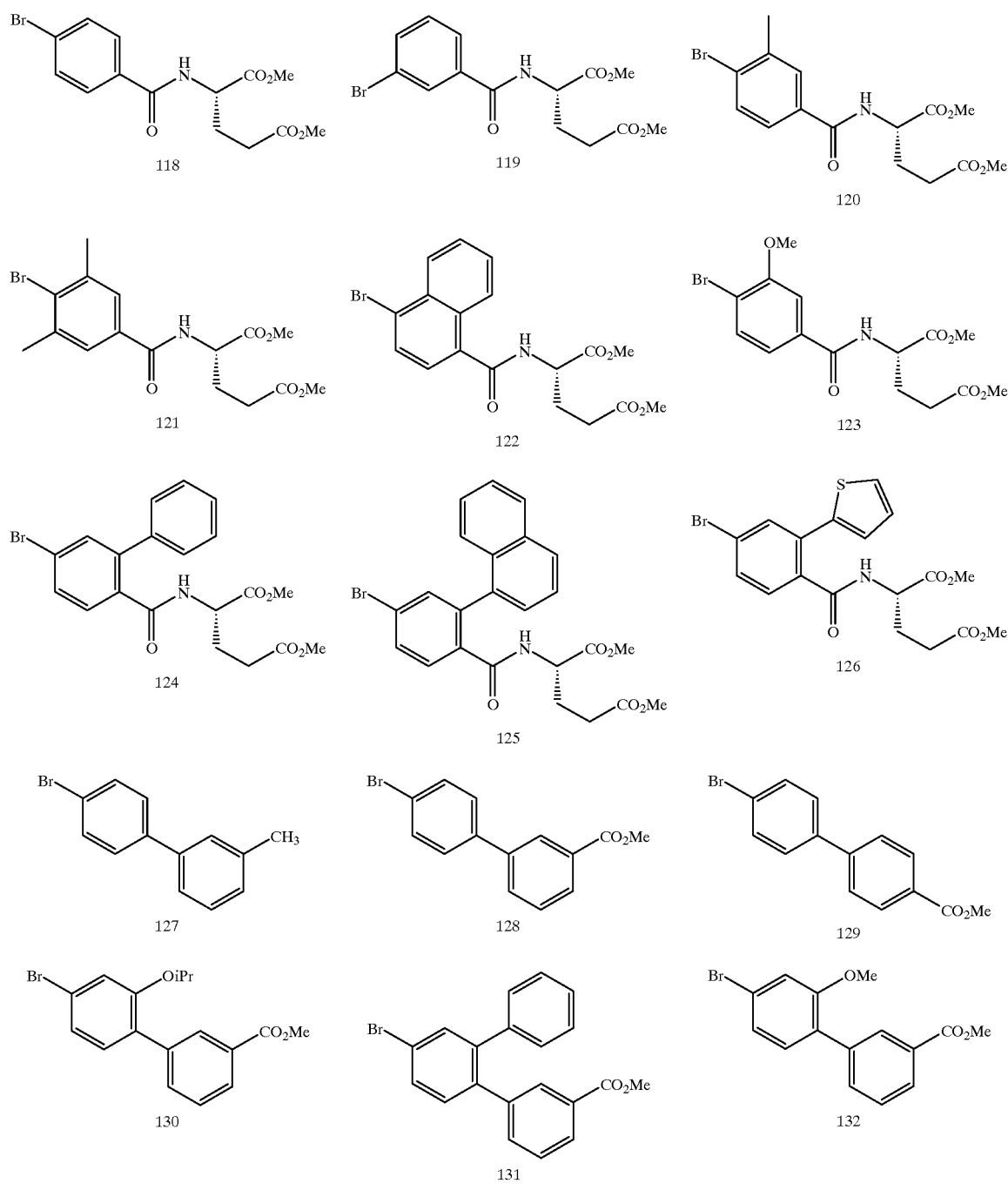

TABLE 12
Amines of the type A—NH₂
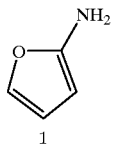
1
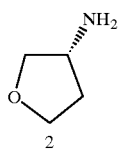
2
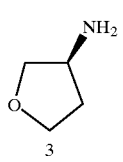
3
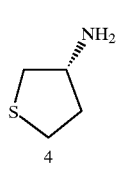
4
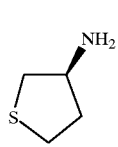
5
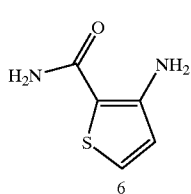
6
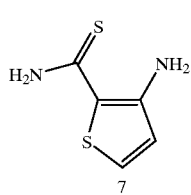
7
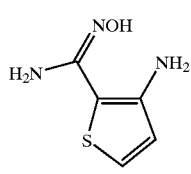
8
TABLE 12-continued
Amines of the type A—NH₂
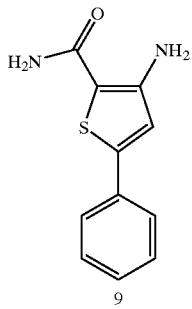
9
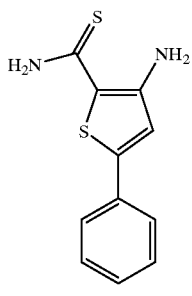
10
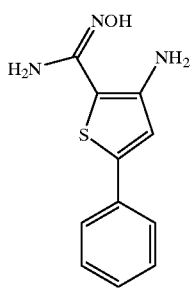
11
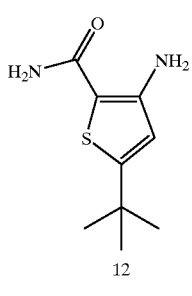
12
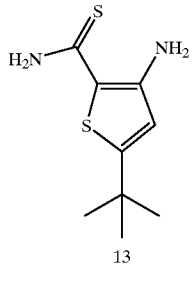
13

TABLE 12-continued
Amines of the type A—NH$_2$
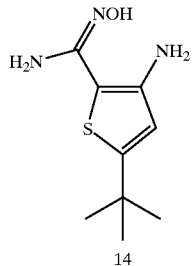
14
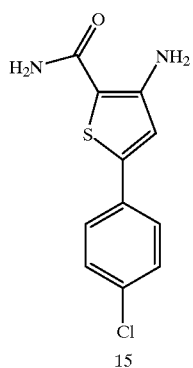
15
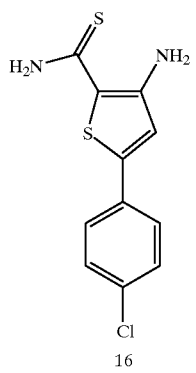
16
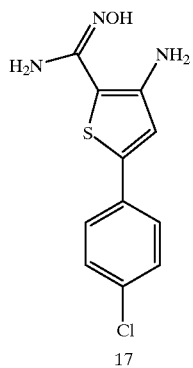
17
TABLE 12-continued
Amines of the type A—NH$_2$
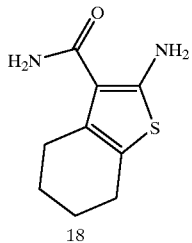
18
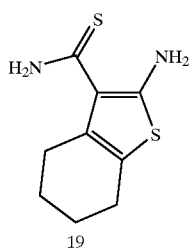
19
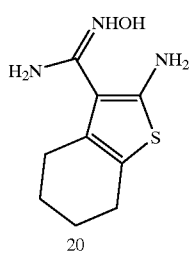
20
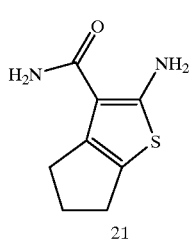
21
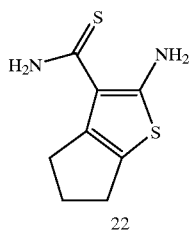
22
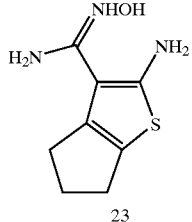
23

TABLE 12-continued
Amines of the type A—NH$_2$
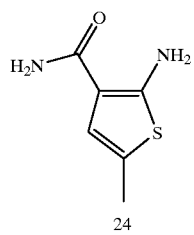
24
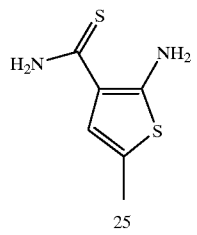
25
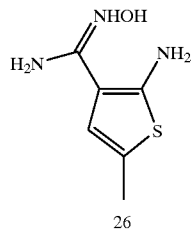
26
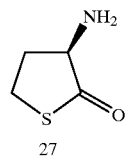
27
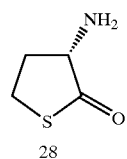
28
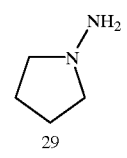
29
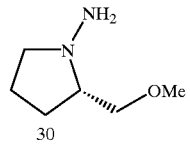
30
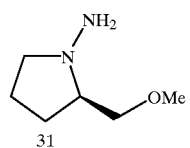
31
TABLE 12-continued
Amines of the type A—NH$_2$
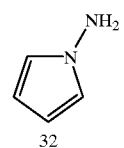
32
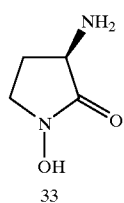
33
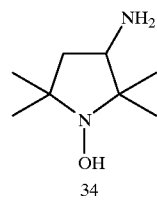
34
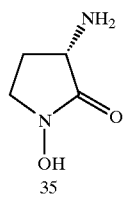
35
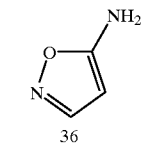
36
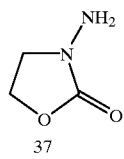
37
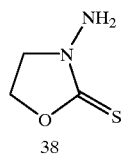
38
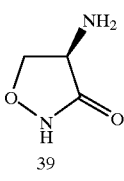
39

TABLE 12-continued
Amines of the type A—NH₂
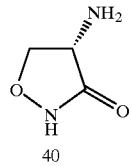
40
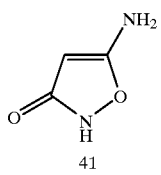
41
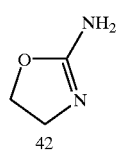
42
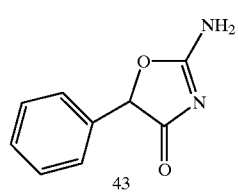
43
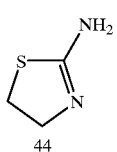
44
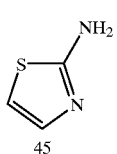
45
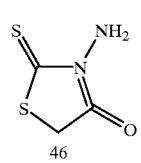
46
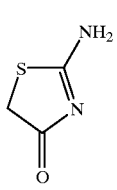
47
TABLE 12-continued
Amines of the type A—NH₂
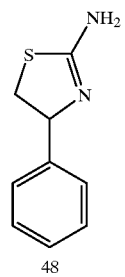
48
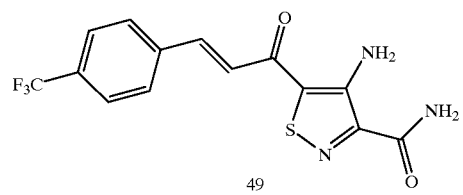
49
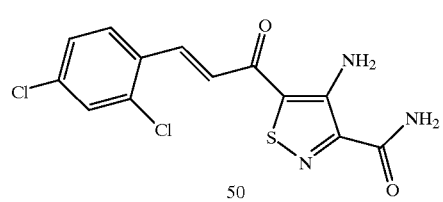
50
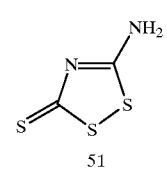
51
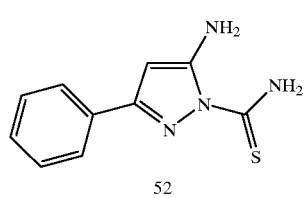
52
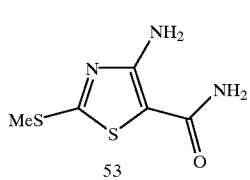
53
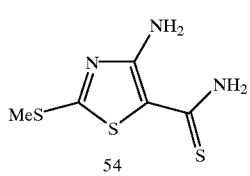
54

TABLE 12-continued
Amines of the type A—NH₂
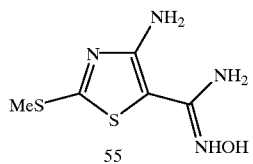
55
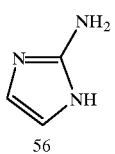
56
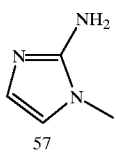
57
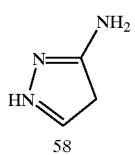
58
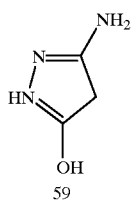
59
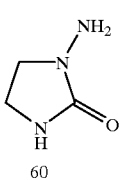
60
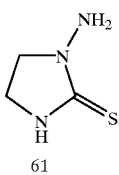
61
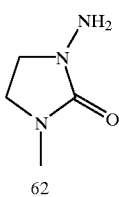
62
TABLE 12-continued
Amines of the type A—NH₂
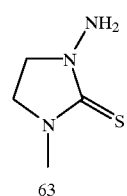
63
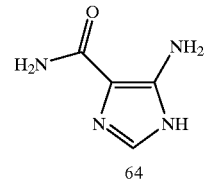
64
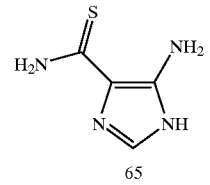
65
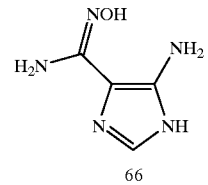
66
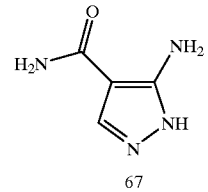
67
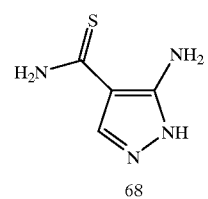
68
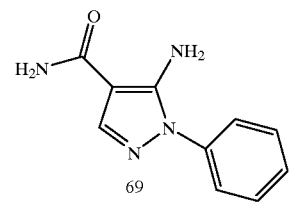
69

TABLE 12-continued
Amines of the type A—NH$_2$
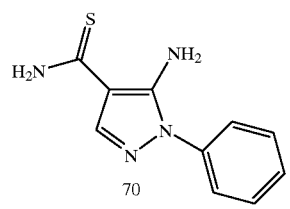
70
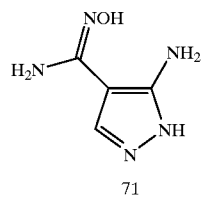
71
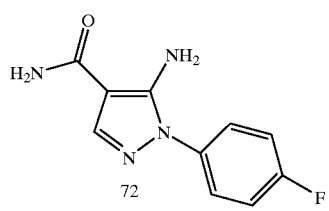
72
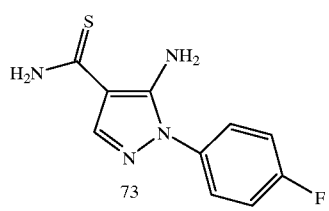
73
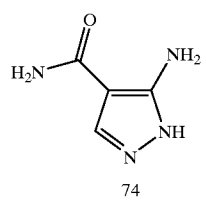
74
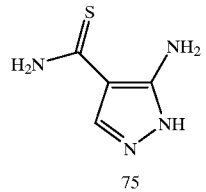
75
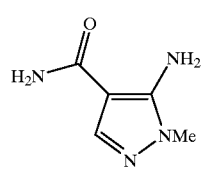
76
TABLE 12-continued
Amines of the type A—NH$_2$
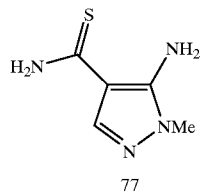
77
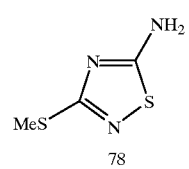
78
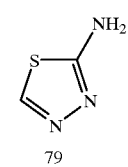
79
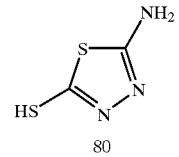
80
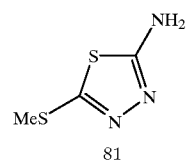
81
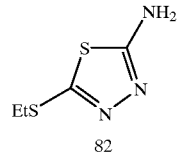
82
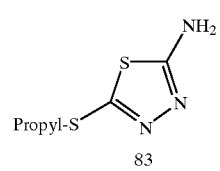
83
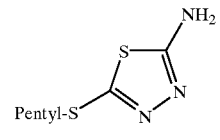
84

TABLE 12-continued
Amines of the type A—NH$_2$
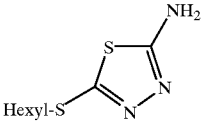
85
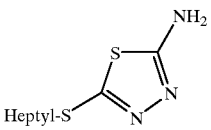
86
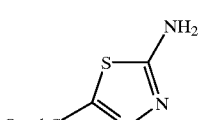
87
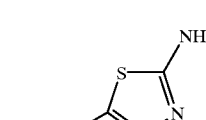
88
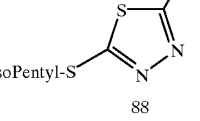
89
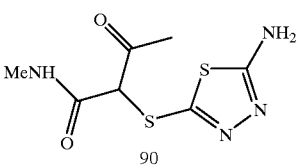
90
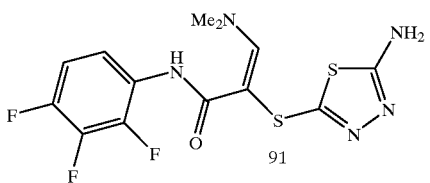
91
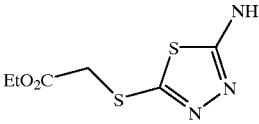
92
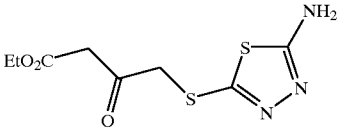
93
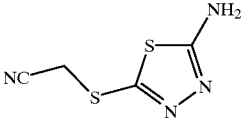
94
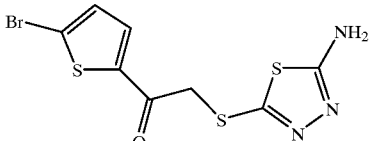
95
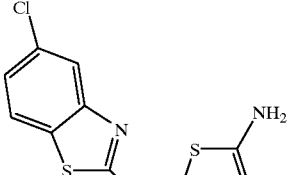
96
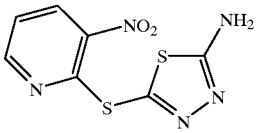
97
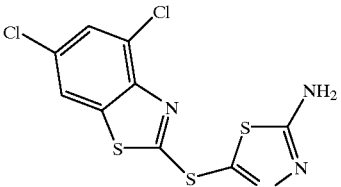
98
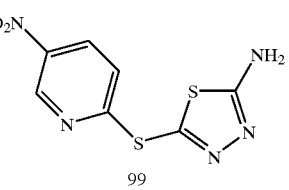
99
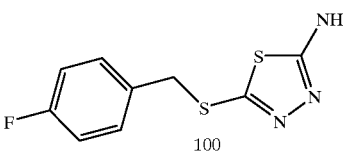
100

TABLE 12-continued
Amines of the type A—NH$_2$
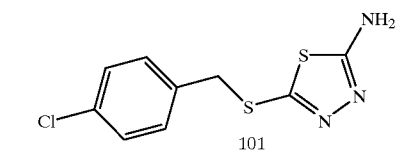
101
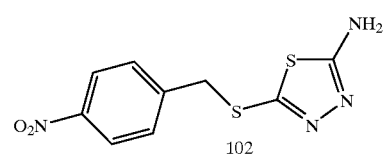
102
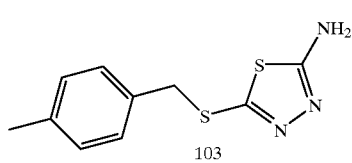
103
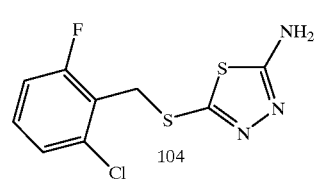
104
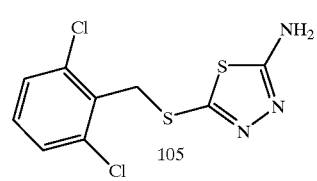
105
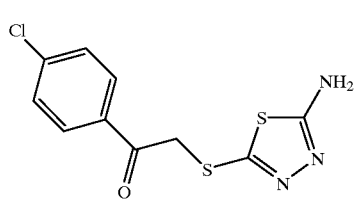
106
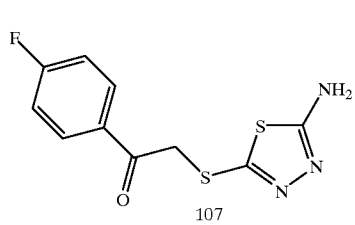
107
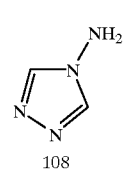
108
TABLE 12-continued
Amines of the type A—NH$_2$
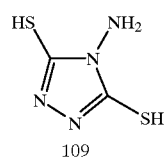
109
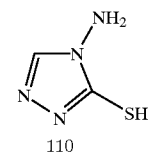
110
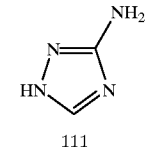
111
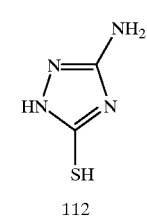
112
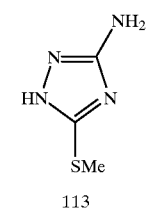
113
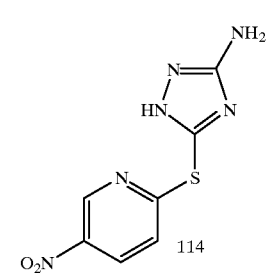
114
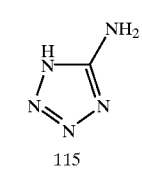
115
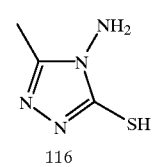
116

TABLE 12-continued
Amines of the type A—NH₂
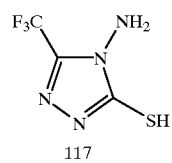
117
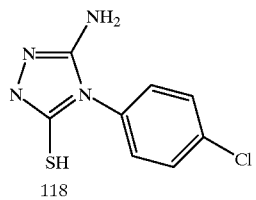
118
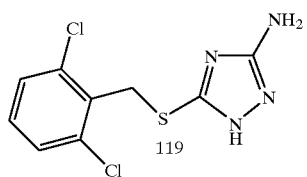
119
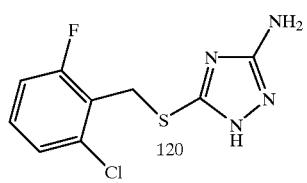
120
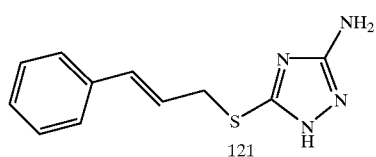
121
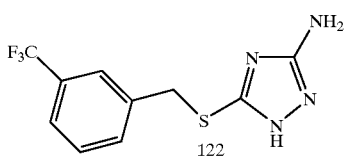
122
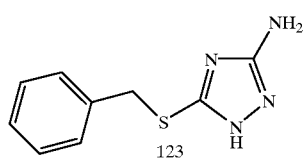
123
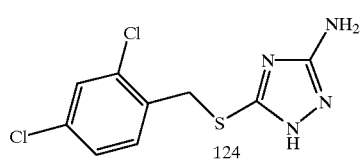
124
TABLE 12-continued
Amines of the type A—NH₂
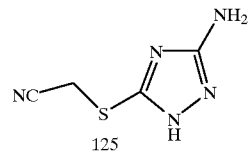
125
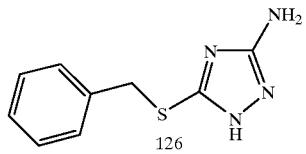
126
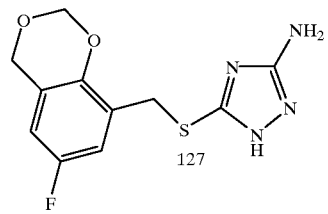
127
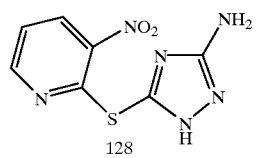
128
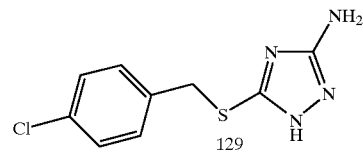
129
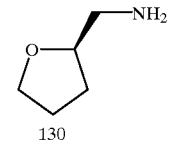
130
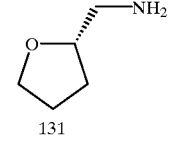
131
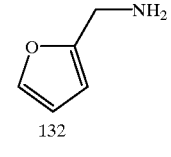
132
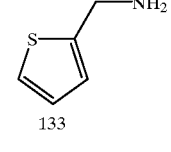
133

TABLE 12-continued
Amines of the type A—NH$_2$
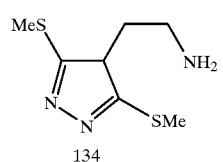
134
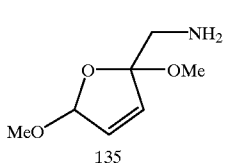
135
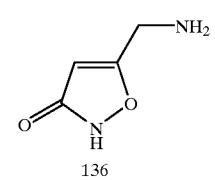
136
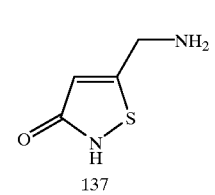
137
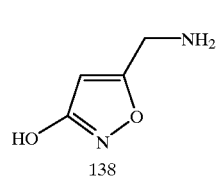
138
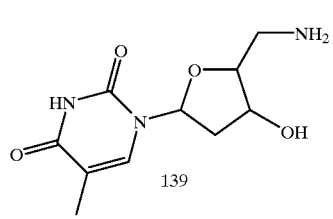
139
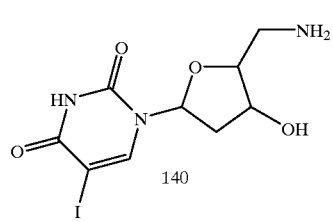
140
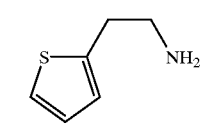
141
TABLE 12-continued
Amines of the type A—NH$_2$
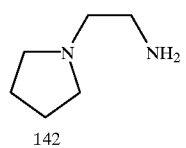
142
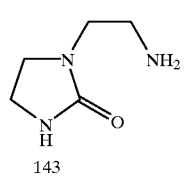
143
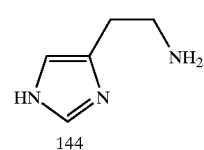
144
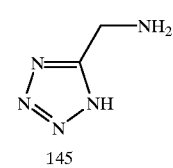
145
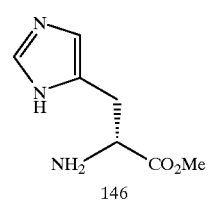
146
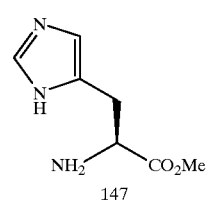
147
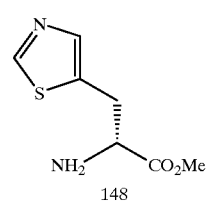
148
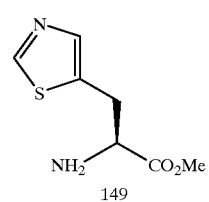
149

TABLE 12-continued
Amines of the type A—NH₂
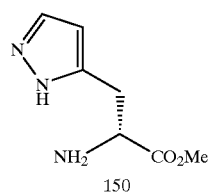
150
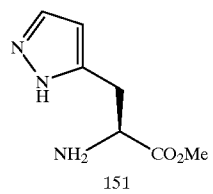
151
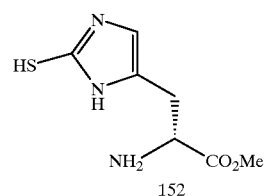
152
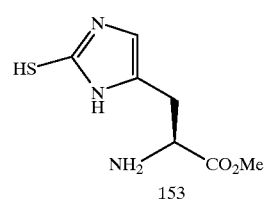
153
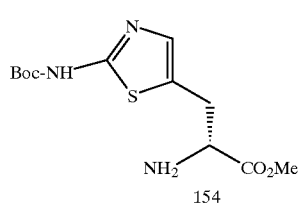
154
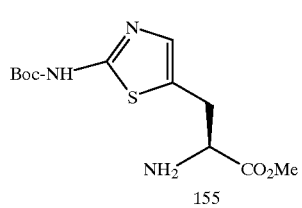
155
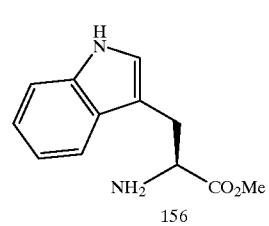
156
TABLE 12-continued
Amines of the type A—NH₂
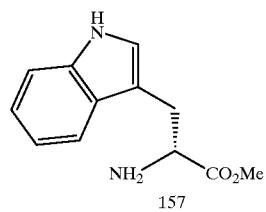
157
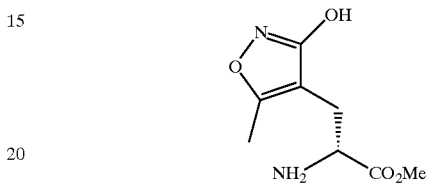
158
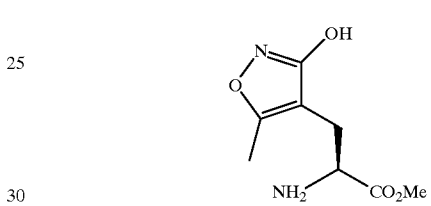
159
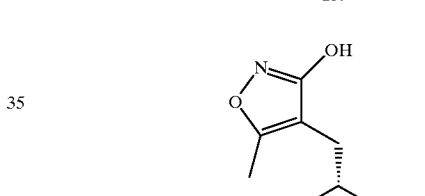
160
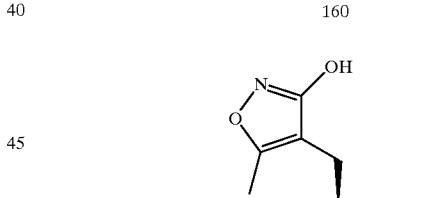
161
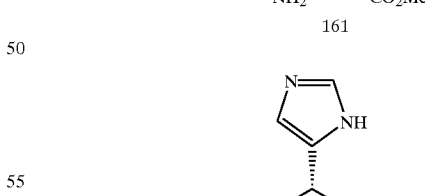
162
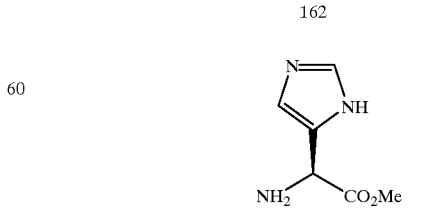
163

TABLE 12-continued
Amines of the type A—NH$_2$
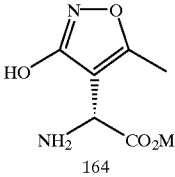
164
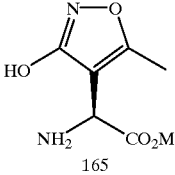
165
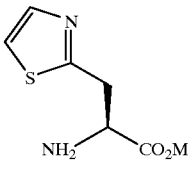
166
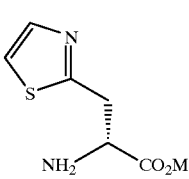
167
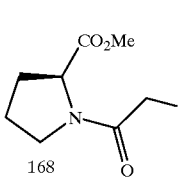
168
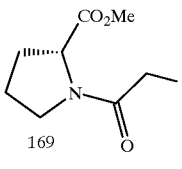
169
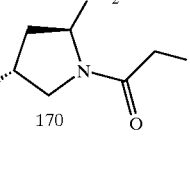
170
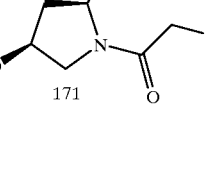
171
TABLE 12-continued
Amines of the type A—NH$_2$
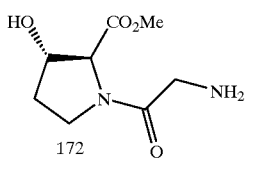
172
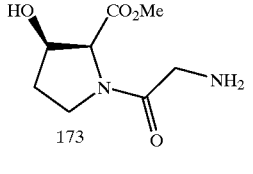
173
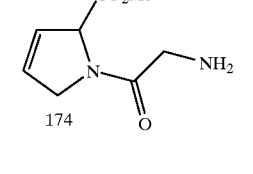
174
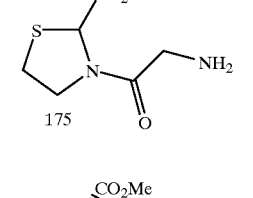
175
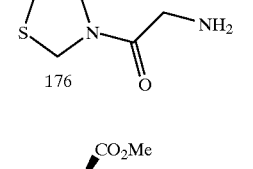
176
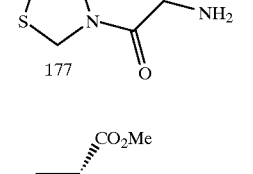
177
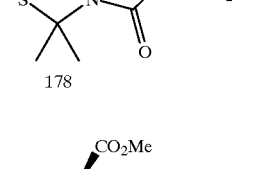
178
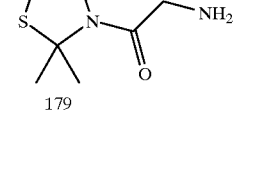
179

TABLE 12-continued
Amines of the type A—NH$_2$
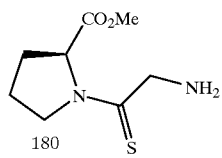
180
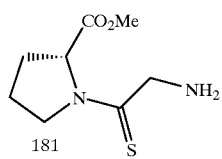
181
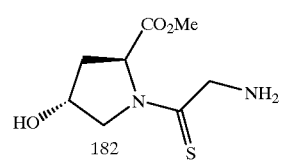
182
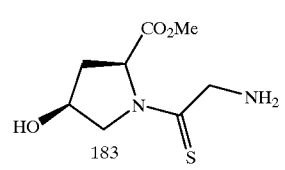
183
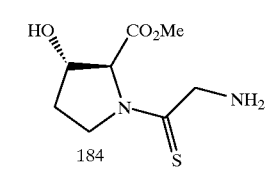
184
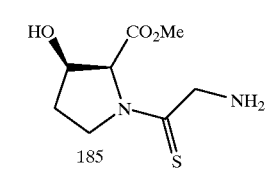
185
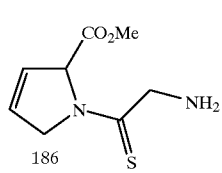
186
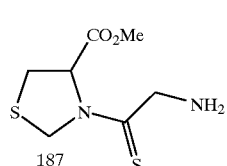
187
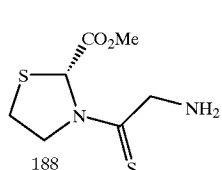
188
TABLE 12-continued
Amines of the type A—NH$_2$
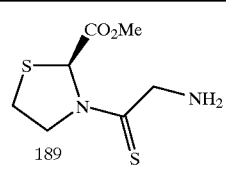
189
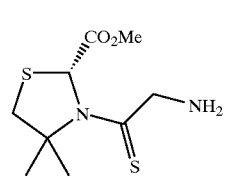
190
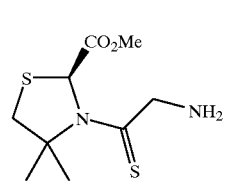
191
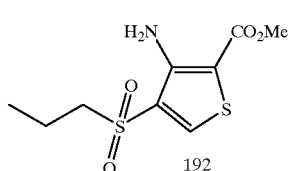
192
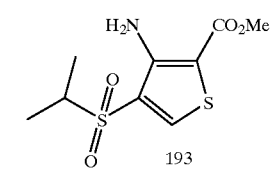
193
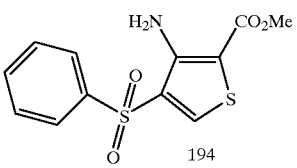
194
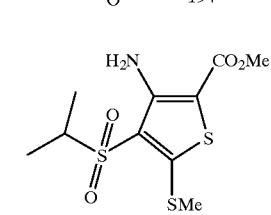
195
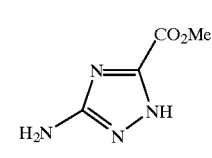
196

TABLE 12-continued
Amines of the type A—NH₂
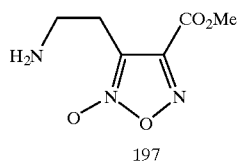
197
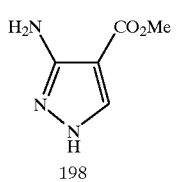
198
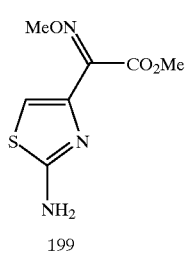
199
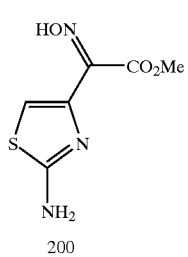
200
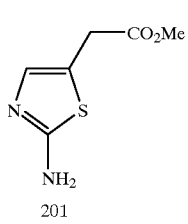
201
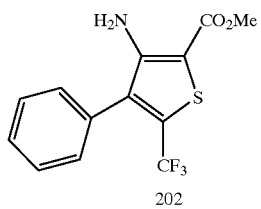
202
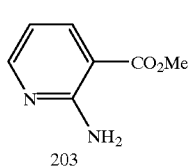
203
TABLE 12-continued
Amines of the type A—NH₂
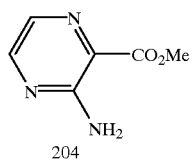
204
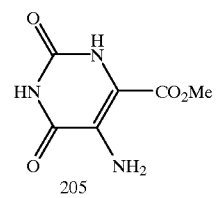
205
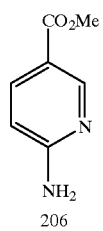
206
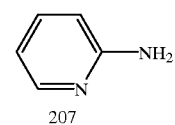
207
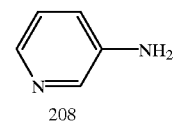
208
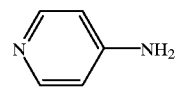
209
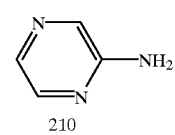
210
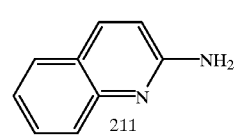
211
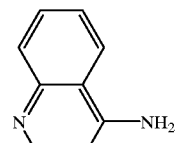
212

TABLE 12-continued
Amines of the type A—NH$_2$
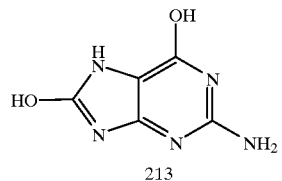
213
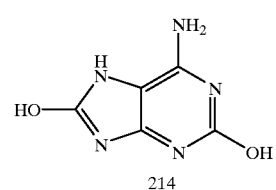
214
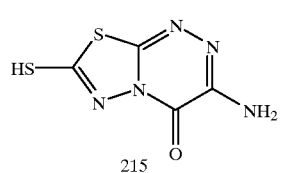
215
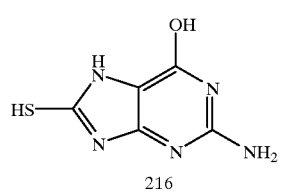
216
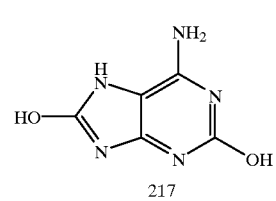
217
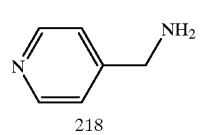
218
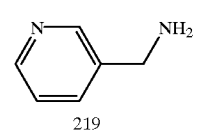
219
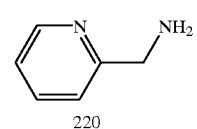
220
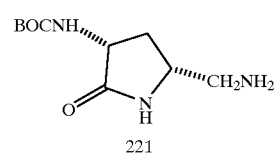
221
TABLE 12-continued
Amines of the type A—NH$_2$
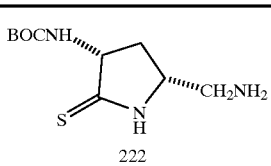
222
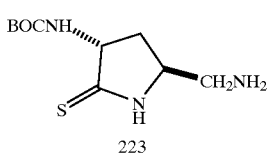
223
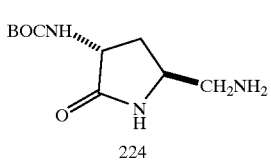
224
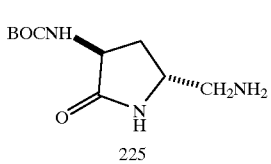
225
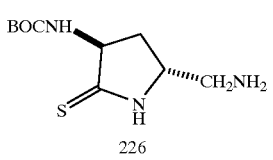
226
227
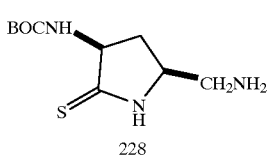
228
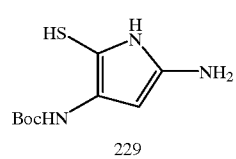
229
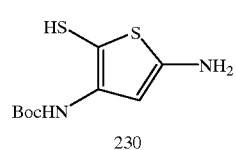
230

TABLE 12-continued
Amines of the type A—NH$_2$
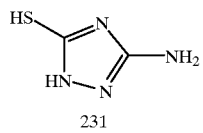
231
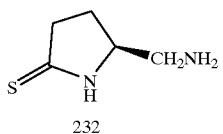
232
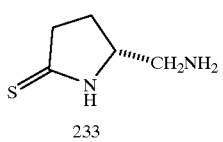
233
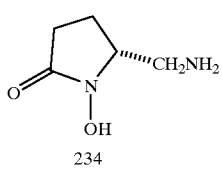
234
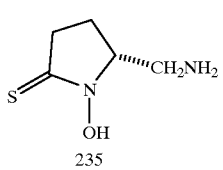
235
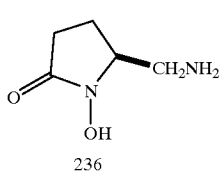
236
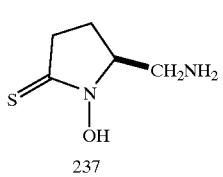
237
TABLE 13
Acids of the type A—CO$_2$H
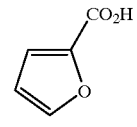
1
TABLE 13-continued
Acids of the type A—CO$_2$H
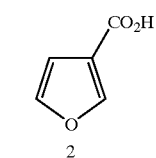
2
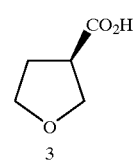
3
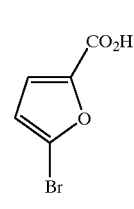
4
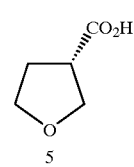
5
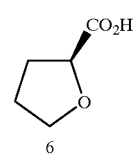
6
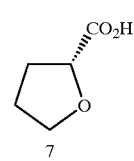
7
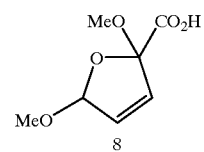
8
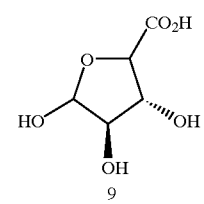
9

TABLE 13-continued
Acids of the type A—CO$_2$H
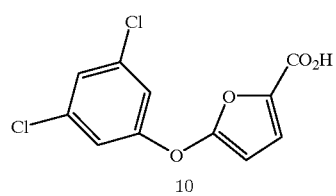
10
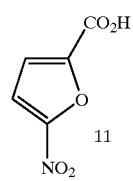
11
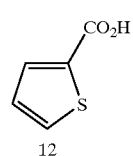
12
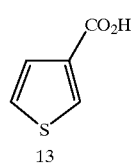
13
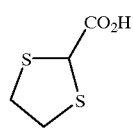
14
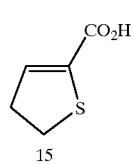
15
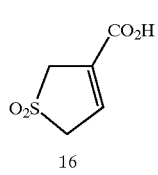
16
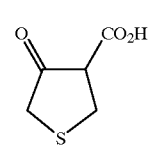
17
TABLE 13-continued
Acids of the type A—CO$_2$H
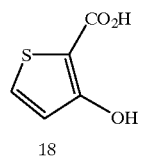
18
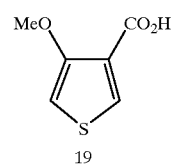
19
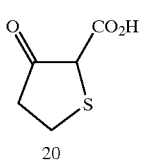
20
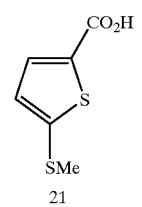
21
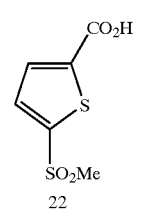
22
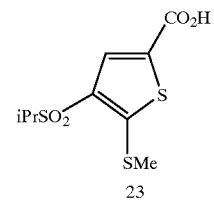
23
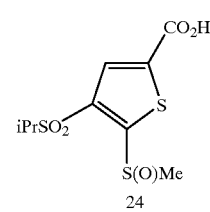
24
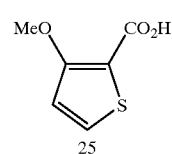
25

TABLE 13-continued
Acids of the type A—CO₂H
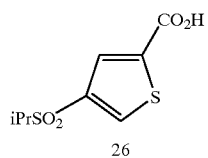
26
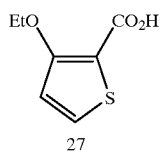
27
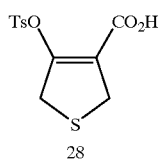
28
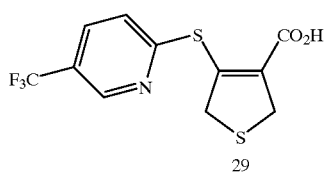
29
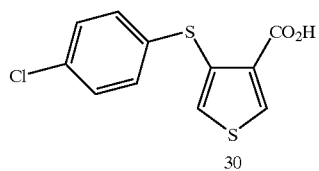
30
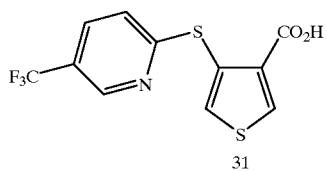
31
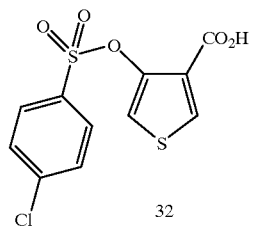
32
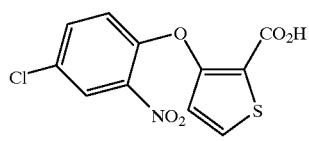
33
TABLE 13-continued
Acids of the type A—CO₂H
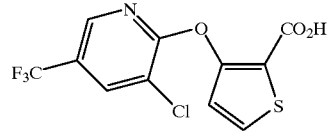
34
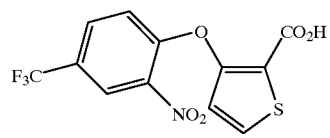
35
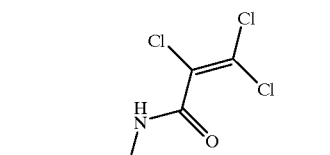
36
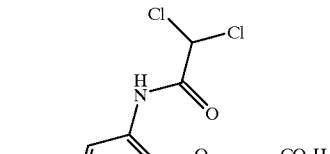
37
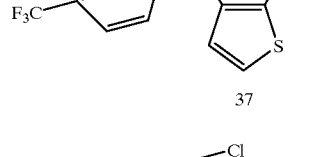
38
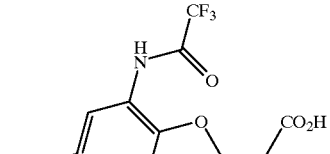
39
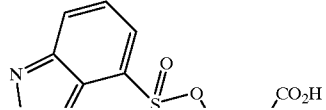

TABLE 13-continued
Acids of the type A—CO₂H
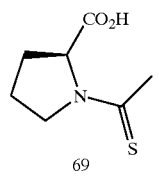
69
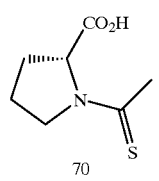
70
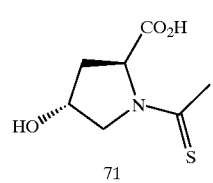
71
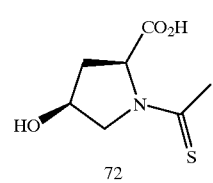
72
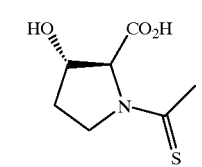
73
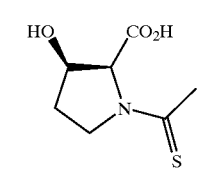
74
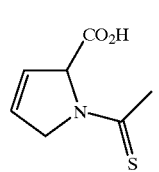
75
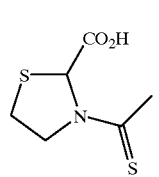
76
TABLE 13-continued
Acids of the type A—CO₂H
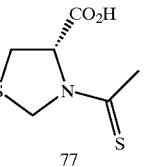
77
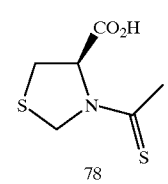
78
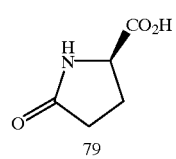
79
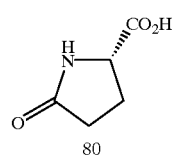
80
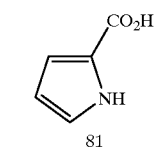
81
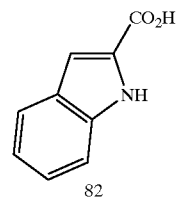
82
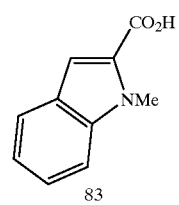
83
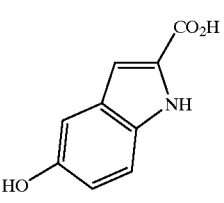
84

TABLE 13-continued
Acids of the type A—CO₂H
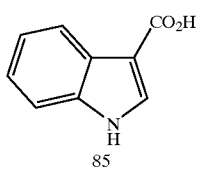
85
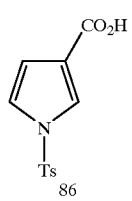
86
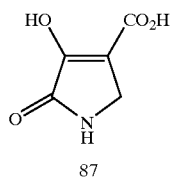
87
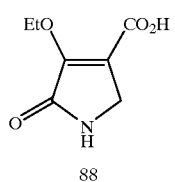
88
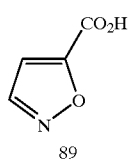
89
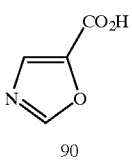
90
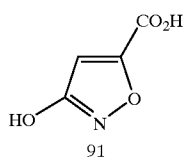
91
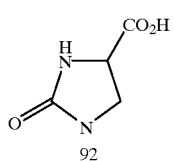
92
TABLE 13-continued
Acids of the type A—CO₂H
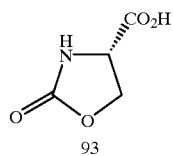
93
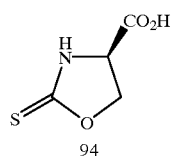
94
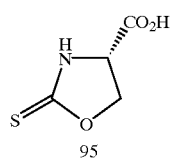
95
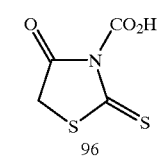
96
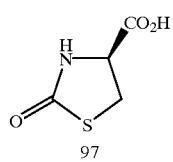
97
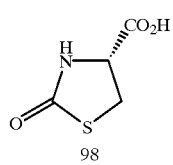
98
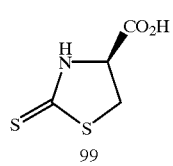
99
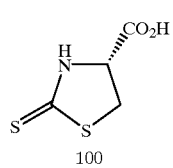
100
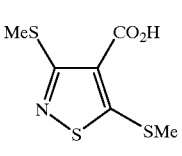
101

TABLE 13-continued
Acids of the type A—CO$_2$H
102
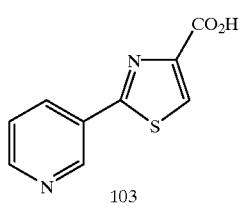
103
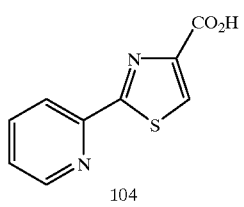
104
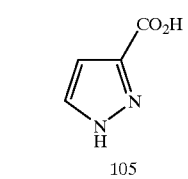
105
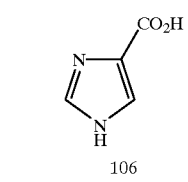
106
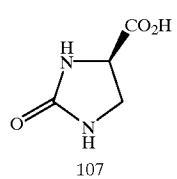
107
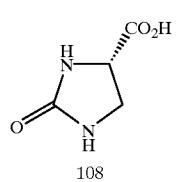
108
TABLE 13-continued
Acids of the type A—CO$_2$H
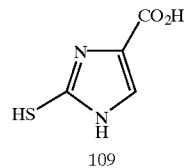
109
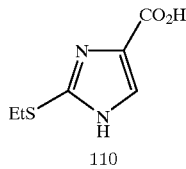
110
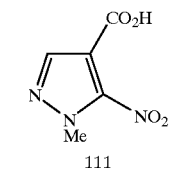
111
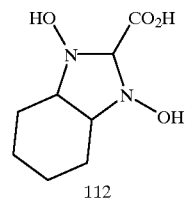
112
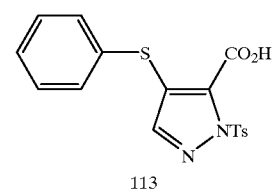
113
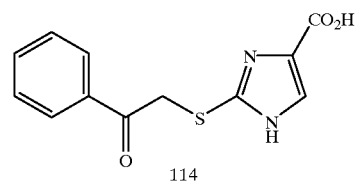
114
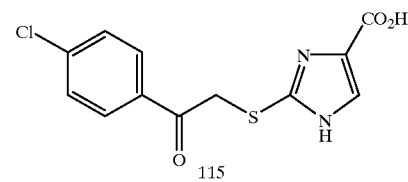
115
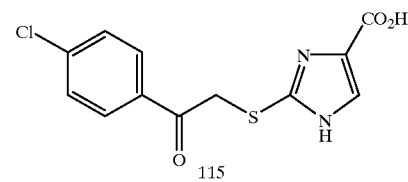
116

TABLE 13-continued
Acids of the type A—CO₂H
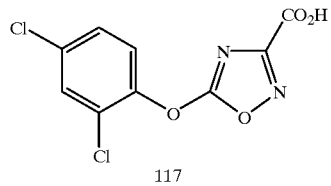
117
118
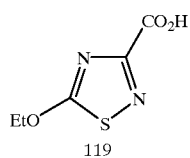
119
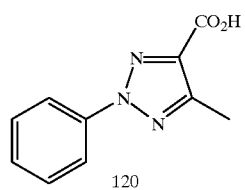
120
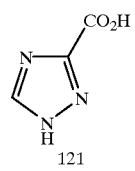
121
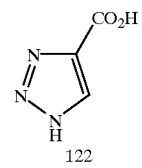
122
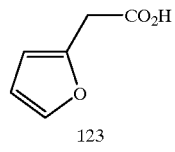
123
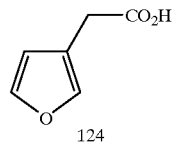
124
TABLE 13-continued
Acids of the type A—CO₂H
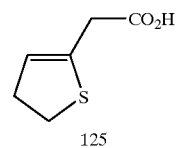
125
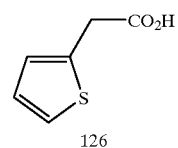
126
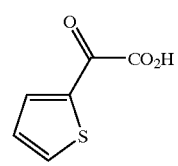
127
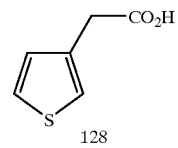
128
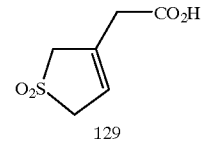
129
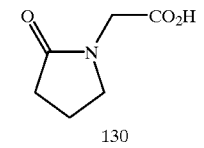
130
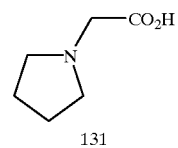
131
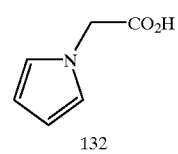
132
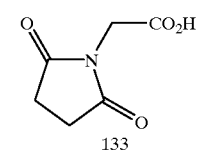
133

TABLE 13-continued
Acids of the type A—CO₂H
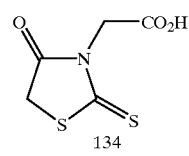
134
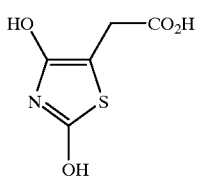
135
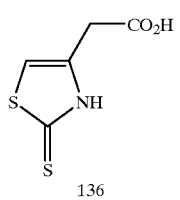
136
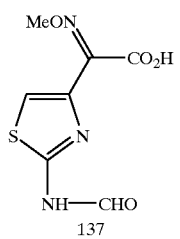
137
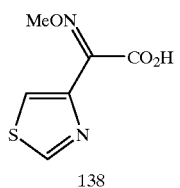
138
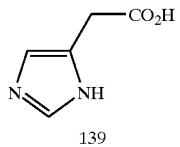
139
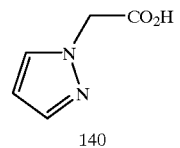
140
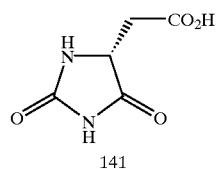
141
TABLE 13-continued
Acids of the type A—CO₂H
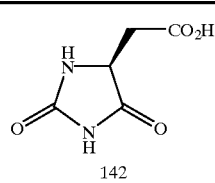
142
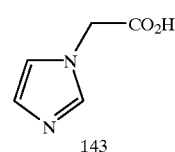
143
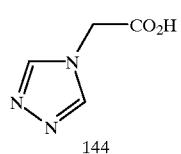
144
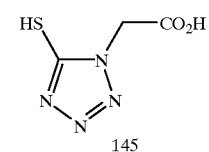
145
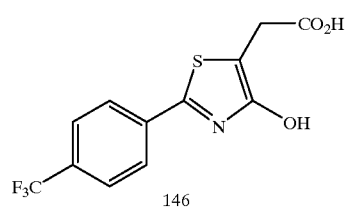
146
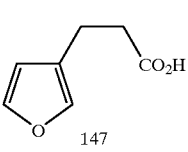
147
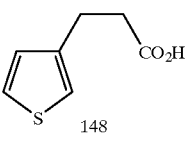
148
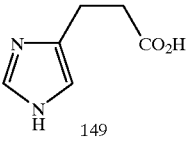
149
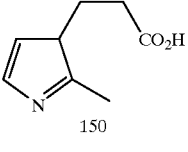
150

TABLE 13-continued
Acids of the type A—CO₂H
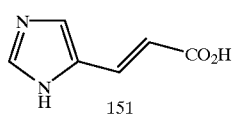
151
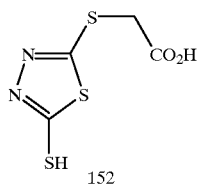
152
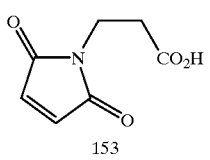
153
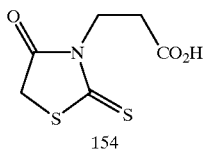
154
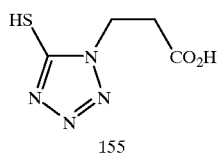
155
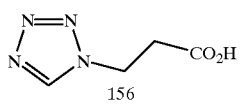
156
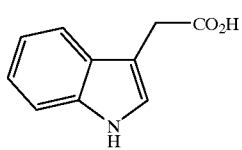
157
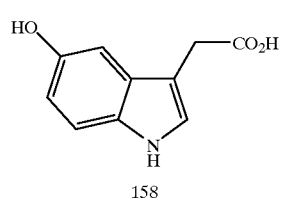
158
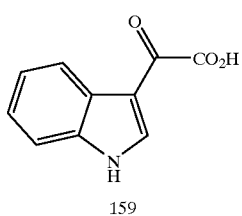
159
TABLE 13-continued
Acids of the type A—CO₂H
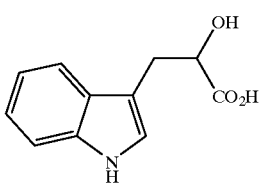
160
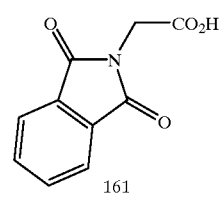
161
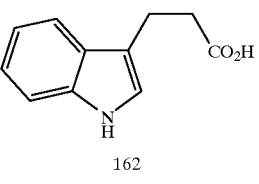
162
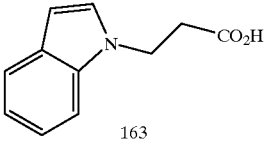
163
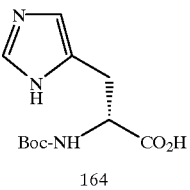
164
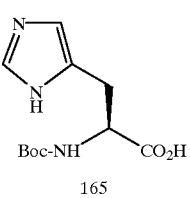
165
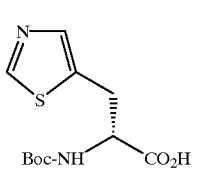
166

TABLE 13-continued
Acids of the type A—CO₂H
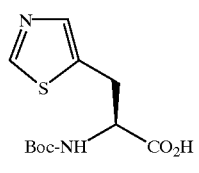
167
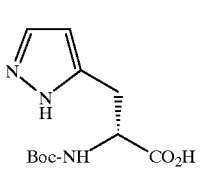
168
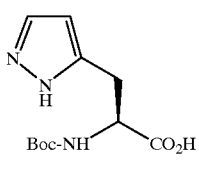
169
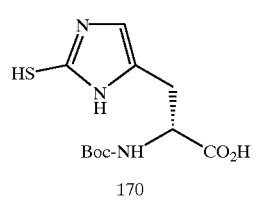
170
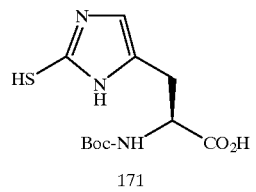
171
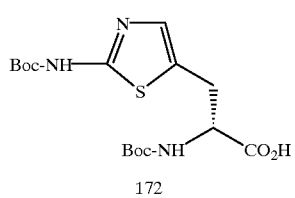
172
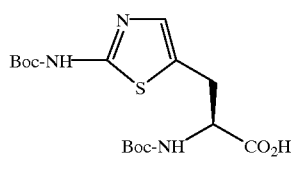
173
TABLE 13-continued
Acids of the type A—CO₂H
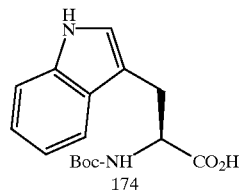
174
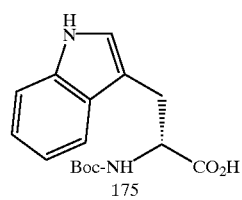
175
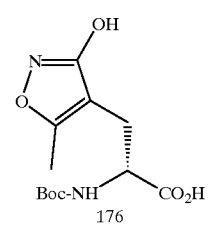
176
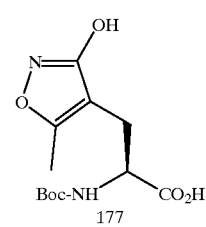
177
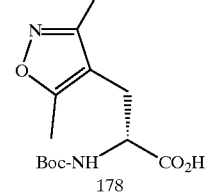
178
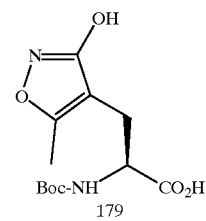
179
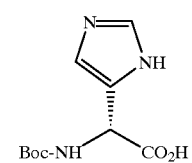
180

TABLE 13-continued
Acids of the type A—CO₂H
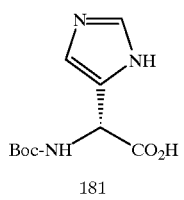
181
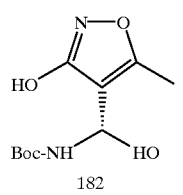
182
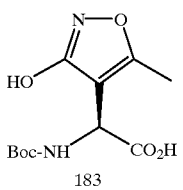
183
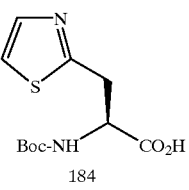
184
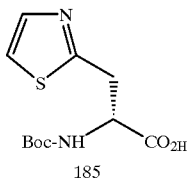
185
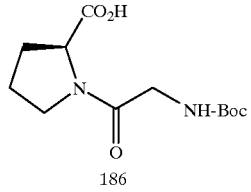
186
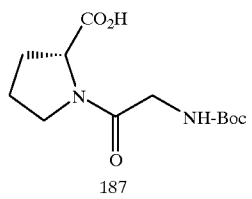
187
TABLE 13-continued
Acids of the type A—CO₂H
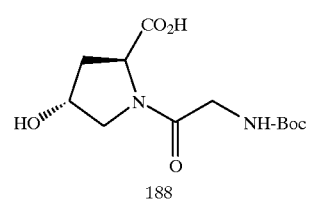
188
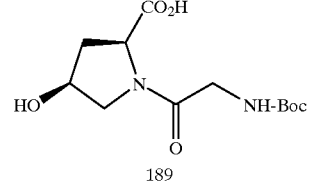
189
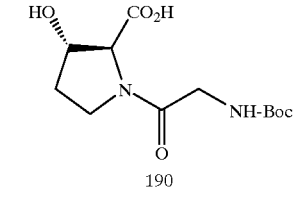
190
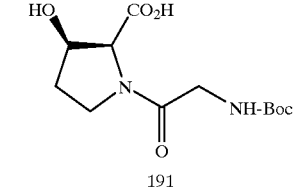
191
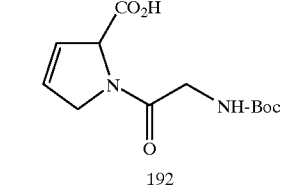
192
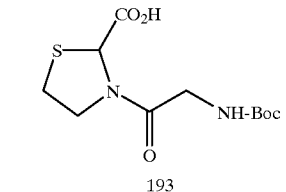
193
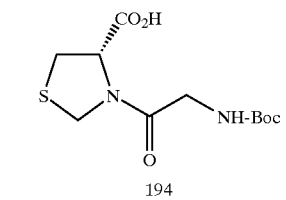
194

TABLE 13-continued
Acids of the type A—CO$_2$H
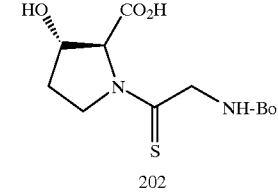
195
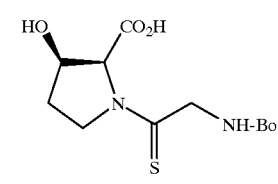
196
197
198
199
200
201
TABLE 13-continued
Acids of the type A—CO$_2$H
202
203
204
205
206
207
208

TABLE 13-continued
Acids of the type A—CO₂H
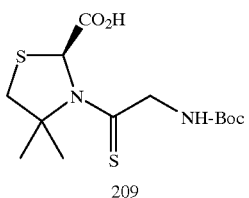
209
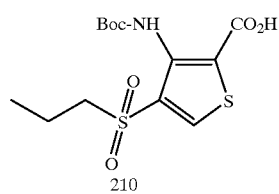
210
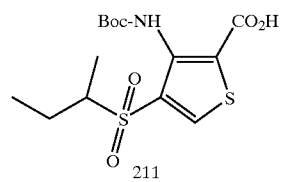
211
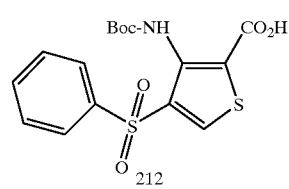
212
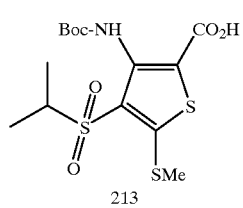
213
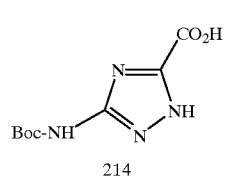
214
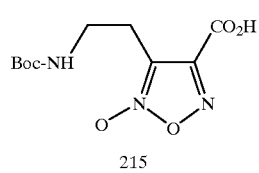
215
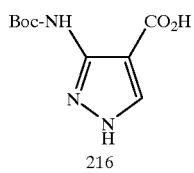
216
TABLE 13-continued
Acids of the type A—CO₂H
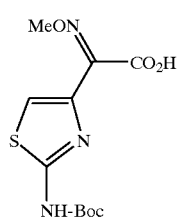
217
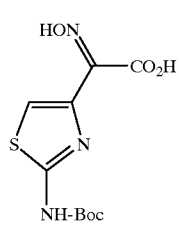
218
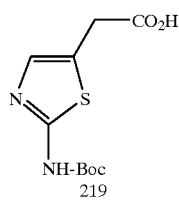
219
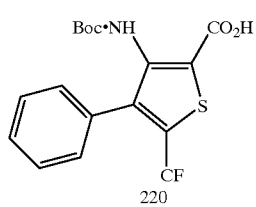
220
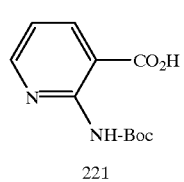
221
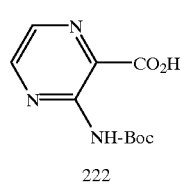
222
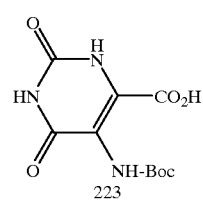
223

TABLE 13-continued
Acids of the type A—CO₂H
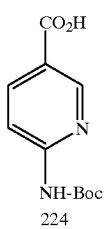
224
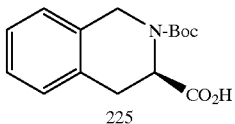
225
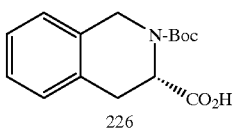
226
227
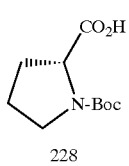
228
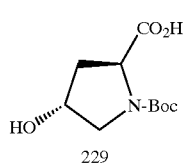
229
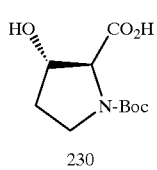
230
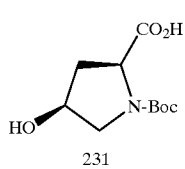
231
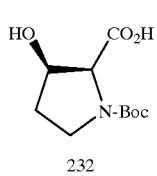
232
TABLE 13-continued
Acids of the type A—CO₂H
233
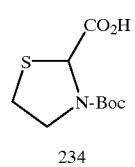
234
235
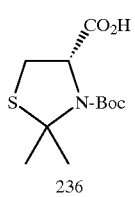
236
237
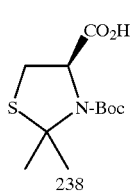
238
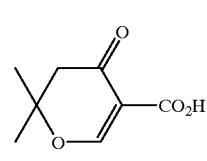
239
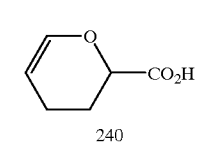
240
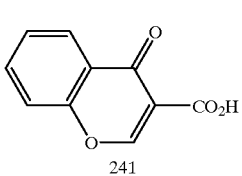
241

TABLE 13-continued
Acids of the type A—CO₂H
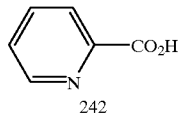
242
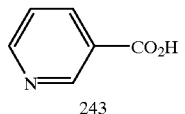
243
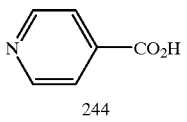
244
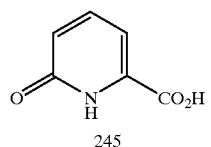
245
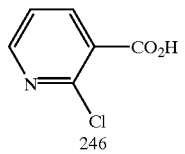
246
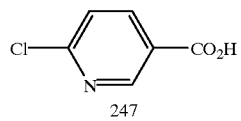
247
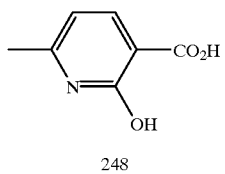
248
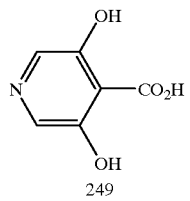
249
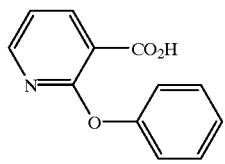
250
TABLE 13-continued
Acids of the type A—CO₂H
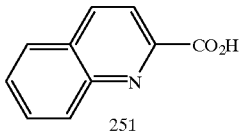
251
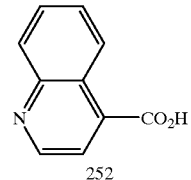
252
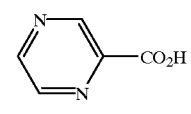
253
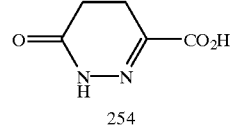
254
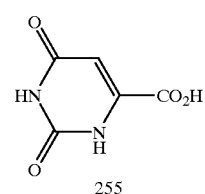
255
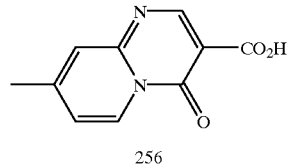
256
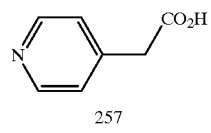
257
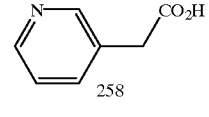
258
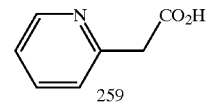
259
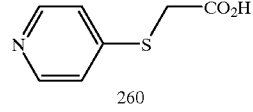
260

TABLE 13-continued
Acids of the type A—CO$_2$H
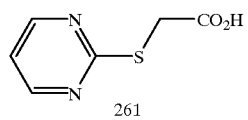
261
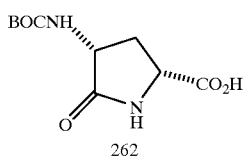
262
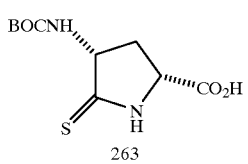
263
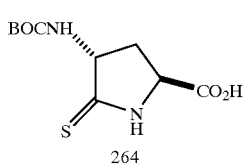
264
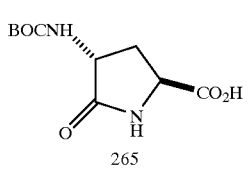
265
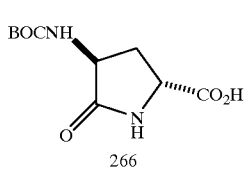
266
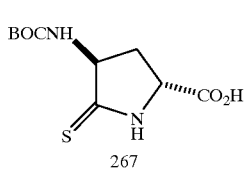
267
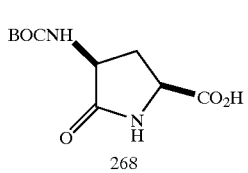
268
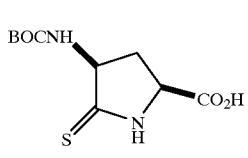
269
TABLE 13-continued
Acids of the type A—CO$_2$H
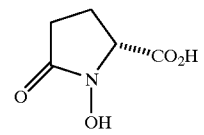
270
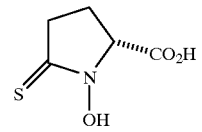
271
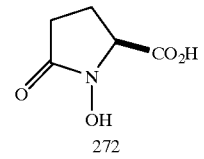
272
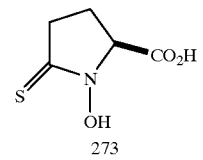
273
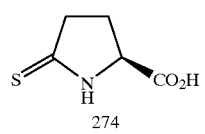
274
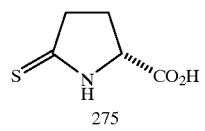
275
TABLE 14
Aldehydes of the type A-CHO
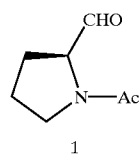
1
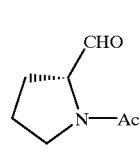
2

TABLE 14-continued
Aldehydes of the type A-CHO
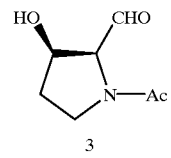
3
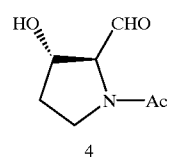
4
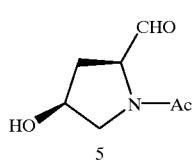
5
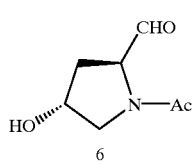
6
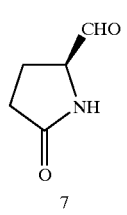
7
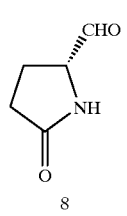
8
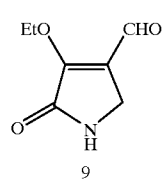
9
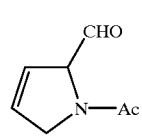
10
TABLE 14-continued
Aldehydes of the type A-CHO
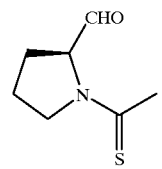
11
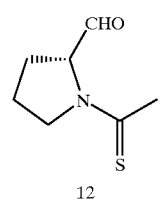
12
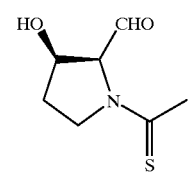
13
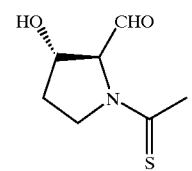
14
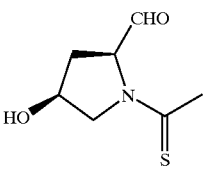
15
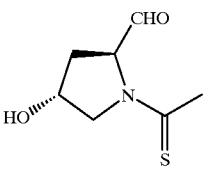
16
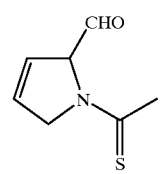
17

TABLE 14-continued
Aldehydes of the type A-CHO
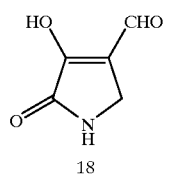
18
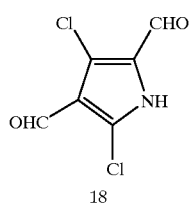
18
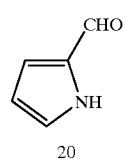
20
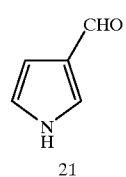
21
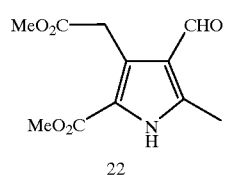
22
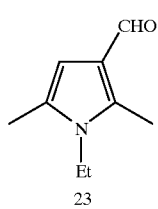
23
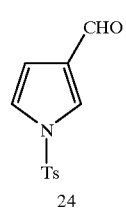
24
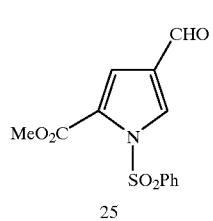
25
TABLE 14-continued
Aldehydes of the type A-CHO
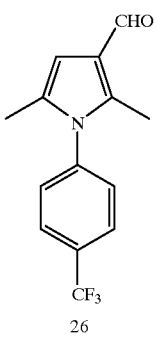
26
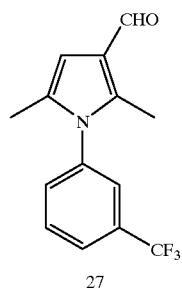
27
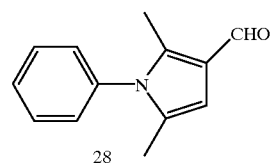
28
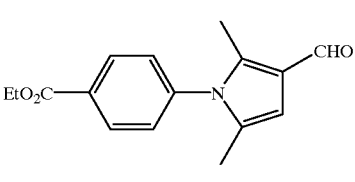
29
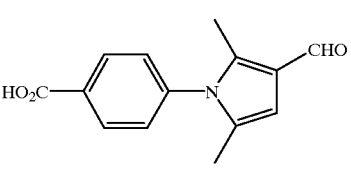
30
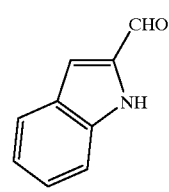
31

TABLE 14-continued
Aldehydes of the type A-CHO
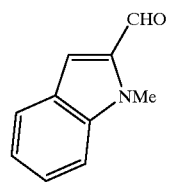
32
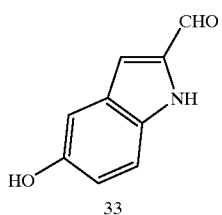
33
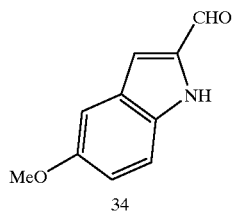
34
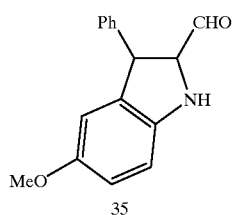
35
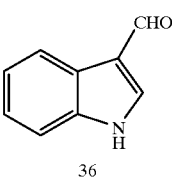
36
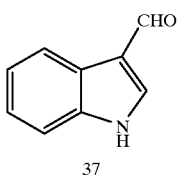
37
38
TABLE 14-continued
Aldehydes of the type A-CHO
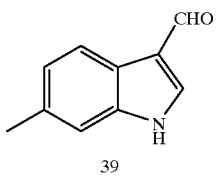
39
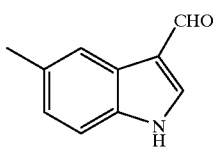
40
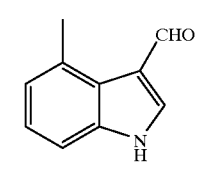
41
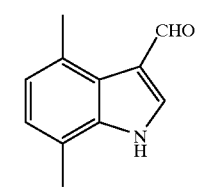
42
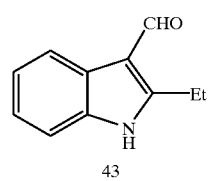
43
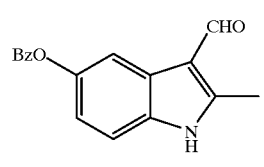
44
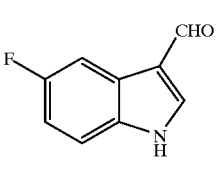
45
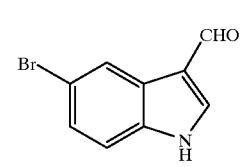
46

TABLE 14-continued
Aldehydes of the type A-CHO
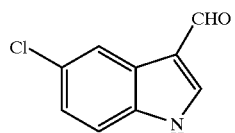
47
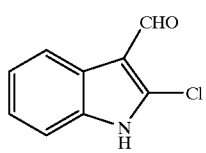
48
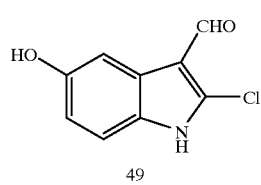
49
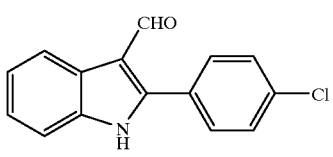
50
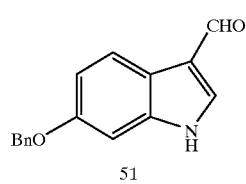
51
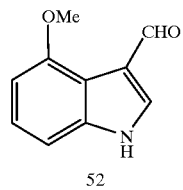
52
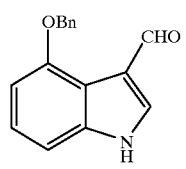
53
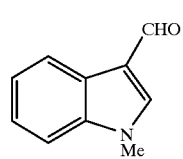
54
TABLE 14-continued
Aldehydes of the type A-CHO
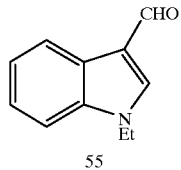
55
56
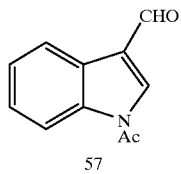
57
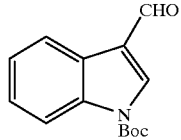
58
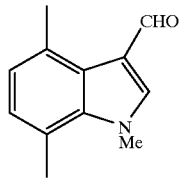
59
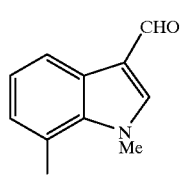
60
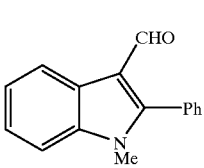
61
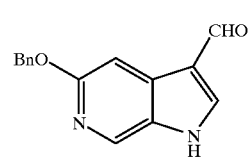
62

TABLE 14-continued
Aldehydes of the type A-CHO
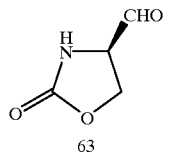
63
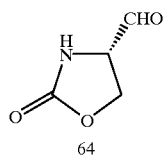
64
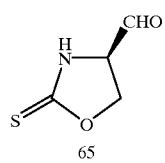
65
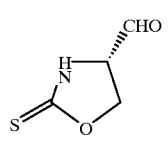
66
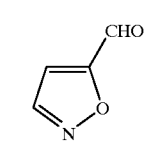
67
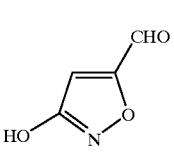
68
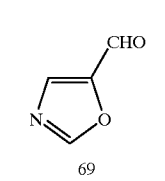
69
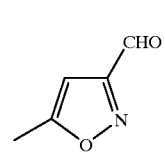
70
TABLE 14-continued
Aldehydes of the type A-CHO
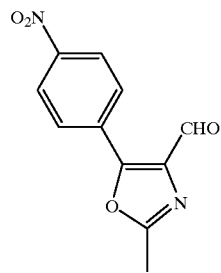
71
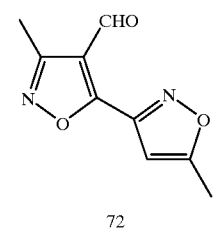
72
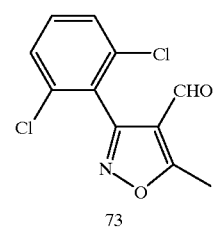
73
74
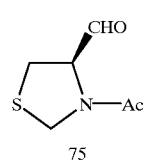
75
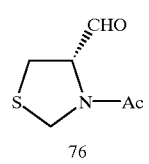
76
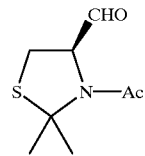
77

TABLE 14-continued
Aldehydes of the type A-CHO
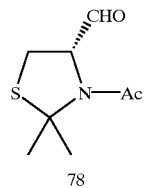
78
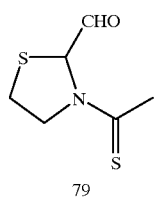
79
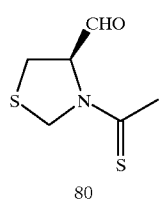
80
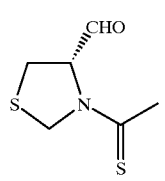
81
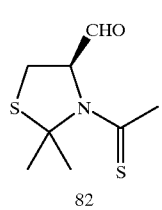
82
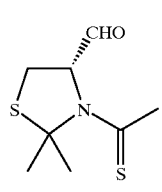
83
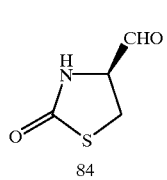
84
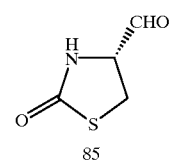
85
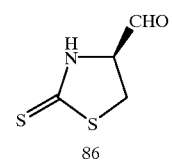
86
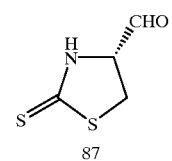
87
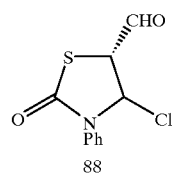
88
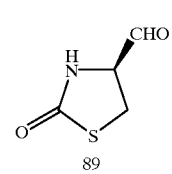
89
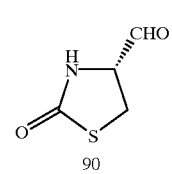
90
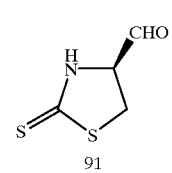
91
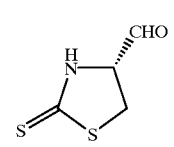
92
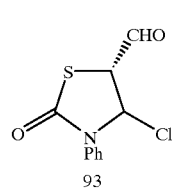
93

TABLE 14-continued
Aldehydes of the type A-CHO
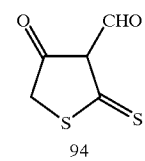
94
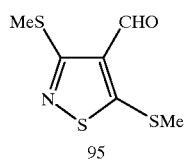
95
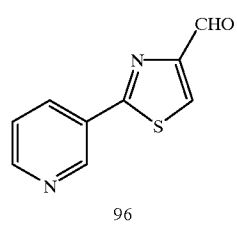
96
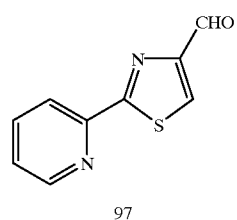
97
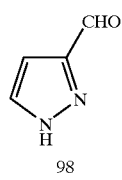
98
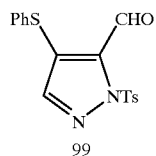
99
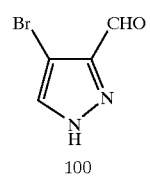
100
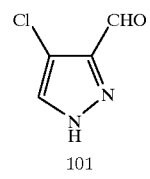
101
TABLE 14-continued
Aldehydes of the type A-CHO
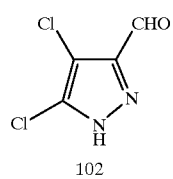
102
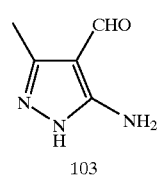
103
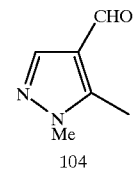
104
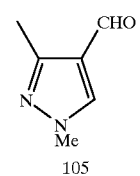
105
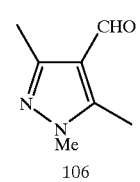
106
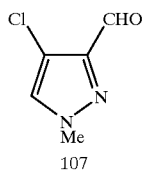
107
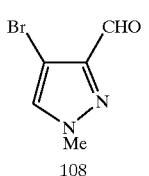
108
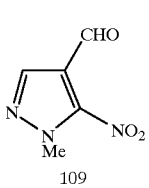
109

TABLE 14-continued
Aldehydes of the type A-CHO
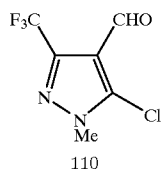
110
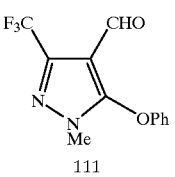
111
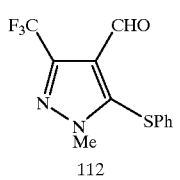
112
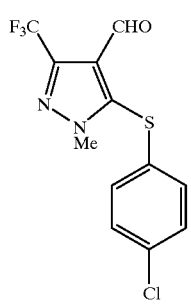
113
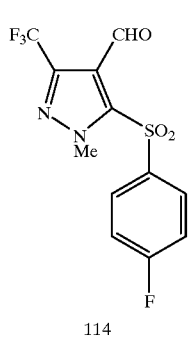
114
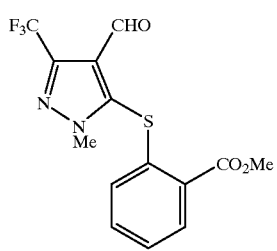
115
TABLE 14-continued
Aldehydes of the type A-CHO
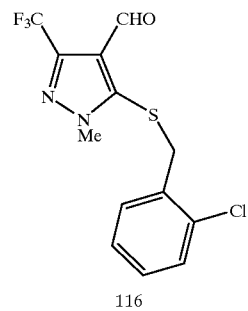
116
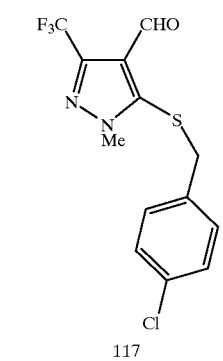
117
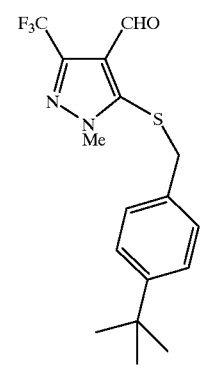
118
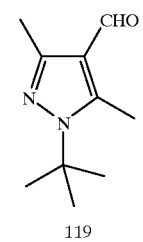
119
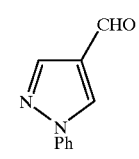
120

TABLE 14-continued
Aldehydes of the type A-CHO
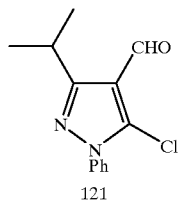
121
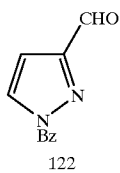
122
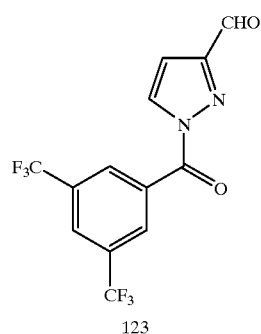
123
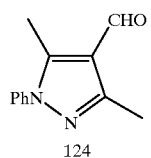
124
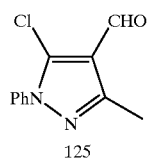
125
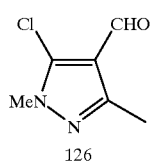
126
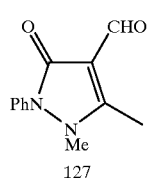
127
TABLE 14-continued
Aldehydes of the type A-CHO
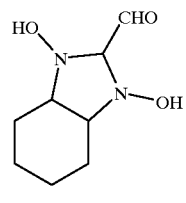
128
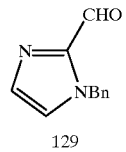
129
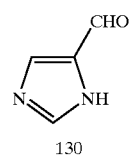
130
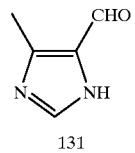
131
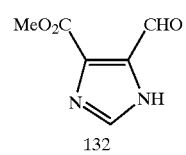
132
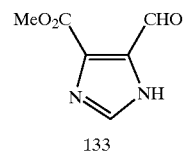
133
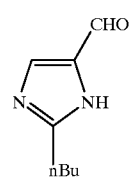
134
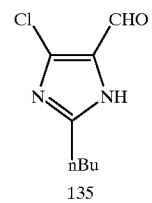
135

TABLE 14-continued
Aldehydes of the type A-CHO
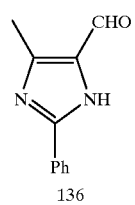
136
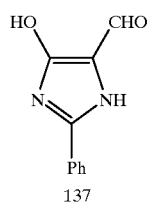
137
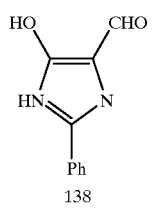
138
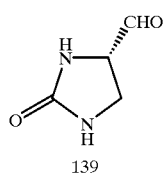
139
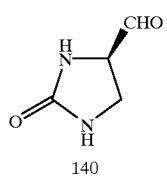
140
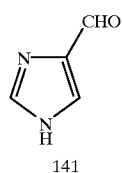
141
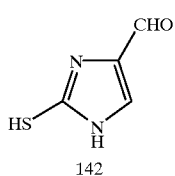
142
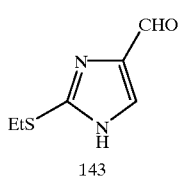
143
TABLE 14-continued
Aldehydes of the type A-CHO
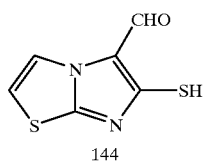
144
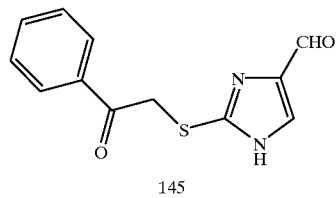
145
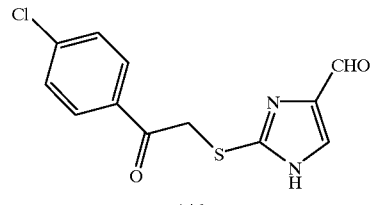
146
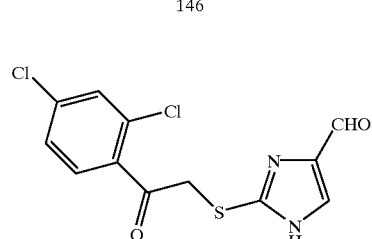
147
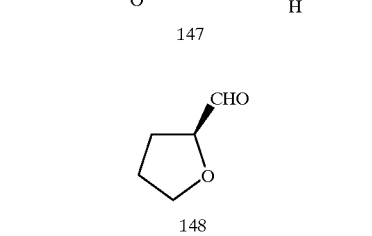
148
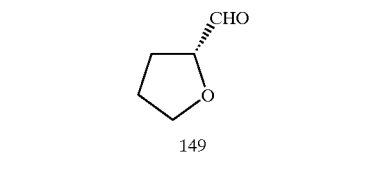
149
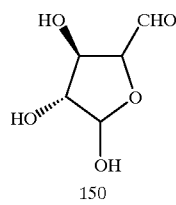
150

TABLE 14-continued
Aldehydes of the type A-CHO
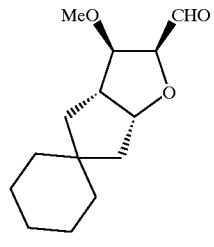
151
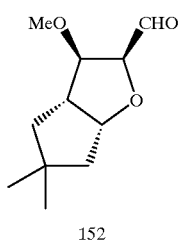
152
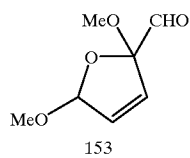
153
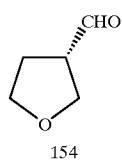
154
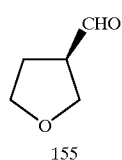
155
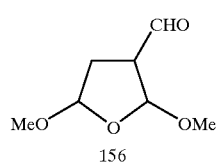
156
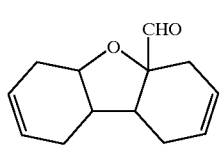
157
TABLE 14-continued
Aldehydes of the type A-CHO
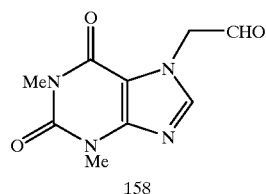
158
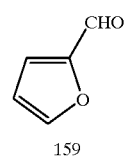
159
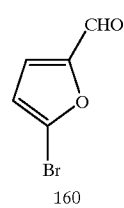
160
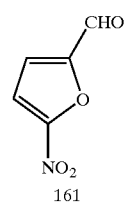
161
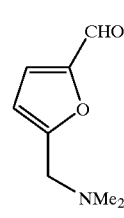
162
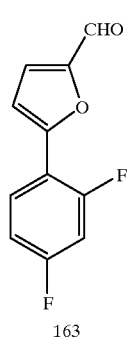
163

TABLE 14-continued
Aldehydes of the type A-CHO
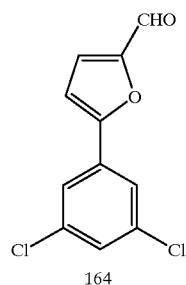
164
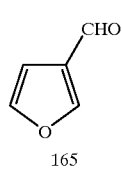
165
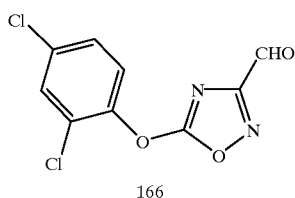
166
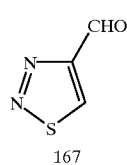
167
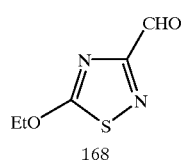
168
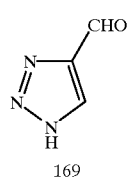
169
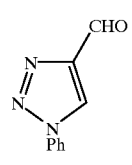
170
TABLE 14-continued
Aldehydes of the type A-CHO
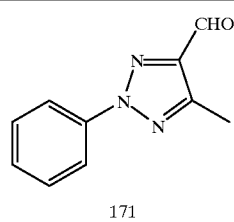
171
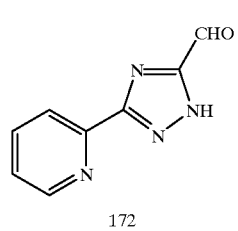
172
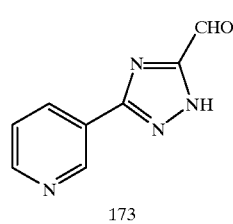
173
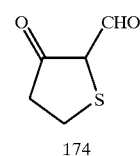
174
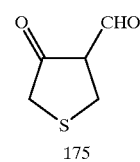
175
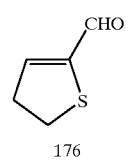
176
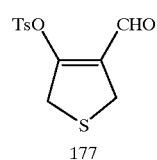
177
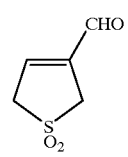
178

TABLE 14-continued
Aldehydes of the type A-CHO
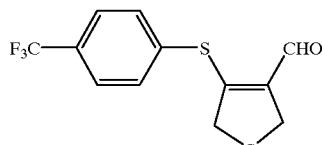
179
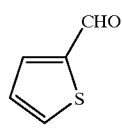
180
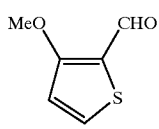
181
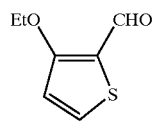
182
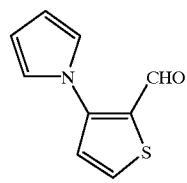
183
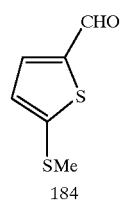
184
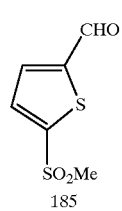
185
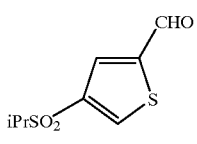
186
TABLE 14-continued
Aldehydes of the type A-CHO
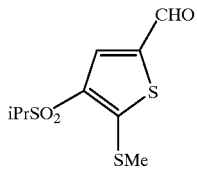
187
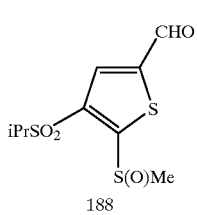
188
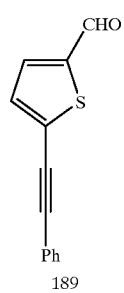
189
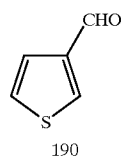
190
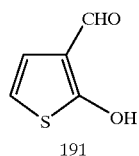
191
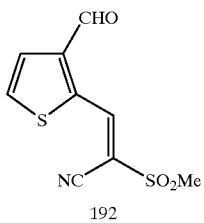
192
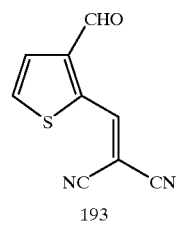
193

TABLE 14-continued
Aldehydes of the type A-CHO
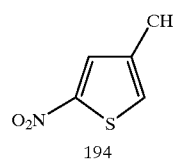
194
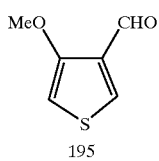
195
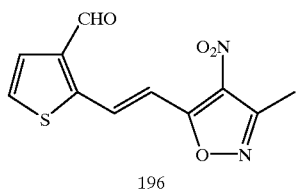
196
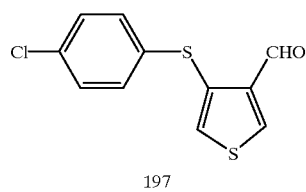
197
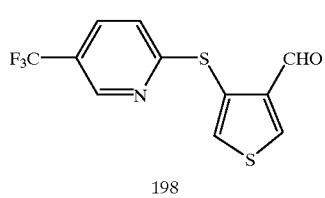
198
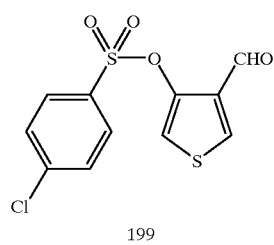
199
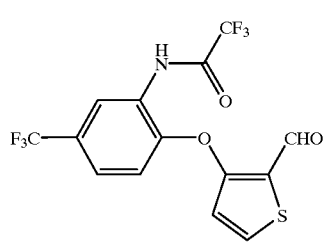
200
TABLE 14-continued
Aldehydes of the type A-CHO
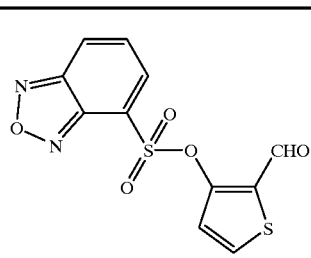
201
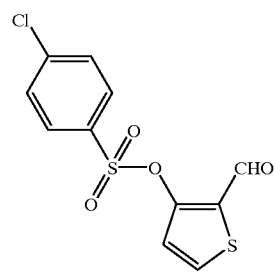
202
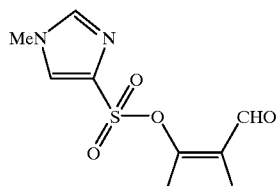
203
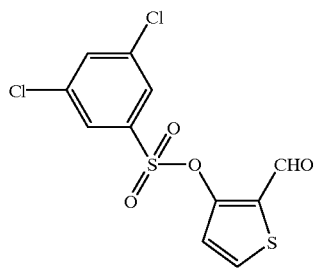
204
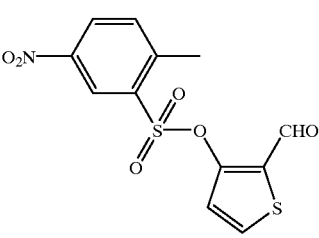
205

TABLE 14-continued
Aldehydes of the type A-CHO
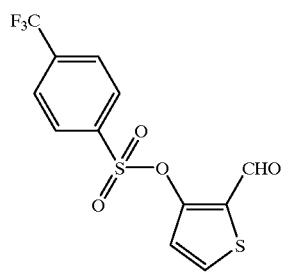
206
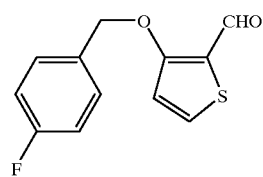
207
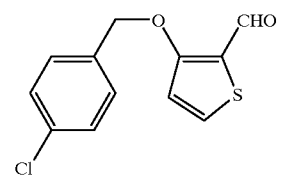
208
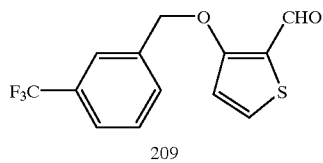
209
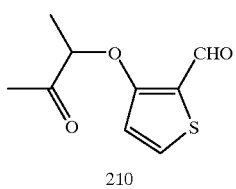
210
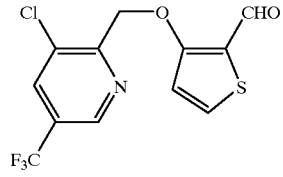
211
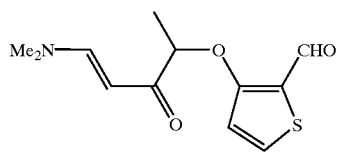
212
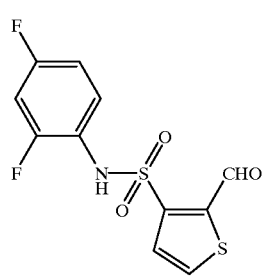
213
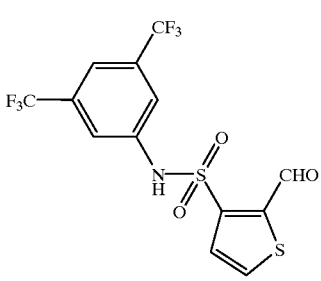
214
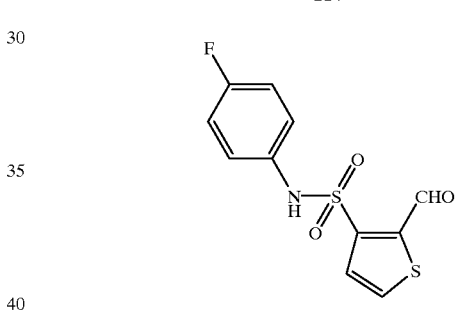
215
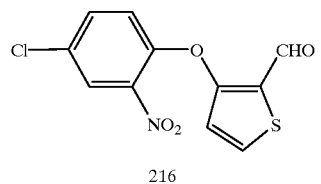
216
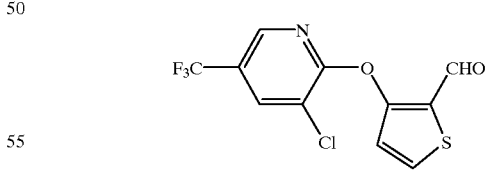
217
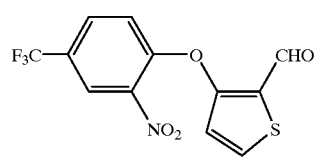
218

TABLE 14-continued
Aldehydes of the type A-CHO
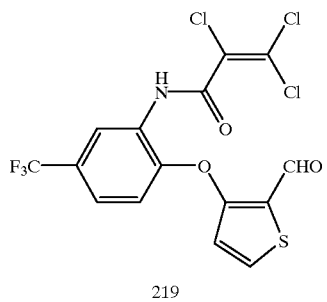
219
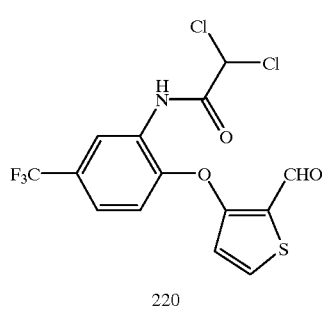
220
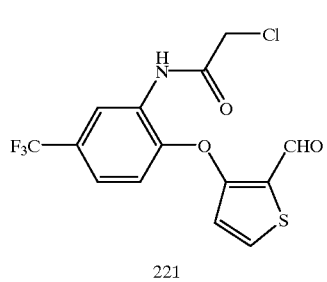
221
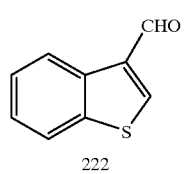
222
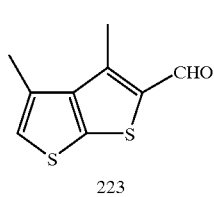
223
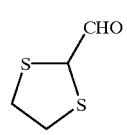
224
TABLE 14-continued
Aldehydes of the type A-CHO
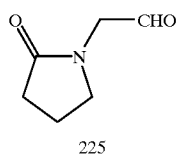
225
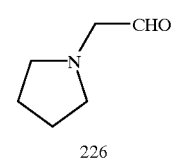
226
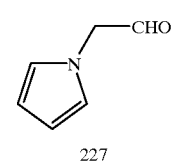
227
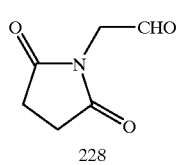
228
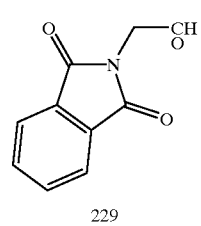
229
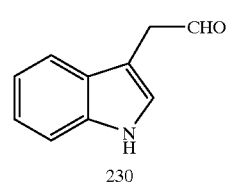
230
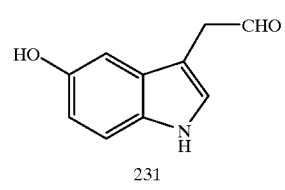
231
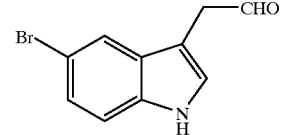
232

TABLE 14-continued
Aldehydes of the type A-CHO
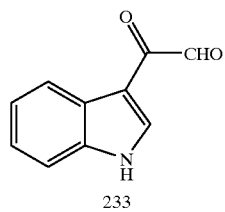
233
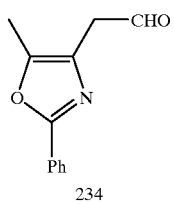
234
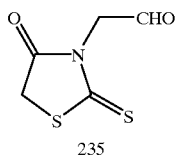
235
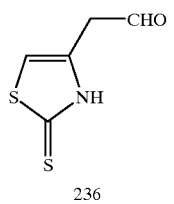
236
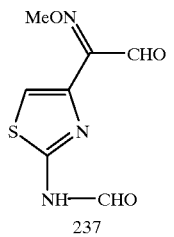
237
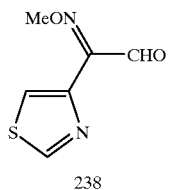
238
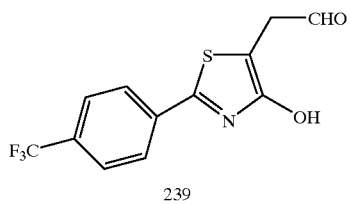
239
240
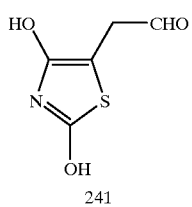
241
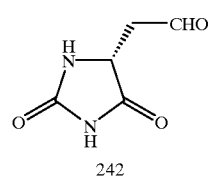
242
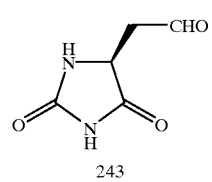
243
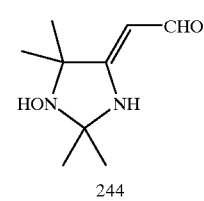
244
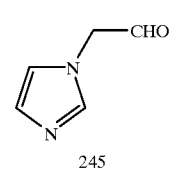
245
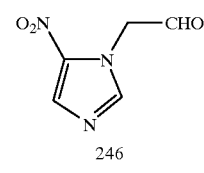
246
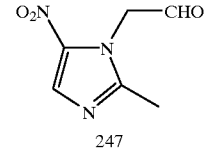
247

TABLE 14-continued
Aldehydes of the type A-CHO
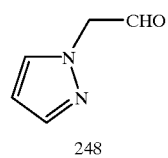
248
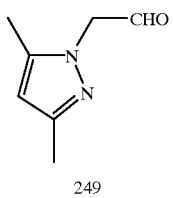
249
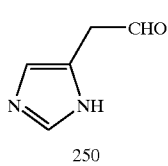
250
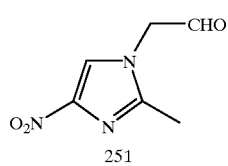
251
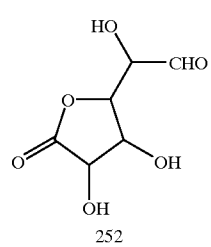
252
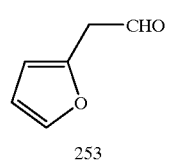
253
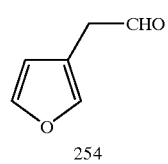
254
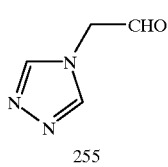
255
TABLE 14-continued
Aldehydes of the type A-CHO
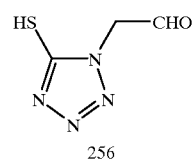
256
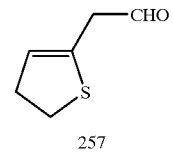
257
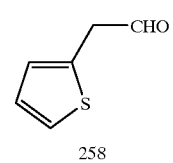
258
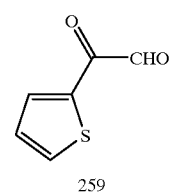
259
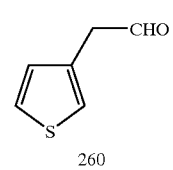
260
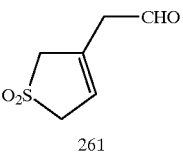
261
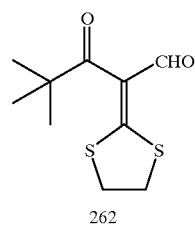
262
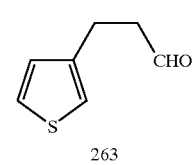
263

TABLE 14-continued
Aldehydes of the type A-CHO
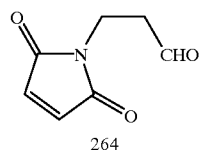
264
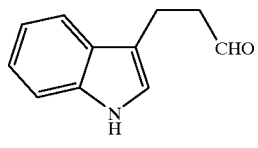
265
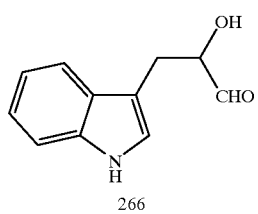
266
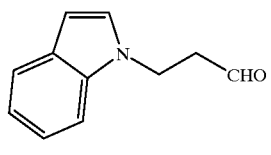
267
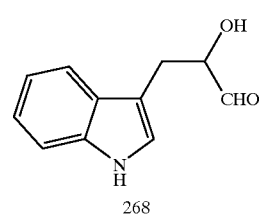
268
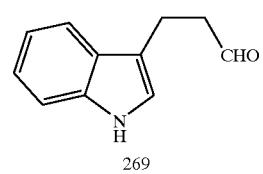
269
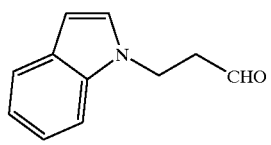
270
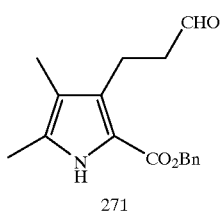
271
TABLE 14-continued
Aldehydes of the type A-CHO
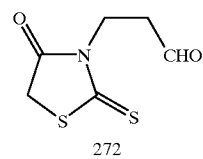
272
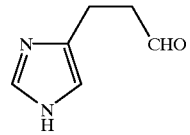
273
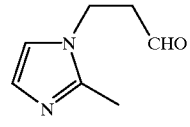
274
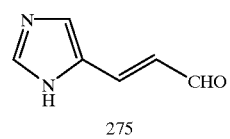
275
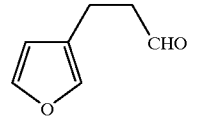
276
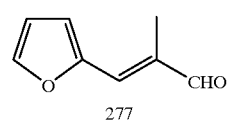
277
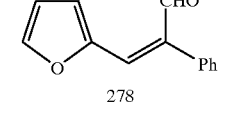
278
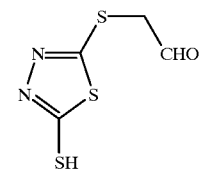
279
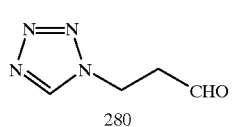
280

TABLE 14-continued

Aldehydes of the type A-CHO

281

282

283

284

284

286

287

288

289

290

291

292

293

294

295

296

TABLE 14-continued

Aldehydes of the type A-CHO 297, 298, 299, 300, 301, 302, 303, 304, 305, 306, 307, 308, 309, 310

TABLE 14-continued
Aldehydes of the type A-CHO
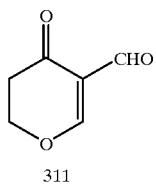
311
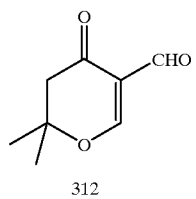
312
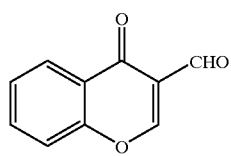
313
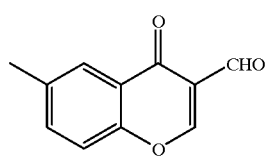
314
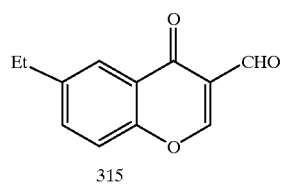
315
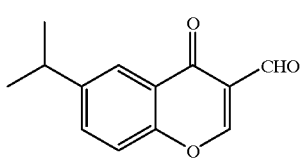
316
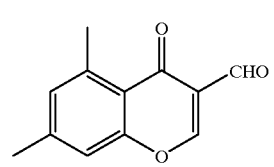
317
TABLE 14-continued
Aldehydes of the type A-CHO
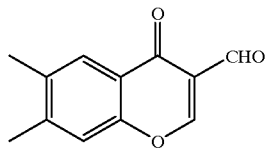
318
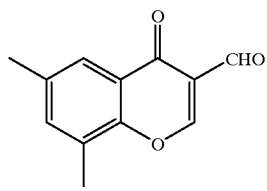
319
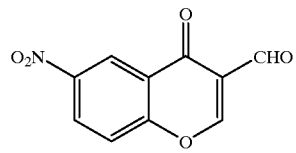
320
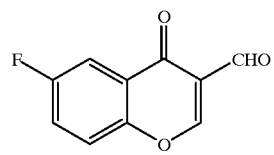
321
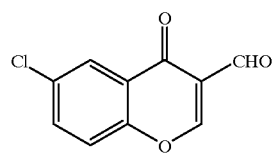
322
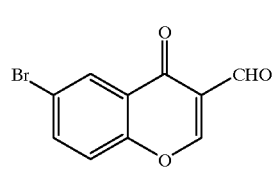
323
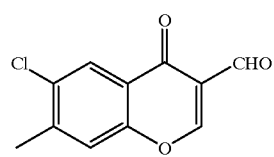
324

TABLE 14-continued
Aldehydes of the type A-CHO
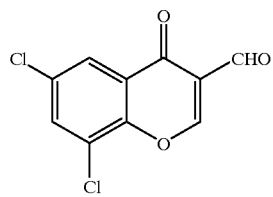
325
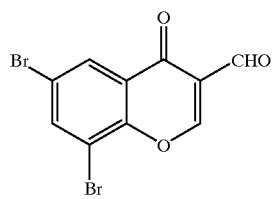
326
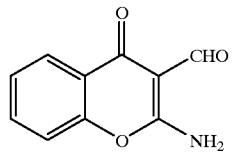
327
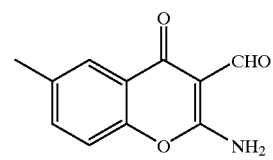
328
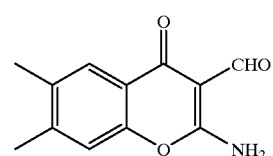
329
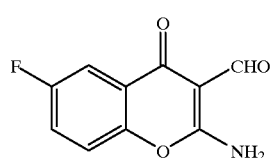
330
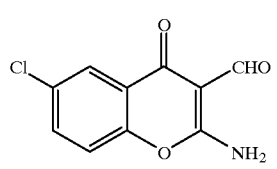
331
TABLE 14-continued
Aldehydes of the type A-CHO
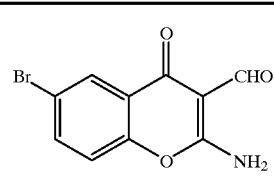
332
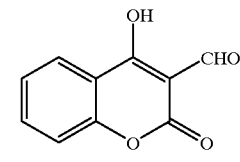
333
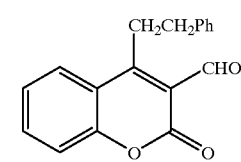
334
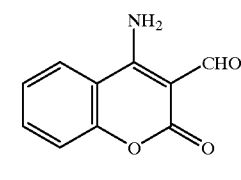
335
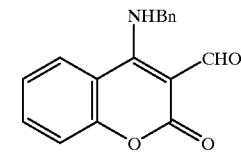
336
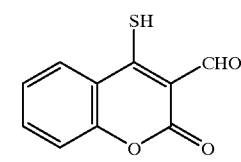
337
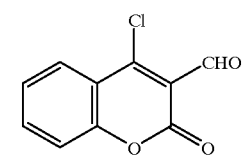
338

TABLE 14-continued
Aldehydes of the type A-CHO
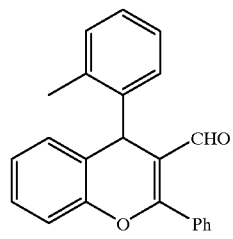
339
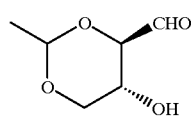
340
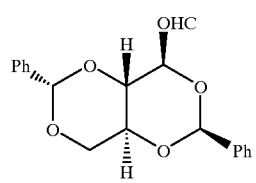
341
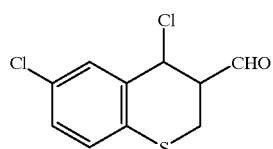
342
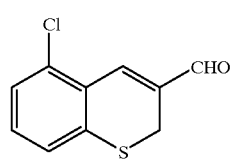
343
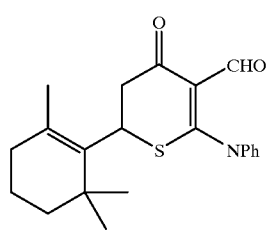
344
TABLE 14-continued
Aldehydes of the type A-CHO
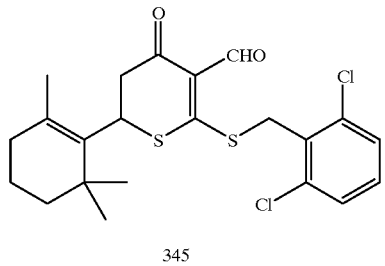
345
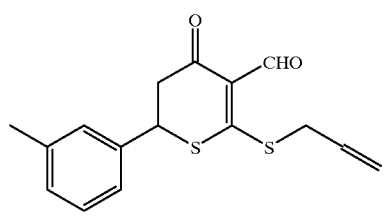
346
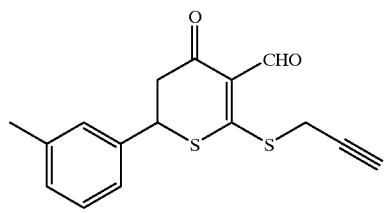
347
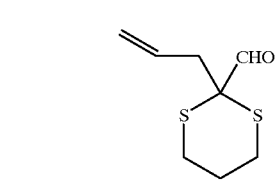
348
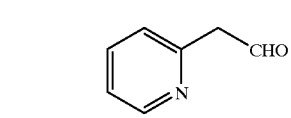
349
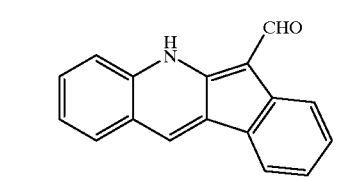
350

TABLE 14-continued
Aldehydes of the type A-CHO
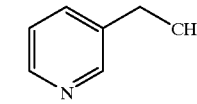
351
352
353
354
355
356
357
358
359
360
361
362
363
364

TABLE 14-continued
Aldehydes of the type A-CHO
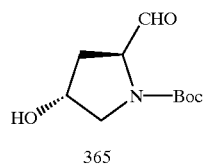
365
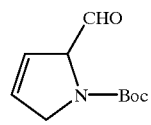
366
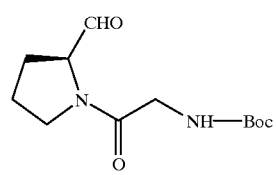
367
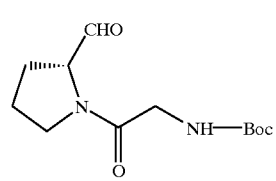
368
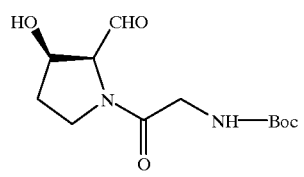
369
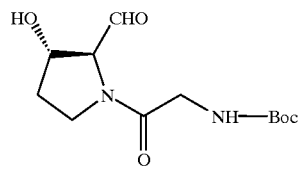
370
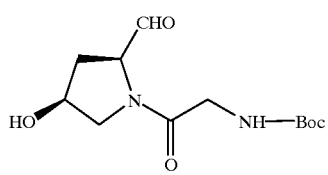
371
TABLE 14-continued
Aldehydes of the type A-CHO
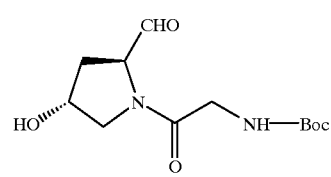
372
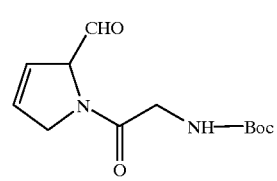
373
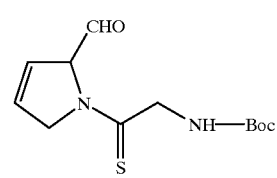
374
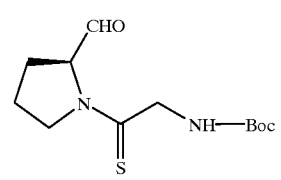
375
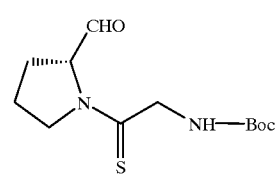
376
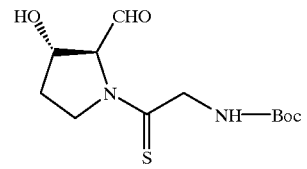
377

TABLE 14-continued
Aldehydes of the type A-CHO
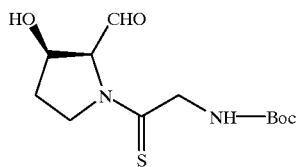
378
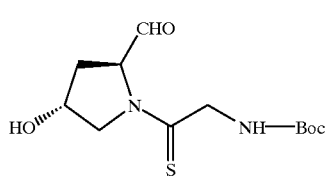
379
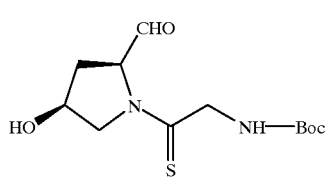
380
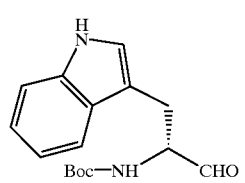
381
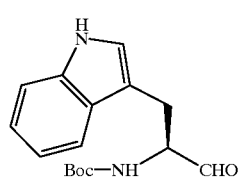
382
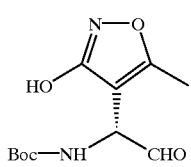
383
TABLE 14-continued
Aldehydes of the type A-CHO
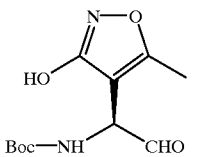
384
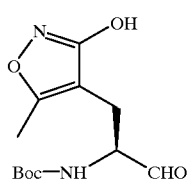
385
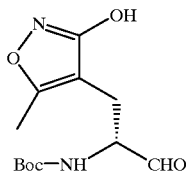
386
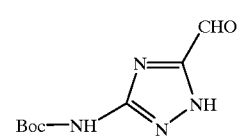
387
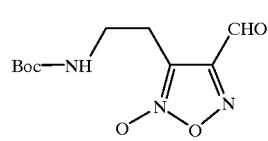
388
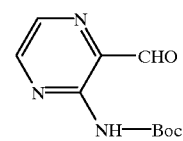
389
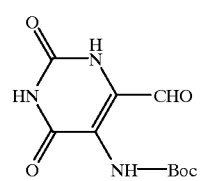
390

TABLE 14-continued
Aldehydes of the type A-CHO
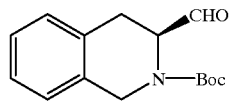
391
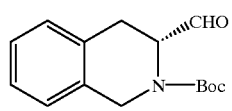
392
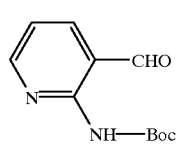
393
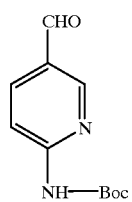
394
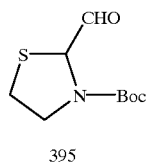
395
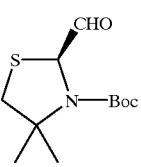
396
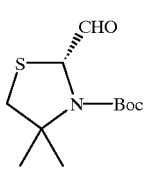
397
TABLE 14-continued
Aldehydes of the type A-CHO
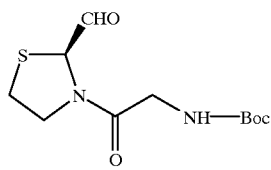
398

399
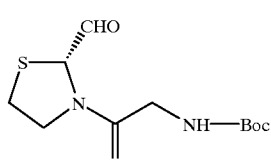
400

401
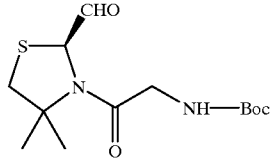
402
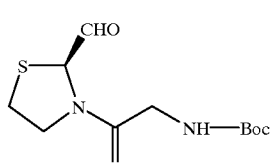
403
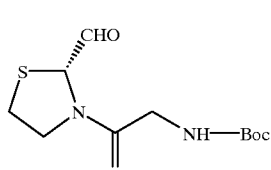
404

US 6,204,293 B1
TABLE 14-continued
Aldehydes of the type A-CHO
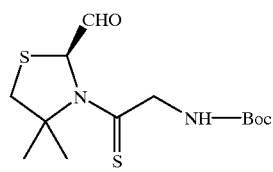
405
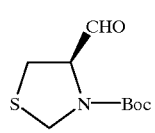
406
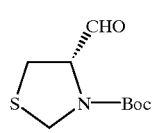
407
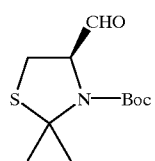
408
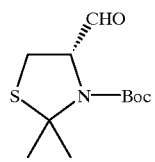
409
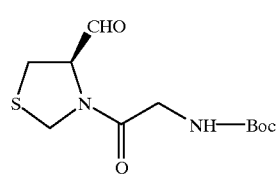
410
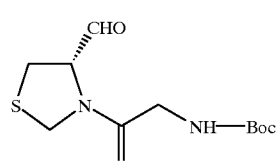
411
TABLE 14-continued
Aldehydes of the type A-CHO
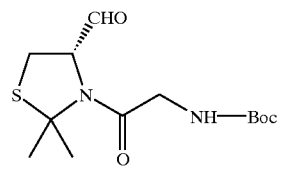
412
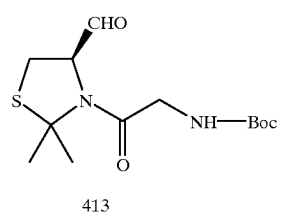
413
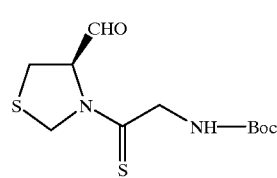
414
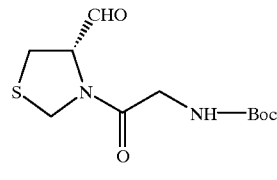
415
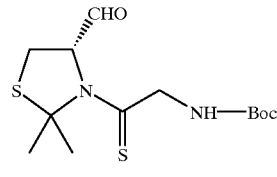
416
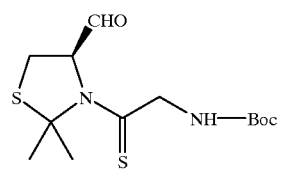
417
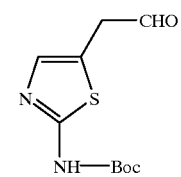
418

TABLE 14-continued
Aldehydes of the type A-CHO
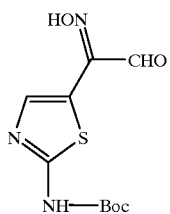
419
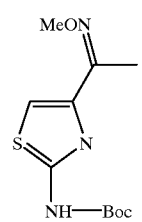
420
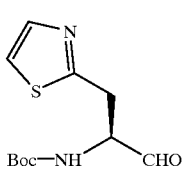
421
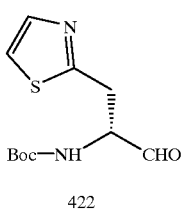
422
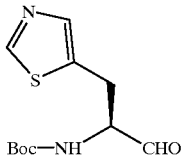
423
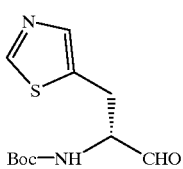
424
TABLE 14-continued
Aldehydes of the type A-CHO
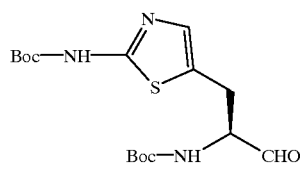
425
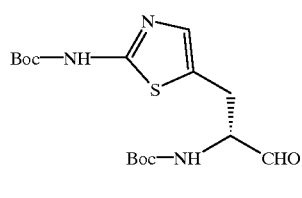
426
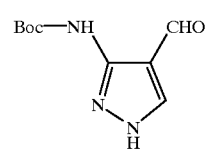
427
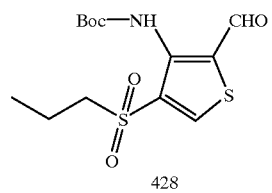
428
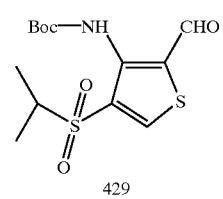
429
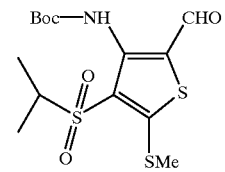
430
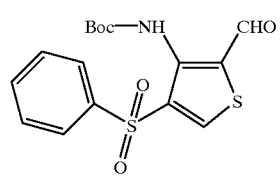
431

TABLE 14-continued
Aldehydes of the type A-CHO
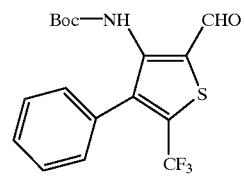
432
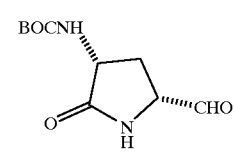
433
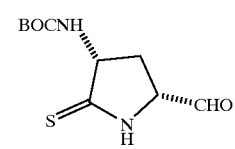
434
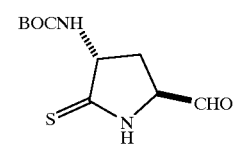
435
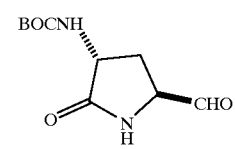
436
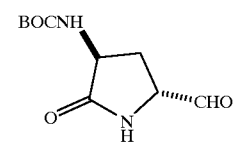
437
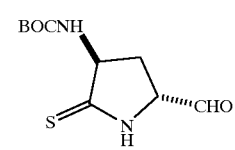
438
TABLE 14-continued
Aldehydes of the type A-CHO
439
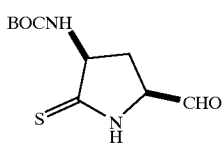
440
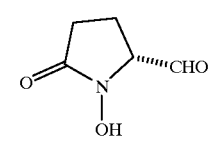
441
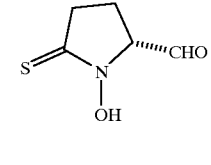
442
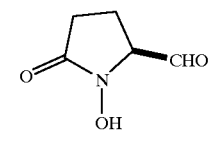
443
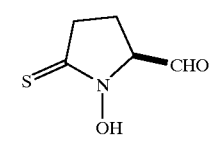
444
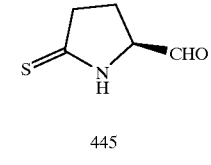
445
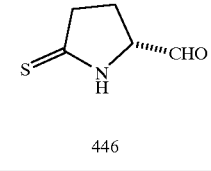
446

TABLE 15
Alcohols of the type A-OH
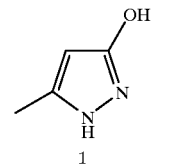
1
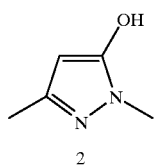
2
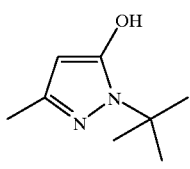
3
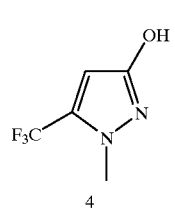
4
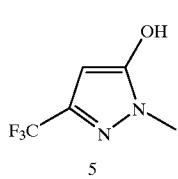
5
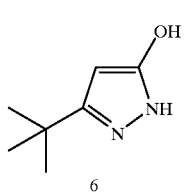
6
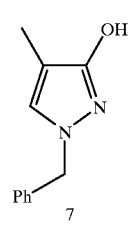
7
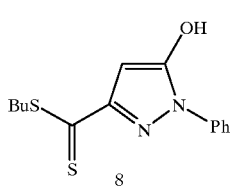
8
TABLE 15-continued
Alcohols of the type A-OH
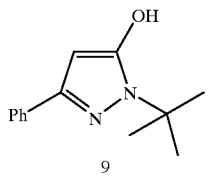
9
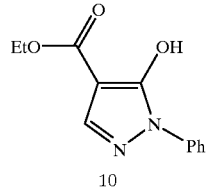
10
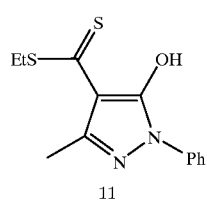
11
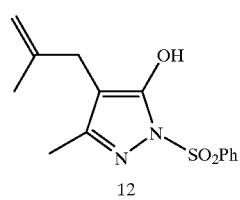
12
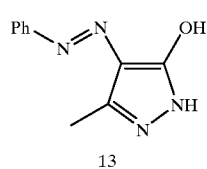
13
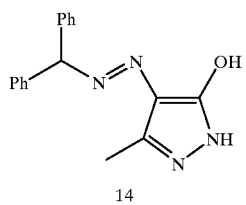
14
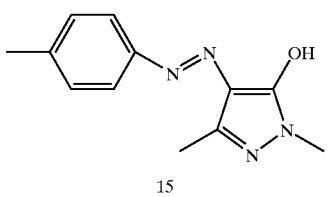
15

TABLE 15-continued
Alcohols of the type A-OH
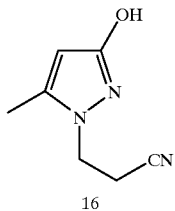
16
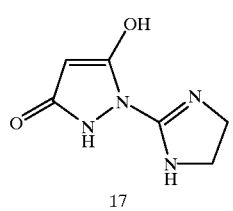
17
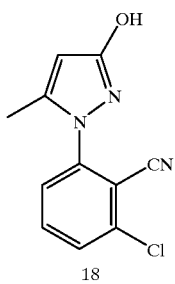
18
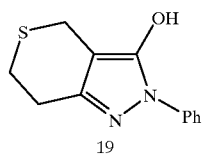
19
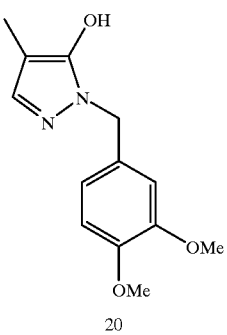
20
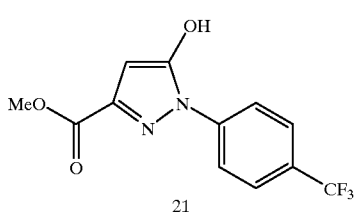
21
TABLE 15-continued
Alcohols of the type A-OH
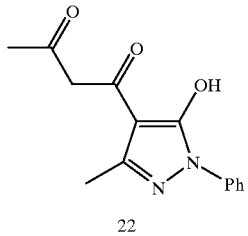
22
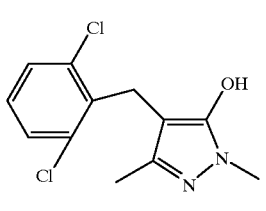
23
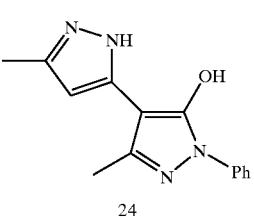
24
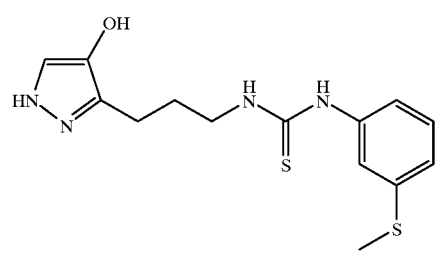
25
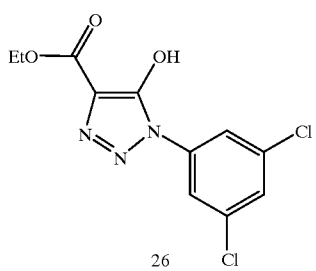
26
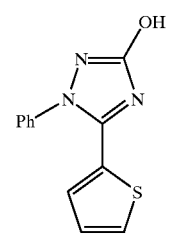
27

TABLE 15-continued
Alcohols of the type A-OH
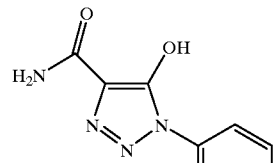
28
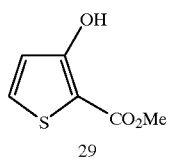
29
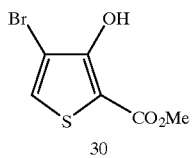
30
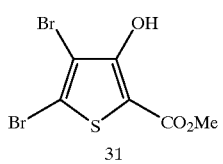
31
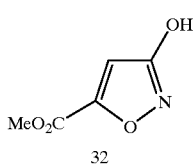
32
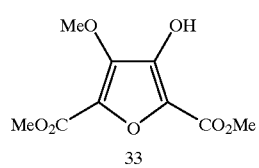
33
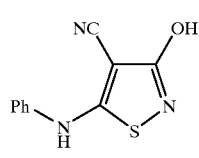
34
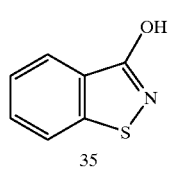
35
TABLE 15-continued
Alcohols of the type A-OH
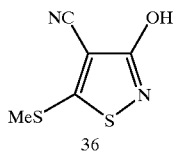
36
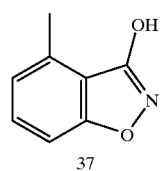
37
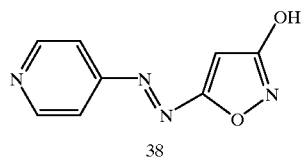
38
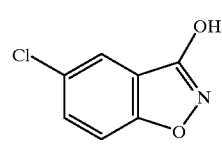
39
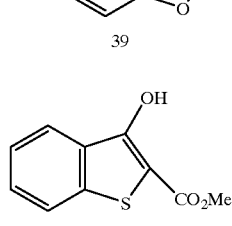
40
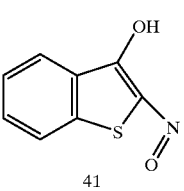
41
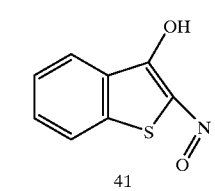
42
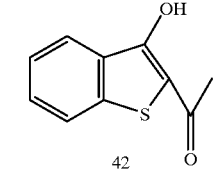
43

TABLE 15-continued
Alcohols of the type A-OH
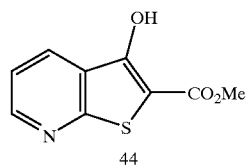
44
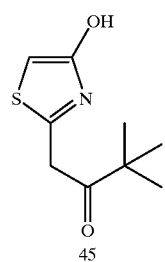
45
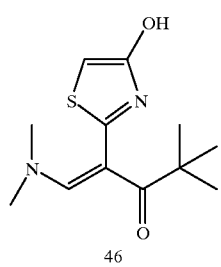
46
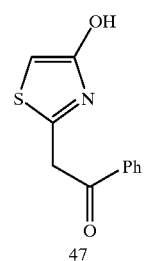
47
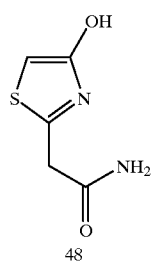
48
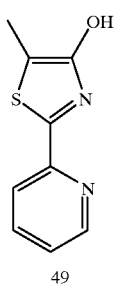
49
TABLE 15-continued
Alcohols of the type A-OH
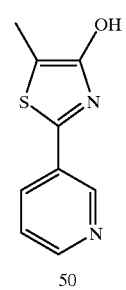
50
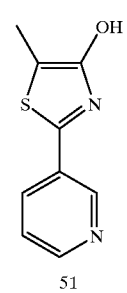
51
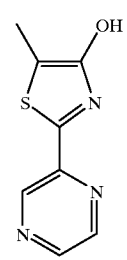
52
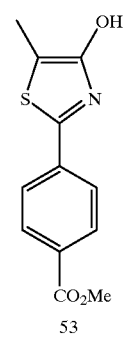
53
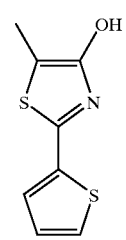
54

TABLE 15-continued
Alcohols of the type A-OH
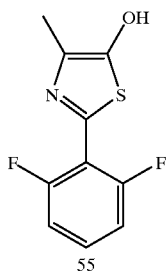
55
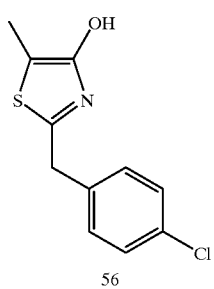
56
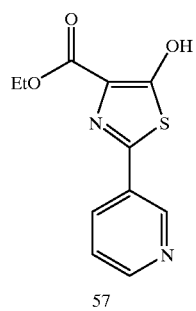
57
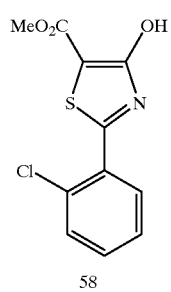
58
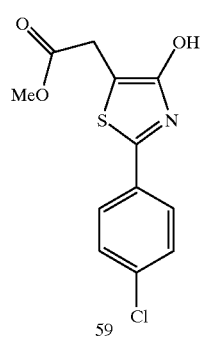
59
TABLE 15-continued
Alcohols of the type A-OH
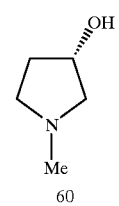
60
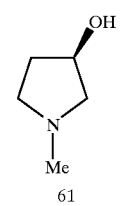
61
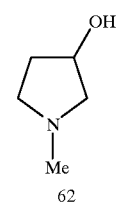
62
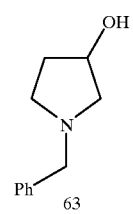
63
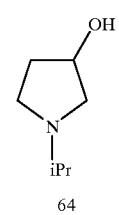
64
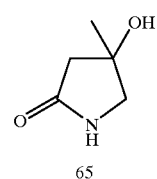
65
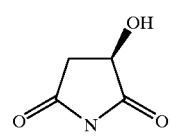
66

TABLE 15-continued
Alcohols of the type A-OH
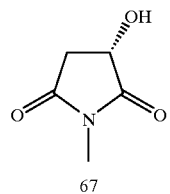
67
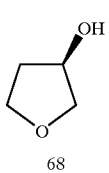
68
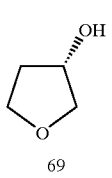
69
70
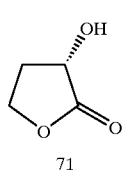
71
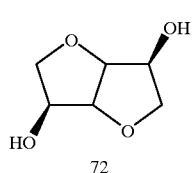
72
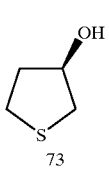
73
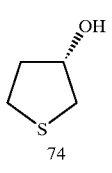
74
TABLE 15-continued
Alcohols of the type A-OH
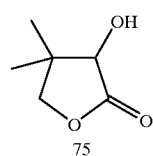
75
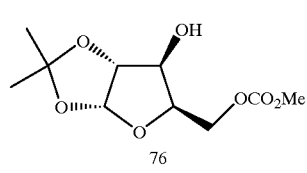
76
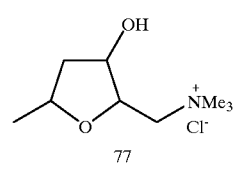
77
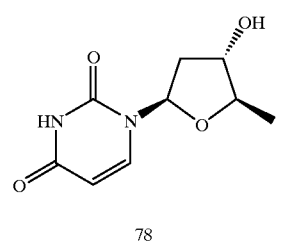
78
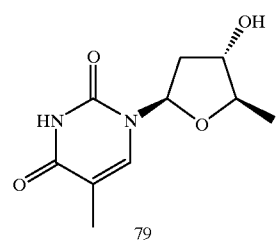
79
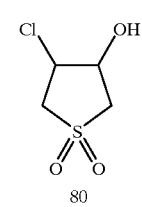
80
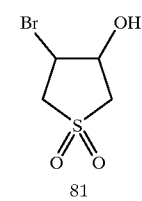
81

TABLE 15-continued
Alcohols of the type A-OH
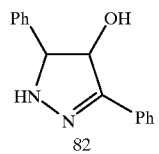
82
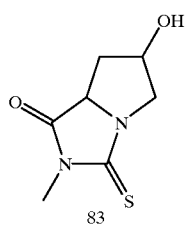
83
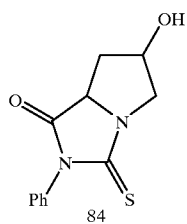
84
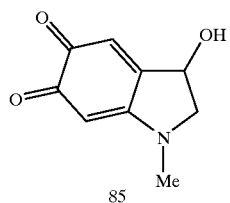
85
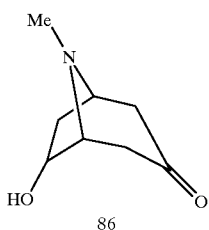
86
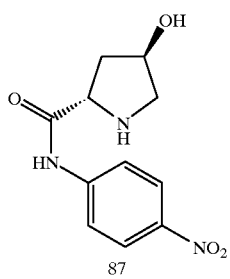
87
TABLE 15-continued
Alcohols of the type A-OH
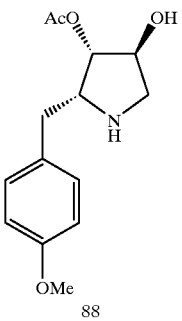
88
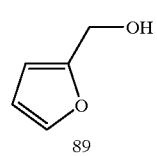
89
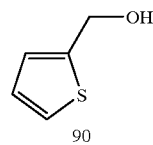
90
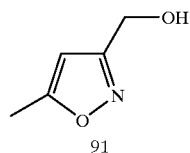
91
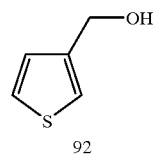
92
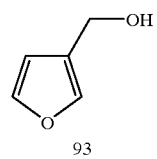
93
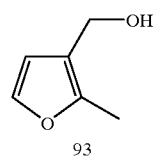
93
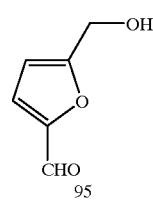
95

TABLE 15-continued
Alcohols of the type A-OH
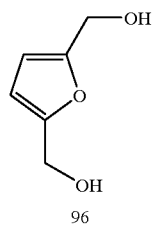
96
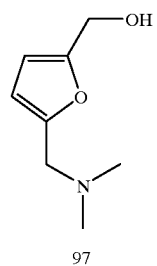
97
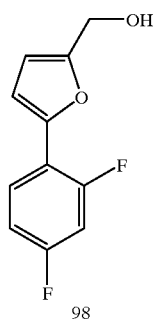
98
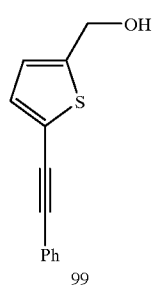
99
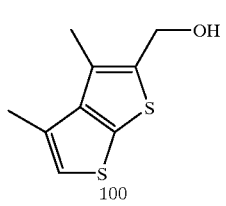
100
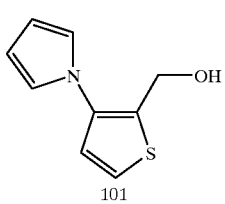
101
TABLE 15-continued
Alcohols of the type A-OH
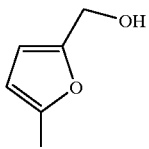
102
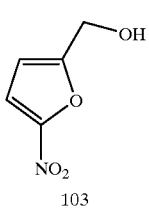
103
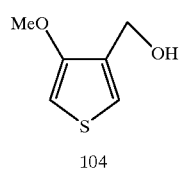
104
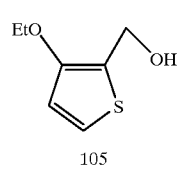
105
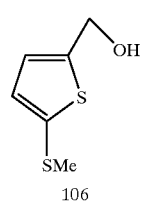
106
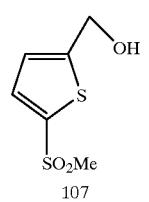
107
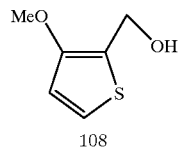
108
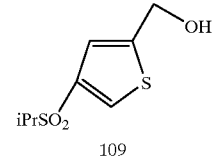
109

TABLE 15-continued
Alcohols of the type A-OH
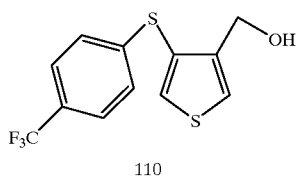
110
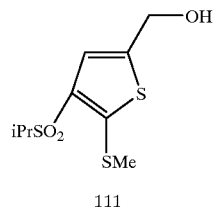
111
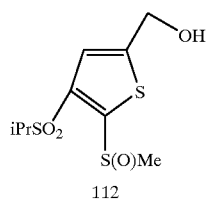
112
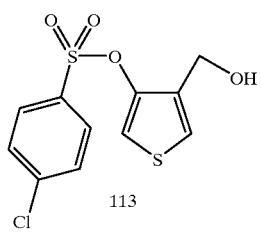
113
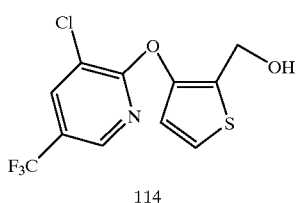
114
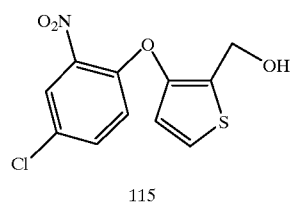
115
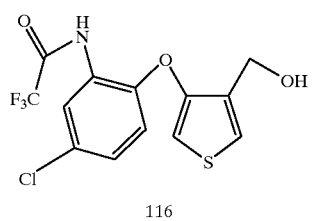
116
TABLE 15-continued
Alcohols of the type A-OH
117
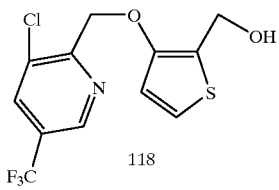
118
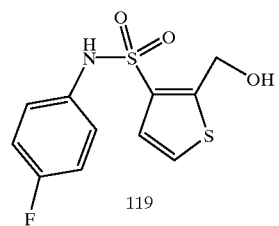
119
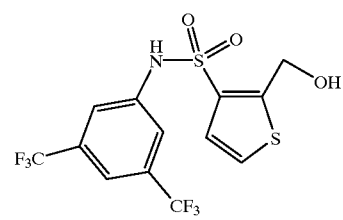
120
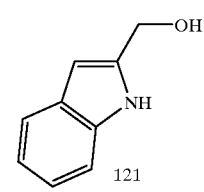
121
122
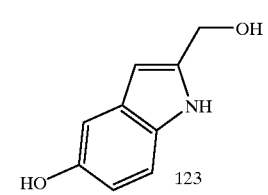
123

TABLE 15-continued
Alcohols of the type A-OH
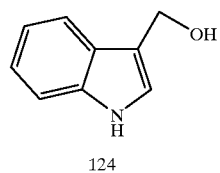
124
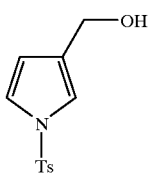
125
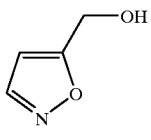
126
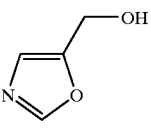
127
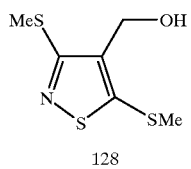
128
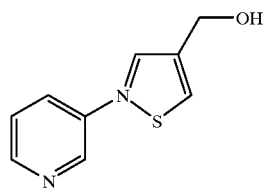
129
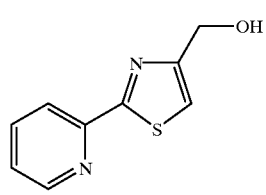
130
TABLE 15-continued
Alcohols of the type A-OH
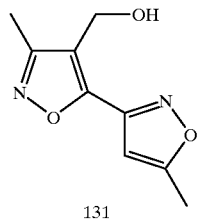
131
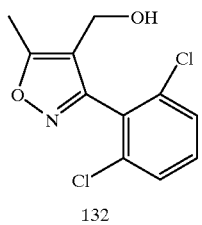
132
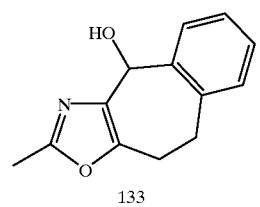
133
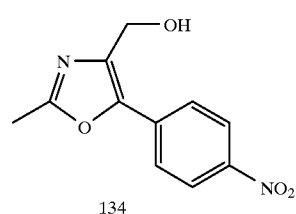
134
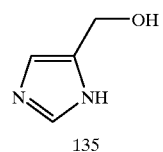
135
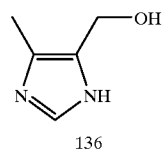
136
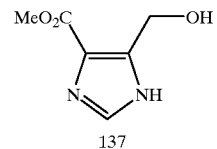
137
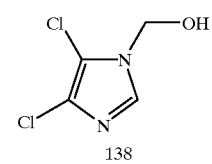
138

TABLE 15-continued
Alcohols of the type A-OH
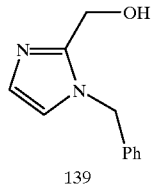
139
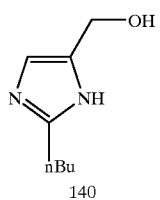
140
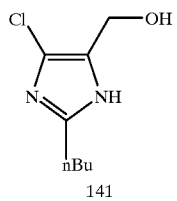
141
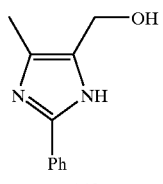
142
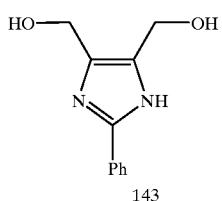
143
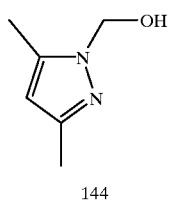
144
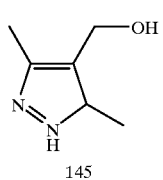
145
TABLE 15-continued
Alcohols of the type A-OH
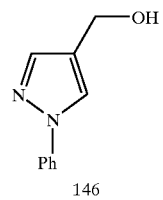
146
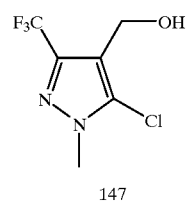
147
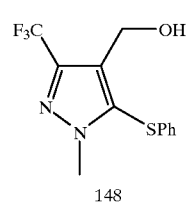
148
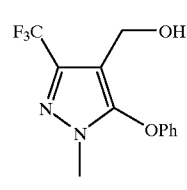
149
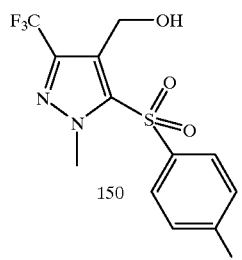
150
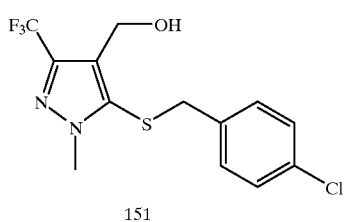
151
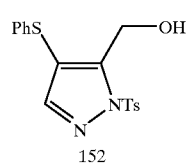
152

TABLE 15-continued
Alcohols of the type A-OH
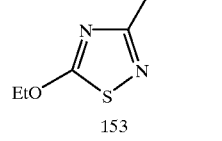
153
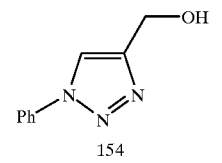
154
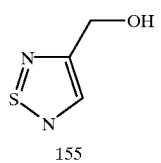
155
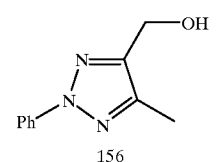
156
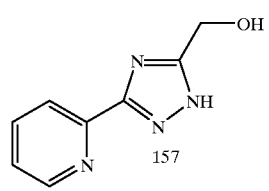
157
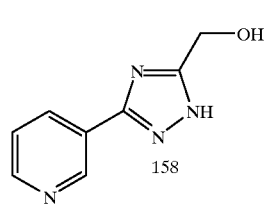
158
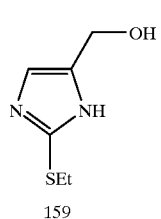
159
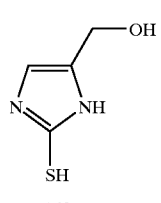
160
TABLE 15-continued
Alcohols of the type A-OH
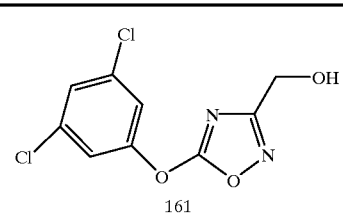
161
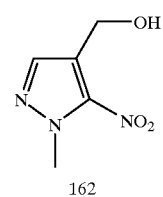
162
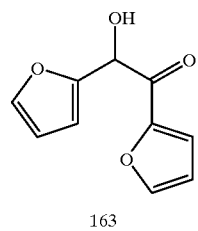
163
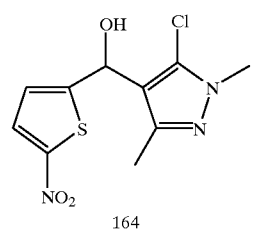
164
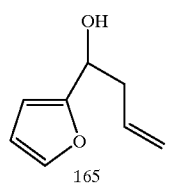
165
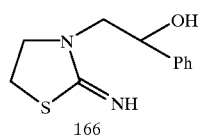
166
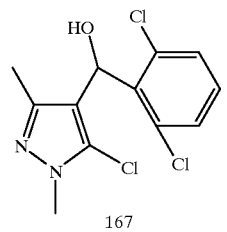
167

TABLE 15-continued
Alcohols of the type A-OH
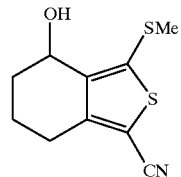
168
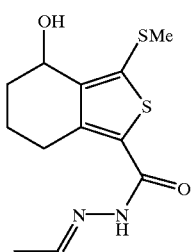
169
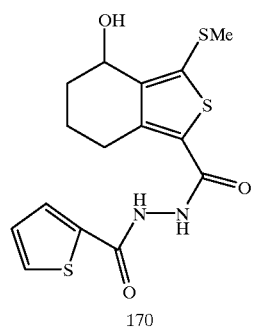
170
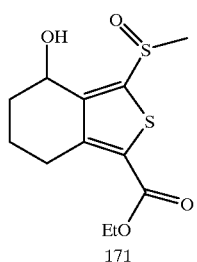
171
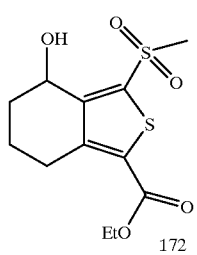
172
TABLE 15-continued
Alcohols of the type A-OH
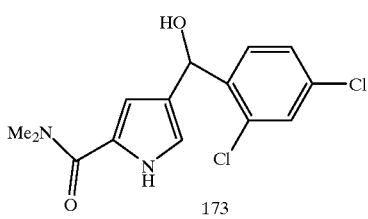
173
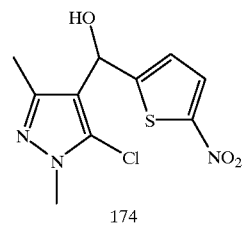
174
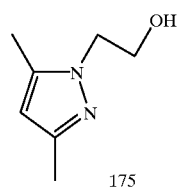
175
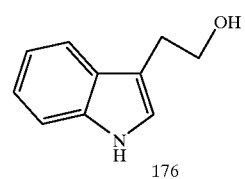
176
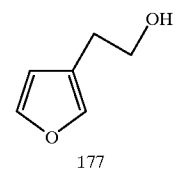
177
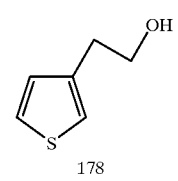
178
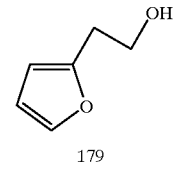
179
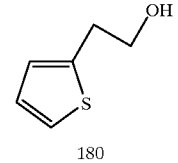
180

TABLE 15-continued
Alcohols of the type A-OH
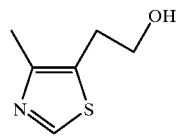
181
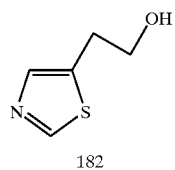
182
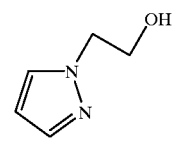
183
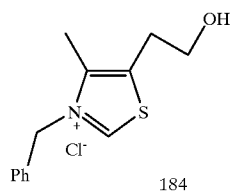
184
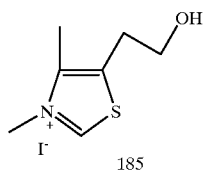
185
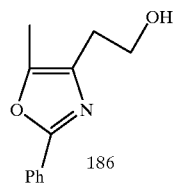
186
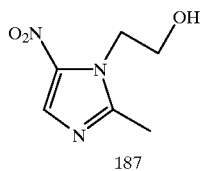
187
188
TABLE 15-continued
Alcohols of the type A-OH
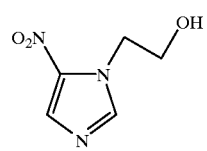
189
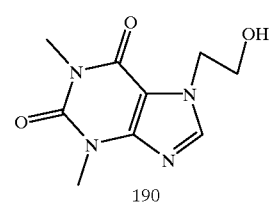
190
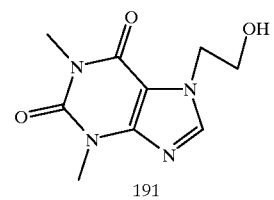
191
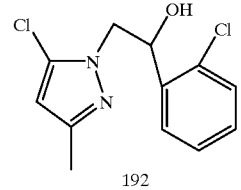
192
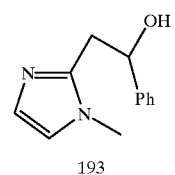
193
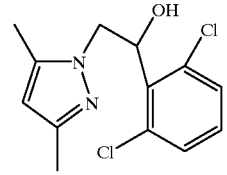
194
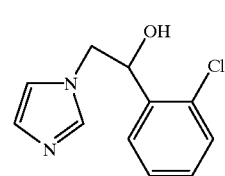
195

TABLE 15-continued
Alcohols of the type A-OH
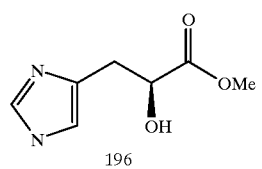
196
197
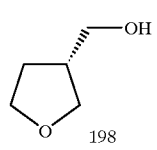
198
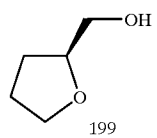
199
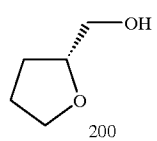
200
201
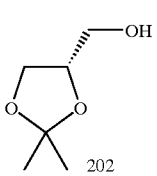
202
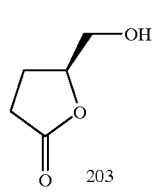
203
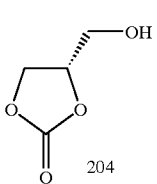
204
TABLE 15-continued
Alcohols of the type A-OH
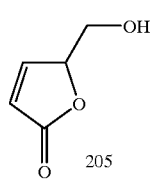
205
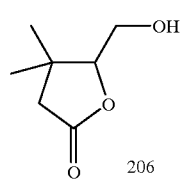
206
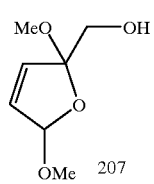
207
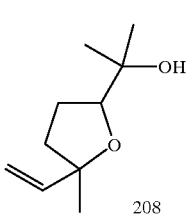
208
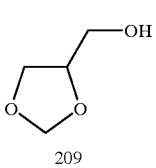
209
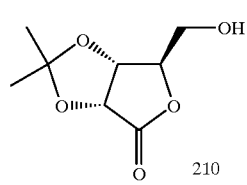
210
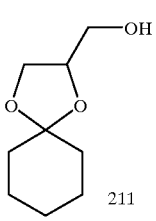
211

441
TABLE 15-continued
Alcohols of the type A-OH
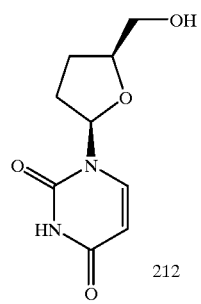
212
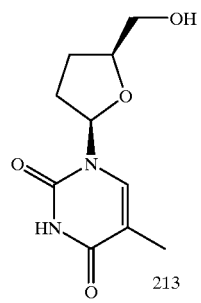
213
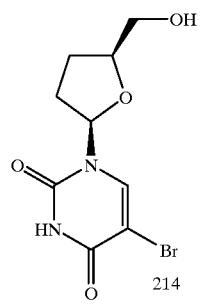
214
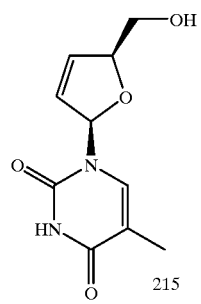
215
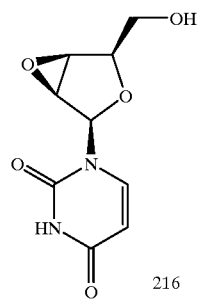
216
442
TABLE 15-continued
Alcohols of the type A-OH
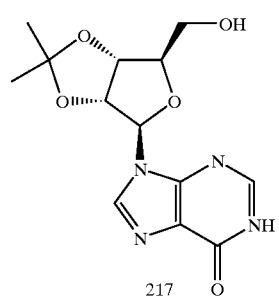
217
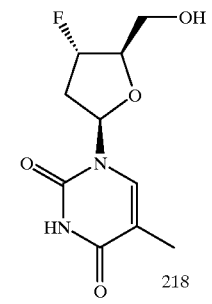
218
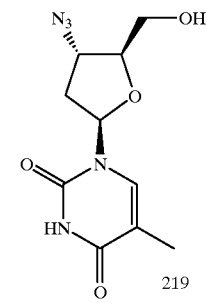
219
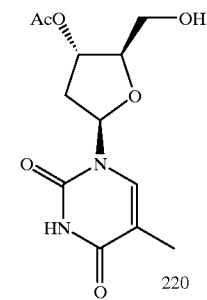
220
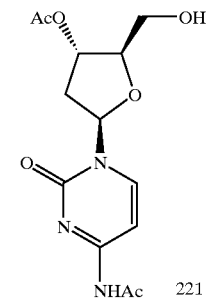
221

TABLE 15-continued
Alcohols of the type A-OH
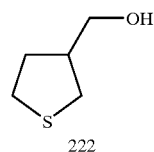
222
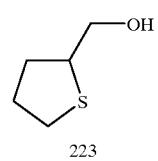
223
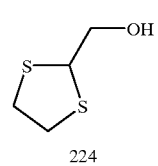
224
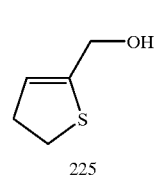
225
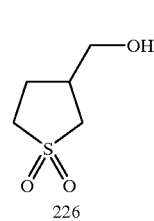
226
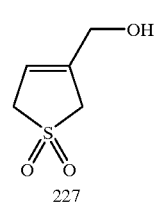
227
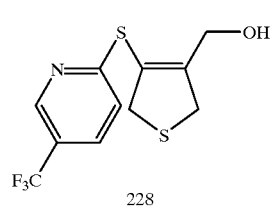
228
229
TABLE 15-continued
Alcohols of the type A-OH
230
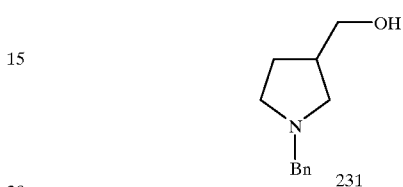
231
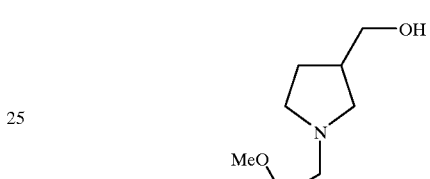
232
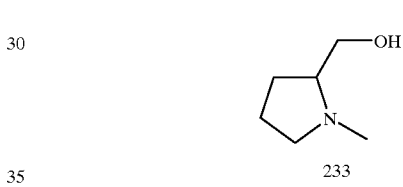
233
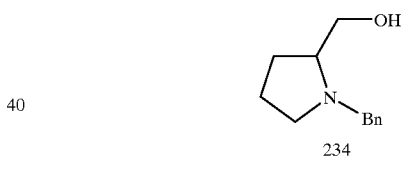
234
235
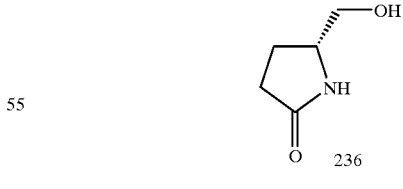
236
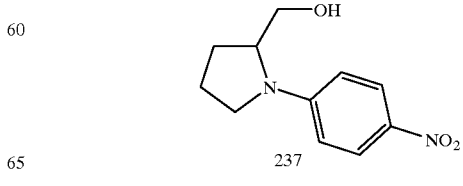
237

TABLE 15-continued
Alcohols of the type A-OH
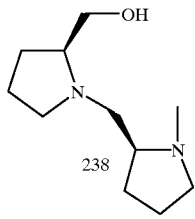
238
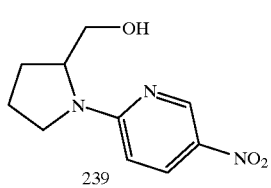
239
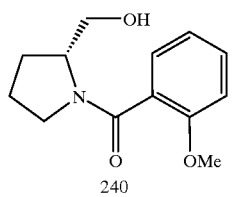
240
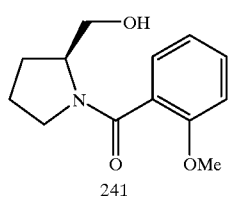
241
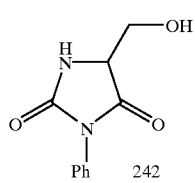
242
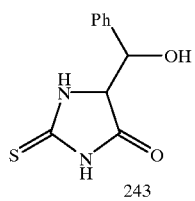
243
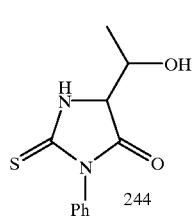
244
TABLE 15-continued
Alcohols of the type A-OH
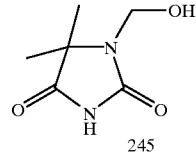
245
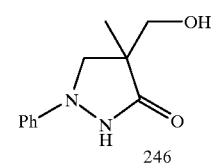
246
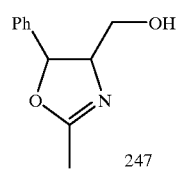
247
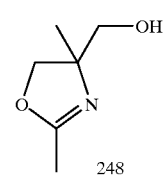
248
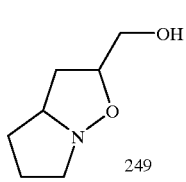
249
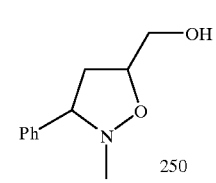
250
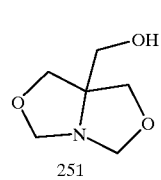
251
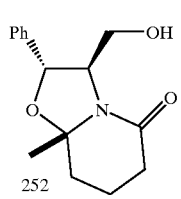
252

TABLE 15-continued
Alcohols of the type A-OH
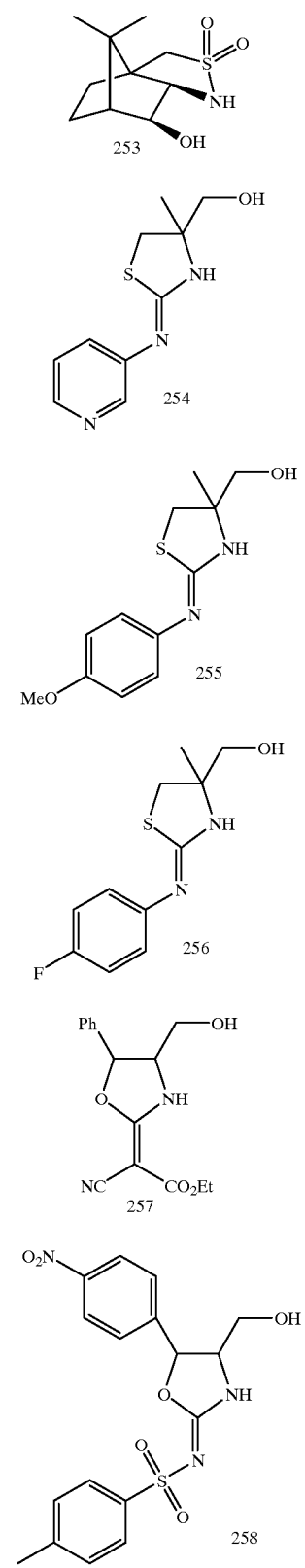
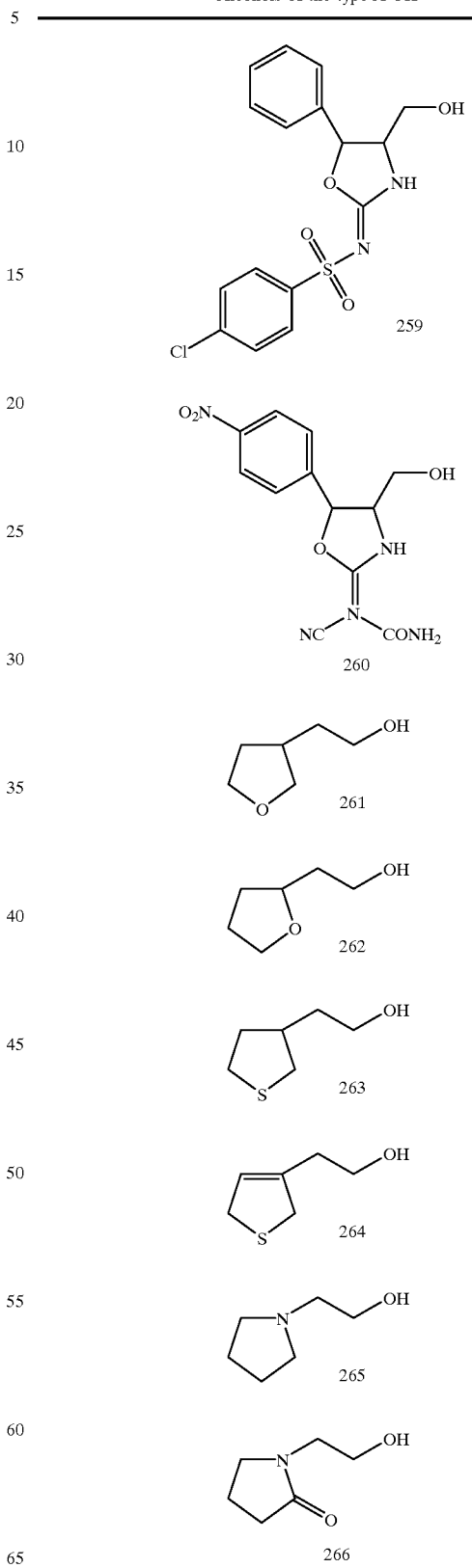

TABLE 15-continued
Alcohols of the type A-OH
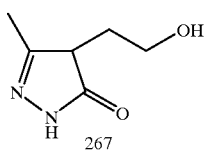
267
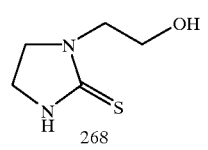
268
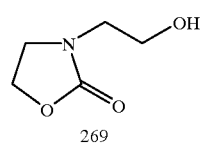
269
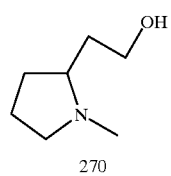
270
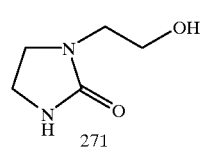
271
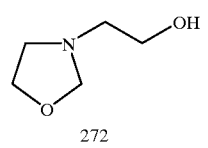
272
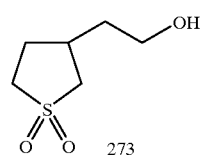
273
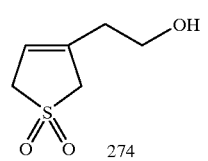
274
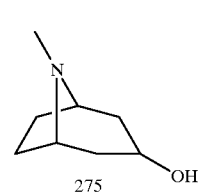
275
TABLE 15-continued
Alcohols of the type A-OH
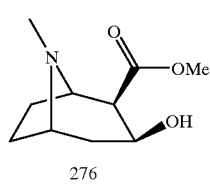
276
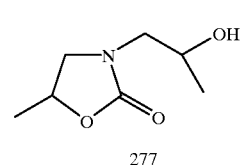
277
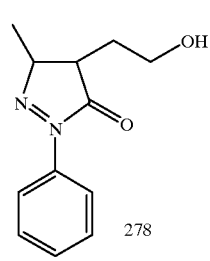
278
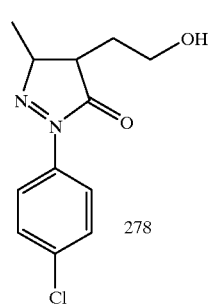
278
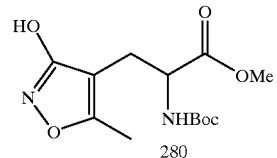
280
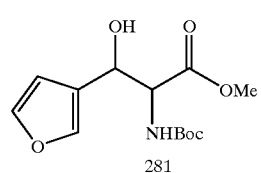
281
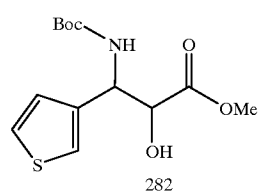
282

TABLE 15-continued
Alcohols of the type A-OH
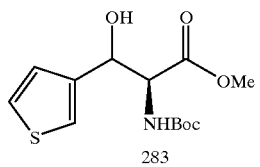
283
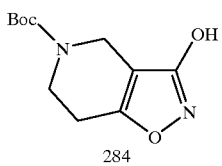
284
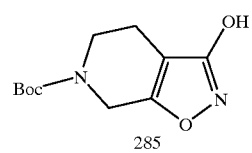
285
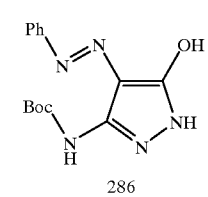
286
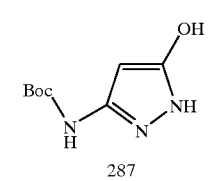
287
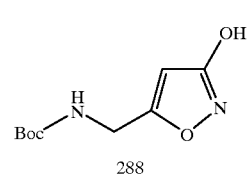
288
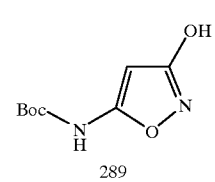
289
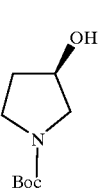
290
TABLE 15-continued
Alcohols of the type A-OH
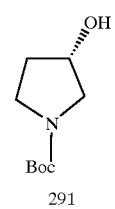
291
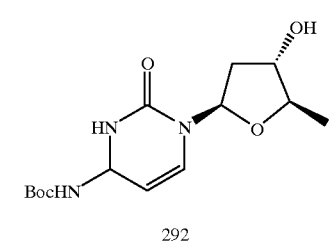
292
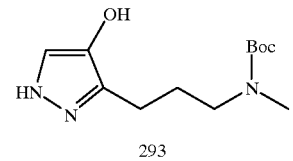
293
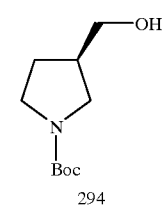
294
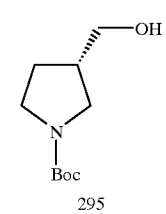
295
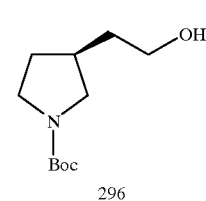
296
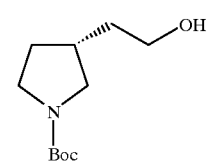
297

TABLE 15-continued
Alcohols of the type A-OH
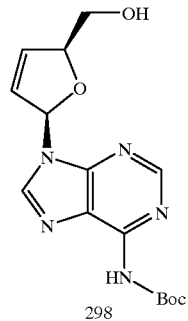
298
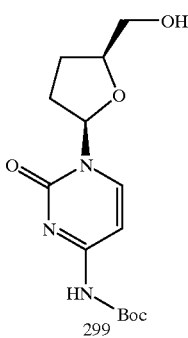
299
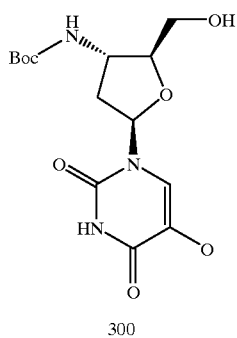
300
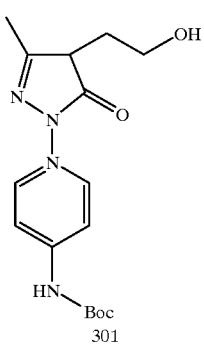
301
TABLE 15-continued
Alcohols of the type A-OH
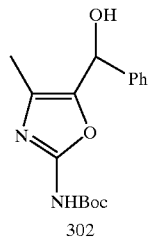
302
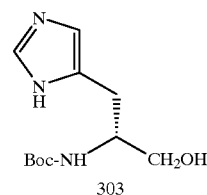
303
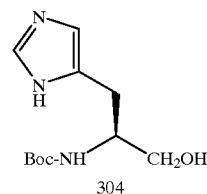
304
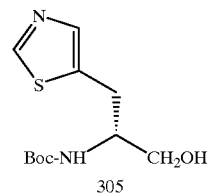
305
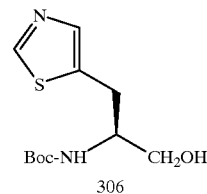
306
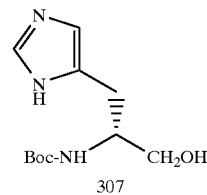
307
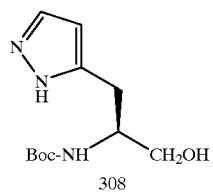
308

TABLE 15-continued
Alcohols of the type A-OH
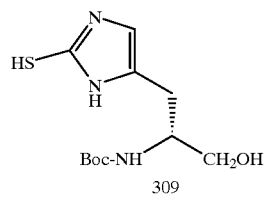
309
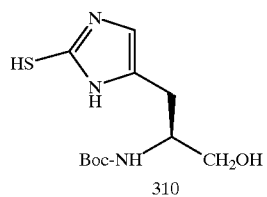
310
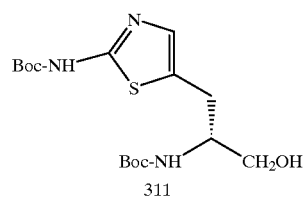
311
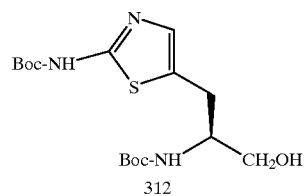
312
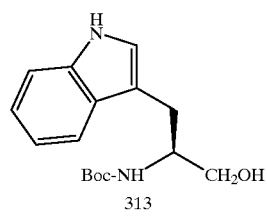
313
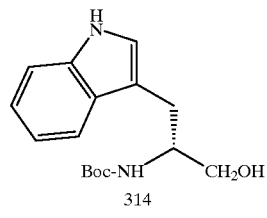
314
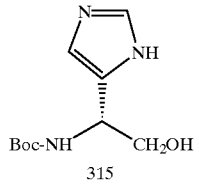
315
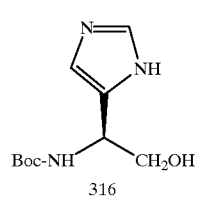
316
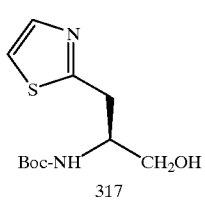
317
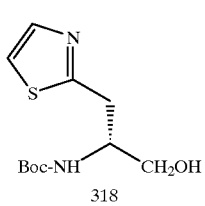
318
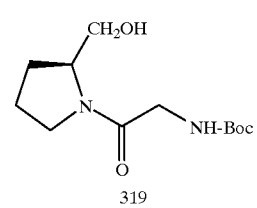
319
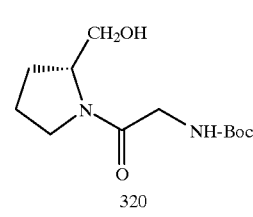
320
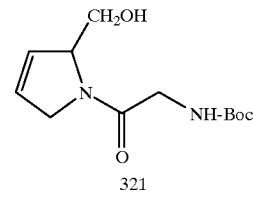
321
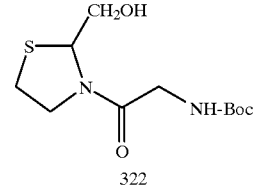
322

TABLE 15-continued

Alcohols of the type A-OH 323, 324, 325, 326, 327, 328, 329, 330, 331, 332, 333, 334, 335, 336

TABLE 15-continued
Alcohols of the type A-OH
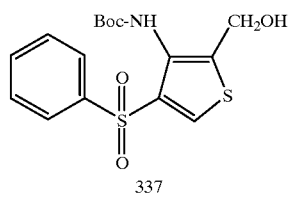
337
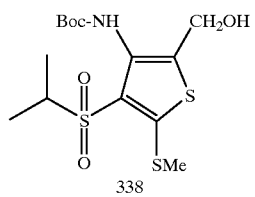
338
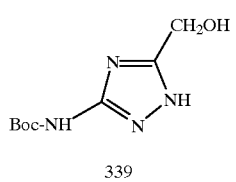
339
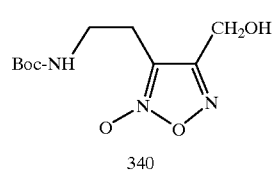
340
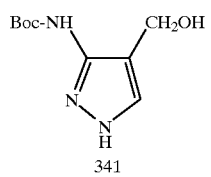
341
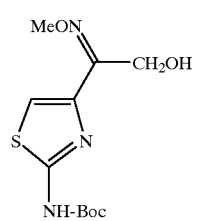
342
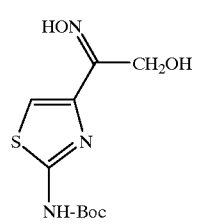
343
TABLE 15-continued
Alcohols of the type A-OH
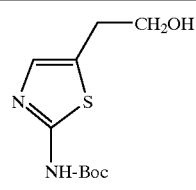
344
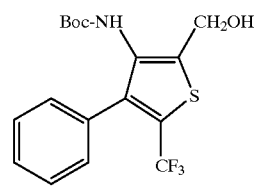
345
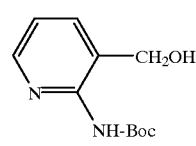
346
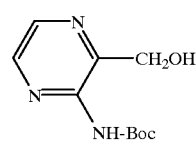
347
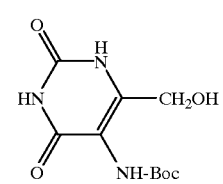
348
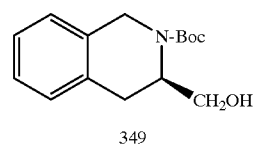
349
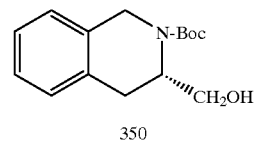
350
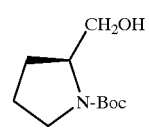
351

TABLE 15-continued
Alcohols of the type A-OH
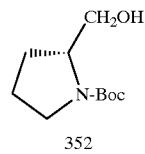
352
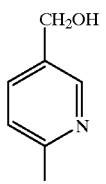
353
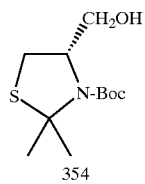
354
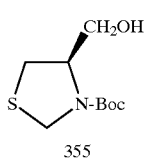
355
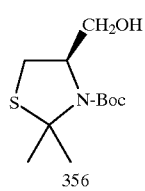
356
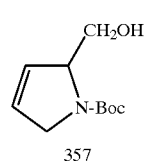
357
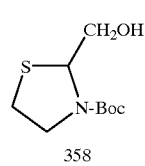
358
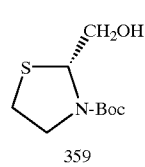
359
TABLE 15-continued
Alcohols of the type A-OH
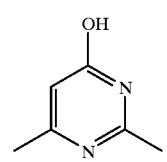
360
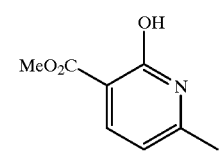
361
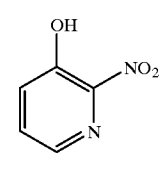
362
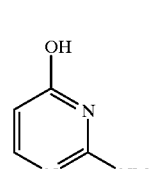
363
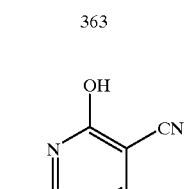
364
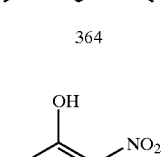
365
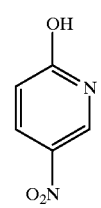
366

TABLE 15-continued
Alcohols of the type A-OH
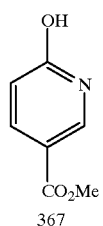
367
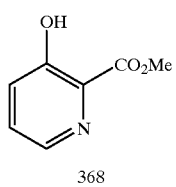
368
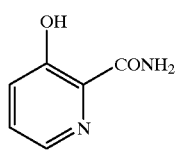
369
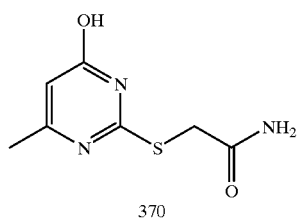
370
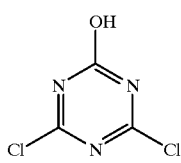
371
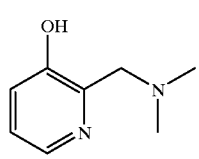
372
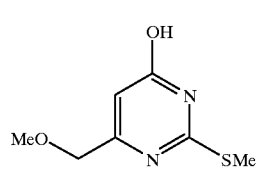
373
TABLE 15-continued
Alcohols of the type A-OH
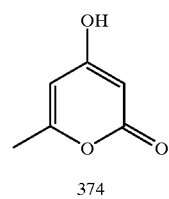
374
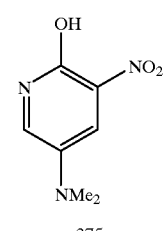
375
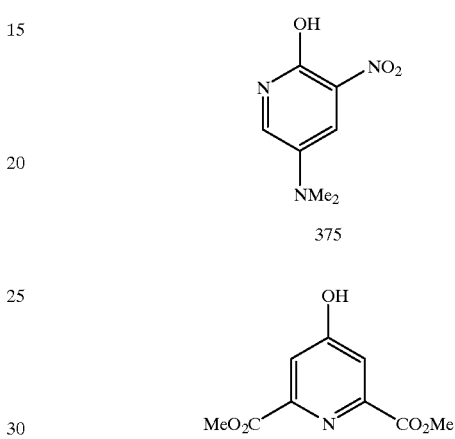
376
377
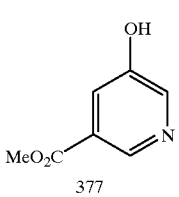
378
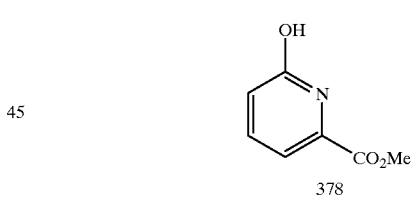
379
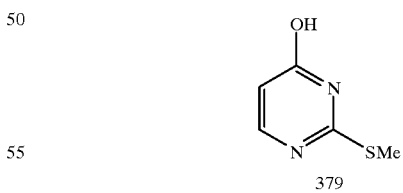
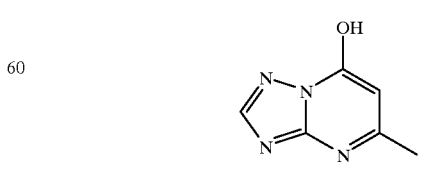
380

TABLE 15-continued
Alcohols of the type A-OH
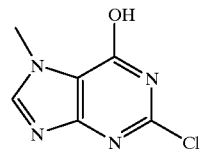
381
382
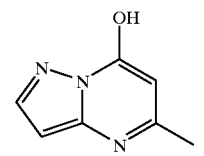
383
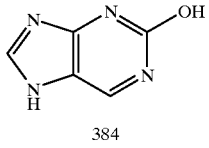
384
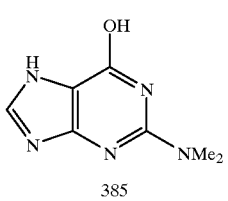
385
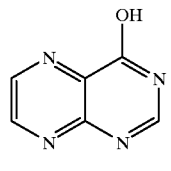
386
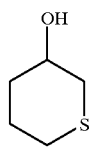
387
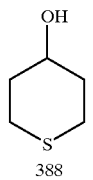
388
TABLE 15-continued
Alcohols of the type A-OH
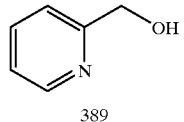
389
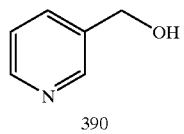
390
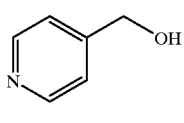
391
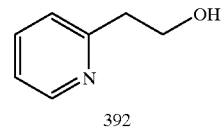
392
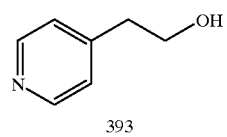
393
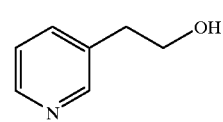
394
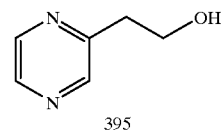
395
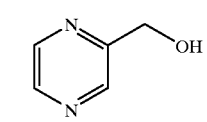
396
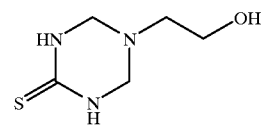
397
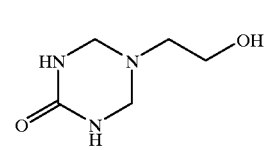
398

TABLE 15-continued
Alcohols of the type A-OH
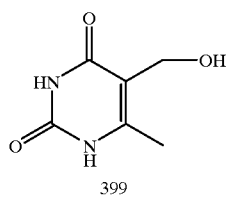
399
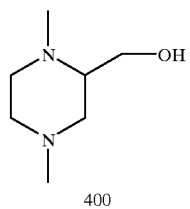
400
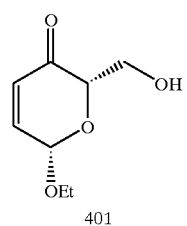
401
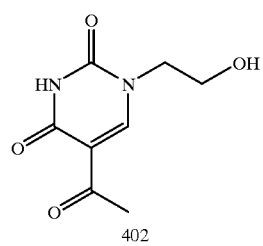
402
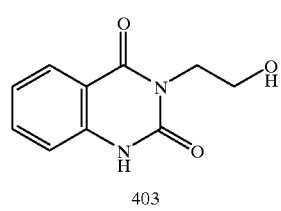
403
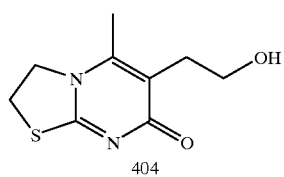
404
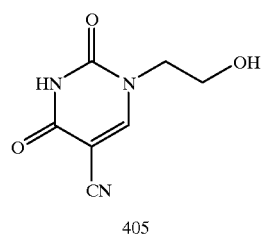
405
TABLE 15-continued
Alcohols of the type A-OH
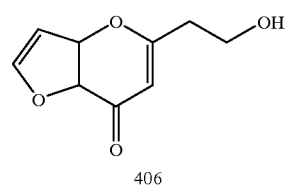
406
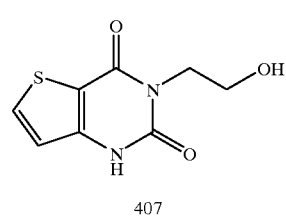
407
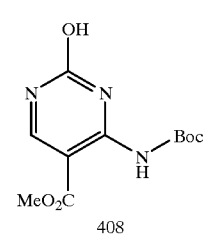
408
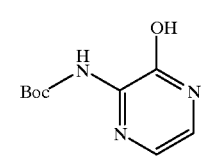
409
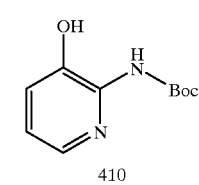
410
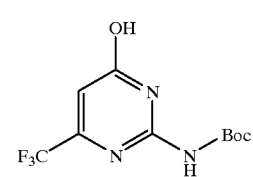
411
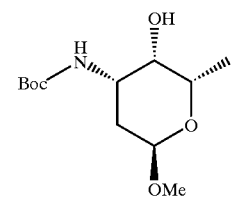
412

TABLE 15-continued
Alcohols of the type A-OH
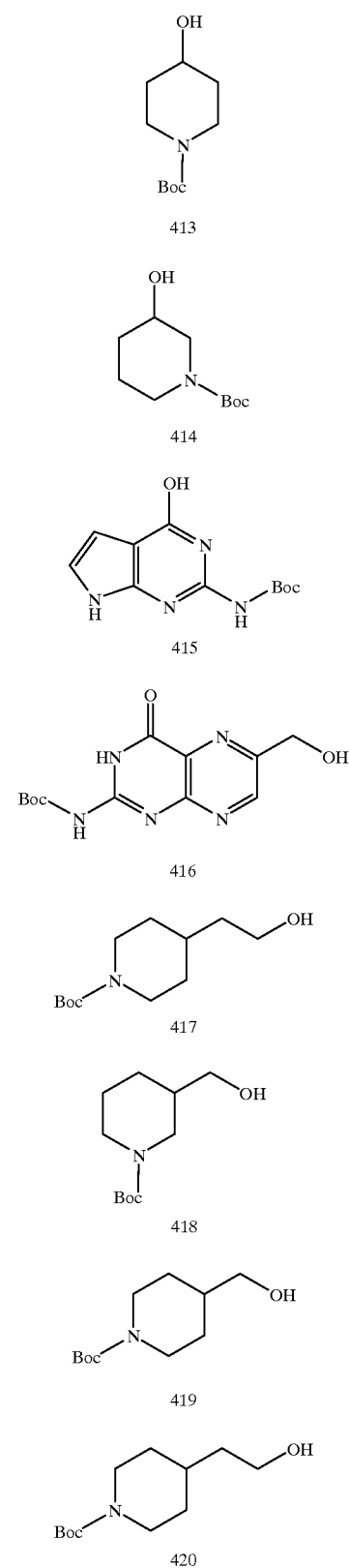
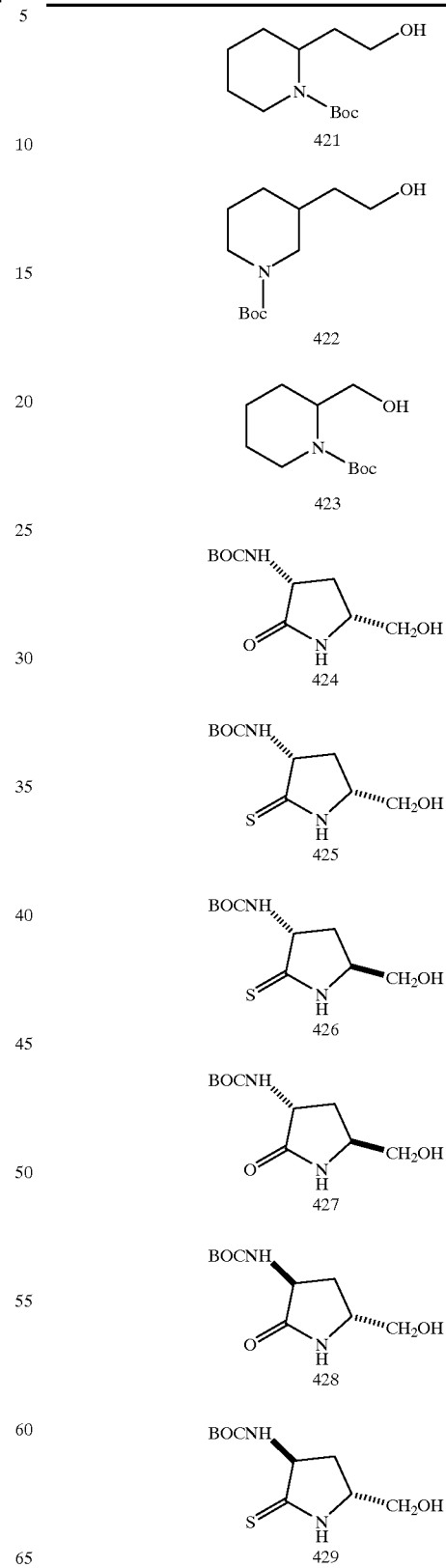

TABLE 15-continued
Alcohols of the type A-OH
430
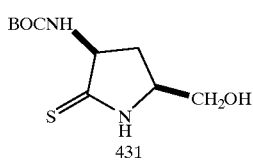
431
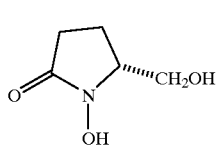
432
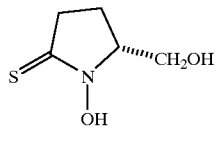
433
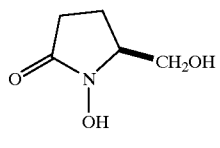
434
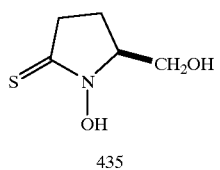
435
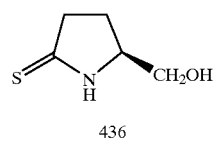
436
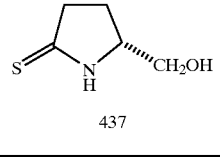
437
TABLE 16
Mercaptans of the type A-SH
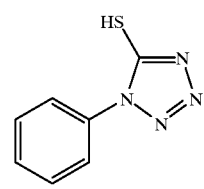
1
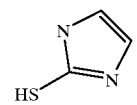
2
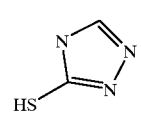
3
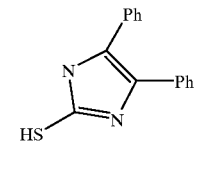
4
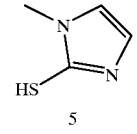
5
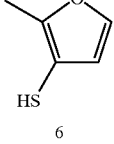
6
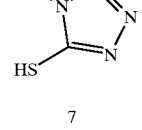
7
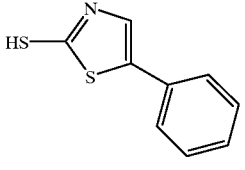
8

TABLE 16-continued
Mercaptans of the type A-SH
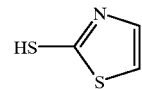
9
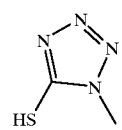
10
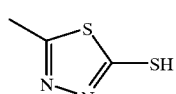
11
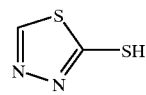
12
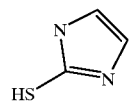
13
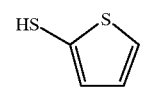
14
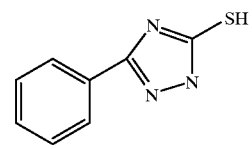
15
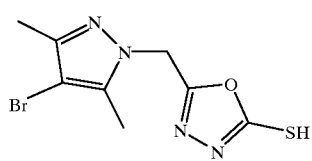
16
TABLE 16-continued
Mercaptans of the type A-SH
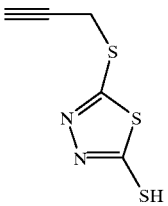
17
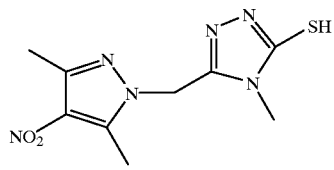
18
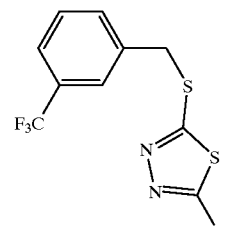
19
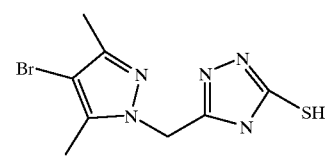
20
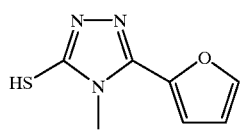
21
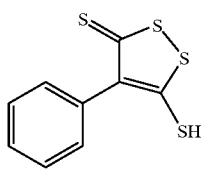
22
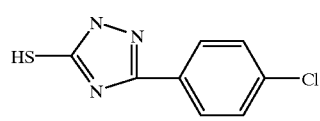
23

TABLE 16-continued
Mercaptans of the type A-SH
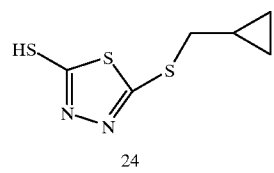
24
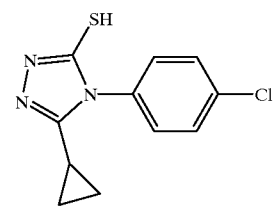
25
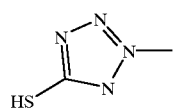
26
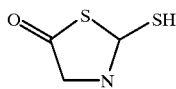
27
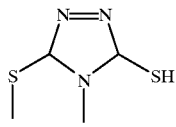
28
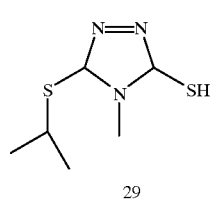
29
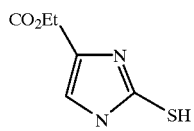
30
TABLE 16-continued
Mercaptans of the type A-SH
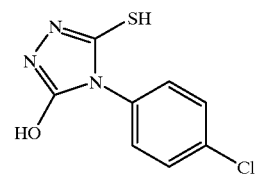
31
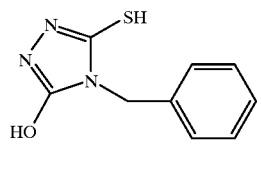
32
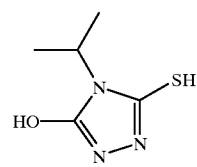
33
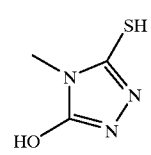
34
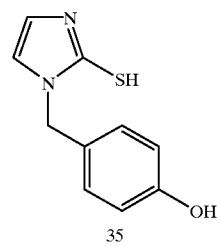
35
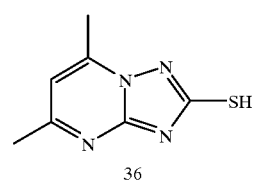
36
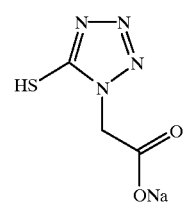
37

TABLE 16-continued
Mercaptans of the type A-SH
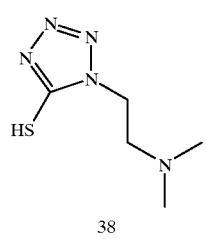
38
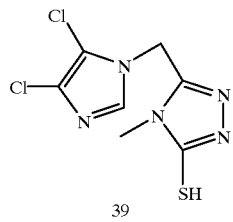
39
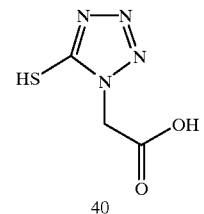
40
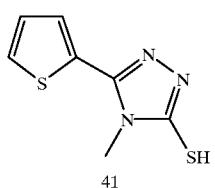
41
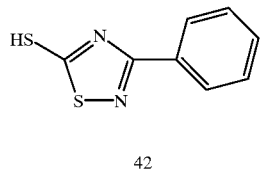
42
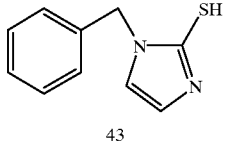
43
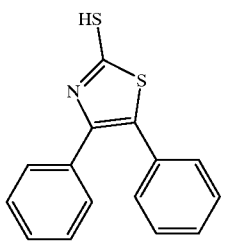
44
TABLE 16-continued
Mercaptans of the type A-SH
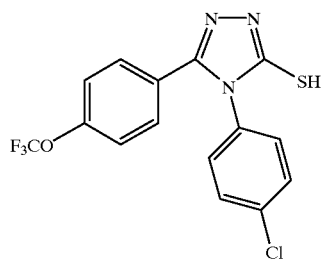
45
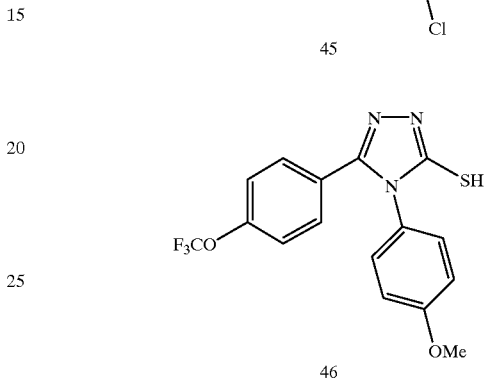
46
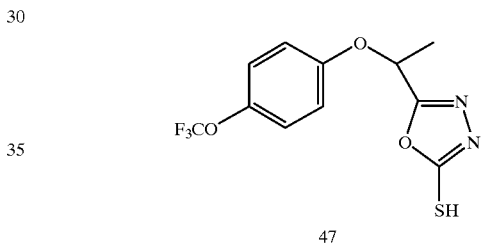
47
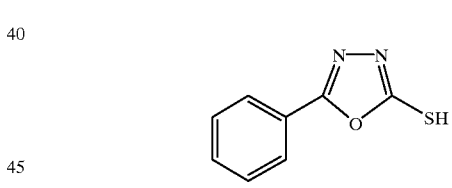
48
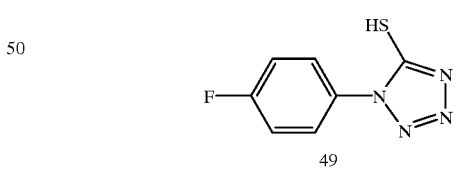
49
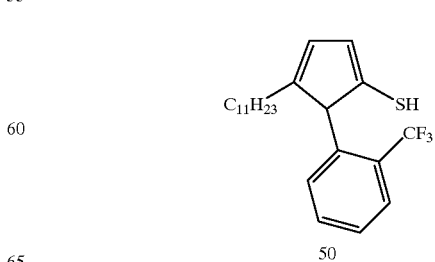
50

TABLE 16-continued
Mercaptans of the type A-SH
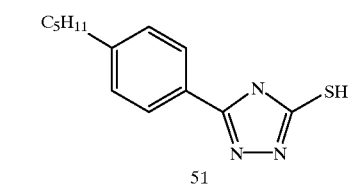
51
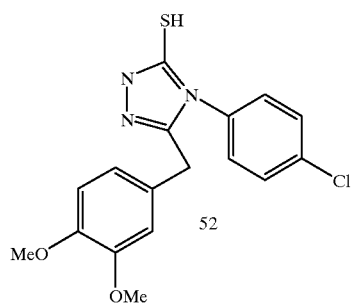
52
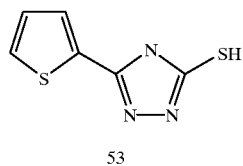
53
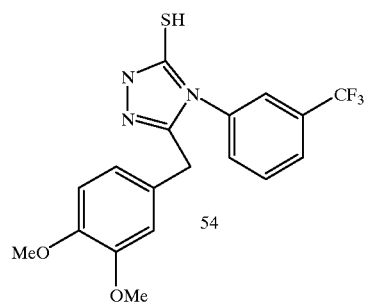
54
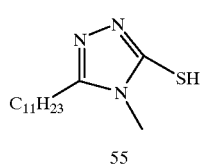
55
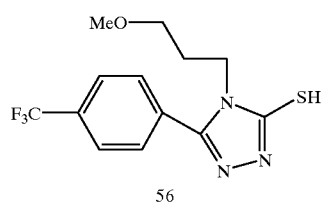
56
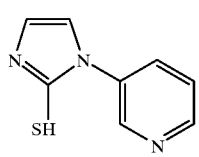
57
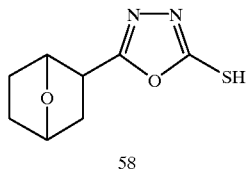
58
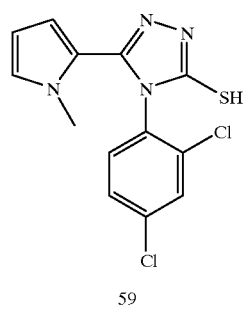
59
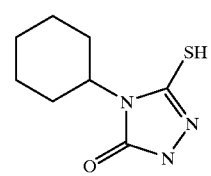
60
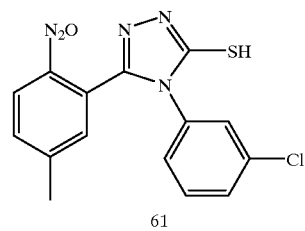
61
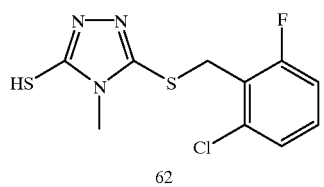
62
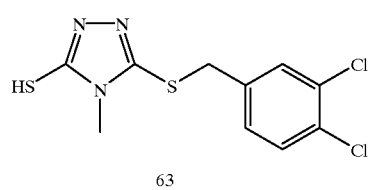
63
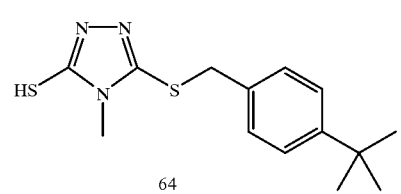
64

TABLE 16-continued
Mercaptans of the type A-SH
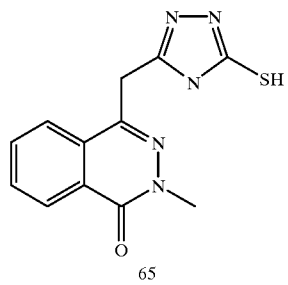
65
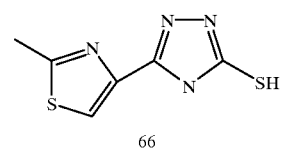
66
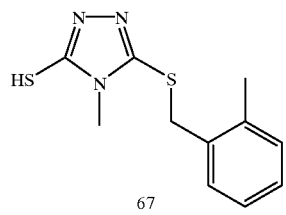
67
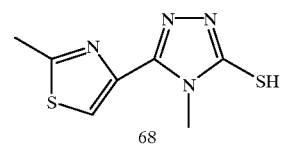
68
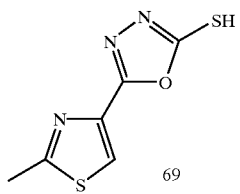
69
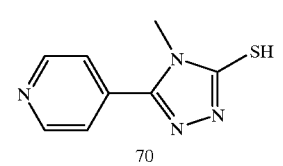
70
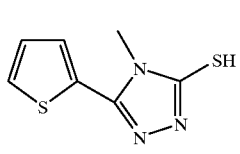
71
TABLE 16-continued
Mercaptans of the type A-SH
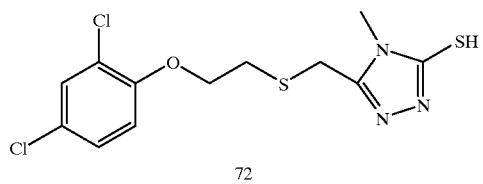
72
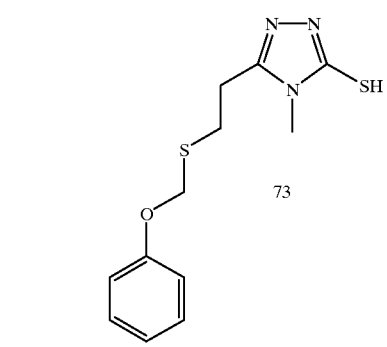
73
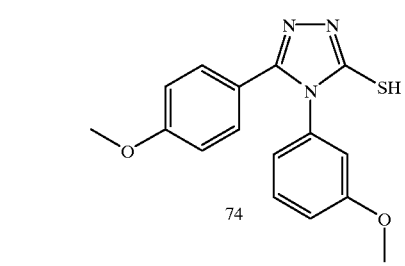
74
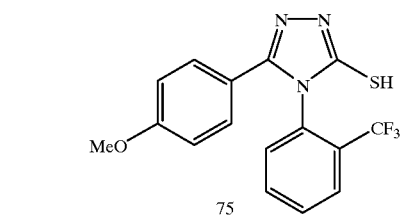
75
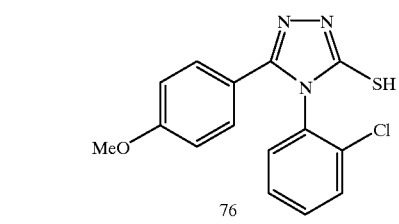
76
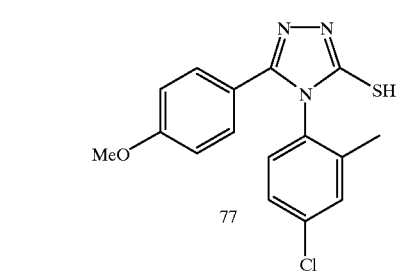
77

TABLE 16-continued

Mercaptans of the type A-SH (Structures 78–90)

TABLE 16-continued
Mercaptans of the type A-SH
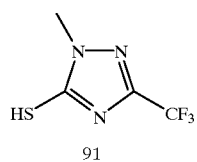
91
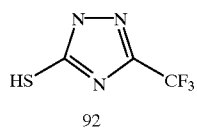
92
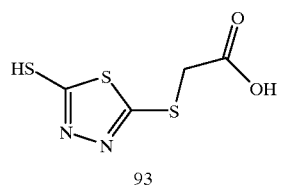
93
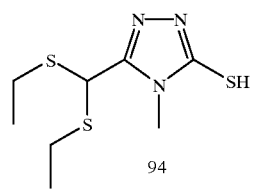
94
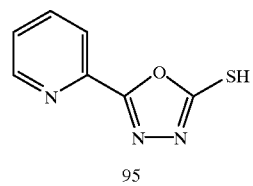
95
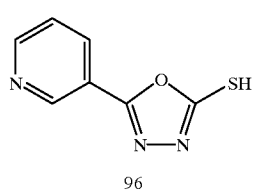
96
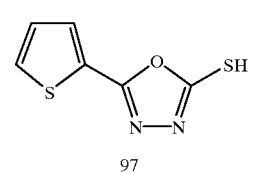
97
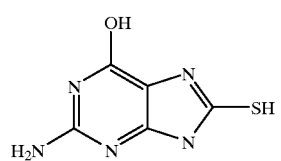
98
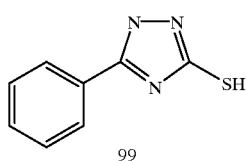
99
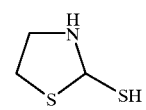
100
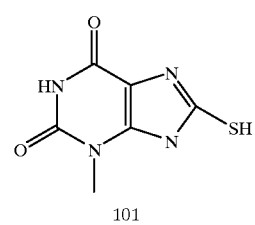
101
102
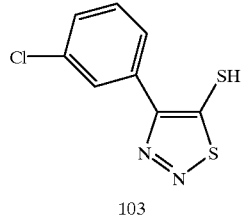
103
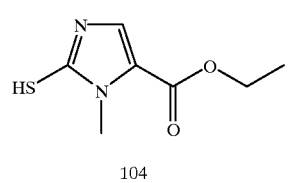
104
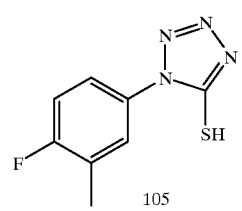
105

TABLE 16-continued
Mercaptans of the type A-SH
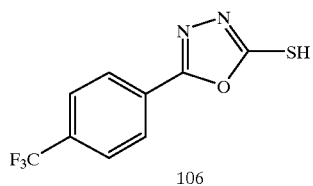
106
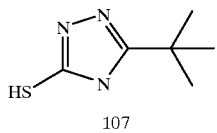
107
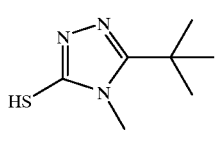
108
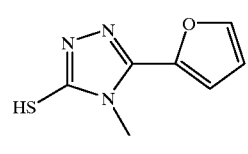
109
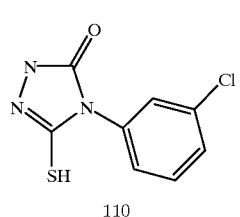
110
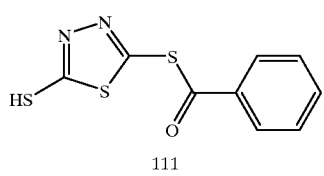
111
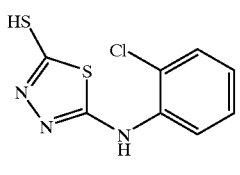
112
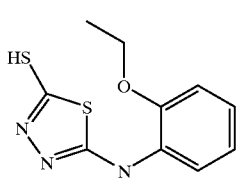
113
TABLE 16-continued
Mercaptans of the type A-SH
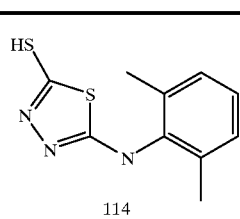
114
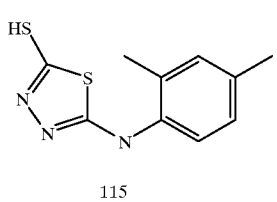
115
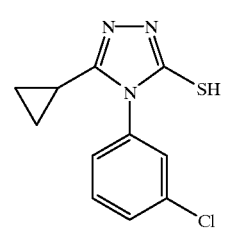
116
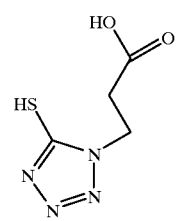
117
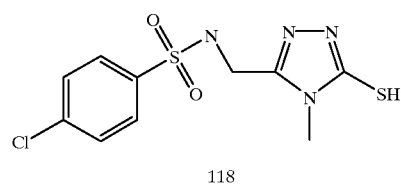
118
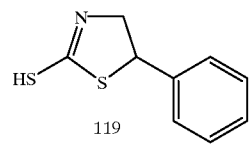
119
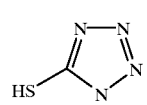
120

TABLE 16-continued
Mercaptans of the type A-SH
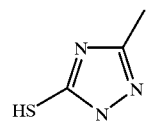
121
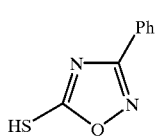
121
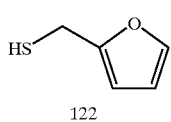
122
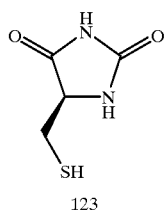
123
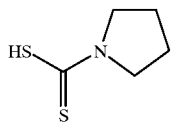
124
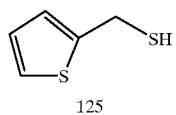
125
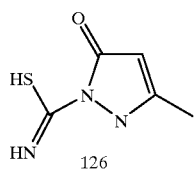
126
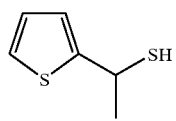
127
TABLE 16-continued
Mercaptans of the type A-SH
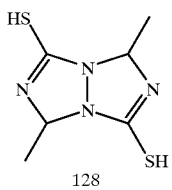
128
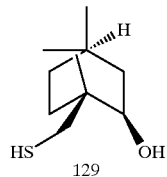
129
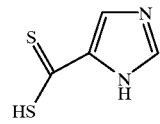
130
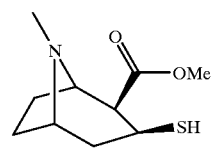
131
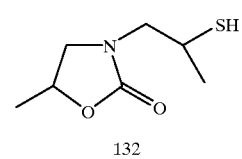
132
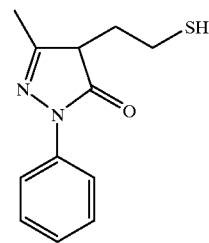
133
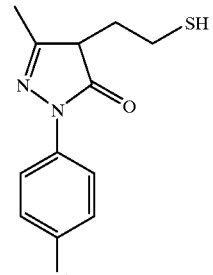
134

TABLE 16-continued
Mercaptans of the type A-SH
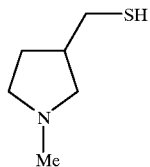
135
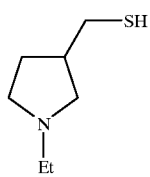
136
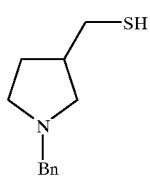
137
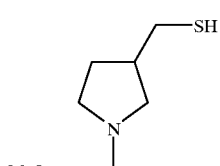
138
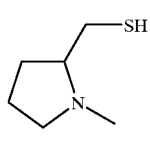
139
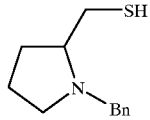
140
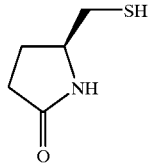
141
TABLE 16-continued
Mercaptans of the type A-SH
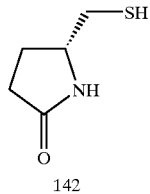
142
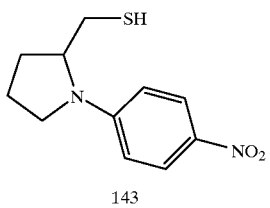
143
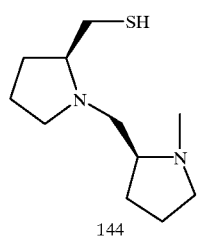
144
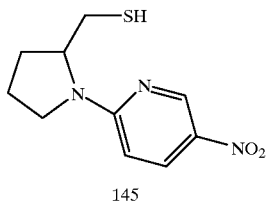
145
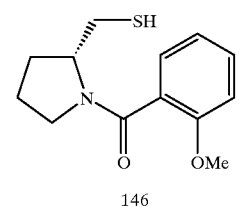
146
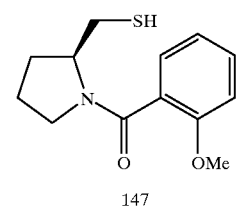
147
148

TABLE 16-continued
Mercaptans of the type A-SH
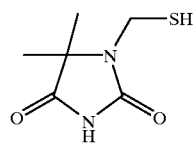
149
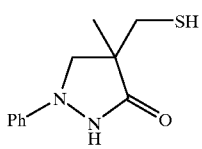
150
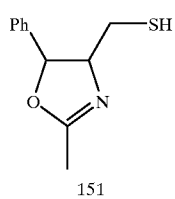
151
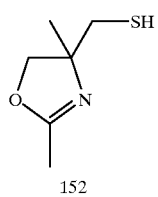
152
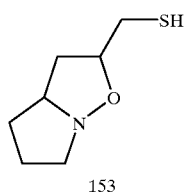
153
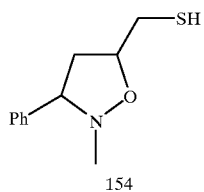
154
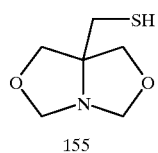
155
TABLE 16-continued
Mercaptans of the type A-SH
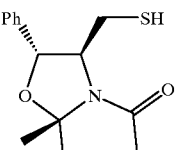
156
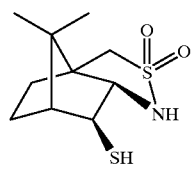
157
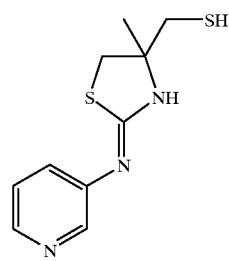
158
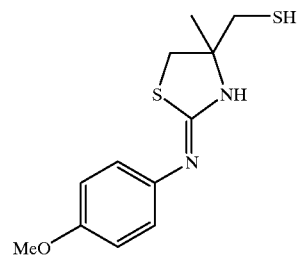
159
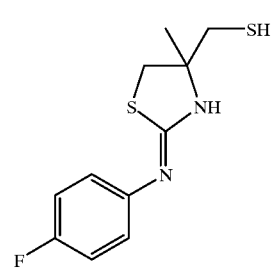
160
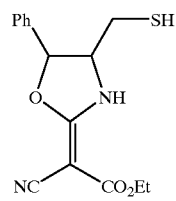
161

TABLE 16-continued
Mercaptans of the type A-SH
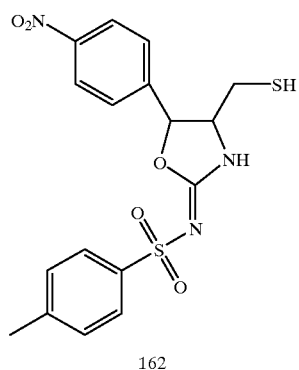
162
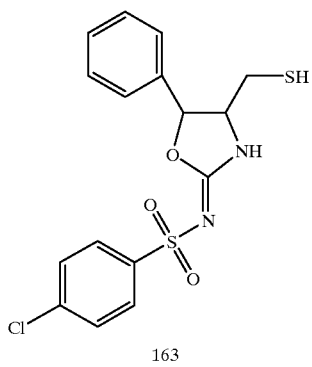
163
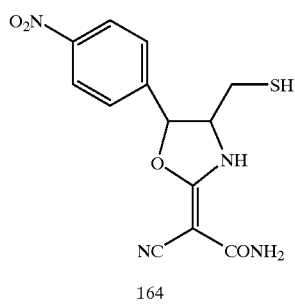
164
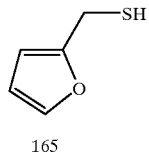
165
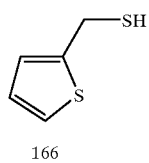
166
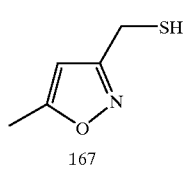
167
TABLE 16-continued
Mercaptans of the type A-SH
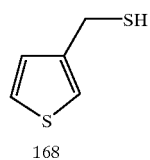
168
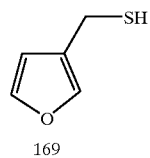
169
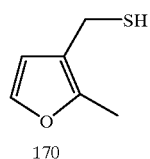
170
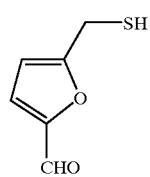
171
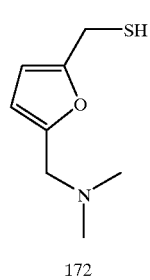
172
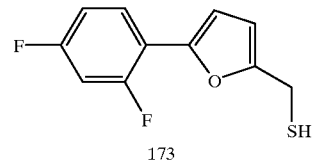
173
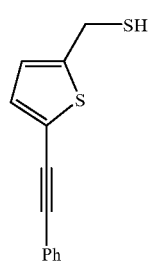
174

TABLE 16-continued

Mercaptans of the type A-SH 175, 176, 177, 178, 179, 180, 181, 182, 183, 184, 185, 186, 187, 188

TABLE 16-continued
Mercaptans of the type A-SH
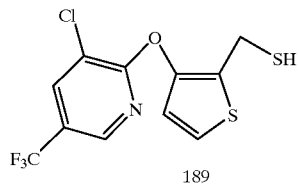
189
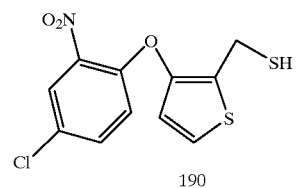
190
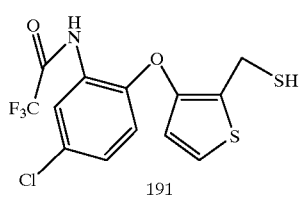
191
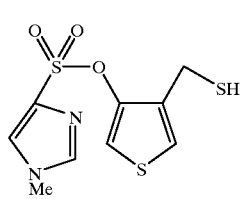
192
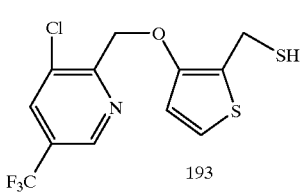
193
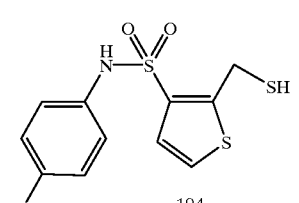
194
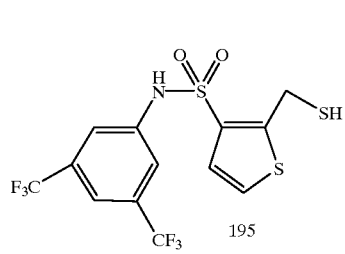
195
TABLE 16-continued
Mercaptans of the type A-SH
196
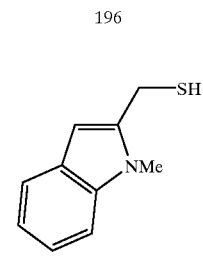
197
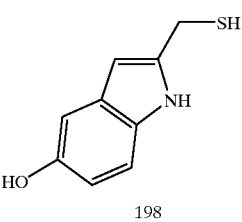
198
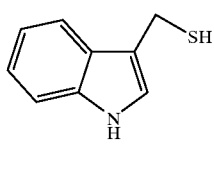
199
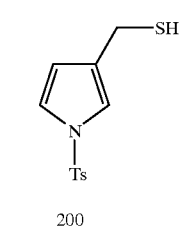
200
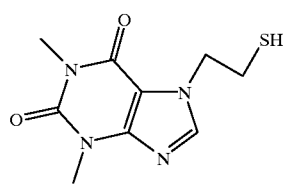
201

TABLE 16-continued
Mercaptans of the type A-SH
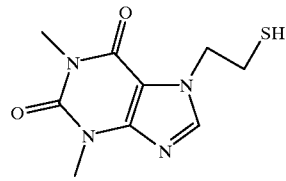
202
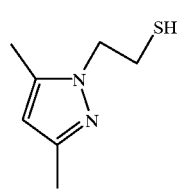
203
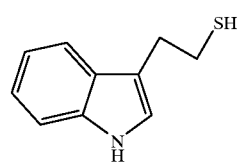
204
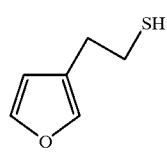
205
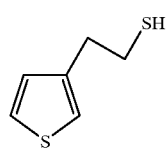
206
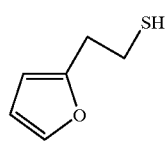
207
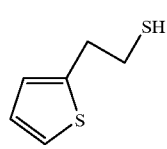
208
TABLE 16-continued
Mercaptans of the type A-SH
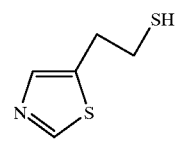
209
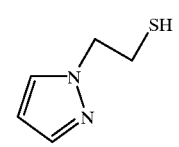
210
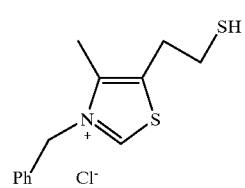
211
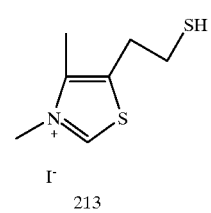
212
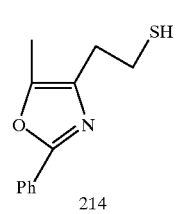
213
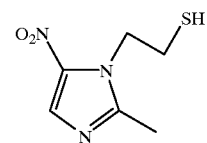
214
215

TABLE 16-continued
Mercaptans of the type A-SH
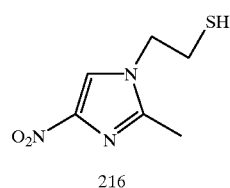
216
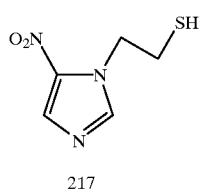
217
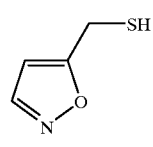
218
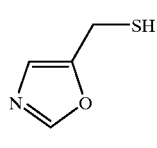
219
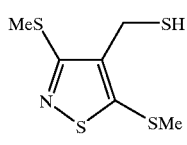
220
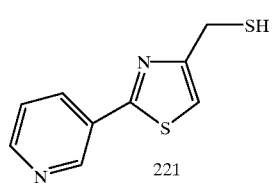
221
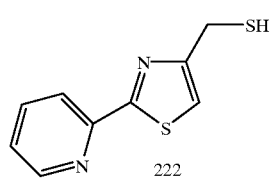
222
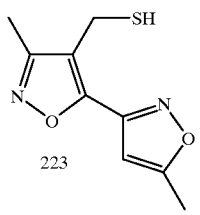
223
TABLE 16-continued
Mercaptans of the type A-SH
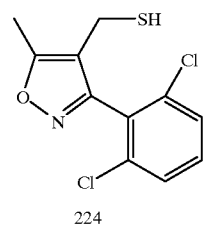
224
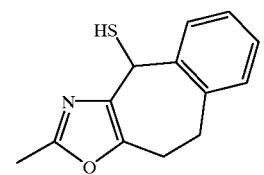
225
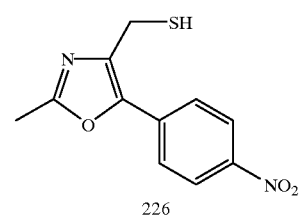
226
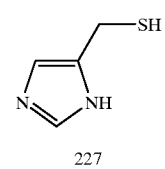
227
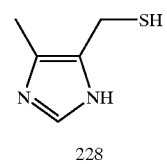
228
229
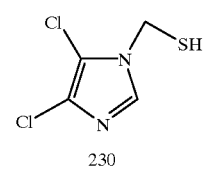
230

TABLE 16-continued
Mercaptans of the type A-SH
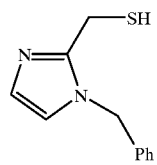
231
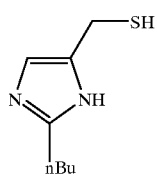
232
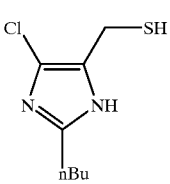
233
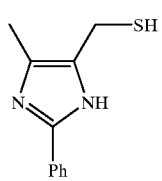
234
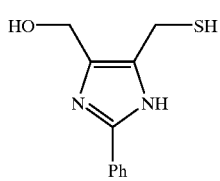
235
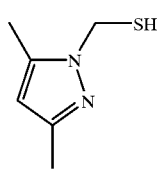
236
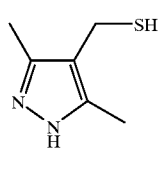
237
TABLE 16-continued
Mercaptans of the type A-SH
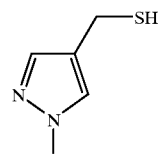
238
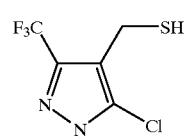
239
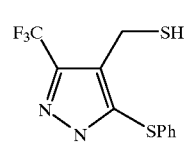
240
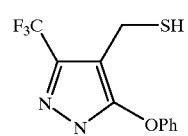
241
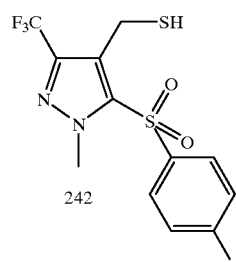
242
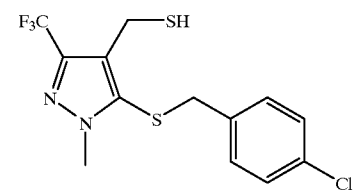
243
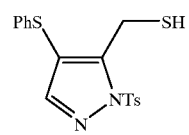
244

TABLE 16-continued

Mercaptans of the type A-SH 245, 246, 247, 248, 249, 250, 251, 252, 253, 254, 255, 256, 257, 258

TABLE 16-continued
Mercaptans of the type A-SH
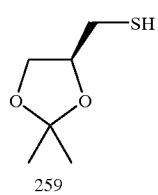
259
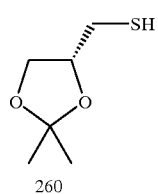
260
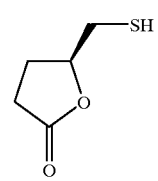
261
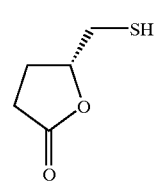
262
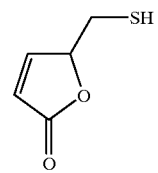
263
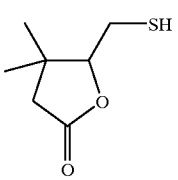
264
TABLE 16-continued
Mercaptans of the type A-SH
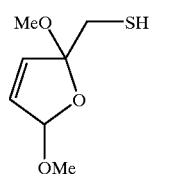
265
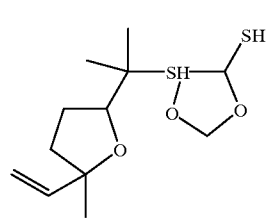
266
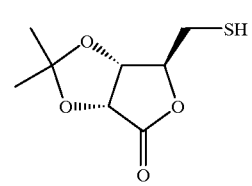
267
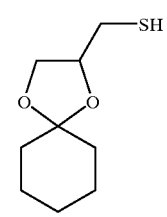
268
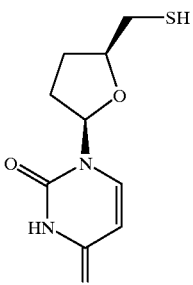
269

TABLE 16-continued
Mercaptans of the type A-SH
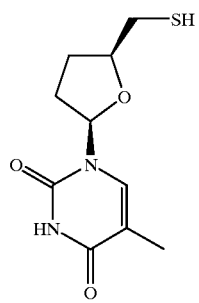
270
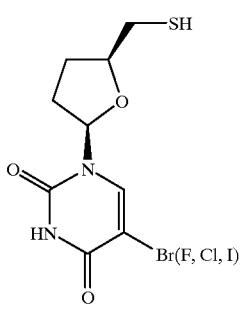
271
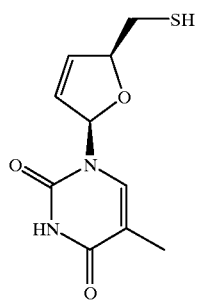
272
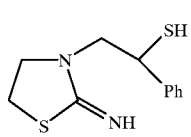
273
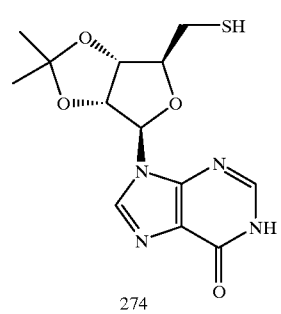
274
TABLE 16-continued
Mercaptans of the type A-SH
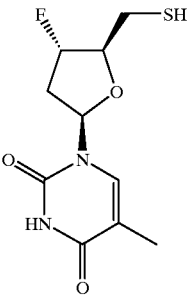
275
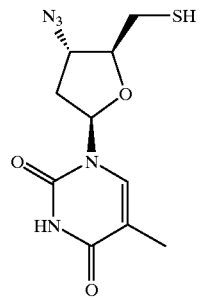
276
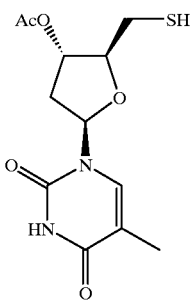
277
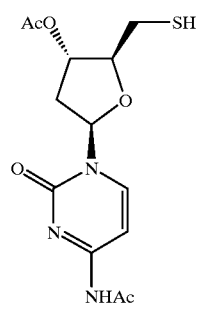
278
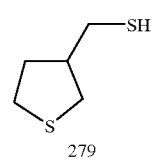
279

TABLE 16-continued

Mercaptans of the type A-SH 280, 281, 282, 283, 284, 285, 286, 287, 288, 289, 290, 291, 292, 293, 294, 295, 296, 297

TABLE 16-continued
Mercaptans of the type A-SH
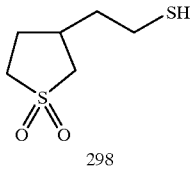
298
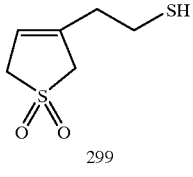
299
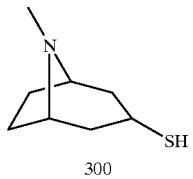
300
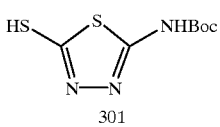
301
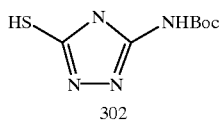
302
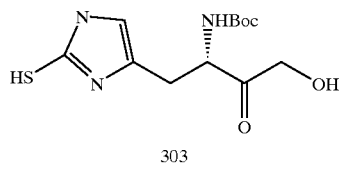
303
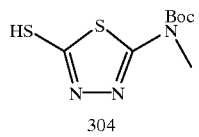
304
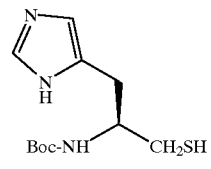
305
TABLE 16-continued
Mercaptans of the type A-SH
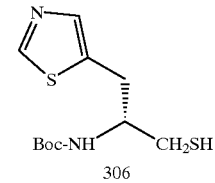
306
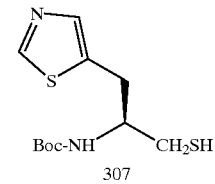
307
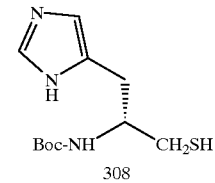
308
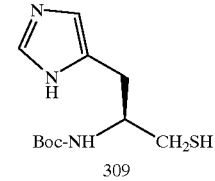
309
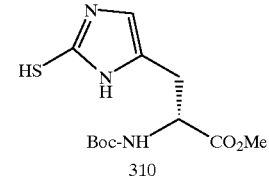
310
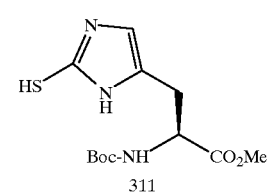
311
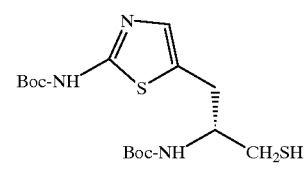
312

TABLE 16-continued
Mercaptans of the type A-SH
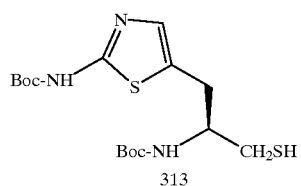
313
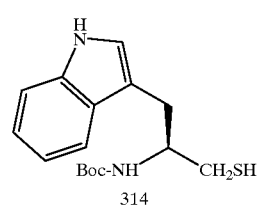
314
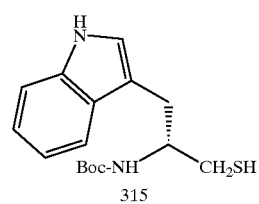
315
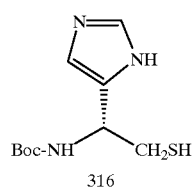
316
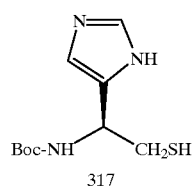
317
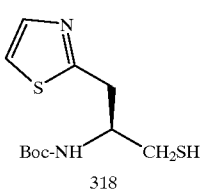
318
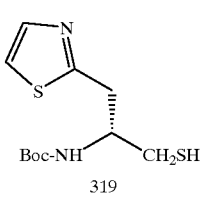
319
TABLE 16-continued
Mercaptans of the type A-SH
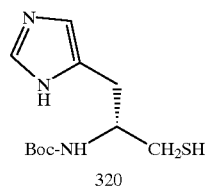
320
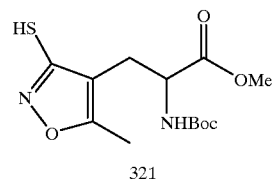
321
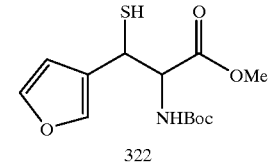
322
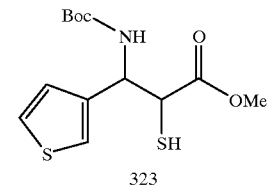
323
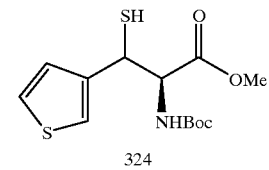
324
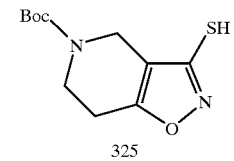
325
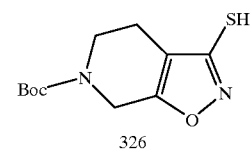
326
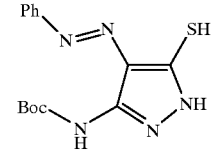
327

TABLE 16-continued
Mercaptans of the type A-SH
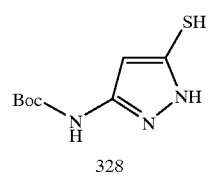
328
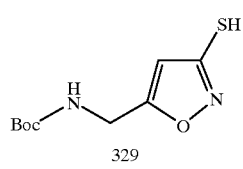
329
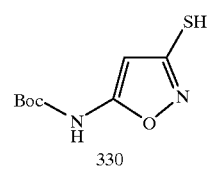
330
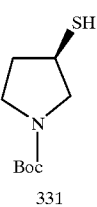
331
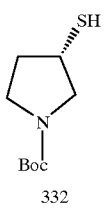
332
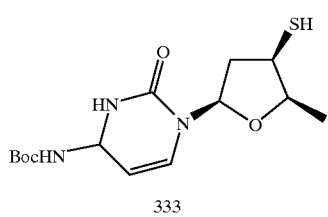
333
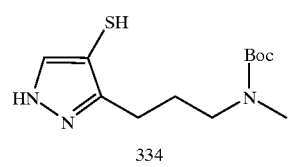
334
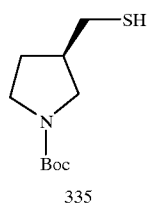
335
TABLE 16-continued
Mercaptans of the type A-SH
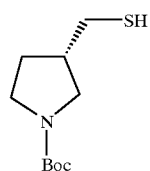
336
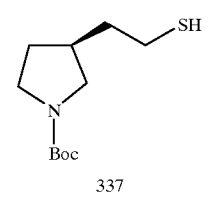
337
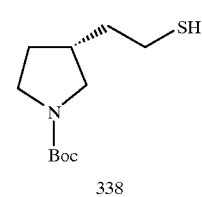
338
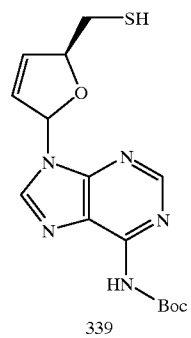
339
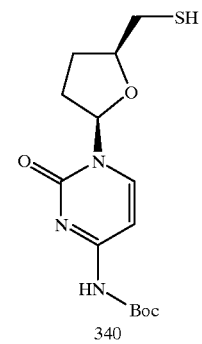
340

TABLE 16-continued
Mercaptans of the type A-SH
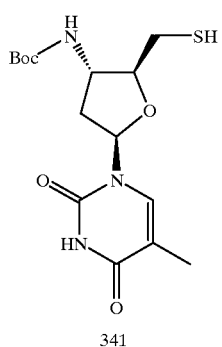
341
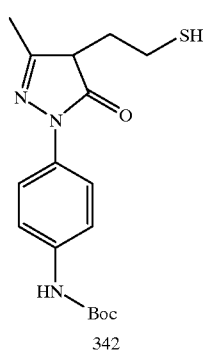
342
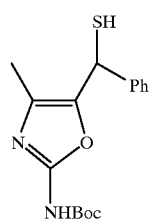
343
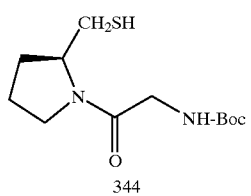
344
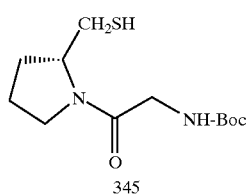
345
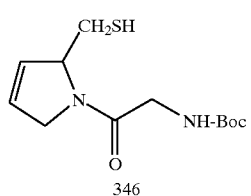
346
TABLE 16-continued
Mercaptans of the type A-SH
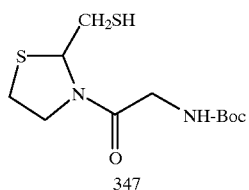
347
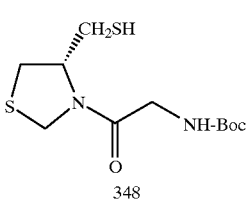
348
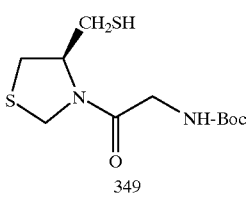
349
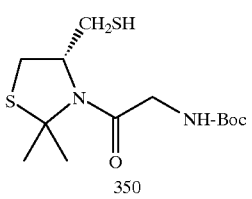
350
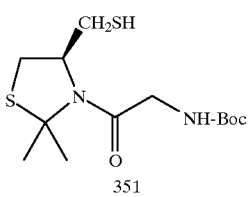
351
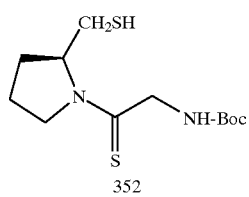
352
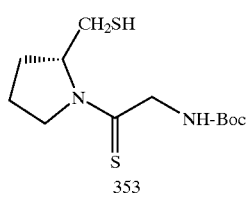
353

TABLE 16-continued
Mercaptans of the type A-SH
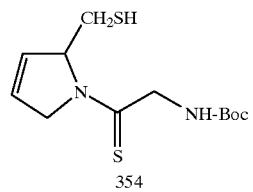
354
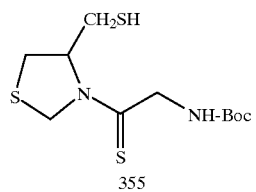
355
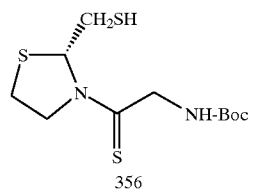
356
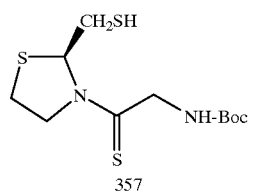
357
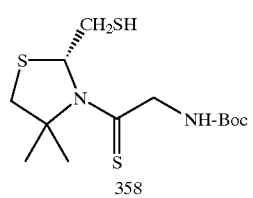
358
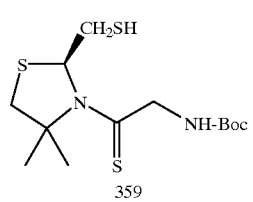
359
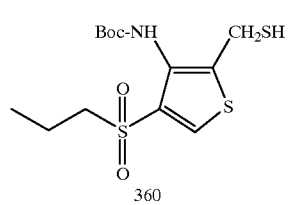
360
TABLE 16-continued
Mercaptans of the type A-SH
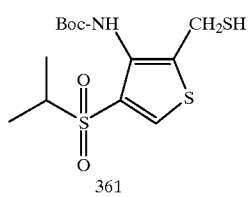
361
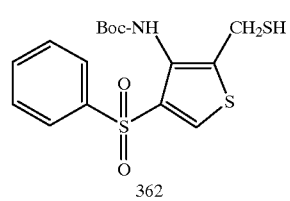
362
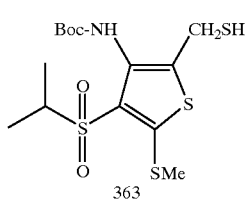
363
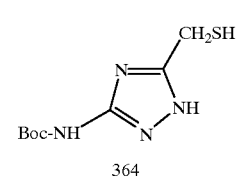
364
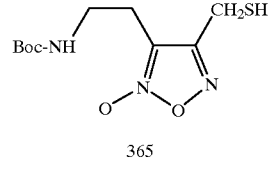
365
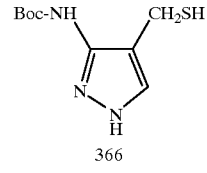
366
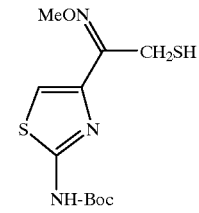
367

TABLE 16-continued

Mercaptans of the type A-SH

368

369

370

371

372

373

374

375

376

377

378

379

380

381

382

TABLE 16-continued
Mercaptans of the type A-SH
383
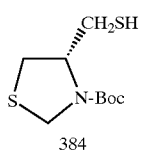
384
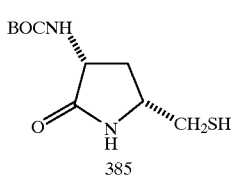
385
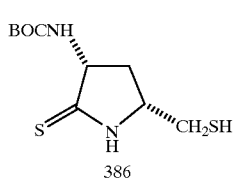
386
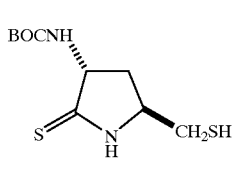
387
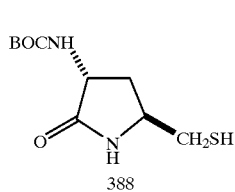
388
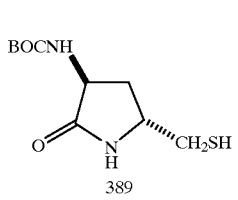
389
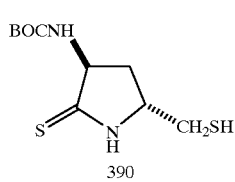
390
TABLE 16-continued
Mercaptans of the type A-SH
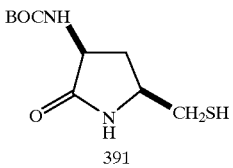
391
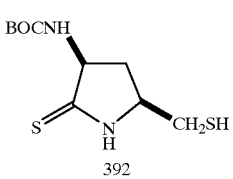
392
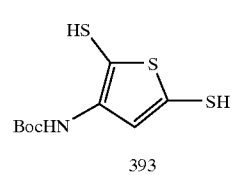
393
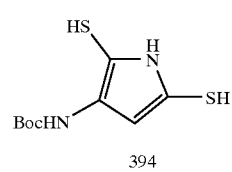
394
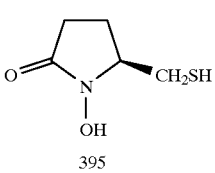
395
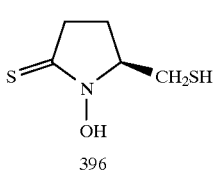
396
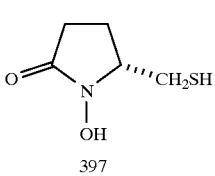
397
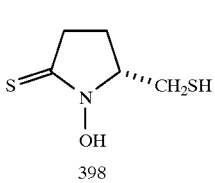
398

TABLE 16-continued

Mercaptans of the type A-SH

399

400

TABLE 17

Halides of the type A-Cl, A-Br and A-I

1

2

3

4

5

6

7

TABLE 17-continued

Halides of the type A-Cl, A-Br and A-I

8

9

10

11

12

13

14

TABLE 17-continued
Halides of the type A-Cl, A-Br and A-I
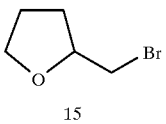
15
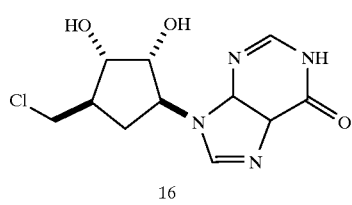
16
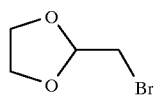
17
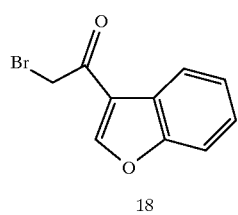
18
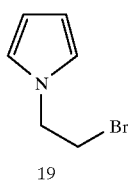
19
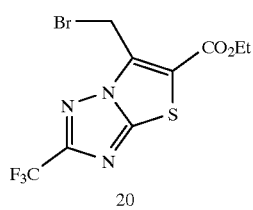
20
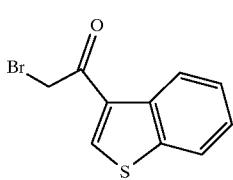
21
TABLE 17-continued
Halides of the type A-Cl, A-Br and A-I
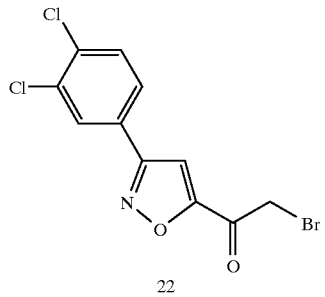
22
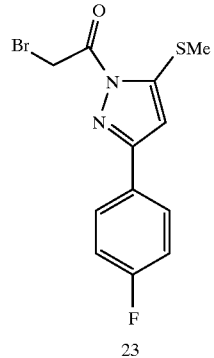
23
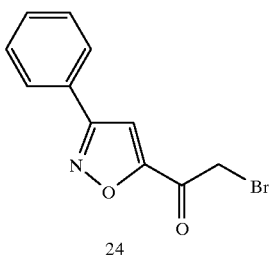
24
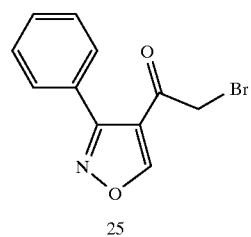
25
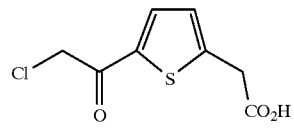
26
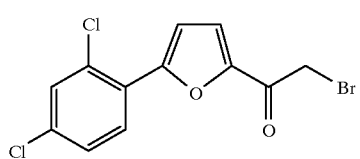
27

TABLE 17-continued
Halides of the type A-Cl, A-Br and A-I
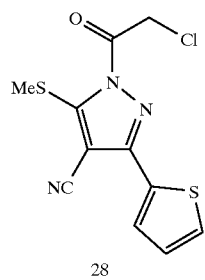
28
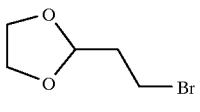
29
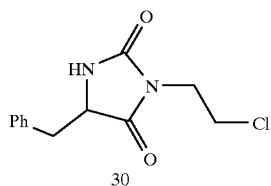
30
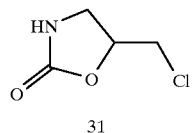
31
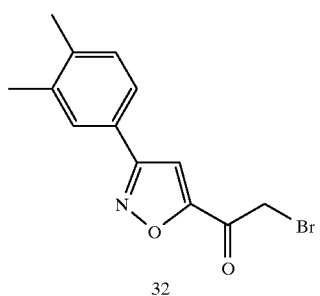
32
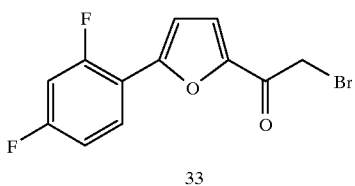
33
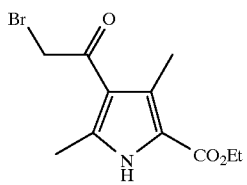
34
TABLE 17-continued
Halides of the type A-Cl, A-Br and A-I
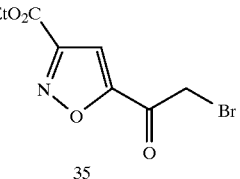
35
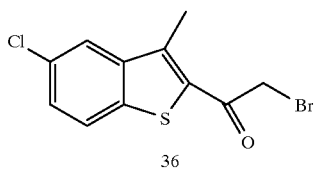
36
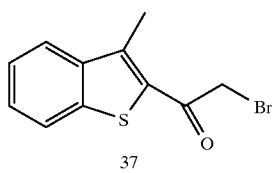
37
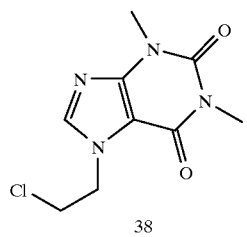
38
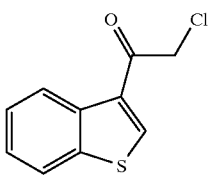
39
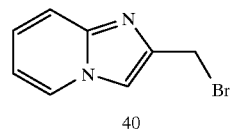
40
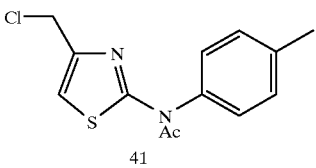
41
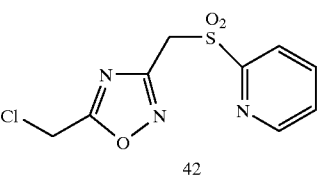
42

TABLE 17-continued
Halides of the type A-Cl, A-Br and A-I
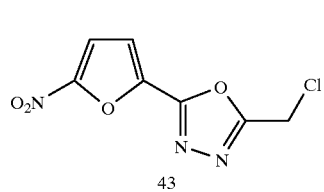
43
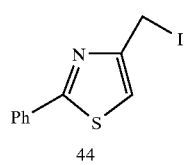
44
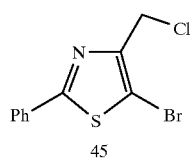
45
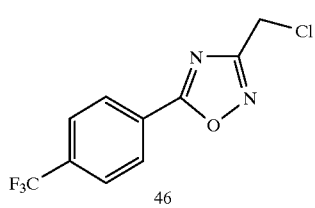
46
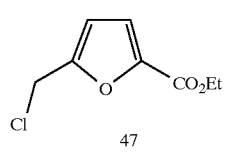
47
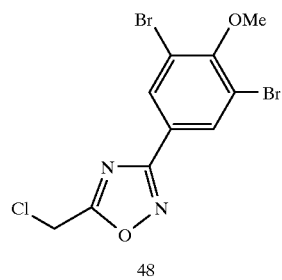
48
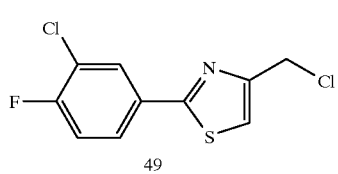
49
TABLE 17-continued
Halides of the type A-Cl, A-Br and A-I
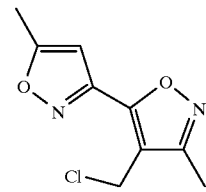
50
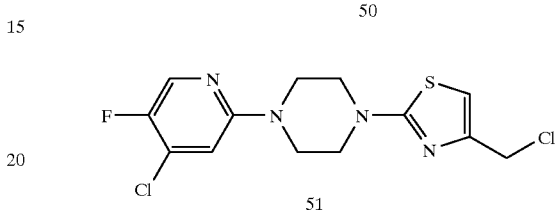
51
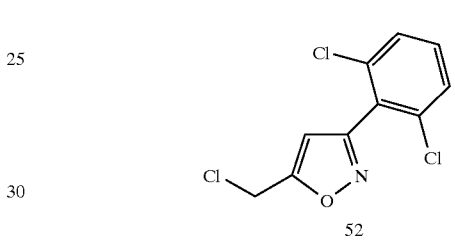
52
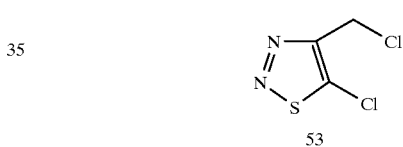
53
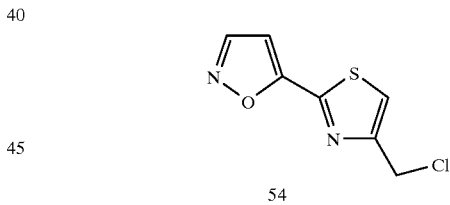
54
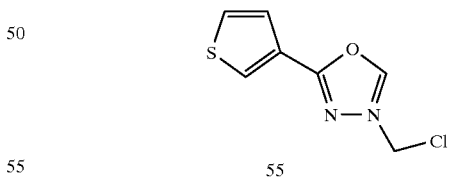
55
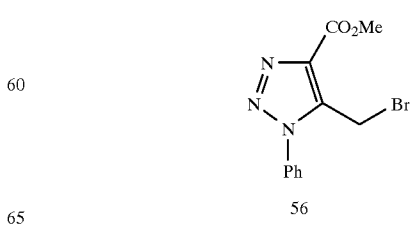
56

TABLE 17-continued
Halides of the type A-Cl, A-Br and A-I
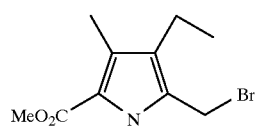
57
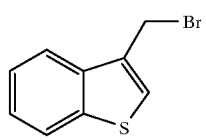
58
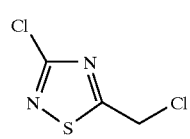
59
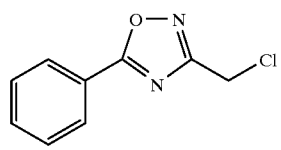
60
61
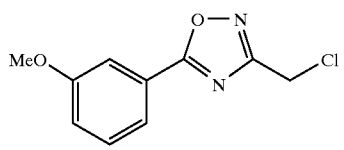
62
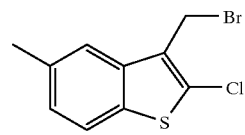
63
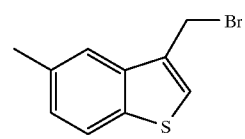
64
TABLE 17-continued
Halides of the type A-Cl, A-Br and A-I
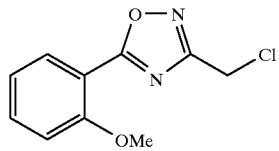
65
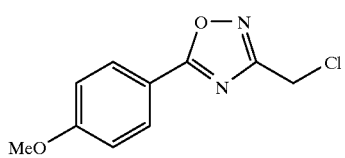
66
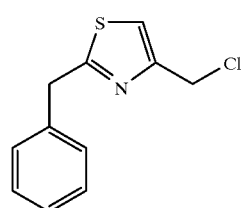
67
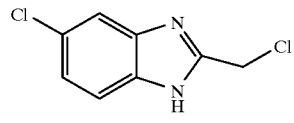
68
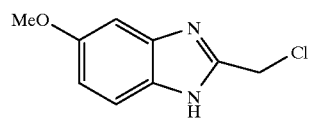
69
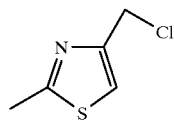
70
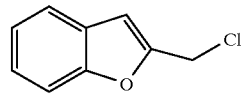
71
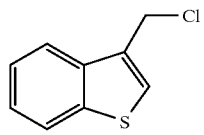
72

TABLE 17-continued
Halides of the type A-Cl, A-Br and A-I
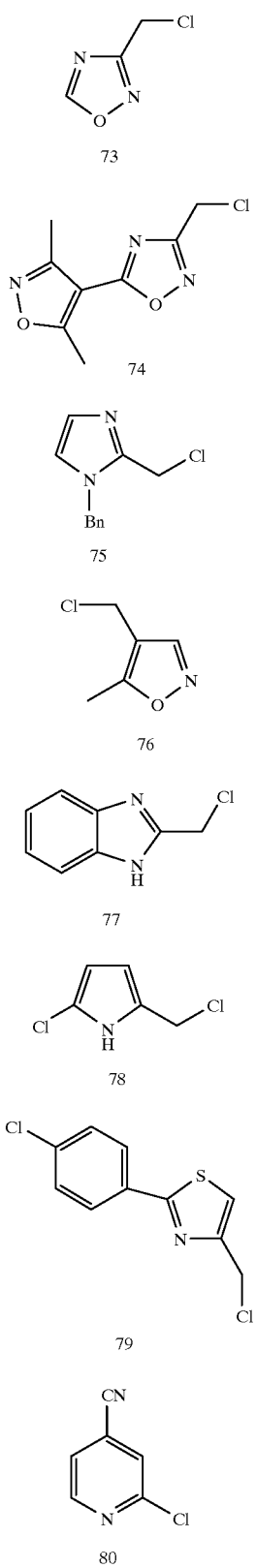
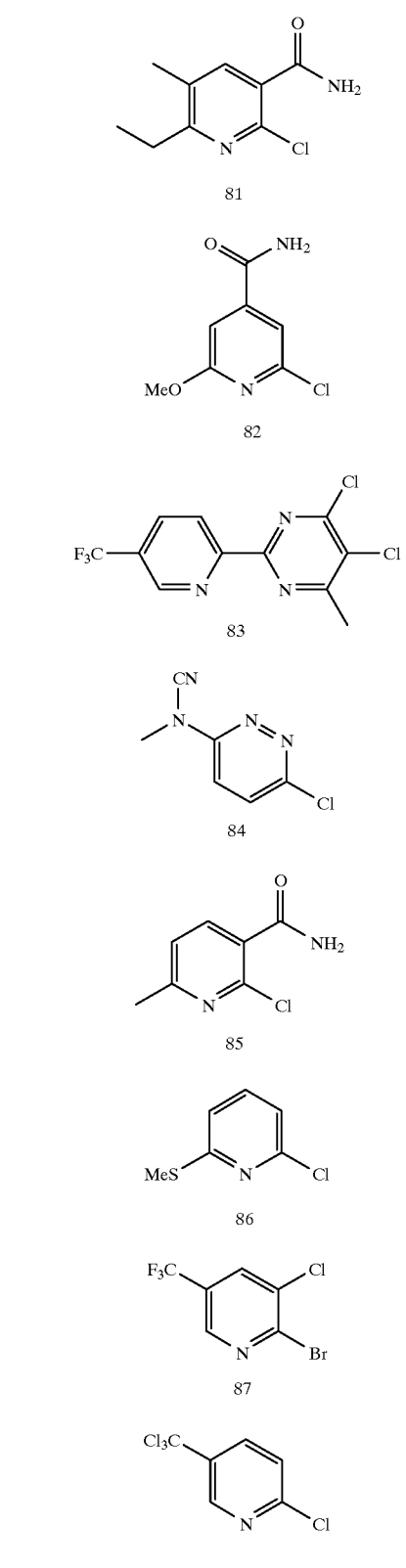

TABLE 17-continued
Halides of the type A-Cl, A-Br and A-I
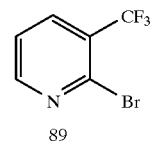
89
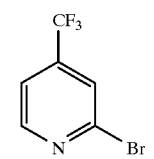
90
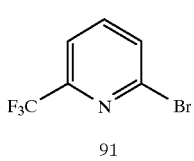
91
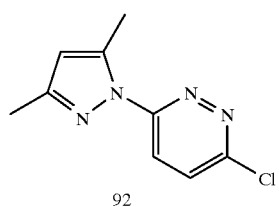
92
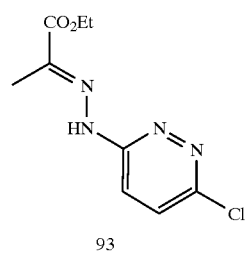
93
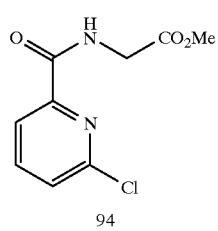
94
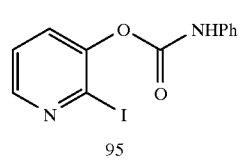
95
TABLE 17-continued
Halides of the type A-Cl, A-Br and A-I
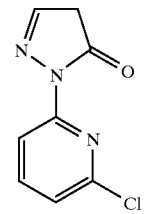
96
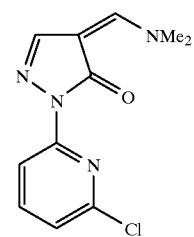
97
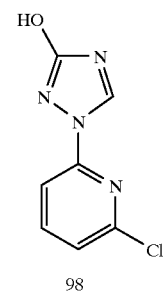
98
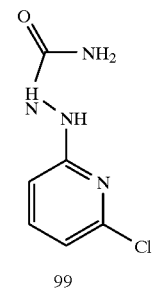
99
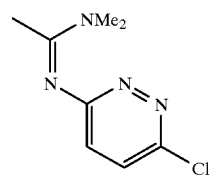
100
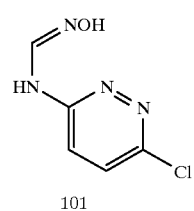
101

TABLE 17-continued
Halides of the type A-Cl, A-Br and A-I
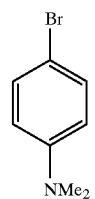
102
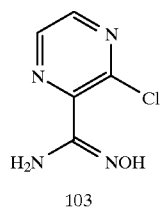
103
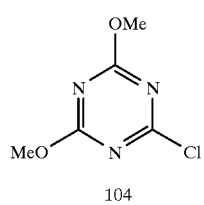
104
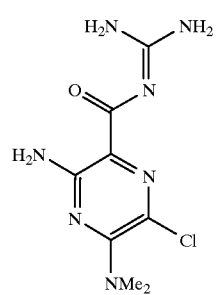
105
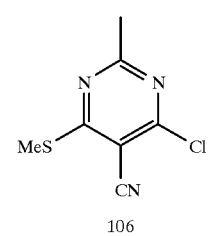
106
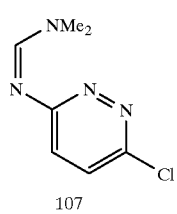
107
TABLE 17-continued
Halides of the type A-Cl, A-Br and A-I
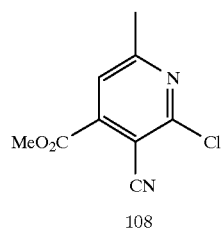
108
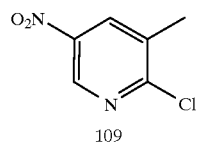
109
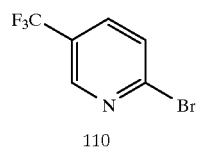
110
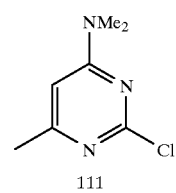
111
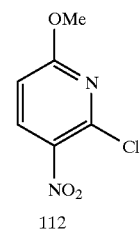
112
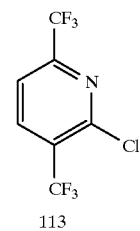
113
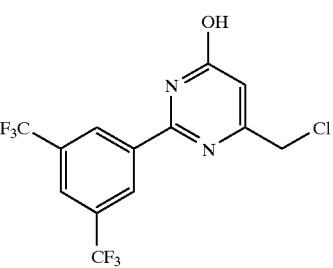
114

TABLE 17-continued
Halides of the type A-Cl, A-Br and A-I
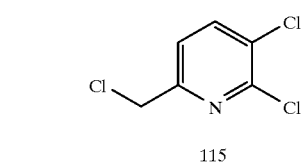
115
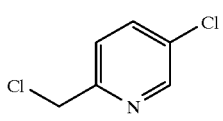
116
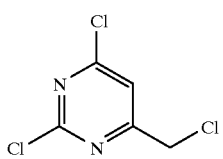
117
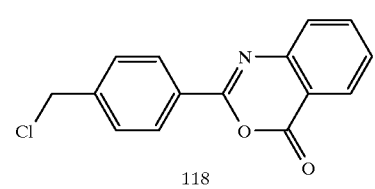
118
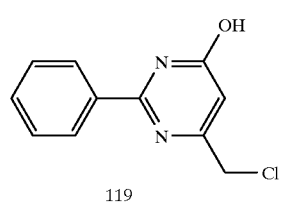
119
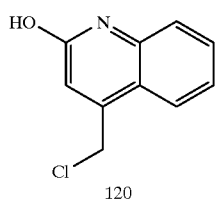
120
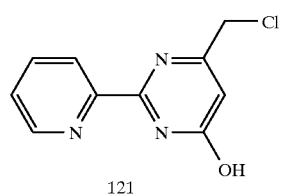
121
TABLE 17-continued
Halides of the type A-Cl, A-Br and A-I
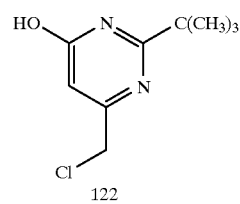
122
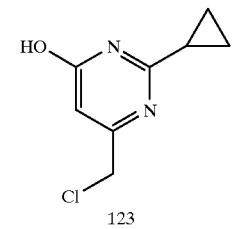
123
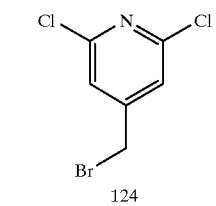
124
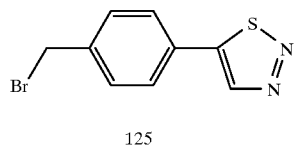
125
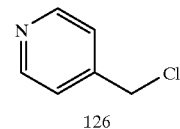
126
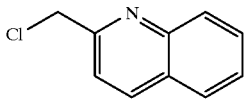
127
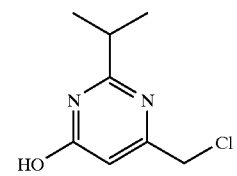
128
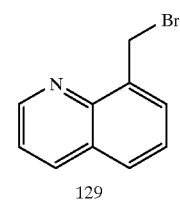
129

TABLE 17-continued
Halides of the type A-Cl, A-Br and A-I
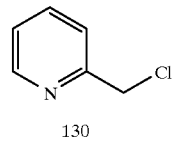
130
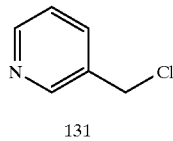
131
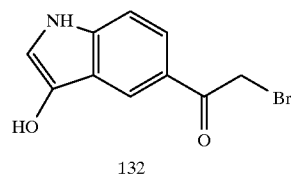
132
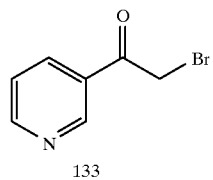
133
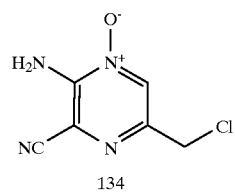
134
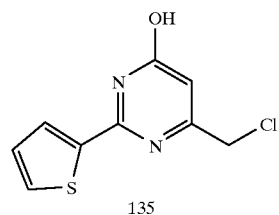
135
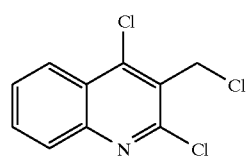
136
TABLE 17-continued
Halides of the type A-Cl, A-Br and A-I
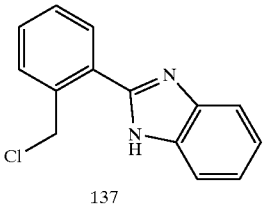
137
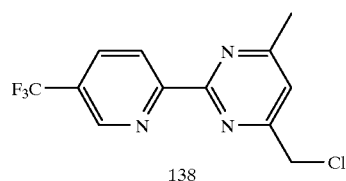
138
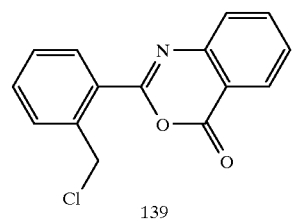
139
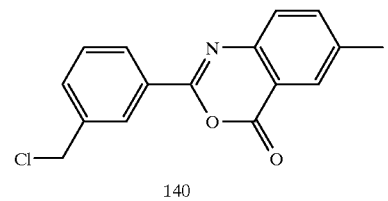
140
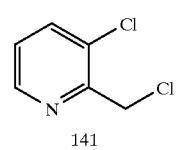
141
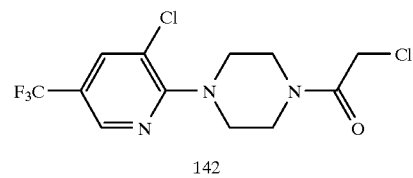
142
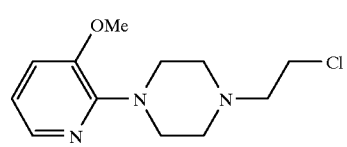
143

TABLE 17-continued
Halides of the type A-Cl, A-Br and A-I
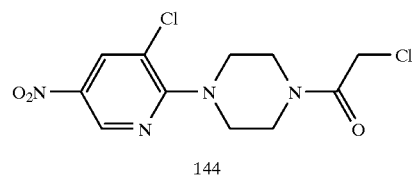
144
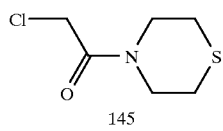
145
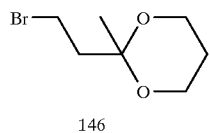
146
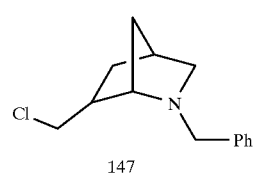
147
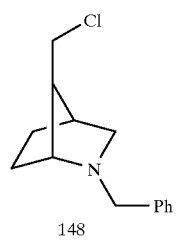
148
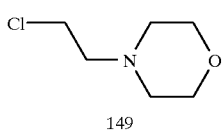
149
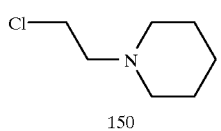
150
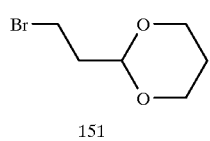
151
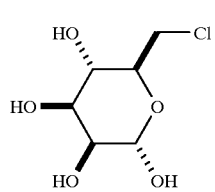
152
TABLE 17-continued
Halides of the type A-Cl, A-Br and A-I
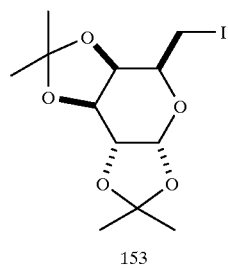
153
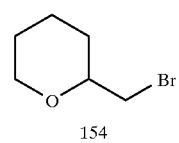
154
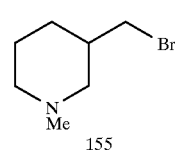
155
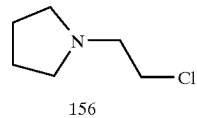
156
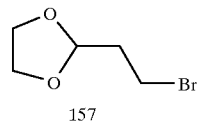
157
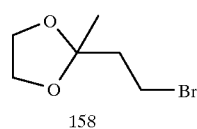
158
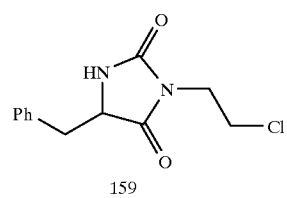
159
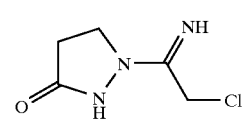
160

TABLE 17-continued
Halides of the type A-Cl, A-Br and A-I
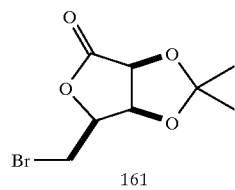
161
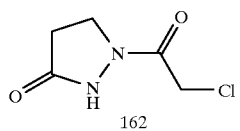
162
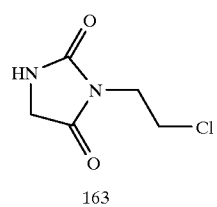
163
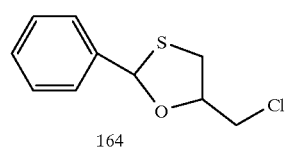
164
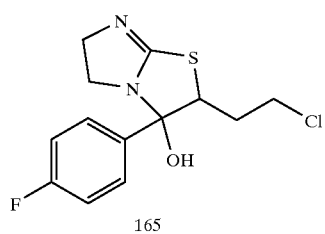
165
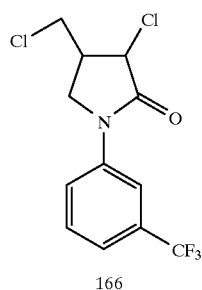
166
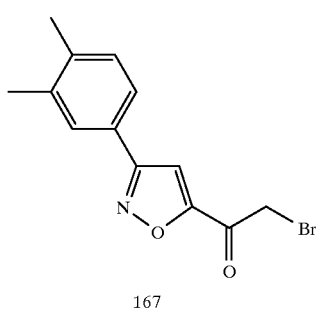
167
TABLE 17-continued
Halides of the type A-Cl, A-Br and A-I
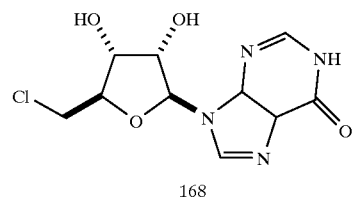
168
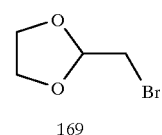
169
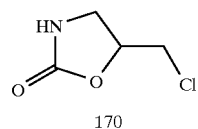
170
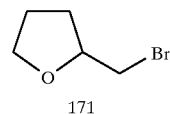
171
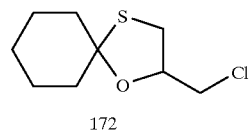
172
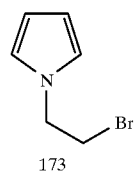
173
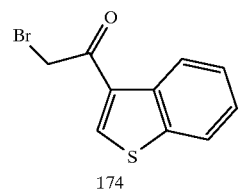
174
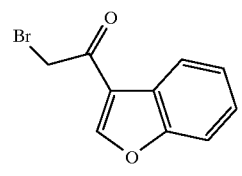
175

TABLE 17-continued
Halides of the type A-Cl, A-Br and A-I
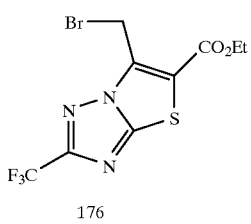
176
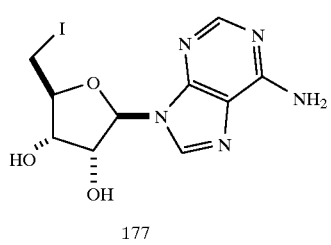
177
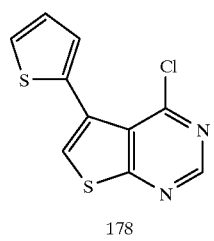
178
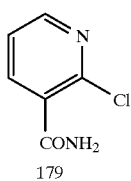
179
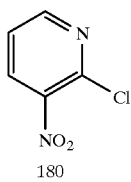
180
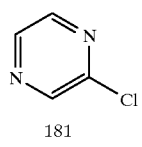
181
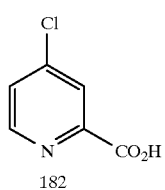
182
TABLE 17-continued
Halides of the type A-Cl, A-Br and A-I
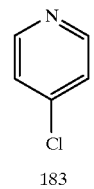
183
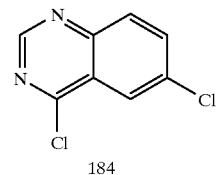
184
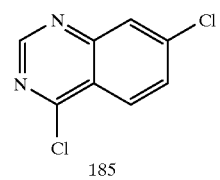
185
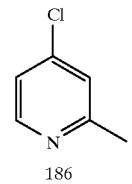
186
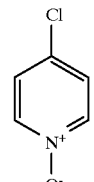
187
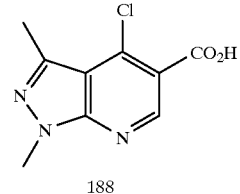
188
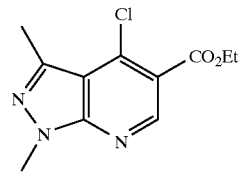
189

TABLE 17-continued
Halides of the type A-Cl, A-Br and A-I
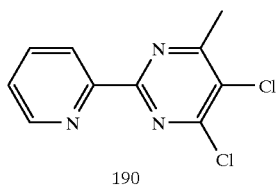
190
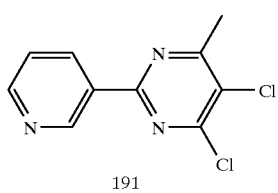
191
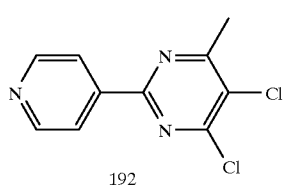
192
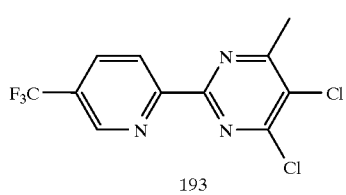
193
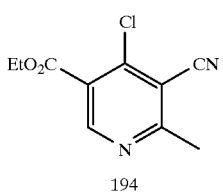
194
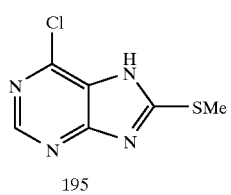
195
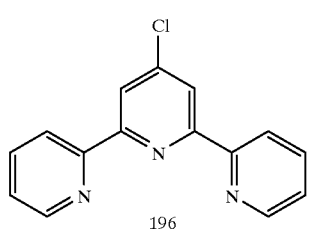
196
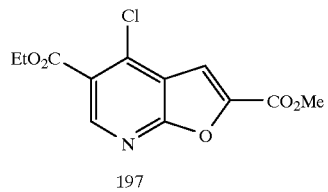
197
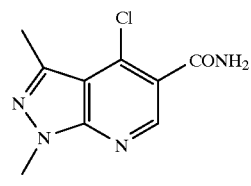
198
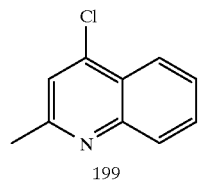
199
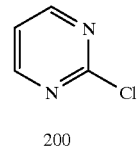
200
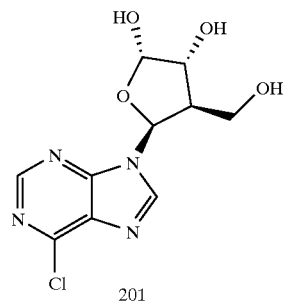
201
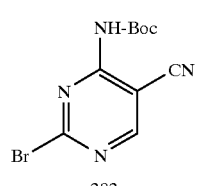
202
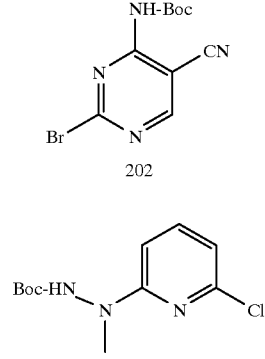
203

TABLE 17-continued
Halides of the type A-Cl, A-Br and A-I
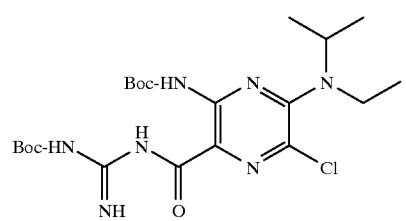
204
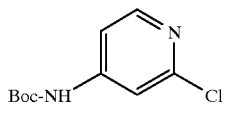
205
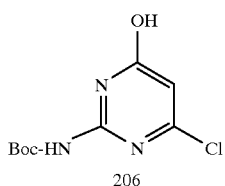
206
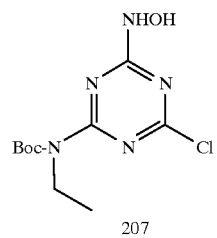
207
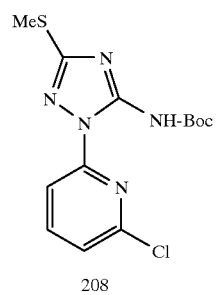
208
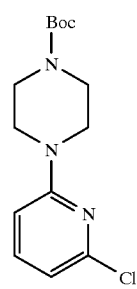
209
TABLE 17-continued
Halides of the type A-Cl, A-Br and A-I
210
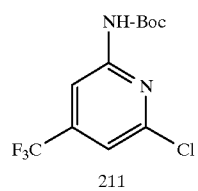
211
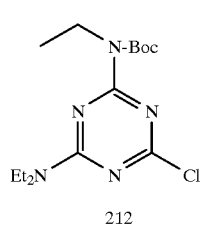
212
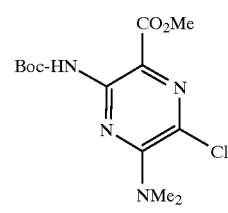
213
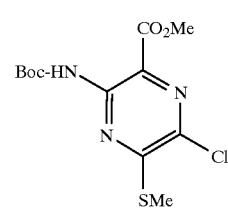
214
215
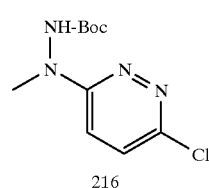
216

TABLE 17-continued
Halides of the type A-Cl, A-Br and A-I
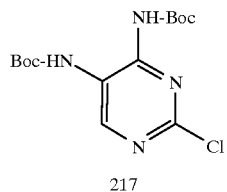
217
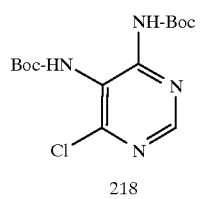
218
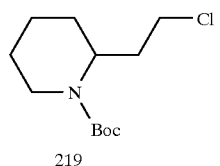
219
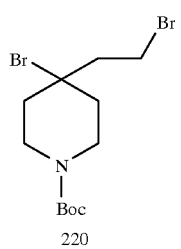
220
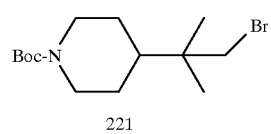
221
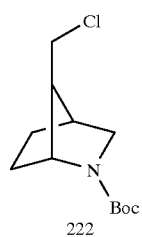
222
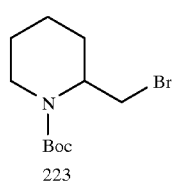
223
TABLE 17-continued
Halides of the type A-Cl, A-Br and A-I
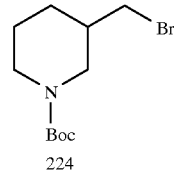
224
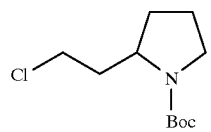
225
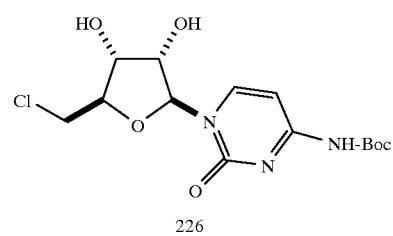
226
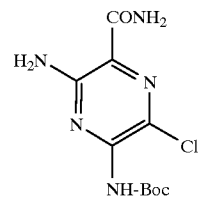
227
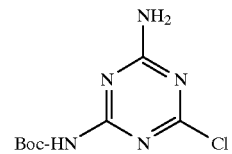
228
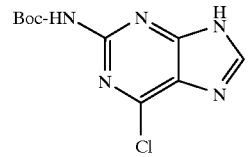
229
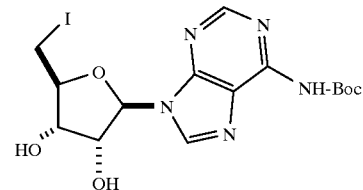
230

TABLE 17-continued
Halides of the type A-Cl, A-Br and A-I
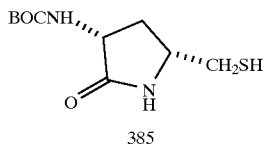
385
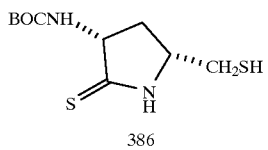
386
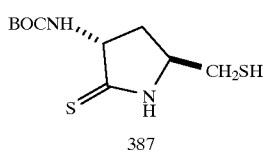
387
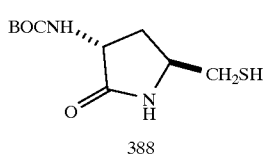
388
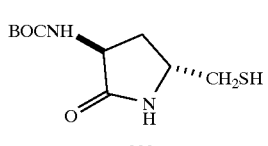
389
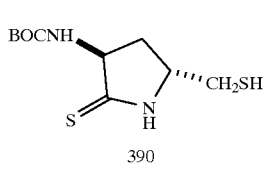
390
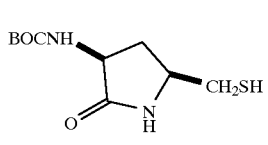
391
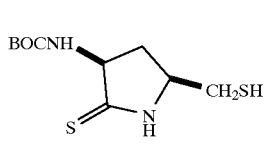
392
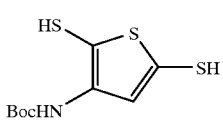
393
TABLE 17-continued
Halides of the type A-Cl, A-Br and A-I
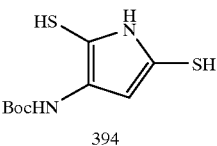
394
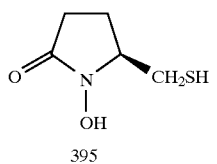
395
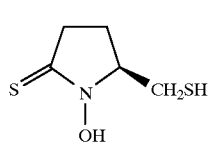
396
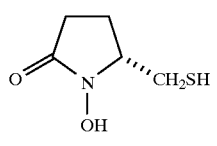
397
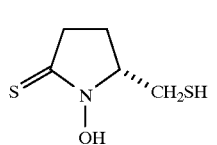
398
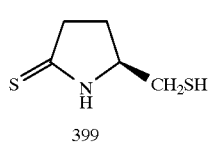
399
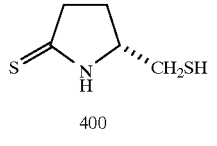
400
TABLE 18
Sulfonyl chlorides of the type A-SO$_2$Cl
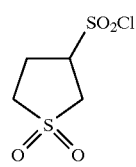
1

TABLE 18-continued
Sulfonyl chlorides of the type A-SO₂Cl
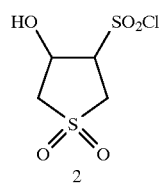
2
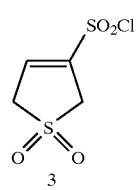
3
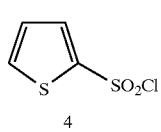
4
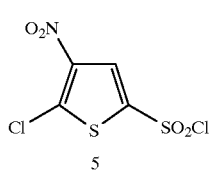
5
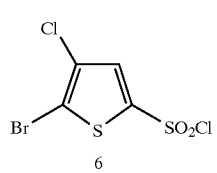
6
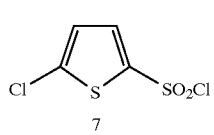
7
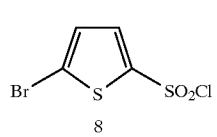
8
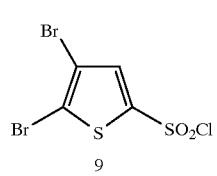
9
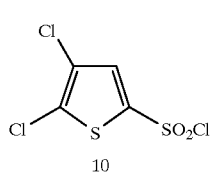
10
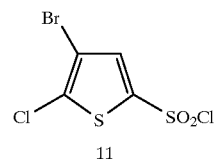
11
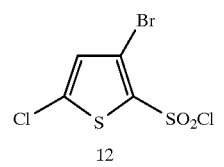
12
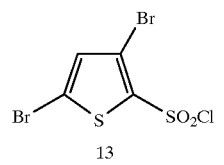
13
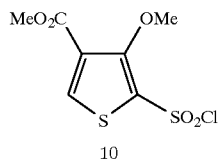
10
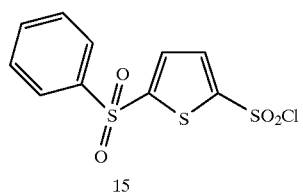
15
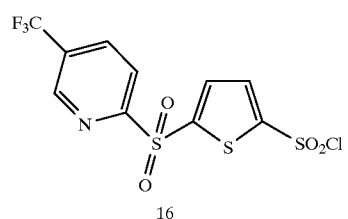
16
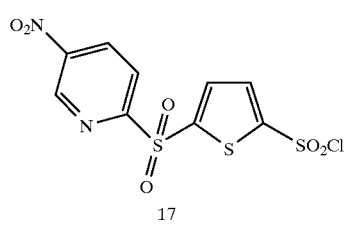
17
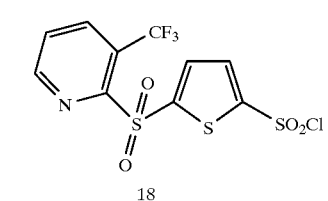
18

TABLE 18-continued
Sulfonyl chlorides of the type A-SO$_2$Cl
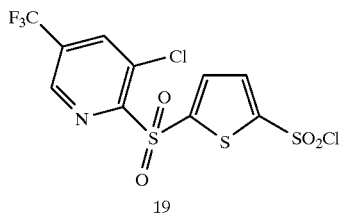
19
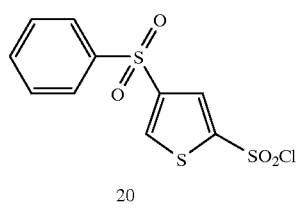
20
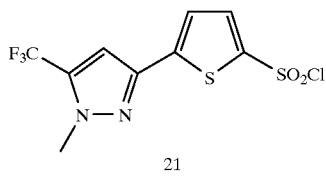
21
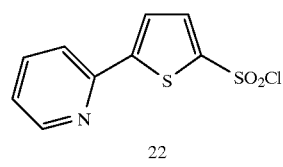
22
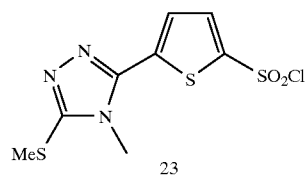
23
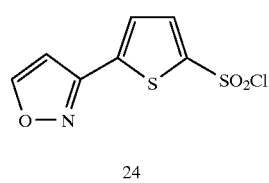
24
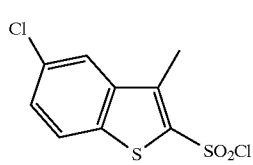
25
TABLE 18-continued
Sulfonyl chlorides of the type A-SO$_2$Cl
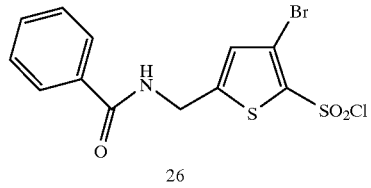
26
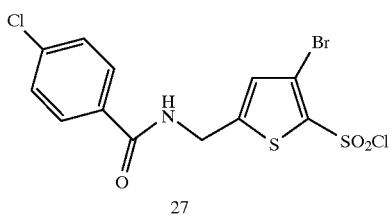
27
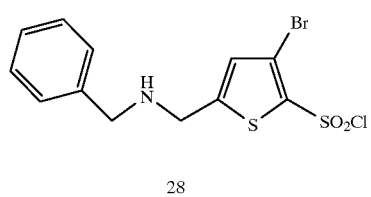
28
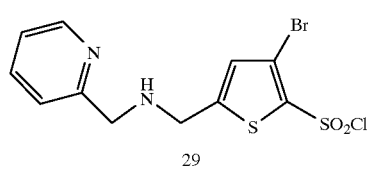
29
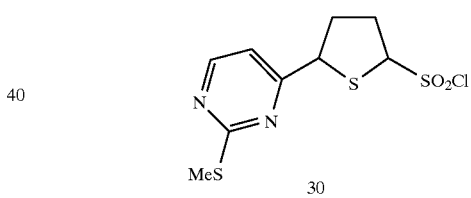
30
31
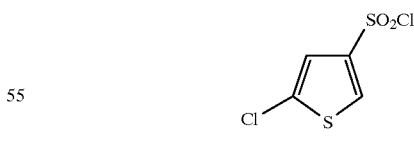
32
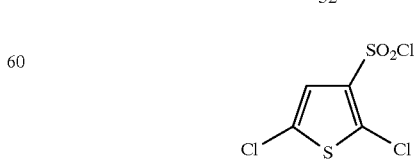
33

TABLE 18-continued
Sulfonyl chlorides of the type A-SO₂Cl
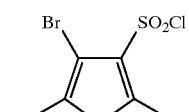
34
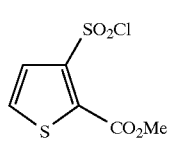
35
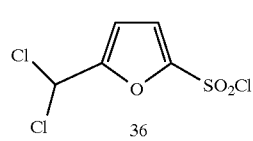
36
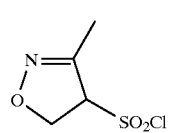
37
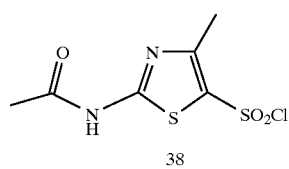
38
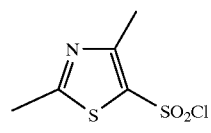
39
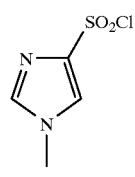
40
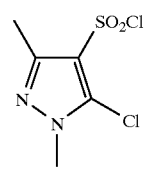
41
TABLE 18-continued
Sulfonyl chlorides of the type A-SO₂Cl
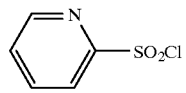
42
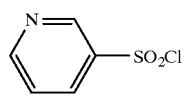
43
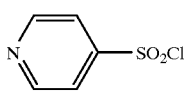
44
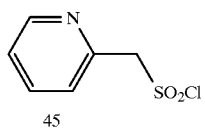
45
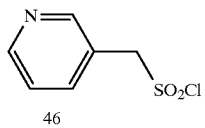
46
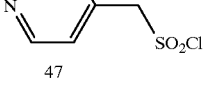
47
48
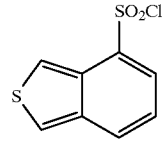
49
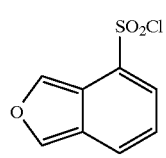
50

TABLE 18-continued

Sulfonyl chlorides of the type A-SO₂Cl

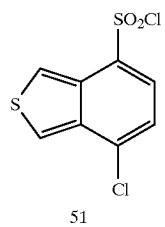

51

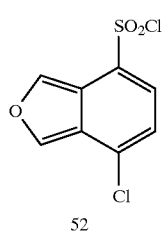

52

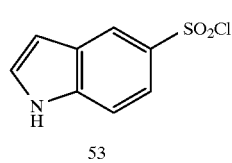

53

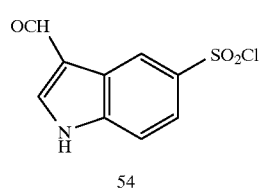

54

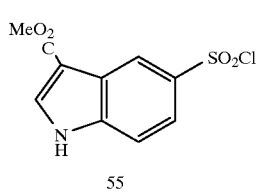

55

The foregoing may be better understood by reference to the following examples which are provided for illustration and not intended to limit the scope of the inventive concept.

In Tables 2–10, the abbreviation bz=benzoyl, bn=benzyl, Ph=phenyl, BOC=t-butyloxycarbonyl and TS=p-toluenesulfonyl.

Compound 1

(3-(Aminomethyl)benzoyl)-Met-OCH₃

Step A (3-(Chloromethyl)benzoyl)-Met-OCH₃

To a solution of methionine methyl ester hydrochloride (2.0 g, 10 mmol) and 3-(chloromethyl)benzoyl chloride (2.08 g, 11.0 mmol) in methylene chloride (50 mL) was slowly added triethylamine (3.07 mL, 22.0 mmol) at ice bath temperature for 2 hours. The mixture was washed with 0.5 N HCl (50 mL×2), brine (50 mL×2) and water (50 mL×2) then dried over anhydrous MgSO₄ and concentrated under reduced pressure. The residue was purified by flash column chromatography (30% ethyl acetate in hexanes) to give the desired product (3.03 g) as a white solid: m.p. 82–83° C.; ¹H NMR (CDCl₃) d 7.82 (1H, s), 7.74 (1H, d, J=7.7 Hz), 7.53 (1H, d, J=7.7 Hz), 7.42 (1H, t, J=7.7 Hz), 7.06 (1H, br d, J=7.6 Hz), 4.92 (1H, ddd, J=7.6, 7.1, 5.1 Hz), 4.59 (2H, s), 3.78 (3H, s), 2.58 (2H, t, J=7.1 Hz) 2.26 (1H, sm), 2.15 (1H, m), 2.10 (3H, s); ¹³C NMR (CDCl₃) d 172.59, 166.54, 138.13, 134.25, 131.95, 129.12, 127.42, 126.97, 52.72, 52.14, 45.55, 31.47, 30.12, 15.55.

Step B (3-(Azidomethyl)benzoyl)-Met-OCH₃

A suspension of (3-(chloromethyl)benzoyl)-Met-OCH₃ (1.58 g, 5.0 mmol) and sodium azide (1.3 g, 20.0 mmol) in DMSO (40 mL) was stirred at 80° C. for 7 hours. The mixture was diluted with methylene chloride (100 mL), washed with brine (70 mL×2) and water (70 mL×2), and then dried over anhydrous MgSO₄. The solvent was evaporated under reduced pressure to give a yellow residue. Chromatography on silica gel (30% ethyl acetate in hexanes) to provide the desired product (1.45 g) as a colorless solid: m.p. 48–49° C.; ¹H NMR (CDCl₃) d 7.78 (2H, m), 7.49 (2H, m), 6.99 (1H, br d, J=7.4 Hz), 4.49 (1H, ddd, J=7.4, 7.1, 5.2 Hz), 4.42 (2H, s), 3.80 (3H,s), 2.60 (2H, t, J=7.4 Hz), 2.29 (1H, m), 2.17 (1H, m), 2.12 (3H, s); ¹³C NMR (CDCl₃) d 177.50. 166.54, 135.97, 134.06, 131.18, 128.89, 126.84, 126.71, 54.09, 52.47, 51.95, 31.38, 30.00,15.30.

Step C (3-(Aminomethyl)benzoyl)-Met-OCH₃

A suspension of (3-(azidomethyl)benzoyl)-Met-OCH₃ (1.29 g, 4.0 mmol) and 5% palladium on carbon (0.2 g) in methanol (40 mL) was stirred under a hydrogen atmosphere (1 atm) for two days at room temperature. The catalyst was removed by filtration through celite (1.5 g) and the solvent was evaporated in vacuo. The residue was washed with water (5 mL×2) and dried to give the desired product (1.12 g) as a colorless foam. ¹H NMR (CDCl₃) d 7.81 (1H, s), 7.68 (1H, d, J=7.4 Hz), 7.45 (1H, d, J=6.5 Hz), 7.36 (1H, t, J=7.4 Hz), 4.91 (1H, ddd, J=7.3, 7.1, 5.1 Hz), 3.90 (2H, s), 3.77 (3H, s), 3.21 (2H, br s), 2.59 (2H, t, J=7.4 Hz), 2.20 (1H, m), 2.12 (1H, m), 2.09 (3H, s).

Compound 2

(4-(Aminomethyl)benzoyl)-Met-OCH₃

The title compound is prepared according to the procedure used to prepare Compound 1 but replacing 3-(chloromethyl)benzoyl chloride with 4-(chloromethyl)benzoyl chloride.

Compound 3

(3-Aminobenzoyl)-Met-OCH₃

The title compound was prepared according to the procedure described in J. Biol. Chem. 269 12410–12413 (1994).

Compound 4

(4-Aminobenzoyl)-Met-OCH₃

Step A

N-BOC-4-Aminobenzoic acid

4-Aminobenzoic acid (10 g, 72.9 mmol) was placed into a mixture of dioxane (145.8 mL) and 0.5 M NaOH (145.8 mL). The solution was cooled to 0° C. and di-t-butyl dicarbonate (23.87 g, 109.5 mmol) was added. The reaction mixture was allowed to warm to room temperature and stirred overnight. The next day, the dioxane was removed, the residue was made acidic and extracted into ethyl acetate. The ethyl acetate fractions were combined and washed with 1N HCl to remove any unreacted starting material. The solution was dried over $Na_2SO_4$ and the solvent was removed in vacuo. The crude material was recrystallized from ethyl acetate/hexanes to provide the desired product (12.2 g): m.p. 189–190° C.; $^1$H NMR ($CD_3OD$) d 1.52 (9H, s), 7.49 (2H, d, J=8.6 Hz), 7.91 (2H, d, J=8.6 Hz), 9.28 (1H, s); $^{13}$C NMR ($CD_3OD$) d 28.59, 81.29, 118.54, 125.30, 131.81, 145.70, 155.00, 169.80; Anal. Calc. for $C_{12}H_{15}NO_4$, C: 60.76, H: 6.37, N: 5.90; Found, C: 60.52, H: 6.43, N: 5.83; HRMS Calc. for $C_{12}H_{15}NO_4$, 237.0961, Found, 237.1001.

Step B (N-BOC-4-Aminobenzoyl)-Met-$OCH_3$

Into a dried, nitrogen filled flask was placed N-BOC4-aminobenzoic acid (8.77 g, 36.97 mmol) in dry methylene chloride (148 mL) along with methionine methyl ester hydrochloride (8.12 g, 40.66 mmol). This solution was cooled in an ice bath and triethylamine (6.7 mL), EDCI (7.80 g, 40.66 mmol) and hydroxybenzotriazole (HOBT, 5.50 g, 40.66 mmol) were added. The mixture was stirred overnight, diluted with more methylene chloride and was extracted three times each with 1 M HCl, 1M $NaHCO_3$ and water. The methylene chloride was dried over $MgSO_4$ and the solvent was removed in vacuo. The resulting solid was recrystallized from ethyl acetate/hexanes to yield the desired product (9.72 g): m.p. 184–185° C.; $^1$H NMR ($CDCl_3$) d 1.53 (9H, s), 2.06–2.18 (4H, m), 2.23–2.33 (1H, m), 2.59 (2H, t, J=7.6 Hz), 3.80 (3H, s), 4.92 (1H, m), 7.45 (2H, d, J=8.7 Hz), 7.77 (2H, d, J=8.7 Hz); $^{13}$C NMR ($CDCl_3$) d 15.59, 28.34, 30.15, 31.64, 52.10, 52.73, 81.20, 117.73, 127.8, 128.33, 141.88, 152.33, 166.50, 172.75; Anal. Calc. for $C_{18}H_{26}N_2O_5S$, C: 56.53, H: 6.85, N: 7.29; Found, C: 56.47, H: 6.86, N: 7.29; m/z (EI) 382 (M).

Step C (4-Aminobenzoyl)-Met-$OCH_3$ hydrochloride

N-BOC-4-aminobenzoyl-Met-$OCH_3$ (3.53 g, 9.59 mmol) was placed into methylene chloride (30–35 mL) and to it was added 3M HCl/$EtO_2$ (38.4 mL). After standing, a white precipitate formed. After two hours the solution was decanted and the crystals were collected by centrifugation. The crystals were then washed several times with fresh ether and dried overnight on the vacuum pump. Meanwhile, the filtrate was left to stand overnight to allow additional product to precipitate. The second fraction was washed with ether and dried overnight on the vacuum pump. The total yield of the desired product was 2.87 g: m.p. 158–164° C.; $^1$H NMR ($CDCl_3$) d 2.10 (3H, s), 2.12–2.29 (1H, m), 2.52–2.71 (1H, m), 2.59 (2H, t, J=7.6 Hz), 3.75 (3H, s), 4.79 (1H, m), 7.02 (2H, d, J=8.6 Hz), 7.55 (2H, d, J=8.6 Hz); $^{13}$C NMR ($CDCl_3$) d 15.23, 31.43, 31.53, 52.91, 52.43, 124.35, 130.56, 135.31, 135.76, 168.95, 173.87; HRMS Calc. for $C_{13}H_{18}N_2O_3S$, 282.1038, Found 282.1009.

Compound 5

(4-Amino-3-methylbenzoyl)-Met-$OCH_3$

Step A

N-BOC-4-Amino-3-methylbenzoic acid

4-Amino-3-methylbenzoic acid (5 g, 33.1 mmol) was reacted according to the same procedure as that used in the process for preparing N-BOC-4-aminobenzoic acid. The resulting orange-brown solid was recrystallized from ethyl acetate and hexanes to provide the desired product (4.99 g) as tan prismatic crystals: m.p. 180–182° C.; 1H NMR ($CD_3OD$) d 1.51 (9h, s), 2.27 (3H, s), 7.66 (1H, d, J=8.1 Hz), 7.79–7.82 (2H, m), 8.32 (1H, s); 13C NMR (CD3OD) d 17.98, 28.62, 81.47, 123.12, 127.05, 129.14, 130.65, 132.99, 142.45, 155.33, 168.70; Anal. Calc. for $C_{13}H_{17}NO_4$, C: 62.15, H: 6.82, N: 5.58; Found C: 62.07, H: 6.86, N: 5.46; m/z (EI) 251; HRMS Calc. for $C_{13}H_{17}NO_4$, 251.1158; Found, 251.1153.

Step B (N-BOC-4-Amino-3-methylbenzoyl)-Met-$OCH_3$

N-BOC-4-amino-3-methylbenzoic acid (2.00 g, 7.96 mmol) was reacted with methionine methyl ester hydrochloride (1.75 g, 8.76 mmol), triethylamine (1.4 mL), EDCI (1.68 g, 8.76 mmol) and hydroxybenzotriazole (HOBT, 1.18 g, 8.76 mmol) in dry methylene chloride (31.8 mL) according to the procedure described for the preparation of N-BOC-4-aminobenzoyl)-Met-$OCH_3$. The resulting solid was recrystallized from ethyl acetate/hexanes to yield the desired product (2.61 g): m.p. 163–165° C.; $^1$H NMR ($CDCl_3$) d 1.54 (9H, s), 2.06–2.18 (4H, m), 2.23–2.34 (4H, m), 2.59 (2H, t, J=6.8 Hz), 3.80 (3H, s), 4.92 (1H, m), 6.45 (1H, s), 6.88 (1H, d, J=7.5 Hz), 7.63 (1H, d, J=8.6 Hz), 7.66 (1H, s), 8.05 (1H, d, J=8.6 Hz); $^{13}$C NMR ($CDCl_3$) d 15.47, 17.61, 28.22, 30.03, 31.55, 51.93, 52.57, 81.04, 118.73, 125.62, 127.66, 129.54, 139.89, 152.34, 166.58, 172.66.

Step C (4-Amino-3-methylbenzoyl)-Met-$OCH_3$ hydrochloride

N-BOC-4-Amino-3-methylbenzoyl-Met-$OCH_3$ (0.99 g, 2.59 mmol) was dissolved in methylene chloride (15–20 mL) and precipitated with 3M HCl/$Et_2O$ (20.7 mL). A pale orange precipitate was obtained, washed with ether and dried overnight on the vacuum pump. The total yield of the desired product was 0.83 g: m.p. 157–159° C.; $^1$H NMR ($CD_3OD$) d 2.04 (3H, s), 2.11–2.25 (1H, m), 2.47 (3H, s), 2.52–2.68 (3H, m), 3.74 (3H, s), 4.75–4.80 (1H, m), 7.48 (1H, d, J=8.2 Hz), 7.81 (2H, d, J=8.2 Hz), 7.87 (1H, s); $^{13}$C NMR ($CD_3OD$) d 15.23, 17.28, 31.43, 31.51, 52.91, 53.37, 124.41, 127.85, 131.99, 133.63, 134.14, 135.65, 169.05, 173.84; Anal. Calc. for $C_{14}H_{21}N_2O_3S$, C: 50.52, H: 6.36, N: 8.42; Found C: 50.71, H: 6.40, N: 8.34.

Compound 6

(4-Amino-3-methoxybenzoyl)-Met-$OCH_3$

Step A

N-BOC-4-Amino-3-methoxybenzoic acid

4-Amino-3-methoxybenzoic acid (1 g, 5.98 mmol) was reacted according to the same procedure as that used in the process for preparing N-BOC-4-aminobenzoic acid. The resulting solid was recrystallized from ethyl acetate and hexanes to provide the desired product (1.5 g) as tan crystals: m.p. 176–178° C.; $^1$H NMR ($CD_3OD$) d 1.52 (9H, s), 3.92 (3H, s), 7.56 (1H, s), 7.62 (1H, d, J=8.4 Hz), 7.96 (1H, s), 8.03 (1H, d, J=8.4 Hz); $^{13}$C NMR ($CD_3OD$) d 28.53, 56.35, 81.78, 112.01, 118.58, 124.20, 125.76, 133.84, 149.04, 154.20, 169.60; HRMS Calc. for $C_{13}H_{17}NO_5$, 267.1107; Found, 267.1103.

Step B

(N-BOC-4-Amino-3-methoxybenzoyl)-Met-OCH$_3$

N-BOC-4-amino-3-methoxybenzoic acid (0.35 g, 1.31 mmol) was reacted with with methionine methyl ester hydrochloride (0.9 g, 1.43 mmol) using EDCI according to the procedure described for the preparation of (N-BOC-4-aminobenzoyl)-Met-OCH$_3$.

The resulting solid was recrystallized from ethyl acetate/hexanes to yield the desired product (0.36 g): m.p. 163–165° C.; $^1$H NMR (CDCl$_3$) d 1.53 (9H, s), 2.09–2.18 (4H, m), 2.23–2.35 (1H, m), 2.60 (2H, t, J=6.9 Hz), 3.80 (3H, s), 3.93 (3H, s), 4.92 (1H, br s), 6.93 (1H, d, J=7.6 Hz), 7.25(1H, m), 7.31 (1H, d, J=10.2 Hz), 7.44 (1H, s), 8.15 (1H, d, J=8.5 Hz); $^{13}$C NMR (CDCl$_3$) d 15.47, 28.23, 30.09, 31.48, 52.06, 52.54, 55.81, 80.82, 98.06, 109.38, 116.66, 119.31, 131.52, 147.23, 152.31, 166.57, 172.58; m/z (FAB) 413 (M+1).

Step C

(4-Amino-3-methoxybenzoyl)-Met-OCH$_3$ hydrochloride

N-BOC-4-Amino-3-methoxybenzoyl-Met-OCH$_3$ (0.71 g, 1.79 mmol) was dissolved in methylene chloride (4 mL) and precipitated with 3M HCl/Et$_2$O (12 mL). A reddish precipitate was obtained, washed with ether and dried overnight on the vacuum pump. The total yield of the desired product was 0.55 g: m.p. 176–177° C.; $^1$H NMR (CD$_3$OD) d 2.08 (3H, s), 2.21 (2H, m), 2.61 (2H, m), 3.74 (3H, s), 4.02 (3H, s), 4.79 (1H, m), 7.50 (1H, d, J=8.2 Hz), 7.57 (1H, d, J=4.1 Hz), 7.67 (1H, s); $^{13}$C NMR (CD$_3$OD) d 15.26, 31.34, 31.42, 52.95, 53.38, 57.12, 112.29, 121.43, 124.57, 124.77, 136.15, 153.67, 168.79, 173.81.

Compound 7

(4-Amino-1-naphthoyl)-Met-OCH$_3$

Step A

4-Amino-1-naphthoic acid

4-Amino-1-naphthalenecarbonitrile (1.5 g, 8.91 mmol) was suspended in a 50% KOH solution (18 mL). The heterogeneous solution was heated at reflux for 2–3 days. Once the solution became homogeneous and TLC showed no more starting material, the deep red solution was cooled and poured over 200 mL of water. The resulting solution was then filtered and the desired product was precipitated with concentrated HCl. The resulting red crystals were filtered and the filtrate was refiltered to give pink crystals. The first fraction of crystals was treated with activated carbon to remove some of the red color. A total of 1.51 g of the desired product was obtained: m.p. 169–171° C.; $^1$H NMR (CD$_3$OD) d 6.69 (1H, d, J=8.2 Hz), 7.38–7.43 (1H, m), 7.48–7.54 (1H, m), 8.03 (1H, d, J=8.5 Hz), 8.13 (1H, d, J=8.2 Hz), 9.09 (1H, d, J=8.5 Hz); $^{13}$C NMR (CD$_3$OD) d 107.39, 114.61, 122.99, 123.92, 125.21, 127.40, 128.48, 135.04, 151.35, 171.44; HRMS Calc. for C$_{11}$H$_7$NO$_2$, 187.0633; Found, 187.0642.

Step B

N-BOC-4-Amino-1-naphthoic acid

4-Amino-1-naphthoic acid (0.86 g, 4.61 mmol) was dissolved in dioxane (9.2 mL). Di-t-butyl dicarbonate (1.11 g, 5.07 mmol) was added and the mixture was stirred overnight. The reaction mixture was worked up as described above for N-BOC-4-aminobenzoic acid to give 0.76 g of the desired product as a reddish pink solid: m.p. 194–195° C.; $^1$H NMR (CD$_3$OD) d 1.56 (9H, s), 7.53–7.62 (2H, m), 7.79 (1H, d, J=8.1 Hz), 8.12 (1H, d, J=8.0 Hz), 8.22 (1H, d, J=8.18 Hz), 9.02 (1H, d, J=8.9 Hz); $^{13}$C NMR (CD$_3$OD) d 26.68, 81.62, 119.06, 123.40, 124.57, 127.03, 127.37, 128.49, 128.77, 131.89, 133.76, 139.86, 155.95, 170.73; Anal. Calc. for C$_{17}$H$_{17}$NO$_4$, C: 66.90, H: 5.96, N: 4.88; Found C: 66.49, H: 6.08, N: 4.79; m/z (EI), 289; HRMS Calc. for C$_{16}$H$_{17}$NO$_4$, 287.1158; Found, 287.1151.

Step C

(N-BOC-4-Amino-1-naphthoyl)-Met-OCH$_3$

N-BOC-4-Amino-naphthoic acid (0.46 g, 1.60 mmol), methionine methyl ester hydrochloride (0.35 g, 1.76 mmol), EDCI (0.43 g, 1.76 mmol), HOBT (0.24 g, 1.76 mmol) and triethylamine (0.27 mL) in methylene chloride (6.4 mL) were reacted as described above for N-BOC-4-aminobenzoyl-Met-OCH3. After workup and recrystallization from ethyl acetate hexanes, the desired product (0.44 g) was obtained as pale pink crystals: m.p. 131–132° C.; $^1$H NMR (CDCl$_3$) d 1.57 (9H, s), 2.11–2.21 (4H, m), 2.29–2.41 (1H, m), 2.65 (2H, t, J=7.1 Hz), 3.83 (3H, s), 4.99–5.06 (1H, m), 6.68 (1H, d, J=8.0 Hz), 7.02 (1H, s), 7.56–7.59 (2H, m) 7.69 (1H, d, J=7.9 Hz), 7.87–7.90 (1H, m), 8.02 (1H, d, J=7.9 Hz), 8.44–8.48 (1H, m); $^{13}$C NMR (CDCl$_3$) d 15.56, 28.31, 30.19, 31.65, 52.06, 52.64, 81.17, 115.82, 120.18, 125.79, 126.37, 126.53, 127.18, 131.02, 135.65, 152.93, 169.04, 172.40; HRMS Calc. for C$_{22}$H$_{28}$N$_2$O$_5$S, 432.1719; Found, 432.1702; m/z (FAB) 433 (M+1).

Step D

(4-Amino-1-naphthoyl)-Met-OCH$_3$ hydrochloride (N-BOC-4-Amino-1-naphtholyl)-Met-OCH$_3$ (0.57 g, 1.31 mmol) was deprotected with HCl/ether to yield the desired product (0.31 g) as a white solid: mp. 178–181° C.; $^1$H NMR (CD$_3$OD) d 2.08–2.16 (4H, m), 2.20–2.30 (1H, m) 2.57–2.75 (2H, m) 3.82 (3H, s), 4.87–4.91 (1H, m), 7.59 (1H, d, J=7.5 Hz), 7.67 (1H, d, J=7.5 Hz) 7.71–7.80 (2H, m), 8.03 (1H, dd, J=7.1, 2.0 Hz), 8.35 (1H, dd, J=6.8, 1.8 Hz); $^{13}$C NMR (CD$_3$OD) d 15.23, 31.40, 53.01, 53.33, 119.90, 122.20, 126.15, 127.41,127.77, 129.09, 129.31, 131.50, 132.33, 135.64, 171.77, 173.83; m/z (FAB), 369 (M+1).

Compound 8

(4-Amino-2-phenylbenzoyl)-Met-OCH$_3$

Step A

4-Nitro-2-phenyltoluene

2-Bromo-4-nitrotoluene (2.16 g, 10.00 mmol) and phenylboric acid (1.46 g, 12.00 mmol) were dissolved in anhydrous DMF (25 mL) under nitrogen. To this mixture was added Pd(Ph$_3$P)$_4$ (0.58 g, 5%). The mixture was heated at 100° C. overnight. The solution was poured onto 1N HCl and extracted with Et$_2$O. The crude product was chromatographed on silica gel using hexanes as eluent. After recrystallization from ethanol, the desired product (1.23 g) was obtained as pale orange needles: m.p. 69–71° C.; $^1$H NMR (CDCl$_3$) d 2.36 (3H, s), 7.29–7.40 (2H, m), 7.41–7.49 (5H, m), 8.07–8.10 (2H, m); $^{13}$C NMR (CDCl$_3$) d 20.68, 121.96, 124.51, 127.78, 128.41, 128.83, 131.06, 139.06, 139.44, 142.97, 143.48, 146.05; Anal. Calc. for $C_{13}H_{11}NO_2$, C: 73.26, H: 5.20, N: 6.57; Found, C: 73.10, H: 5.12, N: 6.50; m/z (EI) 213; HRMS Calc. for $C_{13}H_{11}NO_2$, 213.0790; Found, 213.0793.

Step B

4-Nitro-2-phenylbenzoic acid

4-Nitro-2-phenyltoluene (0.5 g, 2.34 mmol) was dissolved in water (4.6 mL) and pyridine (2.3 mL). The mixture was heated to reflux and $KMnO_4$ (1.85 g, 11.7 mmol) was added. The reaction mixture was heated overnight and the solution was filtered and washed several times with boiling water. The aqueous solution was made acidic and the product was extracted into ethyl acetate. The ethyl acetate solution was dried over $Na_2SO_4$ and the solvent removed in vacuo to provide the desired product (0.37 g): m.p. 174–176° C., $^1$H NMR (CD$_3$OD) d 7.38–7.48 (5H, m), 7.96 (1H, d, J=8.5 Hz), 8.21 (1H, d, J=2.3 Hz), 8.28 (1H, dd, J=8.48, 2.37 Hz); $^{13}$C NMR (CD$_3$OD) d 122.95, 126.09, 129.27, 129.42, 129.49, 131.56, 139.26, 140.42, 144.41, 150.17, 170.52; m/z (EI) 243 (M).

Step C (4-Nitro-2-phenylbenzoyl)-Met-OCH$_3$

4-Nitro-2-phenylbenzoic acid (0.3 g, 1.23 mmol), methionine methyl ester hydrochloride salt (0.27 g, 1.35 mmol), EDCI (0.26 g, 1.35 mmol), HOBT (0.18 g, 1.35 mmol) and triethylamine (0.19 mL) in dry methylene chloride (4.9 mL) were reacted according the procedure described above for (N-BOC-4-aminobenzoyl)-Met-OCH$_3$. After recrystallization of the product from ethyl acetate hexanes, the desired product (0.41 g) was obtained: m.p. 98–101° C.; $^1$H NMR (CDCl$_3$) d 1.62–1.73 (1H, m), 1.79–1.88 (1H, m), 1.91 (3H, s), 1.99 (2H, t, J=7.2 Hz), 3.59 (3H, s), 4.53 (1H, m), 6.45 (1H, d, J=7.8 Hz), 7.33–7.40 (5H, m), 7.67 (1H, d, J=8.3 Hz), 8.07–8.12 (2H, m); $^{13}$C NMR (CDCl$_3$) d 14.92, 29.11, 30.67, 51.51, 52.29, 121.86, 124.74, 128.27, 128.60, 128.69, 129.52, 137.50, 140.56, 141.02, 148.09, 167.23, 171.23; m/z (FAB), 389 (M+1).

Step D (4-Amino-2-phenylbenzoyl)-Met-OCH$_3$ (4-Nitro-2-phenylbenzoyl)-Met-OCH$_3$ (0.35 g, 0.90 mmol) was dissolved in ethyl acetate (9.0 mL). To this mixture was added $SnCl_2 \cdot 2H_2O$ (1.02 g, 4.5 mmol) and the reaction mixture was heated under nitrogen at reflux for one hour. The mixture was poured onto ice, the solution was made basic using NaHCO$_3$ and the product was extracted into ethyl acetate several times (7–8). The ethyl acetate solutions were combined, washed with brine and dried over Na$_2$SO$_4$. The solvent was removed in vacuo to the desired product (0.24 g) as a yellow solid: $^1$H NMR (CDCl$_3$) d 1.58–1.70 (1H, m), 1.80–1.92 (1H, m), 1.98 (3H, s), 2.06 (2H, t, J=7.7 Hz), 3.62 (3H, s), 4.00 (2H, br s), 4.56–4.63 (1H, m), 5.84 (1H, d, J=7.7 Hz), 6.50 (1H, s), 6.61 (1H, d, J=8.4 Hz) 7.29–7.42 (5H, m), 7.58 (1H, d, J=8.3 Hz) $^{13}$C NMR (CDCl$_3$) d 15.02, 29.25, 31.25, 51.57, 52.15, 113.27, 115.88, 123.52, 127.56, 128.37, 128.44, 130.92, 140.66, 141.44, 148.53, 168.58, 171.91.

Compound 9

(4-Amino-2-(2-thienyl)benzoyl)-Met-OCH$_3$

The title compound can be prepared according to the method used to prepare Compound 8, only substituting thiophene-2-boronic acid for phenyl boronic acid.

Compound 10

(4-Amino-2-(1-naphthyl)benzoyl)-Met-OCH$_3$

The title compound can be prepared according to the method used to prepare Compound 8, only substituting 1-naphthylboronic acid for phenylboronic acid.

Compound 11

4-Amino-3'-methylbiphenyl

The title compound was prepared by Suzuki coupling of 1-bromo-4-nitrobenzene and 1-bromo-3-methylbenzene.

Compound 12

4-Amino-4'-biphenyl carboxylic acid

Step A

4-Nitro-4'-methylbiphenyl

The title compound was prepared by Suzuki coupling of 1-bromo-4-nitrobenzene and 1-bromo-4-methylbenzene.

Step B

4-Nitro-4'-biphenyl carboxylic acid

The title compound was prepared by KMnO$_4$ oxidation of 4-nitro-4'-methylbiphenyl.

Step C

4-Amino-4'-biphenyl carboxylic acid

The title compound can be prepared by palladium catalyzed hydrogenation of 4-nitro-4'-biphenyl carboxylic acid.

Compound 13

4-Amino-3'-biphenyl carboxylic acid

Step A

4-Nitro-3'-methylbiphenyl

The title compound was prepared by Suzuki coupling of 1-bromo-4-nitrobenzene and 1-bromo-3-methylbenzene.

Step B

4-Nitro-3'-biphenyl carboxylic acid

The title compound was prepared by KMnO$_4$ oxidation of 4-nitro-3'-methylbiphenyl.

Step C

4-Amino-3'-biphenyl carboxylic acid

The title compound can be prepared by palladium catalyzed hydrogenation of 4-nitro-3'-biphenyl carboxylic acid.

Compound 14

4-Amino-2-methoxy-3'-biphenyl carboxylic acid

Step A

2-Methoxy-4-nitro-3'-methylbiphenyl

The title compound was prepared by reaction of 1-bromo-2-methoxy-4-nitrobenzene with 3-methylphenylboronic acid in the presence of palladium acetate.

Step B

2-Methoxy-4-nitro-3'-biphenylcarboxylic acid

The title compound was prepared by $KMnO_4$ oxidation of 2-methoxy-4-nitro-3'-methylbiphenyl.

Step C

4-Amino-2-methoxy-3'-biphenyl carboxylic acid

The title compound can be prepared by palladium catalyzed hydrogenation of 2-methoxy-4-nitro-3'-biphenyl carboxylic acid.

Compound 15

4-Amino-2-isopropyloxy-3'-biphenyl carboxylic acid

The title compound can be prepared by methods analogous to those used to prepare Compound 14.

Compound 16

4-Amino-2-phenyl-3'-biphenylcarboxylic acid

The title compound can be prepared by methods analogous to those used to prepare Compound 14.

Compound 17

(4-Amino-2-(3,5-dimethylphenylbenzoyl)-Met-OCH$_3$

Step A

2-Bromo-4-nitrobenzoic acid

2-Bromo-4-nitrotoluene (5.0 g, 23.14 mmol) was dissolved in pyridine (23 mL) and water (46 mL). The heterogeneous mixture was heated to 60° C. and $KMnO_4$ (18.29 g, 115.7 mmol) was added carefully. The mixture was then heated under reflux overnight. The reaction mixture was filtered and washed with boiling water. The solution was then made acidic and extracted into ethyl acetate, dried over $Na_2SO_4$ and the solvent was removed in vacuo. The crude product was dissolved in aqueous NaOH and washed with hexanes. The aqueous phase was made acidic and the product was extracted into ethyl acetate. The ethyl acetate solutions were combined and dried over $Na_2SO_4$ and the solvent was removed in vacuo to provide the desired product (3.72 g): m.p. 158–160° C.; $^1$H NMR (CD$_3$OD) d 7.81 (1H, d, J=8.5 Hz), 8.08 (1H, d, J=8.5 Hz), 8.30 (1H, s); $^{13}$C NMR (CD$_3$OD) d 121.96, 122.75, 129.36, 132.24, 139.52, 149.54, 167.75; Anal. Calc. for $C_7H_4BrNO_4$.0.1 ethyl acetate, C: 34.88, H: 1.90, N: 5.50; Found, C: 34.68, H: 1.86, N: 5.82.

Step B

3,5-Dimethylphenylboronic acid

Magnesium turnings (1.44 g, 59.43 mmol) were coverd with dry THF (18.8 mL) in a dried, nitrogen filled flask fitted with an addition funnel and reflux condenser. To this was added 5-bromo-m-xylene (10 g, 54.03 mmol) in THF (15 mL) after initiation of the Grignard reaction. The addition was carried out over several minutes and the reacton mixture was heated at reflux for 1–2 hours until most of the magnesium had reacted. The reaction mixture was then cooled and transferred to an addition funnel fitted to an nitrogen filled flask containing triisopropyl borate (24.9 mL) at −70° C. The dropwise addition was carried out over several minutes and the mixture warmed to room temperature and stirred overnight. The grey solution was poured onto 2 M HCl and immediately turned yellow. The solution was extracted with $Et_2O$ and the $Et_2O$ fractions were combined, dried over $MgSO_4$ and the solvent was removed in vacuo to provide the desired product (2.41 g): m.p. 249–251° C.; $^1$H NMR (CDCl$_3$) d 2.44 (6H, s), 7.23 (1H, s), 7.84 (2H, s); $^{13}$C NMR (CD$_3$OD) d 21.36, 133.28, 134.39, 137.48.

Step C

4-Nitro-2-(3,5-dimethylphenyl)benzoic acid

2-Bromo-4-nitrobenzoic acid (0.43 g, 2.03 mmol) and 3,5-dimethylphenyl boronic acid (0.334 g, 2.23 mmol) were dissolved in anhydrous DMF (25 mL) under nitrogen. To this mixture was added $Cs_2CO_3$ (1.66 g, 5.08 mmol) followed by Pd(Ph$_3$P)$_4$ (0.12 g, 5%). The mixture was heated at 100° C. overnight. The solution was poured onto 1N HCl and extracted with $Et_2O$. It was dried over $MgSO_4$ and the solvent was removed in vacuo. The crude product was chromatographed on silica gel using a 9:1 mixture of hexanes and ethyl acetate to provide the desired product (0.34 g): $^1$H NMR (CDCl$_3$) d 2.36 (6H, s), 6.99 (2H, s), 7.07 (1H, s), 8.03 (1H, d, J=9.0 Hz), 8.23–8.25 (2H, m); $^{13}$C NMR (CDCl$_3$) d 21.28, 121.68, 123.68, 125.74, 126.07, 130.22, 131.19, 131.31, 135.04, 138.21, 144.74, 170.75.

Step D

(4-Nitro-2-(3,5-dimethylphenyl)benzoyl)-Met-OCH$_3$

4-Nitro-2-(3,5-dimethylphenyl)benzoic acid (0.15 g, 0.55 mmol), methionine methyl ester hydrochloride (0.11 g, 0.55 mmol), EDCI (0.11 g, 0.55 mmol), HOBT (0.07 g, 0.55 mmol) and triethylamine (0.08 mL) in dry methylene chloride (2.2 mL) were reacted and worked up according to the procedure for (N-BOC-4-aminobenzoyl)-Met-OCH$_3$ as described above. After recrystallization from ethyl acetate and hexanes, the desired product was obtained (0.13 g): m.p. 122–124° C.; $^1$H NMR (CDCl$_3$) d 1.2–1.84 (1H, m), 1.85–1.97 (1H, m), 2.01 (3H, s), 2.05 (3H, t, J=7.7 Hz), 2.38 (6H, s), 3.70 (3H, s), 4.67–4.74 (1H, m), 6.03 (1H, d, J=7.9 Hz), 7.05 (2H, s), 7.09 (1H, s), 7.84–7.87 (1H, m), 7.84–7.87 (1H, m) 8.23–8.26 (2H, m); $^{13}$C NMR (CDCl$_3$) d 15.20, 21.26, 29.22, 31.15, 51.79, 52.57, 122.07, 125.11, 126.27, 130.03, 130.53, 137.77, 138.82, 140.29, 141.56, 148.41, 167.14, 171.53.

Step E

(4-Amino-2-(3,5-dimethylphenyl)benzoyl)-Met-OCH$_3$ (4-Nitro-2-(3,5-dimethylphenyl)benzoyl)-Met-OCH$_3$ (0.11 g, 0.26 mmol) was dissolved in ethyl acetate (3.0 mL). To this mixture was added SnCl$_2$.2H$_2$O (0.3 g, 1.30 mmol) and the reacton was heated under nitrogen at reflux for 6 hours. The mixture was worked up as described above for (4-amino-2-phenylbenzoyl)-Met-OCH$_3$ to give the desired product (0.15 g): $^1$H NMR (CDCl$_3$) d 1.60–1.70 (1H, m), 1.80–1.90 (1H, m), 1.99 (3H, s), 2.05 (2H, t, J=7.6 Hz), 2.33 (6H, s), 3.64 (3H, s), 3.93 (2H, br s), 4.61–4.64 (1H, m), 5.82 (1H, d, J=7.7 Hz), 6.49 (1H, d, J=2.3 Hz) 6.62 (1H, dd, J=8.4, 2.4 Hz), 6.98 (2H, s), 7.00 (1H, s), 7.65 (1H, d, J=8.3 Hz); $^{13}$C NMR (CDCl$_3$) d 15.08, 21.17, 29.28, 31.49, 51.70, 52.18, 113.30, 115.94, 123.55, 126.36, 129.32, 131.23, 138.15, 140.72, 141.92, 148.40, 168.45, 172.01.

Preparation 1

Anilines of the formula B—NH₂

The anilines from Table 1, entries 10–126 (B—NH₂) are prepared using the procedures for Compounds 1–18 with the exception that methionine methyl ester is replaced by methioninesulfone methyl ester, (S—Me)cysteine methyl ester, serine methyl ester, (O—Me)serine methyl ester, (O—Me)homoserine methyl ester, homoserine lactone, isoleucine methyl ester, leucine methyl ester, norleucine methyl ester, norvaline methyl ester, cyclohexylalanine methyl ester, phenylalanine methyl ester, or glutamic acid dimethyl ester.

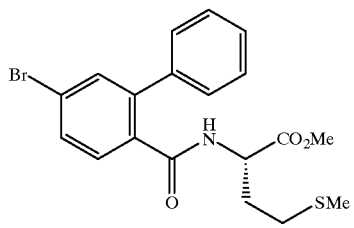

Preparation 2

4-Bromo-2-phenylbenzoyl methionine methyl ester

Preparation 2A

4-Bromo-2-phenylbenzoic acid methyl ester

A solution of methyl 4-amino-2-phenylbenzoic acid (1.0 equivalent) in dilute aqueous HBr is treated with NaNO₂ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

Preparation 2B

4-Bromo-2-phenylbenzoic acid

To a solution of the resultant compound from Preparation 2A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

Preparation 2C

4-Bromo-2-phenylbenzoyl methionine methyl ester

To a solution of the resultant compound from Preparation 2B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

Preparation 2D

4-Bromo-2-phenylbenzoyl methionine methyl ester alternate procedure

A solution of 4-amino-2-phenylbenzoyl methionine methyl ester (1.0 equivalent) in dilute aqueous HBr is treated with NaNO₂ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

Preparation 3

Arylbromides of the formula B-Br

The anilines from Table 1 (B—NH₂) are reacted according to the procedures of Preparation 2 to provide the arylbromides listed in Table 2.

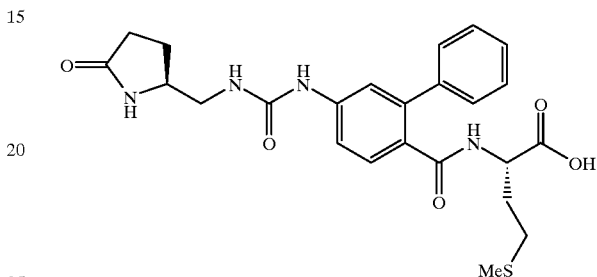

EXAMPLE 1

4-((S)-2-Pyrrolidone-5-aminomethylcarbonyl)amino-2-phenylbenzoyl methionine

EXAMPLE 1A

Methyl 4-((S)-2-Pyrrolidone-5-aminomethylcarbonyl)amino-2-phenylbenzoate

To a solution of methyl 4-amino-2-phenylbenzoate hydrochloride (1.0 equivalent) in toluene is added triphosgene (0.33 equivalent) and the mixture is heated at reflux until judged complete by TLC analysis. The intermediate is reacted without further purification with (S)-5-aminomethyl-2-pyrrolidone (1.0 equivalent) and triethylamine (2.0 equivalents). When judged complete by TLC analysis, the reaction is taken up in ethyl acetate and washed with 1N HCl and brine, evaporated, and purified by chromatography on silica gel.

EXAMPLE 1B

4-((S)-2-Pyrrolidone-5-aminomethylcarbonyl)amino-2-phenylbenzoic acid

To a solution of the resultant compound from Example 1A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

EXAMPLE 1C

4-((S)-2-Pyrrolidone-5-aminomethylcarbonyl)amino-2-phenylbenzoyl methionine methyl ester To a solution of the resultant compound from Example 1B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 1D 4-((S)-2-Pyrrolidone-5-aminomethylcarbonyl) amino-2-phenylbenzoyl methionine methyl ester, alternate preparation To a solution of 4-amino-2-phenylbenzoyl methionine methyl ester (1.0 equivalent) in methylene chloride is added a solution of phosgene in toluene (1.0 equivalent) and triethylamine (2.0 equivalents). The intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 1E 4-((S)-2-Pyrrolidone-5-aminomethylcarbonyl) amino-2-phenylbenzoyl methionine To a solution of the resultant compound from Example 1C in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

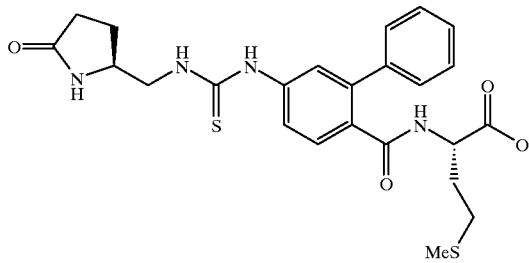

EXAMPLE 2

4-((S)-2-Pyrrolidone-5-aminomethylthiocarbonyl) amino-2-phenylbenzoyl methionine The title compound is prepared as described in Example 1 with the exception that triphosgene (0.33 equivalent) is replaced by thiophosgene (1.0 equivalent).

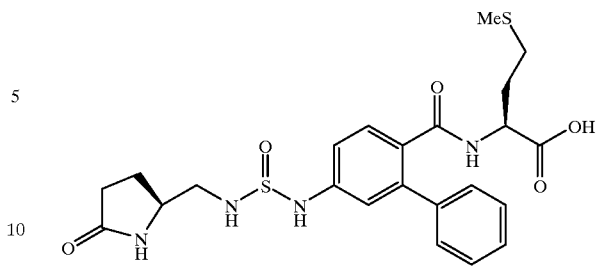

EXAMPLE 3

4-((S)-2-Pyrrolidone-5-aminomethylsulfinyl)amino-2-phenylbenzoyl methionine

EXAMPLE 3A 4-((S)-2-Pyrrolidone-5-aminomethylsulfinyl)amino-2-phenylbenzoyl methionine methyl ester To a solution of 4-amino-2-phenylbenzoyl methionine methyl ester (1.0 equivalent) in methylene chloride is added thionyl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 3B 4-((S)-2-Pyrrolidone-5-aminomethylsulfinyl)amino-2-phenylbenzoyl methionine To a solution of the resultant compound from Example 3A in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

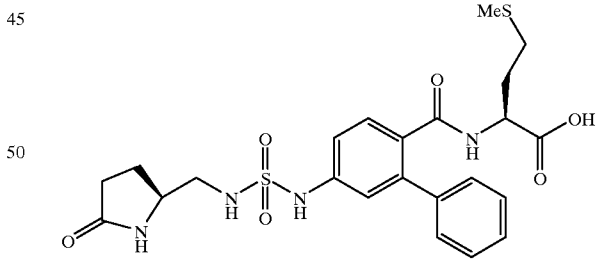

EXAMPLE 4

4-((S)-2-Pyrrolidone-5-aminomethylsulfonyl)amino-2-phenylbenzoyl methionine

EXAMPLE 4A 4-((S)-2-Pyrrolidone-5-aminomethylsulfonyl)amino-2-phenylbenzoyl methionine methyl ester To a solution of 4-amino-2-phenylbenzoyl methionine methyl ester (1.0 equivalent) in methylene chloride is added sulfuryl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 4B 4-((S)-2-Pyrrolidone-5-aminomethylsulfonyl)amino-2-phenylbenzoyl methionine methyl ester, alternate procedure A solution of 1 equivalent of 4-amino-2-phenylbenzoyl methionine methyl ester (1.0 equivalent) and sulfuryl chloride (1.0 equivalent) in acetonitrile with a catalytic amount of antimony(V) chloride is heated to reflux until judged complete by TLC analysis. The solution is then cooled, filtered, and all volatiles are removed under reduced pressure. The residue is taken up in dichloromethane and treated with triethylamine (1 equivalent and (S)-5-aminomethyl-2-pyrrolidone (1.0 equivalent). When the reaction is judged complete by TLC analysis, the product is isolated as described in Example 1A and purified by chromatography on silica gel.

EXAMPLE 4C 4-((S)-2-Pyrrolidone-5-aminomethylsulfonyl)amino-2-phenylbenzoyl methionine methyl ester The resultant compound from Example 4A is hydrolyzed according to the procedure of Example 1B to give the title product.

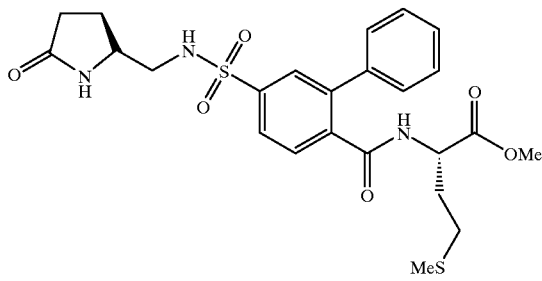

EXAMPLE 5

4-((S)-2-Pyrrolidone-5-methylaminosulfonyl)-2-phenylbenzoyl methionine

EXAMPLE 5A

4-Chlorosulfonyl-2-phenylbenzoic acid methyl ester

To a solution of methyl 4-amino-2-phenylbenzoate (1.0 equivalent) in concentrated HCl is added a solution of sodium nitrite (1.1 equivalents) until an excess of nitrous acid persists. The chlorodiazonium salt is poured into a solution of sulfur dioxide (10 equivalents), copper (II) chloride (0.5 equivalent) and KCl (1.1 equivalents) in dioxane. When TLC analysis indicated that the reaction is complete, the mixture is diluted with water and extracted into benzene which is dried and evaporated to give the title sulfonyl chloride

EXAMPLE 5B 4-((S)-2-Pyrrolidone-5-aminomethyl)sulfonyl)-2-phenylbenzoic acid methyl ester To a solution of the resultant compound from Example 5A (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 5C 4-((S)-2-Pyrrolidone-5-aminomethyl)sulfonyl)-2-phenylbenzoic acid The resultant compound from Example 5B is hydrolyzed according to the procedure of Example 1B to give the title product.

EXAMPLE 5D 4-((S)-2-Pyrrolidone-5-aminomethyl)sulfonyl)-2-phenylbenzoyl methionine methyl ester To a solution of the resultant compound from Example 5C (1.0 equivalent) in (DMF) is added 3-hydroxy-1,2,3-benzotriazin-4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 5E 4-((S)-2-Pyrrolidone-5-aminomethylcarbonyl) amino-2-phenylbenzoyl methionine methyl ester, alternate preparation To a solution of 4-amino-2-phenylbenzoyl methionine methyl ester (1.0 equivalent) in concentrated HCl is added a solution of sodium nitrite (1.1 equivalents) until an excess of nitrous acid persists at which time the chlorodiazonium salt will be treated with gaseous sulfur dioxide and copper (II) chloride to give the sulfonyl chloride (0.1 equivalent). This intermediate is reacted with (S)-5-aminomethyl-2-pyrrolidone (1.0 equivalent) and triethylamine (1.0 equivalent) according to the procedure of Example 5B to give the title compound.

EXAMPLE 5F 4-((S)-2-Pyrrolidone-5-aminomethylcarbonyl) amino-2-phenylbenzoyl methionine To a solution of the resultant compound from Example 5D (1.0 equivalent) in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

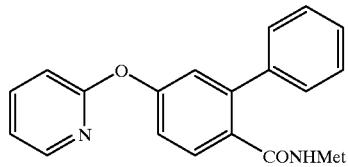

EXAMPLE 6

4-(2-pyridyloxy)-2-phenylbenzoylmethionine

EXAMPLE 6A

4-Hydroxy-2-phenylbenzoic acid methyl ester

A solution of methyl 4-amino-2-phenylbenzoate (1.0 equivalent) in dilute aqueous $H_2SO_4$ is treated with $NaNO_2$ (1.1 equivalents) until an excess of nitrous acid persists to form the diazonium salt. This salt is then diluted further with water and heated. The mixture is extracted into ethyl acetate which is dried and evaporated. The title ester is purified by chromatography on silica gel.

EXAMPLE 6B 4-(2-Pyridyloxy)-2-phenylbenzoic acid methyl ester

A solution of the resultant phenol from Example 6A (1.0 equivalent) is treated with 2-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6C 4-(2-Pyridyloxy)-2-phenylbenzoic acid

A solution of the resultant ester from Example 6B (1.0 equivalent) in aqueous methanol is treated with NaOH (2.0 equivalents) and stirred until the reaction is deemed complete by TLC analysis. The mixture is acidified, diluted with water, and extracted into ethyl acetate which is dried and evaporated. Chromatography on silica gel provides the title product.

EXAMPLE 6D 4-(2-Pyridyloxy)-2-phenylbenzoylmethionine methyl ester

The resultant product from Example 6C is coupled to methionine methyl ester according to the procedure of Example 1C to give the title compound.

EXAMPLE 6E 4-(2-Pyridyloxy)-2-phenylbenzoylmethionine methyl ester, alternate procedure A solution of 4-amino-2-phenylbenzoyl methionine methyl ester (1.0 equivalent) in dilute aqueous $H_2SO_4$ is treated with $NaNO_2$ (1.1 equivalents) until an excess of nitrous acid persists to form the diazonium salt. This salt is then diluted further with water and heated to form the phenol which is purified by chromatography on silica gel. A solution of this phenol (1.0 equivalent) is treated with 3-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6F 4-(2-pyridyloxy)-2-phenylbenzoylmethionine

The resultant compound from Example 6E is hydrolyzed according to the procedure of Example 1B to give the title compound.

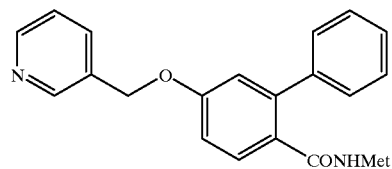

EXAMPLE 7

4-(3-pyridylmethylenoxy)-2-phenylbenzoylmethionine

The title compound is prepared as described in Example 6 with the exception that 2-bromopyridine is replaced by 3-chloromethylpyridine hydrochloride.

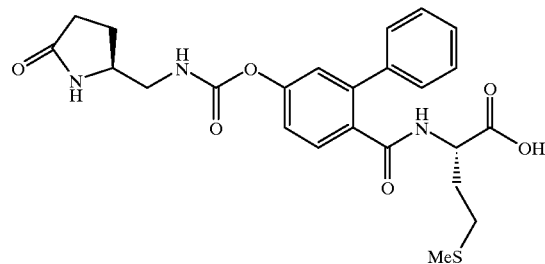

EXAMPLE 8

4-((S)-2-Pyrrolidone-5-aminomethyl)carbonyloxy-2-phenylbenzoyl methionine

EXAMPLE 8A 4-((S)-2-Pyrrolidone-5-aminomethyl)carbonyloxy-2-phenylbenzoyl methionine methyl ester To a solution of 4-hydroxy-2-phenylbenzoyl methionine methyl ester (1.0 equivalent) from Example 6E in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The chloroformate is reacted without further purification with (S)-5-aminomethyl-2-pyrrolidone (1.0 equivalent) and triethylamine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 8B 4-((S)-2-Pyrrolidone-5-aminomethyl)carbonyloxy-2-phenylbenzoyl methionine The resultant compound from Example 8A is hydrolyzed according to the procedure of Example 1B to give the title product.

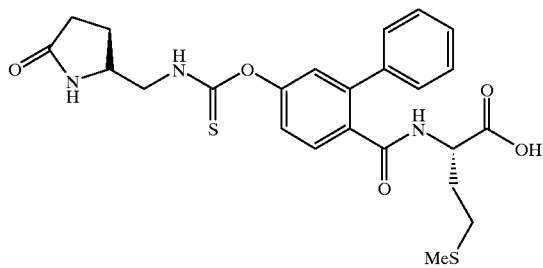

EXAMPLE 9

4-((S)-2-Pyrrolidone-5-aminomethyl)thiocarbonyloxy-2-phenylbenzoyl methionine methyl ester The title compound is prepared as described in Example 8 with the exception that phosgene in toluene is replaced by thiophosgene.

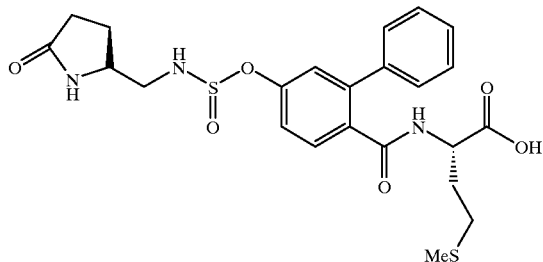

EXAMPLE 10

4-((S)-2-Pyrrolidone-5-aminomethyl)sulfinyloxy)-2-phenylbenzoyl methionine

The title compound is prepared as described in Example 8 with the exception that phosgene in toluene is replaced by thionyl chloride.

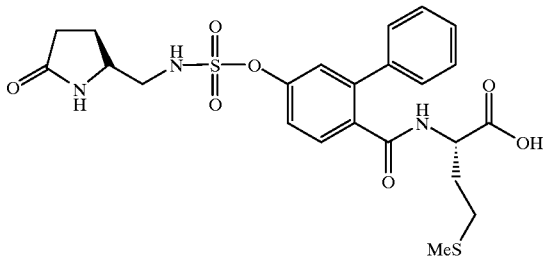

EXAMPLE 11

4-((S)-2-Pyrrolidone-5-aminomethyl)sulfonyloxy)-2-phenylbenzoyl methionine

The title compound is prepared as described in Example 8 with the exception that phosgene in toluene is replaced by sulfuryl chloride.

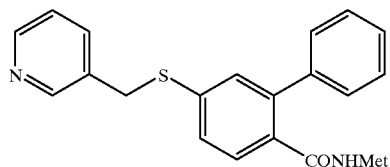

EXAMPLE 12

4-(3-Pyridylmethylenthio)-2-phenylbenzoylmethionine

EXAMPLE 12A

4-Mercapto-2-phenylbenzoic acid methyl ester

A solution of methyl 4-amino-2-phenylbenzoic acid (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel.

EXAMPLE 12B

4-(2-Pyridylmethylenthio)-2-phenylbenzoic acid methyl ester

A solution of the resultant thiophenol (1.0 equivalent) from Example 12A is treated with 2-chloromethylpyridine hydrochloride (1.0 equivalent) in the presence of a NaH (2.0 equivalents), or $K_2CO_3$ (3.0 equivalent)s in DMF or pyridine. The product is isolated by removal of the solvent and chromatography on silica gel.

EXAMPLE 12C

4-(2-Pyridylthiomethylen)-2-phenylbenzoic acid

The resultant compound from Example 12B is hydrolyzed according to the procedure of Example 6C to give the title acid.

EXAMPLE 12D

4-(2-Pyridylthiomethylen)-2-phenylbenzoylmethionine methyl ester

The resultant product from Example 12C is coupled to methionine methyl ester according to the procedure of Example 1C to give the title compound.

EXAMPLE 12E

4-(2-Pyridylthiomethylen)-2-phenylbenzoylmethionine methyl ester, alternate procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated to afford 2-phenyl-4-mercaptobenzoyl-methionine methyl ester. The thiophenol is purified by chromatography on silica gel. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12F 4-(2-Pyridylthiomethylen)-2-phenylbenzoylmethionine methyl ester, alternate procedure 2

Methyl 4-amino-2-phenylbenzoate (100 mmol) is mixed in 50% sulfuric acid, and is cooled by a ice-water bath. To the above mixture with good stirring is added slowly a cold solution of sodium nitrite (110 mmol) in water, the reaction temperature is kept under 10° C. Powdered anhydrous sodium carbonate (100 mmol) is carefully added to the cold reaction mixture in small portions, until the reaction mixture reaches pH 7 to 8. Then, the reaction mixture is added in small portions to a solution of sodium p-methoxybenzylsulfide (prepared from reaction 110 mmol of p-methoxybenzylthiol with 55 mmol of 2.0 M NaOH aqueous solution). After completion of the addition, the reaction mixture is refluxed until judged complete by TLC analysis. The reaction mixture is then extracted with ether, and the organic extracts are washed sequentially with aqueous sodium carbonate solution, water and brine, dried with anhydrous magnesium sulfate, filtered, and concentrated in vacuo. The residue is then purified by column chromatography on silica gel. The product thus obtained is dissolved in methanol and water, followed by addition of lithium hydroxide (200 mmol), and the mixture is refluxed until hydrolysis is judged complete by TLC analysis. The reaction mixture is then acidified with 6 N HCl, and extracted into ethyl acetate. The organic extracts are washed with brine, dried with anhydrous sodium sulfate, and concentrated in vacuo. The crude product obtained is redissolved in methylene chloride, followed by addition of 1-(3-dimethylaminopropyl)-3-ethylcarbodiimide (1.1 equivalent) and 1-hydroxybenzotriazol (1.2 equivalent). The reaction is stirred until it is judged complete by TLC analysis, and then is diluted with ether. The mixture is washed with water, brine, dried over anhydrous magnesium sulfate, filtered, and concentrated in vacuo. The residue is then purified by column chromatography on silica gel. The resulting product is dissolved in trifluoroacetic acid and anisole (1.5 equivalent), and mercury diacetate (1.2 equivalent) is added. After TLC shows no starting material left, the reaction mixture is diluted with ether, washed with water, brine, dried over anhydrous magnesium sulfate, filtered, and concentrated in vacuo. The resulting crude material is purified by column chromatography to afford 2-phenyl-4-mercaptobenzoyl-methionine methyl ester. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12G 4-(3-Pyridylthiomethylen)-2-phenylbenzoylmethionine

The resultant compound from Example 12D is hydrolyzed according to the procedure of Example 1B to give the title product.

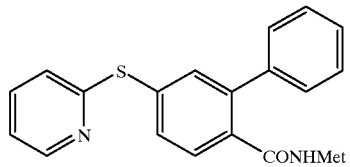

EXAMPLE 13

4-(2-Pyridylthio)-2-phenylbenzoylmethionine

EXAMPLE 13A

4-Fluoro-2-phenyl benzoic acid methyl ester

A solution of methyl 4-amino-2-phenylbenzoate (1.0 equivalent) in dilute aqueous $HBF_4$ is treated with $NaNO_2$ (1.1 equivalents) until an excess of nitrous acid persists. The mixture is extracted into ethyl acetate which is dried and evaporated. The title ester is purified by chromatography on silica gel.

EXAMPLE 13B

4-Fluoro-2-phenyl benzoic acid

The resultant compound from Example 13A is hydrolyzed according to the procedure of Example 6C to give the title acid.

EXAMPLE 13C

4-Fluoro-2-phenyl benzoyl methionine methyl ester

The resultant product from Example 13B is coupled to methionine methyl ester according to the procedure of Example 1C to give the title compound.

EXAMPLE 13D 4-(2-Pyridylthio)-2-phenyl benzoyl methionine methyl ester

A mixture of the resultant fluorobenzoate from Example 13C (1.0 equivalent) and 2-mercaptopyridine (1.0 equivalent) is treated with $K_2CO_3$ (2.0 equivalents) or NaH (1.0 equivalent) in DMF or DMSO and is stirred until the reaction is judged complete by TLC analysis. The mixture is diluted with water and extracted into ethyl acetate which is dried and evaporated. Chromatography of the residue on silica gel affords the title compound.

EXAMPLE 13E 4-(2-Pyridylthio)-2-phenyl benzoyl methionine methyl ester, alternate procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel. A solution of this thiophenol (1.0 equivalent) is treated with 2-bromopyridine hydrobromide (1.0 equivalent) in the presence of a NaH (2.0 equivalent), or $K_2CO_3$ (3.0 equivalent)s in DMF or pyridine. The product is isolated by removal of the solvent and chromatography on silica gel.

EXAMPLE 13F 4-(2-Pyridylthio)-2-phenyl benzoyl methionine methyl ester, alternate procedure 2

A solution of the resultant thiophenol from Example 12A (1.0 equivalent) is treated with 2-bromopyridine hydrobromide (1.0 equivalent) in the presence of a NaH (2.0 equivalents), or $K_2CO_3$ (3.0 equivalents) in DMF or pyridine. The product is isolated by removal of the solvent and chromatography on silica gel. The resultant ester is hydrolyzed according to the procedure of Example 6C and then is coupled to methionine methyl ester according to the procedure of Example 1C to give the title compound.

EXAMPLE 13G 4-(2-Pyridylthio)-2-phenylbenzoylmethionine

The resultant compound from Example 13D is hydrolyzed according to the procedure of Example 1B to give the title product.

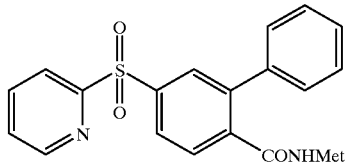

EXAMPLE 14

4-(2-Pyridylsulfonyl)-2-phenylbenzoylmethionine

EXAMPLE 14A 4-(2-Pyridylsulfonyl)-2-phenylbenzoic acid methyl ester

A solution of 4-(2-pyridylthio)-2-phenylbenzoic acid methyl ester (Example 13F) is carefully treated with two equivalents of meta-chloroperbenzoic acid in methylene chloride at low temperature and the reaction is then quenched with aqueous $Na_2SO_3$ when judged complete by TLC analysis. The layers are separated and the organic phase is extracted with aqueous $NaHCO_3$ to remove the m-chlorobenzoic acid. The product is isolated by removal of the solvent and is purified by chromatography on silica gel.

EXAMPLE 14B 4-(2-Pyridylsulfonyl)-2-phenylbenzoic acid

The resultant compound from Example 14A is hydrolyzed according to the procedure of Example 6C to give the title acid.

EXAMPLE 14C 4-(2-pyridylsulfonyl)-2-phenylbenzoylmethionine methyl ester

The resultant product from Example 14B is coupled to methionine methyl ester according to the procedure of Example 1C to give the title compound.

EXAMPLE 14D 4-(2-Pyridylsulfonyl)-2-phenylbenzoylmethionine

The resultant compound from Example 14C is hydrolyzed according to the procedure of Example 1B to give the title product.

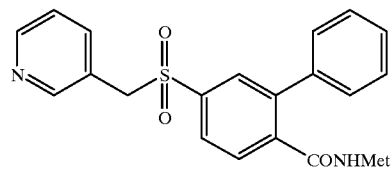

EXAMPLE 15

4-(3-Pyridylthiomethylen)-2-phenylbenzoylmethionine

The title compound is prepared from the resultant product of Example 12B using the procedures from Example 14.

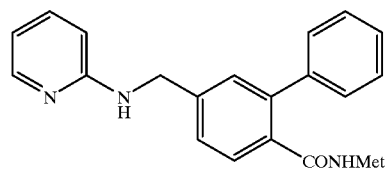

EXAMPLE 16

4-[(2-Aminopyridyl)methylene]-2-phenylbenzoylmethionine

EXAMPLE 16A

2-Phenylterephthalic acid mono methyl ester

A solution of 4-bromo-2-phenylbenzoic acid methyl ester (1.0 equivalent), $Pd(OAc)_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 16B 4-(Hydroxymethyl)-2-phenylbenzoic acid methyl ester

The resultant acid from Example 16A (1.0 equivalent) is treated with a slight excess of N-methylmorpholine (1.1 equivalent) and isobutylchloroformate (1.0 equivalent) in THF at 0° C. The mixture is then treated with $NaBH_4$ (1.0 equivalent) and aqueous $NaHCO_3$ and stirred at 0° C. until the reaction is judged complete by TLC analysis. The mixture is poured into dilute aqueous acid and extracted into ethyl acetate which is dried and evaporated. The product is purified by chromatography on silica gel.

EXAMPLE 16C 4-(Hydroxymethyl)-2-phenylbenzoic acid

The resultant compound from Example 16B is hydrolyzed according to the procedure of EXAMPLE 6C to give the title acid.

EXAMPLE 16D 4-(Hydroxymethyl)-2-phenylbenzoyl methionine methyl ester

The resultant product from Example 16C is coupled to methionine methyl ester according to the procedure of Example 1C to give the title compound.

EXAMPLE 16E 4-formyl-2-phenylbenzoyl methionine methyl ester

A mixture of the resultant alcohol from Example 16D (1.0 equivalent), N-methylmorpholine-N-oxide (1.5 equivalents), molecular sieves, and a catalytic amount of TPAP is stirred in a $CH_2Cl_2$/acetonitrile mixture until the reaction is judged complete by TLC analysis. The mixture is diluted with ethyl ether and filtered through $SiO_2$. The product is purified by chromatography on silica gel.

EXAMPLE 16F 4-(formyl)-2-phenylbenzoyl methionine methyl ester, alternate procedure A mixture of (2-phenyl-4-bromobenzoyl) methionine methyl ester (100 mmol), 4,4,6-trimethyl-2-vinyl-1,3,2-dioxaborinane (100 mmol), tetrakis(triphenylphosphine) palladium (0) (3 mmol) in toluene and 2 M sodium carbonate in water (100 mL) is heated at 80° C. until the starting methyl ester disappears. The resulting mixture is extracted with ether, and washed with water, brine, dried over anhydrous magnesium sulfate, filtered, and concentrated in vacuo. The residue is then purified by column chromatography on silica gel. To a solution of the resulting vinyl compound in dioxane/water (4/1) is added osmium tetraoxide (0.03 equivalent), N-methylmorpholine N-oxide (3 equivalents), and the reaction is stirred at 25° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16G 4-(Hydroxymethyl)-2-phenylbenzoyl methionine methyl ester, alternate procedure To a solution of the resultant compound from Example 16E in ethanol at 0° C. is added sodium borohydride (0.5 equivalent), and the reaction is stirred at 0° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16H

4-[(2-Aminopyridyl)methylene]-2-phenylbenzoylmethionine methyl ester

A mixture of the resultant aldehyde from Example 16E (1.0 equivalent), 2-aminopyridine (1.0 equivalent) and NaCNBH$_3$ (1.5 equivalents) in methanol/acetic acid is stirred until the reaction is judged complete by TLC analysis. The mixture is poured into aqueous $NaHCO_3$ and extracted into ethyl acetate which is dried and evaporated. Chromatography of the residue on silica gel affords the title compound.

EXAMPLE 16I

4-[(2-Aminopyridyl)methylene]-2-phenylbenzoylmethionine

The resultant compound from Example 16H is hydrolyzed according to the procedure of Example 1B to give the title product.

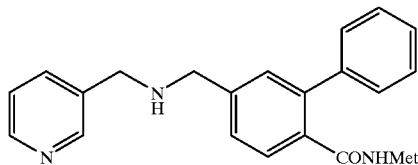

EXAMPLE 17

4-[(3-aminomethylpyridyl)methylene]-2-phenylbenzoylmethionine

Using the procedures of Examples 16F–G and replacing 2-aminopyridine with 3-aminomethylpyridine affords the title product.

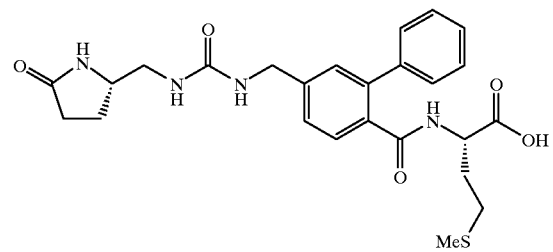

EXAMPLE 18

4-((S)-2-Pyrrolidone-5-aminomethylcarbonyl) aminomethyl-2-phenylbenzoyl methionine

EXAMPLE 18A 4-(Azidomethyl)-2-phenylbenzoyl methionine methyl ester

To triphenylphosphine (1.0 equivalent) in tetrahydrofuran (THF) at −78° C. is added diethyl azodicarboxylate (1.0 equivalent) in THF. To this mixture is added a solution of hydrazoic acid in benzene (2.0 equivalents) and then the resultant compound from Example 16D (1.0 equivalent). After one hour the mixture was warmed to room temperature, stirred until the reaction is judged complete by TLC analysis, evaporated and chromatographed on silica gel to afford the title product.

EXAMPLE 18B 4-(Aminomethyl)-2-phenylbenzoyl methionine methyl ester

To the resultant compound from Example 18A in methanol is added triethylamine (3.0 equivalent) and propane 1,3-dithiol (3.0 equivalents). After the reaction is judged complete by TLC analysis, the mixture is filtered and evaporated. Chromatography of the residue on silica gel provides the title product.

EXAMPLE 18C 4-((S)-2-Pyrrolidone-5-aminomethylcarbonyl) aminomethyl-2-phenylbenzoyl methionine methyl ester To a solution of the resultant compound from Example 18B (1.0 equivalent) in methylene chloride is added triphosgene (0.33 equivalent) and triethyl amine (2.0 equivalents). This intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 18D 4-((S)-2-Pyrrolidone-5-aminomethylcarbonyl) aminomethyl-2-phenylbenzoyl methionine The resultant compound from Example 18C is hydrolyzed according to the procedure of Example 1B to give the title product.

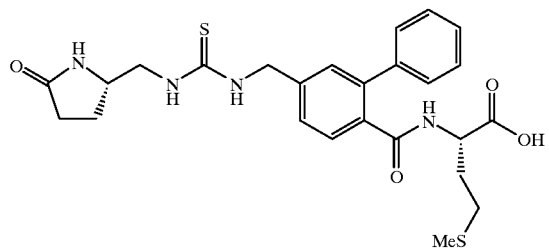

EXAMPLE 19

4-((S)-2-Pyrrolidone-5-aminomethylthiocarbonyl) aminomethyl-2-phenylbenzoyl methionine The title compound is prepared as described in Example 18 with the exception that triphosgene (0.33 equivalent) is replaced by thiophosgene (1.0 equivalent).

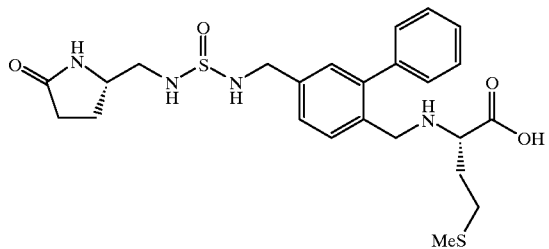

EXAMPLE 20

4-((S)-2-Pyrrolidone-5-aminomethylsulfinyl) aminomethyl-2-phenylbenzoyl methionine The title compound is prepared as described in Example 18 with the exception that triphosgene (0.33 equivalent) is replaced by thionyl chloride (1.0 equivalent).

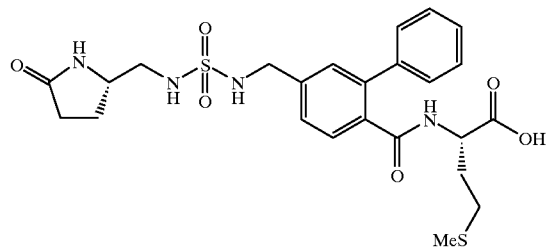

EXAMPLE 21

4-((S)-2-Pyrrolidone-5-aminomethylsulfonyl) aminomethyl-2-phenylbenzoyl methionine Using the Procedure of Example 4 with the resultant compound from Example 18B affords the title product.

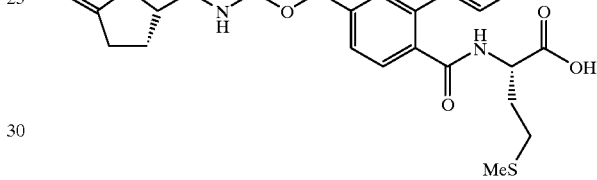

EXAMPLE 22

4-((S)-2-Pyrrolidone-5-aminomethyl) carbonyloxymethylene)-2-phenylbenzoyl methionine Using the procedure of Example 8 with the resultant compound from Example 16D provides the title product.

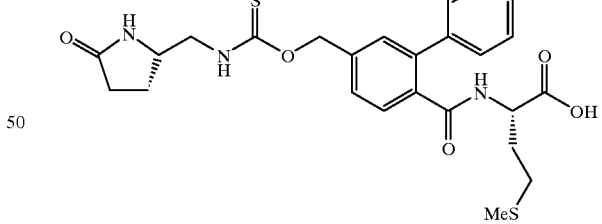

EXAMPLE 23

4-((S)-2-Pyrrolidone-5-aminomethyl) thiocarbonyloxymethylene)-2-phenylbenzoyl methionine Using the procedure of Example 8 with the resultant compound from Example 16D and replacing triphosgene (0.33 equivalent) with thiophosgene (1.0 equivalent) provides the title product.

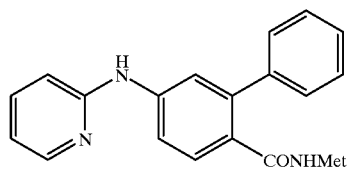

EXAMPLE 24

4-(2-Aminopyridyl)-2-phenylbenzoylmethionine

EXAMPLE 24A 4-(2-Aminopyridyl)-2-phenylbenzoylmethionine methyl ester

4-Amino-2-phenylbenzoyl methionine (1.0 equivalent) methyl ester and 2-bromopyridine hydrobromide (1.0 equivalent) in pyridine are heated until the reaction is judged complete by TLC analysis. The solvent is evaporated and the residue is taken up in ethyl acetate which is washed with water and brine, dried, and evaporated. Chromatography on silica gel affords the title product.

EXAMPLE 24B 4-(2-Aminopyridyl)-2-phenylbenzoylmethionine

The resultant compound from Example 24A is hydrolyzed according to the procedure of Example 1B to give the title product.

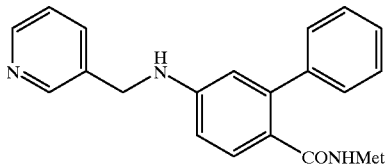

EXAMPLE 25

4-(3-Aminomethylpyridyl)-2-phenylbenzoylmethionine

EXAMPLE 25A 4-(3-Aminomethylpyridyl)-2-phenylbenzoylmethionine methyl ester

A mixture of 3-pyridinecarboxaldehyde (1.0 equivalent), 4-amino-2-phenylbenzoyl methionine methyl ester (1.0 equivalent) and NaCNBH$_3$ (1.0 equivalent) in methanol/acetic acid is stirred until the reaction is judged complete by TLC analysis. The mixture is poured into aqueous NaHCO$_3$ and extracted into ethyl acetate which is dried and evaporated. Chromatography of the residue on silica gel affords the title compound.

EXAMPLE 25B 4-(3-Aminomethylpyridyl)-2-phenylbenzoylmethionine

The resultant compound from Example 25A is hydrolyzed according to the procedure of Example 1B to give the title product.

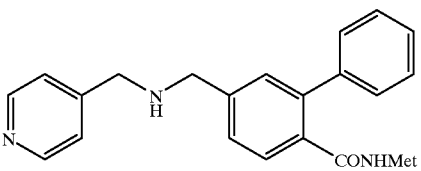

EXAMPLE 26

4-[(4-aminomethylpyridyl)methylene]-2-phenylbenzoylmethionine

Using the procedures of Examples 25 with the resultant amine from Example 18B and 3-pyridinecarboxaldehyde affords the title product.

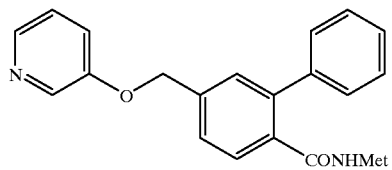

EXAMPLE 27

4-(3-Pyridyloxymethylene)-2-phenylbenzoylmethionine

EXAMPLE 27A 4-(p-Toluenesulfonyloxy)-2-phenylbenzoylmethionine methyl ester

The resultant compound from Example 16D (1.0 equivalent) and p-toluenesulfonyl chloride (1.0 equivalent) in pyridine are stirred until the reaction is judged complete by TLC analysis. The solvent is evaporated and the residue is taken up in ethyl acetate which is washed with water and brine, dried, and evaporated. Chromatography on silica gel affords the title product.

EXAMPLE 27B 4-(3-Pyridyloxymethylene)-2-phenylbenzoylmethionine methyl ester 3-Hydroxypyridine (1.0 equivalent) is treated with sodium hydride (1.0 equivalent) in DMSO, then the resultant compound from Example 27A (1.0 equivalent) is added. When judged complete by TLC analysis, the reaction is diluted with water and ethyl acetate, the organic layer is dried and concentrated, and the crude title compound is purified by chromatography on silica gel.

EXAMPLE 27C 4-(3-Pyridyloxymethylene)-2-phenylbenzoylmethionine

The resultant compound from Example 27B is hydrolyzed according to the procedure of Example 1B to give the title product.

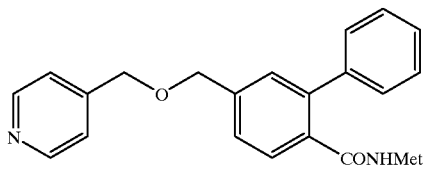

EXAMPLE 28

4-(3-Pyridylmethoxymethylene)-2-phenylbenzoylmethionine

EXAMPLE 28A

4-(3-Pyridylmethoxymethylene)-2-phenylbenzoylmethionine methyl ester

Using the procedure of Example 27B but replacing 3-hydroxypyridine with 3-hydroxymethylpyridine affords the title compound.

EXAMPLE 28B

4-(3-Pyridylmethoxymethylene)-2-phenylbenzoylmethionine methyl ester, alternate procedure The resultant compound from Example 16D (1.0 equivalent) is treated with sodium hydride (2.0 equivalents) in DMSO, then 3-chloromethylpyridine hydrochloride (1.0 equivalent) is added. When judged complete by TLC analysis, the reaction is diluted with water and ethyl acetate, the organic layer is dried and concentrated, and the crude title compound is purified by chromatography on silica gel.

EXAMPLE 28C

4-(3-Pyridylmethoxymethylene)-2-phenylbenzoylmethionine methyl ester

The resultant compound from Example 28A is hydrolyzed according to the procedure of Example 1B to give the title product.

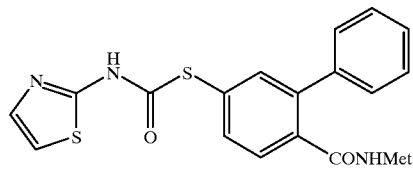

EXAMPLE 29

{2-Phenyl-4-[(thiazol-2-ylamino)carbonylthio]benzoyl}-methionine

EXAMPLE 29A

Thiazol-2-ylisocyanate

A solution of 2-aminothiazol (1.0 mmol), triphosgene (0.34 mmol) and triethylamine (1.0 mmol) in toluene (10 mL) is refluxed until TLC shows no starting amine left. The solvent is then removed in vacuo, and the resulting material is used without further purification.

EXAMPLE 29B

{2-Phenyl-4-[(thiazol-2-ylamino)carbonylthio]benzoyl}-methionine methyl ester A solution of 2-phenyl-4-mercaptobenzoyl-methionine methyl ester from example 12E or 12F (1.0 mmol) and the isocyanate prepared in example 29A (1.0 mmol) in THF is refluxed until TLC shows no thiol left. The solvent is then evaporated in vacuo, and the residue is purified by column chromatography on silica gel to give the title compound.

EXAMPLE 29C

{2-Phenyl-4-[(thiazol-2-ylamino)carbonylthio]benzoyl}-methionine methyl ester, alternate procedure To a solution of 2-phenyl-4-mercaptobenzoyl-methionine methyl ester from example 12E or 12F (1 equivalent) in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The thiochloroformate is reacted without further purification with 2-aminothiazol (1.0 equivalent) and triethylamine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 29D

{2-Phenyl-4-[(thiazol-2-ylamino)carbonylthio]benzoyl}-methionine

The resultant compound from Example 29B is hydrolyzed according to the procedure of Example 1B to give the title product.

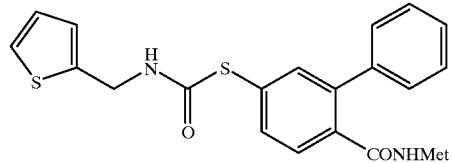

EXAMPLE 30

{2-Phenyl-4-[(thien-2-ylmethylamino)carbonylthio]benzoyl}-methionine

Using the procedure of Example 29 but replacing 2-aminothiazol with thien-2-ylmethylamine affords the title product.

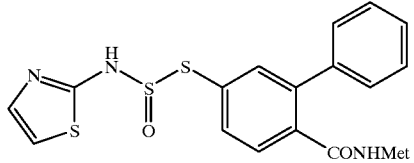

EXAMPLE 31

{2-Phenyl-4-[(thiazol-2-ylamino)thionylthio]benzoyl}-methionine

EXAMPLE 31A

N-Thionyl)thiazol-2-ylamine

A solution of 2-aminothiazol (1.0 mmol), in thionyl chloride is heated at reflux until the reaction is judged to be complete by TLC analysis. Then, the excess thionylchloride is distilled out in vacuo. The resulting material is used without further purification.

EXAMPLE 31B

{2-Phenyl-4-[(thiazol-2-ylamino)thionylthio]benzoyl}-methionine methyl ester

Using the procedure of Example 29B but replacing the resultant product from Example 29A with the resultant product from Example 31A affords the title compound.

EXAMPLE 31C

{2-Phenyl-4-[(thiazol-2-ylamino)thionylthio]benzoyl}-methionine methyl ester, alternate procedure Using the procedure of Example 29C but replacing phosgene in toluene with thionyl chloride affords the title compound.

EXAMPLE 31D

{2-Phenyl-4-[(thiazol-2-ylamino)thionylthio]benzoyl}-methionine

The resultant compound from Example 31B is hydrolyzed according to the procedure of Example 1B to give the title product.

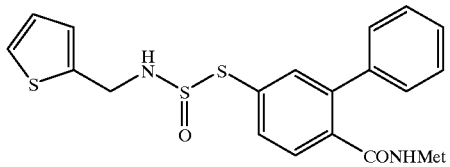

EXAMPLE 32

{2-Phenyl-4-[(thien-2-ylmethylamino)thionylthio]benzoyl}-methionine

Using the procedure of Example 31 but replacing 2-aminothiazol with thien-2-ylmethylamine affords the title product.

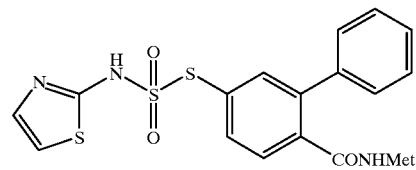

EXAMPLE 33

{2-Phenyl-4-[(thiazol-2-ylamino)sulfonylthio]benzoyl}-methionine methyl ester

Using the procedure of Example 31 but replacing thionyl chloride with sulfuryl chloride affords the title product.

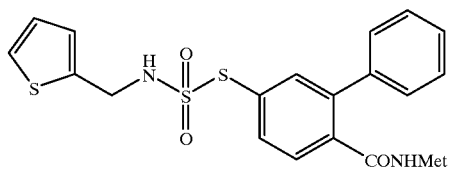

EXAMPLE 34

{2-Phenyl-4-[(thien-2-ylmethylamino)sulfonylthio]benzoyl}-methionine

Using the procedure of Example 31 but replacing 2-aminothiazol with thien-2-ylmethylamine and replacing thionyl chloride with sulfuryl chloride affords the title product.

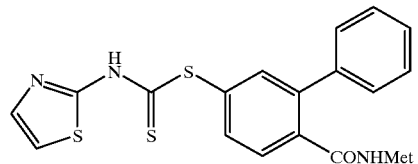

EXAMPLE 35

{2-Phenyl-4-[(thiazol-2-ylamino)thiocarbonylthio]benzoyl}-methionine

Using the procedure of Example 29 and replacing triphosgene (0.34 mmol) or a solution of phosgene in toluene (1.0 equivalent) with thiophosgene (1.0 mmol) affords the title product.

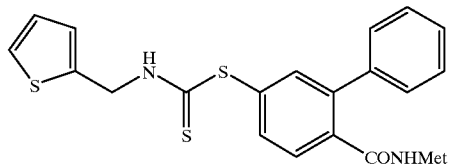

EXAMPLE 36

{2-Phenyl-4-[(thien-2-ylmethylamino)thiocarbonylthio]benzoyl}-methionine

Using the procedure of Example 29 and replacing triphosgene (0.34 mmol) or a solution of phosgene in toluene (1.0 equivalent) with thiophosgene (1.0 mmol) and replacing 2-aminothiazol with thien-2-ylmethylamine affords the title product.

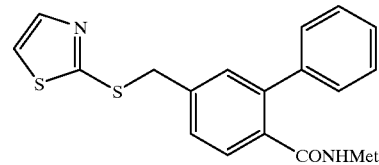

EXAMPLE 37

{2-Phenyl-4-[(thiazol-2-yl)thiomethyl]benzoyl}-methionine

EXAMPLE 37A

{2-Phenyl-4-[(thiomethyl]benzoyl}-methyl ester

The resultant product from Example 27A is dissolved DMF/water (2/1), and sodium hydrosulfide (5 equivalent) is added to the reaction mixture. The reaction is stirred until TLC analysis shows that the reaction is complete. Then, the reaction mixture is acidified with 3 N HCl to about pH 4, extracted with ether, and washed with water and brine, dried over anhydrous magnesium sulfate, filtered, and concentrated in vacuo. The residue is purified with column chromatography on silica gel to give the title compound.

EXAMPLE 37B

{2-Phenyl-4-[thiomethyl]benzoyl}-methionine methyl ester, alternate procedure

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16D (1. equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 37C

{12-Phenyl-4-[(thiazol-2-yl)thiomethyl]benzoyl}-methyl ester

A mixture of the resultant thiol from Example 37A (1 mmol), 2-bromothiazole (1.5 mmol), and anhydrous potassium carbonate (5 mmol) in DMF is stirred at 100° C. until TLC analysis shows that the starting thiol disappeared. Then, the reaction mixture is diluted with water, extracted with ether, and washed with water and brine, dried over anhydrous magnesium sulfate, filtered, and concentrated in vacuo. The residue is purified by column chromatography on silica gel to give the title compound.

{2-Phenyl-4-[(thiazol-2-yl)thiomethyl]benzoyl}-methionine

The resultant compound from Example 37C is hydrolyzed according to the procedure of Example 1B to give the title product.

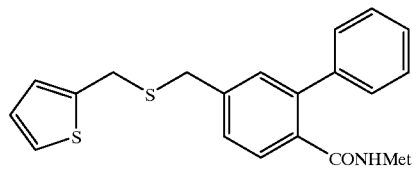

EXAMPLE 38

{2-Phenyl-4-[(thien-2-ylmethyl)thiomethyl]benzoyl}-methionine

Using the procedure of Example 37 and replacing 2-bromothiazole with 2-bromomethylthiophene affords the title product.

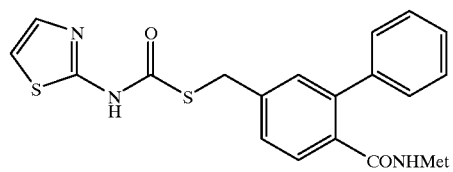

EXAMPLE 39

{2-Phenyl-4-[(thiazol-2-ylamino)carbonylthiomethyl]benzoyl}-methionine

Using the procedure of Example 29 with the resultant product from Example 37A affords the title product.

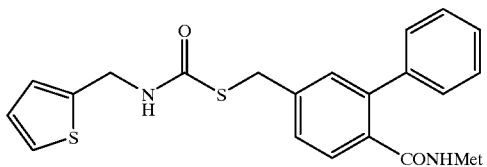

EXAMPLE 40

{2-Phenyl-4-[(thiazol-2-ylamino)carbonylthiomethyl]benzoyl}-methionine

Using the procedure of Example 29 with the resultant product from Example 37A and replacing 2-aminothiazol with thien-2-ylmethylamine affords the title product.

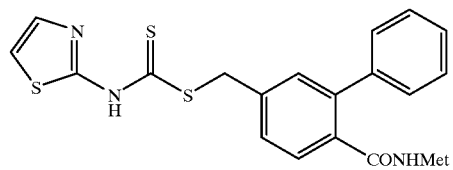

EXAMPLE 41

{2-Phenyl-4-[(thiazol-2-ylamino)thiocarbonylthiomethyl]benzoyl}-methionine

Using the procedure of Example 29 with the resultant product from Example 37A and replacing triphosgene (0.34 mmol) or a solution of phosgene in toluene (1.0 equivalent) with thiophosgene (1.0 mmol) affords the title product.

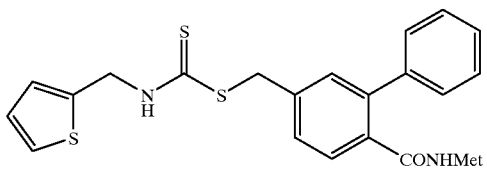

EXAMPLE 42

{2-Phenyl-4-[(thiazol-2-ylamino)thiocarbonylthiomethyl]benzoyl}-methionine

Using the procedure of Example 29 with the resultant product from Example 37A, replacing triphosgene (0.34 mmol) or a solution of phosgene in toluene (1.0 equivalent) with thiophosgene (1.0 mmol), and replacing 2-aminothiazol with thien-2-ylmethylamine affords the title product.

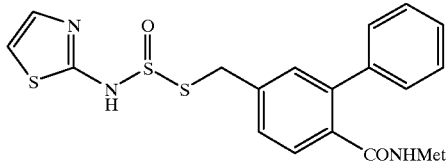

EXAMPLE 43

{2-Phenyl-4-[(thiazol-2-ylamino)thionylthiomethyl]benzoyl}-methionine

Using the procedure of Example 31 with the resultant product from Example 37A affords the title product.

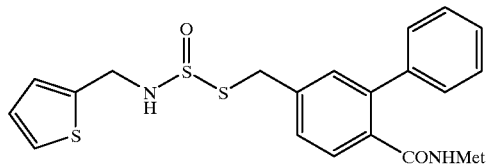

EXAMPLE 44

{2-Phenyl-4-[(thien-2-ylmethylamino)thionylthiomethyl]benzoyl}-methionine

Using the procedure of Example 31 with the resultant product from Example 37A and replacing 2-aminothiazol with thien-2-ylmethylamine affords the title product.

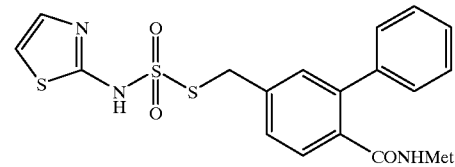

EXAMPLE 45

{2-Phenyl-4-[(thiazol-2-ylamino)sulfonylthiomethyl]benzoyl}-methionine

Using the procedure of Example 31 with the resultant product from Example 37A and replacing thionyl chloride with sulfuryl chloride affords the title product. affords the title product.

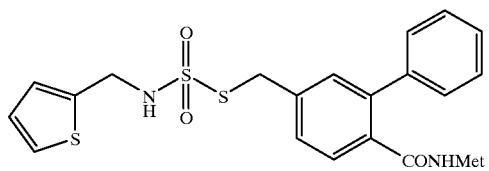

EXAMPLE 46

{2-Phenyl-4-[(thien-2-ylmethylamino)sulfonylthiomethyl]benzoyl}-methionine

Using the procedure of Example 31 with the resultant product from Example 37A, replacing thionyl chloride with sulfuryl chloride, and replacing 2-aminothiazol with thien-2-ylmethylamine affords the title product.

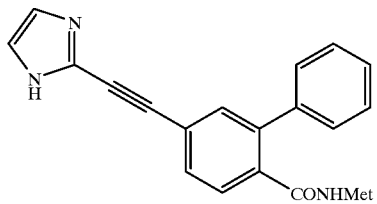

EXAMPLE 47

{4-[2-(Imidazol-2-yl)ethynyl]-2-phenylbenzoyl}methionine

EXAMPLE 47A

4-Ethynyl-2-phenylbenzoyl)methionine methyl ester

A mixture of (2-phenyl-4-bromobenzoyl)-methionine methyl ester (100 mmol), diethylamine (300 mmol), trimethylsilylacetylene (110 mmol), bis(triphenylphosphine) palladium diacetate (5 mmol) and copper (I) iodide (3 mmol) in toluene is heated at 60° C. until TLC analysis indicates the starting methyl ester has disappeared. The reaction mixture is concentrated in vacuo, redissolved in ether, filtered through silica gel, and concentrated. The residue is then dissolved in THF, and is treated with tetrabutylammonium fluoride (120 mmol). After TLC analysis indicates that no starting material is left, the reaction mixture is diluted with ether, washed with water and brine, dried over anhydrous magnesium sulfate, filtered, and concentrated in vacuo. The residue is then purified with column chromatography on silica gel to give the title product.

EXAMPLE 47B

{4-[2-(Imidazol-2-yl)ethynyl]-2-phenylbenzoyl}-methionine methyl ester

The resultant product from Example 47A (5 mmol) is mixed with 4-bromoimidazole (5 mmol), diethylamine (1 mL), bis(triphenylphosphine) palladium diacetate (0.1 mmol) and copper (I) iodide (0.1 mmol) in toluene. The mixture is stirred at 25° C. until TLC analysis indicates the reaction is complete. The reaction mixture is concentrated in vacuo, and the residue is purified with column chromatography on silica gel to give the title product.

EXAMPLE 47C

{4-[2-(Imidazol-2-yl)ethynyl]-2-phenylbenzoyl}-methionine

The resultant compound from Example 47B is hydrolyzed according to the procedure of Example 1B to give the title product.

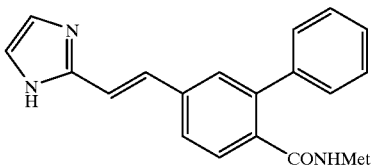

EXAMPLE 48

{4-[2-(Imidazol-4-yl)ethenyl]-2-phenylbenzoyl}-methionine

The resultant acetylene (3 mmol) from Example 47 is mixed with Lindlar catalyst (50 mg), 5 drops of quinoline in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

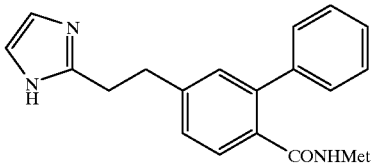

EXAMPLE 49

{4-[2-(Imidazol-4-yl)ethyl]-2-phenylbenzoyl}-methionine

The resultant olefin (1 mmol) from Example 48 is mixed with 5% palladium on carbon (100 mg) in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

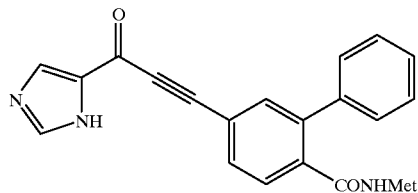

EXAMPLE 50

{4-[2-(Imidazol-4-ylcarbonyl)ethynyl]-2-phenylbenzoyl}-methionine

EXAMPLE 50A

{4-[2-(Imidazol-4-ylcarbonyl)ethynyl]-2-phenylbenzoyl}-methionine methyl ester

A stainless autoclave containing the resultant product from Example 47A (5 mmol), 4-bromoimidazole (5 mmol), 1,1'-bis(diphenylphosphine)-ferrocenepalladium dichloride (0.1 mmol), and triethylamine (10 mL) is flushed with nitrogen, and pressurized to 20 atm with carbon monoxide. The reaction mixture is stirred at 120° C. until judged complete by TLC analysis. After cooling, the triethylamine is evaporated in vacuo, and the residue is purified by column chromatography on silica gel to give the title compound.

EXAMPLE 50B

{4-[2-(Imidazol-4-ylcarbonyl)ethynyl]-2-phenylbenzoyl}-methionine

The resultant compound from Example 50A is hydrolyzed according to the procedure of Example 1B to give the title product.

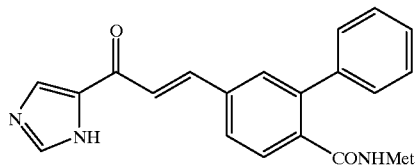

EXAMPLE 51

{4-[2-(Imidazol-4-ylcarbonyl)ethenyl]-2-phenylbanzoyl}-methionine

Using the procedure of Example 48 with the resultant compound from Example 50 affords the title product.

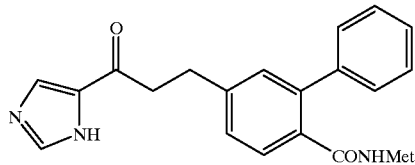

EXAMPLE 52

{4-[2-(Imidazol-4-ylcarbonyl)ethyl]-2-phenylbenzoyl}-methionine

Using the procedure of Example 49 with the resultant compound from Example 51 affords the title product.

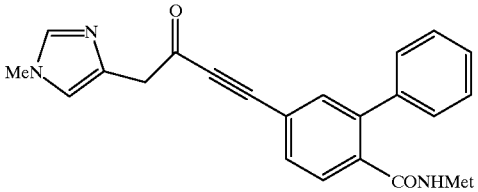

EXAMPLE 53

{4-[4-(1-Methylimidazol-4-yl)-3-keto-1-butynyl]-2-phenylbenzoyl}methionine

EXAMPLE 53A

{4-[4-(1-Methylimidazol-4-yl)-3-keto-1-butynyl]-2-phenylbenzoyl}-methionine methyl ester To a solution of 1-methyl-4-imidazoleacetic acid (5 mmol) in methylene chloride at 0° C. is added oxalyl chloride (6 mmol) and DMF (0.05 mmol). After 30 minute, the solvent is evaporated in vacuo. The residue is redissolved in dichloromethane, followed by the addition of the resultant acetylene from Example 47A (5 mmol), triethylamine (10 mmol), and copper (I) iodide (1 mmol). The reaction is stirred at 25° C. until TLC analysis indicates no starting material is left in the reaction mixture. The reaction is diluted with ether, washed with water and brine, dried over anhydrous magnesium sulfate, filtered, and concentrated in vacuo. The residue is then purified by column chromatography on silica gel to give the title compound.

EXAMPLE 53B

{4-[4-(1-Methylimidazol-4-yl)-3-keto-1-butynyl]-2-phenylbenzoyl}-methionine

The resultant compound from Example 53A is hydrolyzed according to the procedure of Example 1B to give the title product.

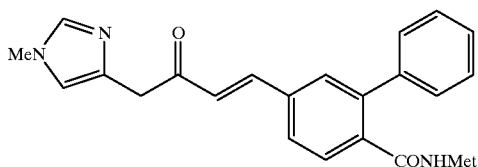

EXAMPLE 54

{4-[4-(1-Methylimidazol-4-yl)-3-keto-1-butenyl]-2-phenylbenzoyl}-methionine

Using the procedure of Example 48 with the resultant compound from Example 53 affords the title product.

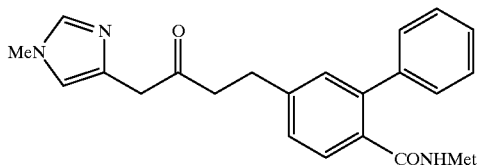

EXAMPLE 55

{4-[4-(1-Methylimidazol-4-yl)-3-keto-1-butyl]-2-phenylbenzoyl}-methionine

Using the procedure of Example 49 with the resultant compound from Example 53 affords the title product.

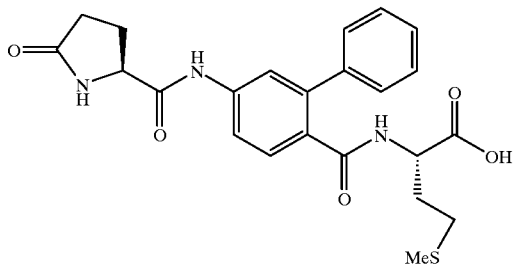

EXAMPLE 56

(S) Pyroglutamyl-(4-amino-2-phenyl)benzoyl methionine

EXAMPLE 56A (S) Pyroglutamyl-(4-amino-2-phenyl)benzoyl methionine methyl ester To a solution of 4-amino-2-phenylbenzoyl methionine methyl ester (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 56B (S) Pyroglutamyl-(4-amino-2-phenyl)benzoyl methionine

The resultant compound from Example 56A is hydrolyzed according to the procedure of Example 1B to give the title product.

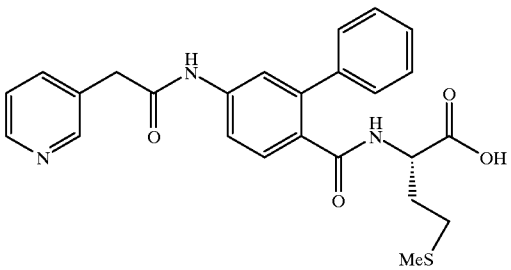

EXAMPLE 57

(S) Pyroglutamyl-(4-amino-2-phenyl)benzoyl methionine

Using the procedure of Example 56 and replacing pyroglutamic acid with 3-pyridylacetic acid affords the title product.

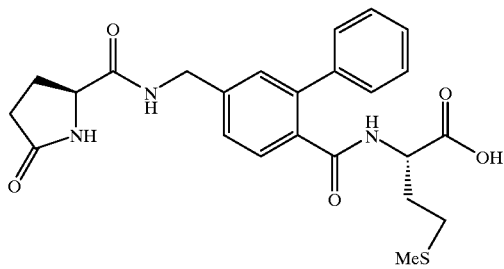

EXAMPLE 58

(S) Pyroglutamyl-(4-aminomethyl-2-phenyl)benzoyl methionine

EXAMPLE 58A (S) Pyroglutamyl-(4-aminomethyl-2-phenyl)benzoyl methionine methyl ester To a solution of the resultant amine from Example 18B (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 58B (S) Pyroglutamyl-(4-aminomethyl-2-phenyl)benzoyl methionine

The resultant compound from Example 58A is hydrolyzed according to the procedure of Example 1B to give the title product.

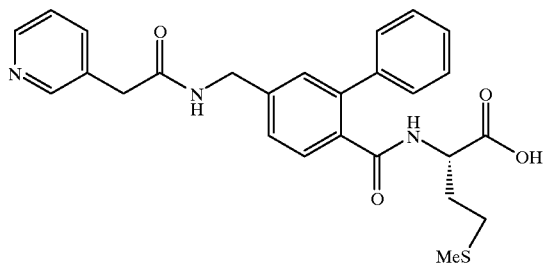

EXAMPLE 59 naming error(S) Pyroglutamyl-(4-aminomethyl-2-phenyl)benzoyl methionine

Using the procedure of Example 58 and replacing pyroglutamic acid with 3-pyridylacetic acid affords the title product.

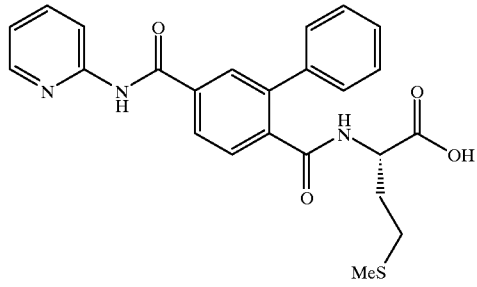

EXAMPLE 60

4-[(Pyridin-2-ylamino)carbonyl]-2-phenylbenzoyl methionine

EXAMPLE 60A

4-Carboxy-2-phenylbenzoyl methionine methyl ester

A solution of 4-bromo-2-phenylbenzoyl methionine methyl ester (1.0 equivalent), Pd(OAc)$_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 60B

4-[(Pyridin-2-ylamino)carbonyl]-2-phenylbenzoyl methionine methyl ester

To a solution of the resultant acid from Example 60A (1.0 equivalent) in DMF is added 3-hydroxy-1,2,3-benzotriazin-4(3H)-one (1.5 equivalents) followed by 2-aminopyridine (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 60C

4-[(Pyridin-2-ylamino)carbonyl]-2-phenylbenzoyl methionine

The resultant compound from Example 60B is hydrolyzed according to the procedure of Example 1B to give the title product.

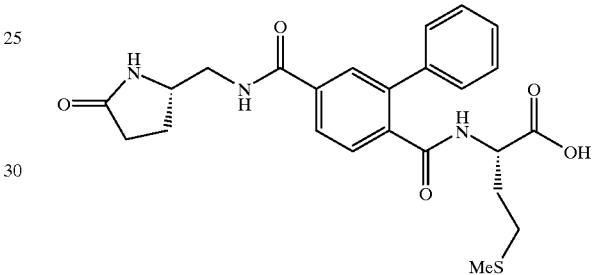

EXAMPLE 61

4-((S)-2-Pyrrolidone-5-aminomethyl)carbonyl)-2-phenylbenzoyl methionine

Using the procedure of Example 60 and replacing 2-aminopyridine with (S)-5-aminomethyl-2-pyrrolidone affords the title product.

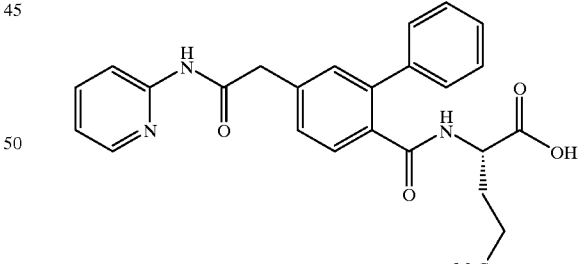

EXAMPLE 62

4-[(Pyridin-2-ylamino)carbonylmethyl]-2-phenylbenzoyl methionine

EXAMPLE 62A

4-Diazocarbonyl-2-phenylbenzoyl methionine methyl ester

The resultant acid from Example 60A (1 equivalent) in dichloromethane is treated with oxalyl chloride (1 equivalent) and DMF (0.05 equivalent). When gas evolution has ceased, the acid chloride solution is added to an ether solution of diazomethane. The reaction is stirred until judged complete by TLC analysis, and then is concentrated to give the crude title compound which is purified by chromatography on silica gel.

EXAMPLE 62B 4-carboxymethyl-2-phenylbenzoyl methionine methyl ester

The resultant compound from Example 62A (1 equivalent) in dioxane is added to a slurry of sodium thiosulfate (1.1 equivalents) and silver (I) oxide (0.5 equivalent) in water. The reaction is stirred until judged complete by TLC analysis, filtered, acidified, and extracted into ethyl acetate which is dried and evaporated. Chromatography of the residue on silica gel affords the title product.

EXAMPLE 62C

4-[(Pyridin-2-ylamino)carbonylmethyl]-2-phenylbenzoyl methionine methyl ester

To a solution of the resultant acid from Example 62B (1.0 equivalent) in dimethylformamide (DMF) is added 3-hydroxy-1,2,3-benzotriazin-4(3H)-one (1.5 equivalents) followed by 2-aminopyridine (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 62D

4-[(Pyridin-2-ylamino)carbonylmethyl]-2-phenylbenzoyl methionine

The resultant compound from Example 62C is hydrolyzed according to the procedure of Example 1B to give the title product.

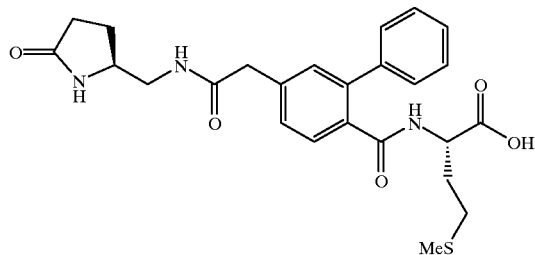

EXAMPLE 63

4-((S)-2-Pyrrolidone-5-aminomethyl)carbonylmethyl)-2-phenylbenzoyl methionine

Using the procedure of Example 62 and replacing 2-aminopyridine with (S)-5-aminomethyl-2-pyrrolidone affords the title product.

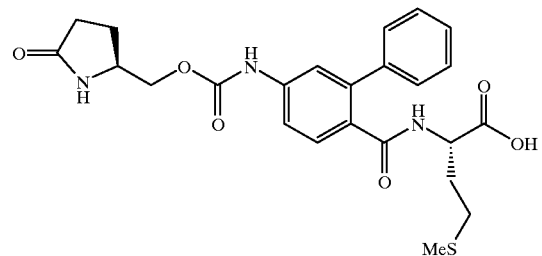

EXAMPLE 64

4-((S)-2-Pyrrolidone-5-methoxycarbonyl)amino-2-phenylbenzoyl methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

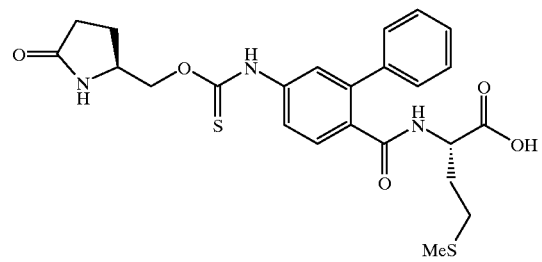

EXAMPLE 65

4-((S)-2-Pyrrolidone-5-methoxythiocarbonyl)amino-2-phenylbenzoyl methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

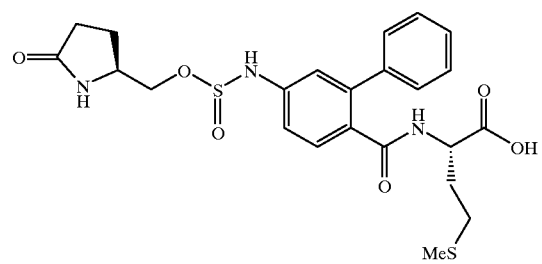

EXAMPLE 66

4-((S)-2-Pyrrolidone-5-methoxysulfinyl)amino-2-phenylbenzoyl methionine

The title compound is prepared as described in Example 3 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

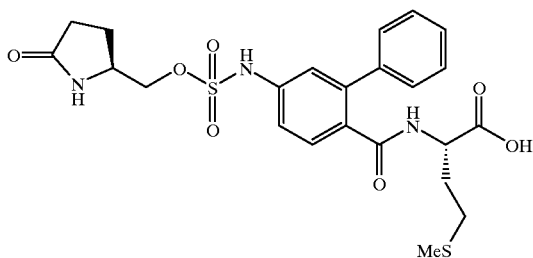

EXAMPLE 67

4-((S)-2-Pyrrolidone-5-methoxysulfonyl)amino-2-phenylbenzoyl methionine

The title compound is prepared as described in Example 4 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

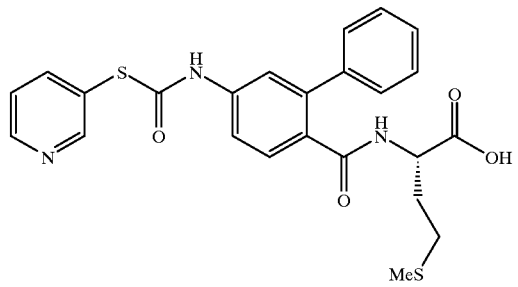

EXAMPLE 68

4-(Pyridin-3-ylmercaptocarbonyl)amino-2-phenylbenzoyl methionine

The title compound is prepared as described in Example 1 with the exception that (S)-5-aminomethyl-2-pyrrolidone (1.0 equivalent) is replaced by 3-mercaptopyridine (1.0 equivalent).

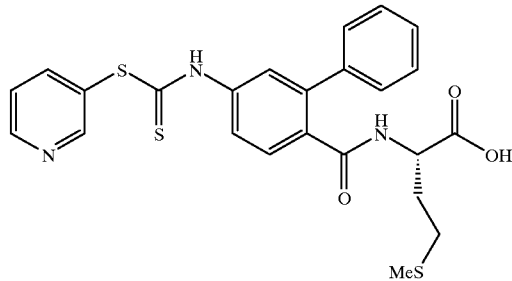

EXAMPLE 69

4-(Pyridin-3-ylmercaptothiocarbonyl)amino-2-phenylbenzoyl methionine

The title compound is prepared as described in Example 1 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

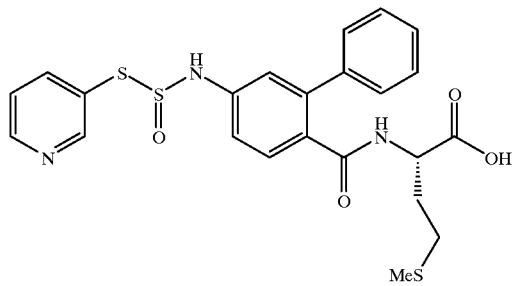

EXAMPLE 70

4-(Pyridin-3-ylmercaptosulfinyl)amino-2-phenylbenzoyl methionine

The title compound is prepared as described in Example 3 with the exception that (S)-5-aminomethyl-2-pyrrolidone (1.0 equivalent) is replaced by 3-mercaptopyridine (1.0 equivalent).

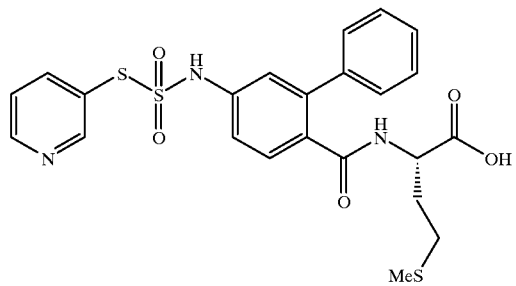

EXAMPLE 71

4-(Pyridin-3-ylmercaptosulfonyl)amino-2-phenylbenzoyl methionine

The title compound is prepared as described in Example 4 with the exception that (S)-5-aminomethyl-2-pyrrolidone (1.0 equivalent) is replaced by 3-mercaptopyridine (1.0 equivalent).

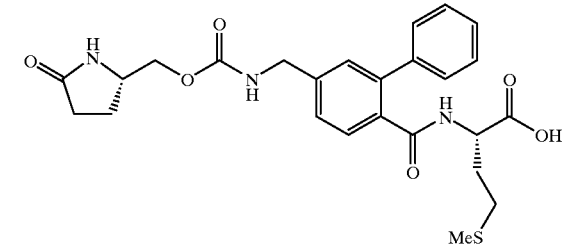

EXAMPLE 72

4-((S)-2-Pyrrolidone-5-methoxycarbonyl) aminomethyl-2-phenylbenzoyl methionine The title compound is prepared as described in Example 18 with the exception that (S)-5-aminomethyl-2-pyrrolidone (1.0 equivalent) is replaced by (S)-5-hydroxymethyl-2- pyrrolidone (1.0 equivalent) and CuCl (0.1 equivalent).

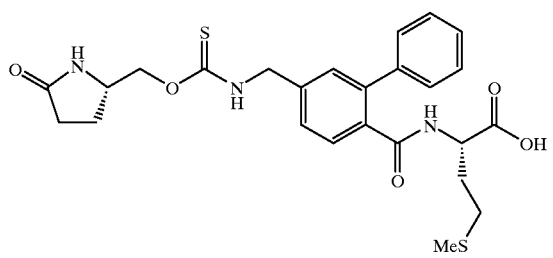

EXAMPLE 73

4-((S)-2-Pyrrolidone-5-methoxythiocarbonyl) aminomethyl-2-phenylbenzoyl methionine The title compound is prepared as described in Example 18 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

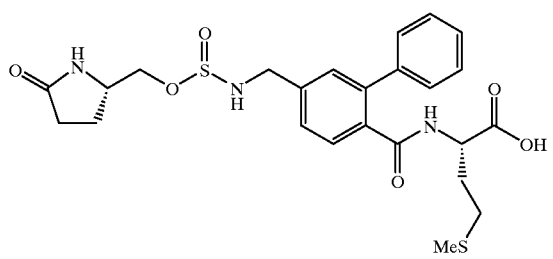

EXAMPLE 74

4-((S)-2-Pyrrolidone-5-methoxysulfinyl) aminomethyl-2-phenylbenzoyl methionine

The title compound is prepared as described in Example 3 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

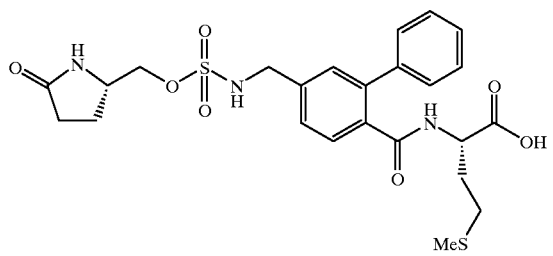

EXAMPLE 75

4-((S)-2-Pyrrolidone-5-methoxysulfonyl) aminomethyl-2-phenylbenzoyl methionine

The title compound is prepared as described in Example 4 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

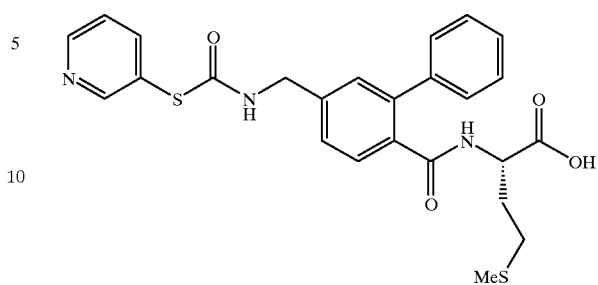

EXAMPLE 76

4-(Pyridin-3-ylmercaptocarbonyl)aminomethyl-2-phenylbenzoyl methionine

The title compound is prepared as described in Example 18 with the exception that (S)-5-aminomethyl-2-pyrrolidone (1.0 equivalent) is replaced by 3-mercaptopyridine (1.0 equivalent).

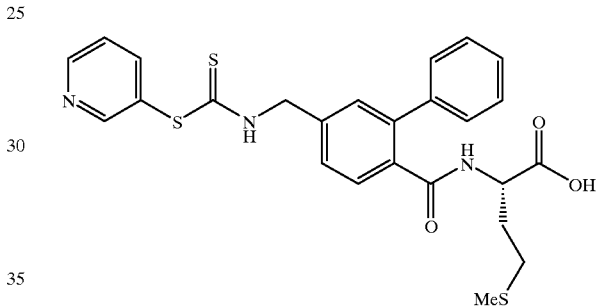

EXAMPLE 77

4-(Pyridin-3-ylmercaptocarbonyl)aminomethyl-2-phenylbenzoyl methionine

The title compound is prepared as described in Example 18 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

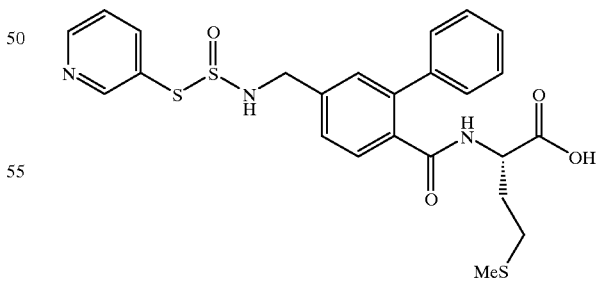

EXAMPLE 78

4-(Pyridin-3-ylmercaptosulfinyl)aminomethyl-2-phenylbenzoyl methionine

The title compound is prepared as described in Example 3 using the resultant amine from Example 18B with the exception that (S)-5-aminomethyl-2-pyrrolidone (1.0 equivalent) is replaced by 3-mercaptopyridine (1.0 equivalent).

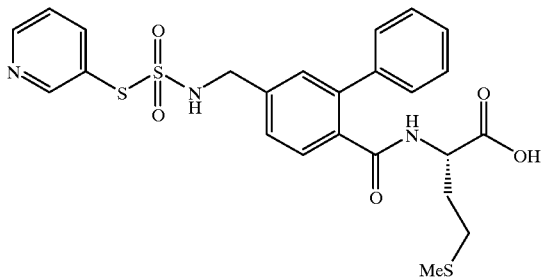

EXAMPLE 79

4-(Pyridin-3-ylmercaptosulfonyl)aminomethyl-2-phenylbenzoyl methionine

The title compound is prepared as described in Example 4 using the resultant amine from Example 18B with the exception that (S)-5-aminomethyl-2-pyrrolidone (1.0 equivalent) is replaced by 3-mercaptopyridine (1.0 equivalent).

EXAMPLE 80

A—NH—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 81

A—NH—CS—NH—B

The procedure of Example 1 is used with the exception that triphosgene (0.33 equivalent) is replaced by thiophosgene (1.0 equivalent), 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 82

A—NH—SO—NH—B

The procedure of Example 3 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 83

A—NH—SO$_2$—NH—B

The procedure of Example 4 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec- butyl, isobutyl, isoamyl, hexyl, octyl, cyclohexyl or phenethyl esters.

EXAMPLE 84

A—NH—SO$_2$—B

The procedure of Example 5 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 85

A—NH—CO—O—B

The anilines from Table 1 (B—NH$_2$) are reacted according to the procedure of Example 6E. The resultant phenols are reacted according to the procedure of Example 8 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 86

A—NH—CS—O—B

The anilines from Table 1 (B—NH$_2$) are reacted according to the procedure of Example 6E. The resultant phenols are reacted according to the procedure of Example 8 with the exception that phosgene in toluene is replaced by thiophosgene and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 87

A—NH—SO—O—B

The anilines from Table 1 (B—NH$_2$) are reacted according to the procedure of Example 6E. The resultant phenols are reacted according to the procedure of Example 8 with the exception that phosgene in toluene is replaced by thionyl chloride and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 88

A—NH—SO$_2$—B

The anilines from Table 1 (B—NH$_2$) are reacted according to the procedure of Example 6E. The resultant phenols are reacted according to the procedure of Example 8 with the exception that phosgene in toluene is replaced by sulfuryl chloride and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 89

A—NH—CH$_2$—B

The procedure of Example 16 is used with the exception that (2-phenyl-4-bromobenzoyl)-methionine methyl ester is replaced by a bromide from Table 2 (B—Br) and 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 90

A—NH—CO—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 91

A—NH—CS—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thiophosgene (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 92

A—NH—SO—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thionyl chloride (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corre-

EXAMPLE 93

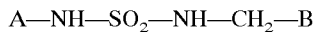

The bromides from Table 2 (B—Br) are reacted according to the procedures of Example 16F–G. The resultant alcohols are reacted according to the procedure of Example 18 with the exception that triphosgene (0.33 equivalent) is replaced by sulfuryl chloride (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 94

A—NH—CO—O—CH$_2$—B

The bromides from Table 2 (B—Br) are reacted according to the procedures of Example 16F–G. The resultant alcohols are reacted according to the procedure of Example 8 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 95

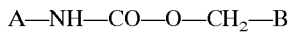

The bromides from Table 2 (B—Br) are reacted according to the procedures of Example 16F–G. The resultant alcohols are reacted according to the procedure of Example 8 with the exception that phosgene in toluene is replaced by thiophosgene and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 96

A—NH—CO—S—B

The anilines Table 1 (B—NH$_2$) are converted into the corresponding mercaptans according to the procedure of Example 12E. These mercaptans are reacted according to the procedure of Example 29 with the exception that 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 97

A—NH—CS—S—B

The anilines Table 1 (B—NH$_2$) are converted into the corresponding mercaptans according to the procedure of Example 12E. These mercaptans are reacted according to the procedure of Example 29 with the exception that phosgene in toluene is replaced by thiophosgene and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 98

A—NH—SO—S—B

The anilines Table 1 (B—NH$_2$) are converted into the corresponding mercaptans according to the procedure of Example 12E. These mercaptans are reacted according to the procedure of Example 29 with the exception that phosgene in toluene is replaced by thionyl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 99

A—NH—SO—S—B

The anilines Table 1 (B—NH$_2$) are converted into the corresponding mercaptans according to the procedure of Example 12E. These mercaptans are reacted according to the procedure of Example 29 with the exception that phosgene in toluene is replaced by sulfuryl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 100

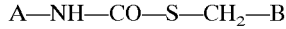
A—NH—CO—S—CH₂—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 101

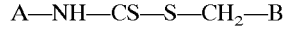
A—NH—CS—S—CH₂—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thiophosgene and 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 102

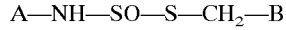
A—NH—SO—S—CH₂—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thionyl chloride and 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 103

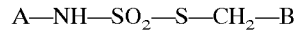
A—NH—SO₂—S—CH₂—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by sulfuryl chloride and 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 104

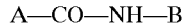
A—CO—NH—B

The procedure of Example 56 is used with the exception that 4-amino-2-phenylbenzoyl methionine methyl ester is replaced by an aniline from Table 1 (B—NH₂) and pyroglutamic acid is replaced by an acid from Table 4 (A—CO₂H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 105

A—CO—NH—CH₂—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 58 with the exception that pyroglutamic acid is replaced by an acid from Table 4 (A—CO₂H). For products derived from acids 164–238 and 262–269 from Table 2, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 106

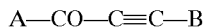
A—CO—C≡C—B

The bromides from Table 2 (B—Br) are reacted according to the procedure of Example 47A. The resultant acetylenes are reacted according to the procedure of Example 53 with the exception that 1-methyl-4-imidazoleacetic acid is replaced by an acid from Table 4 (A—CO$_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 107

A—CO—CH=CH—B

The products from Example 106 are reacted according to the procedure of Example 54.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 108

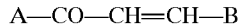
A—CO—CH$_2$—CH$_2$—B

The products from Example 107 are reacted according to the procedure of Example 55.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 109

A—NH—CO—B

The procedure of Example 60 is used with the exception that 4-bromo-2-phenylbenzoyl methionine methyl ester is replaced by a bromide from Table 2 (B—Br) and 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 110

A—NH—CO—CH$_2$—B

The bromides from Table 2 (B—Br) are reacted according to the procedure of Example 60A. The resultant carbocyclic acids are reacted according to the procedure of Example 62 with the exception that 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 111

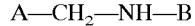
A—CH$_2$—NH—B

The procedure of Example 25 is used with the exception that 4-amino-2-phenylbenzoyl methionine methyl ester is replaced by an amine from Table 1 (B—NH$_2$) and 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 112

A—CH$_2$—NH—CH$_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 25 with the exception that 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

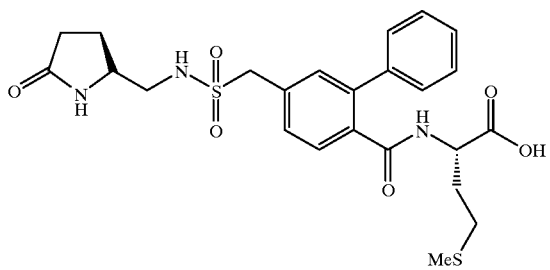

EXAMPLE 113

4-((S)-2-Pyrrolidone-5-aminomethyl) sulfonylmethyl)-2-phenylbenzoyl methionine

EXAMPLE 113A

4-Thioacetoxymethyl-2-phenylbenzoic acid methyl ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16B (1. equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 113B

4-Chlorosulfonylmethylene-2-phenylbenzoic acid methyl ester

The resultant compound from Example 113A in water is stirred vigorously while gaseous chlorine is bubbled through the mixture. When the reaction is judged to be done by TLC analysis, the reaction is extracted with dichloromethane which is dried and evaporated to afford the title product.

EXAMPLE 113C 4-((S)-2-Pyrrolidone-5-aminomethyl) sulfonylmethylene-2-phenylbenzoic acid methyl ester To a solution of the resultant compound from Example 113B (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 113D 4-((S)-2-Pyrrolidone-5-aminomethyl) sulfonylmethylene-2-phenylbenzoic acid The resultant compound from Example 113C is hydrolyzed according to the procedure of Example 1B to give the title product.

EXAMPLE 113E 4-((S)-2-Pyrrolidone-5-aminomethyl) sulfonylmethylene-2-phenylbenzoyl methionine methyl ester To a solution of the resultant compound from Example 113D (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 113F 4-((S)-2-Pyrrolidone-5-aminomethyl) sulfonylmethylene-2-phenylbenzoyl methionine The resultant compound from Example 113E is hydrolyzed according to the procedure of Example 1B to give the title product.

EXAMPLE 114

A—NH—$SO_2$—$CH_2$—B

The procedure of Example 113 is used with the exception that (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

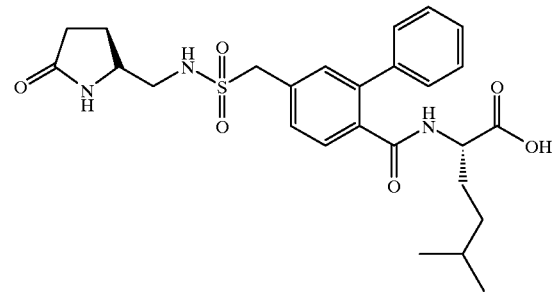

EXAMPLE 115

4-((S)-2-Pyrrolidone-5-aminomethyl) sulfonylmethyl-2-phenylbenzoyl leucine

EXAMPLE 115A 4-(Hydroxymethyl)-2-phenylbenzoyl leucine methyl ester (2-phenylbromobenzoyl)-leucine methyl ester is reacted according to the procedures of Example 16F–G.

EXAMPLE 115B

4-Thioacetoxymethyl-2-phenylbenzoyl leucine methyl ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 115A (1. equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 115C

4-Chlorosulfonylmethylene-2-phenylbenzoyl leucine methyl ester

The resultant compound from Example 115B in water is stirred vigorously while gaseous chlorine is bubbled through the mixture. When the reaction is judged to be done by TLC analysis, the reaction is extracted with dichloromethane which is dried and evaporated to afford the title product.

EXAMPLE 115D 4-((S)-2-Pyrrolidone-5-aminomethyl) sulfonylmethylene-2-phenylbenzoyl leucine methyl ester To a solution of the resultant compound from Example 115C (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 115E 4-((S)-2-Pyrrolidone-5-aminomethyl) sulfonylmethylene-2-phenylbenzoyl leucine The resultant compound from Example 115D is hydrolyzed according to the procedure of Example 1B to give the title product.

EXAMPLE 116

A—NH—SO₂—CH₂—B

The procedure of Example 115 is used with the exception that (2-phenyl1bromobenzoyl)-leucine methyl ester is replaced by a bromide from Table 2, entries 28–132 (B—Br) and (S)-5-aminomethyl-2-pyrrolidone is replaced by an amine from Table 3 (A—NH₂). For products derived from amines 146–206 from Table 3, the final LiOH hydrolysis step also hydrolyzes the ester on the fragment of the final compound that is derived from amines 146–206.

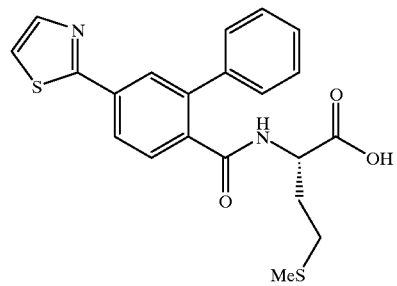

EXAMPLE 117

4-(2-Thiazolyl)-2-phenylbenzoyl methionine

EXAMPLE 117A

2-Thiazole boronic acid

A solution of thiazole (1.0 equivalent) is lithiated with a slight excess of n-butyl lithium in THF (1.05 equivalents) and then treated with trimethyl borate (1.05 equivalents). The reaction mixture is quenched by the addition of aqueous HCl and the resulting boronate ester is cleaved by the addition of excess aqueous NaOH. After acidification and extraction into ethyl acetate the crude boronic acid is used without further purification.

EXAMPLE 117B 4-(2-Thiazolyl)-2-phenylbenzoyl methionine methyl ester

A mixture of 4-bromo-2-phenylbenzoic acid methyl ester (1.0 equivalent), 2-thiazole boronic acid (1.0 equivalent) and catalytic Pd(PPh₃)₄ is heated in a two phase system of toluene and aqueous Na₂CO₃. After cooling, the resulting biaryl compound is isolated by evaporation of the organic phase and is purified by chromatography on silica gel.

EXAMPLE 117C 4-(2-Thiazolyl)-2-phenylbenzoyl methionine

The resultant compound from Example 117C is hydrolyzed according to the procedure of Example 1B to give the tide product.

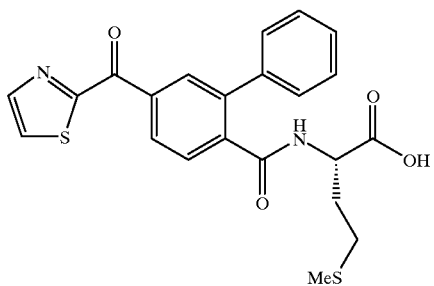

EXAMPLE 118

4-(2-Thiazolylcarbonyl)-2-phenylbenzoyl methionine

EXAMPLE 118A 4-(2-Thiazolylcarbonyl)-2-phenylbenzoyl methionine methyl ester A mixture of 4-bromo-2-phenylbenzoic acid methyl ester (1.0 equivalent), 2-thiazole boronic acid from Example 117A (1.0 equivalent) and catalytic Pd(PPh$_3$)$_4$ is heated in a two phase system of toluene and aqueous Na$_2$CO$_3$ previously purged with a large excess of carbon monoxide. The resulting diaryl ketone is isolated by evaporation of the organic phase and is purified by chromatography on silica gel.

EXAMPLE 118B 4-(2-Thiazolylcarbonyl)-2-phenylbenzoyl methionine

The resultant compound from Example 118A is hydrolyzed according to the procedure of Example 1B to give the tile product.

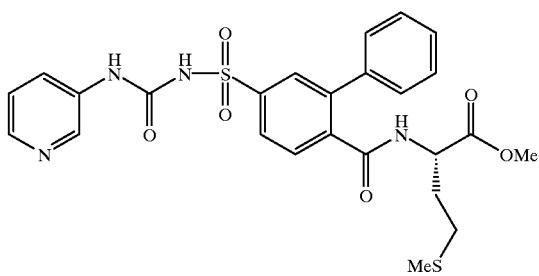

EXAMPLE 119

4[-1(3-Aminopyridyl)carbonylaminosulfonyl]-2-phenylbenzoylmethionine

EXAMPLE 119A

4-Aminosulfonyl-2-phenylbenzoylmethionine methyl ester

To a solution of 4-chlorosulfonyl-2-phenylbenzoyl methionine methyl ester from Example 5E in dichloromethane is added aqueous ammonia and the mixture is stirred until the reaction is judged complete by TLC analysis. The organic phase is separated, dried and evaporated and the product is purified by chromatography on silica gel.

EXAMPLE 119B

4-Isocyanatosulfonyl-2-phenylbenzoylmethionine methyl ester

A mixture of the resultant sulfonamide from Example 119A in chlorobenzene is treated with with oxalyl chloride according to the procedure of Franz et al. (*J. Org. Chem,* 1964, 29, 2592) to give the title compound.

EXAMPLE 119C

4-[(A-aminopyridyl)carbonylaminosulfonyl]-2-phenylbenzoylmethionine methyl ester A mixture of the resultant isocyanate from Example 119B (1 equivalent) in dichloromethane is treated with 3-aminopyridine (1 equivalent) and stirred until the reaction is judged complete by tlc analysis. The solvent is evaporated and the product is purified by chromatography on silica gel.

EXAMPLE 119D

4-[(A-aminopyridyl)carbonylaminosulfonyl]-2-phenylbenzoylmethionine

The resultant compound from Example 119C is hydrolyzed according to the procedure of Example 1B to give the title product.

EXAMPLE 120

A—NH—CO—NH—SO$_2$—B

The anilines from Table 1 (B—NH$_2$) are reacted according to the procedures of Example 5E to afford the corresponding sulfonyl chlorides. These are reacted according to the procedure of Example 119 with the exception that 3-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 121

A—NH—CO—NH—SO$_2$—CH$_2$—B

The bromides from Table 2, entries 28–132 (B—Br) are reacted according to the procedures of Example 115A–C to afford the corresponding sulfonyl chlorides. These are reacted according to the procedure of Example 119 with the exception that 3-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 122

A—O—CH$_2$—B

The bromides from Table 2 (B—Br) are reacted according to the procedures of Example 16F–G. The resultant alcohols are reacted according to the procedure of Example 27 with the exception that 3-hydroxypyridine is replaced by an alcohol from Table 6 (A—OH). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 123

A—O—CO—NH—B

The procedure of Example 1 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 124

A—O—CS—NH—B

The procedure of Example 1 is used with the exception that 4-amino-2-phenylbenzoyl methionine methyl ester is replaced by an aniline from Table 1 (B—NH₂), (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 125

A—O—SO—NH—B

The procedure of Example 3 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 126

A—O—SO₂—NH—B

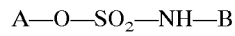

The procedure of Example 4 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 127

A—O—CO—NH—CH₂—B

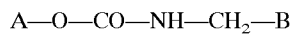

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 128

A—O—CS—NH—CH₂—B

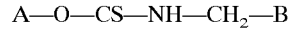

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 129

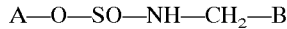
A—O—SO—NH—CH$_2$—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 130

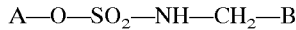
A—O—SO$_2$—NH—CH$_2$—B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 131

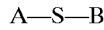
A—S—B

The anilines from Table 1 (B—NH$_2$) are reacted according to the procedures of Example 13A. The resultant fluorides are reacted according to the procedure of Example 13 with the exception that 2-mercaptopyridine is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 132

A—S—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 133

A—S—CS—NH—B

The procedure of Example 1 is used with the exception that 4-amino-2-phenylbenzoyl methionine methyl ester is replaced by an aniline from Table 1 (B—NH$_2$), (S)-5-aminomethyl-2-pyrrolidone (1.0 equivalent) is replaced by a mercaptan from Table 7 (A—SH), and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 134

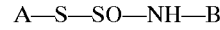
A—S—SO—NH—B

The procedure of Example 3 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 135

A—S—SO₂—NH—B

The procedure of Example 4 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 136

A—S—CO—NH—CH₂—B

The bromides from Table 2 (B—Br) are reacted according to the procedures of Example 16F—G. The resultant alcohols are reacted according to the procedure of Example 18 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 137

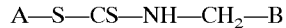
A—S—CS—NH—CH₂—B

The bromides from Table 2 (B—Br) are reacted according to the procedures of Example 16F—G. The resultant alcohols are reacted according to the procedure of Example 18 with the exception that (S)-5-aminomethyl-2-pyrrolidone is replaced by a mercaptan from Table 7 (A—SH) and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 138

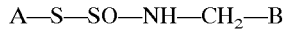
A—S—SO—NH—CH₂—B

The bromides from Table 2 (B—Br) are reacted according to the procedures of Example 16F—G and 18A–B. The resultant amines are reacted according to the procedure of Example 3 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 139

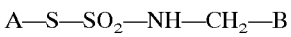
A—S—SO₂—NH—CH₂—B

The bromides from Table 2 (B—Br) are reacted according to the procedures of Example 16F—G and 18A–B. The resultant amines are reacted according to the procedure of Example 4 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 140

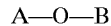
A—O—B

The procedure of Example 6 is used with the exception that 4-amino-2-phenylbenzoyl methionine methyl ester is replaced by an aniline from Table 1 (B—NH$_2$) and 3-bromopyridine is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 141

A—S—B

The procedure of Example 12 is used with the exception that 4-amino-2-phenylbenzoyl methionine methyl ester is replaced by an aniline from Table 1 (B—NH$_2$) and 2-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 142

A—NH—B

The procedure of Example 24 is used with the exception that 4amino-2-phenylbenzoyl methionine methyl ester is replaced by an aniline from Table 1 (B—NH$_2$) and 2-bromopyridine hydrobromide is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 143

A—O—CH$_2$—B

The bromides from Table 2 (B—Br) are reacted according to the procedures of Example 16F–G. The resultant alcohols are reacted according to the procedure of Example 28 with the exception that 3-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 144

A—S—CH$_2$—B

The bromides from Table 2 (B—Br) are reacted according to the procedures of Example 16F–G. The resultant alcohols are reacted according to the procedure of Example 37 with the exception that 2-bromothiazole is replaced by a halide from Table 8(A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 145

A—C≡C—B

The procedure of Example 47 is used with the exception that (2-phenyl-4-bromobenzoyl)-methionine methyl ester is replaced by a bromide from Table 2 (B—Br) and 4-bromoimidazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 146

A—CH=CH—B

The products from Example 145 are reacted according to the procedure of Example 48. This example also encom-

EXAMPLE 147

A—CH₂—CH₂—B

The products from Example 146 are reacted according to the procedure of Example 49. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 148

A—CO—C≡C—B

The bromides from Table 2 (B—Br) are reacted according to the procedure of Example 47A. The resultant acetylenes are reacted according to the procedure of Example 50 with the exception that 4-bromoimidazole is replaced by a halide from Table 8 (A—Cl, A—Br, or A—I). For products derived from halides 202–230 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 149

A—CO—CH=CH—B

The products from Example 148 are reacted according to the procedure of Example 48.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 150

A—CO—CH₂—CH₂—B

The products from Example 149 are reacted according to the procedure of Example 49.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 151

A—SO₂—B

The anilines from Table 1, entries 28–132 (B—NH₂) are reacted according to the procedures of Example 13A. The resultant fluorides are reacted according to the procedure of Example 13 with the exception that 2-mercaptopyridine is replaced by a mercaptan from Table 7 (A—SH). The resultant sulfides are oxidized according to the procedure of Example 14A. For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 152

A—CH₂SO₂—B

The procedure of Example 12 is used with the exception that 4-amino-2-phenylbenzoyl methionine methyl ester is replaced by an aniline from Table 1, entries 28–132 (B—NH₂) and 2-chloromethylpyridine hydrochloride is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 153

A—SO₂—CH₂—B

The bromides from Table 2, entries 28–132 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

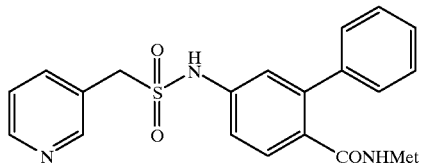

EXAMPLE 154

{4-[(3-sulfonylmethylpyridyl)amino]-2-phenylbenzoyl}methionine

EXAMPLE 154A

{4-[(3-sulfonylmethylpyridyl)amino]-2-phenylbenzoyl}methionine methyl ester

A mixture of 3-chlorosulfonylmethylpyridine hydrochloride (1.0 equivalent) and (4-amino-2-phenylbenzoyl) methionine methyl ester (1.0 equivalent) in dichloromethane is treated with triethylamine (2.2 equivalents). When judged complete by TLC analysis, the reaction is diluted with ethyl acetate, and then is washed with pH 4 water, saturated $NaHCO_3$, and brine. The mixture is dried and concentrated to give the crude title compound which is purified by chromatography on silica gel.

EXAMPLE 154B

{4-[(3-sulfonylmethylpyridyl)amino]-2-phenylbenzoyl}methionine

The resultant compound from Example 154A is hydrolyzed according to the procedure of Example 1B to give the title product.

EXAMPLE 155

$A—CH_2SO_2-NH—B$

The procedure of Example 154 is used with the exception that 4-amino-2-phenylbenzoyl methionine methyl ester is replaced by an aniline from Table 1 (B—NH$_2$) and 3-chlorosulfonylmethylpyridine hydrochloride is replaced by a sulfonyl chloride from Table 9 (A—SO$_2$Cl). This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 156

$A—S_2—NH—CH_2—B$

The bromides from Table 2 (B—Br) are reacted according to the procedures of Example 16F–G. The resultant alcohols are converted to the corresponding amines according to the procedures of Examples 18A–B. These amines are reacted according to the procedure of Example 154 with the exception that -chlorosulfonylmethylpyridine hydrochloride is replaced by a sulfonyl chloride from Table 9 (A—SO$_2$Cl). This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

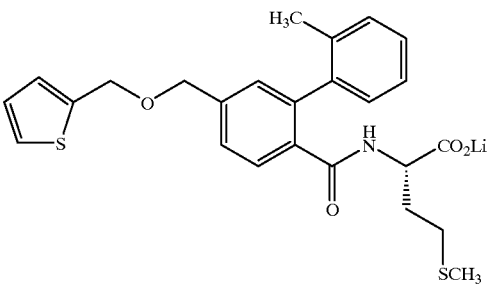

EXAMPLE 273

[4-(2-thienylmethoxymethyl)-2-(2-methylphenyl) benzoyl]methionine Lithium salt

EXAMPLE 273A 4-(2-thienylmethoxymethyl)-2-(2-methylphenyl) benzoic acid methyl ester To a suspension in DMF (3.5 mL) of sodium hydride (60% in mineral oil, 52 mg, 1.3 mmol) was added 2-thiophenemethanol (0.135 mL, 1.4 mmol) and the reaction mixture was stirred for 1.25 hours. 4-bromomethyl-2-(2-methylphenyl)benzoic acid methyl ester (0.35 mL, 1.2 mmol) was added and the reaction mixture was stirred for 2 hours. The reaction mixture was partitioned between water and ether. The aqueous phase was extracted with ether. The combined organic layers were washed with brine, dried over sodium sulfate, filtered and concentrated in vacuo. Chromatography on silica gel (3% ethyl acetate-hexane) gave 4-(2-thienylmethoxymethyl)-2-(2-methylphenyl)benzoic acid methyl ester (250 mg).

EXAMPLE 273B 4-(2-thienylmethoxymethyl)-2-(2-methylphenyl) benzoic acid

To a solution in 1:1 THF-methanol (3.4 mL) was added aqueous 4N sodium hydroxide (0.34 mL) and the reaction mixture was stirred at reflux for 4.5 hours. The reaction mixture was cooled to ambient temperature and concentrated in vacuo. The residue was partitioned between ether and water. Aqueous 2N HCl (1 mL) was added to the aqueous phase. The aqueous phase was extracted with ethyl acetate. The ethyl acetate extract was washed with brine, dried over sodium sulfate, filtered and concentrated in vacuo to give 4-(2-thienylmethoxymethyl)-2-(2-methylphenyl) benzoic acid (230 mg) as a thick oil.

EXAMPLE 273C

[4-(2-thienylmethoxymethyl)-2-(2-methylphenyl) benzoyl]methionine methyl ester

The desired compound was prepared by coupling 4-(2-thienylmethoxymethyl)-2-(2-methylphenyl)benzoic acid, prepared as in Example 272C, with methionine methyl ester hydrochloride using the procedure of Example 184A.

EXAMPLE 273D

[4-(2-thienylmethoxymethyl)-2-(2-methylphenyl)benzoyl]methionine lithium salt

To a solution in 1:1 THF-methanol of [4-(2-thienylmethoxymethyl)-2-(2-methylphenyl)benzoyl] methionine methyl ester, prepared as in Example 272C was added a solution of lithium hydroxide hydrate (40 mg, 0.95 mmol) in water (0.5 mL) and the reaction mixture was stirred for 3.5 hours. The reaction mixture was concentrated in vacuo and the residue was partitioned between ether and water. Aqueous 2N HCl (1 mL) was added to the aqueous phase. The aqueous phase was extracted with ethyl acetate. The ethyl acetate extract was washed with brine, dried over sodium sulfate, filtered and concentrated in vacuo to give [4-(2-thienylmethoxymethyl)-2-(2-methylphenyl)benzoyl] methionine. The acid was dissolved in acetonitrile (5 mL) and a solution of lithium hydroxide hydrate (18 mg, 0.43 mmol) in water (8 mL) was added. The mixture was concentrated and the residue was dissolved in water, frozen and lyophilized to give [4-(2-thienylmethoxymethyl)-2-(2-methylphenyl)benzoyl]methionine lithium salt (204 mg) as a light-yellow solid.

$^1$H NMR (300 MHz, DMSO-$d_6$) δ7.52 (d,1H), 7.50 (dd, 1H), 7.38 (dd, 1H), 7.25–7.10 (envelope, 5H), 7.08 (m, 1H), 7.00 (m, 1H), 6.95 (br d, 1H), 4.70 (s, 2H), 4.60 (s, 2H), 3.70 (m, 1H), 2.20–1.80 (envelope, 8H), 1.68, 1.59 (both m, total 2H).

MS (APCI) 470 (M+H)$^+$.

Anal calcd for $C_{25}H_{26}LiNO_4S_2 \cdot 1.0\ H_2O$: C, 60.84; H, 5.72; N, 2.84. Found: C, 61.10; H, 5.47; N, 2.73.

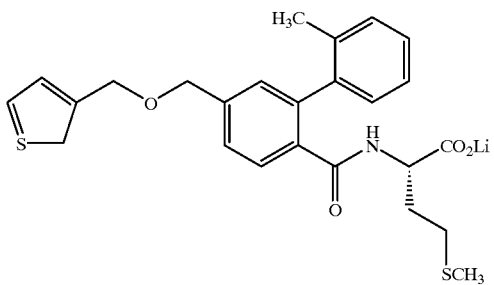

EXAMPLE 274

[4-(3-thienylmethoxymethyl)-2-(2-methylphenyl)benzoyl]methionine Lithium salt

The desired compound was prepared according to the method of Example 272, except substituting 3-thiophenemethanol for 2-thiophenemethanol.

$^1$H NMR (300 MHz, DMSO-$d_6$) δ7.52 (m, 2H), 7.45 (m, 1H), 7.40 (dd, 1H), 7.22, 7.10, 6.95 (all br m, total 7H), 4.59 (s, 2H), 4.55 (s, 2H), 3.68 (m, 1H), 2.20–1.80 (envelope, 8H), 1.68, 1.59 (both m, total 2H).

MS (ESI) m/e 470 (M+H)+, 468 (M−H)−,

Anal calcd for $C_{25}H_{26}LiNO_4S_2 \cdot 0.75\ H_2O$: C, 61.40; H, 5.67; N, 2.86. Found: C, 61.10; H, 5.47; N, 2.73.

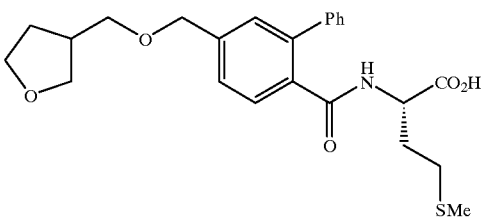

EXAMPLE 287

[4-(3-tetrahydrofurylmethyloxymethyl)-2-phenylbenzoyl]methionine

EXAMPLE 287A 4-chloromethyl-2-phenylbenzoic acid methyl ester

A solution of thionyl chloride (10.0 g, 84.0 mmol) in DMF (10 mL) was added dropwise to a solution of 4-hydroxymethyl-2-phenylbenzoic acid, methyl ester (12.1 g, 50 mmol), prepared as in Example 158C, and LiCl (2.33 g, 55.0 mmol) in DMF (40 mL). After 1 hour, the reaction mixture was poured into H$_2$O and the resulting mixture was extracted with ether (3×). The combined organic extracts were rinsed with H$_2$O (2×), saturated aqueous NaHCO$_3$ (3×) and brine, dried (MgSO$_4$) and concentrated under reduced pressure to provide the desired compound (10.8 g, 83%) as a clear, colorless oil.

EXAMPLE 287B 4-(3-tetrahydrofurylmethyloxymethyl)-2-phenylbenzoic acid methyl ester A solution of the product of Example 287A (2.09 g, 8.00 mmol) and tetrahydro-3-furanmethanol (0.990 g, 9.60 mmol) in DMF (4 mL) was added to a mixture of NaH (6.40 g, 16.0 mmol) (rinsed with THF just prior to use), KI (1.33 g, 9.00 mmol), and Bu$_4$NBr (2.60 g, 0.800 mmol). An exothermic reaction including gas evolution was observed. The mixture was stirred for 30 minutes and then heated at 130° C. for 3.5 hours. The reaction mixture was quenched with by the addition of a few drops of methanol and then treated with H$_2$O (50 mL). The mixture was extracted with a 2:1 mixture of ether and ethyl acetate, followed by ether (2×). The combined organic extracts were rinsed with H$_2$O (4×) and brine, dried (MgSO$_4$), and concentrated under reduced pressure. Flash column chromatography (20% ethyl acetate-hexane) afforded 0.406 g (14.5%) of a 1.6:1 mixture of the methyl and tetrahydro-3-furanmethyl esters, respectively.

EXAMPLE 287C

[4-(3-tetrahydrofurylmethyloxymethyl-2-phenylbenzoyl]methionine methyl ester

A solution of the product of Example 287B (0.406 g, 1.15 mmol) in saturated LiOH-methanol (6 mL) was heated to reflux for 15 hours. The reaction mixture was cooled to ambient temperature and treated with H$_2$O. The mixture was extracted with ether (3×). The ether extracts were discarded and the aqueous phase was made acidic with 3 M HCl. The mixture was extracted with ether (4×), and the organic extracts were dried (Na$_2$SO$_4$) and concentrated under reduced pressure. The resulting amber oil was dissolved in DMF (12 mL) and the solution was treated with L-methionine, methyl ester hydrochloride (0.459 g, 2.30 mmol), 3-hydroxy-1,2,3-benzotriazin-4(3H)-one (0.957 g, 5.75 mmol), 1-(3-dimethylaminopropyl)-3-ethylcarbodiimide (1.12 g, 5.75 mmol), and finally N-methylmorpholine (0.822 g, 8.05 mmol). The reaction mixture was stirred at ambient temperature for 60 hours, diluted with ethyl acetate (36 mL), and extracted with 2 N HCl (3×), followed by saturated aqueous NaHCO$_3$ (3×) and brine. The organic phase was dried (MgSO$_4$) and concentrated to provide a gold oil. Flash column chromatography (30% ethyl acetate-hexane) afforded the desired compound (0.172 g, 29%).

EXAMPLE 287D

[4-(3-tetrahydrofurylmethyloxymethyl)-2-phenylbenzoyl]methionine

Sodium hydroxide (0.776 mL of a 0.979 M aqueous solution, 0.752 mmol) was added to a solution of the product of Example 287C (0.172 g, 0.376 mmol) in methanol (1.5 mL). After 3.5 hours, the mixture was acidified by the addition of 2 N HCl (1 mL) and then extracted with CH$_2$Cl$_2$ (4×). The combined organic extracts were dried (Na$_2$SO$_4$) and then concentrated to provide the title compound (0.126 g, 75%) as a white foam.

$^1$H NMR (CDCl$_3$) δ1.56–1.78 (comp, 2H), 1.85–2.16 (comp, 7H), 2.50–2.64 (m, 1H), 3.36–3.50 (comp, 2H), 3.57–3.64 (m, 1H), 3.69–3.78 (m, 1H), 3.81–3.89 (comp, 2H), 4.56 (s, 2H), 4.56–4.65 (m, 1H), 6.06 (d, J=7.4 Hz, 1H), 7.30–7.45 (comp, 7H), 7.67 (d, J=7.8 Hz, 1H). LRMS (CI) m/e 444 (M+H)$^+$, 461 (M+NH$_4$)$^+$.

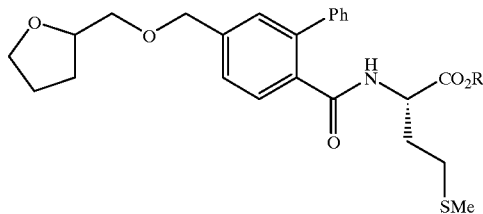

EXAMPLE 288

[4-(2-tetrahydrofurylmethyloxymethyl)-2-phenylbenzoyl]methionine

EXAMPLE 288A 4-(2-tetrahydrofurylmethyloxymethyl)-2-phenylbenzoic acid methyl ester A solution of 4-hydroxymethyl-2-phenylbenzoic acid, methyl ester (1.94 g, 8.00 mmol), prepared as in Example 158C, and tetrahydrofurfuryl chloride (1.18 g, 9.60 mmol) in DMF (4 mL) was added to a mixture of NaH (6.40 g, 16.0 mmol) (rinsed with THF just prior to use), KI (1.33 g, 9.00 mmol), and Bu$_4$NBr (2.60 g, 0.800 mmol). An exothermic reaction including gas evolution was observed. The mixture was stirred 30 minutes and then heated to 130° C. for 3.5 hours. The reaction mixture was quenched by the addition of a few drops of methanol and then treated with H$_2$O. The mixture was extracted with 2:1 ether-ethyl acetate and ether (2×). The combined organic extracts were rinsed with H$_2$O (4×) and chromatography eluting 20% ethyl acetate-hexane) afforded the desired compound (74.9 mg) as an oil shown to be 89% pure by $^1$H NMR.

EXAMPLE 288B

[4-(2-tetrahydrofurylmethyloxymethyl)-2-phenylbenzoyl]methionine

The desired compound was prepared from the product of Example 288A according to the method of Examples 287C and D.

$^1$H NMR (300 MHz, CDCl$_3$) δ1.58–1.64 (m, 1H), 1.64–1.78 (m, 1H), 1.81–1.90 (comp, 4H), 2.00 (s, 3H), 2.04–2.12 (comp, 2H), 3.49–3.52 (comp, 2H), 3.65 (s, 3H), 3.73–3.82 (m, 1H), 3.84–3.92 (m, 1H), 4.06–4.14 (m, 1H), 4.58–4.70 (comp, 3H), 5.86 (d, J=7.8 Hz, 1H), 7.33–7.44 (comp, 7H), 7.70 (d, J=7.8 Hz, 1H). LRMS (CI) m/e 448 (M+H)$^+$, 475 (M+NH$_4$)$^+$.

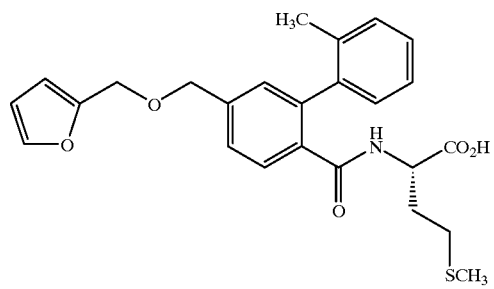

EXAMPLE 299

[4-(2-furylmethyloxymethyl)-2-(2-methylphenyl)benzoyl]methionine

EXAMPLE 299A

Furfuryl Alcohol, Potassium Salt

Potassium hydride (35% in mineral oil) was washed three times with pentane and dried under a N$_2$ sweep to give a grey powder (2.6 g, 65 mmol). THF (20 mL) was added and the mixture cooled in an ice/H$_2$O bath. A solution of furfuryl alcohol (6.4 g, 65 mmol) in THF (10 mL) was then added over 15 minutes. The ice bath was removed and the solution was allowed to warm to ambient temperature and stir for 3 hours. The solvent was removed in vacuo to give 8.6 g of a brown paste which was used as is in the next step.

EXAMPLE 299B 4-(2-furylmethyloxymethyl)-2-(2-methylphenyl)benzoic acid methyl ester To a stirred solution of the 4-chloromethyl-2-(2-methylphenyl)benzoic acid methyl ester (1.12 g , 4.08 mmol) in toluene (20 mL) under N$_2$ was added the furfuryl alcohol potassium salt prepared in Example 299A (0.84 g, 6.1 mmol) followed by 18-crown-6 (1.6 g, 6.1 mmol). The solution was heated at 90° C. for 30 minutes. The reaction mixture was cooled to ambient temperature, diluted with ethyl acetate and washed with H$_2$O (2×), saturated NaHCO$_3$ solution (2×), dried (MgSO$_4$) and concentrated in vacuo. The residue was purified by flash chromatography (10% ethyl acetate-hexane) to give the title compound (0.45 g, 33%) as an orange oil which was contaminated with ~10% of the 2-furanmethyl ester.

EXAMPLE 299C 4-(2-furylmethyloxymethyl)-2-(2-methylphenyl)benzoic acid methyl ester To a stirred solution of the product of Example 299B (0.51 g, 1.5 mmol) in methanol (20 mL) was added saturated LiOH (3 mL) and the resulting solution was heated at reflux for 5 hours. The reaction was cooled to ambient temperature and concentrated in vacuo. The residue was dissolved in formic acid (2 mL) and concentrated in vacuo. The residue was taken up in 3:1 ethyl acetate-H$_2$O and the layers were separated. The aqueous layer was extracted with ethyl acetate. The combined organic layers were washed with H$_2$O (3×), dried (MgSO$_4$) and concentrated in vacuo. The residue was purified by flash chromatography (25%, then 50% ethyl acetate-hexane) to give the desired compound (0.42 g, 85%) as a light yellow oil.

EXAMPLE 299D

[4-(2-furylmethyloxymethyl)-2-(2-methylphenyl)benzoyl]methionine methyl ester

To a stirred solution of the acid (0.41 g, 1.3 mmol), in DMF (6 mL) under N$_2$ was added 3-hydroxy-1,2,3-benzotriazin-4(3H)-one (0.23 g, 1.4 mmol), methionine methyl ester hydrochloride (0.33 g, 1.7 mmol), 1-(3-dimethylaminopropyl)-3-ethylcarbodiimide (0.32 g, 1.7 mmol) and triethylamine (~0.2 mL) to pH=7. The mixture was stirred for 6 hours. The reaction mixture was taken up in ethyl acetate and washed with H$_2$O (5×), saturated NaHCO$_3$ solution (2×) and brine. The organic layer was dried (MgSO$_4$) and concentrated in vacuo. The residue was purified by flash chromatography (5% ethyl acetate-CH$_2$Cl$_2$) and the fractions containing product were concentrated in vacuo to give the desired compound (0.47 g, 80%) as a yellow oil.

EXAMPLE 299E

[4-(2-furylmethyloxmethyl)-2-(2-methylphenyl)benzoyl]methionine

To a stirred solution of the ester (0.47 g, 1.0 mmol) in THF (10 mL) under N$_2$ was added saturated LiOH (2 mL) and the resulting solution stirred for 2 hours at ambient temperature. The reaction mixture was concentrated in vacuo and the residue was azeotroped with formic acid. The residue was taken up in 3:1 ethyl acetate-H$_2$O and the layers were separated. The aqueous layer was extracted with ethyl acetate. The combined organic layers were washed with H$_2$O (3×), dried (MgSO$_4$), and concentrated in vacuo to give the title compound (0.39 g, 85%) as a cloudy pale yellow oil.

$^1$H NMR (300 MHz, CDCl3) δ7.98 (dd, 1 H, J=11.7, 8.1 Hz), 7.44 (dd, 1 H, J=8.1, 1.7 Hz), 7.41 (dd, 1 H, J=1.7, 1.0 Hz), 7.36–7.17 (m, 6 H), 6.36–6.33 (m, 2 H), 5.89 (bt, 1 H, J=7.1 Hz), 4.60–4.53 (2s and m, 5 H), 2.14–2.01 (4s and m, 8 H), 1.96–1.89 (m, 1 H), 1.59–1.43 (m, 1 H).

MS m/z 454 (M$^+$).

Anal. Calcd for C$_{25}$H$_{27}$NO$_5$S (453.55): C, 66.21; H, 6.00; N, 3.09. Found: C, 65.92; H, 6.08; N, 2.79.

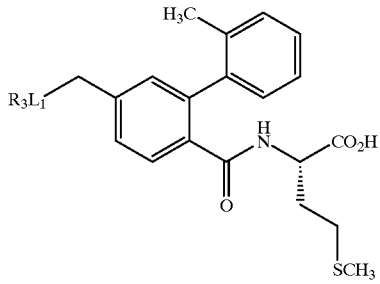

EXAMPLES 321–323

EXAMPLE 321

[4-(2-benzothiazolyloxymethyl)-2-(2-methylphenyl)benzoyl]methionine

To a solution of [4-bromomethyl-2-(2-methylphenyl)benzoyl]methionine methyl ester (160 mg, 0.36 mmol) in DMF (1.5 mL) was added 2-hydroxybenzothiazole (80 mg, 0.53 mmol) and potassium carbonate (100 mg, 0.72 mmol) and the reaction mixture was stirred overnight at ambient temperature. Aqueous workup followed by chromatography on silica gel (40% ethyl acetate-hexanes) gave [4-(2-benzoythiazolyloxymethyl)-2-(2-methylphenyl)benzoyl]methionine (70 mg, 37%). Saponification of the methyl ester using the method of Example 159 gave the title compound (67 mg).

$^1$H NMR (300 MHz, DMSO-d$_6$) δ7.99 (d, 1H), 7.47 (d, 1H), 7.38 (dd, 1H), 7.36 (m, 2H), 7.18 (m, 4H), 7.09 (m, 2H), 5.07 (s, 2H), 4.07 (m, 1H), 1.92–2.20 (m, 8H), 1.60–1.97 (m, 2H).

MS (CI, NH$_3$) m/e 524, 507, 489.

Anal calcd for C$_{27}$H$_{26}$N$_2$O$_4$S$_2$ 1.12 H$_2$O: C, 61.56; H, 5.40; N, 5.32. Found: C, 61.56; H, 5.49; N, 5.16.

EXAMPLE 322

[4-(2-benzoxazolylthiomethyl)-2-(2-methylphenyl)benzoyl]methionine

The desired compound was prepared according to the method of Example 321, except substituting 2-thiobenzoxazole for 2-hydroxybenzothiazole.

$^1$H NMR (300 MHz, DMSO-d$_6$) δ8.14 (bd, 1H), 7.56–7.67 (m, 3H), 7.46 (d, 1H), 7.33 (m, 3H), 7.19 (m, 2H), 7.10 (m, 2H), 4.65 (s, 2H), 4.18 (m, 1H), 1.97–2.21 (m, 5H).

MS (CI, NH$_3$) m/e 524, 507, 489.

Anal calcd for C$_{27}$H$_{26}$N$_2$O$_4$S$_2$.0.60 H$_2$O: C, 62.67; H, 5.30; N, 5.41. Found: C, 62.67; H, 5.41; N, 5.29.

EXAMPLE 323

[4-(2-benzothiazolylthiomethyl)-2-(2-methylphenyl)benzoyl]methionine

The desired compound was prepared according to the method of Example 321, except substituting 2-thiobenzothiazole for 2-hydroxybenzothiazole.

$^1$H NMR (300MHz, DMSO d$_6$) δ8.14 (bd, 1H), 8.01 (d, 1H), 7.86 (d, 1H), 7.59 (d, 1H), 7.47 (m, 2H), 7.35 (m, 2H), 7.19 (m, 2H), 7.08 (m, 2H), 4.70 (s, 2H), 4.19 (m, 1H), 1.94–2.18 (m, 5H), 1.93 (s, 3H), 1.63–1.87 (m, 2H).

MS (CI, NH$_3$) m/e 523, 505.

Anal calcd for $C_{27}H_{26}N_2O_3S_3 \cdot 0.58\ H_2O$: C, 60.83; H, 5.13; N, 5.25. Found C, 60.83; H, 5.06; N, 5.13.

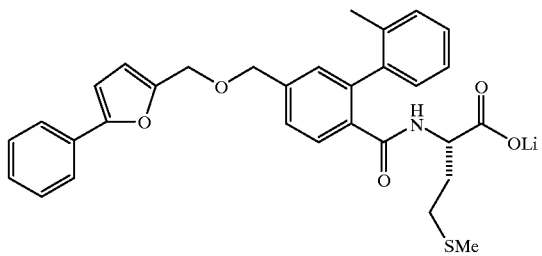

EXAMPLE 327

[4-(5-phenylfur-2-ylmethyloxymethyl)-2-(2-methylphenyl)benzoyl]methionine lithium salt

EXAMPLE 327A 5-bromo-2-hydroxymethylfuran

To a solution of 5-bromofuroic acid (8.97 g, 47.0 mmol) in 200 mL of THF at 0° C. was added N-methylmorpholine (5.23 g, 51.7 mmol) followed by isobutyl chloroformate (6.74 g, 49.5 mmol) and the reaction mixture was stirred for 30 minutes at 0° C. Sodium borohydride (10.7 g, 282 mmol) was added followed by 2 mL of saturated aqueous sodium bicarbonate and the reaction mixture was stirred for 16 hours. The reaction was quenched with 4 mL of 0.5 M phosphoric acid and the reaction was evaporated to a 20 mL volume and extracted with ethyl acetate (3×), dried over $Na_2SO_4$, filtered and evaporated to an oil. Purification by flash chromatography (50% ethyl acetate-hexanes) gave the desired compound as an oil which is unstable to oxygen at ambient temperature.

EXAMPLE 327B 5-phenyl-2-hydroxymethylfuran

The 5-bromo-2-hydroxymethylfuran prepared in Example 327A (1.012 g, 5.72 mmol) was dissolved in 10 mL of DMF and $PdCl_2(PPh_3)_2$ (401 mg, 0.57 mmol) was added followed by phenylboronic acid (1.39 g, 11.4 mmol) and $Cs_2CO_3$ (3.71 g, 11.4 mmol) and the reaction was heated at 80° C. under $N_2$ for 12 hours. The reaction mixture was taken up in ethyl acetate and washed with water (3×) and brine (3×), dried over $Na_2SO_4$, filtered and evaporated to a brown oil that was purified by flash chromatography (50% ethyl acetate-hexanes) to give the desired compound (345 mg, 35%) as an oil.

EXAMPLE 327C 4-(5-phenylfur-2-ylmethyloxymethyl)-2-(2-methylphenyl)benzoic acid methyl ester The 5-phenyl-2-hydroxymethylfuran prepared in Example 327B (345 mg, 1.98 mmol) was dissolved in 5 mL of dry DMF and NaH (50 mg, 1.98 mmol) was added followed by 15-crown-5 (436 mg, 1.98 mmol) and the reaction stirred for 5 minutes at ambient temperature. To the reaction was then added 4-chloromethyl-2-(2-methylphenyl)benzoic acid methyl ester (659 mg, 2.40 mmol) and the reaction was stirred at room temperature for 16 hours. The reaction mixture was taken up in ethyl acetate and washed with water (3×) and brine (3×), dried over $Na_2SO_4$, filtered, evaporated and purified by flash chromatography (15% ethyl acetate-hexanes) to give the desired compound (670 mg, 82%) as an oil.

EXAMPLE 327D

[4-(5-phenylfur-2-ylmethyloxymethyl)-2-(2-methylphenyl)benzoyl]methionine lithium salt The desired compound was prepared from the product of Example 327C according to the method of Examples 304E, F and G.

$^1$H NMR (300 MHz, DMSO-d6) δ7.65–7.68 (m, 2H), 7.54 (d, J=7.8 Hz, 1H), 7.43–7.35 (m, 3H), 7.30–7.10 (m, 6H), 6.96 (bs, 1H), 6.91 (d, J=3.4 Hz, 1H), 6.58 (d, J=3.4 Hz, 1H), 4.62 (s, 2H), 4.58 (s, 2H), 3.71 (bs, 1H), 2.20–1.50 (m, 10H, includes SMe at 1.92 ppm).

MS (ESI) m/e 528 (M–H)$^-$.

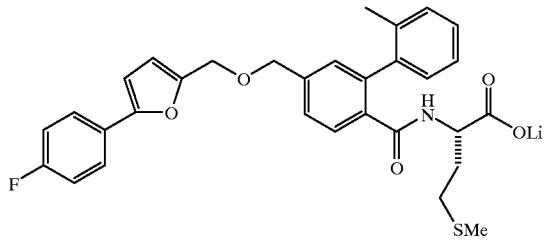

EXAMPLE 328

[4-(5-(4-fluorophenyl)fur-2-ylmethyloxymethyl)-2-(2-methylphenylbenzoyl]methionine lithium salt The desired compound was prepared according to the method of Example 327, except substituting 4-fluorophenylboronic acid for phenylboronic acid.

$^1$H NMR (300 MHz, DMSO-d6) δ7.72–7.68 (m, 2H), 7.54 (d, J=4.3 Hz, 1H), 7.39 (d, J=8.1 Hz, 1H), 7.25–7.05 (m, 7H), 6.92 (bs, 1H), 6.88 (d, J=3.6 Hz, 1H), 6.56 (d, J=3.4 Hz, 1H), 4.61 (s, 2H), 4.54 (s, 2H), 3.68 (bs, 1H), 2.20–1.46 (m, 10H, includes SMe at 1.91 ppm).

MS (ESI) m/e 546 (M–H)$^-$

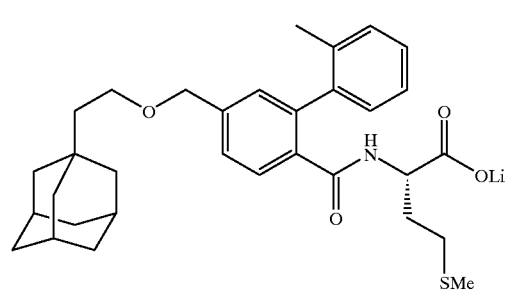

EXAMPLE 404

4-[2-(1-adamantane)ethoxy]methyl-2(2-methylphenyl)benzoylmethionine lithium salt.

The desired compound was prepared according to Example 273 except substituting 1-adamantaneethanol for 2-thiophenemethanol in Example 273A.

$^1$H (DMSO-d$_6$) δ7.52 (d,1H), 7.37 (dd, 1H), 7.20, 7.18, 7.10, 6.97 (all m, total 6H), 4.50 (s, 2H), 3.68 (m, 1H), 3.49

(t, 2H), 2.17, 2.00, 1.90 (all m, total 11H), 1.60 (m, 8H), 1.48 (m, 6H), 1.37 (t, 2H).

MS (ESI) 534 (M−H)−

Anal calcd for $C_{32}H_{40}LiNO_4S$. 1.25 $H_2O$: C, 68.12; H, 7.59; N, 2.48. Found: C, 68.04; H, 7.41; N, 2.87.

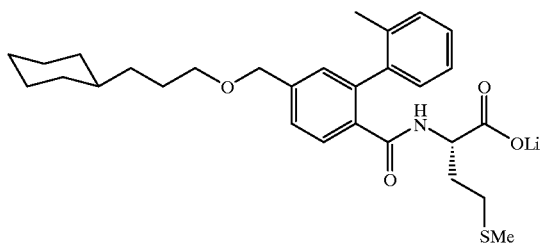

EXAMPLE 405

4-(3-cyclohexylpropoxy)methyl-2-(2-methylphenyl) benzoylmethionine lithium salt.

The desired compound was prepared according to Example 273 except substituting 3-cyclohexylpropanol for 2-thiophenemethanol in Example 273A.

$^1$H (DMSO-$d_6$) δ7.52 (d,1H), 7.37 (d, 1H), 7.20, 7.18, 7.10, 6.97 (all m, total 6H), 4.50 (s, 2H), 3.63 (m, 1H), 3.41 (t, 2H), 2.17, 2.00, 1.90 (all m, total 8H), 1.60 (m, 9H), 1.17 (m, 6H), 0.82 (m, 2H).

MS (ESI) 496 (M−H)−

Anal calcd for $C_{29}H_{38}LiNO_4S$. 0.85 $H_2O$: C, 67.12; H, 7.71; N, 2.70. Found: C, 67.07; H, 7.75; N, 3.00.

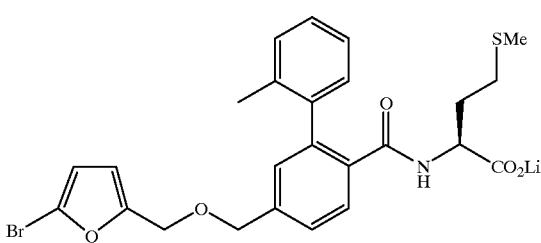

EXAMPLE 434

N-[4-(5-Bromofuran-2-ylmethoxymethyl)-2-(2-methylphenyl)benzoyl]methionine lithium salt The desired compound was prepared according to the method of Examples 157C–H $^1$H NMR (300 MHz, $d_6$DMSO) δ7.51 (d, 1H), 7.38 (bd, 1H), 7.24–6.90 (m, 7H), 6.53 (s, 2H), 4.56 (s, 2H), 4.46 (s, 2H), 3.65 (bs, 1H), 2.16–1.50 (m, 10H, methyl signals at 2.00 and 1.91 buried in multiplet) CIMS, Calcd for $C_{25}H_{26}O_5NSBr$ MH+, 533

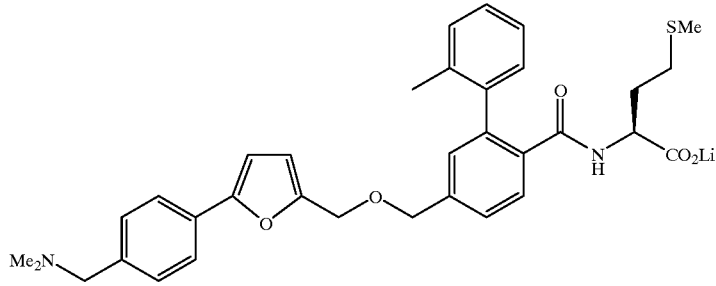

EXAMPLE 435

N-[4-(5-N,N-dimethylaminomethylfuran-2-ylmethoxymethyl)-2-(2-methylphenyl)benzoyl] methionine The desired compound was prepared according to the method of Examples 157C–H $^1$H NMR (300 MHz, $D_2O$) δ7.62 (d, 1H), 7.47 (bd, 1H), 7.35–7.10 (m, 5H), 6.66 (d, 1H), 6.51 (d, 1H), 4.70 (s, 2H), 4.62 (s, 2H), 4.27 (s, 2H), 2.79 (s, 6H), 2.08–1.64 (m, 10H);

MS (CI, isobutane) m/e 511 (511 Calcd for $C_{28}H_{34}O_5N_2S$, MH).

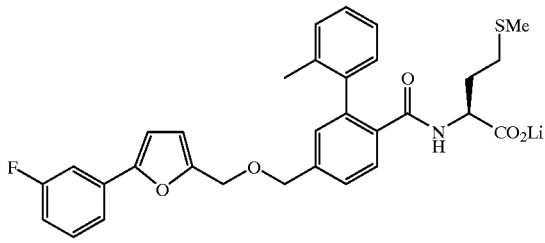

EXAMPLE 436

N-[4-(5-(3-fluorophenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.54–7.38 (m, 4H), 7.21–7.08 (m, 5H), 7.03 (d, 1H), 6.61 (d, 1H), 4.62 (s, 2H), 4.55 (s, 2H), 3.70–3.60 (m, 1H), 2.16–2.14 (m, 2H), 1.99–1.91 (m, 6H) singlet part of multiplet at 1.91, 1.70–1.50 (m, 2H) HRFABMS MH+$C_{31}H_{30}O_5NSFLi$, Calcd 554.1989, Found 554.1996.

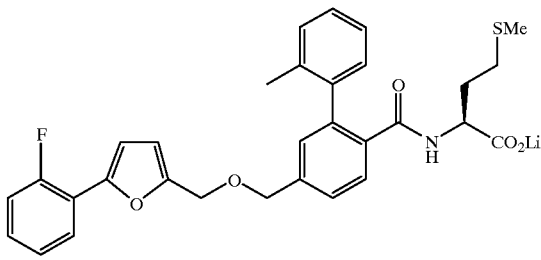

EXAMPLE 437

N-[4-(5-(2-fluorophenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.74 (dt, 1H), 7.54 (d, 1H), 7.42–6.95 (m, 9H), 6.83 (t, 1H), 6.65 (d, 1H), 4.63 (s, 2H), 4.58 (s, 2H), 3.70–3.60 (m, 1H), 2.16–2.10 (m, 2H), 2.02–1.91 (m, 6H) singlet at 1.91 is part of multiplet, 1.70–1.50 (m, 2H). HR FABMS MH+$C_{31}H_{31}O_5$NSF, Calcd 548.1907, Found 548.1916.

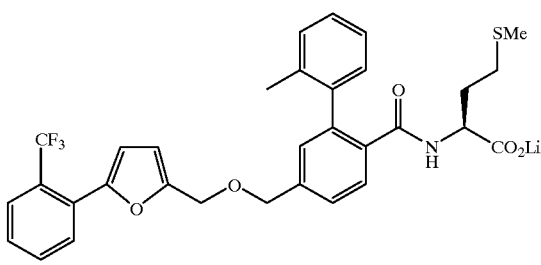

EXAMPLE 438

N-[4-(5-(2-trifluoromethylphenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.84 (d, 1H), 7.79–7.71 (m, 2H), 7.60 (dd, 1H), 7.25–7.10 (m, 5H), 6.95 (bs, 1H), 6.76 (d, 1H), 6.62 (d, 1H), 4.61 (s, 2H), 4.56 (s, 2H), 3.70–3.60 (m, 1H), 2.15–2.10 (m, 2H), 2.01–1.90 (m, 6H), 1.70–1.50 (m, 2H). HR FABMS MH+$C_{32}H_{31}O_5NF_3S$, Calcd 598.1875, Found 598.1868.

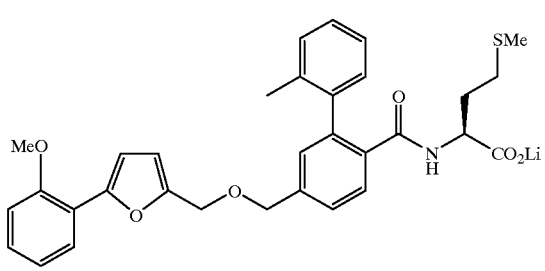

EXAMPLE 439

N-[4-(5-(2-methoxyphenylfuran-2-ylmethoxymethyl)-2-(2-(2-methylphenyl)benzoyl] methionine lithium salt The desired compound was prepared according to the method of Examples 157C–H $^1$H NMR (300 MHz, $d_6$ DMSO) δ7.70 (dd, 1H), 7.54 (d, 1H), 7.40 (bd, 1H), 7.27 (dt, 1H), 7.25–7.08 (m, 7H), 7.00 (dt, 1H), 6.88 (d, 1H), 6.56 (d, 1H), 4.61 (s, 2H), 4.55 (s, 2H), 3.90 (s, 3H), 3.70–3.60 (m, 1H), 2.16–2.12 (m, 2H), 2.02–1.90 (m, 6H), 1.70–1.50 (m, 2H). HR FABMS MH+$C_{32}H_{33}O_6$NSLi, Calcd 566.2189, Found 566.2195.

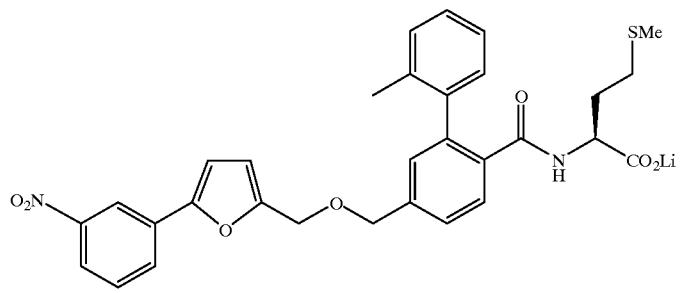

EXAMPLE 440

N-[4-(5-(3-nitrophenyl)furan-2-ylmethoxymethyl)-2-(2-methylphenyl)benzoyl]methionine lithium salt The desired compound was prepared according to the method of Examples 157C–H $^1$H NMR (300 MHz, $d_6$DMSO) δ8.42 (t, 1H), 8.14–8.09 (m, 2H), 7.71 (t, 1H), 7.54 (d, 1H), 7.40 (dd, 1H), 7.22 (d, 1H), 6.66 (d, 1H), 4.64 (s, 2H), 4.59 (s, 2H), 3.70–3.60 (m, 1H), 2.15–2.10 (m, 1H), 2.00–1.95 (m, 1H), 1.91 (s, 3H), 1.68–1.60 (m, 1H), 1.56 (s, 3H), 1.52–1.48 (m, 1H). HRMS MH+$C_{31}H_{31}O_7N_2S$, Calcd 575.1852, Found 575.1846.

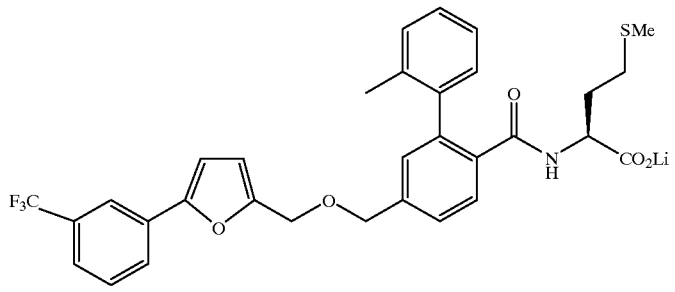

EXAMPLE 441

N-[4-(5-(3-trifluoromethylphenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.98–7.95 (m, 2H), 7.68–7.64 (m, 2H), 7.53 (d, 1H), 7.40 (dd, 1H), 7.25–7.05 (m, 5H), 6.95 (bs, 1H), 6.63 (d, 1H), 4.63 (s, 2H), 4.58 (s, 2H), 3.70–3.60 (m, 1H), 2.18–2.10 (m, 2H), 2.02–1.90 (m, 6H) methyl singlet at 1.91 is part of multiplet, 1.70–1.50 (m, 2H). HR FABMS MH+$C_{32}H_{30}O_5NF_3SLi$, Calcd 604.1957, Found 604.1981.

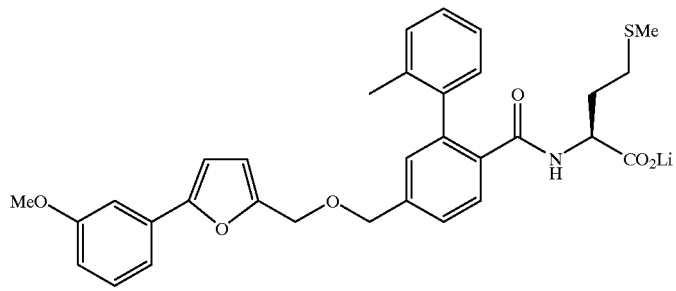

EXAMPLE 442

N-[4-(5-(3-methoxyphenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.53 (d, 1H), 7.40 (dd, 1H), 7.32 (m, 1H), 7.23 (dt, 1H), &.21–7.08 (m, 7H), 6.94 (d, 1H), 6.85 (ddd, 1H), 6.58 (d, 1H), 4.62 (s, 2H), 4.55 (s, 2H), 3.79 (s, 3H), 3.65 (bs, 1H), 2.15–2.10 (m, 2H), 2.00–1.91 (m, 6H), 1.70–1.55 (m, 2H). HR FABMS MH+$C_{32}H_{33}O_6NSLi$, Calcd 566.2189, Found 566.2195.

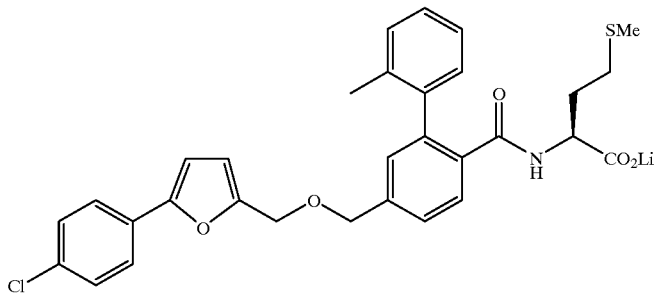

EXAMPLE 443

N-[4-(5-(4-chlorophenyl)furan-2-ylmethoxmethyl)-2-(2-methylphenyl)benzoyl]methionine lithium salt The desired compound was prepared according to the method of Examples 157C–H $^1$H NMR (300 MHz, d$_6$ DMSO) δ7.70–7.66 (m, 2H), 7.52 (d, 1H), 7.48–7.42 (m, 2H), 7.40 (dd, 1H), 7.25–7.13 (m, 5H), 6.96 (d, 1H), 6.96–6.91 (m, 1H), 6.58 (d, 1H), 4.62 (s, 2H), 4.55 (s, 2H), 3.66–3.60 (m, 1H), 2.15–2.10 (m, 2H), 2.01–1.95 (m, 6H, singlet part of multiplet at 1.91), 1.70–0.150 (m, 2H) HRMS MH+C$_{31}$H$_{31}$O$_5$NSCl, Calcd 564.1611, Found 564.1611.

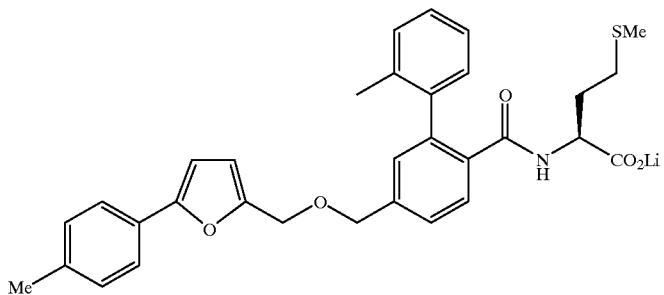

EXAMPLE 444

N-[4-(5-(4-methylphenyl)furan-2-ylmethoxymethyl)-2-(2-methylphenylbenzoyl]methionine lithium salt The desired compound was prepared according to the method of Examples 157C–H $^1$H NMR (300 MHz, d$_6$ DMSO) δ7.60–7.50 (m, 3H), 7.40 (d, 1H), 7.23–7.06 (m,7H), 7.02–6.90 (m, 1H), 6.82 (d, 1H), 6.56 (d, 1H), 4.61 (s, 2H), 4.54 (s, 2H), 3.75–3.65 (m, 1H), 2.31 (s, 3H), 2.18–2.10 (m, 2H), 2.04–1.91 (m, 6H), 1.76–1.50 (m, 2H). HR FABMS MH+C$_{32}$H$_{33}$O$_5$NSLi, Calcd 550.2239, Found 550.2247.

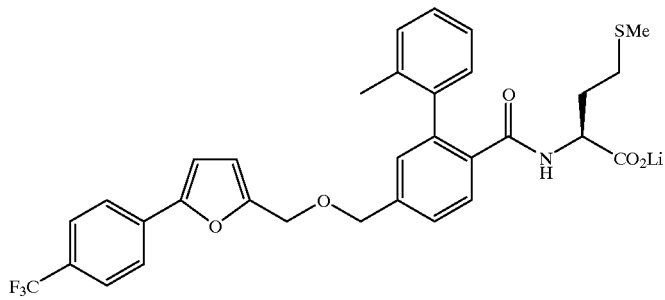

EXAMPLE 445

N-[4-(5-(4-trifluoromethylphenyl)furan-2-ylmethoxymethyl)-2-(2-methylphenyl)benzoyl]methionine lithium salt The desired compound was prepared according to the method of Examples 157C–H 1H NMR (300 MHz, $d_6$ DMSO) δ7.92 (d, 2H), 7.74 (d, 2H), 7.55 (d, 1H), 7.40 (dd, 1H), 7.26–7.06 (5H), 6.94 (bs, 1H), 6.64 (d, 1H), 4.58 (s, 2H), 4.48 (s, 2H), 3.69 (bs, 1H), 2.16–1.50 (m, 10H); CIMS, Calcd for $C_{32}H_{30}O_5NSF_3$ MH+, 598.

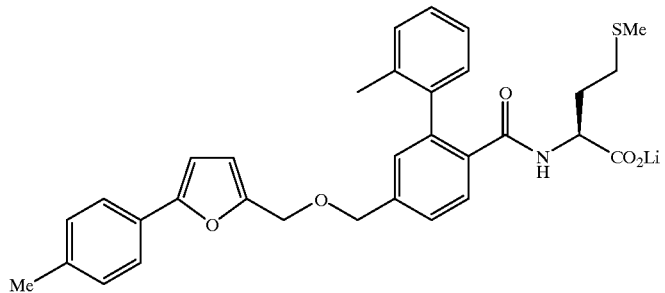

EXAMPLE 446

N-[4-(5-(4-methoxyphenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.64 (d, 1H), 7.60 (d, 2H), 7.42 (bd, 1H), 7.28–7.15 (m, 5H), 6.96 (d, 2H), 6.65 (d, 1H), 6.48 (d, 1H), 4.64 (s, 2H), 4.55 (s, 2H), 3.81 (s, 3H), 2.24–2.20 (m, 2H), 2.08–1.96 (m, 6H), 1.70–1.58 (m, 2H). HR FABMS MH+$C_{32}H_{33}O_6$NSLi, Calcd 566.2189, Found 566.2195

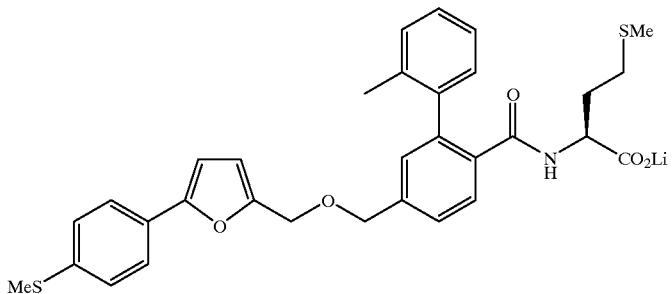

EXAMPLE 447

N-[4-(5-(4-methylthiophenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.60 (d, 2H), 7.55 (d, 1H), 7.40 (d, 1H), 7.27 (d, 2H), 7.21–7.00 (m, 5H), 6.94 (bs, 1H), 6.86 (d, 1H), 6.57 (d, 1H), 4.61 (s, 2H), 4.55 (s, 2H), 3.70–3.62 (m, 1H), 2.18–2.10 (m, 2H), 2.02–1.90 (m, 6H), 1.70–1.50 (m, 2H), HRMS MH+$C_{32}H_{34}O_5NS_2$, Calcd 576.1878, Found 576.1884.

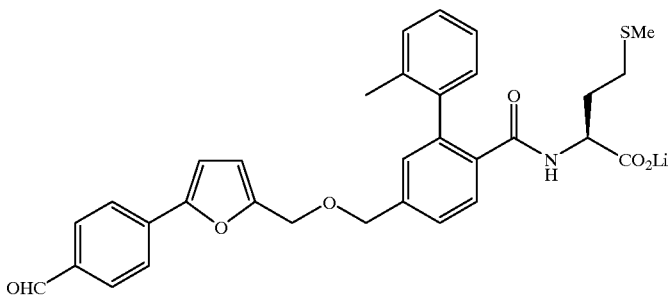

EXAMPLE 448

N-[4-(5-(4-formylphenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ9.16 (s, 1H), 7.93–7.86 (m, 3H), 7.54 (d, 1H), 7.40 (bd, 1H), 7.24–6.94 (m, 7H), 6.66 (d, 1H), 6.00 (d, 1H), 4.63 (s, 2H), 4.59 (s, 2H), 2.16–2.10 (m, 2H), 2.01–1.91 (m, 6H), 1.70–1.55 (m, 2H). HR FABMS MH+$C_{32}H_{31}O_6NSLi$, Calcd 564.2032, Found 564.2034.

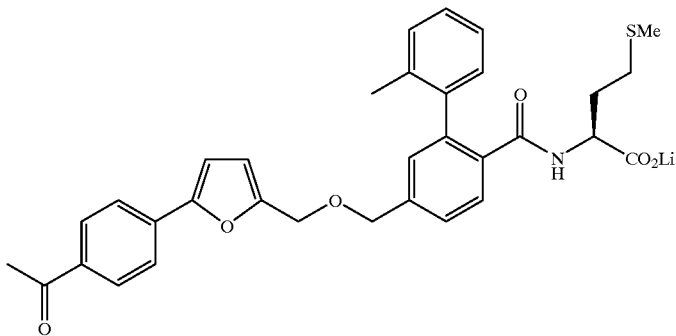

EXAMPLE 449

N-[4-(5-(4-acetylphenyl)furan-2-ylmethoxymethyl)-2-(2-methylphenyl)benzoyl]methionine lithium salt The desired compound was prepared according to the method of Examples 157C–H $^1$H NMR (300 MHz, $d_6$ DMSO) δ7.98 (d, 2H), 7.80 (d, 2H), 7.54 (d, 1H), 7.40 (d, 1H), 7.24–7.06 (m, 6H), 7.02–6.90 (m, 1H), 6.65 (d, 1H), 4.63 (s, 2H), 4.58 (s, 2H), 3.70–3.60 (m, 1H), 2.59 (s, 3H), 2.16–2.10 (m, 2H), 2.02–1.91 (m, 6H) methyl singlet is part of multiplet at 1.91, 1.74–1.55 (m, 2H).HR FABMS MH+$C_{33}H_{33}O_6$NSLi, Calcd 578.2189, Found 578.2178.

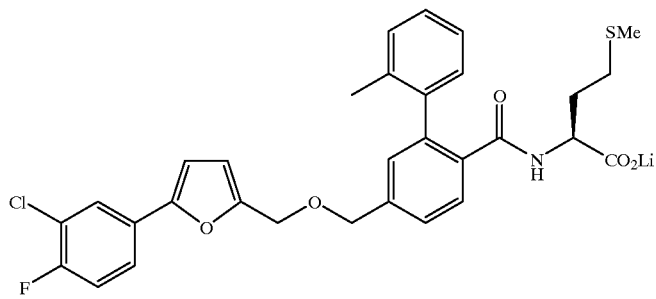

EXAMPLE 450

N-[4-(5-(3-chloro-4-fluorophenyl)furan-2-ylmethoxymethyl)-2-(2-methylphenyl)benzoyl] methionine lithium salt The desired compound was prepared according to the method of Examples 157C–H $^1$H NMR (300 MHz, $d_6$ DMSO) δ7.88 (dd, 1H), 7.66 (ddd, 1H), 7.52 (d, 1H), 7.45 (t, 1H), 7.40 (d, 1H), 7.21–7.06 (m, 6H), 7.02 (d, 1H), 6.99–6.90 (m, 1H), 6.59 (d, 1H), 4.62 (s, 2H), 4.55 (s, 2H), 3.65 (bs, 1H), 2.15–2.10 (m, 2H), 2.00–1.91 (m, 6H), 1.70–1.50 (m, 2H). HR FABMS MH+$C_{31}H_{29}O_5$NFSClLi, Calcd 588.1599, Found 588.1613.

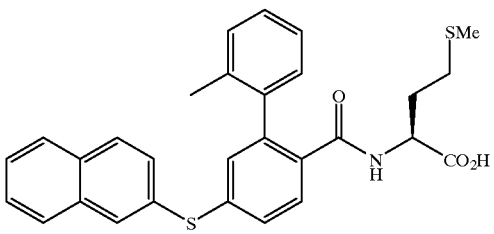

EXAMPLE 497

N-[4-(naphth-2-ylthio)-2-(2-methylphenyl)benzoyl] methionine

The desired compound was prepared according to the method of Examples 13D followed by hydrolysis of the ester.

$^1$H NMR (CDCl$_3$, 300 MHz) δ1.58 (m, 1H), 1.88 (m, 1H), 2.1 (m, 8H), 4.58 (m, 1H), 5.83 (d, 1H, J=8 Hz), 7.10 (m, 1H), 7.25 (m, 5H), 7.53 (m, 3H), 7.82 (m, 4H), 8.01 (m, 1H). MS m/e 502 (M+H)+.

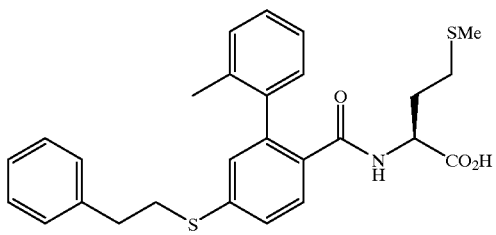

EXAMPLE 498

N-[4-(2-phenylethylthio)-2-(2-methylphenyl)benzoyl]methionine

The desired compound was prepared according to the method of Examples 13D followed by hydrolysis of the ester.

$^1$H NMR (CDCl$_3$, 300 MHz) δ1.57 (m, 1H), 1.89 (m, 1H), 2.1 (m, 8H), 2.99 (m, 2H), 3.12 (m, 2H), 4.58 (m, 1H), 5.84 (t, 1H, J=8 Hz), 7.05 (m, 1H), 7.19–7.29 (m, 10H), 7.96 (m, 1H). MS m/e 480 (M+H)$^+$.

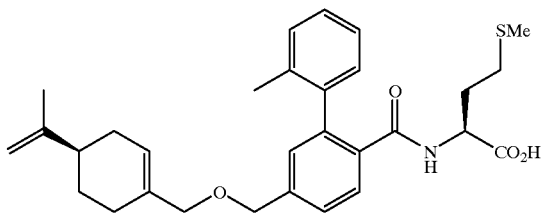

EXAMPLE 521

N-[4-(4-isoprop-2-enylcyclohexen-1-yl)methoxymethyl-2-(2-methylphenyl)benzoyl]methionine lithium salt The desired compound was prepared according to the method of Example 157

$^1$H NMR (300 MHz, DMSO) δ1.33–1.47 (m, 1H), 1.49–1.62 (m, 1H), 1.68 (s, 3H), 1.70–2.18 (m, 12H), 1.93 (s, 3H), 3.60–3.73 (m, 1H), 3.86 (s, 2H), 4.47 (s, 2H), 4.71 (s, 2H), 5.68 (brs, 1H), 6.93–7.01 (m, 2H), 7.07–7.26 (m, 5H), 7.37 (dd, J=8, 1 Hz, 1H), 7.54 (d, J=8 Hz, 1H).

MS (ESI(+)) m/z 508 (M+H)$^+$.

Anal calcd for C$_{30}$H$_{36}$NO$_4$SLi.0.40H$_2$O.0.25LiOTf: C, 66.69; H, 6.80; N, 2.55. Found: C, 66.64; H, 6.81; N, 2.58.

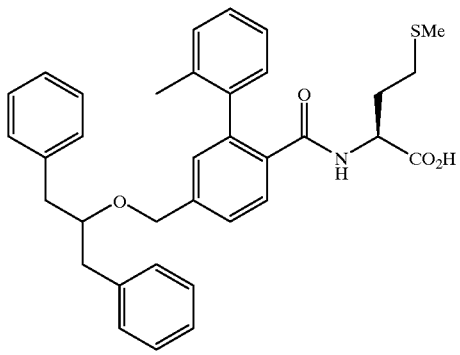

EXAMPLE 522

N-[4-(1,3-diphenylpropan-2-yl)oxymethyl-2-(2-methylphenyl)benzoyl]methionine lithium salt The desired compound was prepared according to the method of Example 157

$^1$H NMR (300 MHz, DMSO) δ1.47–1.74 (m, 2H), 1.74–1.88 (m, 1H), 1.90 (s, 3H), 1.95 (m, 3H), 2.04–2.13 (m, 1H), 2.78 (m, 4H), 3.57–3.69 (brs, 1H), 3.86 (pentet, J=6Hz, 1H), 4.43 (s, 2H), 6.82 (brs, 1H), 6.92 (m, 1H), 7.04–7.26 (m, 16H), 7.37 (d, J=8 Hz, 1H).

MS (APCI(–)) m/z 566 (M–H)$^-$.

Anal calcd for C$_{35}$H$_{36}$NO$_4$SLi.0.80H$_2$O: C, 71.48; H, 6.44; N, 2.38. Found: C, 71.51; H, 6.15; N, 2.31.

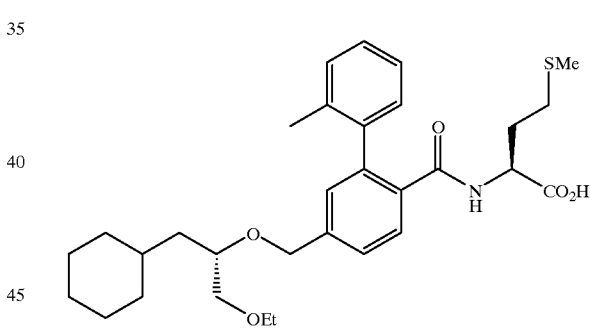

EXAMPLE 525

N-[4-(3-Cyclohexyl-1-ethoxypropan-2-yl)oxymethyl-2-(2-methylphenyl)benzoyl]methionine lithium salt The desired compound was prepared according to the method of Example 157

$^1$H NMR (300 MHz, DMSO) δ0.72–0.97 (m, 2H), 1.07 (t, J=7 Hz, 3H), 1.08 (m, 2H), 1.20–1.42 (m, 4H), 1.53–1.74 (m, 8H), 1.79–2.18 (m, 4H), 1.91 (s, 3H), 3.34–3.37 (m, 4H), 3.54–3.71 (m, 2H), 4.55 (d, J=12.9 Hz, 1H), 4.68 (d, J=12.9 Hz, 1H), 6.97 (brd, 1H), 7.06–7.23 (m, 5H), 7.36 (dd, J=8.1, 1.0 Hz, 1H), 7.52 (d, J=7.8 Hz, 1H).

MS (ESI(–)) m/z 540 (M–H)$^-$.

Anal. calcd for C$_{31}$H$_{42}$NO$^5$SLi.0.70H$^2$O: C, 66.45; H, 7.81; N, 2.50. Found: C, 66.45; H, 7.64; N, 2.27.

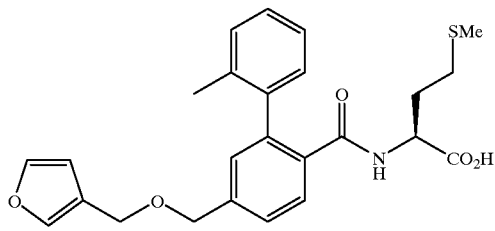

EXAMPLE 530

N-[4-(furan-3-ylmethoxymethyl)-2-(2-methylphenyl)benzoyl]methionine litihium salt The desired compound was prepared according to the method of Example 157

$^1$H NMR (DMSO-d$_6$) δ7.63 (d, 1 H, J=22.6 Hz), 7.53 (d, 1 H, J=8.0 Hz), 7.38 (d, 1 H, J=8.0 Hz), 7.22–7.11 (m, 5 H), 7.03–6.95 (m, 2 H), 6.50 (s, 1 H), 4.55 (s, 2 H), 4.41 (s, 2 H), 3.69–3.58 (m, 1 H), 2.18–1.85 (m, 8 H), 1.78–1.66 (m, 1 H), 1.59–1.52 (m, 1 H);

MS m/z 452 (M$^+$−1, 100).

Exact mass calcd for C$_{25}$H$_{28}$NO$_5$S 454.1688, found 454.1693.

Anal. Calcd for C$_{25}$H$_{26}$LiNO$_5$S.H$_2$O (477.50): C, 62.88; H, 5.91; N, 2.93. Found: C, 62.80; H, 5.72; N, 2.86.

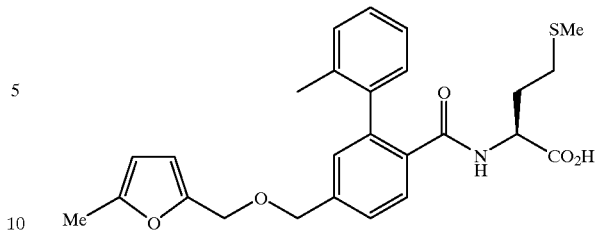

EXAMPLE 532

N-[4-(5-methylfuran-2-ylmethoxymethyl)-2-(2-methylphenyl)benzoyl]methionine lithium salt The desired compound was prepared according to the method of Example 157

$^1$H NMR (DMSO-d$_6$) δ7.52 (d, 1 H, J=7.9 Hz), 7.36 (d, 1 H, J=7.9 Hz), 7.22–6.95 (m, 6 H), 6.29 (d, 1 H, J=3.1 Hz), 6.01 (d, 1 H, J=3.1 Hz), 4.54 (s, 2 H), 4.41 (s, 2 H), 3.69–3.60 (m, 1 H), 2.23 (s, 3 H), 2.18–1.86 (m, 8 H), 1.78–1.65 (m, 1 H), 1.59–1.52 (m, 1 H);

MS m/z 468 (M$^+$+1, 100).

Exact mass calcd for C$_{26}$H$_{30}$NO$_5$S 468.1845, found 468.1847.

Anal. Calcd for C$_{26}$H$_{28}$LiNO$_5$S.0.67 H$_2$O (485.52): C, 64.32; H, 6.09; N, 2.88. Found: C, 64.17; H, 5.70; N, 2.90.

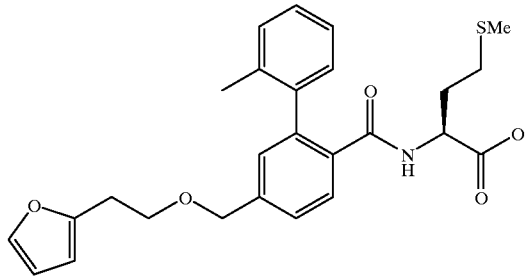

EXAMPLE 531

N-[4-(2-furan-2-ylethoxymethyl)-2-(2-methylphenyl)benzoyl]methionine lithium salt The desired compound was prepared according to the method of Example 157

$^1$H NMR (DMSO-d$_6$) δ7.52 (d, 1 H, J=7.9 Hz), 7.46 (s, 1 H), 7.34 (d, 1 H, J=7.9 Hz), 7.23–6.91 (m, 6 H), 6.34–6,31 (m, 1 H), 6.17–6.14 (m, 1 H), 4.57 (s, 2 H), 3.68 (t, 2 H, J=7.9 Hz),3.68–3.63 (m, 1 H), 2.89 (t, 2 H, J=7.9 Hz), 2.17–1.81 (m, 8 H), 1.72–1.65 (m, 1 H), 1.59–1.53 (m, 1 H);

MS m/z 468 (M$^+$+1, 100).

Anal. Calcd for C$_{26}$H$_{28}$LiNO$_5$S.0.5 H$_2$O (482.52): C, 64.72; H, 6.06; N, 2.90. Found: C, 64.79; H, 6.02; N, 2.78.

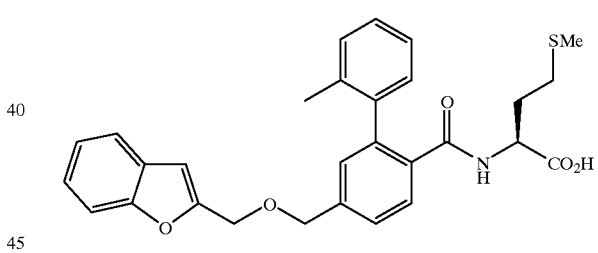

EXAMPLE 533

N-[4-(benzofuran-2-ylmethoxymethyl)-2-(2-methylphenyl)benzoyl]methionine lithium salt The desired compound was prepared according to the method of Example 157

$^1$H NMR (DMSO-d$_6$) δ7.62 (d, 1 H, J=8.0 Hz), 7.54 (d, 1 H, J=6.1 Hz), 7.73 (d, 1 H, J=4.9 Hz), 7.41 (d, 1 H, J=8.0 Hz), 7.30 (dt, 1 H, J=7.3, 1.2 Hz), 7.25–7.14 (m, 6 H), 6.96–6.91 (m, 2 H), 4.68 (s, 2 H), 4.65 (s, 2 H), 3.69–3.61 (m, 1 H), 2.18–1.86 (m, 8 H), 1.78–1.65 (m, 1 H), 1.59–1.52 (m, 1 H);

MS m/z 504 (M$^+$+1, 100).

Anal. Calcd for C$_{29}$H$_{28}$LiNO$_5$S. H$_2$O (527.57): C, 66.02; H, 5.73; N, 2.65. Found: C, 65.76; H, 5.37; N, 2.73.

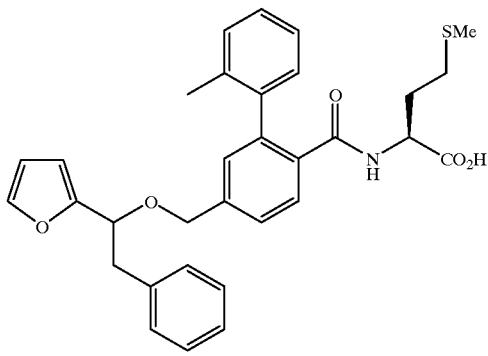

EXAMPLE 534

N-[4-(1-furan-2-yl-2-phenylethoxymethyl)-2-(2-methylphenyl)benzoyl]methionine lithium salt The desired compound was prepared according to the method of Example 157

$^1$H NMR (DMSO-d$_6$) δ7.57 (d, 1 H, J=1.7 Hz), 7.37 (dd, 1 H, J=7.5, 1.7 Hz), 7.18–7.01 (m, 9 H), 6.84–6.80 (m, 3 H), 6.34–6.31 (m, 2 H), 4.58 (dd, 1 H, J=13.9, 6.3 Hz), 4.40 (d, 1 H, J=12.8 Hz), 4.31 (d, 1 H, J=12.8 Hz), 3.62–3.60 (m, 1 H), 3.11 (ddd, 1 H, J=13.9, 7.5, 3.5 Hz), 2.11–1.85 (m, 8 H), 1.79–1.61 (m, 1 H), 1.51–1.46 (m, 1 H);

MS m/z 544 (M$^+$+1, 100).

Anal. Calcd for C$_{32}$H$_{32}$LiNO$_5$S. H$_2$O (567.63): C, 67.71; H, 6.04; N, 2.47. Found: C, 67.84; H, 6.10; N, 2.83.

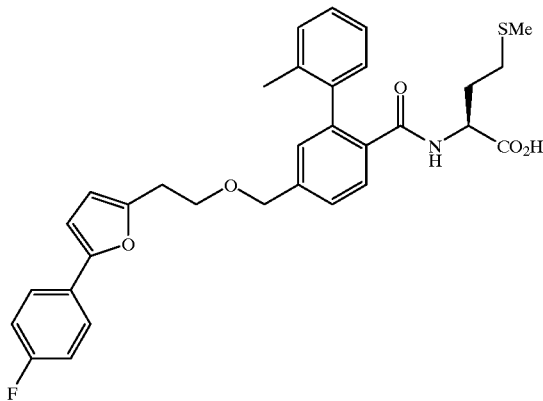

EXAMPLE 535

N-[4-(5-(4-fluorophenyl)furan-2-ylethoxymethyl)-2-(2-methylphenyl)benzoyl]methionine lithium salt The desired compound was prepared according to the method of Example 157

$^1$H NMR (DMSO-d$_6$) δ7.64–7.60 (m, 1 H), 7.51–7.33 (m, 4 H), 7.19–7.09 (m, 6 H), 6.69–6.91 (m, 1 H), 6.86 (d, 1 H, J=3.1 Hz), 6.27 (d, 1 H, J=3.4 Hz), 4.58 (s, 2 H), 3.76 (t, 2 H, J=6.6 Hz), 3.68–3.58 (m, 1 H), 2.97 (t, 2 H, J=6.6 Hz), 2.18–1.85 (m, 8 H), 1.78–1.66 (m, 1 H), 1.59–1.52 (m, 1 H); MS m/z 562 (M$^+$+1, 100).

Exact mass calcd for C$_{32}$H$_{33}$FNO$_5$S 562.2063, found 562.2068.

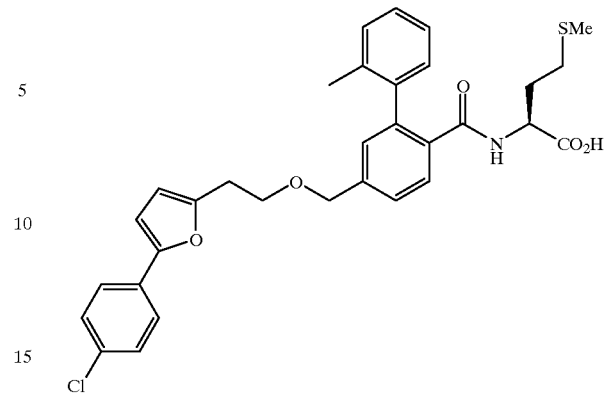

EXAMPLE 536

N-[4-(5-(4-chlorophenyl)furan-2-ylethoxymethyl)-2-(2-methylphenyl)benzoyl]methionine lithium salt The desired compound was prepared according to the method of Example 157

$^1$H NMR (DMSO-d$_6$) δ7.67–7.62 (m, 2 H), 7.49 (d, 1 H, J=7.8 Hz), 7.58–7.54 (m, 1 H), 7.25–7.08 (m, 6 H), 6.97–6.92 (m, 2 H), 6.78 (d, 1 H, J=3.1 Hz), 6.26 (d, 1 H, J=3.4 Hz), 4.58 (s, 2 H), 3.76 (t, 2 H, J=6.4 Hz), 3.67–3.58 (m, 1 H), 2.96 (t, 2 H, J=6.4 Hz), 2.17–1.86 (m, 8 H), 1.79–1.66 (m, 1 H), 1.59–1.52 (m, 1 H);

MS m/z 578 (M$^+$+1, 100).

Exact mass calcd for C$_{32}$H$_{33}$ClNO$_5$S 578.1768, found 578.1784.

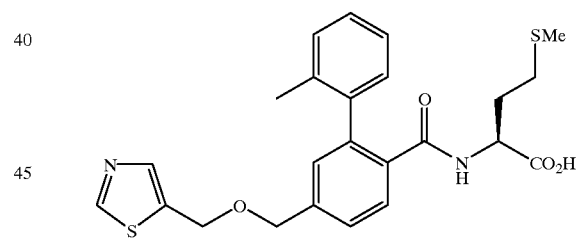

EXAMPLE 539

N-[4-(thiazol-5-ylmethoxymethyl)-2-(2-methylphenyl)benzoyl]methionine lithium salt The desired compound was prepared according to the method of Example 157

$^1$H NMR (DMSO-d$_6$) δ9.08 (d, 1 H, J=0.7 Hz), 7.88 (d, 1 H, J=1.0 Hz), 7.53 (d, 1 H, J=7.8 Hz), 7.38 (dd, 1 H, J=7.8, 1.4 Hz), 7.21–7.12 (m, 4 H), 6.96–6.91 (m, 2 H), 4.80 (s, 2 H), 4.60 (s, 2 H), 3.72–3.64 (m, 1 H), 2.18–1.85 (m, 8 H), 1.78–1.65 (m, 1 H), 1.60–1.51 (m, 1 H);

MS m/z 471 (M$^+$+1, 100).

Exact mass calcd for C$_{24}$H$_{27}$N$_2$O$_4$S$_2$ 471.1412, found 471.1420.

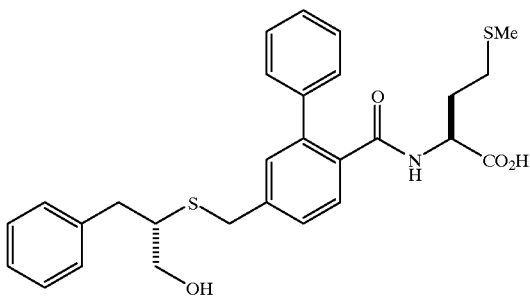

EXAMPLE 545

N-[4-(3-phenylpropan-1-ol-2-ylthiomethyl)-2-phenylbenzoyl]methionine, sodium salt The desired compound was prepared according to the method of Example 157

$^1$H NMR (300 MHz, d$_6$-DMSO) δ1.65–1.85 (m, 1H), 1.97 (s, 3H), 1.98–2.10 (m, 1H), 2.65 (dd, J=15.7, 10.8 Hz, 1H), 2.82 (m, 1H), 3.01 (m, 1H), 3.17 (brd, 2H), 3.39 (m, 1H), 3.54 (dd, J=11.4, 4.8 Hz, 1H), 3.75 (m, 2H), 4.90 (brm, 1H), 7.07–7.42 (m, 13H);

MS (FAB) m/e (M+H)$^+$ 510, (M−H)$^−$ 508.

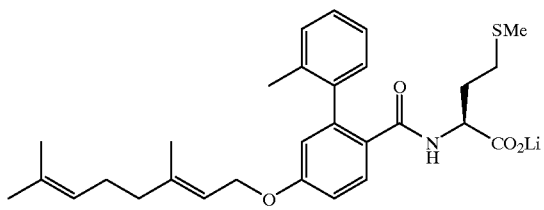

EXAMPLE 546

N-[4-geranyloxy-2-(2-methylphenyl)benzoyl] methionine, lithium salt

The desired compound was prepared according to the method of Example 6E–F $^1$H nmr (300 MHz, DMSO d$_6$): δ7.50, d, 1H; 7.20, m, 3H; 6.94, m, 2H; 6.79, m, 1H; 6.66, m, 1H; 5.43, t, 1H; 5.09, m, 1H; 4.60, d, 2H; 3.68, m, 1H; 1.88–2.23, m, 13H; 1.83, m, 1H; 1.67, s, 3H; 1.63, s, 3H; 1.58, s, 3H.

MS (APCI(+)): 494 (MH+). Calc'd for C$_{29}$H$_{36}$LiNO$_4$S.2.11 H$_2$O: C, 64.55; H, 7.51; N, 2.60: Found: C, 64.56; H, 6.94; N, 2.60.

EXAMPLE 547

N-[4-farnesyloxy-2-(2-methylphenyl)benzoyl] methionine, lithium salt

The desired compound was prepared according to the method of Example 6E–F $^1$H nmr (300 MHz, D$_2$O): δ7.73, m, 1H; 7.19, m, 3H; 6.82, m, 2H; 6.52, m, 1H; 5.24, m, 1H; 4.90, m, 2H; 4.24, m, 3H; 1.71–2.12, m, 18H; 1.40, m, 12H.

MS (APCI(+)) 5644 (MH+). Calc'd for C$_{34}$H$_{44}$LiNO$_4$S.1.67 H$_2$O: C, 68.08; H, 7.96; N, 2.34: Found: C, 68.09; H, 7.94; N, 2.26.

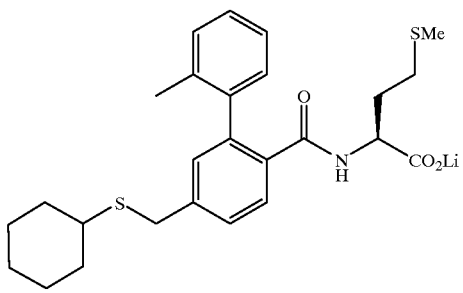

EXAMPLE 550

N-[4-cyclohexylthiomethyl-2-(2-methylphenyl) benzoyl]methionine, lithium salt

The desired compound was prepared according to the method of Example 157 $^1$H nmr (300 MHz, D$_2$O): δ7.64, d, 1H; 6.98–7.37, m, 6H; 4.20, m, 1H; 3.69, s, 2H; 2.49, m, 1H; 2.07, bs, 2H; 1.99, s, 3H; 1.97, s, 3H; 1.03–1.95, m, 12H.

MS (FAB(+)) 472 (MH+); FAB (−): 470 (M−H)$^−$. Calc'd for C$_{26}$H$_{32}$LiNO$_3$S$_2$.1.30 H$_2$O: C, 62.33; H, 6.96; N, 2.80: Found: C, 62.33; H, 6.85; N, 2.60.

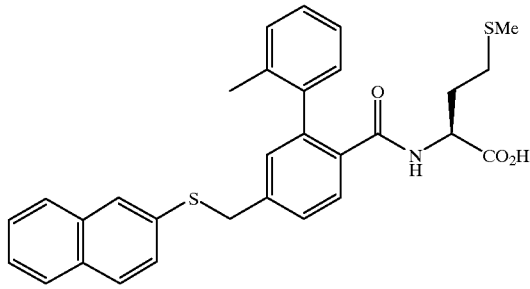

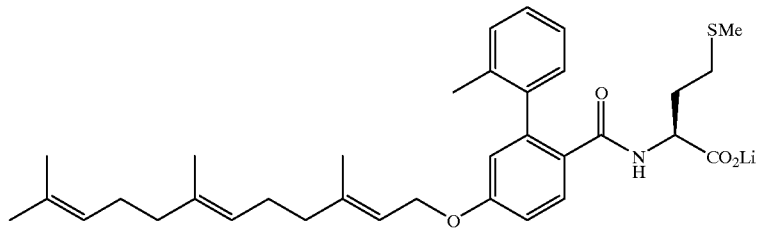

EXAMPLE 551

N-[4-naphth-2-ylthiomethyl-2-(2-methylphenyl)benzoyl]methionine

The desired compound was prepared according to the method of Example 157 $^1$H nmr (300 MHz, DMSO d$_6$): δ8.12d, 1H; 7.83, m, 4H; 7.47, m, 5H; 1.16, m, 3H; 7.06, m, 1H; 6.99, m, 1H; 4.42, s, 2H; 4.18, m, 1H; 1.61–2.20, m, 10H.

MS (APCI(+)) 516 (MH+). Calc'd for C$_{30}$H$_{29}$NO$_3$S$_2$.0.82 H$_2$O: C, 67.93; H, 5.82; N, 2.64: Found: C, 67.92; H, 5.64; N, 2.51.

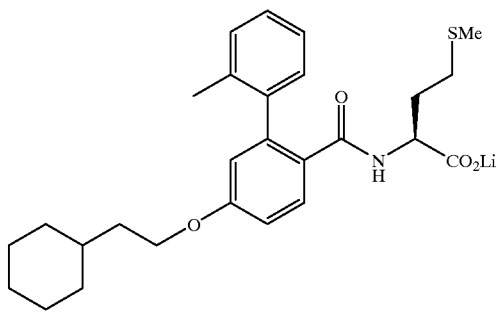

EXAMPLE 552

N-[4-(2-cyclohexylethoxy)-2-(2-methylphenyl)benzoyl]methionine, lithium salt

The desired compound was prepared according to the method of Example 6E–F $^1$H nmr (300 MHz, DMSO d$_6$): δ7.50, d, 1H; 7.20, m, 2H; 6.96, dd, 1H; 6.79, m, 1H; 6.64, m, 1H; 4.04, t, 2H; 3.67, m, 1H; 2.16, m, 1H; 1.99, m, 2H; 1.91, s, 3H; 1.38–1.90, m, 14H; 1.18, m, 2H; 0.93, m, 2H.

MS (ESI(+)) 468 (M−H)$^-$. Calc'd for C$_{27}$H$_{34}$LiNO$_4$S.1.62 H$_2$O: C, 64.25; H, 7.44; N, 2.77: Found: C, 64.25; H, 7.44; N, 2.72.

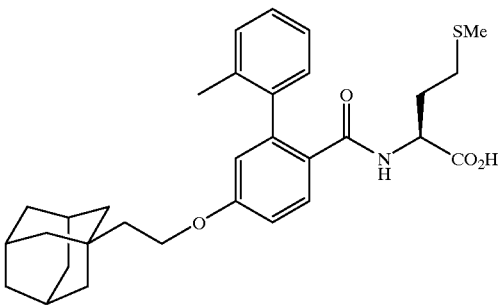

EXAMPLE 553

N-[4-(2-adamantan-1-ylethoxy)-2-(2-methylphenyl)benzoyl]methionine

The desired compound was prepared according to the method of Example 6E–F $^1$H nmr (300 MHz, DMSO d$_6$): δ12.53, bs, 1H; 7.79, d, 1H; 7.50, d, 1H; 7.18, m, 4H; 6.99 dd, 1H; 6.67, bs, 1H; 4.21, m, 1H; 4.06, m, 2H; 1.99–2.24, m, 3H; 1.87–1.97, m, 4H; 1.50–1.84, m, 20H.

MS (APCI(+)) 522 (MH+).

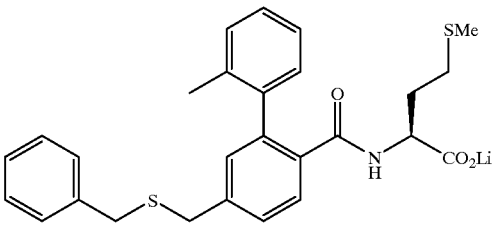

EXAMPLE 554

N-[4-benzylthiomethyl-2-(2-methylphenyl)benzoyl]methionine, lithium salt

The desired compound was prepared according to the method of Example 157 $^1$H nmr (300 MHz, DMSO d$_6$): δ7.63, d, 1H; 7.37, d, 1H; 7.25, m, 9H; 7.10, bd, 2H; 4.24, m, 1H; 3.68, s, 2H; 3.65, s, 2H; 2.26, bs, 1H; 1.57–2.13, m, 8H.

MS (APCI(+)) 480 (MH+). Calc'd for C$_{27}$H$_{28}$LiNO$_3$S$_2$.1.67 H$_2$O: C, 62.89; H, 6.13; N, 2.72: Found: C, 62.81; H, 5.35; N, 3.32.

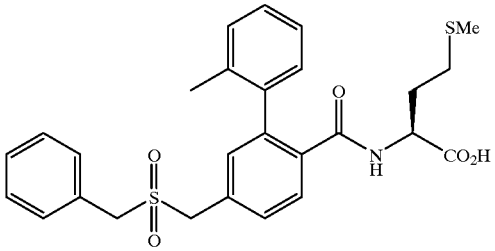

EXAMPLE 555

N-[4-benzylsulfonylmethyl-2-(2-methylphenyl)benzoyl]methionine

The desired compound was prepared according to the method of Example 157, employing the sodium salt of benzylsulfinic as the nucleophilic partner $^1$H nmr (300 MHz, DMSO d$_6$): δ8.28, m, 1H; 7.50, m, 2H; 7.39, m, 5H; 7.22, m, 3H; 7.14, m, 2H; 4.57, s, 2H; 4.49, s, 2H; 4.22, m, 1H; 2.00, 2.22, m, 5H; 1.94. s. 3H; 1.65–1.92, m, 2H.

MS (APCI(+)) 512 (MH+). Calc'd for C$_{27}$H$_{29}$NO$_5$S$_2$.0.26 H$_2$O: C, 62.81; H, 5.76; N, 2.71: Found: C, 62.80; H, 6.01; N, 2.57.

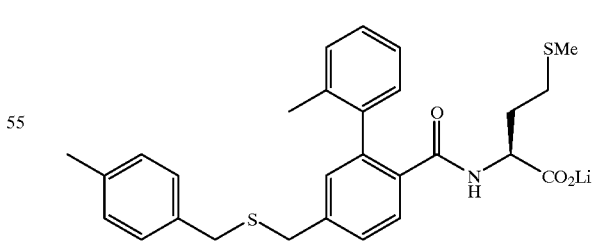

EXAMPLE 556

N-[4-(4-methylbenzyl)thiomethyl-2-(2-methylphenyl)benzoyl]methionine, lithium salt The desired compound was prepared according to the method of Example 157 $^1$H nmr (300 MHz, D$_2$O): δ7.60, d, 1H; 6.86–7.22, m, 5H; 6.75, m, 3H; 6.66, m, 2H; 4.22, m, 1H; 3.23, s, 2H; 3.20, s, 2H; 1.60–2.09, m, 13H.

MS (APCI(+)) 494 (MH+). Calc'd for $C_{28}H_{30}LiNO_3S_2 \cdot 1.34\ H_2O$: C, 64.21; H, 6.29; N, 2.67: Found: C, 64.21; H, 5.74; N, 2.46.

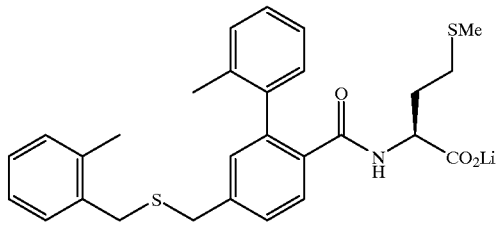

EXAMPLE 557

N-[4-(2-methylbenzyl)thiomethyl-2-(2-methylphenyl)benzoyl]methionine, lithium salt The desired compound was prepared according to the method of Example 157 $^1$H nmr (300 MHz, D$_2$O): δ7.61, d, 1H; 7.03–7.26, m, 5H; 6.80, m, 5H; 4.22, m, 1H; 3.37, s, 2H; 3.31, s, 2H; 1.59–2.06, m, 13H.

MS (APCI(+)) 494 (MH+). Calc'd for $C_{30}H_{29}NO_3S_2 \cdot 0.94\ H_2O$: C, 65.11; H, 6.22; N, 2.71: Found: C, 65.12; H, 6.05; N, 2.68.

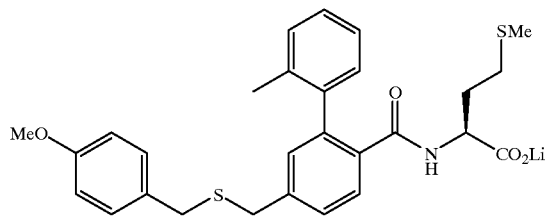

EXAMPLE 558

N-[4-(4-methoxybenzyl)thiomethyl-2-(2-methylphenyl)benzoyl]methionine, lithium salt The desired compound was prepared according to the method of Example 157 $^1$H nmr (300 MHz, D$_2$O): δ7.58, d, 1H; 7.03–7.15, m, 5H; 6.93, d, 2H; 6.82, d, 1H; 6.59, d, 2H; 4.19, m, 1H; 3.48, s, 3H; 3.41, s, 2H; 3.37, s, 2H; 1.55–2.07, m, 10H.

MS (APCI(+)) 509 (MH+). Calc'd for $C_{28}H_{31}Li_2NO_6S_2 \cdot 0.73\ H_2O$: C, 59.14; H, 5.75; N, 2.46: Found: C, 59.13; H, 5.80; N, 2.21.

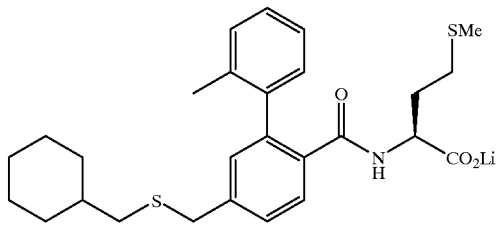

EXAMPLE 559

N-[4-cyclohexylmethylthiomethyl-2-(2-methylphenyl)benzoyl]methionine, lithium salt The desired compound was prepared according to the method of Example 157 $^1$H nmr (300 MHz, D$_2$O): d 7.67, d, 1H; 6.95–7.34, m, 6H; 4.22, m, 1H; 3.52, m, 2H; 0.63–2.19, m, 23H.

MS (APCI(+)) 486 (MH+). Calc'd for $C_{27}H_{34}LiNO_3S_2 \cdot 1.77\ H_2O$: C, 61.94; H, 7.23; N, 2.68: Found: C, 61.94; H, 7.18; N, 2.53.

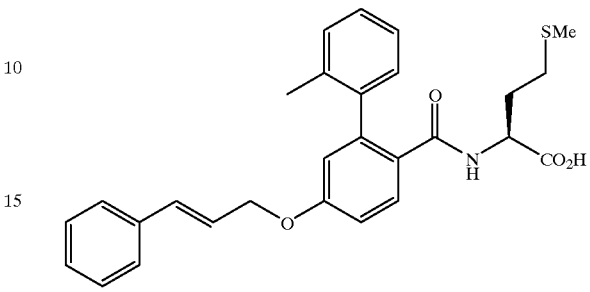

EXAMPLE 560

N-[4-(3-phenyl)prop-2-en-1-yloxy-2-(2-methylphenyl)benzoyl]methionine

The desired compound was prepared according to the method of Example 6E–F $^1$H nmr (300 MHz, DMSO d$_6$): d 7.89, bd, 1H; 7.48, m, 3H; 7.36, m, 2H; 7.27, m, 1H; 7.10–7.24, m, 4H; 7.08, dd, 1H; 6.75, m, 2H; 6.51, dt, 1H; 4.82, d, 2H; 4.19, m, 1H; 1.98–2.25, m, 5H; 1.97, s, 3H; 1.63–1.93, m, 2H.

MS (APCI(+)) 476 (MH+). Calc'd for $C_{28}H_{29}NO_4S \cdot 0.29\ H_2O$: C, 69.95; H, 6.20; N, 2.91: Found: C, 69.95; H, 5.93; N, 2.81.

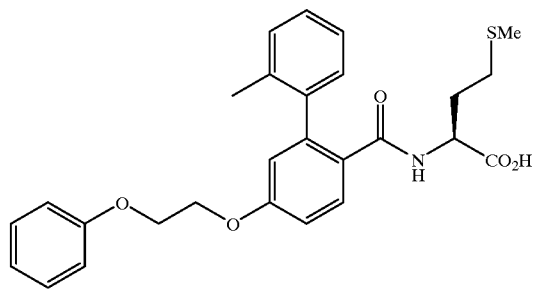

EXAMPLE 561

N-[4-(2-phenoxy)ethoxy-2-(2-methylphenyl)benzoyl]methionine

The desired compound was prepared according to the method of Example 6E–F $^1$H nmr (300 MHz, D$_2$O): d 7.89, d, 1H; 7.53, d, 1H; 7.30, dd, 2H; 7.10–7.25, m, 4H; 7.07, dd, 1H; 6.97, m, 3H; 6.74, bs, 1H; 4.39, m, 2H; 4.31, m, 2H; 4.22, m, 1H; 2.02–2.29, m, 5H; 1.97, s, 3H; 1.63–1.91, m, 2H.

MS (APCI(+)) 480 (MH+). Calc'd for $C_{27}H_{29}NO_5S \cdot 0.67\ H_2O$: C, 65.91; H, 6.22; N, 2.85: Found: C, 65.95; H, 6.14; N, 3.31.

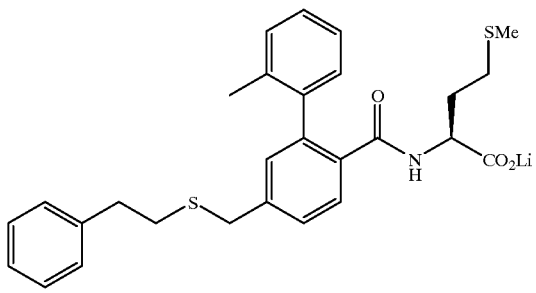

EXAMPLE 562

N-[4-(2-phenyl)ethylthiomethyl-2-(2-methylphenyl)benzoyl]methionine, lithium salt The desired compound was prepared according to the method of Example 157 $^1$H nmr (300 MHz, D$_2$O): d 7.62, d, 1H; 7.08–7.19, m, 5H; 6.90–7.01, m, 4H; 6.83, d, 2H; 4.17, m, 1H; 3.44, s, 2H; 2.51, m, 2H; 2.38, m, 2H; 1.60–2.05, m, 10H.

MS (APCI(+)) 494 (MH+). Calc'd for C$_{28}$H$_{31}$LiNO$_3$S$_2$.1.24 H$_2$O: C, 64.31; H, 6.45; N, 2.68: Found: C, 64.30; H, 5.93; N, 2.20.

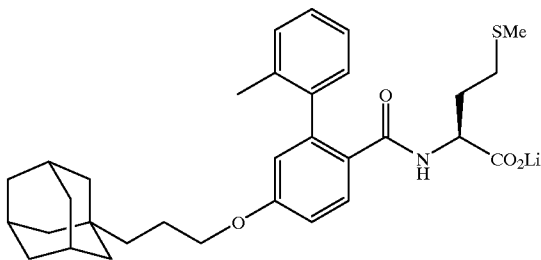

EXAMPLE 563

N-[4-(2-adamantan-1-ylpropoxy)-2-(2-methylphenyl)benzoyl]methionine, lithium salt The desired compound was prepared according to the method of Example 6E–F $^1$H nmr (300 MHz, DMSO d$_6$): δ7.5, d, 2H; 7.17, m, 4H; 6.96, dd, 1H; 6.80, m, 1H; 6.63, bs, 1H; 3.96, t, 2H; 3.65, m, 1H; 2.17, m, 1H; 1.50–2.08, m, 29H.

MS (APCI(+)) 535 (MH+). Calc'd for C$_{32}$H$_{38}$LiNO$_4$S.1.51 H$_2$O: C, 67.80; H, 7.29; N, 2.47: Found: C, 67.81; H, 7.03; N, 2.23.

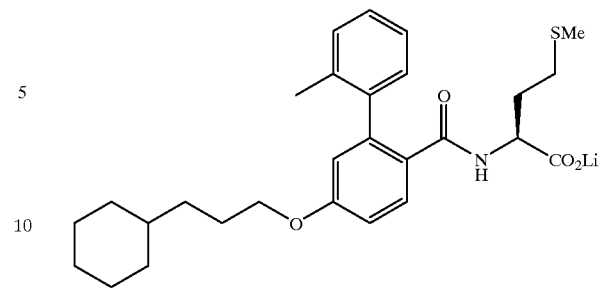

EXAMPLE 564

N-[4-(3-cyclohexylpropoxy)-2-(2-methylphenylbenzoyl]methionine, lithium salt

The desired compound was prepared according to the method of Example 6E–F $^1$H nmr (300 MHz, D$_2$O): δ7.72, m, 1H; 7.18, m, 3H; 6.80, m, 2H; 6.51, m, 1H; 4.22, m, 1H; 3.64, m, 2H; 0.55–2.17, m, 26H.

MS (APCI(+)) 484 (MH+). Calc'd for C$_{28}$H$_{36}$LiNO$_4$S.0.87 H$_2$O: C, 66.56; H, 7.53; N, 2.77: Found: C, 66.57; H, 7.75; N, 2.53.

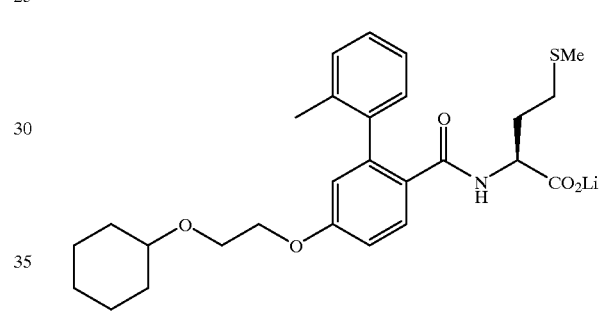

EXAMPLE 565

N-[4-(2-cyclohexyloxy)ethoxy-2-(2-methylphenyl)benzoyl]methionine, lithium salt

The desired compound was prepared according to the method of Example 6E–F $^1$H nmr (300 MHz, DMSO d$_6$): δ7.50, d, 1H; 7.20, m, 4H; 6.97, dd, 1H; 6.81, m, 1H; 6.66, bs, 1H; 4.12, m, 2H; 3.66, m, 2H; 3.63, m, 1H; 1.11–2.24, m, 20H.

MS (APCI(+)) 486 (MH+). Calc'd for C$_{27}$H$_{34}$LiNO$_5$S.1.94 H$_2$O: C, 61.59; H, 7.25; N, 2.66: Found: C, 61.59; H, 6.97; N, 2.556.

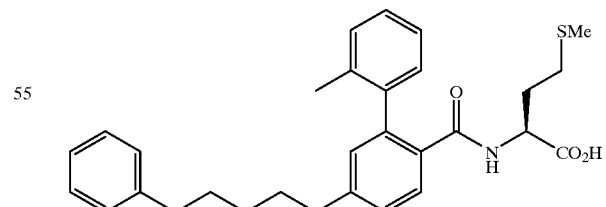

EXAMPLE 566

N-[4-(3-phenoxy)propoxy-2-(2-methylphenyl)benzoyl]methionine

The desired compound was prepared according to the method of Example 6E–F $^1$H nmr (300 MHz, D$_2$O): δ7.66, m, 1H; 7.01–7.22, m, 4H; 6.80, m, 3H; 6.67, m, 4H; 4.19, m, 1H; 3.72, m, 2H; 3.60, m, 2H; 1.52–2.08, m, 12H.

MS (APCI(+)) 493 (MH+). Calc'd for C$_{28}$H$_{30}$LiNO$_5$S.1.34 H$_2$O: C, 64.22; H, 6.29; N, 2.67: Found: C, 64.23; H, 6.01; N, 2.38.

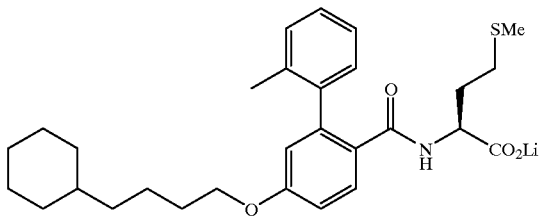

EXAMPLE 567

N-[4-(4-cyclohexyl)butoxy-2-(2-methylphenyl) benzoyl]methionine, lithium salt

The desired compound was prepared according to the method of Example 6E–F $^1$H nmr (300 MHz, DMSO d$_6$): δ7.50, d, 1H; 7.20, m, 4H; 6.95, dd, 1H; 6.80, m, 1H; 6.63, m, 1H; 4.00, t, 2H; 3.68, m, 1H; 0.78–2.20, m, 27H.

MS (ESI(−)) 496 (M−H)$^-$. Calc'd for C$_{29}$H$_{38}$LiNO$_4$S.1.08 H$_2$O: C, 66.59; H, 7.74; N, 2.68: Found: C, 66.60; H, 7.47; N, 2.52.

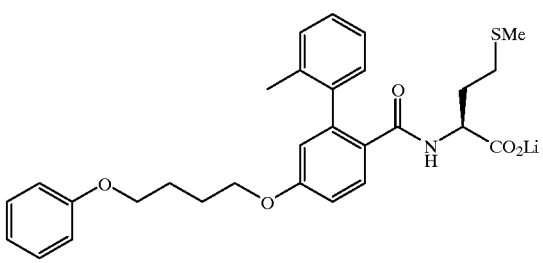

EXAMPLE 568

N-[4-(3-phenoxy)butoxy-2-(2-methylphenyl) benzoyl]methionine. lithium salt

The desired compound was prepared according to the method of Example 6E–F $^1$H nmr (300 MHz, DMSO d$_6$): δ7.68, m, 1H; 6.86–7.20, m, 4H; 6.77, m, 3H; 6.45, m, 4H; 4.19, m, 1H; 3.51, m, 2H; 3.39, m, 2H; 1.33–2.06, m, 14H.

MS (APCI(+)) 508 (MH+). Calc'd for C$_{29}$H$_{32}$LiNO$_5$S.1.19 H$_2$O: C, 65.11; H, 6.48; N, 2.62: Found: C, 65.10; H, 6.25; N, 2.73.

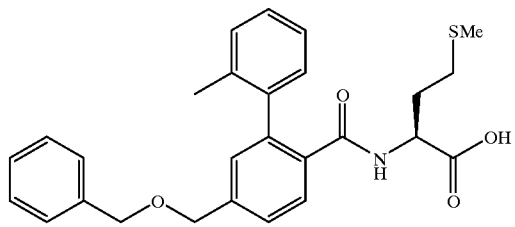

EXAMPLE 571

N-[4-(benzyloxymethyl)-2-(2-methylphenyl) benzoyl]methionine lithium salt

The desired compound was prepared according to the method of Example 157

(DMSO-d$_6$) δ7.55 (d,1H), 7.41 (dd, 1H), 7.37, 7.30, 7.18, 6.97 (all m, total 11H), 4.60 (s, 2H), 4.56 (s, 2H), 3.65 (m, 1H), 2.17, 2.00, 1.90 (all m, total 8H), 1.70 (m, 1H), 1.58 (m, 1H).

MS (APCI) 464 (M+H)$^+$.

Anal calcd for C$_{27}$H$_{28}$LiNO$_4$S.0.50 H$_2$O: C, 67.77; H, 6.11; N, 2.93. Found: C, 67.64; H, 5.93; N, 3.00.

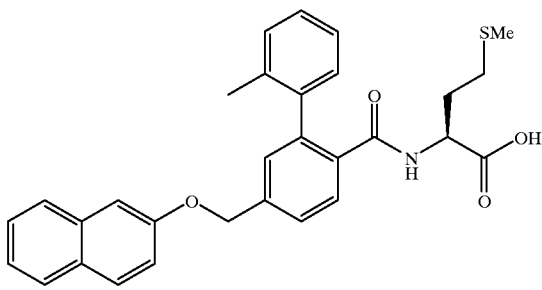

EXAMPLE 573

N-[4-(naphth-2-yloxymethyl)-2-(2-methylphenyl) benzoyl]methionine

The desired compound was prepared according to the method of Example 157

(DMSO-d$_6$) δ8.20 (d, 1H), 7.83 (d, 2H), 7.78 (d, 1H), 7.55 (m, 2H), 7.45 (m, 2H), 7.37 (m, 2H), 7.24 (dd, 1H), 7.20 (m, 4H), 5.24 (s, 2H), 4.22 (m, 1H), 2.10 (m, 5H), 1.96 (s, 3H), 1.80 (m, 2H).

MS (APCI) 500 (M+H)$^+$.

Anal calcd for C$_{30}$H$_{29}$NO$_4$S.0.40 H$_2$O: C, 71.09; H, 5.93; N, 2.76. Found: C, 71.01; H, 5.83; N, 2.59.

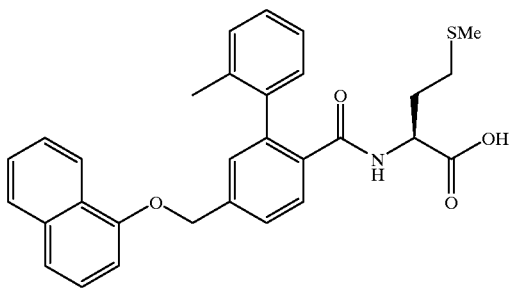

EXAMPLE 574

N-[4-(naphth-1-yloxymethyl)-2-(2-methylphenyl) benzoyl]methionine

The desired compound was prepared according to the method of Example 157

(DMSO-d$_6$) δ8.20 (m, 2H), 7.87 (m, 1H), 7.64 (d,1H), 7.50 (m, 4H), 7.42 (d, 1H), 7.39 (m, 1H), 7.21 (m, 2H), 7.15 (m, 2H), 7.09 (d, 1H), 5.40 (s, 2H), 4.22 (m, 1H), 2.10 (m, 5H), 1.96 (s, 3H), 1.80 (m, 2H).

MS (APCI) 500 (M+H)$^+$.

Anal calcd for C$_{30}$H$_{29}$NO$_4$S.0.40 H$_2$O: C, 71.09; H, 5.93; N, 2.76. Found: C, 71.07; H, 5.81; N, 2.61.

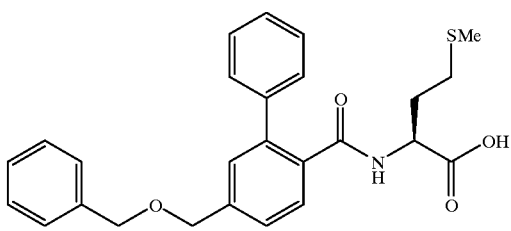

EXAMPLE 575

N-[4-(benzyloxymethyl)-2-phenylbenzoyl] methionine

The desired compound was prepared according to the method of Example 157

(DMSO-d$_6$) δ8.53 (d,1H), 7.38 (m, 13H), 4.62 (s, 2H), 4.58 (s, 2H), 4.30 (m, 1H), 2.23 (m, 2H), 2.00 (s, 3H), 1.84 (m, 2H).

MS (APCI) 450 (M+H)$^+$.

Anal calcd for C$_{26}$H$_{27}$NO$_4$S: C, 69.46; H, 6.05; N, 3.12. Found: C, 69.15; H, 5.99; N, 3.08.

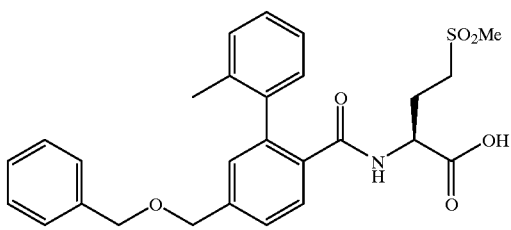

EXAMPLE 576

N-2-[4-(benzyloxymethyl)-2-(2-methylphenyl)benzoyl]amino-4-methanesulfonylbutanoic acid lithium salt The desired compound was prepared according to the method of Example 157

(DMSO-d$_6$) δ7.59 (d,1H), 7.41 (dd, 1H), 7.37, 7.30, 7.18, 7.01 (all m, total 11H), 4.60 (s, 2H), 4.56 (s, 2H), 3.70 (m, 1H), 2.80 (s, 3H), 2.53 (m, 2H), 2.17, 2.00, 1.82 (all m, total 5H).

MS (ESI) 494 (M–H)$^-$.

Anal calcd for C$_{27}$H$_{28}$LiNO$_6$S.1.00 H$_2$O: C, 62.42; H, 5.82; N, 2.70. Found: C, 62.19; H, 5.61; N, 2.70.

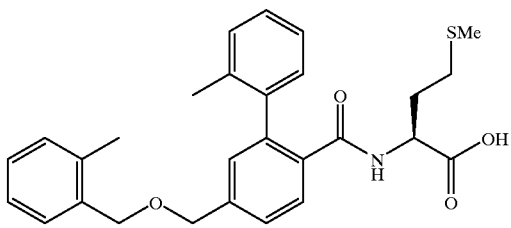

EXAMPLE 577

N-[4-(2-methylbenzyloxymethyl)-2-(2-methylphenyl)benzoyl]methionine lithium salt The desired compound was prepared according to the method of Example 157

(DMSO-d$_6$) δ7.55 (d,1H), 7.41 (dd, 1H), 7.32 (m, 1H), 7.18, 6.97 (both m, total 9H), 4.61 (s, 2H), 4.57 (s, 2H), 3.68 (m, 1H), 2.25 (s, 3H), 2.17, 2.00, 1.90 (all m, total 8H), 1.60 (m, 2H).

MS (APCI) 478 (M+H)$^+$.

Anal calcd for C$_{28}$H$_{30}$LiNO$_4$S.0.75 H$_2$O: C, 67.66; H, 6.39; N, 2.82. Found: C, 67.70; H, 6.23; N, 2.79.

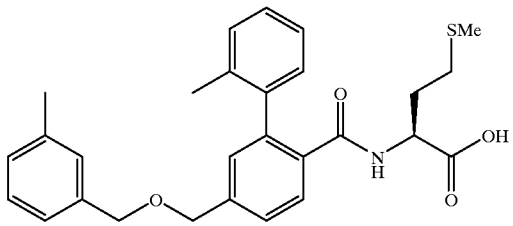

EXAMPLE 578

N-[4-(3-methylbenzyloxymethyl)-2-(2-methylphenyl)benzoyl]methionine lithium salt The desired compound was prepared according to the method of Example 157

(DMSO-d$_6$) δ7.55 (d,1H), 7.40 (dd, 1H), 7.22, 7.15, 6.97 (all m, total 10H), 4.60 (s, 2H), 4.53 (s, 2H), 3.68 (m, 1H), 2.30 (s, 3H), 2.17, 2.00, 1.90 (all m, total 8H), 1.62 (m, 2H).

MS (APCI) 478 (M+H)$^+$.

Anal calcd for C$_{28}$H$_{30}$LiNO$_4$S.0.75 H$_2$O: C, 67.66; H, 6.39; N, 2.82. Found: C, 67.83; H, 6.12; N, 2.82.

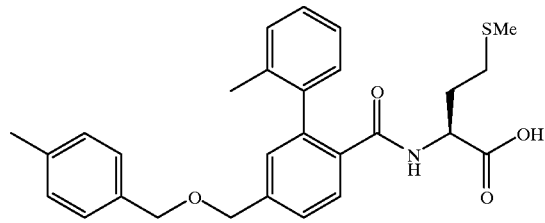

EXAMPLE 579

N-[4-(4-methylbenzyloxymethyl)-2-(2-methylphenyl)benzoyl]methionine lithium salt The desired compound was prepared according to the method of Example 157

(DMSO-d$_6$) δ7.55 (d,1H), 7.39 (dd, 1H), 7.22, 7.15, 6.95 (all m, total 10H), 4.59 (s, 2H), 4.50 (s, 2H), 3.68 (m, 1H), 2.28 (s, 3H), 2.17, 2.00, 1.90 (all m, total 8H), 1.62 (m, 2H).

MS (APCI) 478 (M+H)$^+$.

Anal calcd for C$_{28}$H$_{30}$LiNO$_4$S.0.75 H$_2$O: C, 67.66; H, 6.39; N, 2.82. Found: C, 67.51; H, 6.21; N, 2.72.

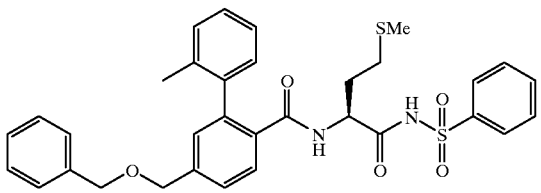

EXAMPLE 580

Benzenesulfonyl N-2-[4-(benzyloxymethyl)-2-(2-methylphenyl)benzoyl]amino-4-methylthiobutanamide The desired compound was prepared according to the method of Example 157. The resultant acid was reacted with 1,1'-carbonyldiimidazole and benzenesulfonamide to yield the title compound. (DMSO-$d_6$) δ7.75 (m, 2H), 7.52, 7.40, 7.37, 7.30, 7.15 (all m, total 16H), 4.60 (s, 2H), 4.57 (s, 2H), 4.00 (m, 1H), 2.17, 2.00, 1.90 (all m, total 8H), 1.60 (m, 2H).

MS (ESI) 601 (M–H)$^-$

Anal calcd for $C_{33}H_{34}N_2O_5S_2 \cdot 1.00\ H_2O$: C, 63.85; H, 5.85; N, 4.51. Found: C, 63.77; H, 5.40; N, 4.37.

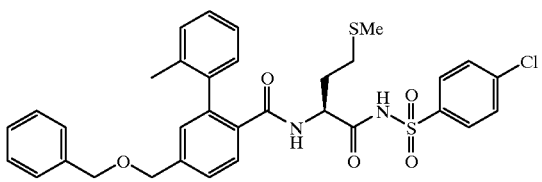

EXAMPLE 581

4-chlorobenzenesulfonyl N-2-[4-(benzyloxymethyl)-2-(2-methylphenyl)benzoyl]amino-4-methylthiobutanamide The desired compound was prepared according to the method of Example 157. The resultant acid was reacted with 1,1'-carbonyldiimidazole and 4-chlorobenzenesulfonamide to yield the title compound. (DMSO-$d_6$) δ7.65 (m, 2H), 7.52, 7.40, 7.37, 7.30, 7.15 (all m, total 16H), 4.60 (s, 2H), 4.57 (s, 2H), 4.00 (m, 1H), 2.17, 2.00, 1.90 (all m, total 8H), 1.60 (m, 2H).

MS (ESI) 601 (M–H)$^-$

Anal calcd for $C_{33}H_{34}N_2O_5S_2 \cdot 1.00\ H_2O$: C, 63.85; H, 5.85; N, 4.51. Found: C, 63.77; H, 5.40; N, 4.37.

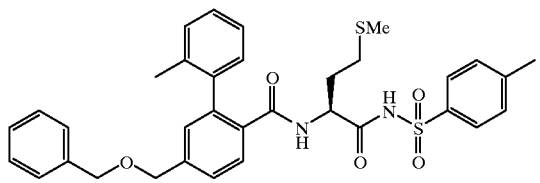

EXAMPLE 582

4-methylbenzenesulfonyl N-2-[4-(benzyloxymethyl)-2-(2-methylphenyl)benzoyl]amino-4-methylthiobutanamide The desired compound was prepared according to the method of Example 157. The resultant acid was reacted with 1,1'-carbonyldiimidazole and 4-methylbenzenesulfonamide to yield the title compound. (DMSO-$d_6$) δ7.60 (m, 2H), 7.50, 7.40, 7.37, 7.30, 7.15 (all m, total 15H), 4.60 (s, 2H), 4.57 (s, 2H), 4.00 (m, 1H), 2.34 (s, 3H), 2.17, 2.00, 1.90 (all m, total 8H), 1.60 (m, 2H).

MS (ESI) 617 (M+H)$^+$

Anal calcd for $C_{34}H_{36}N_2O_5S_2 \cdot 0.25\ H_2O$ and 1.00 HOAc: C, 63.46; H, 5.99; N, 4.11. Found: C, 63.31; H, 5.53; N, 4.26.

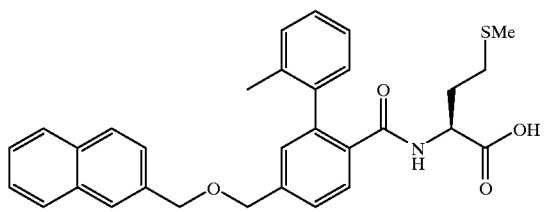

EXAMPLE 583

N-[4-(naphth-2-ylmethoxymethyl)-2-(2-methylphenyl)benzoyl]methionine lithium salt The desired compound was prepared according to the method of Example 157.

(DMSO-$d_6$) δ7.90 (m, 4H), 7.50 (m, 5H), 7.20, 6.98 (both m, total 6H), 4.72 (s, 2H), 4.65 (s, 2H), 3.70 (m, 1H), 2.17, 2.00, 1.90 (all m, total 8H), 1.63 (m, 2H).

MS (APCI) 514 (M+H)$^+$.

Anal calcd for $C_{31}H_{30}LiNO_4S \cdot 1.00\ H_2O$: C, 69.26; H, 6.00; N, 2.61. Found: C, 69.26; H, 5.82; N, 2.55.

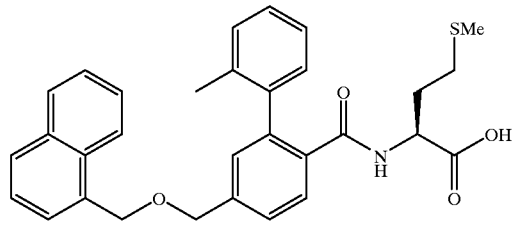

EXAMPLE 584

N-[4-(naphth-1-ylmethoxymethyl)-2-(2-methylphenyl)benzoyl]methionine lithium salt The desired compound was prepared according to the method of Example 157.

(DMSO-$d_6$) δ8.09 (m, 1H), 7.95 (m, 1H), 7.90 (m, 1H), 7.52 (m, 5H), 7.42 (m, 1H), 7.20, 6.98 (both m, total 6H), 5.01 (s, 2H), 4.68 (s, 2H), 3.70 (m, 1H), 2.17, 2.00, 1.90 (all m, total 8H), 1.63 (m, 2H).

MS (APCI) 514 (M+H)$^+$.

Anal calcd for $C_{31}H_{30}LiNO_4S \cdot 1.00\ H_2O$: C, 69.26; H, 6.00; N, 2.61. Found: C, 69.14; H, 5.72; N, 2.47.

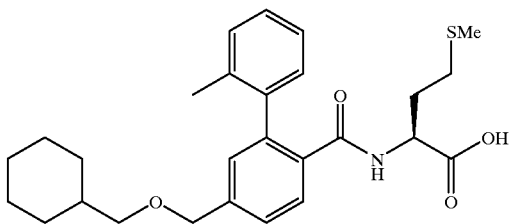

EXAMPLE 585

N-[4-(cyclohexylmethoxymethyl)-2-(2-methylphenyl)benzoyl]methionine lithium salt The desired compound was prepared according to the method of Example 157.

(DMSO-$d_6$) δ7.55 (d, 1H), 7.38 (dd, 1H), 7.20, 7.00 (both m, total 6H), 4.50 (s, 2H), 3.72 (m, 1H), 3.25 (d, 2H), 2.17, 2.00, 1.90 (all m, total 8H), 1.63 (m, 8H), 1.18 (m, 3H), 0.91 (m, 2H).

MS (ESI) 468 (M−H)⁻.

Anal calcd for $C_{27}H_{34}LiNO_4S \cdot 0.75\ H_2O$: C, 66.31; H, 7.32; N, 2.86. Found: C, 66.19; H, 7.36; N, 2.89.

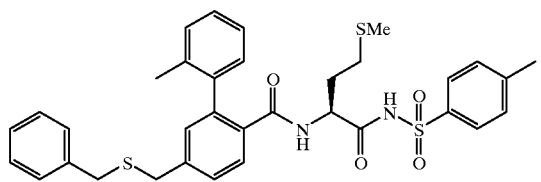

EXAMPLE 568

4-methylbenzenesulfonyl N-2-[4-(benzylthiomethyl)-2-(2-methylphenyl)benzoyl]amino-4-methylthiobutanamide The desired compound was prepared according to the method of Example 582.

(DMSO-$d_6$) δ7.67 (m, 2H), 7.44 (m, 1H), 7.30 (m, 14H), 4.02 (m, 1H), 3.73 (s, 2H), 3.68 (s, 2H), 2.37 (s, 3H), 2.17, 2.00, 1.90 (all m, total 8H), 1.60 (m, 2H).

MS (APCI) 633 (M+H)⁺

Anal calcd for $C_{34}H_{36}N_2O_4S_3 \cdot 2.25\ H_2O$: C, 60.64; H, 6.06; N, 4.16. Found: C, 60.51; H, 5.58; N, 4.37.

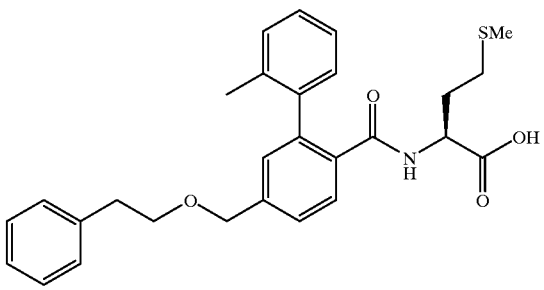

EXAMPLE 587

N-[4-(2-phenylethoxymethyl)-2-(2-methylphenyl)benzoyl]methionine lithium salt

The desired compound was prepared according to the method of Example 157. (DMSO-$d_6$) δ7.50 (d,1H), 7.33 (d, 1H), 7.20, 7.05 (both m, total 11H), 4.56 (s, 2H), 3.72 (m, 1H), 3.66 (t, 2H), 2.85 (t, 2H), 2.17, 2.00, 1.90 (all m, total 8H), 1.70 (m, 1H), 1.58 (m, 1H).

MS (APCI) 478 (M+H)⁺.

Anal calcd for $C_{28}H_{30}LiNO_4S \cdot 1.00\ H_2O$: C, 67.26; H, 6.43; N, 2.79. Found: C, 67.29; H, 6.31; N, 2.78.

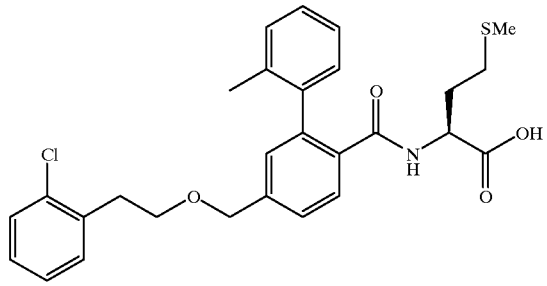

EXAMPLE 588

N-[4-(2-(2-chlorophenyl)ethoxymethyl)-2-(2-methylphenyl)benzoyl]methionine lithium salt The desired compound was prepared according to the method of Example 157.

(DMSO-$d_6$) δ7.50 (d,1H), 7.38 (d, 2H), 7.31 (d, 1H), 7.20, 7.05 (both m, total 8H), 4.56 (s, 2H), 3.82 (m, 1H), 3.66 (t, 2H), 3.00 (t, 2H), 2.17, 2.00, 1.90 (all m, total 8H), 1.70 (m, 1H), 1.58 (m, 1H).

MS (APCI) 512/514 (M+H)⁺.

Anal calcd for $C_{28}H_{29}ClLiNO_4S \cdot 0.50\ H_2O$: C, 63.81; H, 5.74; N, 2.66. Found: C, 63.84; H, 5.62; N, 2.62.

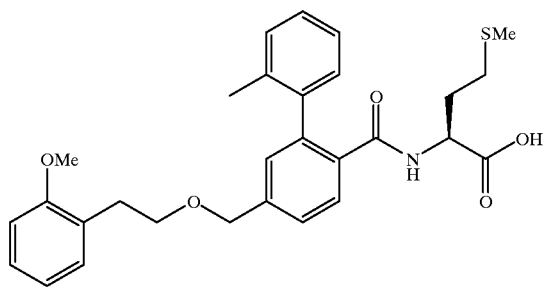

EXAMPLE 589

N-[4-(2-(2-methoxyphenyl)ethoxymethyl)-2-(2-methylphenyl)benzoyl]methionine lithium salt The desired compound was prepared according to the method of Example 157.

(DMSO-$d_6$) δ7.50 (d,1H), 7.33 (dd, 1H), 7.20, 7.16, 7.05, 6.99 (all m, total 8H), 6.92, (m, 1H), 6.82 (ddd, 1H), 4.54 (s, 2H), 3.74 (s, 3H), 3.72 (m, 1H), 3.60 (t, 2H), 2.83 (t, 2H), 2.17, 2.00, 1.90 (all m, total 8H), 1.70 (m, 1H), 1.58 (m, 1H).

MS (ESI) 506 (M−H)⁻.

Anal calcd for $C_{29}H_{32}LiNO_5S \cdot 0.40\ H_2O$: C, 66.88; H, 6.35; N, 2.69. Found: C, 66.90; H, 6.31; N, 2.66.

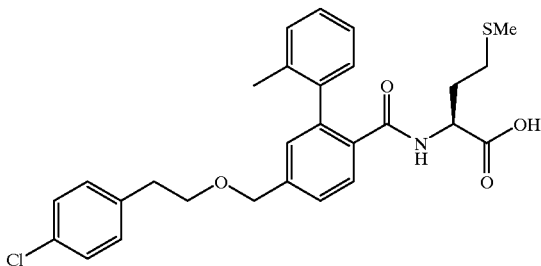

EXAMPLE 590

N-[4-(2-(4-chlorophenyl)ethoxymethyl)-2-(2-methylphenyl)benzoyl]methionine lithium salt The desired compound was prepared according to the method of Example 157.

(DMSO-$d_6$) δ7.50 (d,1H), 7.32, 7.27, 7.22, 7.15, 7.04 (all m, total 11H), 4.54 (s, 2H), 3.79 (m, 1H), 3.66 (t, 2H), 2.85 (t, 2H), 2.17, 2.00, 1.90 (all m, total 8H), 1.72 (m, 1H), 1.60 (m, 1H).

MS (ESI) 512/514 (M+H)$^+$.

Anal calcd for $C_{28}H_{29}ClLiNO_4S \cdot 1.00 \, H_2O$: C, 62.74; H, 5.83; N, 2.61. Found: C, 62.83; H, 5.50; N, 2.52.

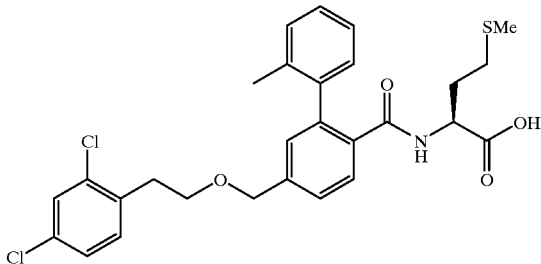

EXAMPLE 591

N-[4-(2-(2,4-dichlorophenyl)ethoxymethyl)-2-(2-methylphenyl)benzoyl]methionine lithium salt The desired compound was prepared according to the method of Example 157.

(DMSO-$d_6$) δ7.53 (d,1H) 7.50 (d, 1H), 7.41 (d, 1H), 7.21, 7.12, 7.03 (all m, total 8H), 4.56 (s, 2H), 3.75 (m, 1H), 3.67 (t, 2H), 2.98 (t, 2H), 2.17, 2.00, 1.90 (all m, total 8H), 1.70 (m, 1H), 1.58 (m, 1H).

MS (ESI) 544/546 (M−H)$^−$.

Anal calcd for $C_{28}H_{29}Cl_2LiNO_4S$: C, 60.88; H, 5.11; N, 2.54. Found: C, 60.57; H, 5.19; N, 2.42.

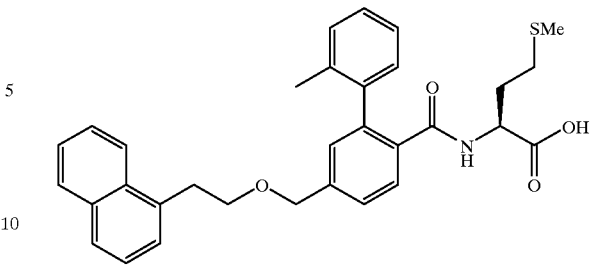

EXAMPLE 592

N-[4-(2-naphth-1-ylethoxymethyl)-2-(2-methylphenyl)benzoyl]methionine lithium salt The desired compound was prepared according to the method of Example 157.

(DMSO-$d_6$) δ8.09 (m, 1H), 7.90 (m, 1H), 7.78 (m, 1H), 7.48 (m, 3H), 7.42 (m, 2H), 7.31 (m, 1H), 7.22, 7.10, 6.98 (all m, total 6H), 4.59 (s, 2H), 3.80 (t, 2H), 3.73 (m, 1H), 3.33 (t, 2H), 2.17, 2.00, 1.90 (all m, total 8H), 1.70 (m, 1H), 1.58 (m, 1H).

MS (ESI) 526 (M−H)$^−$.

Anal calcd for $C_{32}H_{32}LiNO_4S \cdot 0.75 \, H_2O$: C, 70.25; H, 6.17; N, 2.56. Found: C, 70.27; H, 6.03; N, 2.49.

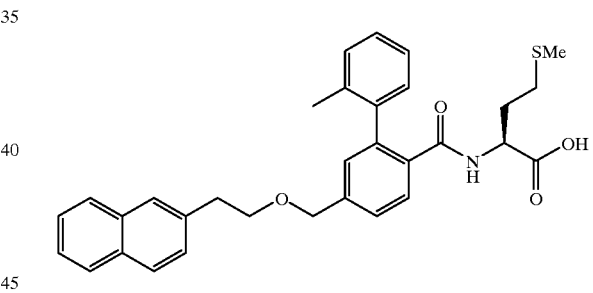

EXAMPLE 593

N-[4-(2-naphth-2-ylethoxymethyl)-2-(2-methylphenyl)benzoyl]methionine lithium salt The desired compound was prepared according to the method of Example 158.

(DMSO-$d_6$) (500 MHz) δ7.82 (d, 1H), 7.78 (m, 2H), 7.72 (s, 1H), 7.50 (d, 1H), 7.45 (m, 2H), 7.40 (d, 1H), 7.32 (d,1H), 7.20, 7.10, 6.98 (all m, total 6H), 4.57 (s, 2H), 3.81 (m, 1H), 3.79 (t, 2H), 3.02 (t, 2H), 2.17, 2.00, 1.90 (all m, total 8H), 1.70 (m, 1H), 1.58 (m, 1H).

MS (ESI) 526 (M−H)$^−$.

Anal calcd for $C_{32}H_{32}LiNO_4S \cdot 0.50 \, H_2O$: C, 70.83; H, 6.13; N, 2.58. Found: C, 70.90; H, 5.83; N, 2.45.

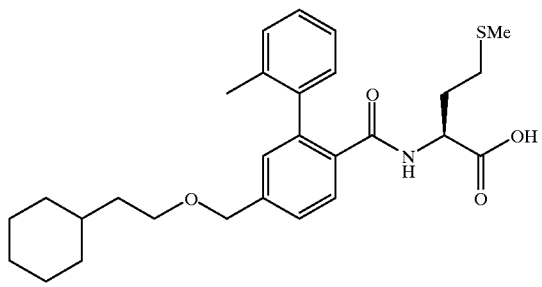

EXAMPLE 594

N-[4-(2-cyclohexylethoxymethyl)-2-(2-methylphenyl)benzoyl]methionine lithium salt The desired compound was prepared according to the method of Example 157.

(DMSO-$d_6$) δ7.55 (d, 1H), 7.38 (dd, 1H), 7.19, 7.10, 6.96 (all m, total 6H), 4.50 (s, 2H), 3.66 (m, 1H), 3.45 (t, 2H), 2.17, 2.00, 1.90 (all m, total 8H), 1.60 (m, 7H), 1.40 (m, 3H), 1.15 (m, 3H), 0.86 (m, 2H).

MS (ESI) 482 (M−H)⁻.

Anal calcd for $C_{28}H_{36}LiNO_4S.0.85\ H_2O$: C, 66.61; H, 7.53; N, 2.77. Found: C, 66.55; H, 7.56; N, 3.03.

EXAMPLE 595

N-[4-(3-phenylpropoxymethyl)-2-(2-methylphenyl)benzoyl]methionine lithium salt

The desired compound was prepared according to the method of Example 157.

(DMSO-$d_6$) δ7.54 (d,1H), 7.39 (dd, 1H), 7.20, 7.15, 7.10, 6.95 (all m, total 11H), 4.53 (s, 2H), 3.67 (m, 1H), 3.43 (t, 2H), 2.62 (t, 2H), 2.17, 2.00, 1.90, 1.84 (all m, total 10H), 1.70 (m, 1H), 1.58 (m, 1H).

MS (ESI) 492 (M+H)⁺.

Anal calcd for $C_{29}H_{32}LiNO_4S.0.60\ H_2O$: C, 68.51; H, 6.58; N, 2.75. Found: C, 68.49; H, 6.45; N, 2.77.

EXAMPLE 597

N-[4-(3-cyclohexylpropoxymethyl)-2-(2-methylphenyl)benzoyl]-N-methylmethionine lithium salt The desired compound was prepared according to the method of Example 157.

(DMSO-$d_6$) δ7.37, 7.20, 7.10 (all m, total 7H), 4.50 (m, 1H), 4.49, 4.46 (both s, total 2H), 3.42 (t, 2H), 2.62, 2.45, 2.17, 2.00, 1.90 (all m, total 11H), 1.60 (m, 8H), 1.17 (m, 7H), 0.83 (m, 2H).

MS (ESI) 510 (M−H)⁻.

Anal calcd for $C_{30}H_{40}LiNO_4S.0.50\ H_2O$: C, 68.42; H, 7.85; N, 2.66. Found: C, 68.33; H, 7.72; N, 2.82.

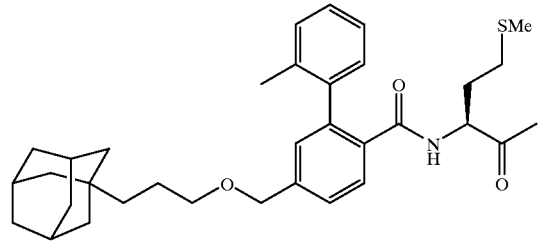

EXAMPLE 599

N-[4-(3-adamant-1-ylpropoxymethyl)-2-(2-methylphenyl)benzoyl]methionine lithium salt The desired compound was prepared according to the method of Example 157.

(DMSO-$d_6$) δ7.52 (d, 1H), 7.40 (m, 1H), 7.37 (dd, 1H), 7.20, 7.15, 7.10 (all m, total 5H), 4.50 (s, 2H), 3.86 (m, 1H), 3.40 (t, 2H), 2.17, 2.00, 1.90 (all m, total 10H), 1.60, 1.47, 1.40 (all m, total 17H), 1.04 (m, 2H).

MS (ESI) 548 (M−H)⁻.

Anal calcd for $C_{33}H_{42}LiNO_4S.0.25\ H_2O$: C, 70.75; H, 7.65; N, 2.50. Found: C, 70.56; H, 7.69; N, 2.66.

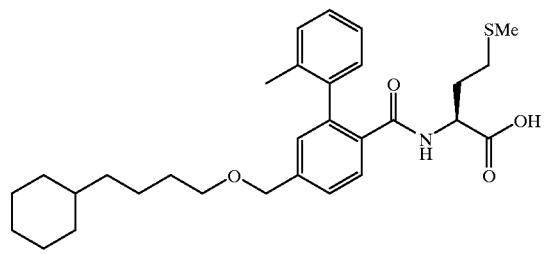

EXAMPLE 600

N-[4-(4-cyclohexylbutoxymethyl)-2-(2-methylphenyl)benzoyl]-N-methylmethionine

The desired compound was prepared according to the method of Example 157.

(DMSO-$d_6$) δ7.52 (d, 1H), 7.36 (d, 1H), 7.20, 7.10, 6.96 (all m, total 6H), 4.50 (s, 2H), 3.66 (m, 1H), 3.43 (t, 2H), 2.17, 2.00, 1.90 (all m, total 8H), 1.60 (m, 9H), 1.30 (m, 2H), 1.17 (m, 6H), 0.83 (m, 2H).

MS (APCI) 512 (M+H)⁺.

Anal calcd for $C_{30}H_{40}LiNO_4S.1.00\ H_2O$: C, 67.27; H, 7.90; N, 2.61. Found: C, 67.32; H, 7.70; N, 2.51.

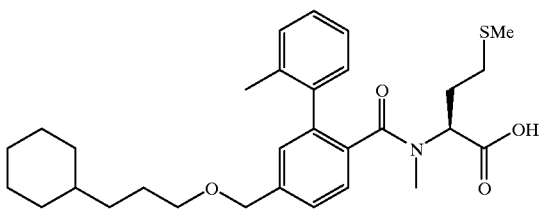

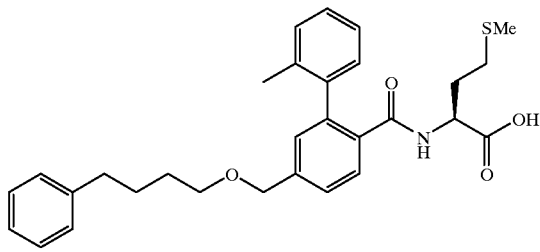

EXAMPLE 601

N-[4-(4-phenylbutoxymethyl)-2-(2-methylphenyl)benzoyl]-N-methylmethionine

The desired compound was prepared according to the method of Example 157.

(DMSO-$d_6$) δ7.52 (d,1H), 7.37 (dd, 1H), 7.20, 7.15, 7.10, 6.95 (all m, total 11H), 4.50 (s, 2H), 3.67 (m, 1H), 3.43 (t, 2H), 2.58 (t, 2H), 2.17, 2.00, 1.90 (all m, total 8H), 1.60 (m, 6H).

MS (APCI) 506 (M+H)$^+$.

Anal calcd for $C_{30}H_{34}LiNO_4S \cdot 0.50\ H_2O$: C, 69.21; H, 6.78; N, 2.69. Found: C, 69.08; H, 6.61; N, 2.78.

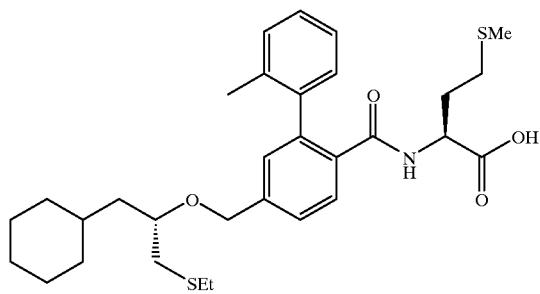

EXAMPLE 606

N-[4-(3-cyclohexyl-1-ethylthiopropan-2-ylaminomethyl)-2-(2-methylphenyl)benzoyl]methionine Lithium Salt The desired compound was prepared according to the method of Example 157.

MS (CI/NH$_3$) m/z: (M−H)$^−$556;

$^1$H NMR (DMSO-$d_6$, 300 MHz) δ7.53 (d, J=8 Hz, 1H), 7.37 (dd, J=8, 1 Hz, 1H), 7.21–7.12 (m, 4H), 6.94 (m, 1H), 4.66 (d, J=12 Hz, 1H), 4.51 (d, J=12 Hz, 3.75–3.55 (m, 2H), 2.78–2.45 (m, 4H), 2.18–1.92 (m, 7H), 1.74–1.54 (m, 7H), 1.46–1.23 (m, 3H), 1.18–1.04 (m, 7H), 0.94–0.85 (m, 2H);

Anal. Calcd for $C_{31}H_{42}LiNO_4S_2 \cdot 1.10\ H_2O$: C, 63.80; H, 7.63; N, 2.40. Found: C, 63.79; H, 7.28; N, 2.28.

Examples 729–747 were prepared by the procedure described in Example 157

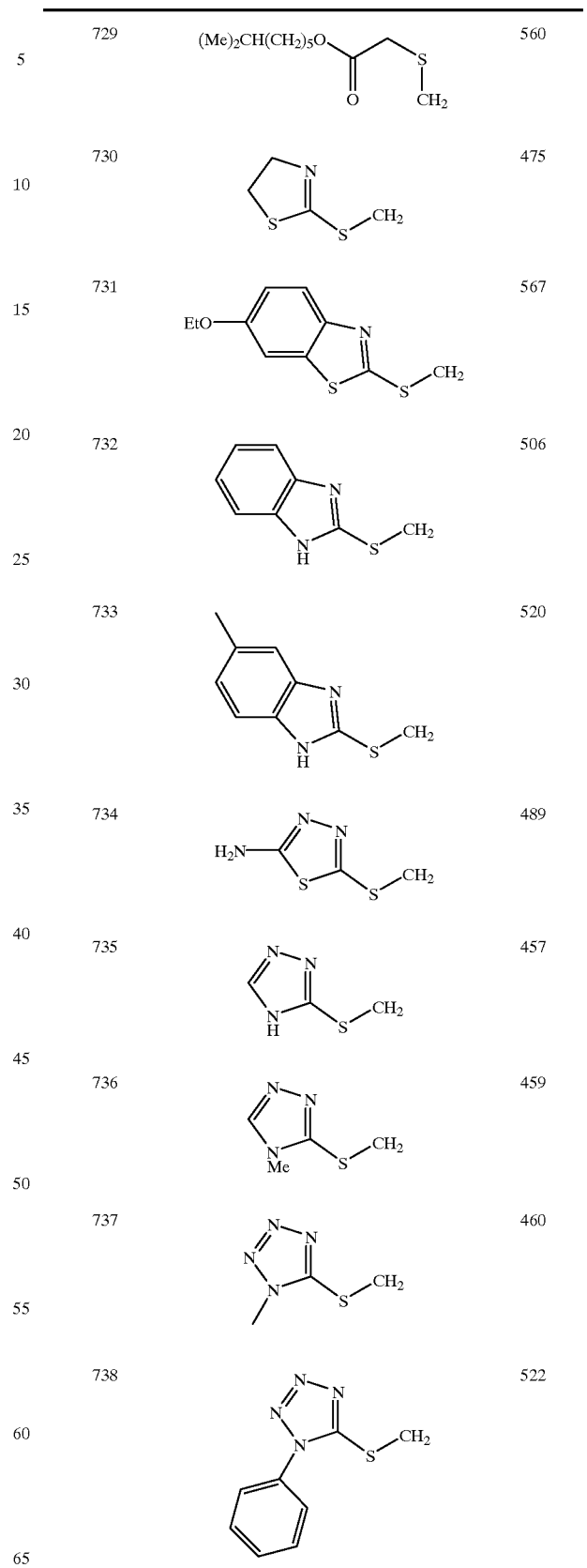

-continued

| | | |
|---|---|---|
| 739 | 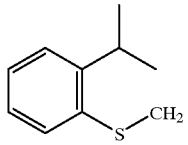 | 508 |
| 740 | 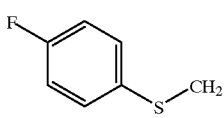 | 484 |
| 741 | 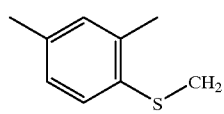 | 494 |
| 742 | 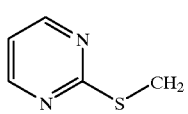 | 470 |
| 743 | 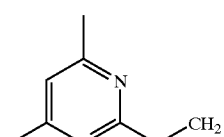 | 496 |
| 744 | 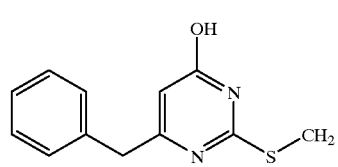 | 574 |
| 745 | 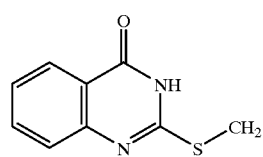 | 534 |
| 746 | 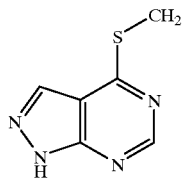 | 508 |
| 747 | 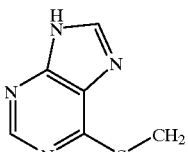 | 508 |

-continued

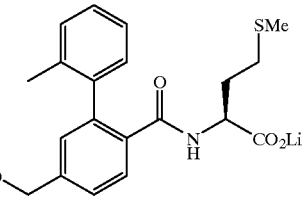

EXAMPLE 795

N-[4-(4-phenoxyphenoxymethyl)-2-(2-methylphenyl)benzoyl]methionine lithium salt

The desired compound was prepared according to the method of Example 157. $^1$H nmr (300 MHz, DMSO-d$_6$): δ7.58 (d, 1 H), 7.51 (d, 1 H), 7.35 (t, 2 H), 730–7.10 (m, 5 H), 7.10–6.96 (m, 7 H), 6.90 (dt, 1 H), 5.18 (s, 2 H), 2.12 (m, 2 H), 2.00 (br s, 3 H), 1.92 (br s, 3 H), 1.72 (m, 1 H), 1.58 (m, 1 H).

MS (ESI–): m/e 540 (M–H)$^-$.

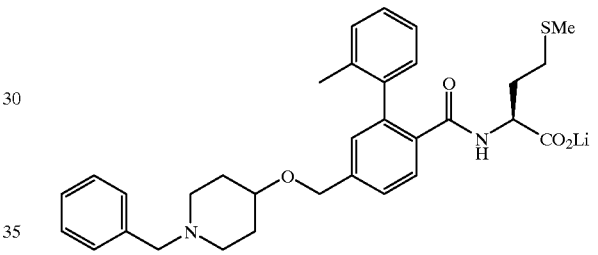

EXAMPLE 807

N-[4-(1-benzylpiperidin-4-yloxymethyl)-2-(2-methylphenyl)benzoyl]methionine lithium salt The desired compound was prepared according to the method of Example 157. $^1$H nmr (300 MHz, DMSO-d$_6$): δ7.52 (d, 1 H), 7.40–7.16 (m, 10 H), 7.10 (m, 1 H), 6.95 (m, 1 H), 4.55 (s, 2 H), 3.66 (m, 1 H), 3.43 (s, 2 H), 3.40 (m, 1 H), 3.16 (s, 2 H), 2.65 (m, 2 H), 2.18–1.98 (m, 6 H), 1.91 (br s, 3 H), 1.92–1.80 (m, 2 H), 1.70–1.44 (m, 3 H).

MS (ESI–): m/e 545 (M–H)$^-$.

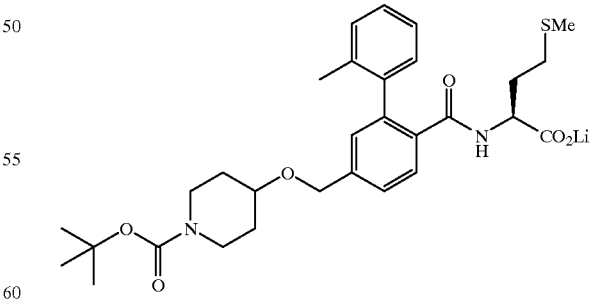

EXAMPLE 808

N-[4-(1-t-butoxycarbonylpiperidin-4-yloxymethyl)-2-(2-methylphenyl)benzoyl]methionine lithium salt The desired compound was prepared according to the method of Example 157. $^1$H nmr (300 MHz, DMSO-d$_6$):

δ7.52 (d, 1 H), 7.39 (dd, 1 H), 7.25–7.10 (m, 5 H), 6.94 (m, 1 H), 4.58 (s, 2 H), 4.10 (m, 1 H), 3.70–3.50 (m, 3 H), 3.17 (m, 2 H), 3.03 (m, 2 H), 2.18 (m, 2 H), 2.00 (br s, 3 H), 1.92 (br s, 3 H), 1.90–1.45 (m, 4 H), 1.39 (s, 9 H).

MS (ESI–): m/e 555 (M–H)⁻.

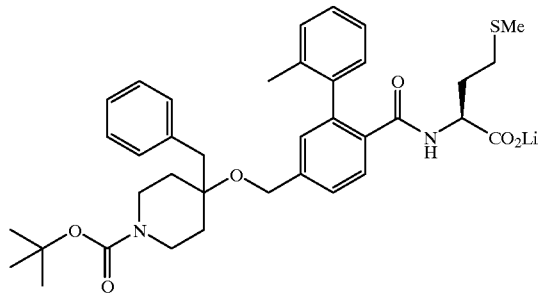

EXAMPLE 809

N-[4-(1-t-butoxycarbonyl-4-benzylpiperidin-4-yloxymethyl)-2-(2-methylphenyl)benzoyl]methionine lithium salt The desired compound was prepared according to the method of Example 157. $^1$H nmr (300 MHz, DMSO-d$_6$): δ7.52 (d, 1 H), 7.41 (dd, 1 H), 7.25–7.10 (m, 10 H), 6.94 (m, 1 H), 4.66 (s, 2 H), 3.72–3.60 (m, 3 H), 2.95 (m, 2 H), 2.91 (s, 2 H), 2.18 (m, 2 H), 2.00 (br s, 3 H), 1.92 (br s, 3 H), 1.80–1.37 (m, 6 H), 1.35 (s, 9 H).

MS (ESI–): m/e 645 (M–H)⁻.

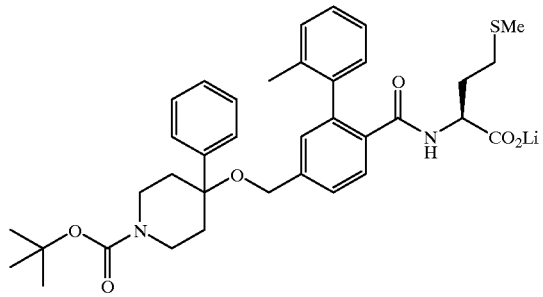

EXAMPLE 816

N-[4-(1-t-butoxycarbonyl-4-phenylpiperidin-4-yloxymethyl)-2-(2-methylphenyl)benzoyl]methionine lithium salt The desired compound was prepared according to the method of Example 157. $^1$H nmr (300 MHz, DMSO-d$_6$): δ7.49 (m, 3 H), 7.39 (m, 3 H), 7.30 (t, 1 H), 7.27–7.07 (m, 5 H), 6.95 (d, 1 H), 4.14 (s, 2 H), 3.85 (m, 32 H), 3.68 (m, 1 H), 3.10–3.05 (m, 2 H), 2.20–1.95 (m, 7 H), 1.92 (br s, 3 H), 1.83 (dt, 2 H), 1.70 (m, 1 H), 1.57 (m, 1 H), 1.40 (s, 9 H).

MS (ESI–): m/e 631 (M–H)⁻.

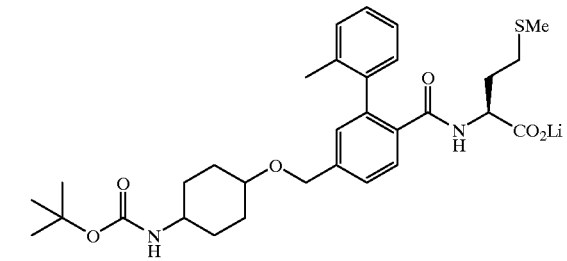

EXAMPLE 817

N-[4-(4-t-butoxycarbonylaminocyclohexyloxymethyl)-2-(2-methylphenyl)benzoyl]methionine lithium salt The desired compound was prepared according to the method of Example 157. $^1$H nmr (300 MHz, DMSO-d$_6$): δ7.51 (d, 1 H), 7.36 (dd, 1 H), 7.26–7.12 (m, 3 H), 7.10 (m, 1 H), 6.94 (m, 1 H), 6.70 (d, 1 H), 4.55 (s, 2 H), 3.67 (m, 1 H), 3.30–3.12 (m, 2 H), 2.16 (m, 2 H), 2.05–1.93 (m, 5 H), 1.91 (br s, 3 H), 1.82–1.50 (m, 4 H), 1.37 (s, 9 H), 1.30–1.10 (m, 4 H).

MS (ESI–): m/e 569 (M–H)⁻.

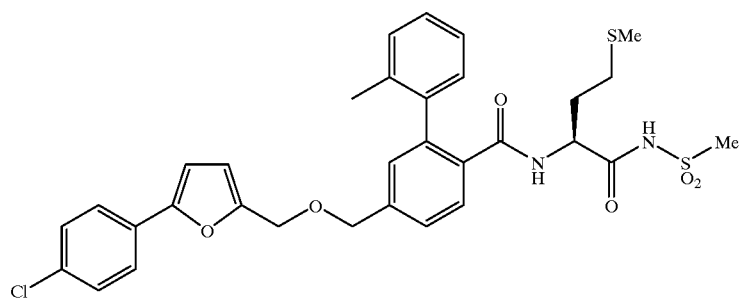

EXAMPLE 818

N-[4-(5-(4-chlorophenyl)furan-2-ylmethoxymethyl)-2-(2-methylphenyl)benzoyl]methionine methanesulfonimide The desired compound was prepared according to the method of Example 157.

$^1$H NMR (300 MHz, CDCl$_3$) δ7.99 (s, 1H), 7.57 (d, 2H), 7.48–7.40 (m, 2H), 7.36–7.18 (m, 6H), 6.60 (d, 1H), 6.42 (d, 1H), 4.66 (s, 2H), 4.58 (s, 2H), 3.23 (s, 3H), 2.16–1.40 (m, 10H, methyl signals at 2.16 and 2.13 buried in multiplet) CIMS, Calcd for C$_{32}$H$_{33}$O$_6$N$_2$S$_2$Cl APCI-Q1MS, MH- 639

EXAMPLE 820

N-[4-(5-(4-isopropylphenyl)furan-2-ylmethoxymethyl)-2-(2-methylphenyl)benzoyl] methionine lithium salt The desired compound was prepared according to the method of Example 157.

$^1$H NMR (300 MHz, d$_6$ DMSO) δ7.59–7.51 (m, 3H), 7.40 (bd, 1H), 7.28–7.11 (m, 7H), 7.00–6.91 (m, 1H), 6.82 (d, 1H), 6.55 (d, 1H), 4.61 (s, 2H), 4.54 (s, 2H), 3.70–3.61 (m, 1H), 2.92 (dq, 1H), 2.16–1.50 (m, 10H, methyl signals at 2.00 and 1.91 buried in multiplet),1.22 (d, 6H). Calcd for the acid C$_{34}$H$_{37}$O$_5$NS APCI-Q1MS, MH- 570

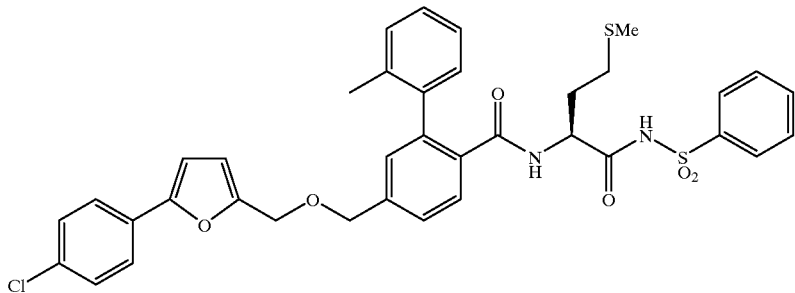

EXAMPLE 819

N-[4-(5-(4-chlorophenyl)furan-2-ylmethoxymethyl)-2-(2-methylphenyl)benzoyl]methionine benzenesulfonimide The desired compound was prepared according to the method of Example 157.

$^1$H NMR (300 MHz, d$_6$ DMSO) δ7.89–7.28 (m, 16H), 6.96 (d, 1H), 6.58 (d, 1H), 4.61 (s, 2H), 4.54 (s, 2H), 2.16–1.50 (m, 10H) Calcd for C$_{37}$H$_{35}$O$_6$N$_2$S$_2$Cl APCI-Q1MS, MH- 701

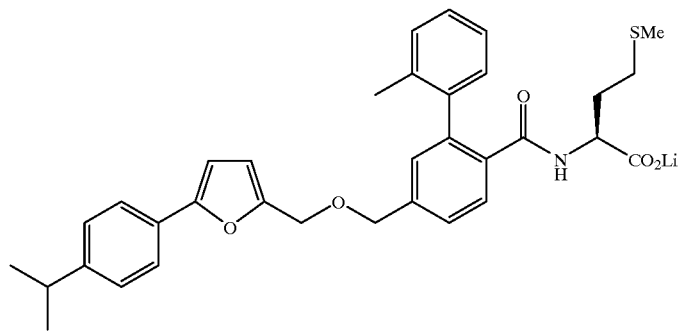

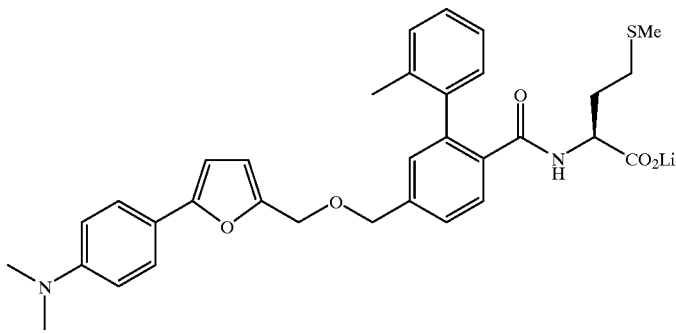

EXAMPLE 821

N-[4-(5-(4-N,N-dimethylaminophenyl)furan-2-ylmethoxymethyl)-2-(2-methylphenyl)benzoyl] methionine lithium salt The desired compound was prepared according to the method of Example 157.

$^1$H NMR (300 MHz, $d_6$ DMSO) δ7.54–7.44 (m, 3H), 7.40 (dd, 1H), 7.21–6.90 (m, 6H), 6.74–6.71 (m, 2H), 6.47 (d, 1H), 4.60 (s, 2H), 4.51 (s, 2H), 3.70–3.61 (m, 1H), 2.93 (s, 6H), 2.16–1.50 (m, 10H, Calcd for the acid $C_{33}H_{36}O_5N_2S$ APCI-Q1MS, MH– 571

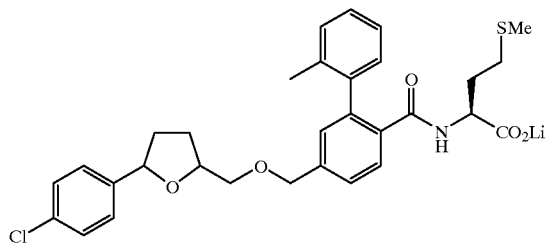

EXAMPLE 822

N-[4-(5-syn(4chlorophenyl)tetrahydrofuran-2-ylmethoxymethyl)-2-(2-methylphenyl)benzoyl] methionine lithium salt The desired compound was prepared according to the method of Example 157.

$^1$H NMR (300 MHz, $d_6$ DMSO) δ7.54 (d, 1H), 7.41–7.06 (m, 9H), 7.02–6.90 (m, 1H), 4.81 (dd, 1H), 4.62 (s, 2H), 4.18 (m, 1H), 3.70–3.50 (m, 3H), 2.31–1.48 (m, 14H).

Calcd for the acid $C_{31}H_{34}O_5NSCl$ FT HRMS MH+ 568.1919, found 568.1921.

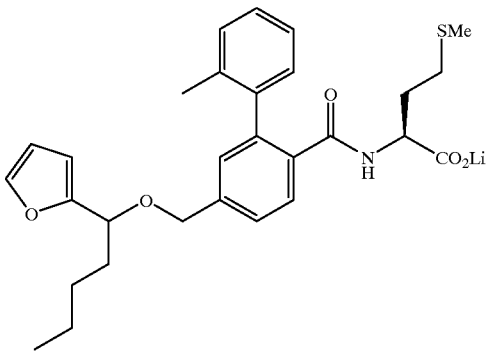

EXAMPLE 825

N-[4-(1-furan-2-ylpentyloxymethyl)-2-(2-methylphenyl)benzoyl]methionine lithium salt The desired compound was prepared according to the method of Example 157.

$^1$H NMR (DMSO-$d_6$,) δ7.63 (s, 1 H), 7.50 (d, 1 H, J=8.1 Hz), 7.32 (d, 1 H, J=7.5 Hz), 7.21–6.92 (m, 6 H), 6.43–6.40 (m, 1 H), 4.48–4.36 (m, 3 H), 3.67–3.61 (m, 1 H), 2.18–1.53 (m, 12 H), 1.28–1.14 (m, 4 H), 0.83–0.78 (m, 3 H); MS m/z 508 (M$^+$–1, 100).

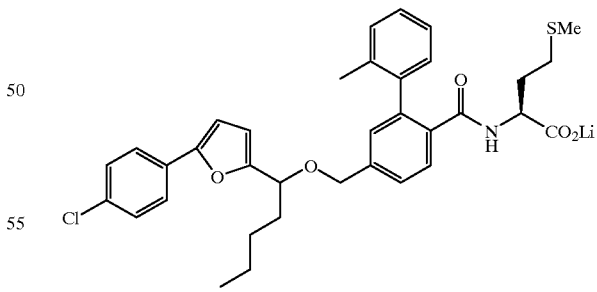

EXAMPLE 826

N-[4-(1-(5-(4-chlorophenyl)furan-2-yl)pentyloxymethyl)-2-(2-methylphenyl)benzoyl] methionine lithium salt The desired compound was prepared according to the method of Example 157.

¹H NMR (DMSO-d₆,) δ7.69–7.65 (m, 2 H), 7.50 (d, 1 H, J=7.8 Hz), 7.47–7.43 (m, 2 H), 7.37–7.33 (m, 1 H), 7.20–7.08 (m, 4 H), 6.96–6.92 (m, 2 H), 6.54 (dd, 1 H, J=3.4, 1.0 Hz), 4.57–4.43 (m, 3 H), 3.65–3.60 (m, 1 H), 2.18–1.1.51 (m, 12 H), 1.37–1.23 (m, 4 H), 0.86–0.80 (m, 3 H);

MS m/z 618 (M⁺–1, 100).

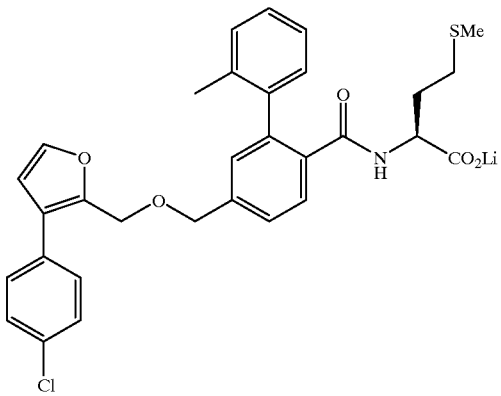

EXAMPLE 827

N-[4-(3-(4-chlorophenyl)furan-2-ylmethoxymethyl)-2-(2-methylphenyl)benzoyl]methionine lithium salt The desired compound was prepared according to the method of Example 157.

¹H NMR (DMSO-d₆,) δ7.67 (d, 1 H, J=2.0 Hz), 7.47–7.41 (m, 3 H), 7.38–7.29 (m, 3 H), 7.17–7.03 (m, 5 H), 6.92–6.87 (m, 1 H), 6.75 (d, 1 H, J=2.0 Hz), 4.54 (s, 2 H), 4.49 (s, 2 H), 3.61–3.56 (m, 1 H), 2.18–1.81 (m, 8 H), 1.74–1.64 (m, 1 H), 1.59–1.53 (m, 1 H);

MS m/z 562 (M⁺–1, 100).

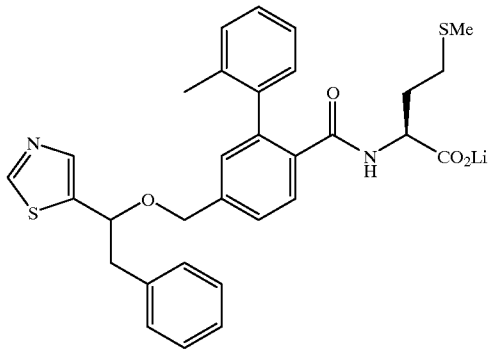

EXAMPLE 828

N-[4-(1-thiazol-5-yl-2-phenylethoxymethyl)-2-(2-methylphenyl)benzoyl]methionine lithium salt The desired compound was prepared according to the method of Example 157.

¹H NMR (DMSO-d₆,) δ9.06 (s, 1 H), 7.78 and 7.77 (2s, 1 H total), 7.43 (dd, 1 H, J=7.8, 2.4 Hz), 7.19–7.04 (m, 10 H), 6.97–6.88 (m, 2 H), 5.09–5.03 (m, 1 H), 4.50–4.45 (m, 1 H), 4.41–4.37 (M, 1 H), 3.68–3.59 (m, 1 H), 3.24–3.16 (m, 1 H), 3.07–2.98 (m, 1 H), 2.17–1.82 (m, 8 H), 1.73–1.64 (m, 1 H), 1.59–1.53 (m, 1 H);

MS m/z 559 (M⁺–1, 100).

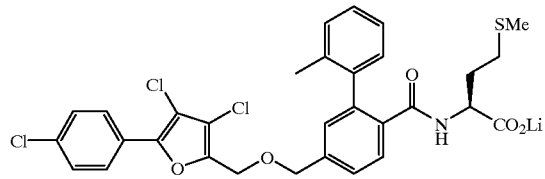

EXAMPLE 829

N-[4-(3,4-dichloro-5-(4-chlorophenyl)furan-2-ylmethoxymethyl)-2-(2-methylphenyl)benzoyl] methionine lithium salt The desired compound was prepared according to the method of Example 157.

¹H NMR (DMSO-d₆,) δ7.86–7.81 (m, 2 H), 7.61–7.56 (m, 2 H), 7.52 (d, 1 H, J=7.8 Hz), 7.39 (dd, 1 H, J=7.8, 1.7 Hz), 7.21–7.10 (m, 4 H), 6.97–6.92 (m, 2 H), 4.64 (s, 2 H), 4.62 (s, 2 H), 3.67–3.61 (m, 1 H), 2.18–1.83 (m, 8 H), 1.73–1.64 (m, 1 H) 1.59–1.52 (m, 1 H);

MS m/z 632 (M⁺–1, 100).

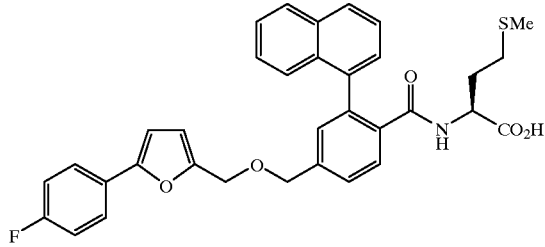

EXAMPLE 868

N-[4-(5-(4-fluorophenyl)furan-2-ylmethoxymethyl)-2-naphth-1-ylbenzoyl]methionine lithium salt The desired compound was prepared according to the method of Example 157.

¹H NMR(CD₃OD-d₄, 500 MHz) δ: 7.88 (m, 3H), 7.77 (d, J=7.5 Hz, 1H), 7.67 (d, J=7.5 Hz, 1H), 7.60–7.44 (m, 8H), 7.34 (m, 2H), 7.01 (m, 1H), 6.60 (d, J=2.5 Hz, 1H), 6.42 (d, J=2.5 Hz, 1H), 4.65 (s, 2H), 4.53 (s, 2H), 4.01–4.08 (m, 1H), 1.78 (s, 3H), 1.64–1.11(m, 4H).

MS: ESI (−) m/z: (M−H)⁻ 582

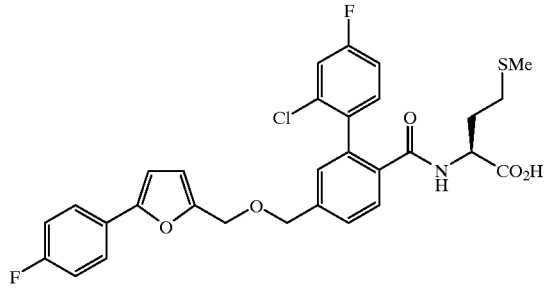

EXAMPLE 869

N-[4-(5-(4-fluorophenyl)furan-2-ylmethoxymethyl)-2-(2-chloro-4-fluorophenyl)benzoyl]methionine lithium salt The desired compound was prepared according to the method of Example 157.

707

$^1$H NMR(CD$_3$OD-d$_4$, 500 MHz) δ7.64 (m, 3H), 7.45 (m, 2H), 7.22 (m, 2H), 7.08 (m, 3H), 6.64 (d, J=2.5 Hz, 1H), 6.45 (d, J=2.5 Hz, 1H), 4.64 (s, 2H), 4.57 (s, 2H), 4.26 (m, 1H), 2.70–2.50 (M, 1H), 2.20 (m, 2H), 2.02 (s, 3H), 1.79 (m 1H). MS: ESI (–) m/z: (M–H)$^-$ 584

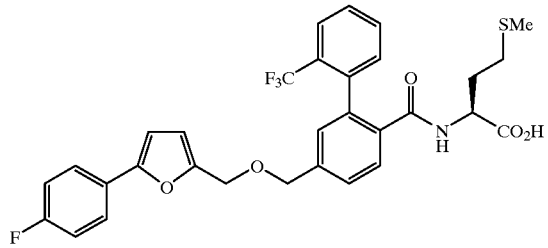

EXAMPLE 872

N-[4-(5-(4-fluorophenyl)furan-2-ylmethoxymethyl)-2-(2-trifluoromethylphenyl)benzoyl]methionine Lithium salt The desired compound was prepared according to the method of Example 157.

$^1$H NMR(CD$_3$OD-d$_4$, 500 MHz) δ7.88 (m,1H), 7.84 (m, 1H), 7.71 (m, 2H), 7.56–7.36 (m, 5H), 7.12 (m, 2H), 6.67 (d, J=2.5 Hz, 1H),6.46 (d, J=2.5 Hz, 1H), 4.55 (s, 4H), 2.30–2.20 (m, 2H), 2.10 (s, 3H), 2.09–2.0 (m, 2H).

MS: ESI (–) m/z: (M–H$_2$O)$^-$ 582

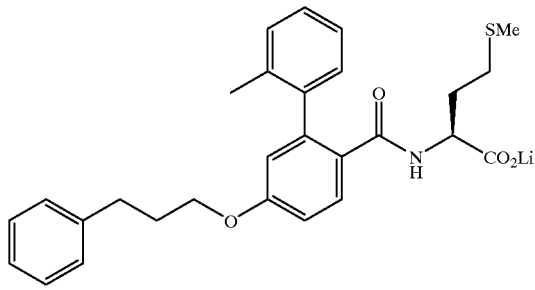

EXAMPLE 879

N-[4-(3-phenylpropoxy)-2-(2-methylphenyl)benzoyl]methionine, lithium salt

The desired compound was prepared according to the method of Example 6E–F $^1$H (300 MHz, D$_2$O): δ7.67, m, 1H; 7.00–7.23, m, 4H; 6.68–6.94, m, 6H; 6.40, s, 1H; 4.20, m, 1H; 3.51, m, 2H; 2.29, m, 2H; 1.69–2.05, m, 9H; 1.50–1.68, m, 3H.

MS (APCI(+)): 478 (MH+). Calc'd for C$_{28}$H$_{30}$LiNO$_4$S+ 1.22 (H$_2$O): C, 66.53; H, 6.47; N 2.77: Found: C, 66.53; H, 6.31; N, 2.44.

708

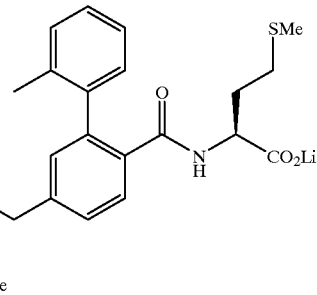

EXAMPLE 882

N-[4-(3-Cyclohexyl-1-methylthiopropan-2-yl)oxymethyl-2-(2-methylphenyl)benzoyl]methionine lithium salt The desired compound was prepared according to the method of Example 157.

$^1$H NMR (300 MHz, DMSO) δ0.70–0.95 (m, 2H), 1.00–1.15 (m, 3H), 1.30–1.50 (m, 3H), 1.50–1.70 (m, 7H), 1.93 (s, 3H), 2.00 (brs, 2H), 2.06 (s, 3H), 2.16 (brs, 2H) 2.59 (dd, J=13.5, 6.3 Hz, 1H), 2.71 (dd, J=13.5, 4.8 Hz, 1H), 3.60 (brs, 2H), 4.51 (d, J=12 Hz, 1H), 4.66 (d, J=12 Hz, 1H), 6.96 (brs, 1H), 7.10–7.28 (m, 5H), 7.38 (d, J=8 Hz, 1H), 7.52 (d, J=8 Hz, 1H).

MS (APCI(+)) m/z 544 (M+H);

Analysis calc'd for C$_{30}$H$_{40}$LiNO$_4$S$_2$.0.50 H2O: C, 64.49; H, 7.40; N, 2.51; found: C, 64.51; H, 7.21; N, 2.53.

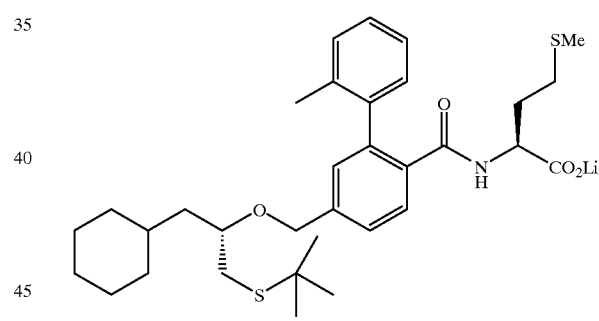

EXAMPLE 883

N-[4-(3-Cyclohexyl-1-t-butylthiopropan-2-yl)oxymethyl-2-(2-methylphenyl)benzoyl]methionine lithium salt The desired compound was prepared according to the method of Example 157.

$^1$H NMR (300 MHz, DMSO) δ0.70–0.95 (m, 2H), 1.01–1.15 (m, 3H), 1.24 (s, 9H), 1.35–1.43 (m, 3H), 1.50–1.65 (m, 7H), 1.91 (brs, 3H), 1.95–2.05 (m, 2H), 2.10–2.19 (m, 1H), 2.59 (dd, J=12.6, 6.8 Hz, 1H), 2.76 (dd, J=12.6, 4.8 Hz, 1H), 3.53–3.71 (m, 2H), 4.54 (d, J=12.5 Hz, 1H), 4.68 (d, J=12.6 Hz, 1H), 6.96 (brd, J=6 Hz, 1H), 7.10–7.25 (m, 5H), 7.37 (dd, J=8.0, 1.4 Hz, 1H), 7.52 (d, J=8.0 Hz, 1H).

MS (APCI(+)) m/z 586 (M+H);

Analysis calc'd for C$_{33}$H$_{46}$LiNO$_4$S$_2$.1.05H2O: C, 64.90; H, 7.94; N, 2.29; found: C, 64.88; H, 7.89; N, 2.28.

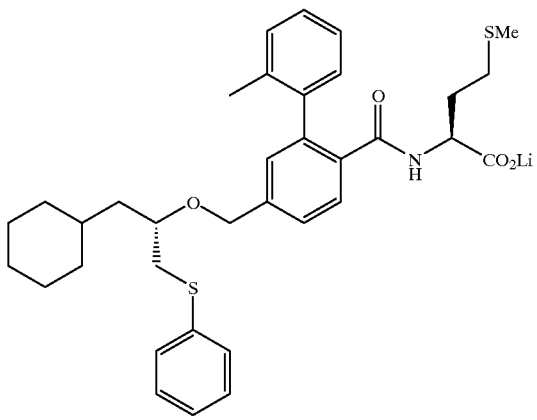

EXAMPLE 884

N-[4-(3-Cyclohexyl-1-phenylthiopropan-2-yl)oxymethyl-2-(2-methylphenyl)benzoyl]methionine lithium salt The desired compound was prepared according to the method of Example 157.

$^1$H NMR (300 MHz, DMSO) δ0.65–0.92 (m, 2H), 0.96–1.20 (m, 3H), 1.26–1.74 (m, 10H), 1.75–1.87 (m, 1H), 1.91 (s, 3H), 1.91–2.03 (m, 2H), 2.07–2.18 (m, 1H), 2.99–3.10 (m, 1H), 3.24 (dd, J=13.2, 4.7 Hz, 1H), 3.52–3.73 (m, 2H), 4.44 (d, J=12.6 Hz, 1H), 4.62 (d, J=12.6 Hz, 1H), 6.89–7.02 (m, 2H), 7.06–7.16 (m, 2H), 7.18–7.27 (m, 4H), 7.28–7.37 (m, 3H), 7.50 (d, J=7.8 Hz, 1H).

MS (APCI(–)) m/z 604 (M–1);

Analysis calc'd for $C_{35}H_{42}LiNO_4S_2$·1.10 H2O: C, 66.56; H, 7.05; N, 2.22; found: C, 66.57; H, 6.89; N, 2.18.

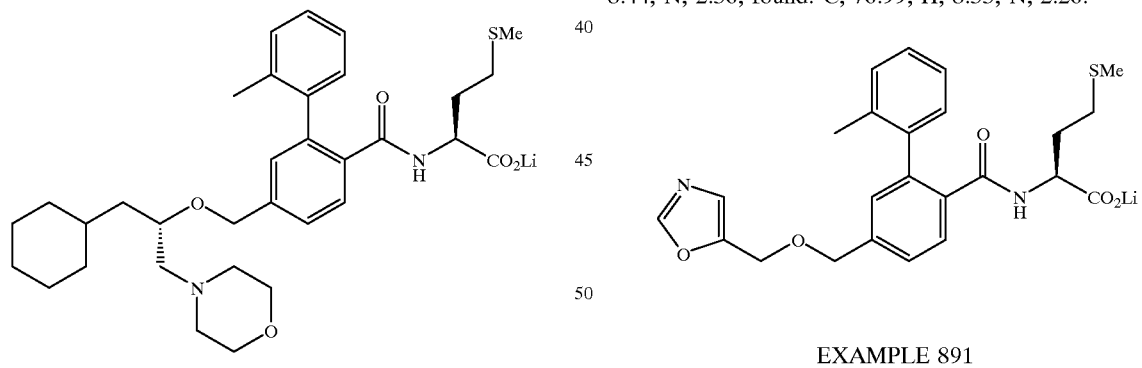

EXAMPLE 885

N-[4-(3-Cyclohexyl-1-morpholin-4-ylpropan-2-yl)oxymethyl-2-(2-methylphenyl)benzoyl]methionine trifluoroacetate salt The desired compound was prepared according to the method of Example 157.

$^1$H NMR (300 MHz, DMSO) δ0.86–1.00 (m, 2H), 1.12–1.39 (m, 5H), 1.56–1.76 (m, 8H), 1.95 (s, 3H), 2.00–2.20 (m, 5H), 3.03–3.78 (m, 7H), 3.85–3.99 (m, 2H), 4.23 (brs, 1H), 4.63 (s, 2H), 7.10–7.26 (m, 5H), 7.43 (dd, J=7.8, 1.3 Hz, 1H), 7.53 (d, J=7.8 Hz, 1H), 8.04 (m, 1H).

MS (APCI(–)) m/z 581 ((M–H);

Analysis calc'd for $C_{33}H_{46}N_2O_5S$·0.40H2O+1.25TFA: C, 58.21; H, 6.61; N, 3.82; found: C, 58.20; H, 6.62; N, 3.80.

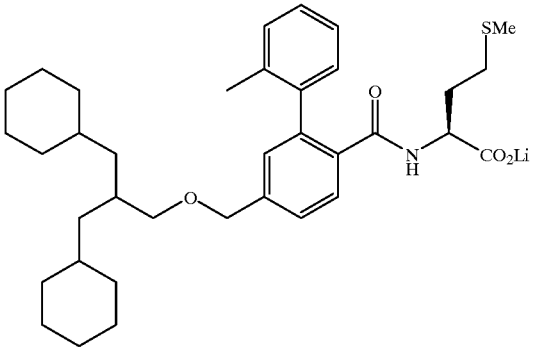

EXAMPLE 889

N-[4-(3-Cyclohexyl-2-cyclohexylmethylpropan-2-yl)oxymethyl-2-(2-methylphenyl)benzoyl]methionine lithium salt The desired compound was prepared according to the method of Example 157.

$^1$H NMR (300 MHz, DMSO) δ0.70–0.84 (m, 4H), 0.93–1.31 (m, 13H), 1.51–1.77 (m, 14H), 1.89 (s, 3H), 1.93–2.16 (m, 4H), 3.28 (s, 2H), 3.64 (brs, 1H), 4.50 (s, 2H), 6.92–6.98 (m, 1H), 7.09–7.24 (m, 5H), 7.33 (dd, J=7.8, 1.3 Hz, 1H), 7.52 (d, J=7.8 Hz, 1H).

MS (ESI(–)) m/z 592 ((M–H);

Analysis calc'd for $C_{36}H_{50}LiNO_4S$·0.5H2O: C, 71.02; H, 8.44; N, 2.30; found: C, 70.99; H, 8.33; N, 2.20.

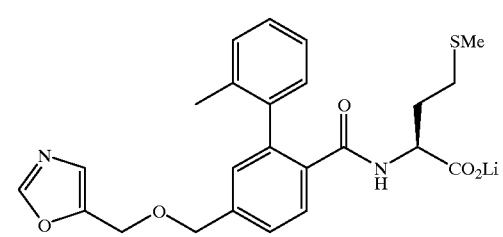

EXAMPLE 891

N-[4-(oxazol-5-ylmethoxymethyl)-2-(2-methylphenyl)benzoyl]methionine lithium salt The desired compound was prepared according to the method of Example 157.

$^1$H NMR (DMSO-d$_6$,) δ8.34 (s, 1 H), 7.53 (d, 1 H, J=7.9 Hz), 7.37 (d, 1 H, J=8.0 Hz), 7.22–7.07 (m, 6 H), 6.96–6.91 (m, 1 H), 4.59 (s, 2 H), 4.58 (s, 2 H), 3.73–3.69 (m, 1 H), 2.18–1.82 (m, 8 H), 1.74–1.64 (m, 1 H), 1.59–1.53 (m, 1 H);

MS m/z 453 (M$^+$–1, 100).

Exact mass calcd for $C_{24}H_{27}N_2O_5S$ 455.1629, found 455.1635.

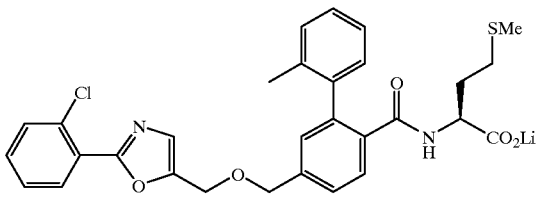

EXAMPLE 892

N-[4-(2-(2-chlorophenyl)oxazol-5-ylmethoxymethyl)-2-(2-methylphenyl)benzoyl]methionine lithium salt The desired compound was prepared according to the method of Example 157.

$^1$H NMR (DMSO-d$_6$,) δ8.49 (s, 1 H), 7.52–7.31 (m, 5 H), 7.26–7.22 (m, 5 H), 6.92–6.87 (m, 2 H), 4.53 (s, 2 H), 4.50 (m, 2 H), 3.68–3.62 (m, 1 H), 2.18–1.80 (m, 8 H ), 1.77–1.65 (m, 1 H), 1.58–1.52 (m, 1 H);

MS m/z 563 (M+–1, 100).

Exact mass calcd for C$_{30}$H$_{30}$ClN$_2$O$_5$S 565.1564, found 565.1578.

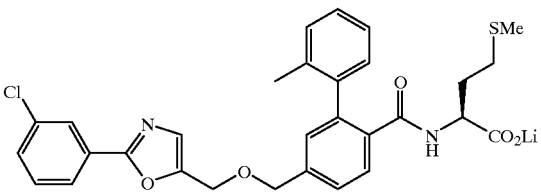

EXAMPLE 893

N-[4-(2-(3-chlorophenyl)oxazol-5-ylmethoxymethyl)-2-(2-methylphenyl)benzoyl]methionine lithium salt The desired compound was prepared according to the method of Example 157.

$^1$H NMR (DMSO-d$_6$,) δ8.49 (s, 1 H), 7.74–7.72 (m, 1 H), 7.64–7.61 (m, 1 H), 7.53 (d, 1 H, J=7.8 Hz), 7.48–7.38 (m, 3 H), 7.21–7.12 (m, 5 H), 6.99–6.94 (m, 1 H), 4.76 (s, 2 H), 4.64 (m, 2 H), 3.68–3.62 (m, 1 H), 2.15–1.80 (m, 8 H), 1.77–1.64 (m, 1 H), 1.58–1.52 (m, 1 H);

MS m/z 563 (M+–1, 100).

Exact mass calcd for C$_{30}$H$_{30}$ClN$_2$O$_5$S 565.1564, found 565.1588.

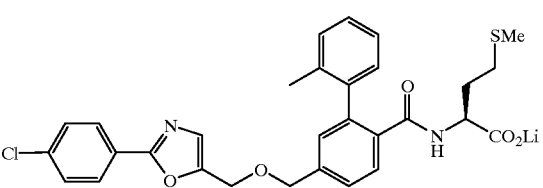

EXAMPLE 894

N-[4-(2-(4-chlorophenyl)oxazol-5-ylmethoxymethyl)-2-(2-methylphenyl)benzoyl]methionine lithium salt The desired compound was prepared according to the method of Example 157.

$^1$H NMR (DMSO-d$_6$,) δ8.46 (s, 1 H), 7.71–7.67 (m, 2 H), 7.54–7.46 (m, 3 H), 7.40–7.37 (m, 1 H), 7.21–7.12 (m, 5 H), 6.99–6.94 (m, 1 H), 4.74 (s, 2 H), 4.64 (m, 2 H), 3.68–3.62 (m, 1 H), 2.17–1.79 (m, 8 H), 1.77–1.63 (m, 1 H), 1.60–1.52 (m, 1 H);

MS m/z 563 (M+–1, 100).

Exact mass calcd for C$_{30}$H$_{30}$ClN$_2$O$_5$S 565.1564, found 565.1578.

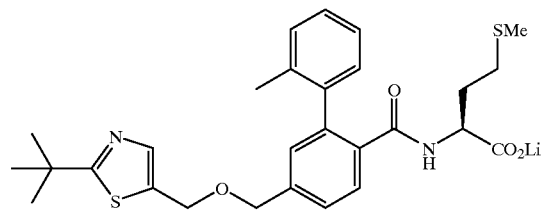

EXAMPLE 895

N-[4-(2-t-butylthiazol-5-ylmethoxymethyl)-2-(2-methylphenyl)benzoyl]methionine lithium salt The desired compound was prepared according to the method of Example 157.

$^1$H NMR (DMSO-d$_6$,) δ7.60 (s, 1 H), 7.53 (d, 1 H, J=7.8 Hz), 7.38 (dd, 1 H, J=7.8, 1.4 Hz), 7.21–7.11 (m, 5 H), 6.97–6.93 (m, 1 H), 4.72 (s, 2 H), 4.59 (m, 2 H), 3.68–3.62 (m, 1 H), 2.18–1.80 (m, 8 H), 1.77–1.63 (m, 1 H), 1.60–1.53 (m, 1 H), 1.35 (s, 9 H);

MS m/z 525 (M+–1, 100).

Exact mass calcd for C$_{28}$H$_{35}$N$_2$O$_4$S$_2$ 527.2033, found 527.2037.

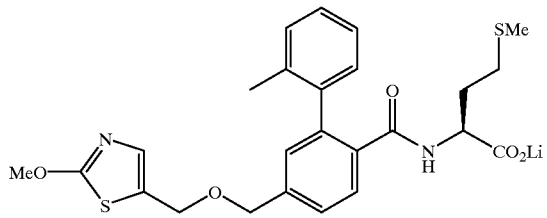

EXAMPLE 896

N-[4-(2-methoxythiazol-5-ylmethoxymethyl)-2-(2-methylphenylbenzoyl]methionine lithium salt The desired compound was prepared according to the method of Example 157.

$^1$H NMR (DMSO-d$_6$,) δ7.53 (d, 1 H, J=8.0 Hz), 7.37 (d, 1 H, J=7.9 Hz), 7.22–7.06 (m, 6 H), 6.97–6.87 (m, 1 H), 4.60 (s, 2 H), 4.56 (s, 2 H), 3.99 (s, 3 H), 3.71–3.64 (m, 1 H), 2.17–1.79 (m, 8 H), 1.73–1.64 (m, 1 H), 1.59–1.53 (m, 1 H);

MS m/z 501 (M++1, 100).

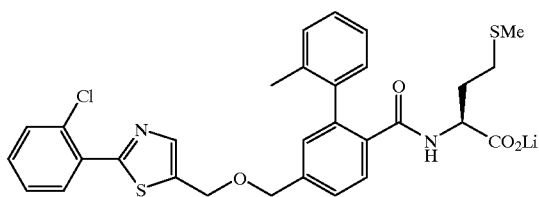

EXAMPLE 897

N-[4-(2-(2-chlorophenyl)thiazol-5-ylmethoxymethyl)-2-(2-methylphenyl)benzoyl]methionine lithium salt The desired compound was prepared according to the method of Example 157.

$^1$H NMR (DMSO-$d_6$,) δ8.19–8.14 (m, 1 H), 7.96 (s, 1 H), 7.67–7.61 (m, 1 H), 7.56–7.47 (m, 3 H), 7.41 (dd, 1 H, J=7.8, 1.4 Hz), 7.21–7.15 (m, 5 H), 6.98–6.95 (m, 1 H), 4.86 (s, 2 H), 4.66 (m, 2 H), 3.69–3.63 (m, 1 H), 2.18–1.82 (m, 8 H), 1.77–1.63 (m, 1 H), 1.60–1.53 (m, 1 H);

MS m/z 579 (M+−1, 100).

Exact mass calcd for $C_{30}H_{30}ClN_2O_4S_2$ 581.1336, found 581.1316.

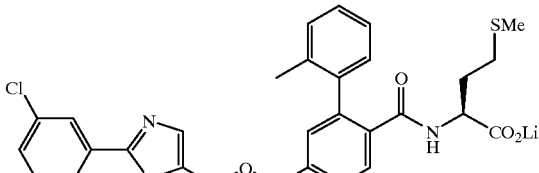

EXAMPLE 898

N-[4-(2-(3-fluorophenyl)thiazol-5-ylmethoxymethyl)-2-(2-methylphenyl)benzoyl]methionine lithium salt The desired compound was prepared according to the method of Example 157.

$^1$H NMR (DMSO-$d_6$,) δ7.90 (s, 1 H), 7.79–7.70 (m, 2 H), 7.59–7.52 (m, 2 H), 7.4–7.40 (m, 1 H), 7.37–7.31 (m, 1 H), 7.21–7.14 (m, 5 H), 6.98–6.95 (m, 1 H), 4.83 (s, 2 H), 4.64 (m, 2 H), 3.69–3.63 (m, 1 H), 2.17–1.79 (m, 8 H), 1.77–1.63 (m, 1 H), 1.60–1.53 (m, 1 H);

MS m/z 563 (M+−1, 100).

Exact mass calcd for $C_{30}H_{30}FN_2O_4S_2$ 565.1631, found 565.1624.

EXAMPLE 899

N-[4-(2-(3-chlorophenyl)thiazol-5-ylmethoxymethyl)-2-(2-methylphenyl)benzoyl]methionine lithium salt The desired compound was prepared according to the method of Example 157. $^1$H NMR (DMSO-$d_6$,) δ7.96–7.94 (m, 1 H), 7.91 (s, 1 H), 7.90–7.86 (m, 1 H), 7.56–7.53 (m, 3 H), 7.43–7.40 (m, 1 H), 7.21–7.14 (m, 5 H), 6.98–6.96 (m, 1 H), 4.83 (s, 2 H), 4.64 (m, 2 H), 3.69–3.63 (m, 1 H), 2.17–1.79 (m, 8 H), 1.77–1.63 (m, 1 H), 1.60–1.53 (m, 1 H);

MS m/z 579 (M+−1, 100).

Exact mass calcd for $C_{30}H_{30}ClN_2O_4S_2$ 581.1336, found 581.1339.

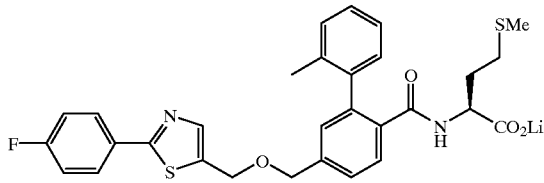

EXAMPLE 900

N-[4-(2-(4-fluorophenylthiazol-5-ylmethoxymethyl)-2-(2-methylphenyl)benzoyl]methionine lithium salt The desired compound was prepared according to the method of Example 157.

$^1$H NMR (DMSO-$d_6$,) δ8.00–7.95 (m, 2 H), 7.85 (s, 1 H), 7.54 (d, 1 H, J=7.7 Hz), 7.42–7.39 (m, 1 H), 7.37–7.31 (m, 2 H), 7.22–7.13 (m, 5 H), 6.98–6.95 (m, 1 H), 4.81 (s, 2 H), 4.63 (m, 2 H), 3.69–3.63 (m, 1 H), 2.17–1.79 (m, 8 H), 1.77–1.63 (m, 1 H), 1.60–1.53 (m, 1 H);

MS m/z 563 (M+−1, 100).

Exact mass calcd for $C_{30}H_{29}LiFN_2O_4S_2$ 571.1708, found 571.1707.

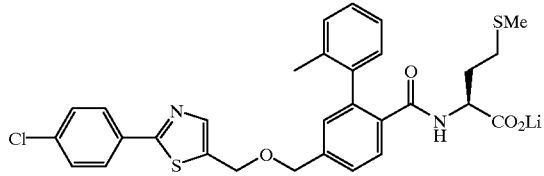

EXAMPLE 901

N-[4-(2-(4-chlorophenyl)thiazol-5-ylmethoxymethyl)-2-(2-methylphenyl)benzoyl]methionine lithium salt The desired compound was prepared according to the method of Example 157.

$^1$H NMR (DMSO-$d_6$,) δ7.97–7.92 (m, 2 H), 7.88 (s, 1 H), 7.58–7.53 (m, 3 H), 7.42–7.40 (m, 1 H), 7.22–7.13 (m, 5 H), 6.98–6.96 (m, 1 H), 4.82 (s, 2 H), 4.64 (m, 2 H), 3.69–3.62 (m, 1 H), 2.17–1.79 (m, 8 H), 1.77–1.63 (m, 1 H), 1.60–1.53 (m, 1 H);

MS m/z 579 (M+−1, 100).

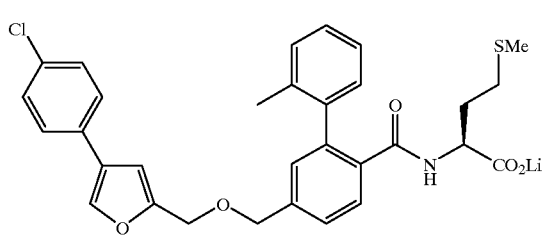

EXAMPLE 904

N-[4-(4-(4-chlorophenyl)furan-2-ylmethoxymethyl)-2-(2-methylphenyl)benzoyl]methionine lithium salt The desired compound was prepared according to the method of Example 157.

$^1$H NMR (DMSO-d$_6$,) δ8.20 (s, 1 H), 7.64–7.60 (m, 2 H), 7.55–7.52 (m, 1 H), 7.44–7.38 (m, 3 H), 7.21–7.11 (m, 5 H), 6.96–6.93 (m, 2 H), 4.60 (s, 2 H), 4.52 (s, 2 H), 3.71–3.64 (m, 1 H), 2.18–1.82 (m, 8 H), 1.74–1.64 (m, 1 H), 1.59–1.53 (m, 1 H);

MS m/z 562 (M+−1, 100).

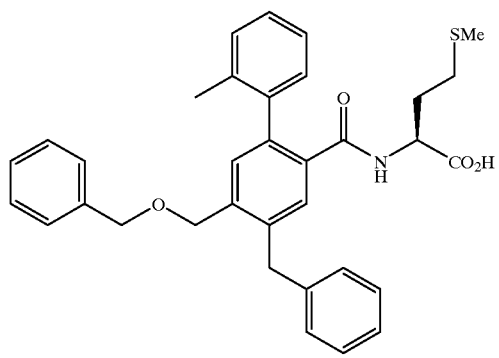

EXAMPLE 923

N-[5-Benzyl-4-benzyloxymethyl-2-(2-methylphenyl)benzoyl]methionine

The desired compound was prepared according to the method of Example 343 using 9-benzyl-9-BBN as the coupling partner. $^1$H (300 MHz, DMSO-d6, δ) 12.55 (1H, bs), 8.00 (1H, bd, J=12 Hz), 7.40–7.25 (8H, m), 7.25–7.10 (8H, m), 4.59 (2H, s), 4.50 (2H, s), 4.18 (1H, m), 4.07 (2H, s), 2.25–1.95 (4H, m), 1.93 (3H, s), 1.90–1.60 (3H, m). m/z ESI) 554 (MH+)

Anal.calc. for C$_{34}$H$_{35}$NO$_4$S C 73.75, H 6.37, N 2.53 Found C 73.47, H 6.12, N 2.27

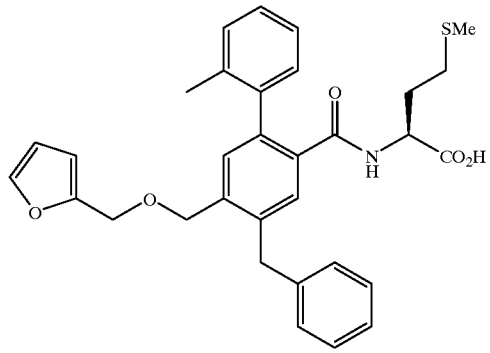

EXAMPLE 924

N-[5-Benzyl-4-(furan-2-yloxymethyl)-2-(2-methylphenyl)benzoyl]methionine

The desired compound was prepared according to the method of Example 343 using 9-benzyl-9-BBN as the coupling partner. $^1$H (300 MHz, DMSO-d6, δ) 12.55 (1H, bs), 7.98 (1H, bd, J=12 Hz), 7.63 (1H, m), 7.40–7.25 (4H, m), 7.25–7.00 (7H, m), 6.41 (2H, m), 4.47 (2H, s), 4.50 (2H, s), 4.18 (1H, m), 4.04 (2H, s), 2.25–1.90 (5H, m), 1.92 (3H, s), 1.90–1.60 (2H, m). m/z (ESI) 544 (MH+)

Anal.calc. for C$_{32}$H$_{33}$NO$_5$S.0.50 H$_2$O C 69.54, H 6.20, N 2.53 Found C 69.57, H 6.69, N 2.57

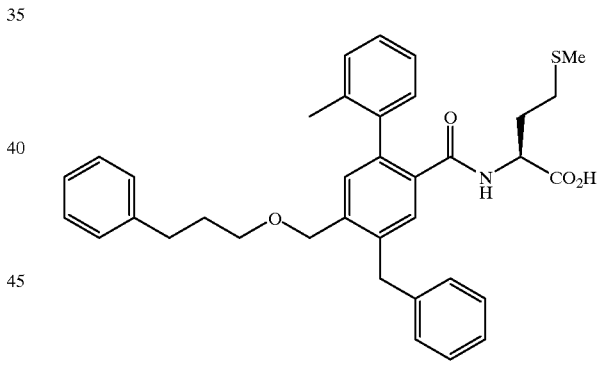

EXAMPLE 925

N-[5-Benzyl4-(2-phenylethoxymethyl)-2-(2-methylphenyl)benzoyl]methionine

The desired compound was prepared according to the method of Example 343 using 9-benzyl-9-BBN as the coupling partner. $^1$H (300 MHz, DMSO-d6, δ) 7.40–7.00 (16H, m), 6.86 (1H, bd, J=10 Hz), 4.51(2H, s), 4.18 (2H, s), 3.62 (1H, m), 3.41 (2H, t, J=8 Hz), 2.59 (2H, t, J=8 Hz), 2.25–1.95 (4H, m), 1.94 (3H, s), 1.80 (2H, m) 1.80–1.60 (3H, m). m/z (ESI) 580 (MH−)

Anal.calc. for C$_{36}$H$_{38}$LiNO$_4$S.1.70 H$_2$O C 69.93, H 6.75, N 2.27 Found C 69.61, H 6.30, N 2.06

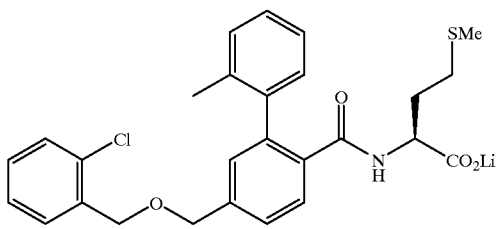

EXAMPLE 930

N-[4-(2-chlorobenzyloxymethyl)-2-(2-methylphenyl)benzoyl]methionine lithium salt The desired compound was prepared according to the method of Example 157

(DMSO-d6) δ7.56 (m, 2H), 7.43 (m, 2H), 7.35 (m, 2H), 7.18, 6.97 (both m, total 8H), 4.65 (s, 2H), 4.61 (s, 2H), 3.70 (m, 1H), 2.17, 2.00, 1.90 (all m, total 8H), 1.68, 1.59 (both m, total 2H).

MS (ESI) 498/500 (M+H)$^+$.

Anal calcd for $C_{27}H_{27}ClLiNO_4S \cdot 0.25\ H_2O$: C, 63.78; H, 5.45; N, 2.75. Found: C, 63.75; H, 5.41; N, 2.70.

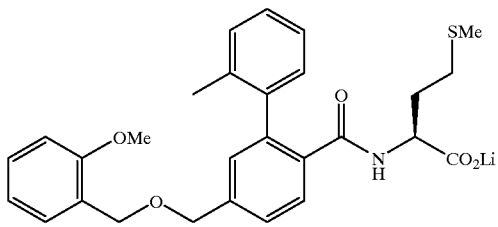

EXAMPLE 931

N-[4-(2-methoxybenzyloxymethyl)-2-(2-methylphenyl)benzoyl]methionine lithium salt The desired compound was prepared according to the method of Example 157

(DMSO-d$_6$) δ7.55 (d,1H), 7.40 (dd, 1H), 7.36 (dd, 1H), 7.26 (m, 1H), 7.18, 7.10 (both m, total 6H), 6.98 (d, 1H), 6.93 (ddd, 1H), 4.62 (s, 2H), 4.53 (s, 2H), 3.75 (m, 1H), 3.74 (s, 3H), 2.17, 2.00, 1.90 (all m, total 8H), 1.63 (m, 2H).

MS (ESI) 492 (M–H)$^-$.

Anal calcd for $C_{28}H_{30}LiNO_5S \cdot 0.50\ H_2O$: C, 66.13; H, 6.14; N, 2.75. Found: C, 65.99; H, 5.99; N, 2.66.

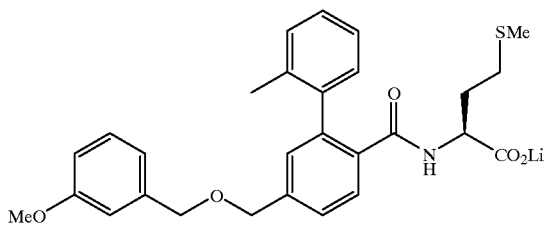

EXAMPLE 932

N-[4-(3-methoxybenzyloxymethyl)-2-(2-methylphenyl)benzoyl]methionine lithium salt The desired compound was prepared according to the method of Example 157

(DMSO-d$_6$) δ7.55 (d,1H), 7.41 (dd, 1H), 7.25, 7.18, 7.12, 6.97, 6.93 (all m, total 9H), 6.84 (m, 1H), 4.60 (s, 2H), 4.54 (s, 2H), 3.74 (s, 3H), 3.72 (m, 1H), 2.17, 2.00 1.90 (all m, total 8H), 1.63 (m, 2H).

MS (ESI) 492 (M–H)$^-$.

Anal calcd for $C_{28}H_{30}LiNO_5S \cdot 0.50\ H_2O$: C, 66.13; H, 6.14; N, 2.75. Found: C, 66.27; H, 5.82; N, 2.63.

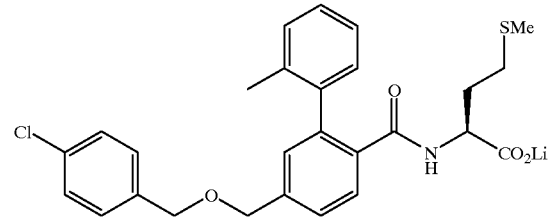

EXAMPLE 933

N-[4-(4-chlorobenzyloxymethyl)-2-(2-methylphenyl)benzoyl]methionine lithium salt The desired compound was prepared according to the method of Example 157 (D$_2$O) δ7.60 (d, 1H), 7.25, 7.13, 6.94, 6.88 (all m, total 11H), 4.20 (m, 5H), 2.05, 1.97, 1.90, 1.80, 1.70 (all m, 10H).

MS (ESI) 498/500 (M+H)$^+$.

Anal calcd for $C_{27}H_{27}ClLiNO_4S \cdot 0.25\ H_2O$: C, 63.78; H, 5.45; N, 2.75. Found: C, 63.52; H, 5.33; N, 2.72.

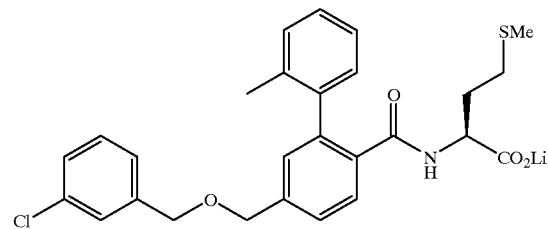

EXAMPLE 934

N-[4-(3-chlorobenzyloxymethyl)-2-(2-methylphenyl)benzoyl]methionine lithium salt The desired compound was prepared according to the method of Example 157

(DMSO-d$_6$) δ7.55 (d, 1H), 7.41 (m, 2H), 7.35 (m, 2H), 7.17, 6.97 (both m, total 7H), 4.61 (s, 2H), 4.58 (s, 2H), 3.69 (m, 1H), 2.17, 2.00, 1.90 (all m, total 8H), 1.68, 1.59 (both m, total 2H).

MS (ESI) 498/500 (M+H)$^+$.

Anal calcd for $C_{27}H_{27}ClLiNO_4S \cdot 0.25\ H_2O$: C, 63.78; H, 5.45; N, 2.75. Found: C, 63.72; H, 5.30; N, 2.71.

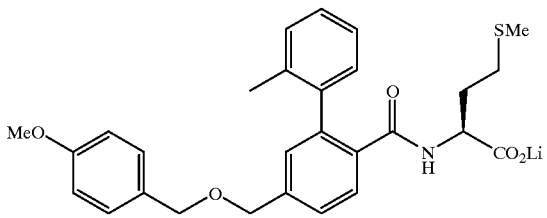

EXAMPLE 935

N-[4-(4-methoxybenzyloxymethyl)-2-(2-methylphenyl)benzoyl]methionine lithium salt The desired compound was prepared according to the method of Example 157

(DMSO-$d_6$) δ7.55 (d,1H), 7.39 (dd, 1H), 7.27 (dd, 2H), 7.20, 7.10, 6.97 (all m, total 7H), 6.90 (dd, 1H), 4.57 (s, 2H), 4.46 (s, 2H), 3.74 (s, 3H), 3.69 (m, 1H), 2.17, 2.00, 1.90 (all m, total 8H), 1.63 (m, 2H).

MS (ESI) 492 (M–H)⁻.

Anal calcd for $C_{28}H_{30}LiNO_5S\cdot 0.50\ H_2O$: C, 66.13; H, 6.14; N, 2.75. Found: C, 66.21; H, 5.93; N, 2.72.

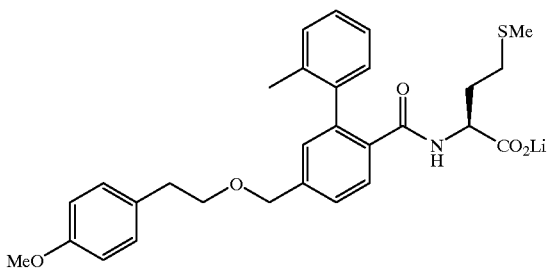

EXAMPLE 937

N-[4-(2-(4-methoxyphenyl)ethoxymethyl)-2-(2-methylphenylbenzoyl]methionine lithium salt The desired compound was prepared according to the method of Example 157

(DMSO-$d_6$) δ7.51 (d,1H), 7.32 (dd, 1H), 7.20, 7.07, 6.97 (all m, total 5H), 7.13 (dd, 2H), 6.80 (dd, 1H), 4.55 (s, 2H), 3.70 (s, 3H), 3.70 (m, 1H), 3.60 (t, 2H), 2.79 (t, 2H), 2.17, 2.00, 1.90 (all m, total 8H), 1.63 (m, 2H).

MS (ESI) 506 (M–H)⁻.

Anal calcd for $C_{29}H_{32}LiNO_5S\cdot 0.50\ H_2O$: C, 66.65; H, 6.36; N, 2.68. Found: C, 66.73; H, 6.33; N, 2.65.

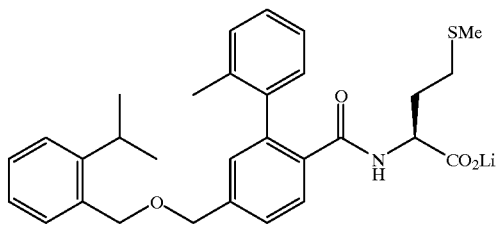

EXAMPLE 938

N-[4-(2-isopropylbenzyloxymethyl)-2-(2-methylphenyl)benzoyl]methionine lithium salt The desired compound was prepared according to the method of Example 157 (DMSO-$d_6$) δ7.55 (d,1H), 7.40 (d, 1H), 7.30, 7.20, 7.13, 6.98 (all m, total 10H), 4.61 (s, 2H), 4.59 (s, 2H), 3.70 (m, 1H), 3.18 (m, 1H), 2.17, 2.00, 1.90 (all m, total 8H), 1.62 (m, 2H), 1.15 (d, 6H).

MS (ESI) 504 (M–H)⁻.

Anal calcd for $C_{30}H_{34}LiNO_4S\cdot 0.85\ H_2O$: C, 68.38; H, 6.83; N, 2.66. Found: C, 68.04; H, 6.50; N, 3.06.

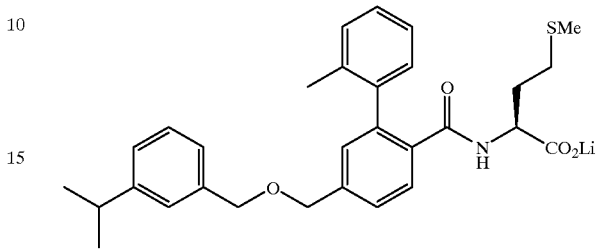

EXAMPLE 939

N-[4-(3-isopropylbenzyloxymethyl)-2-(2-methylphenyl)benzoyl]methionine lithium salt The desired compound was prepared according to the method of Example 157

(DMSO-$d_6$) δ7.55 (d,1H), 7.40 (d, 1H), 7.20, 7.15, 6.98 (all m, total 10H), 4.60 (s, 2H), 4.54 (s, 2H), 3.64 (m, 1H), 2.85 (m, 1H), 2.17, 2.00, 1.90 (all m, total 8H), 1.62 (m, 2H), 1.19 (d, 6H).

MS (ESI) 504 (M–H)⁻.

Anal calcd for $C_{30}H_{34}LiNO_4S\cdot 1.00\ H_2O$: C, 68.04; H, 6.85; N, 2.64. Found: C, 68.21; H, 6.51; N, 2.85.

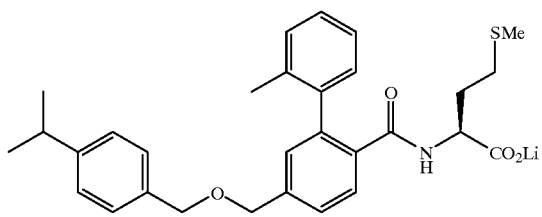

EXAMPLE 940

N-[4-(4-isopropylbenzyloxymethyl)-2-(2-methylphenyl)benzoyl]methionine lithium salt The desired compound was prepared according to the method of Example 157

(DMSO-$d_6$) δ7.55 (d,1H), 7.40 (dd, 1H), 7.25, 7.20, 7.15, 7.00 (all m, total 10H), 4.59 (s, 2H), 4.52 (s, 2H), 3.70 (m, 1H), 2.85 (m, 1H), 2.17, 2.00, 1.90 (all m, total 8H), 1.62 (m, 2H), 1.19 (d, 6H).

MS (ESI) 504 (M–H)⁻.

Anal calcd for $C_{30}H_{34}LiNO_4S\cdot 0.50\ H_2O$: C, 69.21; H, 6.78; N, 2.69. Found: C, 69.26; H, 6.72; N, 2.71.

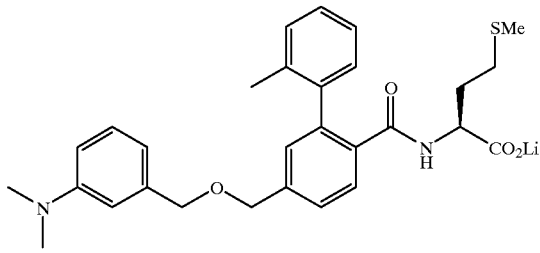

EXAMPLE 941

N-[4-(3-N,N-dimethylaminobenzyloxymethyl)-2-(2-methylphenyl)benzoyl]methionine lithium salt The desired compound was prepared according to the method of Example 157

(DMSO-d$_6$) δ7.55 (d,1H), 7.40 (dd, 1H), 7.27 (dd, 2H), 7.20, 7.15, 6.98 (all m, total 7H), 6.69 (m, 1H), 6.64 (dd, 2H), 4.49 (s, 2H), 4.54 (s, 2H), 3.69 (m, 1H), 2.85 (s, 6H), 2.17, 2.00, 1.90 (all m, total 8H), 1.62 (m, 2H).

MS (ESI) 505 (M–H)$^-$.

Anal calcd for C$_{29}$H$_{33}$LiN$_2$O$_4$S . 0.33 H$_2$O: C, 67.17; H, 6.54; N, 5.40. Found: C, 66.87; H, 6.13; N, 5.28.

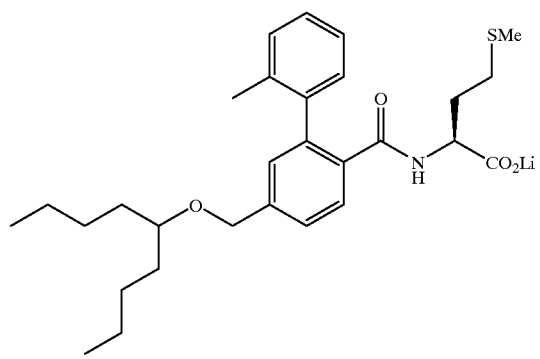

EXAMPLE 942

N-[4-(nonan-5-yloxymethyl)-2-(2-methylphenyl)benzoyl]methionine lithium salt

The desired compound was prepared according to the method of Example 157

(DMSO-d$_6$) δ7.55 (d,1H), 7.37 (d, 1H), 7.20, 7.10, 6.97 (all m, total 6H), 4.53 (s, 2H), 3.66 (m, 1H), 3.35 (m, 1H), 2.17, 2.00, 1.90, 1.60, 1.44, 1.25 (all m, total 16H), 0.84 (m, 6H).

MS (ESI) 498 (M–H)$^-$.

Anal calcd for C$_{29}$H$_{40}$LiNO$_4$S . 0.50 H$_2$O: C, 67.68; H, 8.03; N, 2.72. Found: C, 67.84; H,8.22; N, 2.63.

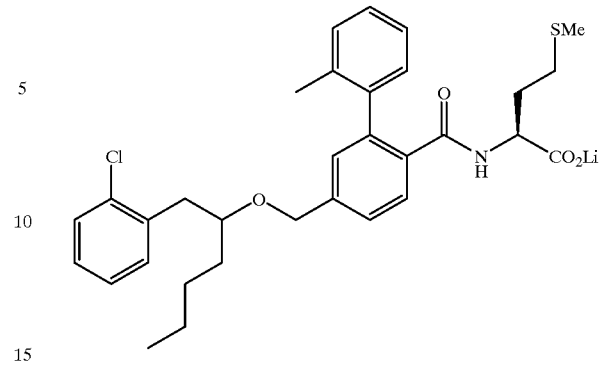

EXAMPLE 943

N-[4-(1-(2-chlorophenyl)hexan-2-yloxymethyl)-2-(2-methylphenyl)benzoyl]methionine lithium salt The desired compound was prepared according to the method of Example 157

(DMSO-d$_6$) δ7.45 (dd, 1H), 7.36 (m, 2H), 7.20, 6.96 (both m, total 9H), 4.54 (d, 1H), 4.44 (d, 1H), 3.66 (m, 2H), 2.98 (m, 1H), 2.85 (m, 1H), 2.17–1.20 (envelope, 16H), 0.83 (m, 3H).

MS (ESI) 566 (M–H)$^-$.

Anal calcd for C$_{32}$H$_{37}$ClLiNO$_4$S . 0.75 H$_2$O: C, 65.41; H, 6.60; N, 2.34. Found: C, 65.41; H,6.25; N, 2.38.

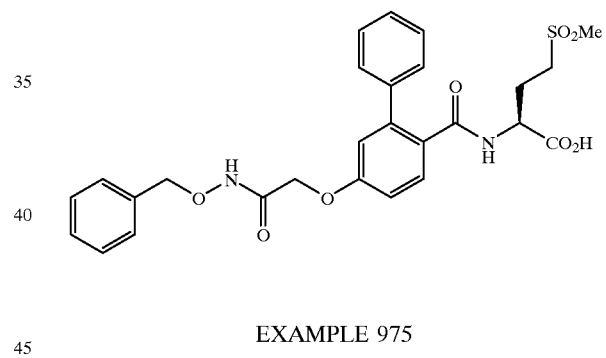

EXAMPLE 975

2-N-[4-(N-benzyloxyacetmidoxy)-2-phenylbenzoyl]amino-4-methanesulfonylbutanoic acid

EXAMPLE 975A

Methyl 4-Benzyloxy-2-phenylbenzoate

The methoxy group of compound methyl 4-methoxy-2-phenylbenzoate was deprotected to give methyl 4-hydroxy-2-phenylbenzoate by using the method described previously (EtSH—AlCl$_3$). The crude product (7.83 g, 34.3 mmol) was dissolved in 200 mL of acetone. To this solution was added benzylbromide (5.87 g, 34.3 mmol) and potassium carbonate (9.47 g, 2.0 eq). The mixture was refluxed for 12 hr. The reaction mixture was filtered and the filtrate was evaporated to dryness. The residue was dissolved in ether and washed with 1N HCl and 1N NaOH solution. The ether solution was evaporated. The pale yellow solid was recrystallized from 5% ethyl acetate in hexane to give the title compound as white crystals (7.53 g, yield 87%).

$^1$H NMR (CDCl$_3$) δ7.87 (d, J=8.6 Hz, 1H), 7.27–7.44 (m, 10H), 6.98 (d, J=8.6 Hz, 1H), 6.95 (s, 1H), 5.13 (s, 2H), 3.61 (s, 3H).

EXAMPLE 975B

N-[4-Benzyloxy-2-phenylbenzoyl]methionine methyl ester

The compound prepared in Example 975A was hydrolyzed with 1N aqueous NaOH and the carboxylic acid was coupled with (L)-methionine methyl ester by using coupling reagents. After flash column chromatography (1.5:1 =hexane/ethyl acetate), the desired compound was obtained (82% yield).

$^1$H NMR (CDCl$_3$) δ7.69 (d, J=8.5 Hz, 1H), 7.28–7.41 (m, 10H), 6.97 (d, J=8.5 Hz, 1H), 6.94 (s, 1H), 6.02 (d, J=7.7 Hz, 1H), 5.09 (s, 2H), 4.64 (ddd, J=5.1 and 7.7 Hz, 1H), 3.64 (s, 3H), 2.09 (t, J=7.6 Hz, 2H), 2.00 (s, 3H), 1.86–1.96 (m, 1H), 1.68–1.77 (m, 1H); $^{13}$C NMR (CDCl$_3$) δ171.4, 168.2, 159.3, 141.2, 139.8, 135.9, 130.3, 128.2, 128.1, 127.6, 127.4, 127.1, 126.9, 116.1, 113.0, 69.4, 51.7, 51.3, 30.7, 29.0, 14.7.

EXAMPLE 975C

Methyl N-[4-benzyloxy-2-phenylbenzoyl]amino-4-methanesulfonylbutanoate

The compound resulting from Example 975B (2.07 g, 4.67 mmol) was dissolved in a mixture of 60 mL of acetone and 15 mL of water. To this solution was added 4-methylmopholine-N-oxide (1.64 g, 3.0 eq) and 1.0 mL (0.019 eq) of OsO$_4$ solution (2.5% in tert-butanol). The mixture was stirred at r.t for 5 hr. The solvents were evaporated and the residue was extracted with ethyl acetate and water. After evaporation of solvents, the desired compound was obtained (2.22 g, 100% yield).

$^1$H NMR (CDCl$_3$) δ7.71 (d, J=8.6 Hz, 1H), 7.34–7.48 (m, 10 H), 7.02 (d, J=8.6 Hz, 1H), 6.93 (s, 1H), 5.88 (d, J=7.4 Hz, 1H), 5.13 (s, 2H), 4.65 (ddd, J=5.1 and 7.4 Hz, 1H), 3.67 (s, 3H), 2.85 (s, 3H), 2.62–2.82 (m, 2H), 2.20–2.28 (m, 1H), 1.88–1.98 (m, 1 H).

EXAMPLE 975D

Methyl 2-N-[4-(benzyloxycarbonylmethoxy)-2-phenylbenzoyl]amino-4-methanesulfonylbutanoate The compound resulting from Example 975C (2.44 g, 4.25 mmol) was hydrogenated at 1 atm in THF-CH$_3$OH to remove the benzyl group (yield 100%). The resulting compound (1.66 g, 4.25 mmol) was reacted with benzyl bromoacetate (1.07 g, 4.67 mmol) in acetone in the presence of K$_2$CO$_3$ (1.22 g, 8.84 mmol). After stirring at r.t for 10 hrs, the reaction mixture was worked up. The crude product was purified by recrystalization from 20% of ethyl acetate in hexane to give the title compound (2.17 g, 95% yield for 2 steps).

$^1$H NMR (CDCl$_3$) δ7.68 (d, J=8.7 hz, 1H), 7.41–7.47 (m, 3H), 7.31–7.39 (m, 7H), 6.92 (d, J=8.7 Hz, 1H), 6.84 (s, 1H), 5.87 (d, J=7.5 Hz, 1H), 5.24 (s, 2H), 4.73 (s, 2H), 4.64 (ddd, J=5.1 and 7.5 Hz, 1H), 3.67 (s, 3H), 2.84 (s, 3H), 2.62–2.81 (m, 2.22–2.28 (m, 1H), 1.92–2.00 (m, 1H).

EXAMPLE 975E

2-N-[4-(N-benzyloxyacetamidoxy)-2-phenylbenzoyl]amino-4-methanesulfonylbutanoic acid The compound resulting from Example 975D (279 mg, 0.50 mmol) was suspended in 6 mL of methanol and 2.0 mL of 0.5 N LiOH solution. After stirring at 0° C. for 2 hr and at r.t for 2 hr, the solvents were evaporated and the residue was dissolved in 20 mL of water. The aqueous solution was filtered and the filtrate was acidified with 1 N HCl solution. The white precipitate was collected (263 mg, 97% yield).

$^1$H NMR (CDCl$_3$ and 1 drop of CD$_3$OD) δ8.92 (s, 1H), 7.67 (d, J=8.5 Hz, 1H), 7.40–7.47 (m, 3H), 7.26–7.38 (m, 7H), 6.85 (d, J=8.5 Hz, 1H), 6.78 (s, 1H), 6.00 (d, J=7.5 Hz, 1H), 4.93 (s, 2H), 4.60–4.67 (m, 3H), 2.84 (s, 3H), 2.64–2.78 (m, 2H), 2.20–2.24 (m, 1H), 1.90–1.95 (m, 1H).

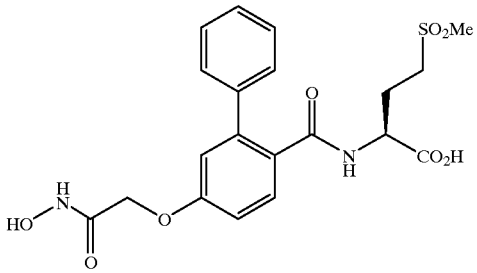

EXAMPLE 976

2-N-[4-(N-hydroxyacetamidoxy)-2-phenylbenzoyl] amino-4-methanesulfonylbutanoic acid The compound resulting from Example 975D (279 mg, 0.50 mmol) was suspended in 6 mL of methanol and 2.0 mL of 0.5 N LiOH solution. After stirring at 0° C. for 2 hr and at r.t for 2 hr, the solvents were evaporated and the residue was dissolved in 20 mL of water. The aqueous solution was filtered and the filtrate was acidified with 1 N HCl solution. The white precipitate was collected (263 mg, 97% yield). TLC showed this compound was pure (R$_f$=0.50, 30:3:1 =CH$_2$Cl$_2$/CH$_3$OH/HOAc). This compound (176 mg) was dissolved in 4 mL of THF and 4 mL of methanol. The solution was hydrogenated at 1 atm in the presence of catalytic amount of Pd/C. After 1 hr, the reaction mixture was filtered. The filtrate was evaporated to dryness. The residue was dissolved in 10 mL of water and the aqueous solution was lyophilized to give the title compound as a white solid (141 mg, 96% yield).

$^1$H NMR (CD$_3$OD) δ7.52 (d, J=8.4 Hz, 1H), 7.35–7.45 (m, 5H), 7.04 (d, J=8.4 Hz, 1H), 7.00 (s, 1H), 4.62 (s, 2H), 4.44 (dd, J=4.6 and 9.2 Hz, 1H), 2.88 (s, 3H), 2.77–2.82 (m, 1H), 2.59–2.68 (m, 1H), 2.21–2.29 (m, 1H), 1.96–2.00 (m, 1H); $^{13}$C NMR (CD$_3$OD) δ173.6, 172.7, 167.4, 160.2, 143.5, 141.5, 130.9, 130.5, 129.8, 129.6, 129.1, 117.5, 114.3, 67.3, 52.6, 51.8, 40.7, 25.3.

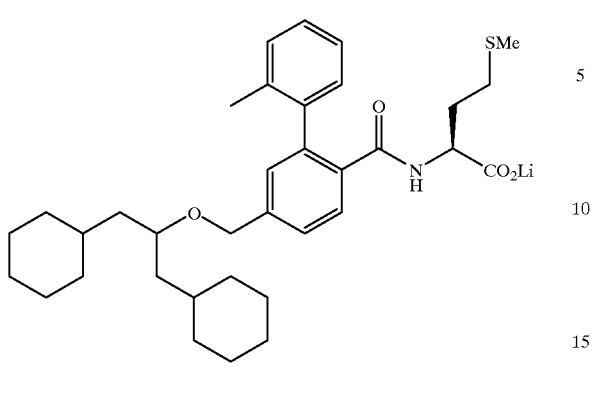

EXAMPLE 981

N-[4-(1,3-dicyclohexylpropan-2-yloxymethyl)-2-(2-methylphenyl)benzoyl]methionine lithium salt The desired compound was prepared according to the method of Example 157

$^1$H NMR (300 MHz, CDCl$_3$) δ0.81–1.00 (m, 6H), 1.09–1.78 (m, 20H), 1.86 (2.20, J=m Hz, 3H), 2.08 (s, 3H), 2.16 (m, 3H), 3.58 (m, 1H), 4.50–4.59 (m, 3H), 5.84–5.96 (m, 1H), 7.18 (brs, 1H), 7.26–7.47 (m, 6H), 7.94–8.02 (m, 1H).

MS (DCI(NH$_3$)) m/z 580 (M+H);

Analysis calc'd for C$_{35}$H$_{48}$NO$_4$SLi+1.0LiOTf+0.25H$_2$O: C, 69.30; H, 7.68; N, 2.69; found: C, 62.60; H, 6.93; N, 1.96.

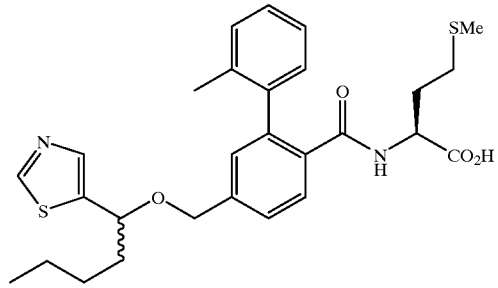

EXAMPLE 985

N-[4-(2-thiazol-5-ylbut-2-oxymethyl)-2-(2-methylphenyl)benzoyl]methionine

The desired compound was prepared according to the method of Example 157 $^1$H nmr (300 MHz, DMSO d$_6$): δ12.57, bs, 1H; 9.08, s, 1H; 8.09, bd, 1H; 7.86, d, 1H; 7.50, d, 1H; 7.33, dd, 1H; 7.20, m, 2H; 7.07–7.17, m, 3H; 4.78, t, 1H; 4.45, q (AA'), 2H; 4.23, ddd, 1H; 2.00–2.24, m, 4H; 1.97, s, 3H; 1.62–1.95, m, 4H; 1.24, m, 4H; 0.82, t, 1.5H; 0.81, t, 1.5H.

MS (ESI(−)): 525 (M−H); (ESI(+)): 527. Calc'd for C$_{28}$H$_{34}$N$_2$O$_4$S$_2$: C 63.85, H 6.51, N 5.32: Found: C 63.62, H 6.54, N 5.16.

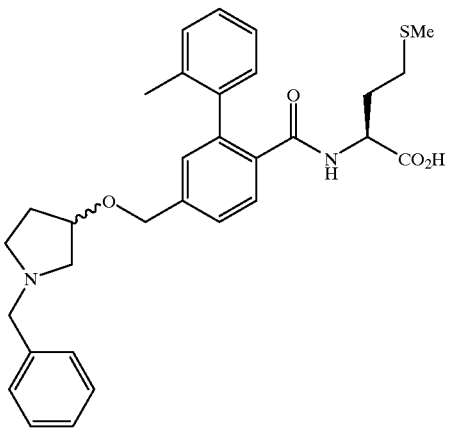

EXAMPLE 987

N-[4-(1-benzylpyrrolidin-3-oxymethyl)-2-(2-methylphenyl)benzoyl]methionine

The desired compound was prepared according to the method of Example 157 $^1$H nmr (300 MHz, DMSO d$_6$): δ8.05, m, 2H; 7.49, d, 1H; 7.38, m, 1H; 7.03–7.26, m, 8H; 6.99, m, 2H; 4.50, m, 2H; 4.07–4.31, m, 4H; 3.20–3.75, m, 2H; 2.53–2.96, m, 2H; 1.62–2.24, m, 12H.

MS (ESI(−)): 531 (M−H); (ESI(+)): 533. Calc'd for C$_{31}$H$_{36}$N$_2$O$_4$S+1.40 H$_2$O: C 68.72 H 7.01, N 5.02: Found: C 66.73, H 6.28, N 4.59.

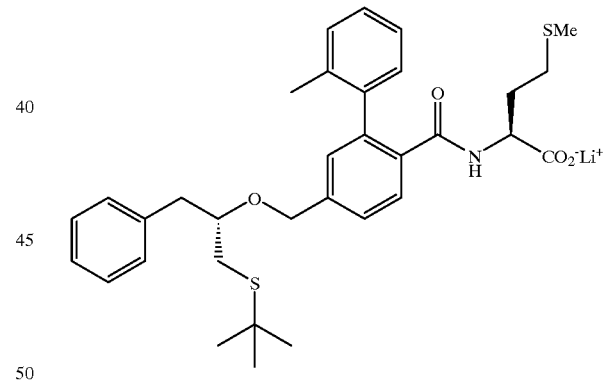

EXAMPLE 994

N-[4-(1-t-butylthio-3-phenylprop-2-oxymethyl)-2-(2-methylphenyl)benzoyl]methionine The desired compound was prepared according to the method of Example 157 $^1$H (300 MHz, DMSO–d6, δ) 7.43 (1H, d, J=8 Hz), 7.24 (1H, d, J=3 Hz), 7.22–7.10 (9H, m), 7.10 (1H, bs), 6.92 (1H, m), 4.63 (1H, d, J=12Hz), 4.52 (1H, d, J=12 Hz), 3.75 (1H, m), 3.67 (1H, m), 2.86 (2H, m), 2.64 (2H, m), 2.20–1.95 (4H, m), 1.90 (3H, s), 1.80–1.50 (3H, m), 1.20 (9H, s). m/e (ESI) 578 (MH$^-$)

Anal.calc. for C$_{33}$H$_{40}$LiNO$_4$S$_2$. 1.00 H$_2$O C 65.65, H 7.01, N 2.32 Found C 65.65, H 6.73, N 2.22

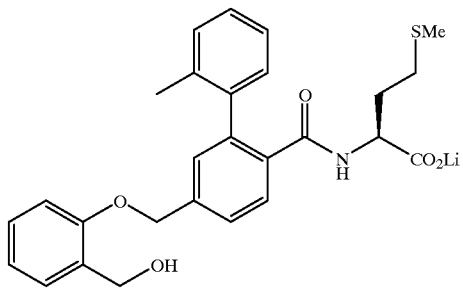

EXAMPLE 1042

N-[4-(2-hydroxymethylphenoxymethyl)-2-(2-methylphenyl)benzoyl]methionine. lithium salt

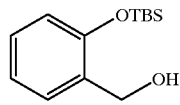

EXAMPLE 1042A 2-hydroxymethyltert-butyldimethylsiloxybenzene

To a solution of methyl salycilate (1.0 g) in DMF (15mL) was added imidazole (0.56 g) and TBDMS—Cl (1.1 g). After 21 h, the reaction was diluted with water (150 mL) and extracted into hexane (100 mL). The organic extracts were washed with brine (20 mL), dried (MgSO$_4$), filtered and concentrated to give a colorless oil (1.77 g). A portion of this product (0.5 g) was dissolved in THF (5 mL), and 1M LiAlH$_4$ (THF, 1.4 mL) was added at −78° C. The reaction was warmed immediately to 0° C. After 15 min, the reaction was quenched by addition of 10% sodium potassium tartrate (20 mL). After stirring vigorously for 5 min, the mixture was extracted with EtOAc/hexane (1:1, 2×50 mL). The organic extracts were washed with brine (20 mL), dried (MgSO$_4$), filtered and concentrated. The residue was purified by silica gel chromatography eluting with 20% EtOAc/hexane to afford a colorless oil (250 mg).

MS (ESI(−)) m/e (M−H)$^-$237.

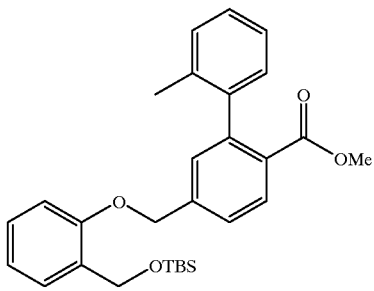

EXAMPLE 1042B 4-(2-tert-butyldimethylsiloxymethylphenoxymethyl)-2-(2-methylphenyl)benzoic acid, methyl ester 2-Hydroxymethyltert-butyldimethylsiloxybenzene (250 mg) was converted to the title compound by the procedure in Example 1308F. The product was purified by silica gel chromatography eluting with 5% EtOAc/hexane to afford a colorless oil (400 mg).

MS (ESI(+)) m/e (M+NH$_4$)$^+$494.

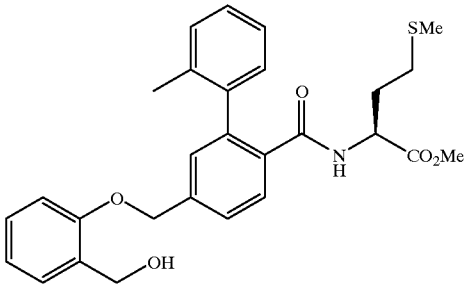

EXAMPLE 1042C

N-[4-(2-hydroxymethylphenoxymethyl)-2-methylphenyl)benzoyl]methionine, methyl ester 4-(2-tert-butyldimethylsiloxymethylphenoxymethyl)-2-(2-methylphenyl)benzoic acid methyl ester (400 mg) was dissolved in THF (3 mL), and IM TBAF (THF, 1 mL) was added. After 15 min, the reaction was diluted with EtOAC (50 mL), and washed with water. The organic extracts were washed with brine (20 mL), dried (MgSO$_4$), filtered and concentrated to give a light yellow oil. This material was converted to the title compound by the procedure in examples 608C and D. The product was isolated as a colorless glassy foam (0.336 g).

MS (APCI(+) m/e (M+H)$^+$494,
MS (APCI(−) m/e (M−H)$^-$492.

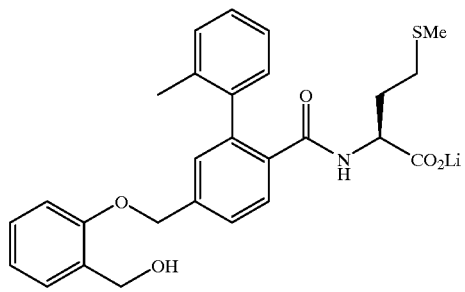

EXAMPLE 1042D

N-[4-(2-hydroxymethylphenoxymethyl)-2-(2-methylphenyl)benzoyl]methionine, lithium salt N-[4-(2-Hydroxymethylphenoxymethyl)-2-(2-methylphenyl)benzoyl]methionine methyl ester (330 mg) was converted into the title compound by the procedure in example 608E. The product was isolated as a white powder (320 mg).

$^1$H NMR (300 MHz, DMS O) δ1.48–1.70 (m, 4H), 1.92 (s, 3H), 1.95–2.15 (m, 3H), 3.58–3.70 (m, 1H), 4.56 (brs, 2H), 4.97–5.06 (m, 1H), 5.19 (brs, 2H), 6.90–7.03 (m, 3H), 7.14–7.25 (m, 6H), 7.39 (brd, J=7 Hz, 1H), 7.50 (d, J=8 Hz, 1H), 7.56 (d, J=8 Hz, 1H).

MS (APCI(−)) m/e 478 (M−H);

Analysis calc'd for $C_{27}H_{28}LiNO_5S \cdot 3.45H_2O$: C, 59.21; H, 6.42; N, 2.56; found: C, 59.14; H, 5.92; N, 2.51.

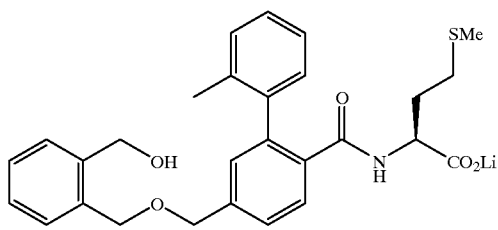

EXAMPLE 1043

N-[4-(2-hydroxymethylbenzyloxymethyl)-2-(2-methylphenyl)benzoyl]methionine, lithium salt

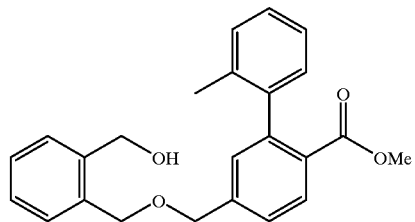

EXAMPLE 1043A 4-(2-hydroxymethylbenzyloxymethyl)-2-(2-methylphenyl)benzoic acid, methyl ester The title compound was prepared in 74% yield according to the procedure described in example 1308F.

MS(ESI) 394 $(M+NH_4)^+$.

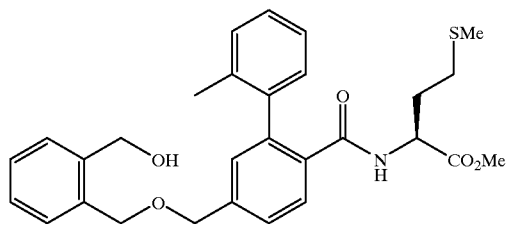

EXAMPLE 1043B

N-[4-(2-hydroxymethylbenzyloxymethyl)-2-(2-methylphenyl)benzoyl]methionine, methyl ester The title compound was prepared from 4-(2-hydroxymethylbenzyloxymethyl)-2-(2-methylphenyl) benzoic acid methyl ester according to the procedures in examples 608C and D.

MS (APCI(+) m/e $(M+H)^+$ 508,

MS (APCI(−) m/e $(M-H)^-$ 506.

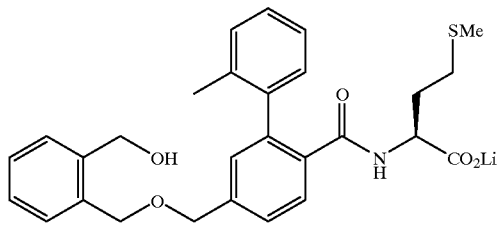

EXAMPLE 1043C

N-[4-($^2$-hydroxymethylbenzyloxymethyl)-2-(2-methylphenyl)benzoyl]methionine, lithium salt N-[4-(2-Hydroxymethylbenzyloxymethyl)-2-(2-methylphenyl)benzoyl]methionine methyl ester was converted to the title compound by the procedure in example 608E. The product was isolated as a white powder.

$^1$H NMR (300 MHz, DMSO) δ1.50–1.87 (m, 4H), 1.91 (s, 3H), 1.94–2.19 (m, 3H), 3.60–3.72 (m, 1H), 4.56 (brs, 2H), 4.59 (s, 4H), 5.07–5.14 (m, 1H), 6.91–7.00 (m, 1H), 7.09–7.46 (m, 10H), 7.54 (d, J=8.1 Hz, 1H).

MS (APCI(−)) m/e 492 (M−H);

Analysis calc'd for $C_{28}H_{30}LiNO_5S \cdot 0.75H_2O$: C, 65.55; H, 6.19; N, 2.73; found: C, 65.56; H, 6.22; N, 2.69.

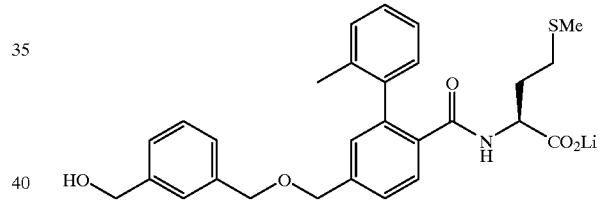

EXAMPLE 1044

N-[4-(3-hydroxymethylbenzyloxymethyl)-2-(2-methylphenyl)benzoyl]methionine, lithium salt

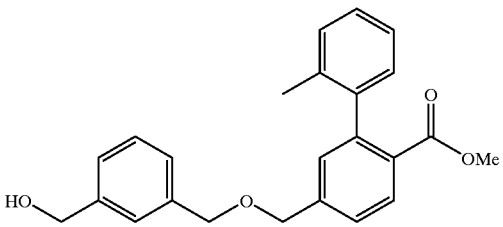

EXAMPLE 1044A 4-(3-hydroxymethylbenzyloxymethyl)-2-(2-methylphenyl)benzoic acid, methyl ester The title compound was prepared according to the procedure described in example 1308F.

MS (ESI) 394 (M+NH₄)⁺.

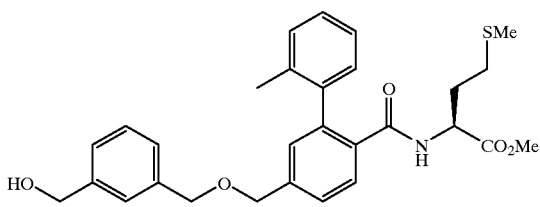

EXAMPLE 1044B

N-[4-(3-hydroxymethylbenzyloxymethyl)-2-(2-methylphenyl)benzoyl]methionine, methyl ester The title compound was prepared from 4-(3-hydroxymethylbenzyloxymethyl)-2-(2-methylphenyl) benzoic acid methyl ester according to the procedures in examples 608C and D.

MS (APCI(+)) m/e (M+H)⁺508,

MS (APCI(−)) m/e (M−H)⁻506.

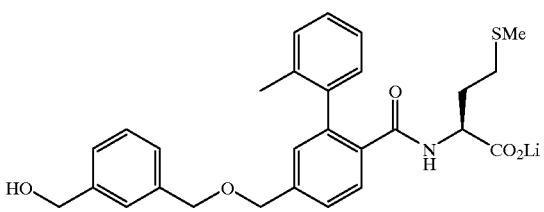

EXAMPLE 1044C

N-[4-(3-hydroxymethylbenzyloxymethyl)-2-(2-methylphenylbenzoyl]methionine, lithium salt N-[4-(3-Hydroxymethylbenzyloxymethyl)-2-(2-methylphenyl)benzoyl]methionine methyl ester was converted to the title compound by the procedure in example 608E. The product was isolated as a white powder.

¹H NMR (300 MHz, DMS O) δ1.48–1.87 (m, 4H), 1.93 (s, 3H), 1.95–2.18 (m, 3H), 3.60–3.72 (m, 1H), 4.48 (brs, 2H), 4.52 (s, 2H), 4.59 (s, 2H), 5.20 (brs, 1H), 6.90–7.00 (m, 1H), 7.09–7.26 (m, 5H), 7.29 (s, 4H), 7.40 (d, J=7.8 Hz, 1H), 7.53 (d, J=7.8 Hz, 1H).

MS (APCI(−)) m/e 492 (M−H);

Analysis calc'd for $C_{28}H_{30}LiNO_5S \cdot 1.05H_2O$: C, 64.87; H, 6.24; N, 2.70; found: C, 64.91; H, 6.16; N, 2.62.

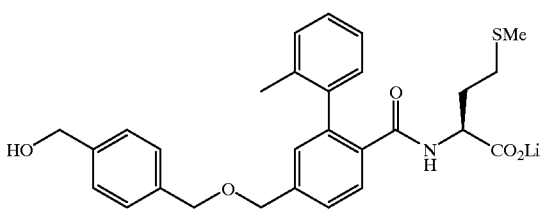

EXAMPLE 1045

N-[4-(4-hydroxymethylbenzyloxymethyl)-2-(2-methylphenyl)benzoyl]methionine, lithium salt

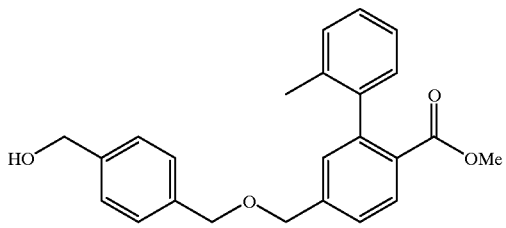

EXAMPLE 1045A 4-(4-hydroxymethylbenzyloxymethyl)-2-(2-methylphenyl)benzoic acid, methyl ester The title compound was prepared according to the procedure described in example 1308F.

MS (ESI) 394 (M+NH₄)⁺.

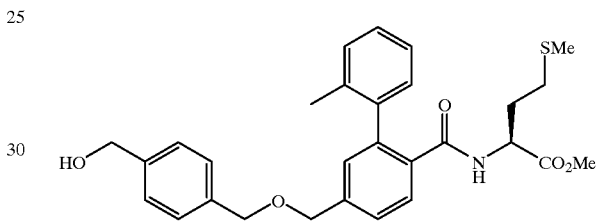

EXAMPLE 1045B

N-[4-(4-hydroxymethylbenzyloxymethyl)-2-(2-methylphenylbenzoyl]methionine, methyl ester The title compound was prepared from 4-(4-hydroxymethylbenzyloxymethyl)-2-(2-methylphenyl) benzoic acid methyl ester according to the procedures in examples 608C and D.

MS (APCI(+)) m/e (M+H)⁺508,

MS (APCI(−)) m/e (M−H)⁻506.

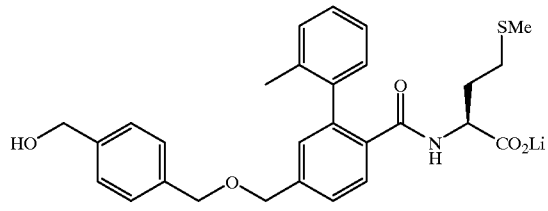

EXAMPLE 1045C

N-[4-(4-hydroxymethylbenzyloxymethyl)-2-(2-methylphenyl)benzoyl]methionine, lithium salt N-[4-(4-Hydroxymethylbenzyloxymethyl)-2-(2-methylphenyl)benzoyl]methionine methyl ester was converted to the title compound by the procedure in example 608E. The product was isolated as a white powder.

¹H NMR (300 MHz, DMS O) 5 1.50–1.87 (m, 4H), 1.92 (s, 3H), 1.95–2.19 (m, 3H), 3.60–3.72 (m, 1H), 4.48 (d, J=6

Hz, 2H), 4.54 (s, 2H), 4.60 (s, 2H), 5.20 (t, J=6.0 Hz, 1H), 6.91–7.00 (m, 1H), 7.09–7.24 (m, 7H), 7.30 (d, J=14.7 Hz, 1H), 7.30 (s, 1H), 7.41 (dd, J=7.8, 1.2 Hz, 1H), 7.53 (d, J=7.8 Hz, 1 H).

MS (APCI(−)) m/e 492 (M−H).

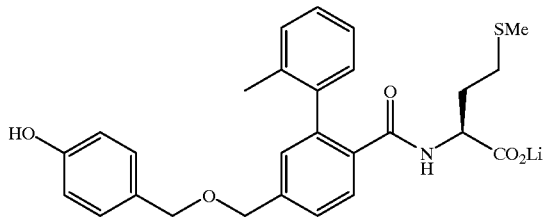

EXAMPLE 1046

N-[4-(4-hydroxybenzyloxymethyl)-2-(2-methylphenyl)benzoyl]methionine, lithium salt

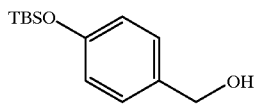

EXAMPLE 1046A 4-hydroxymethyltert-butyldimethylsiloxybenzene

The title compound was prepared according to the procedure in example 1042A, replacing methyl salycilate with methyl 4-hydroxybenzoate, and was isolated as a colorless oil.

$^1$H NMR (300 MHz, CDCl$_3$) δ0.19 (s, 6H), 0.98 (s, 9H), 4.61 (s, 2H), 6.82 (d, J=8.4 Hz, 2H), 7.23 (d, J=8.1 Hz, 2H).

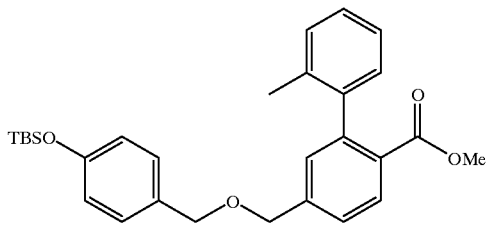

EXAMPLE 1046B 4-(4-tert-butyldimethylsiloxybenzyloxymethyl)-2-(2-methylphenyl)benzoic acid, methyl ester The title compound was prepared according to the procedure described in example 1308F, and was isolated as a colorless oil.

MS (APCI(+)) 494 (M+NH$_4$)$^+$.

MS (APCI(−)) m/e 475 (M−H)$^-$.

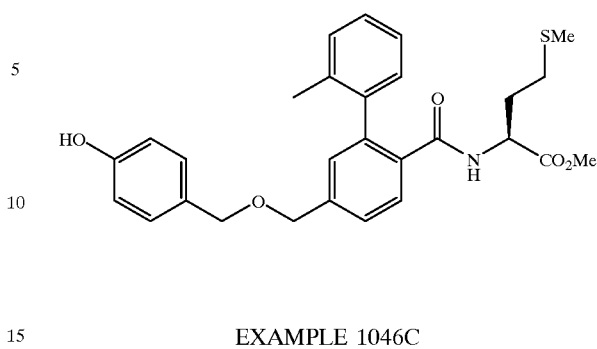

EXAMPLE 1046C

N-[4-(4-hydroxybenzyloxymethyl)-2-(2-methylphenyl)benzoyl]methionine, methyl ester The title compound was prepared from 4-(4-tert-butyldimethylsiloxybenzyloxymethyl)-2-(2-methylphenyl)benzoic acid methyl ester according to the procedures in examples 608C and D.

MS (APCI(+) m/e (M+H)$^+$494,

MS (APCI(−) m/e (M−H)$^-$492.

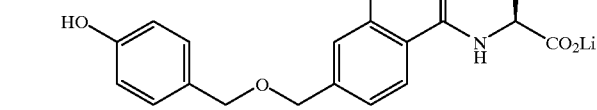

EXAMPLE 1046D

N-[4-(4-hydroxybenzyloxymethyl)-2-(2-methylphenyl)benzoyl]methionine, lithium salt N-[4-(4-hydroxybenzyloxymethyl)-2-(2-methylphenyl)benzoyl]methionine methyl ester was converted to the title compound by the procedure in example 608E. The product was isolated as a white powder.

$^1$H NMR (300 MHz, DMSO) δ1.50–1.76 (m, 4H), 1.91 (s, 3H), 1.95–2.16 (m, 3H), 3.62–3.74 (m, 1H), 4.39 (brd, J=5 Hz, 2H), 5.03–5.09 (m, 1H), 5.17 (s, 2H), 6.93–7.00 (m, 3H), 7.13–7.26 (m, 7H), 7.48 (d, J=7.8 Hz, 1H), 7.55 (d, J=7.8 Hz, 1H).

MS (APCI(−)) m/e 478 (M−H);

Analysis calc'd for C$_{27}$H$_{28}$LiNO$_5$S.1.30H$_2$O: C, 63.72; H, 6.06; N, 2.75; found: C, 63.66; H, 5.89; N, 2.57.

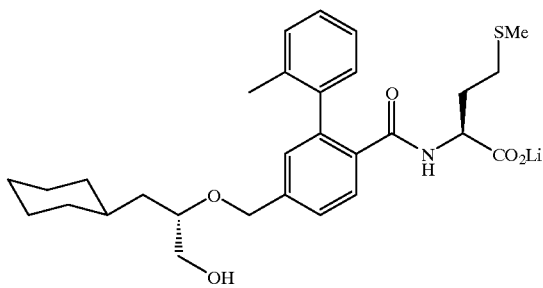

EXAMPLE 1049

N-[4-(3-cyclohexyl-1-hydroxyprop-2-yloxymethyl)-2-(2-methylphenyl)benzoyl]methionine, lithium salt

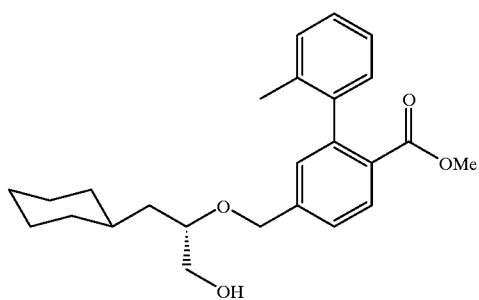

EXAMPLE 1049A 4-(3-cyclohexyl-1-hydroxyprop-2-yloxymethyl)-2-(2-methylphenyl)benzoic acid, methyl ester To a solution of N-[4-(3-cyclohexyl-1-(4-methoxybenzyloxy)prop-2-yloxymethyl)-2-(2-methylphenyl)benzoic acid methyl ester (Example 1051B, 360 mg) in dichloromethane (2 mL) was added water (5 drops), and 2,3-dichloro-5,6-dicyano-1,4-benzoquinone (190 mg). After 50 min, the reaction was diluted with EtOAc/hexane (1:1, 10 mL), dried (MgSO$_4$), and filtered through a pad of silica gel. The filtrate was concentrated, and the residue was purified by silica gel chromatography eluting with 20%–30% EtOAc/hexane to give the title compound (230 mg, 90%) as a colorless oil.

MS (DCI/NH$_3$) 414 (M+NH$_4$)$^+$.

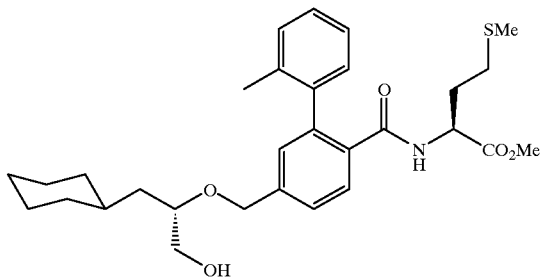

EXAMPLE 1049B

N-[4-(3-cyclohexyl-1-hydroxyprop-2-yloxymethyl)-2-(2-methylphenyl)benzoyl]methionine, methyl ester The title compound was prepared from 4-(3-cyclohexyl-1-hydroxyprop-2-yloxymethyl)-2-(2-methylphenyl)benzoic acid methyl ester according to the procedure described in examples 608C and D, and was isolated as a colorless oil.

MS (APCI(+)) 528 (M+H)$^+$

MS (APCI(−)) 526 (M+H)$^-$, 562 (M+Cl)$^-$, 586 (M+CH$_3$COO)$^-$.

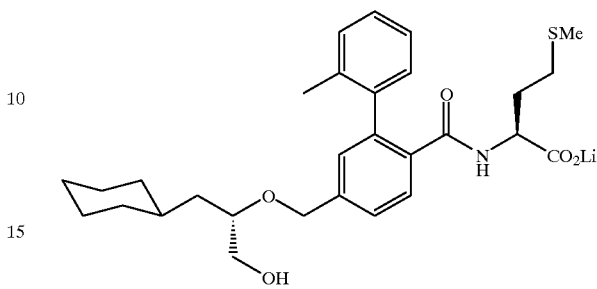

EXAMPLE 1049C

N-[4-(3-cyclohexyl-1-hydroxyprop-2-yloxymethyl)-2-(2-methylphenyl)benzoyl]methionine, lithium salt The title compound was prepared from N-[4-(3-cyclohexyl-1-hydroxyprop-2-yloxymethyl)-2-(2-methylphenyl)benzoyl]methionine methyl ester according to example 608E, and was isolated as a white powder.

$^1$H NMR (300 MHz, DMS O) δ0.70–0.94 (m, 2H), 1.00–1.89 (m, 15H), 1.91 (s, 3H), 1.95–2.19 (m, 3H), 3.36–3.48 (m, 3H), 3.60–3.70 (m, 1H), 4.51 (d, J=12.3 Hz), 4.52–4.61 (m, 1H), 4.69 (d, J=12.9 Hz, 1H), 6.89–6.98 (m, 1H), 7.08–7.24 (m, 5H), 7.37 (d, J=7.8 Hz, 1H), 7.51 (d, J=7.8 Hz, 1H).

MS (APCI(−)) m/e 512 (M−H);

Analysis calc'd for C$_{29}$H$_{38}$LiNO$_5$S.1.25H$_2$O: C, 64.25; H, 7.53; N, 2.58; found: C, 64.28; H, 7.29; N, 2.50.

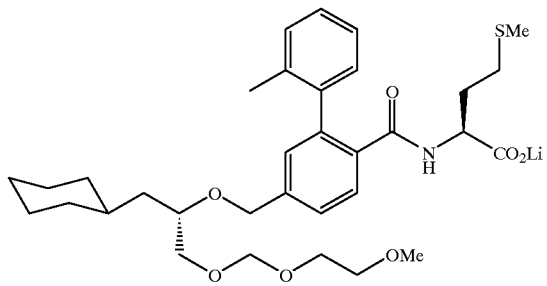

EXAMPLE 1050

N-[4-(3-cyclohexyl-1-(2-methoxyethoxymethyleneoxy)prop-2-yloxymethyl)-2-(2-methylphenyl)benzoyl]methionine, lithium salt

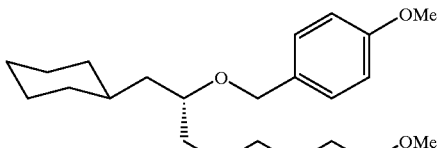

EXAMPLE 1050A (S)-3-cyclohexyl-2-(4-methoxybenzyloxy)-1-methoxyethoxymethyleneoxypropane To a solution of (S)-3-cyclohexyl-2-(4-methoxybenzyloxy)-1-propanol (Example 1316B, 425 mg)

in dichloromethane (5 mL) at ambient temperature was added diisopropylethylamine (0.533 mL), then methoxyethoxymethylchloride (0.21 mL). After 6 h, additional methoxyethoxymethyl chloride (0.04 mL) was added. After a total of 8 h, the reaction was concentrated and the residue was purified by silica gel chromatography eluting with 30% EtOAc/hexane to give the title compound as a colorless oil (450 mg, 80%).

$^1$H NMR (300 MHz, CDCl$_3$) δ0.70–0.95 (m, 2H), 1.08–1.70 (m, 11H), 3.40 (s, 3H), 3.54–3.73 (m, 7H), 3.80 (s, 3H), 4.47 (d, J=11.4 Hz, 1H), 4.62 (d, J=11.4 Hz, 1H), 4.75 (s, 2H), 6.86 (d, J=8.4 Hz, 2H), 7.26 (d, J=8.4 Hz, 2H).

MS (DCI/NH$_3$) m/e 384 (M+NH$_4$)$^+$.

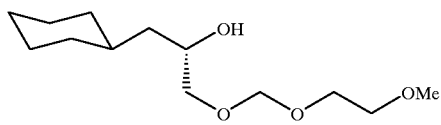

EXAMPLE 1050B (S)-3-cyclohexyl-1-methoxyethoxymethyleneoxy-2-propanol

To a solution of (S)-3-cyclohexyl-2-(4-methoxybenzyloxy)-1-methoxyethoxymethyleneoxy propane (450 mg) in methylenechloride (4 mL) was added water (0.4 mL) and 2,3-dichloro-5,6-dicyano-1,4-benzoquinone (335 mg). After 2 h, the reaction was diluted with EtOAc/hexane (1:1, 40 mL), dried (MgSO$_4$), and filtered through a pad of silica gel. The solution was concentrated, and the residue was purified by silica gel chromatography eluting with 40% EtOAc/hexane to afford the title compound as a colorless oil (280 mg, 92%).

MS(DCI/NH$_3$) 264 (M+NH$_4$)$^+$.

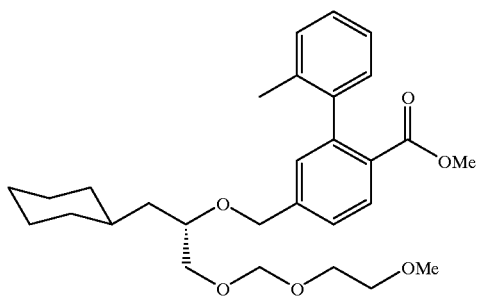

EXAMPLE 1050C 4-(3-cyclohexyl-1-(2-methoxyethoxymethyleneoxy) prop-2-yloxymethyl)-2-(2-methylphenyl)benzoic acid, methyl ester The title compound was prepared from (S)-3-cyclohexyl-1-ethoxyethoxymethyleneoxy-2-propanol according to the procedure in example 1308F. MS (DCI/NH$_3$) 502 (M+NH$_4$)$^+$.

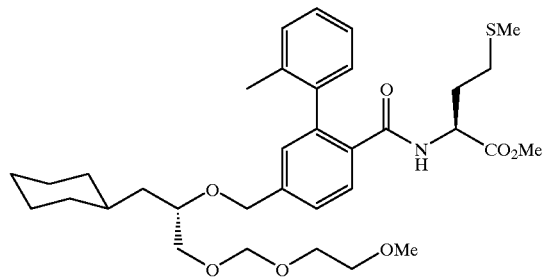

EXAMPLE 1050D

N-[4-(3-cyclohexyl-1-(2-methoxyethoxymethyleneoxy)prop-2-yloxymethyl)-2-(2-methylphenyl)benzoyl]methionine, methyl ester The title compound was prepared from 4-(3-cyclohexyl-1-(2-methoxyethoxymethyleneoxy)prop-2-yloxymethyl)-2-(2-methylphenyl)benzoic acid methyl ester according to the procedure in examples 608C and D.

MS (APCI(+)) 616 (M+H)$^+$.

MS (APCI(–)) 614 (M+H)$^-$.

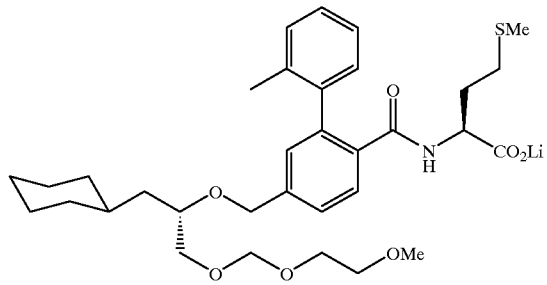

EXAMPLE 1050E

N-[4-(3-cyclohexyl-1-(2-methoxyethoxymethyleneoxy)prop-2-yloxymethyl)-2-(2-methylphenyl)benzoyl]methionine, lithium salt The title compound was prepared from N-[4-(3-cyclohexyl-1-(2-methoxyethoxymethyleneoxy)prop-2-2-yloxymethyl)-2-(2-methylphenyl)benzoyl]methionine methyl ester according to the procedure in example 608E, and was isolated as a white powder.

$^1$H NMR (300 MHz, DMS O) δ0.72–1.87 (m, 17H), 1.91 (s, 3H), 1.98–2.16 (m, 3H), 3.21 (s, 3H), 3.39–3.43 (m, 2H), 3.49–3.57 (m, 4H), 3.58–3.73 (m, 2H), 4.53 (d, J=12.6 Hz, 1H), 4.61 (s, 2H), 4.68 (d, J=12.6 Hz, 1H), 6.90–6.98 (m, 1H), 7.08–7.24 (m, 5H), 7.35 (brd, J=7.8 Hz, 1H), 7.51 (d, J=7.8 Hz, 1H).

MS (APCI(+0)) m/e 600 (M–H);

Analysis calc'd for C$_{33}$H$_{46}$LiNO$_7$S.0.8H$_2$O; C, 63.71; H, 7.71; N, 2.25; found: C, 63.72; H, 7.66; N, 2.08.

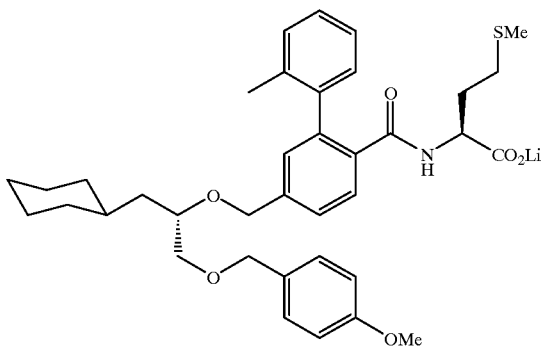

EXAMPLE 1051

N-[4-(3-cyclohexyl-1-methoxybenzyloxy)prop-2-yloxymethyl)-2-(2-methylphenyl)benzoyl]methionine, lithium salt

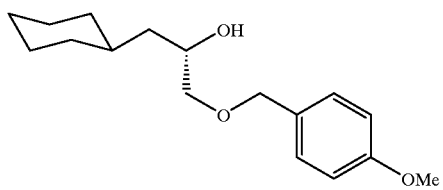

EXAMPLE 1051A 3-cyclohexyl-1-(4-methoxybenzyloxy)-2-propanol

The title compound was prepared according to example 1308D, replacing n-butanol with 4-methoxybenzyl alcohol.

MS (Cl/NH$_3$) 296 (M+NH$_4$)$^+$.

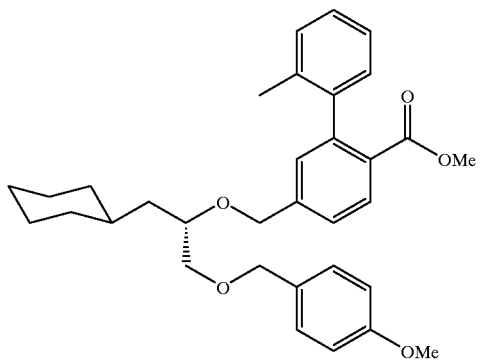

EXAMPLE 1051B

N-[4-(3-cyclohexyl-1-(4-methoxybenzyloxy)prop-2-yloxymethyl)-2-(2-methylphenyl)benzoic acid, methyl ester The title compound was prepared from 3-cyclohexyl-1-(4-methoxybenzyloxy)-2-propanol according to example 1308F.

MS(Cl/NH$_3$) 534 (M+NH$_3$)$^+$.

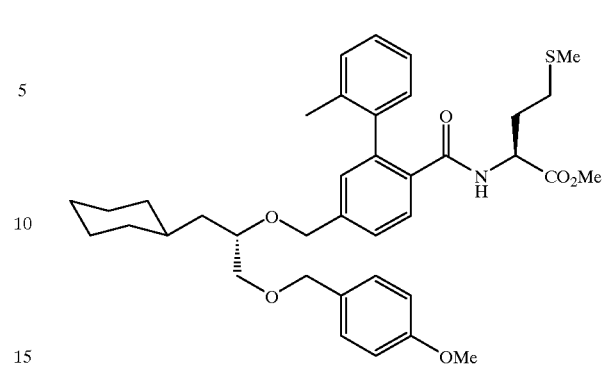

EXAMPLE 1051C

N-[4-(3-cyclohexyl-1-(4-methoxybenzyloxy)prop-2-yloxymethyl)-2-(2-methylphenyl)benzoyl]methionine, methyl ester The title compound was prepared from N-[4-(3-cyclohexyl-1-(4-methoxybenzyloxy)prop-2-yloxymethyl)-2-(2-methylphenyl)benzoic acid methyl ester according to the procedures in examples 608C and D.

MS(APCl(+)) 648 (M+H)$^+$.
MS(APCl(−)) 646 (M−H)$^-$.

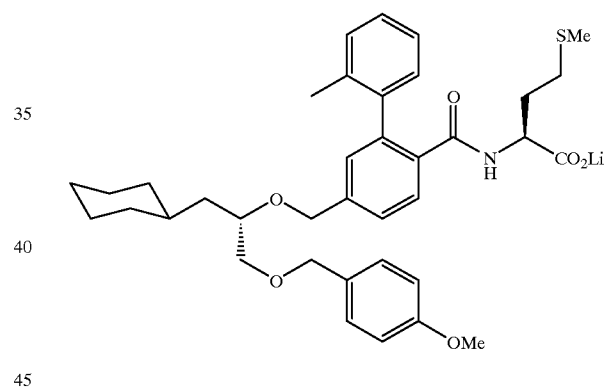

EXAMPLE 1051D

N-[4-(3-cyclohexyl-1-(4-methoxybenzyloxy)prop-2-yloxymethyl)-2-(2-methylphenylbenzoyl]methionine, lithium salt The title compound was prepared from N-[4-(3-cyclohexyl-1-(4-methoxybenzyloxy)prop-2-yloxymethyl)-2-(2-methylphenyl)benzoyl]methionine methyl ester according to the procedure in example 608E, and was isolated as a white powder.

$^1$H NMR (300 MHz, DMSO) δ 0.70–0.93 (m, 2H), 1.02–1.87 (m, 15H), 1.91 (s, 3H), 1.95–2.18 (m, 3H), 3.40–3.47 (m, 2H), 3.57–3.70 (m, 2H), 3.72 (s, 3H), 4.39 (ABq, Δν$_{AB}$=24 Hz, J$_{AB}$=11.7 Hz, 2H), 4.53 (d, J=12.6 Hz, 1H), 4.67 (d, J=12.6 Hz, 1H), 6.85 (d, J=8.4 Hz, 2H), 6.92–6.99 (m, 1H), 7.07–7.20 (m, 5H), 7.21 (d, J=8.4 Hz, 2H), 7.34 (dd, J=7.8, 0.9 Hz, 1H), 7.51 (d, J=7.8 Hz, 1H).

MS (APCl(−)) m/e 632 (M−H);

Analysis calc'd for C$_3$H$_{46}$LiNO$_6$S·0.5H$_2$O: C, 68.50; H, 7.30; N, 2.16; found: C, 68.50; H, 7.21; N, 2.09.

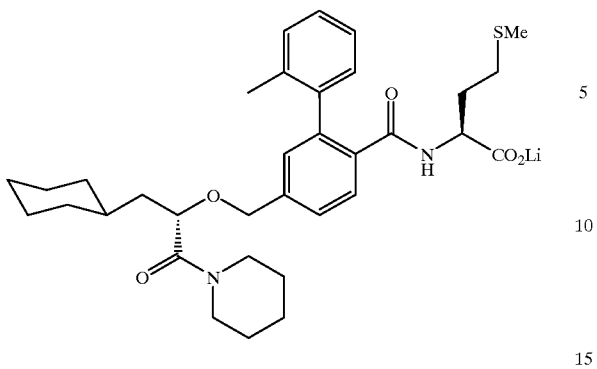

EXAMPLE 1052

N-[4-(3-cyclohexyl-N-piperidin-1-ylpropion-2-yloxymethyl)-2-(2-methylphenyl)benzoyl] methionine, lithium salt

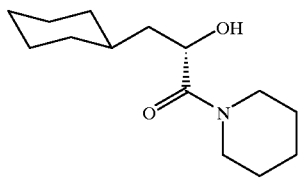

EXAMPLE 1052A (S)-3-cyclohexyl-2-hydroxy-N-piperidin-1-ylpropionamide

To a solution of (S)-3-cyclohexyllactic acid (Example 1308A, 260 mg) in DMF (8 mL) was added piperidine (0.326 mL), 1-hydroxybenzotriazole (222 mg), and 1-ethyl-3-(3-dimethylaminopropyl) carbodiimide (344 mg). After stirring at ambient temperature for 6 h, the reaction was poured into EtOAc (100 mL), washed with water (2×50 mL), and brine (10 mL). The organic solution was dried (MgSO$_4$), filtered and concentrated to afford a light yellow oil which was purified by silica gel chromatography eluting with 40% EtOAc/hexane to give a white solid (399 mg, 94%).

$^1$H NMR (300 MHz, CDCl$_3$) δ0.80–1.03 (m, 2H), 1.06–1.23 (m, 5H), 1.52–1.78 (m, 12H), 1.91–2.00 (m, 1H), 3.30 (m, 2H), 3.51–3.68 (m, 2H), 3.79 (brd, J=6 Hz, 1H), 4.41 (m, 1H).

MS (DCI/NH$_3$) m/e 240 (M+H)$^+$.

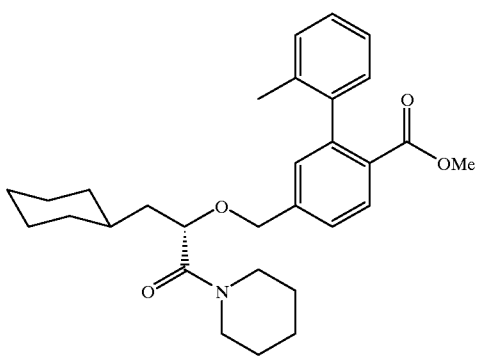

EXAMPLE 1052B 4-(3-cyclohexyl-N-piperidin-1-ylpropion-2-yloxymethyl)-2-(2-methylphenyl)benzoic acid, methyl ester The title compound was prepared from (S)-3-cyclohexyl-2-hydroxy-N-piperidin-1-ylpropionamide according to the procedure in example 1308F as a colorless oil.

MS (APCI(+)) 478 (M+H)$^+$.

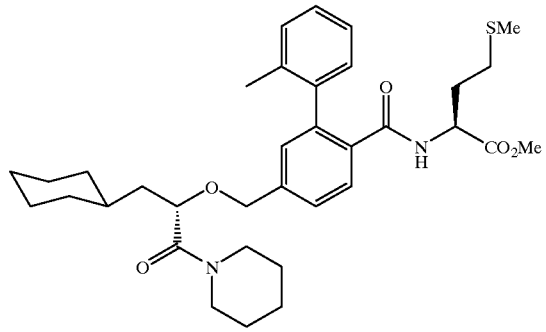

EXAMPLE 1052C

N-[4-(3-cyclohexyl-N-piperidin-1-ylpropion-2-yloxymethyl)-2-(2-methylphenyl)benzoyl] methionine, methyl ester The title compound was prepared from 4-(3-cyclohexyl-N-piperidin-1-ylpropion-2-yloxymethyl)-2-(2-methylphenyl)benzoic acid methyl ester according to the procedure in example 608C and D as a colorless oil.

MS(APCI(+)) 609 (M+H)$^+$.

MS(APCI(−)) 607 (M−H)⁻.

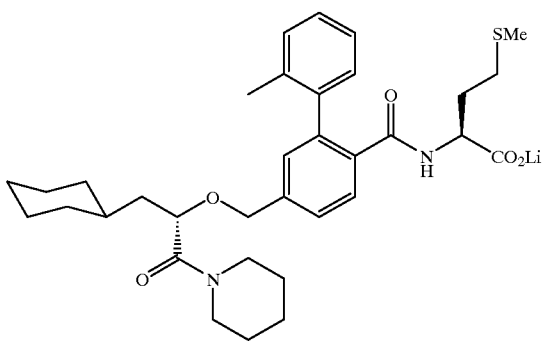

EXAMPLE 1052D

N-[4-(3-cyclohexyl-N-piperidin-1-ylpropion-2-yloxymethyl)-2-(2-methylphenyl)benzoyl] methionine, lithium salt The title compound was prepared from N-[4-(3-cyclohexyl-N-piperidin-1-ylpropion-2-yloxymethyl)-2-(2-methylphenyl)benzoyl]methionine methyl ester according to the procedure in example 608E as a white powder.

$^1$H NMR (300 MHz, DMS O) δ0.64–0.93 (m, 2H), 1.02–1.14 (m, 3H), 1.32–1.70 (m, 14H), 1.73–2.18 (m, 7H), 1.91 (s, 3H), 3.37–3.50 (m, 4H), 3.62–3.74 (m, 1H), 4.32 (dd, J=9, 2.4 Hz, 1H), 4.37 (d, J=12.3 Hz, 1H), 4.55 (d, J=12.3 Hz, 1H), 6.92–6.99 (m, 1H), 7.09–7.24 (m, 5H), 7.35 (dd, J=7.8, 1 Hz, 1H), 7.52 (d, J=8.1 Hz, 1H).

MS (APCI(−)) m/e 593 (M-H);

Analysis calc'd for $C_{34}H_{45}LiN_2O_5S \cdot 1.60H_2O$: C, 64.87; H, 7.72; N, 4.45; found: C, 64.87; H, 7.61; N, 4.46.

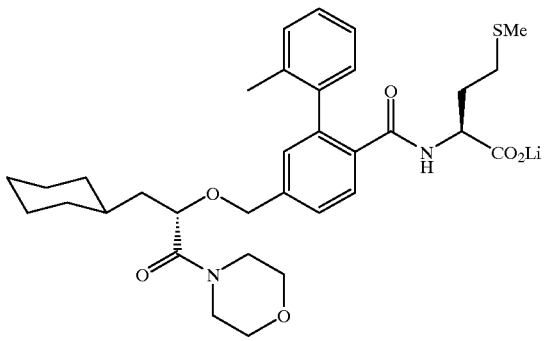

EXAMPLE 1053

N-[4-(3-cyclohexyl-N-morpholin-4-ylpropion-2-yloxymethyl)-2-(2-methylphenyl)benzoyl] methionine, lithium salt

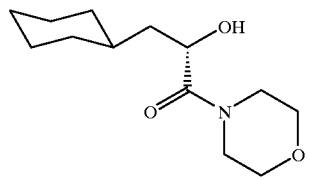

EXAMPLE 1053A (S)-3-cyclohexyl-2-hydroxy-N-morpholin-1-ylpropionamide

The title compound was prepared as a colorless oil according to example 1052A, substituting morpholine for piperidine.

MS (DCI/NH₃) 242 (M+H)⁺.

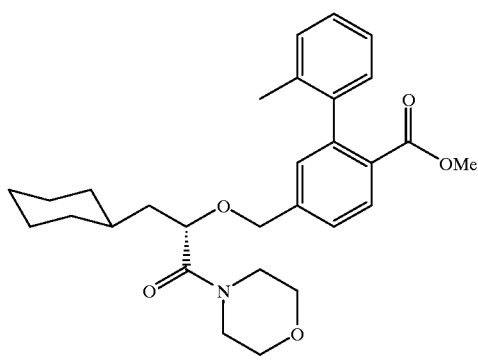

EXAMPLE 1053B 4-(3-cyclohexyl-N-morpholin4-ylpropion-2-yloxymethyl)-2-(2-methylphenyl)benzoic acid, methyl ester The title compound was prepared from (S)-3-cyclohexyl-2-hydroxy-N-morpholin-1-ylpropionamide as a colorless oil according to the procedure in example 1308F.

MS(APCI(+)) 480 (M+H)⁺.

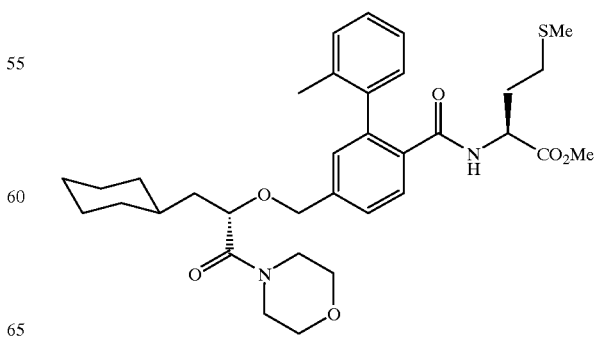

EXAMPLE 1053C

N-[4-(3-cyclohexyl-N-morpholin4-ylpropion-2-yloxymethyl)-2-(2-methylphenyl)benzoyl]methionine, methyl ester The title compound was prepared from 4-(3-cyclohexyl-N-morpholin-4-ylpropion-2-yloxymethyl)-2-(2-methylphenyl)benzoic acid methyl ester according to the procedure in examples 608C, and D.

MS(APCI(+)) 611 (M+H)$^+$.

MS(APCI(−)) 609 (M−H)$^-$.

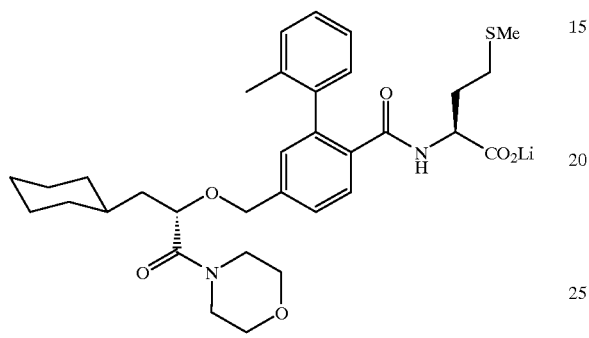

EXAMPLE 1053D

N-[4-(3-cyclohexyl-N-morpholin-4-ylpropion-2-yloxymethyl)-2-(2-methylphenyl)benzoyl]methionine, lithium salt N-[4-(3-Cyclohexyl-N-morpholin-4-ylpropion-2-yloxymethyl)-2-(2-methylphenyl)benzoyl]methionine methyl ester was converted into the title compound according to the procedure in example 608E, and was isolated as a white powder.

$^1$H NMR (300 MHz, DMS O) δ0.75–0.97 (m, 2H), 1.00–1.19 (m, 3H), 1.33–1.46 (m, 2H), 1.48–1.74 (m, 6H), 1.75–2.20 (m, 7H), 1.91 (s, 3H), 3.41–3.49 (m, 2H), 3.50–3.58 (m, 6H), 3.62–3.73 (m, 1H), 4.33 (dd, J=8.9, 3 Hz, 1H), 4.39 (d, J=12.6 Hz, 1H), 4.57 (d, J=12.3 Hz, 1H), 6.92–7.02 (m, 1H), 7.08–7.24 (m, 5H), 7.36 (d, J=8.1 Hz, 1H), 7.54 (d, J=8.1 Hz, 1H).

MS (APCI(−)) m/e 595 (M−H);

Analysis calc'd for $C_{33}H_{43}N_2O_6SLi.1.85H_2O$: C, 62.32; H, 7.40; N, 4.40; found: C, 62.31; H, 7.29; N, 4.43.

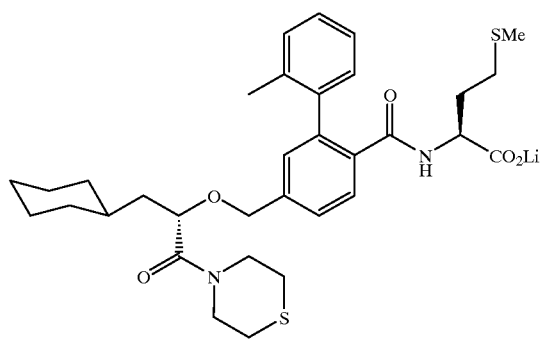

EXAMPLE 1054

N-[4-(3-cyclohexyl-N-thiomorpholin-4-ylpropion-2-yloxymethyl)-2-(2-methylphenyl)benzoyl]methionine, lithium salt

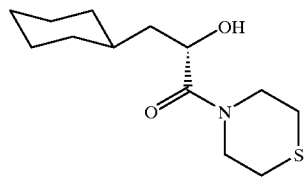

EXAMPLE 1054A (S)-3-cyclohexyl-2-hydroxy-N-thiomorpholin-1-ylpropionamide

The title compound was prepared as a colorless oil according to example 1052A, substituting thiomorpholine for piperidine.

MS (DCI/NH$_3$) 258 (M+H)$^+$.

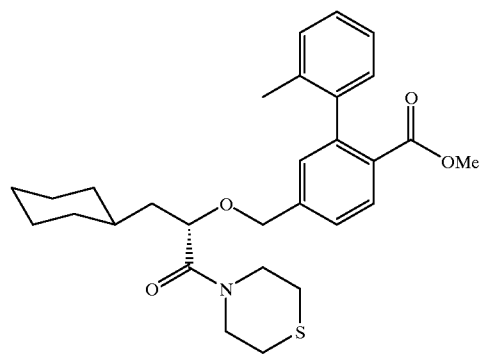

EXAMPLE 1054B 4-(3-cyclohexyl-N-thiomorpholin-4-ylproion-2-yloxymethyl)-2-(2-methylphenyl)benzoic acid, methyl ester The title compound was prepared from (S)-3-cyclohexyl-2-hydroxy-N-thiomorpholin-1-ylpropionamide as a colorless oil according to the procedure in example 1308F.

MS(APCI(+)) 496 (M+H)$^+$.

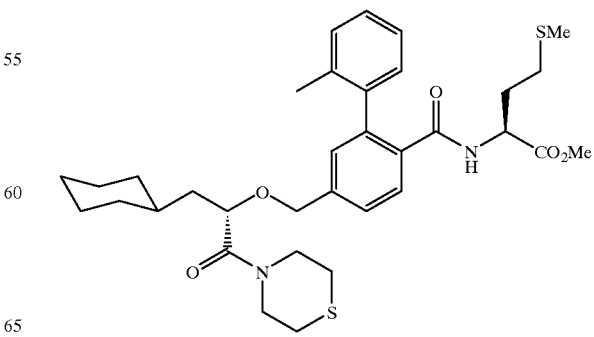

EXAMPLE 1054C

N-[4-(3-cyclohexyl-N-thiomorpholin-4-ylpropion-2-yloxymethyl)-2-(2-methylphenyl)benzoyl]methionine, methyl ester The title compound was prepared from 4-(3-cyclohexyl-N-thiomorpholin-4-ylpropion-2-yloxymethyl)-2-(2-methylphenyl)benzoic acid methyl ester according to the procedure in examples 608C, and D.

MS(APCI(+)) 627 (M+H)⁺.

MS(APCI(−)) 625 (M−H)⁻.

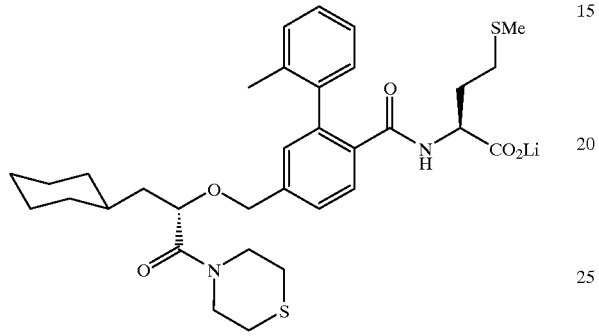

EXAMPLE 1054D

N-[4-(3-cyclohexyl-N-thiomorpholin-4-ylpropion-2-yloxymethyl)-2-(2-methylphenyl)benzoyl]methionine, lithium salt N-[4-(3-Cyclohexyl-N-thiomorpholin-4-ylpropion-2-yloxymethyl)-2-(2-methylphenyl)benzoyl]methionine methyl ester was converted into the title compound according to the procedure in example 608E, and was isolated as a white powder.

$^1$H NMR (300 MHz, DMS O) δ0.76–0.98 (m, 2H), 1.03–1.19 (m, 2H), 1.32–1.74 (m, 9H), 1.75–2.18 (m, 7H), 1.92 (s, 3H), 2.52–2.59 (m, 4H), 3.60–3.82 (m, 5H), 432 (dd, J=9.1, 3.8 Hz, 1H), 4.39 (d, J=12.3 Hz, 1H), 4.57 (d, J=12.3 Hz, 1H), 6.92–6.98 (m, 1H), 7.08–7.23 (m, 5H), 7.36 (d, J=8.1 Hz, 1H), 7.53 (d, J=8.1 Hz, 1H).

MS (APCI(−)) m/e 611 (M−H);

Analysis calc'd for C$_{33}$H$_{43}$N$_3$O$_5$S$_2$Li.2.05H$_2$O: C, 60.45; H, 7.24; N, 4.27; found C, 60.48; H, 7.16; N, 4.22.

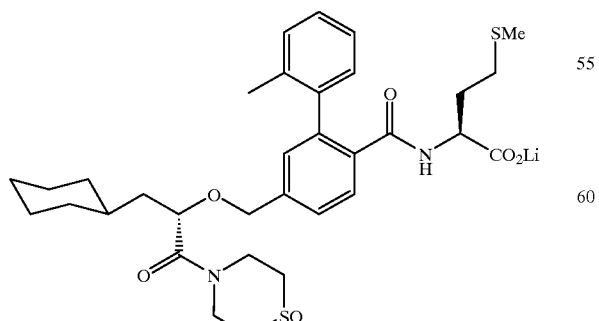

EXAMPLE 1055

N-[4-(3-cyclohexyl-N-thiomorpholin-S-oxide-4-ylpropion-2-yloxymethyl)-2-(2-methylphenyl)benzoyl]methionine, lithium salt

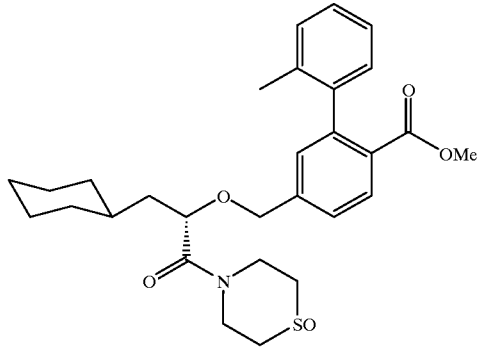

EXAMPLE 1055A 4-(3-cyclohexyl-N-thiomorpholin-S-oxide-4-ylpropion-2-yloxymethyl)-2-(2-methylphenyl)benzoic acid, methyl ester To a solution of 4-(3-cyclohexyl-N-thiomorpholin-4-ylpropion-2-yloxymethyl)-2-(2-methylphenyl)benzoic acid methyl ester (example 1054B, 250 mg) in dichloromethane (2.5 mL) at 0° C. was added m-chloroperbenzoic acid (174 mg, 55% pure). After 1.5 h at 0° C., the reaction was quenched by the addition of dilute aqueous sodium sulfite. The reaction was diluted with ether (50 mL), and washed with 1M NaOH (2×5 mL), and brine (2×5 mL). The organic solution was dried (MgSO$_4$), filtered and concentrated to afford a light yellow oil which was purified by silica gel chromatography eluting with 2.5 %–5.0% MeOH/EtOAc to give a colorless oil (240 mg, 94%).

MS(APCI(+)) 512 M+H)⁺.

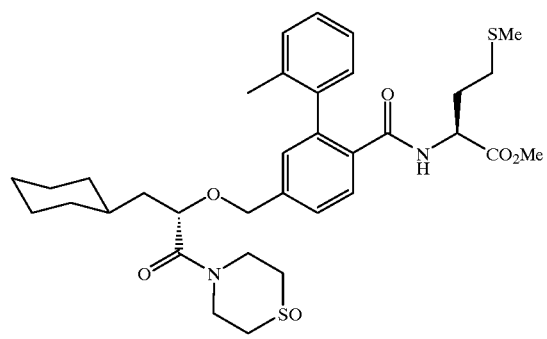

EXAMPLE 1055B

N-[4-(3-cyclohexyl-N-thiomorpholin-S-oxide-4-ylproion-2-yloxymethyl)-2-(2-methylphenyl)benzoyl]methionine, methyl ester The title compound was prepared from 4-(3-cyclohexyl-N-thiomorpholin-S-oxide-4-ylpropion-2-yloxymethyl)-2-(2-methylphenyl)benzoic acid methyl ester according to the procedure in examples 608C, and D.

MS(APCI(+)) 643 (M+H)⁺.

MS(APCI(−)) 641 (M−H)⁻.

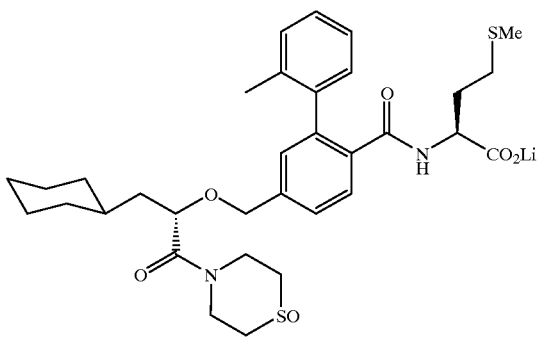

EXAMPLE 1055C

N-[4-(3-cyclohexyl-N-thiomorpholin-S-oxide-4-ylpropion-2-yloxymethyl)-2-(2-methylphenyl)benzoyl]methionine, lithium salt N-[4-(3-Cyclohexyl-N-thiomorpholin-S-oxide-4-ylpropion-2-yloxymethyl)-2-(2-methylphenyl)benzoyl] methionine methyl ester was converted into the title compound according to the procedure in example 608E, and was isolated as a white powder.

$^1$H NMR (300 MHz, DMS O) δ0.76–0.97 (m, 2H), 1.04–1.18 (m, 3H), 1.34–1.74 (m, 8H), 1.75–2.18 (m, 7H), 1.92 (s, 3H), 2.68–2.90 (m, 4H), 3.40–3.70 (m, 2H), 3.77–4.06 (m, 2H), 4.16–4.27 (m, 1H), 4.32–4.41 (m, 2H), 4.54–4.67 (m, 1H), 6.97 (brs, 1H) 7.11–7.26 (m, 5H), 7.39 (d, J=7.8 Hz, 1H), 7.54 (d, J=7.8 Hz, 1H).

MS (ESI(−)) m/e 627 (M−H);

Analysis calc'd for $C_{33}H_{43}N_2O_6S_2Li.2.10H_2O$: C58.93, 58.90; H, 7.07; N, 4.16; found: C58.93,; H, 7.01; N, 4.01.

mL, 55 mmol) and p-toluenesulfonic acid (0.1 g). The solution was refluxed overnight and the water collected in a Dean-Stark trap. The reaction was cooled and concentrated in vacuo. The residue was taken up in EtOAc (150 mL) and washed with water (3×50 mL), dried (MgSO₄) and concentrated in vacuo. The residue was purified by flash chromatography (hexane EtOAc 19:1) to give 8.1 g (89%) of a colorless liquid;

MS m/z 185 (M⁺+1, 100)

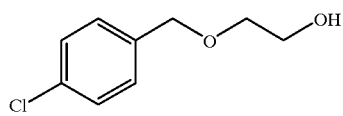

EXAMPLE 1084B

To a stirred suspension of zirconium (IV) chloride (5.1 g, 22 mmol) in ether (100 mL) was added a 1 M solution of LAH in ether (10.9 mL, 10.9 mmol) and the resulting black mixture stirred for 30 min. A solution of the acetal (2.0 g, 11 mmol) in ether (20 mL) was then added and the mixture refluxed overnight. The reaction was cooled and a solution of 10% aqueous $K_2CO_3$ (50 mL) was added carefully over 20 min and stirred for 45 min. The reaction was filtered thru Celite and the bed was washed well with ether. The ether layer was separated, dried (MgSO₄), and concentrated in vacuo. The residue was purified by flash chromatography (hexane/EtOAc 7:3) to get 0.17 g (8%) of a colorless liquid;

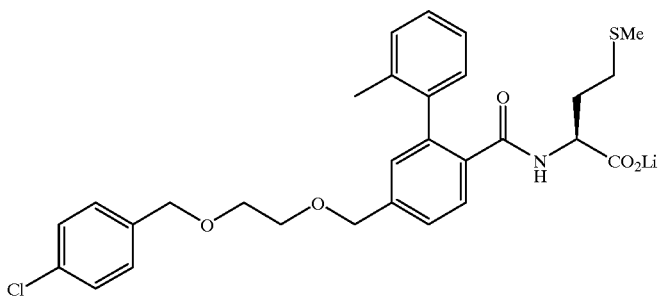

EXAMPLE 1084
N-[4-(2-(4-chlorobenzyloxy)ethoxymethyl)-2-(2-methylphenyl)benzoyl]methionine lithium salt

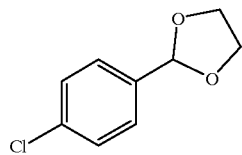

EXAMPLE 1084A
To a stirred solution of p-chlorobenzaldehyde (7.0 g, 50 mmol) in toluene (100 mL) was added ethylene glycol (3.1

MS m/z 204 (M$^+$+18, 100).

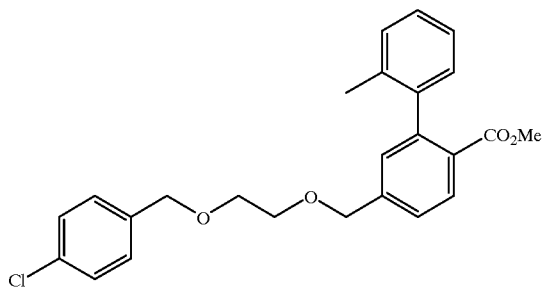

EXAMPLE 1084C

To an ice-cooled suspension of sodium hydride (0.032 g, 1.4 mmol) in DMF (3 mL) was added 15-crown-5 (0.2 mL, 1 mmol) and the core benzyl bromide (see example 1178D) (0.34 g, 1.1 mmol) and the resulting mixture stirred for 30 min. The reaction was quenched with H$_2$O (2 mL) and taken up in EtOAc (30 mL). The organic layer was washed with H$_2$O (5×10 mL), dried (MgSO$_4$) and concentrated in vacuo. The residue was purified by flash chromatography (hexane/EtOAc 9:1) to give 0.124 g (33%) of a colorless oil;

MS m/z 442 (M$^+$+18, 100).

mL) and the resulting solution heated to 60° C. overnight. The reaction was concentrated in vacuo and the residue taken up in 1:1 EtOAc/H$_2$O (30 mL) and acidified to pH=3 with 1N HCl. The layers were separated and the organic washed with H$_2$O (2×10 mL), dried (MgSO$_4$) and concentrated in vacuo to give 0.105 g (95%) of a colorless oil which was used as is in the following coupling.

To a stirred solution of the acid (0.105 g, 0.255 mmol) in DMF (3 mL) was added L-methionine methyl ester hdrochloride (0.066 g, 0.33 mmol), 1-hydroxybenzotriazole hydrate (0.045 g, 0.33 mmol), 1-(3-dimethylaminopropyl)-3-ethylcarbodiimide hydrochloride (0.065 g, 0.33 mmol) and triethylamine to pH=7 and the resulting mixture stirred overnight at rt. The reaction was poured into EtOAc (20 mL) and washed with H$_2$O (5×20 mL) and saturated aqueous NaHCO$_3$ (2×20 mL). The organic layer was dried (MgSO$_4$) and concentrated in vacuo. The residue was purified by flash chromatography (hexane/EtOAc 3:1) to give 0.129 g (91%) of a colorless oil;

MS m/z 556 (M$^+$+1, 100).

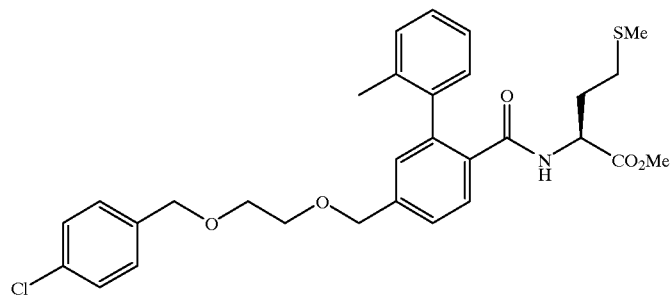

EXAMPLE 1084D

N-[4-(2-(4-chlorobenzyloxy)ethoxymethyl)-2-(2-methylphenyl)benzoyl]methionine, methyl ester To a solution of the ester (0.115 g, 0.271 mmol) in MeOH (5 mL) was added a saturated solution of LiOH in H$_2$O (1

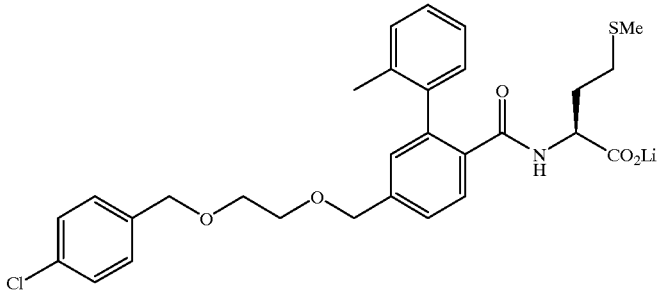

EXAMPLE 1084E

N-[4-(2-(4-chlorobenzyloxy)ethoxymethyl)-2-(2-methylphenyl)benzoyl]methionine lithium salt To a stirred solution of the ester (0.124 g, 0.223 mmol) in THF (5 mL) was added a solution of LiOH.H$_2$O (0.0103 g, 0.245 mmol) in H$_2$O (1 mL) and the resulting solution stirred for 3 h at rt. The reaction was concentrated in vacuo and lyopholized to give 0.122 g (100%) of a white powder:

$^1$H NMR (DMS O-d$_6$,) δ7.53 (d, 1 H, J=7.8 Hz), 7.38–7.29 (m, 5 H), 7.22–7.12 (m, 5H), 6.97–6.93 (m, 1 H), 4.57 (s, 2 H), 4.48 (s, 2 H), 3.73–3.60 (m, 5 H), 2.17–1.79 (m, 8 H), 1.68–1.63 (m, 1 H), 1.59–1.53 (m, 1 H);

MS m/z 540 (M$^+$–1, 100).

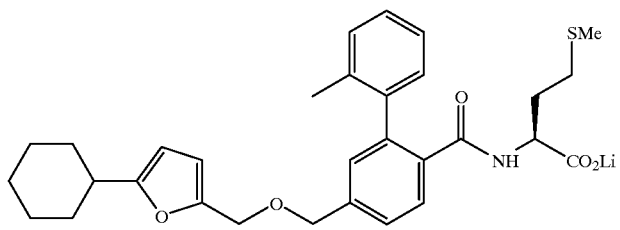

EXAMPLE 1090

[4-(2-(5-cyclohexylfuranyl)methoxymethyl)-2-(2-methylphenyl)-benzoyl]methionine, lithium salt

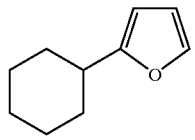

EXAMPLE 1090A

To a stirred solution of dichloroethane (70 mL) cooled –20° C. was added aluminum chloride (23 g, 0.17 mol) and cyclohexane carbonyl chloride (25 g, 0.17 mol) and the resulting mixture stirred for 10 min. Allyl chloride (15 mL, 0.18 mol) was added over 15 min, keeping the temperature between –15 to –25° C., and the resulting mixture stirred 1 h at –20° C. The reaction was quenched with 1N Hcl (200 mL) very carefully. The layers were separated and the aqueous extracted with ether (2×50 mL). The combined organic layers were washed with H$_2$O (200 mL), 5% aqueous NaHCO$_3$ (150 mL), dried (MgSO$_4$) and the solvent removed by distillation up to 85° C. The residue was put under vacuum (30 mmHg) and heated to 70° C. for 30 min. The residue was purified by flash chromatography (hexane) and the solvent removed by distillation to give 5 g (20%) of a colorless liquid;

$^1$H NMR (CDCl$_3$) δ7.29–7.28 (m, 1 H), 6.28–6.26 (m, 1 H), 5.95–5.93 (m, 1 H) 2.65–2.57 (m, 1 H), 2.06–1.96 (m, 2 H), 1.82–1.66 (m, 3 H), 1.43–1.19 (m, 5 H).

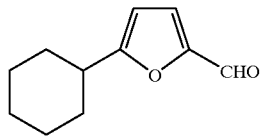

EXAMPLE 1090B

To a stirred solution of the cyclohexyl furan (0.75 g, 5.0 mmol) in DMF (1.6 mL, 20 mmol) was added phosphorus oxychloride (1.9 mL, 20 mmol) and the mixture heated to 90° C. for 2.5 h. The reaction was cooled, poured onto ice, and brought to pH=8 with 6N NaOH. The solution was extracted with ether (2×50 mL) and the combines ether layers were washed with H$_2$O (25 mL), dried (MgSO$_4$) and concentrated in vacuo. The residue was purified by flash chromatography (hexane/EtOAc 20:1 then 10:1) to give 0.48 g (54%) of a yellow liquid;

$^1$H NMR (CDCl$_3$) δ9.52 (s, 1 H), 7.17 (d, 1 H, J=3.5 Hz), 6.20 (dd, 1 H, J=3.5, 0.7 Hz), 2.79–2.68 (m, 1 H), 2.12–2.05 (m, 2 H), 1.86–1.69 (m, 3 H), 1.53–1.21 (m, 5 H).

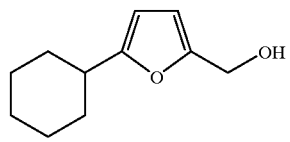

EXAMPLE 1090C

To a stirred solution of the aldehyde (0.48 g, 2.7 mmol) in MeOH (10 mL) at 0° C. was added sodium borohydride (0.20 g, 5.3 mmol) portionwise and the resulting solution stirredfor 1 h. The reaction was quenched with 1N HCl (10 mL) and concentrated in vacuo. The residue was taken up in EtOAC (25 mL) and washed with H$_2$O (15 mL), dried (MgSO$_4$) and concentrated in vacuo. The residue was purified by flash chromatography (hexane/EtOAc 6:1) to give 0.30 g (63%) of a colorless liquid;

MS m/z 181 (M⁺+1, 100).

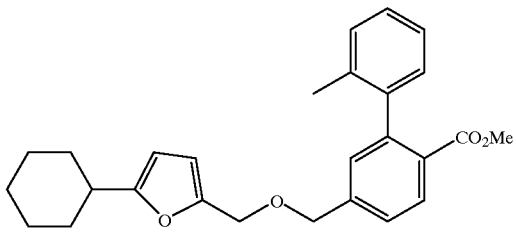

EXAMPLE 1090D

The alcohol (0.30 g, 1.7 mmol) was coupled to the core benzyl bromide (see example 1178 D) by procedure 1084 C. Flash chromatography (hexane/EtOAc 20:1) gave 0.48 g (68%) of a colorless oil;

MS m/z 436 (M⁺+18, 100).

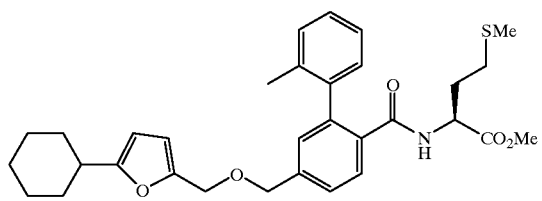

EXAMPLE 1090E

The ester (0.47 g, 1.1 mmol) was hydrolyzed as in example 1084 D and coupled to L-methionine methyl ester hydrochloride as in example 1084 D. Flash chromatography (hexane/EtOAc 3:1) gave 0.37 g (60%) of an yellow oil;

MS m/z 550 (M⁺+1, 100).

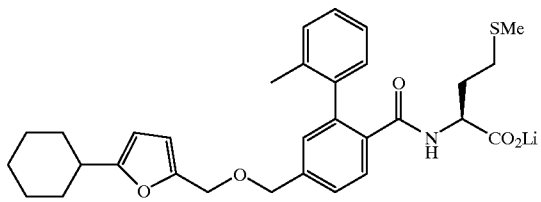

EXAMPLE 1090F

The ester (0.37 g, 0.67 mmol) was hydrolyzed as in example 1084 E to give 0.37 g of a white powder;

¹H NMR (DMSO-d₆,) δ7.52 (d, 1 H, J=7.8 Hz), 7.35 (d, 1 H, J=7.8 Hz), 7.21–7.07 (m, 5 H), 7.00–6.92 (m, 1 H), 6.31 (d, 1 H, J=3.1 Hz), 5 99 (d, 1 H, J=3.1 Hz), 4.54 (s, 2 H), 4.41 (s, 2 H), 3.72–3.66 (m, 1 H), 2.17–1.14 (m, 21 H);

MS m/z 534 (M⁺−1, 100).

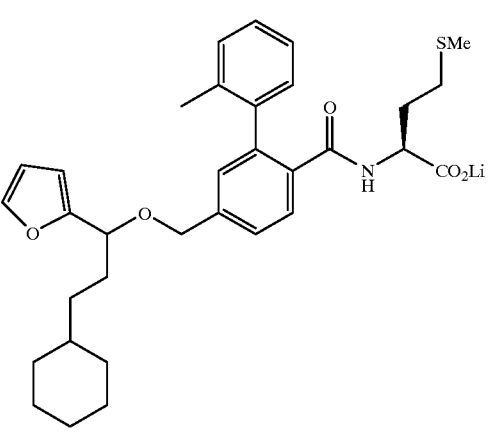

EXAMPLE 1091

N-[4-(1-furan-2-yl-3-cyclohexylpropoxymethyl)-2-(2-methylphenyl)benzoyl]methionine lithium salt

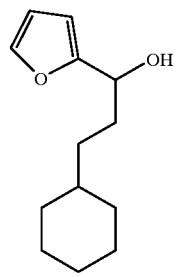

EXAMPLE 1091A

To a stirred suspension of magnesium (0.55 g, 23 mmol) in ether (20 mL) was added cyclohexylethyl bromide (3.6g, 19 mmol) and a crystal of iodine and the reaction was stirred 90 min. In another flask a stirred solution of 2-furanaldehyde (1.5 g, 16 mmol) in 1:1 THF/ether (20 mL) was cooled in an ice/MeOH bath. The Grignard solution was added to the aldehyde and stirred for 30 min. The reaction was quenched with saturated aqueous ammonium chloride (20 mL) and the reaction concentrated in vacuo. The residue was taken up in EtOAc (50 mL) and washed with H₂O (2×15 mL), dried (MgSO₄) and concentrated in vacuo. The residue was purified by flash chromatography (hexane/EtOAc 6:1) to give 1.5 g (45%) of a yellow oil;

MS m/z 208 (M$^+$+1, 100).

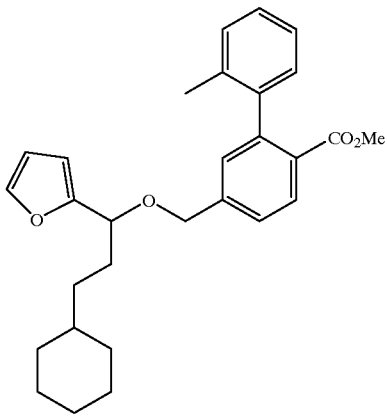

EXAMPLE 1091B

The alcohol (0.50 g, 2.4 mmol) was coupled to the core benzyl bromide (see example 1178 D) by procedure 1084 C. Flash chromatography (hexane/EtOAc 20:1) gave 0.60 g (60%) of a colorless oil;

MS m/z 446 (M$^+$+1, 100).

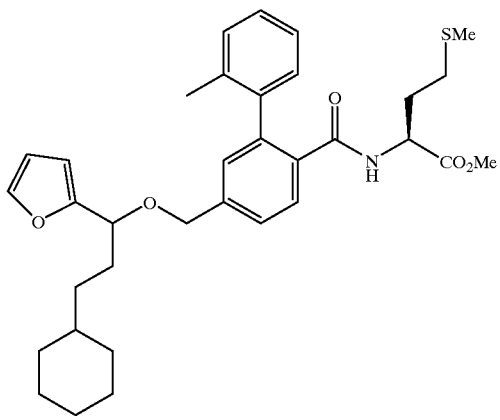

EXAMPLE 1091C

N-[4-(1-furan-2-yl-3-cyclohexylpropoxymethyl)-2-(2methylphenyl)benzoyl]methionine, methyl ester The ester (0.59 g, 1.3 mmol) was hydrolyzed as in example 1084 D and coupled to L-methionine methyl ester hydrochloride as in example 1084 D. Flash chromatography (hexane/EtOAc 6:1) gave 0.51 g (67%) of a colorless oil;

MS m/z 565 (M$^+$+1, 100).

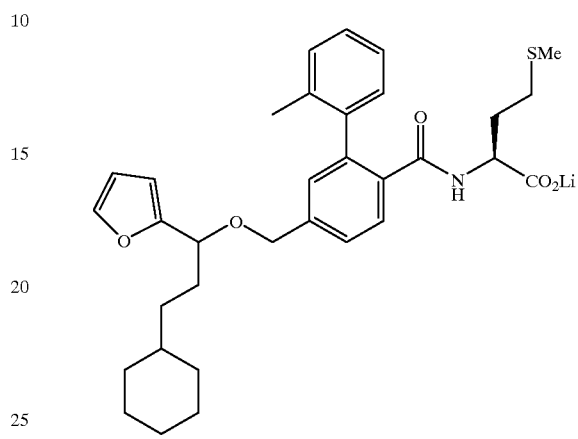

EXAMPLE 1091D

N-[4-(1-furan-2-yl-3-cyclohexylpropoxymethyl)-2-(2-methylphenyl)benzoyl]methionine lithium salt The ester (0.51 g, 0.90 mmol) was hydrolyzed as in example 1084 E to give 0.50 g of a light pink powder;

$^1$H NMR (DMS O-d$_6$,) δ7.62 (s, 1 H), 7.50 (d, 1 H, J=7.8 Hz), 7.32–7.30 (m, 1 H), 7.21–6.91 (m, 6 H), 6.42–6.39 (m, 2 H), 4.48–4.34 (m, 3 H), 3.72–3.65 (m, 1 H), 2.18–1.52 (m, 17 H), 1.27–1.02 (m, 6 H), 0.85–0.75 (m, 2 H);

MS m/z 562 (M$^+$–1, 100).

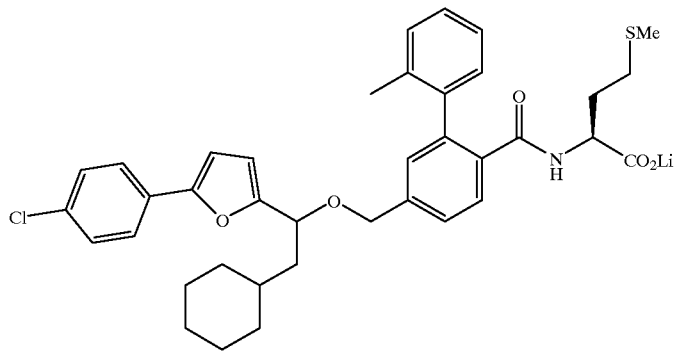

EXAMPLE 1092

N-[4-(1-(5-(4-chlorophenyl)furan-2-yl)-2-cyclohexylethoxymethyl)-2-(2-methylphenyl)benzoyl]methionine lithium salt

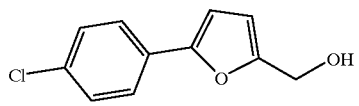

EXAMPLE 1092A

To a stirred suspension of LAH (0.78 g, 21 mmol) in THF (10 mL) was added a solution of 5-(4-chlorophenyl)-2-furoic acid (3.8 g, 17 mmol) in THF (30 mL) at a rate to maintain a gentle reflux. The reaction was stirred for 2 h at rt and heated to 50° C. for 30 min. The reaction was cooled in an ice bath and quenched with $H_2O$ (0.8 mL), 15% NaOH (0.8 mL), and $H_2O$ (2.1 mL). The reaction was filtered and concentrated in vacuo. The residue was taken up in EtOAc (50 mL) and washed with $H_2O$ (25 mL), dried ($MgSO_4$) and concentrated in vacuo. The residue was purified by flash chromatography ($CH_2Cl_2$) to give 1.3 g (36%) of a yellow oil;

MS m/z 208 ($M^+$+1, 100).

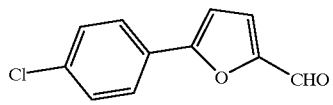

EXAMPLE 1092B

To a stirred solution of the alcohol (1.3 g, 6.2 mmol) in 9:1 $CH_2Cl_2/CH_3CN$ (20 mL) was added powdered sieves (6 g), N-methylmorpholine N-oxide (1.1 g, 9.3 mmol), and tetrapropylammonium perruthenate (0.11 g, 0.31 mmol) and stirred for 2 h at rt. The reaction was filtered through a silica gel bed, eluting with EtOAc (25 mL). The filtrate was concentrated in vacuo to give 1.0 g (78%) of a pink powder;

MS m/z 206 ($M^+$+1, 100).

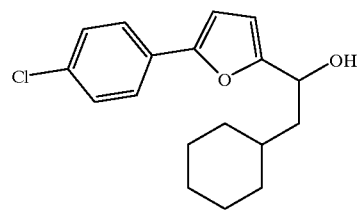

EXAMPLE 1092C

A Grignard reaction was run on the aldehyde (1.0 g, 4.9 mmol) as in example 1091 A using cyclohexylmethyl bromide. Flash chromatography (hexane/EtOAc 9:1) gave 0.73 g (48%) of an orange oil;

MS m/z 304 ($M^+$+1, 100).

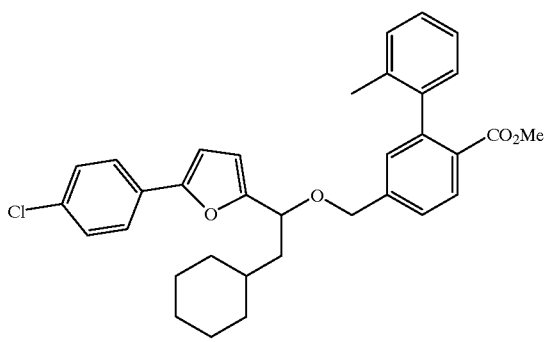

EXAMPLE 1092D

The alcohol (0.79 g, 2.6 mmol) was coupled to the core benzyl bromide (see example 1178 D) by procedure 1084 C. Flash chromatography (hexane/EtOAc 20:1) gave 0.50 g (36%) of a colorless oil;

MS m/z 543 ($M^+$+1, 100).

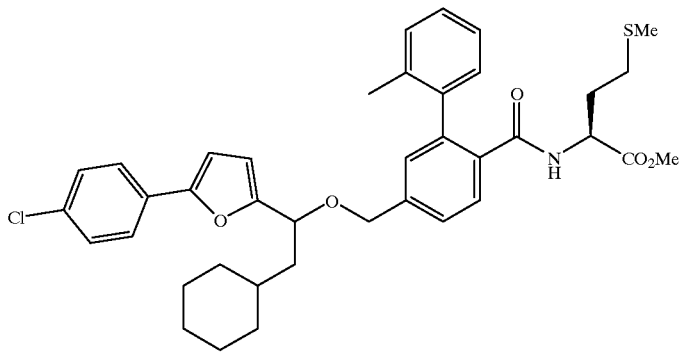

EXAMPLE 1092E

N-[4-(1-(5-(4-chlorophenyl)furan-2-yl)-2-cyclohexylethoxymethyl)-2-(2-methylphenyl)benzoyl]methionine, methyl ester The ester (0.50 g, 0.92 mmol) was hydrolyzed as in example 1084 D and coupled to L-methionine methyl ester hydrochloride as in example 1084 D. Flash chromatography (hexane/EtOAc 3:1) gave 0.37 g (59%) of colorless oil;

MS m/z 674 (M$^+$+1, 100).

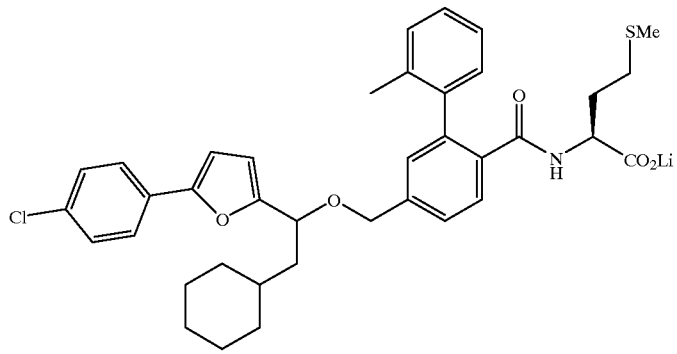

EXAMPLE 1092F

N-[4-(1-(5-(4-chlorophenyl)furan-2-yl)-2-cyclohexylethoxymethyl)-2-(2-methylphenyl)benzoyl]methionine lithium salt The ester (0.35 g, 0.52 mmol) was hydrolyzed as in example 1084 E to give 0.35 g of a white powder;

$^1$H NMR (DMS O-d$_6$) δ7.68 (dd, 2 H, J=8.8, 3.3 Hz), 7.50 (d, 1 H, J=7.8 Hz), 7.46 (dd, 2 H, J=8.8, 2.6 Hz), 7.33 (d, 1 H, J=8.1 Hz), 7.21–7.09 (m, 5 H), 6.97–6.87 (m, 2 H), 6.56 (dd, 1 H, J=3.3, 0.73 Hz), 4.56–4.42 (m, 3 H), 3.74–3.66 (m, 1 H), 2.17–0.83 (m, 23 H);

MS m/z 658 (M$^+$−1, 100).

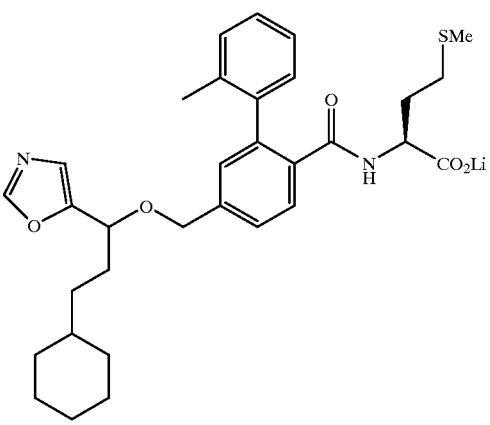

EXAMPLE 1093

N-[4-(1-oxazol-5-yl-3-cyclohexylpropoxymethyl)-2-(2-methylphenyl]methionine lithium salt

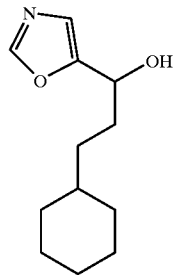

EXAMPLE 1093A

To a stirrred solution of toluenesulfonyl chloride (500 g, 2.6 mol) in quinoline (900 g) at 75° C. was added slowly N-methylformamide (100 g, 1.69 mol). The product distills from the reaction and is collected in a dry ice/acetone cooled receiving flask. Heating was discontinued and the addition was added at a rate to maintain a pot temperature of 75–80° C. After the addition was complete the reaction was stirred until distillation ceased. The distillate contained 48 g (69%) of a colorless liquid which was used as is in the next step.

To a stirred solution of methyl isocyanate (48 g, 1.17 mol) in THF (800 mL) in a dry ice/EtOH bath was added a 1.6M BuLi solution (730 mL) over 90 min, and the reaction was stirred an additional 20 min. A solution of ethyl diethoxy-acetate (206 g, 1.17 mol) in THF (200 mL) was then added over 1 h. The reaction was allowd to warm to −10° C. over 90 min. Cool in an ice bath and quench with glacial AcOH (75 mL) and stir overnight. The reaction was concentrated in vacuo, taken up in EtOAc (300 mL) and washed with $H_2O$ (2×100 mL), dried ($MgSO_4$) and concentrated in vacuo. Flash chromatography (hexane/EtOAc 4:1) gave 94 g (47%) of a golen liquid which was used as is in the next step.

To a flask containing the acetal (11 g, 64 mmol) in an ice bath was added a 1:1 mixture of $TFA/CH_2Cl_2$ (70 mL) followed by $H_2O$ (4 mL) and the solution stirred for 2 h. The reaction was concentrated in vacuo. Flash chromatography (hexane/EtOAc 7:3) gave 7.1 g of a brown liquid which was used as is in the next step.

A Grignard reaction was run on the aldehyde (0.59 g, 6.1 mmol) as in example I using cyclohexylethyl bromide. Flash chromatography ($CH_2Cl_2$/EtOAc 9:1) gave 0.15 g (13%) of a yellow powder;

MS m/z 209 ($M^+$+1, 100).

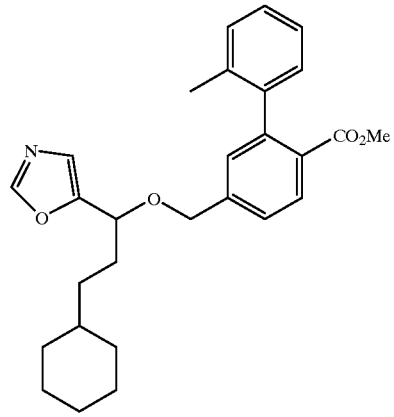

EXAMPLE 1093B

The alcohol (0.15 g, 0.75 mmol) was coupled to the core benzyl bromide (see example 1178 D) by procedure 1084 C. Flash chromatography (hexane/EtOAc 6:1) gave 0.20 g (61%) of a colorless oil;

MS m/z 448 ($M^+$+1, 100).

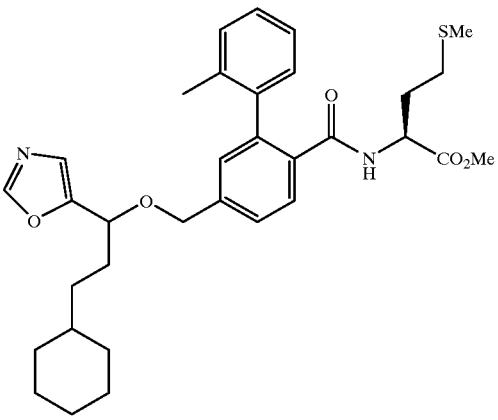

EXAMPLE 1093C

N-[4-(1-oxazol-5-yl-3-cyclohexylpropoxymethyl)-2-(2-methylphenyl)benzoyl]methionine, methyl ester The ester (0.19 g, 0.44 mmol) was hydrolyzed as in example 1084 D and coupled to L-methionine methyl ester hydrochloride as in example 1084 D. Flash chromatography (hexane/EtOAc 3:2) gave 0.20 g (84%) of colorless oil;

MS m/z 579 (M+ +1, 100).

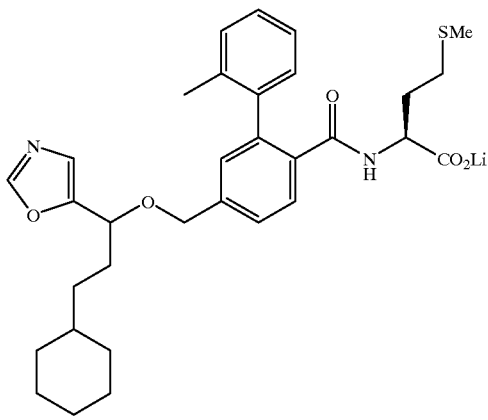

EXAMPLE 1093D

N-[4-(1-oxazol-5-yl-3-cyclohexylpropoxymethyl)-2-(2-methylphenyl)benzoyl]methionine lithium salt The ester (0.18 g, 0.31 mmol) was hydrolyzed as in example 1084 E to give 0.18 g of a white powder;

$^1$H NMR (DMS O-d$_6$,) δ8.34 (d, 1 H, J=1.1 Hz), 7.52 (d, 1 H, J=8.1 Hz), 7.33 (dd, 1 H, J=7.7, 1.1 Hz), 7.22–6.95 (m, 7 H), 4.53–4.40 (m, 3 H), 3.74–3.63 (m, 1 H), 2.18–1.52 (m, 17 H), 1.29–1.02 (m, 6 H), 0.88–0.75 (m, 2 H);

MS m/z 563 (M+ –1, 100).

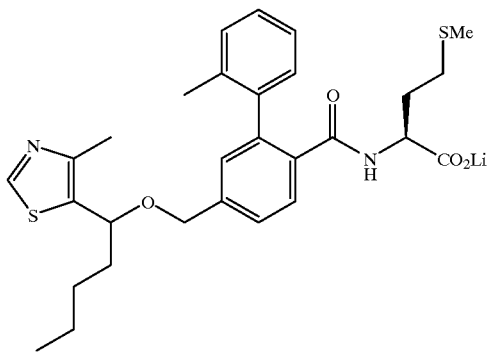

EXAMPLE 1095

N-[4-(1-(4-methylthiazol-5-yl)pentyloxy)methyl)-2-(2-methylphenyl)benzoyl]methionine lithium salt Step 1: 2-amino-4-methyl-thiazole ethyl ester A 50 mL round-bottom flask was charged with ethylthioacetate (6.4 mL, 50 mmol) and water (25 mL). Bromine (2.8 mL, 51 mmol) was added over 30 min. An orange solution was formed. The reaction was added to Et$_2$O (100 mL). The organic layer was dried over MgSO$_4$ and solvent removed under vacuum. The orange gel was added to a refluxing solution of thiourea (8.95 g, 117.5 mL) in ethanol (25 mL). The reaction was refluxed for about 2 h, then cooled slightly and poured into 50 mL of ice water. The pH was adjusted to 7–9 with NH$_3$(aq.). A thick white precipitate formed. The mixture was filtered to collect the solid. The product was recrystalized from 95% EtOH. Yield: 7.3 g (78%), white fluffy crystalline solid.

$^1$H NMR (δ, CDCl$_3$): 5.4 (2H), 4.25 (3H), 2.55 (3H), 1.35 (2H). Mass spec (DCI): 187 (M+1).

Step 2: 4-methylthiazole ethyl ester

A 50 mL round-bottom flask was charged with 4 N H$_2$SO$_4$ (80 mL) and 2-amino-4-methyl-thiazole ethyl ester (2.23 g,12 mmol). The reaction was cooled to –5° C. Sodium nitrite (0.99 g, 14.4 mmol) in 5 mL H$_2$O, was added over 5 min. The reaction was stirred for about 30 min. 50%(by wt) H$_3$PO$_2$ (15.84 mL, 120 mmol) was slowly added. A thick orange foam formed. The reaction was allowed to stir about 3 h until the foam had subsided. 50 mL of water was added. The pH was adjusted to 4–5 with potassium hydrogen phosphate tribasic. The reaction was extracted with Et$_2$O (3×50 mL), dried over Na$_2$SO$_4$ and concentrated under vacuum. Purified by silica gel column (3:1 Hexane/EtOAc). Yield: 1.50 g (67% ), orange oil.

$^1$H NMR (δ, CDCl$_3$): 8.8 (1H), 4.35 (3H), 2.8 (3H), 1.4 (2H).

N-[4-(1-(4-methylthiazol-5-yl)pentyloxy)methyl)-2-(2-methylphenyl)benzoyl]methionine lithium salt Steps 3–9: Follow Steps 1–7 in example 1098.
Yield: 30.6 mg, pale peach solid.

$^1$H NMR (δ, DMS O): 8.95 (1H), 6.8–7.6 (7H), 7.2 (1H), 4.4 (2H), 3.7 (1H), 2.3 (3H), 0.7–2.2 (17H) Mass spec (ESI): 541 (M+1), 539 (M–1) C$_{29}$H$_{35}$LiN$_2$O$_4$S$_2$.4.30 H$_2$O Calc'd.: C 55.81 H 7.04 N 4.49 Found: C 55.82 H 6.16 N 3.86

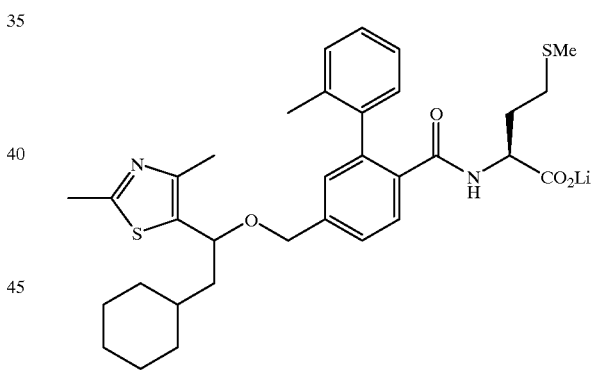

EXAMPLE 1096

N-[4-(1-(2,4-dimethylthiazol-5-yl)-2-cyclohexylethoxy)methyl)-2-(2-methylphenyl)benzoyl]methionine lithium salt Procedure: Follow step 1–7 in example 1098 except in step 3 use cyclohexylmagnesium bromide (1 M in Et$_2$O) instead of n-butylmagnesium bromide. Yield: 286.7 mg, pale yellow fluffy solid.

$^1$H NMR (δ, DMS O): 6.85–7.6 (7H), 4.7 (1H), 4.4 (2H), 3.68 (1H), 2.56 (3H), 2.22 (3H), 2.2 (3 H), 1.9 (3H), 0.7–1.85 & 1.95–2.19 (18H) Mass spec (ESI): 595 (M+1), 593 (M–1) C$_{33}$H$_4$ LiN$_2$O$_4$S$_2$.2.00 H$_2$O Calc'd: C 62.24 H 7.12 N 4.40 Found: C 62.21 H 6.75 N 4.23

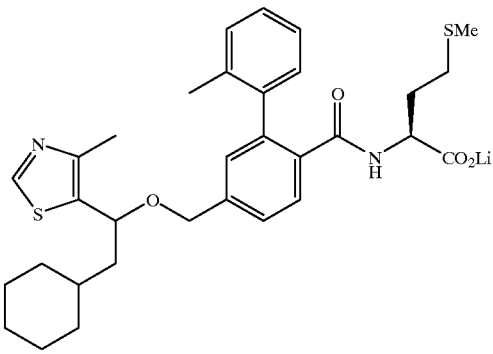

EXAMPLE 1097

N-[4-(1-(4-methylthiazol-5-yl)-2-cyclohexylethoxy)methyl)-2-(2-methylphenyl)benzoyl]methionine lithium salt Procedure: Follow step 1–7 in example 1095 except use cyclohexylmagnesium bromide (1 M in Et2O) instead of n-butylmagnesium bromide. Yield: 122.1 mg, pale yellow fluffy solid.

$^1$H NMR (δ, CDCl$_3$): 8.7 (1H), 6.8–7.4 (7H), 5.7 (1H), 4.38 (2H), 4.1 (1H), 2.95 (3H), 2.9 (3H), 0.8–2.6 (21H) Mass spec (ESI): 581 (M+1), 579 (M−1) C$_{32}$H$_{39}$LiN$_2$O$_4$S$_2$.3.45 H$_2$O Calc'd.: C 59.23 H 7.13 N 4.32 Found: C 59.19 H 6.98 N 4.38

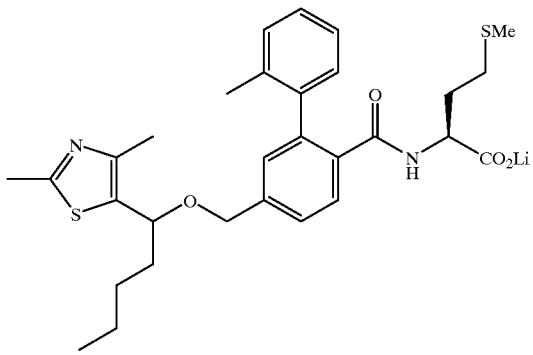

EXAMPLE 1098

N-[4-(1-(2.4-dimethylthiazol-5-yl)pentyloxy)methyl)-2-(2-methylphenyl)benzoyl]methionine lithium salt

Step 1: 2,4-dimethylthiazole-5-methanol

A 3-neck 100 mL round-bottom flask under N$_2$ atmosphere was charged with ethyl-2,4-dimethylthiazole-5-carboxylate (1.85 g, 10 mmol) in anhydrous CH$_2$Cl$_2$ (20 mL). The mixture was cooled to −78° C. 22 mL of di-isobutylaluminum hydride (1.0 M in CH$_2$Cl$_2$) was added dropwise via syringe. The reaction was allowed to warm to room temperature slowly and stirred for 14 h. TLC (1:1 Hexane/EtOAc) showed no starting material. The reaction was cooled to 0° C. MeOH(2 mL) and then 1 M HCl (10 mL) were slowly added. The bath was removed and the reaction stirred for 20 min. Extract with Et$_2$O (3×10 mL). Wash the combined organic layers with brine (10 mL). Dry over MgSO$_4$, filter and remove solvent under vacuum. Yield: 1.363 g (95%), orange oil.

$^1$H NMR (δ, CDCl$_3$): 2.65(3H), 2.36 (3H), 2.05 (1H), 1.7 (2H).

Step 2: 2,4-dimethylthiazole-5-carbaldehyde

A 3-neck 100 mL round-bottom flask was charged with anhydrous CH$_2$Cl$_2$ (20 mL) and oxalyl chloride (1.0 mL, 11.25 mmol) under N$_2$ atmosphere. The mixture was cooled to −78° C. Anhydrous DMSO (1.1 mL, 15 mmol) was slowly added. The reaction was allowed to stir for 30 min. 2,4-dimethylthiazole-5-methanol (1.181 g, 7.5 mmol) in CH$_2$Cl$_2$ (5 mL) was slowly added. The reaction was allowed to stir for about 3 h, until TLC (1:1 EtOAc/Hexane) showed no starting material. The reaction was quenched with triethylamine (4.3 mL, 30 mmol) and stirred for 10 min. before warming to room temperature. The reaction was poured into Et$_2$O (100 mL) and then extracted with water (2×25 mL). The organic phase was washed with NaHCO$_3$(aq) (25 mL) and brine (25 mL). Dry over MgSO$_4$ and concentrated under vacuum. The product was stored in the freezer. Yield: 1.04 g (89%) orange crystalline solid.

$^1$H NMR (δ, CDCl$_3$): 10.0 (1H), 2.72 (d, 6H).

Step 3: 2,4-dimethylthiazol-5-pentanol

A 3-neck 100 mL round-bottom flask was charged with 2,4-dimethylthiazole-5-carbaldehyde (1.164 g, 7.5 mmol) and anhydrous THF (20 mL) under N$_2$ atmosphere. The reaction was cooled to −10° C. n-Butylmagnesium chloride (7.5 mL, 2.0 M (in THF)) was added dropwise. The reaction was stirred for 1 h, then warmed to room temperature and stirred for an additional 3 h. The reaction was quenched with 4 mL MeOH/1 M HCl (1:1). The aqueous and organic layers were separated. The pH of the aqueous layer was adjusted to 3 with 1 M HCl. The aqueous layer was extracted with EtOAc (3×10 mL). All organic layers were combined and washed with brine (10 mL), dried over MgSO$_4$ and concentrated under vacuum. Purify by silica gel column (1:1 EtOAc/Hexane). Yield: 1.76 g, orange oil.

$^1$H NMR (δ, CDCl$_3$): 2.65 (3H), 2.35 (3H), 1.2–2.0 (7H), 0.9 (3H).

Step 4: 4-(1-(2,4-dimethylthiazol-5-yl)pentyloxy)methyl)-2-(2-methylphenyl)benzoic acid A 50-mL round-bottom flask was charged with 2,4-dimethylthiazol-5-pentanol (523.2 mg, 2.4 mmol), 4-bromomethyl-2-(2-methylphenyl)benzoic acid, methyl ester (639.3 mg, 2 mmol) (as prepared by examples 1178A–1178D) and anhydrous dmf (3 mL). The reaction was cooled to 0° C. Sodium hydride (60% dispersion in mineral oil) (126.9 mg, 3 mmol) was added. After stirring at 0° C. for 15 min., the bath was removed and the reaction was allowed to stir at ambient temperature for 2 h. After the TLC showed no 4-bromomethyl-2-(2-methylphenyl)phenylacetate was present, the reaction was quenched with 6 M H$_3$PO$_4$ buffer (2 mL). Extract with Et$_2$O (3×10 mL). The pH of the aqueous layer was adjusted to 3 with 1 M H$_3$PO$_4$ and then extracted with EtOAc (3×10 mL). The combined organic layers were washed with water (10 mL) and brine (10 mL), dried over MgSO$_4$, filtered and concentrated under vacuum. The product was redissolved in EtOH (10 mL) and 4 N NaOH (4 mL, 16 mmol) was added. The reaction was refluxed for 2 h, then allowed to cool. Water (10 mL) was added and the mixture was extracted with Et$_2$O (3×10 mL). The pH of the aqueous layer was adjusted to 3 with 1 M H$_3$PO$_4$ and then extracted with EtOAc (3×10 mL). The combined organic layers were washed with brine, dried over MgSO$_4$, filtered and concentrated under vacuum. Yield: 309 mg (35%), orange solid.

¹H NMR (δ, CDCl₃): 7.0–7.4 (7H), 4.35 (d, 1H), 2.65 (3H), 2.25 (3H), 2.1 (3H), 1.2–2.0 (6 H), 0.85 (3H).

Step 5: N-[4-1-(2,4-dimethylthiazol-5-yl)pentyloxy) methyl-2-(2-methylphenyl)benzoyl]methionine A 50 mL round-bottom flasks was charged with 4-(1-(2, 4-dimethylthiazol-5-yl)pentyloxy)methyl)-2-(2-methylphenyl)benzoic acid (174.9 mg, 0.4 mmol), 1-(3-dimethylaminopropyl-3-ethylcarbodiimide hydrochloride (EDAC) (85.7 mg, 0.44 mmol), L-methionine methyl ester hydrochloride (106.6 mg, 0.52 mmol), 1-hydroxybenzotriazole (61.0 mg, 0.44 mmol) and dmf (3 mL). The reagents were stirred until completely dissolved and then triethylamine (0.11 mL, 0.72 mmol) was added. The reaction was stirred about 48 h until no starting material was present. Water (2 mL) and EtOAc (2 mL) were added to dissolve the precipitate. The mixture was extracted with EtOAc (3×10 mL). The combined organic layers were washed with 2 M Na₂CO₃ (10 mL), water (10 mL) and brine (10 mL), dried over MgSO₄, filtered and concentrated under vacuum. Yield: 74.7 mg (33%), yellow oil.

¹H NMR (δ, CDCl₃): 7.0–7.4 (7H), 4.55 (2H), 4.33 (1H), 3.75 (3H), 2.95 (3H), 2.65 (3H), 2.0–2.4 (5H), 0.8–2.0 (9H). Mass spec(ESI): 569 (M+1), 567 (M−1).

Step 6: N-[4-1-(2,4-dimethylthiazol-5-yl)pentyloxy) methyl-2-(2-methylphenyl)benzoyl]methionine carboxylic acid A 25 mL round-bottom flask was charged with N-[4-1-(2,4-dimethylthiazol-5-yl)pentyloxy)methyl-2-(2-methylphenyl)benzoyl]methionine (74.7 mg, 0.13 mmol) and 3 mL of MeOH/THF (1:1). The flask was cooled to 0° C. and 1 M lithium hydroxide (0.260 mL, 0.26 mmol) was added. The bath was removed and the reaction stirred for about 3 h, monitoring by TLC (1:1 EtOAc/Hexane). The solvent was removed under vacuum and the reaction diluted with water. The mixture was extracted with EtOAc (3×10 mL), washed with brine (10 mL), dried over MgSO₄, filtered and concentrated under vacuum. Yield: 59.1 mg (81%), yellow oil.

¹H NMR (δ, CDCl₃): 7.1–7.5 (7H), 4.55 (2H), 4.35 (1H), 2.65 (3H), 2.3 (3H), 1.8–2.2 (5H), 0.8–2.0 (9H). Mass spec(ESI): 555 (M+1), 553 (M −1).

Step 7: N-[4-1-(2,4-dimethylthiazol-5-yl)pentyloxy) methyl-2-(2-methylphenyl)benzoyl]methionine lithium salt A 25 mL round-bottom flask was charged with N-[4-1-(2,4-dimethylthiazol-5-yl)pentyloxy)methyl-2-(2-methylphenyl)benzoyl]methionine-carboxylic acid (53.1 mg, 0.095 mmol) and 2 mL MeOH/H₂O (1:1). 1 M lithium hydroxide (0.110 mL, 0.105 mmol) was added. The reaction was allowed to stir for a few minutes and then the solvent was removed under vacuum. The reaction was frozen at −78° C. and lyophilized to dryness. Yield: 48.5 mg, white fluffy powder.

¹H NMR (δ, DMS O): 6.8–7.6 (7H), 4.62 (1H), 4.4 (2H), 3.65 (1H), 2.56 (3H) 2.22 (3H), 2.2 (3H), 1.9 (3 H), 0.7–1.85 & 1.92–2.8 (14H) Mass spec (ESI): 555 (M+1), 553 (M−1) C₃₀H₃₇LiN₂O₄S₂.4.45 H₂O Calc'd.: C 56.23 H 7.22 N 4.37 Found: C 56.23 H6.25 N 3.75

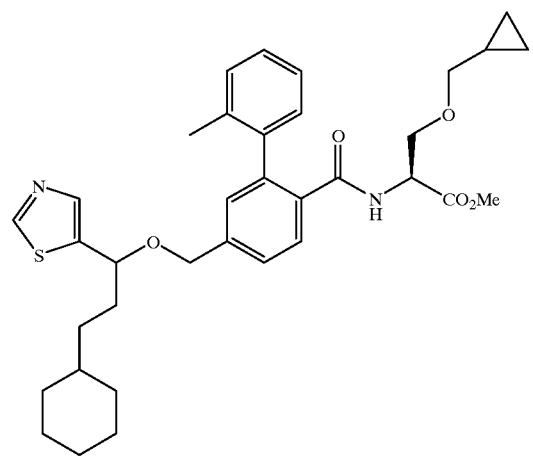

EXAMPLE 1113

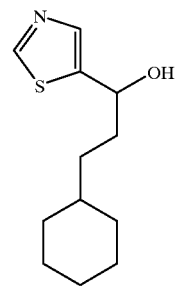

EXAMPLE 1113A 1-(5-thiazolyl)-3-cyclohexylpropan-1-ol

A solution of thiazole-5-carboxaldehyde (2.31 g, 20.4 mmol) in 20 mL of in THF was added to a cold (0° C.) solution of 2-cyclohexylethylmagnesium bromide (prepared from 2-bromoethylcyclohexane (7.88 g) and magnesium turnings (1.22 g)) in 30 mL of ethyl ether and the mixture stirred 30 minutes. The cold bath was removed and the mixture stirred for 2 hours more and then quenched by the addition of 3N aqueous HCl. The solution was stirred until 2 clear phases resulted and then the layers were separated. The pH of the aqueous phase was adjusted to 4 with 2M aqueous sodium carbonate and then extracted with 3 portions of ethyl acetate. All the organic phases were combined and washed with brine, dried, filtered and concentrated. The residue was purified by column chromatography on silica gel (125 g, 50% ethyl acetate/hexanes) to provide 2.69 g (58%) of the title compound.

MS (DCI, NH$_3$): 226 (MH$^+$); 243 (M+NH$_4$)$^+$.

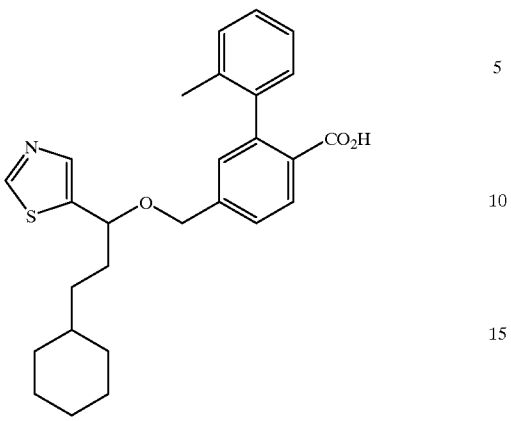

EXAMPLE 1113B 4-(1-thiazol-5-yl-3-cyclohexylpropoxy)methyl)-2-(2-methylphenyl)benzoic acid A solution of example 1113A (270 mg, 1.2 mmol) and example 1178D (319 mg, 1.0 mmol) in 1 mL of DMF were cooled in an ice bath and treated with sodium hydride (60%, 60 mg, 1.5 mmol). The bath was removed and the mixture stirred for 1 hour and quenched by the addition of water. The mixture was diluted with water and the pH adjusted to ~2 with phosphoric acid. The mixture was extracted with 3 portions of ethyl acetate. The combined organic fractions were washed with water and brine, dried filtered and concentrated. The residue was dissolved in 10 mL of ethanol and treated with 2 mL of 4N aqueous sodium hydroxide and then heated to reflux for 2 hours. The solution was cooled to room temperature and concentrated to dryness. The residue was dissolved in water and extracted with 2 portions of ethyl ether. The ether extracts were combined and washed with water. The pH of the combined aqueous phases was adjusted to ~4 with phosphoric acid and then the mixture was extracted with three portions of ethyl acetate. The combined ethyl acetate layers were washed with water and brine, dried, filtered and concentrated to provide 369 mg (82%) of the title compound.

MS (DCI, NH$_3$): 450 (MH$^+$).

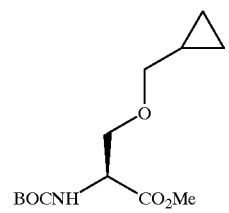

EXAMPLE 1113C

O-cyclopropylmethyl-N-t-butoxycarbonyl-L-serine, methyl ester

A solution example 1109A (268 mg, 1.09 mmol) in 5 mL of ether was treated with ethereal diazomethane until a light yellow color persisted. The excess diazomethane was removed in a stream of nitrogen and the solution of the methyl ester was treated with palladium (II) acetate (12 mg, 0.05 mmol) and excess ethereal diazomethane was added in portions over 1 hour and stirring continued for an additional 30 minutes. The resulting dark mixture was filtered through alumina and alumina pad washed well with ether. The filtrate was concentrate to provide 273 mg (92%) of the title compound.

MS (DCI, NH$_3$): 274 (MH$^+$).

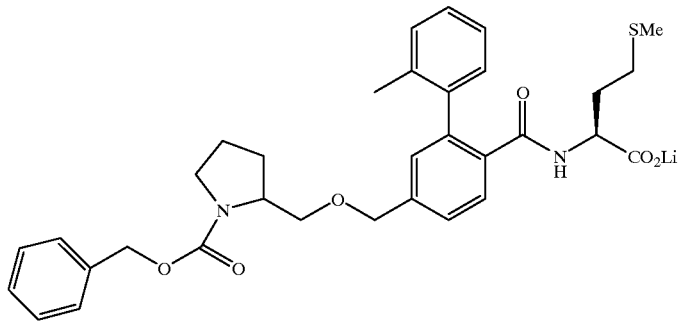

EXAMPLE 1128

N-[4-(N-benzyloxycarbonylpyrrolin-2-ylmethoxymethyl)-2-(2-methylphenyl)benzoyl] methionine lithium salt

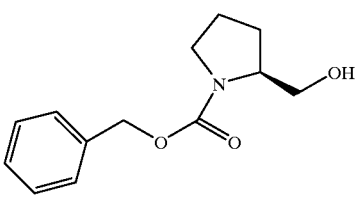

EXAMPLE 1128A

N-Benzyloxycarbonyl-2(S)-hydroxymethylpyrrolidine

2(S)-hydroxymethylpyrrolidine (1.01 g, 10.00 mmol) was dissolved in 10 mL of methylene chloride and cooled in an ice bath. The solution was treated with 10 mL of 2M sodium carbonate and vigorously stirred while a solution of benzylchloroformate (1.6 mL, 11.0 mmol) in 5 mL of methylene chloride was added dropwise. The mixture was stirred overnight during which time the ice bath melted. The layers were separated and the aqueous layer extracted with methylene chloride. The combined organic extracts were dried, filtered and concentrated to provide 2.35 g (100%) of the title compound.

MS (DCI, $NH_3$): 236 $(MH)^+$; 253 $(M+NH_4)^+$.

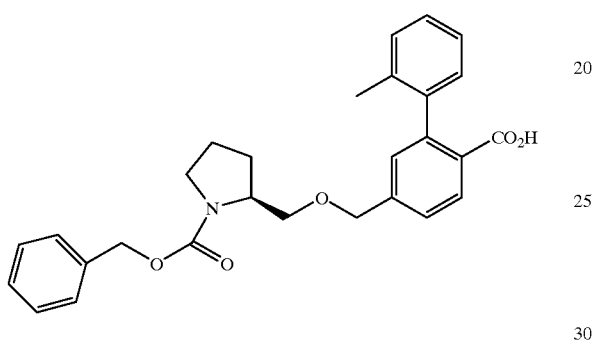

EXAMPLE 1128B

N-[4-(N-benzyloxycarbonylpyrrolin-2-ylmethoxymethyl)-2-(2-methylphenyl)benzoic acid Following the procedure described in example 1113B, example 1128A (265 mg. 1.2 mmol) provided 363 mg (77%) of the title compound.

MS (ESI+): 460 (MH+): (ESI−): 458 (M−H).

EXAMPLE 1128C

N-[4-(N-benzyloxycarbonylpyrrolin-2-ylmethoxymethyl)-2-(2-methylphenyl)benzoyl] methionine methyl ester Following the procedure of example 1178I, example 1128B (300 mg, 0.65 mmol) provided 280 mg (71%) of the title compound.

MS (ESI+): 605 (MH+): (ESI−): 603 (M−H).

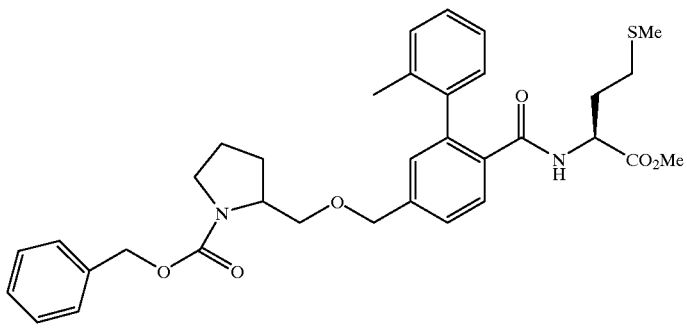

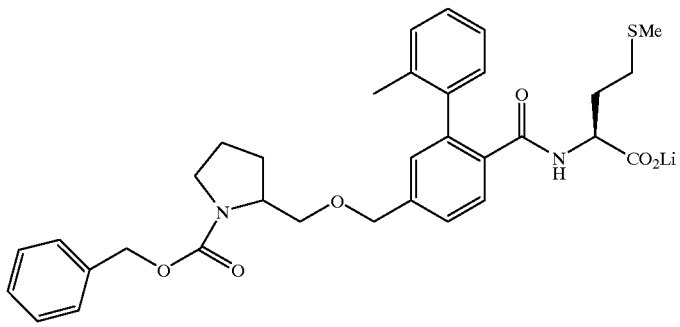

EXAMPLE 1128D

N-[4-(N-benzyloxycarbonylpyrrolin-2-ylmethoxymethyl)-2-(2-methylphenyl)benzoyl] methionine lithium salt Using the procedure described in example 1178J, example 1128C (270 mg, 0.45 mmol) provided 226 mg of the title compound.

$^1$H nmr (300 MHz., dmso d6): δ7.52, d, 1H; 6.90–7.40, 12H; 5.03, s, 2H; 4.51, d, 2H; 33.93, m, 1H; 3.68, m, 1H; 3.23–3.59, m, 4H; 1.46–2.18, 14H.

MS (ESI+): 591 (MH+): (ESI−): 589 (M−H).

Calc'd for $C_{33}H_{37}LiN_2O_6S \cdot 1.20\, H_2O$; C 64.11; H 6.42; N 4.53; Found: C 64.10; H6.23; N 4.38.

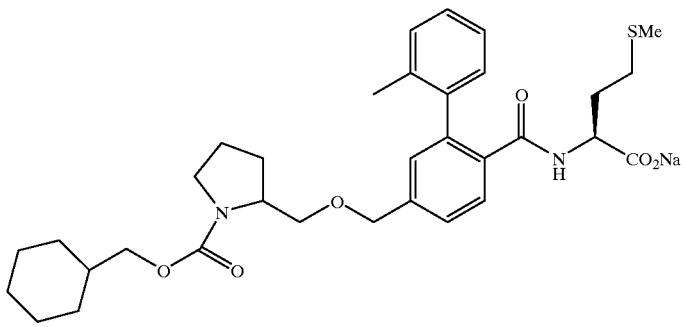

EXAMPLE 1129

N-[4-(N-cyclohexylmethoxycarbonylpyrrolin-2-ylmethoxymethyl)-2-(2-methylphenyl)benzoyl] methionine Sodium salt Following the procedure of example 1128 and substituting cyclohexylmethylchloroformate for benzylchloroformate in example A, the title compound was prepared. Additionally, sodium hydroxide was was substituted for lithium hydroxide prior to lyphilization.

$^1$H nmr (300 MHz., dmso d6): δ7.52, d, 1H; 7.36, dd, 1H; 6.94–7.26, m, 5H; 6.92, m, 1H; 4.53, s, 2H; 3.88, m, 1H; 3.75, d, 2H; 3.67, m, 1H; 3.51, m, 3.40, m, 1H; 3.25, m, 1H; 2.15, bs, 1.5H; 2.00, bs, 1.5H; 1.91, s, 3H; 1.43–1.97, 17H; 1.12, bm 3H; 0.92, m, 2H.

MS (ESI+): 597 (MH+): (ESI−): 595 (M−H).

Calc'd for $C_{33}H_{43}NaN_2O_6S \cdot 1.65\, H_2O$; C 61.12; H 7.20; N 4.32; Found: C 61.13; H 7.02; N 4.18.

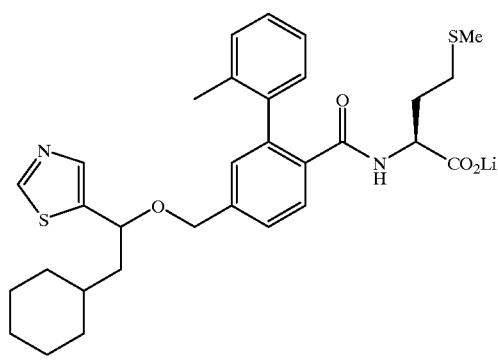

EXAMPLE 1131

N-[4-(2-cyclohexyl-1-thiazol-5-ylethoxymethyl)-2-(2-methylphenyl)benzoyl]methionine lithium salt

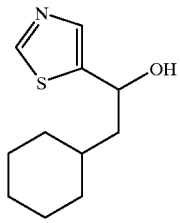

EXAMPLE 1131A 1-(5-thiazolyl)-2-cyclohexylethanol

Using the procedure of example 1113A and substituting cyclohexymethylmagnesium bromide, 0.98 g (46%) of the title compound was prepared.
MS (DCI, NH$_3$): 212 (MH)$^+$; 229 (M+NH$_4$)$^+$.

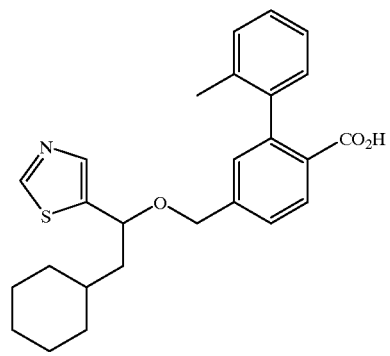

EXAMPLE 1131B

N-[4-(2-cyclohexyl-1-thiazol-5-ylethoxymethyl)-2-(2-methylphenyl)benzoic acid

Following the procedure of example 1113B, example 1131A (0.96 g, 4.54 mmol) provided 1.48 g (90%) of the title compound.
MS (DCI, NH$_3$): 212 (MH)$^+$.

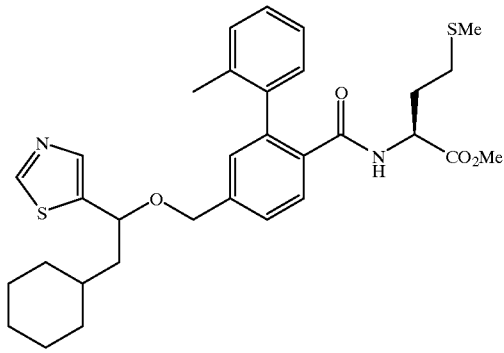

EXAMPLE 1131C

N-[4-(2-cyclohexyl-1-thiazol-5-ylethoxymethyl)-2-(2-methylphenyl)benzoyl]methionine methyl ester Following the procedure of example 1178I, example 1131B (1.48 g, 3.48 mmol) provided 1.64 g (81%) of the title compound.

MS (ESI+): 581 (MH+): (ESI−): 579 (M−H).

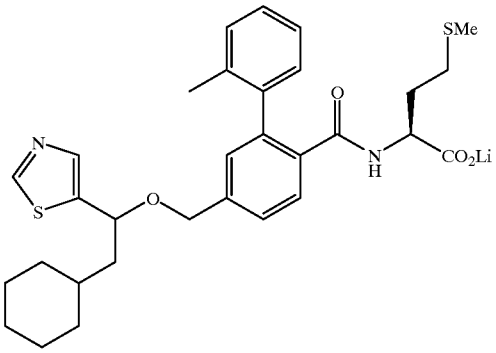

EXAMPLE 1131D

N-[4-(2-cyclohexyl-1-thiazol-5-ylethoxymethyl)-2-(2-methylphenyl)benzoyl]methionine lithium salt Following the procedure of example 1178J, example 1131C (1.63 g, 2.80 mmol) provided 1.61 g (89%) of the title compound.

$^1$H nmr (300 MHz., dmso d6): δ9.08, s, 1H; 7.89, s, 1H; 7.52, d, 1H; 7.33, dd, 1H; 7.10–7.26, m, 4H; 7.07, bs, 1H; 6.96, bs, 1H; 4.88, m, 1H; 4.42, q, 2H; 3.71, m, 3H; 1.95–2.20, m, 4H; 1.92, s, 3H; 1.81, bm, 2H; 1.57, bm, 8H; 1.32, m, 1H; 1.07, m, 3H; 0.89, m, 2H.

MS (ESI+): 567 (MH+): (ESI−): 575 (M−H).

Calc'd for C$_{31}$H$_{37}$LiN$_2$O$_4$S$_2$. 1.35 H$_2$O; C 62.37; H 6.70; N 4.69; Found: C 62.37; H 6.48; N 4.57.

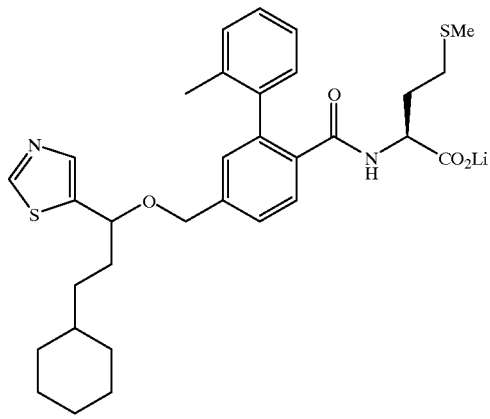

EXAMPLE 1132

N-[4-(3-cyclohexyl-1-thiazol-5-ylpropoxymethyl)-2-(2-methylphenyl)benzoyl]methionine lithium salt

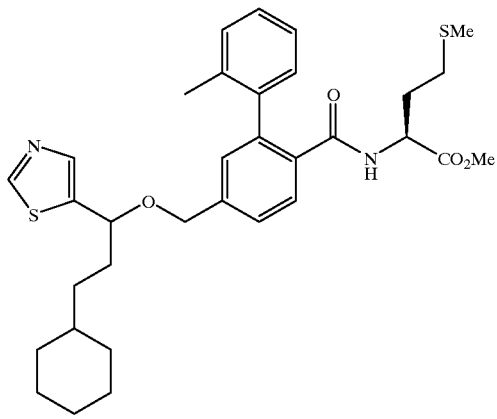

EXAMPLE 1132A

N-[4-(3-cyclohexyl-1-thiazol-5-ylpropoxymethyl)-2-(2-methylphenyl)benzoyl]methionine, methyl ester Following the procedure of example 1178I, example 1113B (0.36 g, 0.80 mmol) provided 0.41 g (87%) of the title compound.

MS (ESI+): 595 (MH+): (ESI−): 593 (M−H).

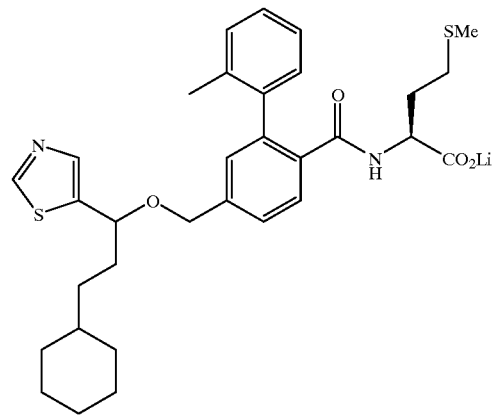

EXAMPLE 1132B

N-[4-(3-cyclohexyl-1-thiazol-5-ylpropoxymethyl)-2-(2-methylphenyl)benzoyl]methionine lithium salt Following the procedure of example 1178J, example 1132A (405 mg, 0.68 mmol) provided 362 mg (91%) of the title compound.

$^1$H nmr (300 MHz., dmso d6): δ9.08, s, 1H; 7.87, s, 1H; 7.51, d, 1H; 7.32, d, 1H; 719, bm, 4H; 7.08, bs, 1H; 6.95, m, 1H; 4.74, t, 1H; 4.43, q, 2H; 3.69, m, 1H; envelope 1.78–2.20, 8H; 1.62, bm, 8H; 1.11, bm, 6H; 0.79, m, 2H.

MS (ESI+): 581 (MH+): (ESI−): 579 (M−H).

Calc'd for $C_{32}H_{39}LiN_2O_4S_2$. 1.15 $H_2O$; C 63.27; H 6.85; N 4.61; Found: C 69.30; H 6.64; N 4.50.

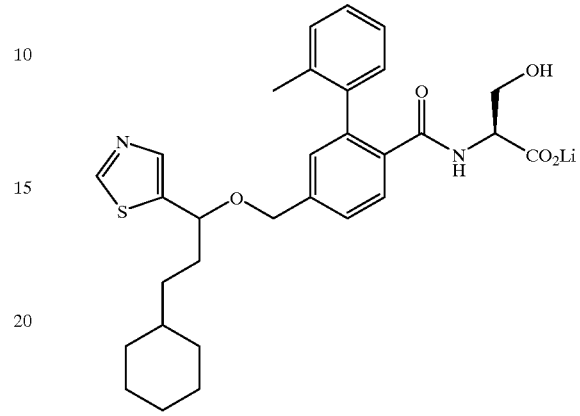

EXAMPLE 1133

N-[4-(3-cyclohexyl-1-thiazol-5-ylpropoxymethyl)-2-(2-methylphenyl)benzoyl]serine lithium salt

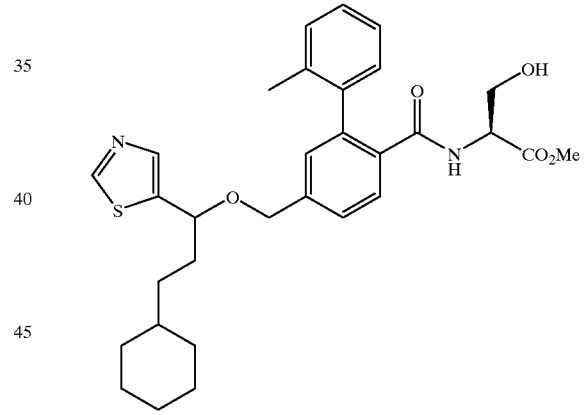

EXAMPLE 1133A

N-[4-(3-cyclohexyl-1-thiazol-5-ylpropoxymethyl)-2-(2-methylphenyl)benzoyl]serine methyl ester Using the procedure described in example 1178I and substituting L-serine methyl ester for L-methionine methyl ester, example 1113B provided the title compound.

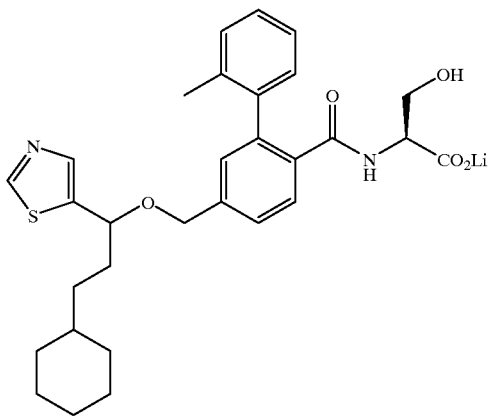

EXAMPLE 1133B

N-[4-(3-cyclohexyl-1-thiazol-5-ylpropoxymethyl)-2-(2-methylphenyl)benzoyl]serine lithium salt Using the procedure described in example 1178J, example 1133A provided the title compound.

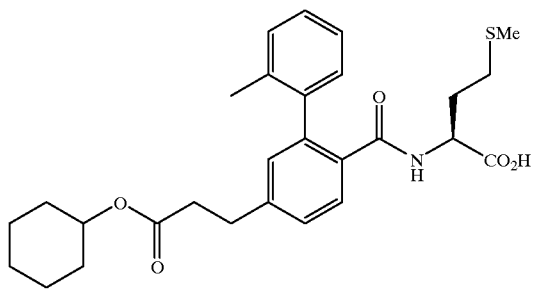

EXAMPLE 1152

N-[4-(cyclohexyloxycarbonylethyl)-2-(2-methylphenyl)benzoyl]methionine

EXAMPLE 1152A

N-[4-(cyclohexyloxycarbonylethyl)-2-(2-methylphenyl)benzoyl]methionine tert-butyl ester The procedures described in the Example 1147C were used here to convert 1147B (50 mg) to the title diester (35 mg, 55%). ¹HNMR (300 MHz, CDCl₃) δ7.82 (2 d's, 1 H), 7.31–7.15 (m, 5 H), 7.03 (br s, 1 H), 5.85 (br d, 1 H), 4.75 (m, 1 H), 4.50 (m, 1 H), 3.00 (t, 2 H), 2.63 (t, 2 H), 2.20–1.90 (m, 8 H), 1.90–1.20 (m, 12 H), 1.40 (s, 9 H).

MS(CI/NH₃) m/z: 554 (M+H)⁺.

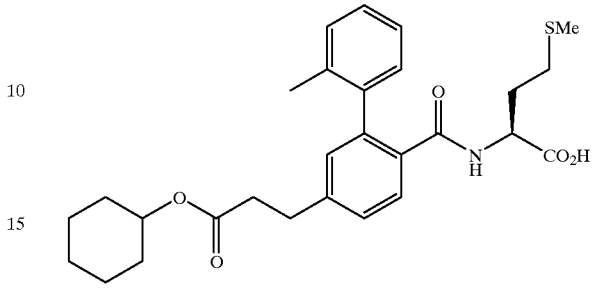

EXAMPLE 1152B

N-[4-(cyclohexyloxycarbonylethyl)-2-(2-methylphenyl)benzoyl]methionine

The intermediate 1152A (30 mg) was stirred with HCl (4.0 N in dioxane, 1.0 mL) in DCM (1 mL) at room temperature for 15 hours. Solvent was then evaporated to give the title compound without purification. ¹HNMR (300 MHz, CDCl₃) δ7.96 (2 d's, 1 H), 7.37–7.15 (m, 5 H), 7.05 (br s, 1 H), 5.87 (m, 1 H), 4.75 (m, 1 H), 4.52 (m, 1 H), 3.01 (t, 2 H), 2.64 (t, 2 H), 2.20–2.00 (m, 8 H), 2.00–1.20 (m, 12 H).

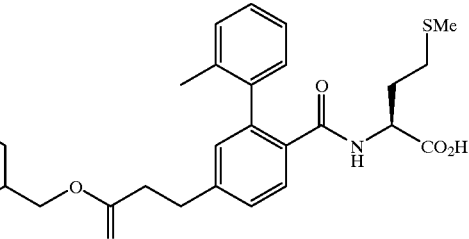

EXAMPLE 1153

N-[4-(cyclohexylmethoxycarbonylethyl)-2-(2-methylphenyl)benzoyl]methionine

The procedures described in the Example 1152A and 1152B were used here to 1147B (50 mg) to the title compound (33 mg, 56%). ¹HNMR (300 MHz, CDCl₃) δ7.96 (2 d's, 1 H), 7.37–7.15 (m, 5 H), 7.05 (br s, 1 H), 5.87 (m, 1 H), 4.60 (m, 1 H), 3.87 (d, 2 H), 3.01 (dt, 2 H), 2.64 (t, 2 H), 2.20–1.97 (m, 8 H), 1.80–0.85 (m, 13 H).

MS(ESI–) m/z: 510 (M–H)⁻.

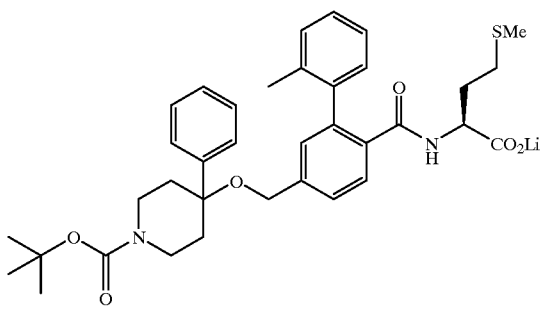

EXAMPLE 1156

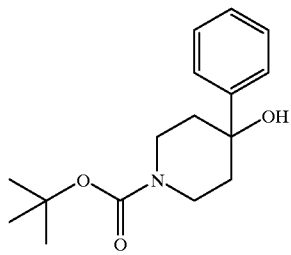

EXAMPLE 1156A 1-t-butoxycarbonyl-4-hydroxy-4-phenylpiperidine

To a solution of 4-hydroxy-4-phenylpiperidine (1.77 g, 10.0 mmol) and triethylamine (2 mL) in DCM (40 mL) was addede di-tert-butyl dicarbonate (2.29 g, 10.5 mmol). After 15 hopurs at room temperature, the reaction mixture was then partitioned between ether (80 mL) and water (20 mL). The organic layer was washed with water (2×20 mL), brine (20 mL), dried over anhydrous magnesium sulfate, filtered and concentrated. The residue was purified by column chromatography with 90:10:5 of hexane:ethyl acetate:chloroform to give the title compound (1.01 g, 36%). ¹HNMR (300 MHz, CDCl₃) δ7.48 (dq, 2 H), 7.37 (tt, 1 H), 7.30 (dt, 1 H), 4.02 (br loop, 2 H), 3.15 (br t, 2 H), 2.01 (br dt, 2 H), 1.74 (dq, 2 H), 1.48 (s, 9 H).

MS(CI/NH₃) m/z: 278 (M+H)⁺.

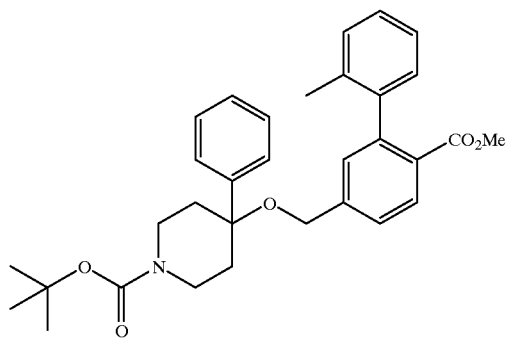

EXAMPLE 1156B

Methyl 4-(N-t-butoxycarbonyl4-phenylpiperidin-4-yloxymethyl)-2-(2-methylphenyl)benzoate To a suspension of of sodium hydride (95%, 22 mg, 0.85 mmol) in DMF (1.5 mL) was added 1156A (208 mg, 0.75 mmol). After 15 min., a solution of 4-bromomethyl-2-(2-methylphenyl)benzoic acid, methyl ester (example 1178D, 160 mg, 0.50 mmol), 15-crown-5 (22 mg), and tetrabutylammonium iodide (37 mg) in DMF (2 mL) was added to the reaction mixture through a cannula. After 3 hours, the reaction mixture was then partitioned between ethyl acetate (80 mL) and water (20 mL). The organic layer was washed with water (2×20 mL), brine (20 mL), dried over anhydrous magnesium sulfate, filtered and concentrated. The residue was purified wibyth column chromatography with 20% ethyl acetate in hexane to give the title compound (145 mg, 56%). ¹HNMR (300 MHz, CDCl₃) δ7.94 (d, 1 H), 7.46–7.19 (m, 9 H), 7.18 (d, 1 H), 7.07 (br d, 1 H), 4.18 (s, 2 H), 4.02 (br loop, 2 H), 3.60 (s, 3 H), 3.25 (br loop, 2 H), 2.15 (m, 2 H), 2.066 (s, 3 H), 1.93 (m,2 H), 1.47 (s, 9 H).

MS(CI/NH₃) m/z: 533 (M+NH₄)⁺.

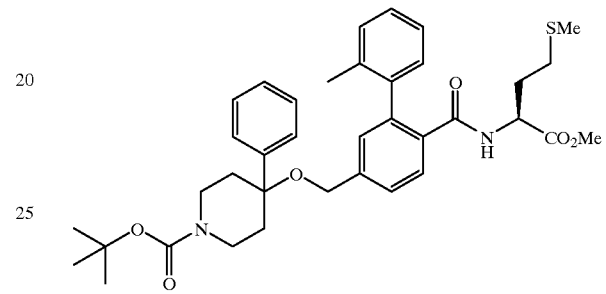

EXAMPLE 1156C

N-[4-(N-t-butoxycarbonyl-4-phenylpiperidin-4-yloxymethyl)-2-(2-methylphenyl)benzoyl] methionine methyl ester The procedures descriped in the Example 403E and 403F were used here to convert the above intermediate 1156B (411 mg, 0.80 mmol) to the title methyl ester (275 mg, 53%).

¹HNMR (300 MHz, CDCl₃) δ7.94 (2 d's, 1 H), 7.43 (2 d's, 1 H), 7.36–7.25 (m, 9 H), 7.18 (m, 1 H), 5.88 (br d, 1 H), 4.62 (m, 1 H), 4.61 (s, 2 H), 3.77 (m, 2 H), 3.66 (s, 3 H), 3.12 (m, 2 H), 2.20–2.00 (m, 9 H), 1.87 (m, 3 H), 1.61 (m, 2 H), 1.46 (s, 9 H).

MS(CI/NH₃) m/z: 664 (M+NH₄)⁺.

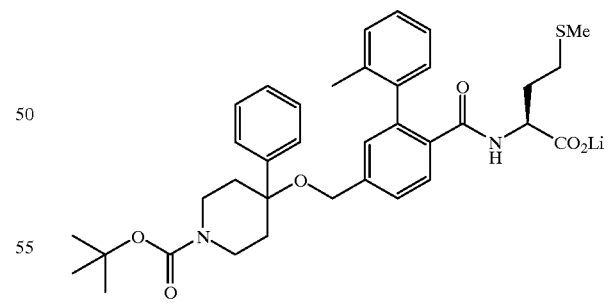

EXAMPLE 1156C

N-[4-(N-t-butoxycarbonyl4-phenylpiperidin-4-yloxymethyl)-2-(2-methylphenyl)benzoyl] methionine lithium salt The procedure described in the Example 403I was used here to convert the intermediate 1156B (265 mg) to the title lithium salt (264 mg, 100%).

¹H nmr (300 MHz, DMS O-d₆): δ7.49 (m, 3 H), 7.39 (m, 3 H), 7.30 (t, 1 H), 7.27–7.07 (m, 5 H), 6.95 (d, 1 H), 4.14 (s, 2 H), 3.85 (m, 32 H), 3.68 (m, 1 H), 3.10–3.05 (M, 2 H), 2.20–1.95 (m, 7 H), 1.92 (br s, 3 H), 1.83 (dt, 2 H), 1.70 (m, 1 H), 1.57 (m, 1 H), 1.40 (s, 9 H).

MS (ESI–): m/e 631 (M–H)⁻.

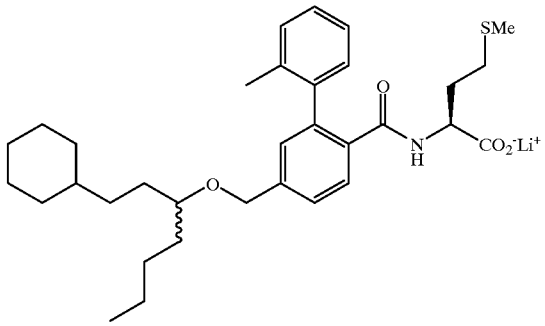

EXAMPLE 1192

N-[4-(1-Cyclohexylheptan-3-yloxymethyl-2-(2-methylphenyl)benzoyl]methionine lithium salt

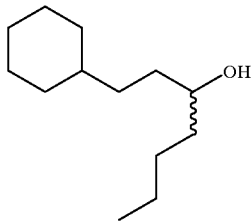

EXAMPLE 1192A

1-Cyclohexylheptan-3-ol

The alcohol was prepared using the method described in Example 1206A starting with 3-cyclohexylpropyl carboxaldehyde (prepared by Swern oxidation of 3-cyclohexyl-1-propanol) and butylmagnesium chloride.

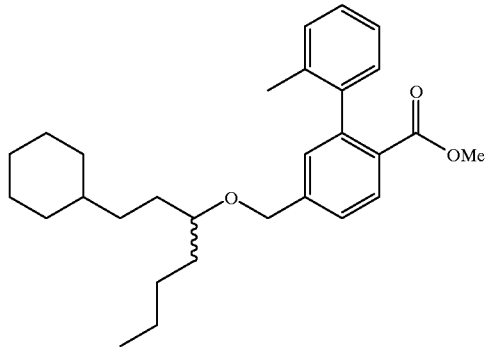

EXAMPLE 1192B 4-(1-Cyclohexylheptan-3-yloxymethyl-2-(2-methylphenyl)benzoic acid methyl ester The ether was prepared using the method described in Example 1205B starting with the compound from Example 1192A and 4-bromomethyl-2-(2-methylphenyl)benzoic acid methyl ester, prepared as in Example 1132A–D. m/e (ESI) 437 (MH⁺)

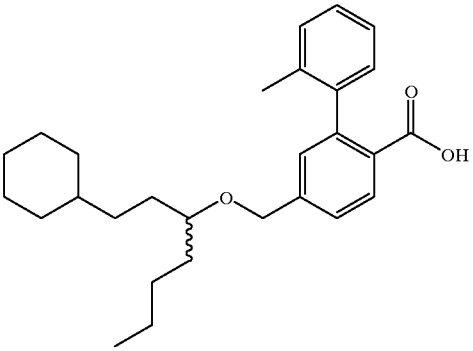

EXAMPLE 1192C 4-(1-Cyclohexylheptan-3-yloxymethyl-2-(2-methylphenyl)benzoic acid The acid was prepared using the method described in Example 1205C starting with the compound from Example 1192B.

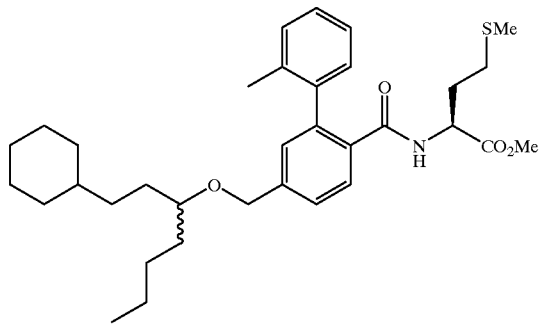

EXAMPLE 1192D cl N-[4-(1-Cyclohexylheptan-3-yloxymethyl-2-(2-methylphenyl)benzoyl]methionine methyl ester The compound was prepared using the method described in Example 1132G starting with the compound from Example 1192C. m/e (ESI) 566 (MH⁻)

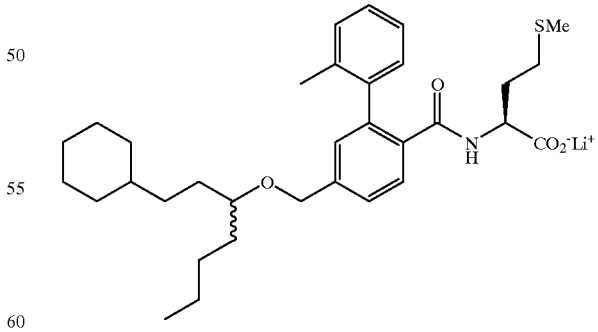

EXAMPLE 1192E

N-[4-(1-Cyclohexylheptan-3-yloxymethyl-2-(2-methylphenyl)benzoyl]methionine lithium salt The desired compound was prepared according to the method of Example 1132H starting with the compound from Example 1192D. $^1$H (300 MHz, CDCl$_3$, d) (rotamer) 8.00 (7.96) (1H, d, J=9 Hz), 7.44 (1H, dd, J=7&2 Hz), 7.40–7.10 (5H, m), 5.87 (1H, m), 4.57 (2H, s), 4.56 (1H, m), 3.36 (1H, m), 2.20–2.00 (8H, m), 1.91 (1H, m), 1.67 (4H, m), 1.53 (4H, m), 1.30 (6H, m), 1.20 (6H, m), 0.88 (5H, m). m/e (ESI) 552 (MH$^-$)

Anal.calc. for C$_{33}$H$_{46}$LiNO$_4$S. 1.25 H$_2$O C 68.07, H 8.40, N 2.41 Found C 68.19, H 8.22, N 2.48

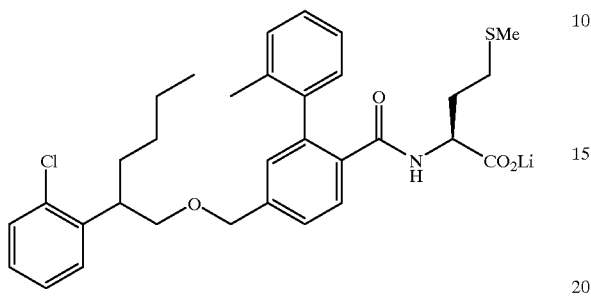

EXAMPLE 1205

N-[4-(2-(2-chlorophenyl)hexan-1-yloxymethyl)-2-(2-methylphenyl)benzoyl]methionine lithium salt

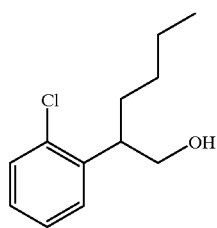

EXAMPLE 1205A 2-(2-chlorophenyl)hexan-1-ol

THF (45 mL) was cooled to –10° C., then 1.5M LDA. THF in cyclohexane was added followed by 1.7 g (10 mmol) 2-chlorophenylacetic acid in THF (15 mL) which was added dropwise. Stirred reaction at –10° C. under N$_2$ for 30 min., warmed to RT over 30 min., then recooled to –10° C. Added 5.5 g (3.4 mL, 30 mmol) 1-iodobutane, then allowed reaction to warm to RT overnight. Next day filtered through celite, then added the filtrate to 2N HCl and Et$_2$O. Washed organic layer with brine, extracted combined aqueous layers with Et$_2$O, then dried combined organic layers over Na$_2$SO$_4$. After filtration and concentration had 1.9 g dark brown oil that was reduced without purification.

That oil was dissolved in THF (10 mL), cooled to –10° C., then 1.0M BH$_3$ in THF was added dropwise under N$_2$. After allowing the reaction to warm to RT overnight, it was cooled to 0° C., and 1N NaOH (17 mL) was added dropwise. The reaction was stirred for 15 min., then partitioned between water and Et$_2$O. Washed organic layer with brine, extracted combined aqueous layers with Et$_2$O, then dried combined organic layers over Na$_2$SO$_4$. After filtration and concentration the crude material was purified by chromatography using 88/12 hex/EtOAc. Recovered 0.72 g (34% from 2-chlorophenylacetic acid).

$^1$H NMR (CDCl$_3$) δ7.40 (d, 1H), 7.28 (m, 2H), 7.17 (m, 1H), 3.79 (t, 2H), 3.48 (m, 1H), 1.79 (m, 1H), 1.64 (m, 1H), 1.29 (m, 4H), 0.86 (t, 3H).

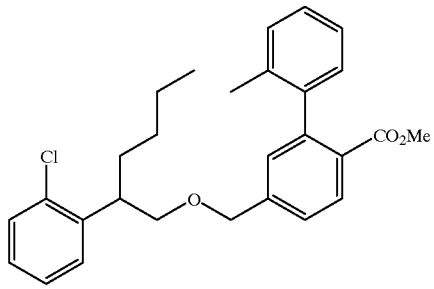

EXAMPLE 1205B 4-(2-(2-chlorophenyl)hexan-1-yloxymethyl)-2-(2-methylphenyl)benzoic acid methyl ester The alcohol described in Example 1205A (240 mg, 1.13 mmol) and the bromide described in Example 1178D (315 mg, 1.00 mmol) were dissolved in DMF (0.5 mL), then 45 mg 60% NaH (1.12 mmol) was added. After stirring at RT overnight, the reaction was partitioned between EtOAc and water. The organic layer was washed with brine, then dried over Na$_2$SO$_4$. After filtration and concentration the crude material was purified by chromatography using 98/2 hex/EtOAc. Recovered 170 mg (38%).

MS (APCI) 451/453 (M+H)$^+$.

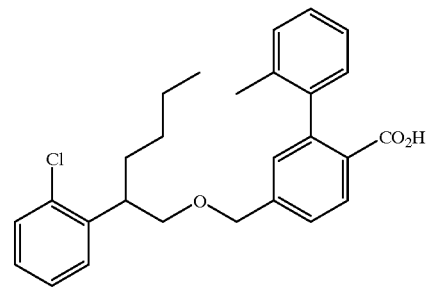

EXAMPLE 1205C 4-(2-(2-chlorophenyl)hexan-1-yloxymethyl)-2-(2-methylphenyl)benzoic acid The title compound was prepared from the compound described in Example 1205B by the method described in EXAMPLE 1178H.

MS (APCI) 454/456 (M+H+NH$_3$)$^+$.

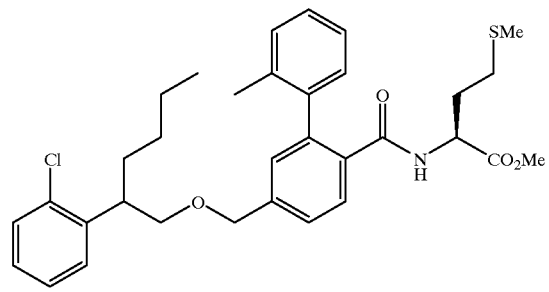

EXAMPLE 1205D

N-[4-(2-(2-chlorophenyl)hexan-1-yloxymethyl)-2-(2-methylphenyl)benzoyl]methionine methyl ester The compound described in Example 1205D (148 mg, 0.34 mmol) was dissolved in DMF (1.5 mL), then 74 mg (0.37 mmol) HCl.Met-OMe, 70 mg (0.37 mmol) EDCI.HCl, 54 mg (0.35 mmol) HOBT.H₂O, and 38mg (41μL, 0.37 mmol) N-methylmorpholine were added. The reaction was stirred at RT overnight, then partitioned between 2N HCl and EtOAc. The organic layer was washed with saturated aqueous NaHCO₃ and brine, then dried over Na₂SO₄. After filtration and concentration the crude material was purified by chromatography using 4/1 hex/EtOAc. Recovered 160 mg (81%).

MS (APCI) 582/584 (M+H)⁺.

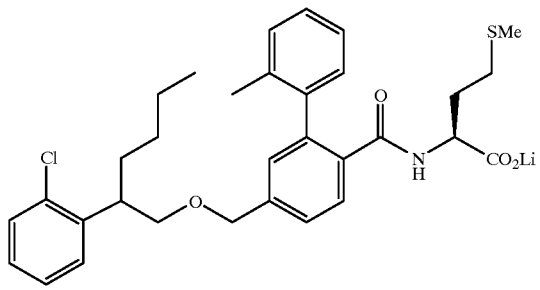

EXAMPLE 1205E

N-[4-(2-(2-chlorophenyl)hexan-1-yloxymethyl)-2-(2-methylphenyl)benzoyl]methionine lithium salt The above compound was prepared from the compound described in Example 1205D according to the method of Example 1178J.

¹H NMR (DMS O-d₆) δ7.47 (d, 1H), 7.37 (m, 2H), 7.20, 6.96 (both m, total 9H), 4.50 (dd, 2H), 3.66 (m, 1H), 3.60 (d, 2H), 3.45 (m, 1H), 2.10, 1.97, 1.90, 1.75, 1.58 (all m, total 12H), 1.18 (m, 4H), 0.79 (m, 3H).

MS (ESI) 566/568 (M−H)⁻.

Anal calcd for C₃₂H₃₇ClLiNO₄S. 0.50 H₂O: C, 65.91; H, 6.46; N, 2.40. Found: C, 65.85; H,6.57; N, 2.40.

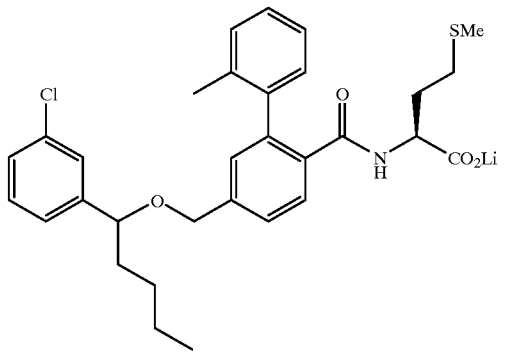

EXAMPLE 1206

N-[4-(1-(3-chlorophenyl)pentan-1-yloxymethyl)-2-(2-methylphenyl)benzoyl]methionine lithium salt

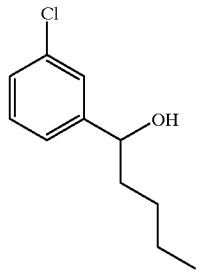

EXAMPLE 1206A 1-(3-chlorophenyl)pentan-1-ol

A solution of 3-chlorobenzaldehyde (1.4 g, 10 mmol) in THF (10 mL) was cooled to −10° C., then 2.0 M n-butylmagnesium chloride (10 mL) was added. The reaction was allowed to warm to RT under N₂ overnight. Next day the reaction was cooled to 0–5° C., water (5 mL) was added, followed by 2N HCl—Et₂O partition. The organic layer was washed with brine, then dried over Na₂SO₄. After filtration and concentration the crude material was purified by chromatography using 9/1 hex/EtOAc. Recovered 1.25 g (63%).

¹H NMR (CDCl₃) δ7.37 (m, 1H), 7.23 (m, 3H), 4.43 (ddd, 1H), 1.82 (d, 1H), 1.72 (m, 2H), 1.35 (m, 4H), 0.90 (t, 3H).

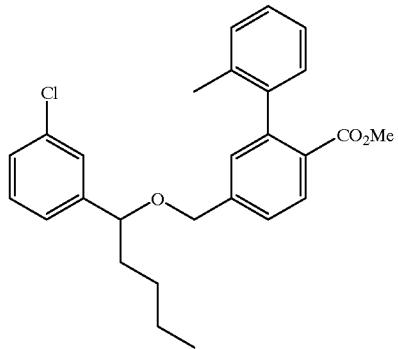

EXAMPLE 1206B 4-(1-(3-chlorophenyl)pentan-1-yloxymethyl)-2-(2-methylphenyl)benzoic acid methyl ester The title compound was prepared from the compound described in Example 1206A and the bromide described in Example 1178D using the method of Example 1205B.

MS (DCI/NH$_3$) 454/456 (M+H+NH$_3$)$^+$.

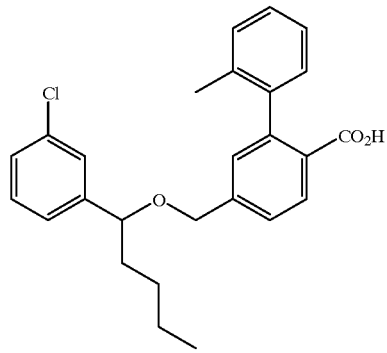

EXAMPLE 1206C 4-(1-(3-chlorophenyl)pentan-1-yloxymethyl)-2-(2-methylphenyl)benzoic acid The title compound was prepared from the compound described in Example 1206B using the method of Example 1178H.

MS (APCI) 440/442 (M+H+NH$_3$)$^+$.

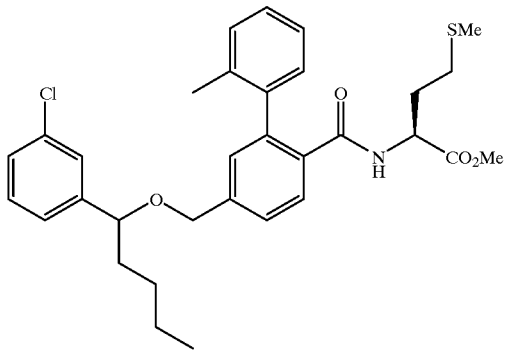

EXAMPLE 1206D

N-[4-(1-(3-chlorophenyl)pentan-1-yloxymethyl)-2-(2-methylphenyl)benzoyl]methionine methyl ester The title compound was prepared from the compound described in Example 1206C using the method of Example 1205D.

MS (APCI) 568/570 (M+H)$^+$.

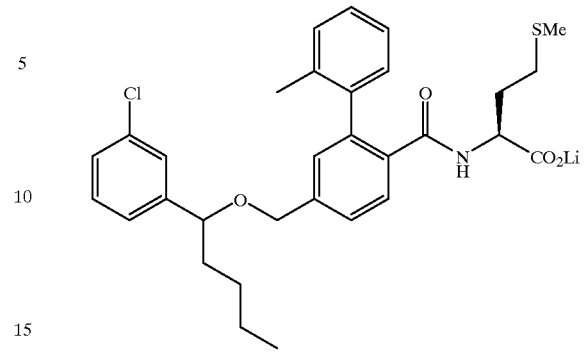

EXAMPLE 1206E

N-[4-(1-(3-chlorophenyl)pentan-1-yloxymethyl)-2-(2-methylphenyl)benzoyl]methionine lithium salt The above compound was prepared from the compound described in Example 1206D according to the method of Example 1178J.

$^1$H NMR (DMS O-d$_6$) δ7.50 (d, 1H), 7.37 (m, 5H), 7.20, 7.08, 6.96 (all m, total 6H), 4.40 (m, 3H), 3.66 (m, 1H), 2.17, 2.00, 1.90, 1.75, 1.60 (all m, total 12H), 1.23 (m, 4H), 0.80 (m, 3H).

MS (ESI) 552 (M–H)$^-$.

Anal calcd for C$_{31}$H$_{35}$ClLiNO$_4$S. 0.50 H$_2$O: C, 65.43; H, 6.38; N, 2.46. Found: C, 65.35; H, 6.19; N, 2.42.

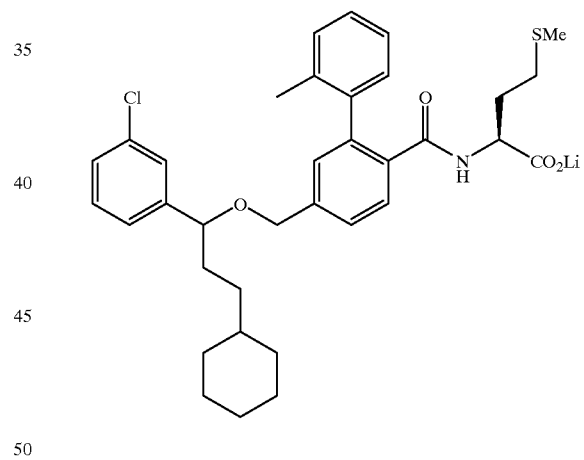

EXAMPLE 1207

N-[4-(1-(3-chlorophenyl)-3-cyclohexylpropan-1-yloxymethyl)-2-(2-methylphenyl)benzoyl]methionine lithium salt

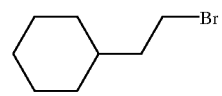

EXAMPLE 1207A 2-cyclohexylethyl bromide

The title compound was prepared from the alcohol by the method of Example 1178D.

¹H NMR (CDCl₃) δ3.63 (t, 2H), 1.75 (m, 7H), 1.45 (m, 1H), 1.22 (m, 3H), 0.90 (m, 2H).

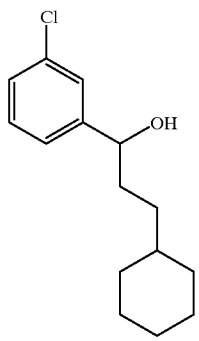

EXAMPLE 1207B 1-(3-chlorophenyl)-3-cyclohexylpropan-1-ol

The bromide described in Example 1207A was converted to the Grignard reagent, then reacted with 3-chlorobenzaldehyde using the method of Example 1206A to give the title compound.

¹H NMR (CDCl₃) δ7.37 (s, 1H), 7.23 (m, 3H), 4.42 (m, 1H), 1.70 (m, 8H), 1.20 (m, 6H), 0.88 (m, 2H).

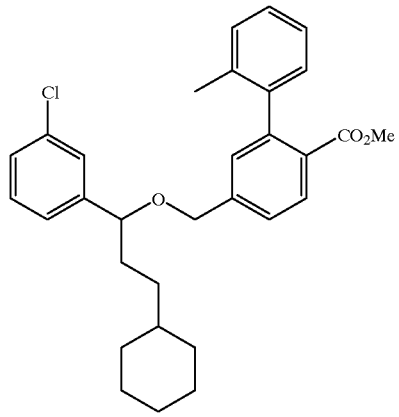

EXAMPLE 1207C 4-(1-(3-chlorophenyl)-3-cyclohexylpropan-1-yloxymethyl)-2-(2-methylphenyl)benzoic acid methyl ester The title compound was prepared from the compound described in Example 1207B and the bromide described in Example 1178D using the method of Example 1205B.

MS (APCI) 491/493 (M+H)⁺.

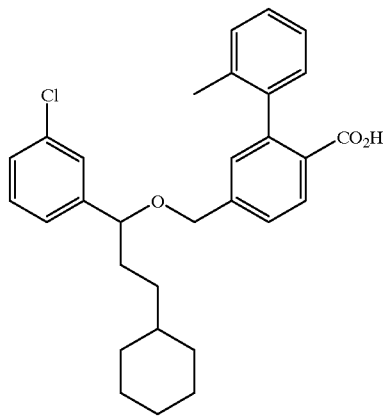

EXAMPLE 1207D 4-(1-(3-chlorophenyl)-3-cyclohexylpropan-1-yloxymethyl)-2-(2-methylphenyl)benzoic acid The title compound was prepared from the compound described in Example 1207C using the method of Example 1178H.

MS (APCI) 475/477 (M−H)⁻.

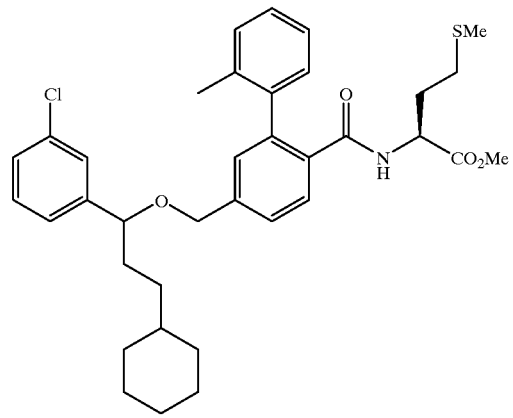

EXAMPLE 1207E

N-[4-(1-(3-chlorophenyl)-3-cyclohexylpropan-1-yloxymethyl)-2-(2-methylphenyl)benzoyl] methionine methyl ester The above compound was prepared from the compound described in Example 1207D using the method of Example 1205D.

MS (APCI) 622/624 (M+H)+.

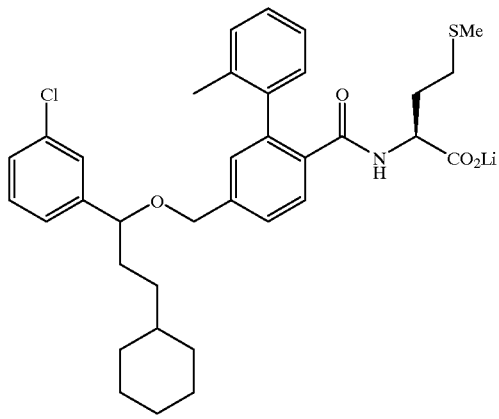

EXAMPLE 1207F

N-[4-(1-(3-chlorophenyl)-3-cyclohexylpropan-1-yloxymethyl)-2-(2-methylphenyl)benzoyl]methionine lithium salt The above compound was prepared from the compound described in Example 1207E according to the method of Example 1178J.

$^1$H NMR (DMS O-$d_6$) δ7.50 (d, 1H), 7.37 (m, 5H), 7.20, 7.08, 6.96 (all m, total 6H), 4.40 (m, 3H), 3.66 (m, 1H), 2.20–1.50 (envelope, 17H), 1.10 (m, 6H), 0.80 (m, 2H).

MS (ESI) 606 (M–H)−.

Anal calcd for $C_{35}H_{41}ClLiNO_4S$. 0.75 $H_2O$: C, 66.97; H, 6.82; N, 2.23. Found: C, 66.84; H, 6.42; N, 1.81.

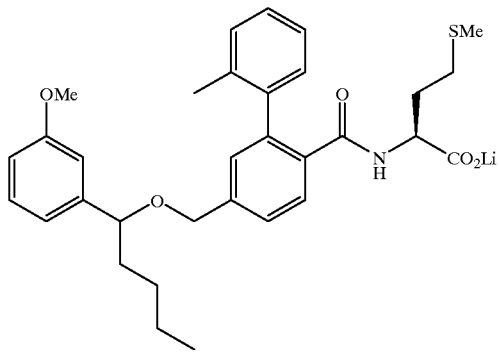

EXAMPLE 1208

N-[4-(1-(3-Methoxyphenyl)pentan-1-yloxymethyl)-2-(2-methylphenyl)benzoyl]methionine lithium salt

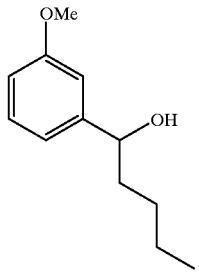

EXAMPLE 1208A 1-(3-Methoxyphenyl)pentan-1-ol

The title compound was prepared from 3-methoxybenzaldehyde using the method of EXAMPLE 1206A.

$^1$H NMR (CDCl$_3$) δ7.26 (m, 1H), 6.94 (m, 2H), 6.82 (m, 1H), 4.63 (m, 1H), 3.82 (s 3H), 1.82 (d, 1H), 1.75 (m, 2H), 1.35 (m, 4H), 0.90 (t, 3H).

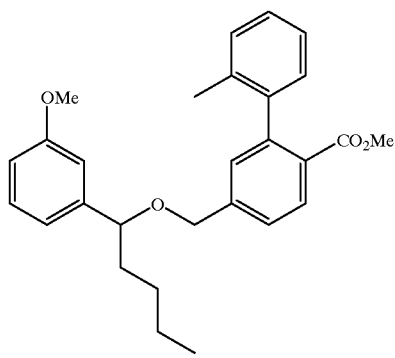

EXAMPLE 1208B 4-(1-(3-Methoxyphenyl)pentan-1-yloxymethyl)-2-(2-methylphenyl)benzoic acid methyl ester The title compound was prepared from the compound described in Example 1208A and the bromide described in Example 1178D using the method of Example 1205B.

MS (DCI/NH$_3$) 450 (M+H+NH$_3$)$^+$.

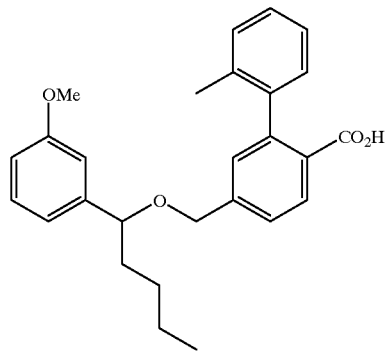

EXAMPLE 1208C 4-(1-(3-Methoxyphenyl)pentan-1-yloxymethyl)-2-(2-methylphenyl)benzoic acid The title compound was prepared from the compound described in Example 1208B using the method of Example 1178H.

MS (APCI) 436 (M+H+NH$_3$)$^+$.

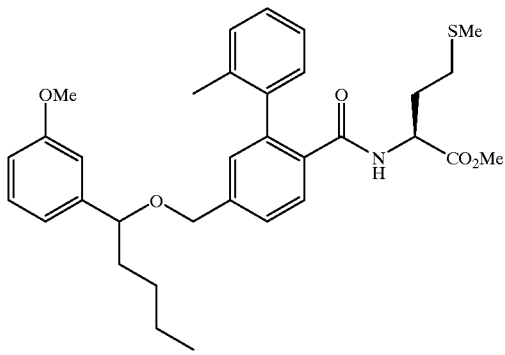

EXAMPLE 1208D

N-[4-(1-(3-Methoxyphenyl)pentan-1-yloxymethyl)-2-(2-methylphenyl)benzoyl]methionine methyl ester The title compound was prepared from the compound described in Example 1208C using the method of Example 1205D.

MS (APCI) 564 (M+H)$^+$.

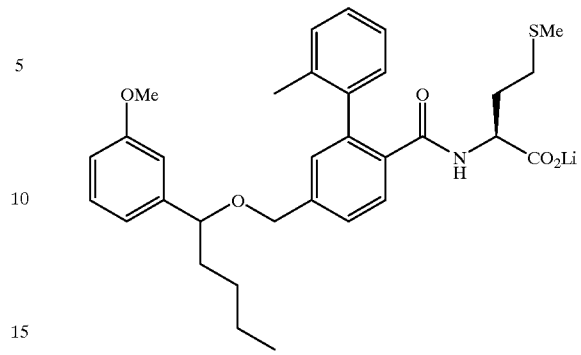

EXAMPLE 1208E

N-[4-(1-(3-Methoxyphenyl)pentan-1-yloxymethyl)-2-(2-methylphenyl)benzoyl]methionine lithium salt The above compound was prepared from the compound described in Example 1208D according to the method of Example 1178J.

$^1$H NMR (DMS O-d$_6$) δ 7.39 (d, 1H), 7.20–6.68 (envelope, 11H), 4.22 (m, 2H), 4.18 (m, 1H), 3.60 (s, 3H), 3.56 (m, 1H), 2.20–1.40 (envelope, 12H), 1.10 (m, 4H), 0.65 (m, 3H).

MS (ESI) 548 (M–H)$^-$.

Anal calcd for C$_{32}$H$_{38}$ClLiNO$_5$S·0.65 H$_2$O: C, 67.74; H, 6.98; N, 2.47. Found: C, 67.76; H, 6.95; N, 2.42.

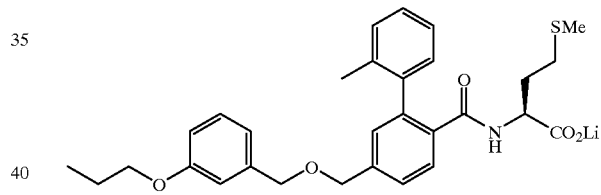

EXAMPLE 1209

N-[4-(3-(1-Propoxy)benzyloxymethyl)-2-(2-methylphenyl)benzoyl]methionine lithium salt

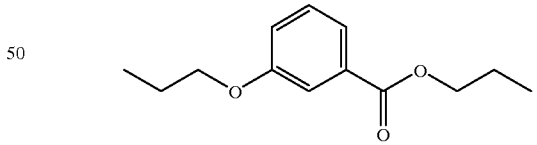

EXAMPLE 1209A 3-(1-Propoxy)benzoic acid propyl ester

3-Hydroxybenzoic acid (2.88 g, 20.9 mmol) and potassium carbonate (14.0 g, 101 mmol) were slurried in DMF (50 mL), then 1-bromopropane (8.0 mL, 10.8 g, 88 mmol) was added. The reaction was stirred at RT overnight, then partitioned between water and Et$_2$O. The organic layer was washed with brine, then dried over Na$_2$SO$_4$. After filtration and concentration recovered 4.6 g (100%).

$^1$H NMR (CDCl$_3$) δ 7.62 (m, 1H), 7.57 (m, 1H), 7.33 (dd, 1H), 7.09 (m, 1H), 4.26 (t, 2H), 3.98 (t, 2H), 1.80 (m, 4H), 1.05 (t, 3H), 1.04 (t, 3H).

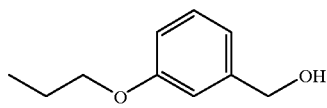

EXAMPLE 1209B 3-(1-Propoxy)benzyl alcohol

The compound described in Example 1209A (2.2 g, 10 mmol) was dissolved in THF (10 mL), then added to 1.0M LAH in THF (10.5 mL). Stirred reaction at RT for 1 h, cooled in an ice-water bath, then successively added water (0.6 mL), 15% NaOH (0.6 mL), and water (1.8 mL). The bath was removed, and after 15 min. stirring added $Et_2O$ (60 mL) and $MgSO_4$. Stirred reaction for another 15 min., then filtered through a plug (10–15 g) of silica gel, rinsing the plug with $Et_2O$ (200 mL). Concentrated filtrate to give 1.5 g (83%) of the title compound.

$^1$H NMR (CDCl$_3$) δ7.27 (dd, 1H), 6.90 (m, 2H), 6.82 (m, 1H), 4.63 (s, 2H), 3.91 (t, 2H), 1.95 (s, 1H), 1.80 (m, 2H), 1.04 (t, 3H).

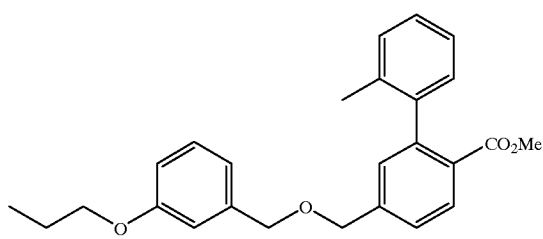

EXAMPLE 1209C 4-(3-(1-Propoxy)benzyloxymethyl)-2-(2-methylphenyl)benzoic acid methyl ester The title compound was prepared from the compound described in Example 1209B and the bromide described in Example 1178D using the method of Example 1205B.

MS (DCI/NH$_3$) 422 (M+H+NH$_3$)$^+$.

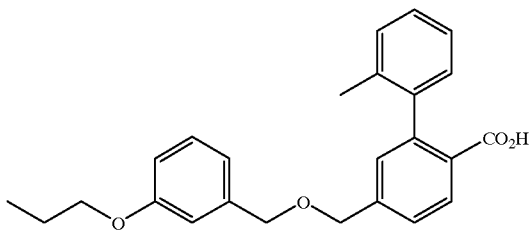

EXAMPLE 1209D 4-(3-(1-Propoxy)benzyloxymethyl)-2-(2-methylphenyl)benzoic acid The title compound was prepared from the compound described in Example 1209C using the method of Example 1178H.

MS (DCI/NH$_3$) 408 (M+H+NH$_3$)$^+$.

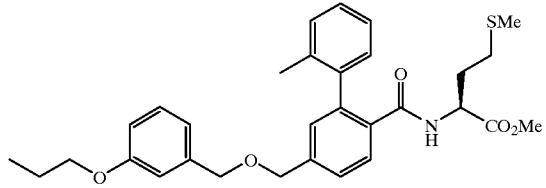

EXAMPLE 1209E

N-[4-(3-(1-Propoxy)benzyloxymethyl)-2-(2-methylphenyl)benzoyl]methionine methyl ester The title compound was prepared from the compound described in Example 1209D using the method of Example 1205D.

MS (APCI) 536 (M+H)$^+$.

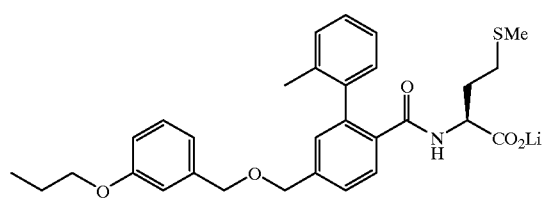

EXAMPLE 1209F

N-[4-(3-(1-Propoxy)benzyloxymethyl)-2-(2-methylphenyl)benzoyl]methionine lithium salt The above compound was prepared from the compound described in Example 1209E according to the method of Example 1178J.

$^1$H NMR (DMSO-d$_6$) δ7.55 (d,1H), 7.40 (d, 1H), 7.20, 7.07 (both m, total 7H), 6.90 (m, 2H), 6.82 (m, 1H), 4.60 (s, 2H), 4.54 (s, 2H), 3.90 (t, 2H), 3.78 (m, 1H), 2.17, 2.00, 1.90 (all m, total 8H), 1.70 (m, 3H), 1.60 (m, 1H), 0.96 (t, 3H).

MS (ESI) 520 (M−H)$^−$.

Anal calcd for C$_{30}$H$_{34}$LiNO$_5$S: C, 68.30; H, 6.50; N, 2.65. Found: C, 67.90; H, 6.55; N, 2.68.

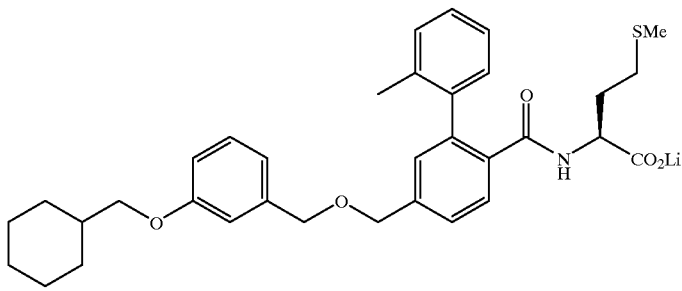

EXAMPLE 1210

N-[4-(3-cyclohexylmethyloxybenzyloxymethyl)-2-(2-methylphenyl)benzoyl]methionine lithium salt

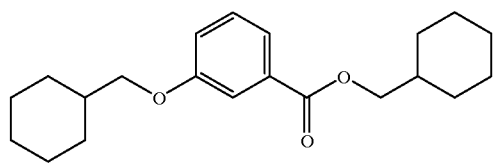

EXAMPLE 1210A 3-(cyclohexylmethyloxy)benzoic acid cyclohexylmethyl ester

The above compound was prepared from 3-hydroxybenzoic acid and bromomethylcyclohexane using the method of Example 1209A, except with this bromide the compound had to be purified by chromatography using 97/3 hex/EtOAc which gave a 9% yield.

MS (DCI/NH$_3$) 331/348 (M+H)$^+$/(M+H+NH$_3$)$^+$.

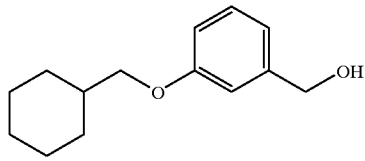

EXAMPLE 1210B 3-(cyclohexylmethyloxy)benzyl alcohol

The title compound was prepared from the compound described in Example 1210A using the method of Example 1209B.

MS (DCI/NH$_3$) 221/238 (M+H)$^+$/(M+H+NH$_3$)$^+$.

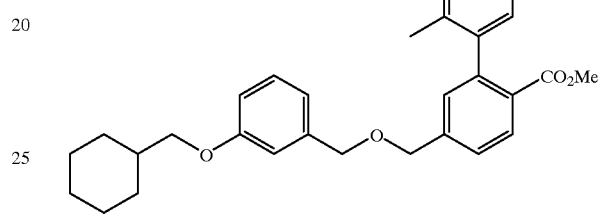

EXAMPLE 1210C 4-(3-cyclohexylmethyloxybenzyloxymethyl)-2-(2-methylphenyl)benzoic acid methyl ester The title compound was prepared from the compound described in Example 1210B and the bromide described in Example 1178D using the method of Example 1205B.

MS (DCI/NH$_3$) 476 (M+H+NH$_3$)$^+$.

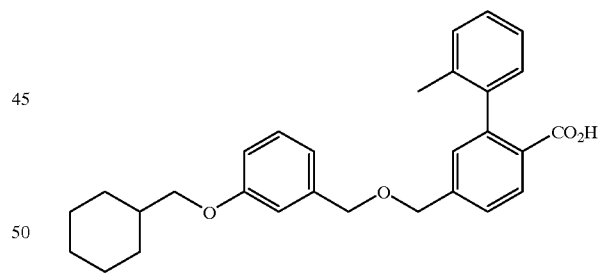

EXAMPLE 1210D 4-(3-cyclohexylmethyloxybenzyloxymethyl)-2-(2-methylphenyl)benzoic acid The title compound was prepared from the compound described in Example 1210C using the method of Example 1178H.

MS (DCI/NH$_3$) 462 (M+H+NH$_3$)$^+$.

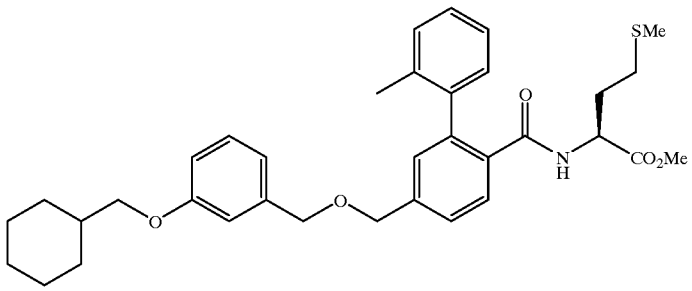

EXAMPLE 1210E

N-[4-(3-cyclohexylmethyloxybenzyloxymethyl)-2-(2-methylphenyl)benzoyl]methionine methyl ester The title compound was prepared from the compound described in Example 1210D using the method of Example 1205D.

MS (APCI) 590 (M+H)⁺.

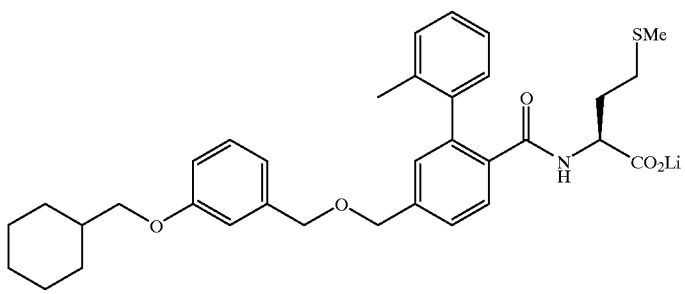

EXAMPLE 1210F

N-[4-(3-cyclohexylmethyloxybenzyloxymethyl)-2-(2-methylphenyl)benzoyl]methionine lithium salt The above compound was prepared from the compound described in Example 1210E according to the method of Example 1178J.

$^1$H NMR (DMS O-$d_6$) δ7.55 (d, 1H), 7.40 (dd, 1H), 7.20, 6.97 (both m, total 7H), 6.90 (m, 2H), 6.82 (m, 1H), 4.60 (s, 2H), 4.52 (s, 2H), 3.73 (d, 2H), 4.48 (m, 1H), 2.17, 2.00, 1.90 (all m, total 7H), 1.70 (m, 9H), 1.20 (m, 3H), 1.03 (m, 2H).

MS (ESI) 574 (M−H)⁻.

Anal calcd for $C_{34}H_{40}LiNO_5S \cdot 0.70 \, H_2O$: C, 68.71; H, 6.84; N, 2.17. Found: C, 68.70; H, 7.02; N, 2.36.

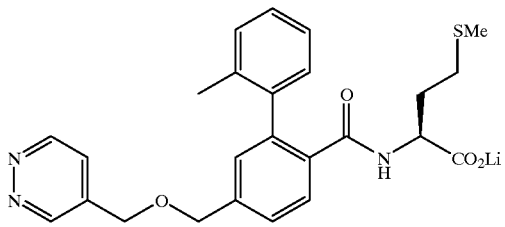

EXAMPLE 1221

N-[4-(Pyridazin-4-ylmethoxymethyl)-2-(2-methylphenyl)benzoyl]methionine lithium salt

EXAMPLE 1221A 3.6-Dichlopyridazine-4-carboxylic acid ethyl ester 3,6-Dichloropyridazine-4-carboxylic acid was preapared by the methods in JACS, 76, 2201 (1954) and Chem.Pharm.Bull., 5, 587 (1957). That acid (9.15 g, 47.4 mmol) was dissolved in THF (50 mL), then EtOH (6.5 mL, 5.1 g, 111 mmol), EDCI.HCl (10.0 g, 52.5 mmol), and DMAP (0.64 g, 5.2 mmol) were added. The reaction was stirred at RT overnight, concentrated, and partitioned between EtOAc and water. The organic layer washed with 2M aq. $Na_2CO_3$, then water several times to clarify the organic layer. The combined aqueous layers were-extracted with EtOAc, then the combined organic layers were dried over $Na_2SO_4$. After filtration and concentration the crude material was purified by chromatography using 4/1 hex/EtOAc. Recovered 6.45 g (61%). MS (DCI/NH₃) 221/223 (M+H)⁺ and 238/240 (M+H+NH₃)⁺.

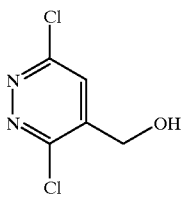

EXAMPLE 1221B 3.6-Dichlopyridazine-4-methanol

The compound descibed in Example 1221A (5.4 g, 24 mmol) was dissolved in toluene (75 mL), cooled to −10° C., then 1.5M DIBAL in toluene (32 mL) was added dropwise, keeping the reaction temperature under 0° C. (the addition took ca. 15 min.). After another 5 min. saturated aqueous Rochelle's salt (25 mL) was added carefully. That mixture was stirred cold for 20 min., at RT for 20 min., then $Na_2SO_4$ was added. That slurry was stirred for 30 min., then filtered through celite. The solids on top of the celite were partitioned between 2N HCl (to dissolve Al salts) and EtOAc. Solid $NaHCO_3$ was used to adjust the aqueous layer to pH 7–8, twice extracted with EtOAc, then the combined EtOAc layers were washed with brine, combined with the toluene filtrate from the celite filtration, and dried over $Na_2SO_4$. After filtration and concentration the crude material was purified by chromatography (had to dissolve the 4.2 g crude solids in $CHCl_3$/MeOH and preadsorb on 12 g silica gel) using 65/35 hex/EtOAc. Recovered 1.8 g (41%). MS (DCI/$NH_3$) 179/181 (M+H)$^+$ and 196/198 (M+H+$NH_3$)$^+$.

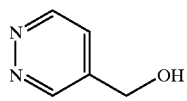

EXAMPLE 1221C

Pyridazine-4-methanol

The compound descibed in Example 1221B (1.8 g, 10 mmol) was dissolved in absolute EtOH (65 mL), then 10% palladium on carbon (335 mg) and triethylamine (6.0 mL, 4.4 g, 43 mmol) were added. The slurry was stirred at RT under $H_2$ balloon for 3 h, then filtered through celite and concentrated. The 3.5 g solids were slurried in EtOAc (100 mL), and mechanically stirred at RT overnight. The slurry was filtered, the filtrate concentrated, and that material was purified by chromatography using EtOAc/EtOH 9/1. Recovered 0.83 g (75%) MS (DCI/$NH_3$) 111 (M+H)$^+$ and 128 (M+H+$NH_3$)$^+$.

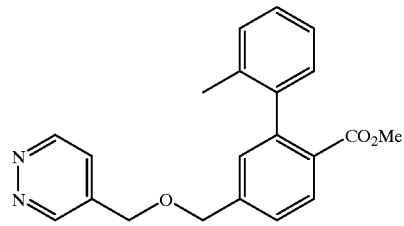

EXAMPLE 1221D 4-(Pyridazin-4-ylmethoxymethyl)-2-(2-methylphenyl)benzoic acid methyl ester The bromide described in Example 1178D (230 mg, 0.72 mmol) was dissolved in DMF (0.8 mL), cooled to –10° C., then added 29 mg 60% NaH (so 17 mg, 0.72 mmol NaH), followed by the alcohol described in Example 1221C (79 mg, 0.72 mmol). Stired the reaction at –10° C. for 45 min., then partitioned between EtOAc and water. The EtOAc layer was washed with brine, the combined aqueous layers extracted with EtOAc, then the combined organic layers were dried over $Na_2SO_4$. After filtration and concentration the crude material was purified by chromatography using EtOAc. Recovered 150 mg (60%).

MS (APCI) 349 (M+H)$^+$.

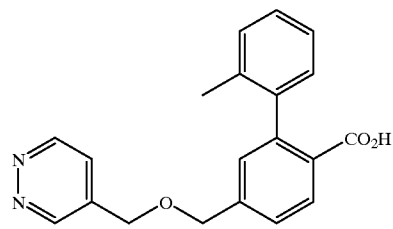

EXAMPLE 1221E 4-(Pyridazin-4-ylmethoxymethyl)-2-(2-methylphenyl)benzoic acid Starting with the compound described in Example 1221D, the title compound was prepared by the method of Example 1178H, except that during the work-up, the aqueous layer was water and enough 2N HCl to get pH 3–4. MS (ESI) 333 (M–H)$^-$.

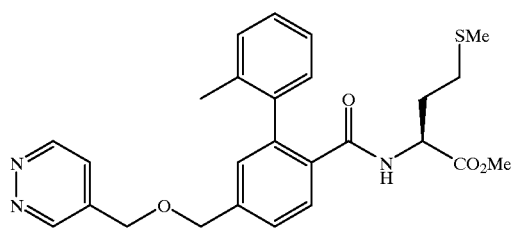

EXAMPLE 1221F

N-[4-(Pyridazin-4-ylmethoxymethyl)-2-(2-methylphenyl)benzoyl]methionine methyl ester Starting with the compound described in Example 1221E, the title compound was prepared by the method of Example 1205D, except that during the work-up, the 2N HCl wash was eliminated, and the chromatography used successively hex/EtOAc 1/3, EtOAc, EtOAc/EtOH 98/2. MS (APCI) 480 (M+H)$^+$.

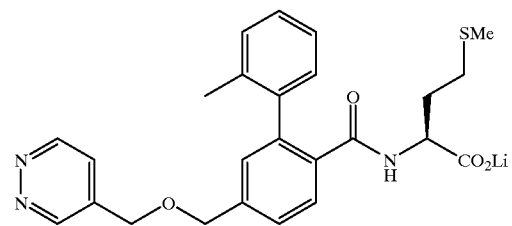

EXAMPLE 1221G

N-[4-(Pyridazin-4-ylmethoxymethyl)-2-(2-methylphenyl)benzoyl]methionine lithium salt Starting with the compound described in Example 1221F, the title compound was prepared by the method of Example 1178J. $^1$H NMR (DMSO-d6) δ9.22 (m, 1H), 9.18 (dd, 1H), 7.65 (m, 1H), 7.55 (d, 1H), 7.45 (d, 1H), 7.20, 6.95 (both m, total 6H), 4.69 (s, 2H), 4.66 (s, 2H), 3.68 (m, 1H), 2.15–1.50 (envelope, 10H). MS (ESI) 464 (M–H)$^-$. HRMS (FAB+)

calcd for $C_{25}H_{27}LiN_3O_4S$: 472.1882. Found: 472.1898.

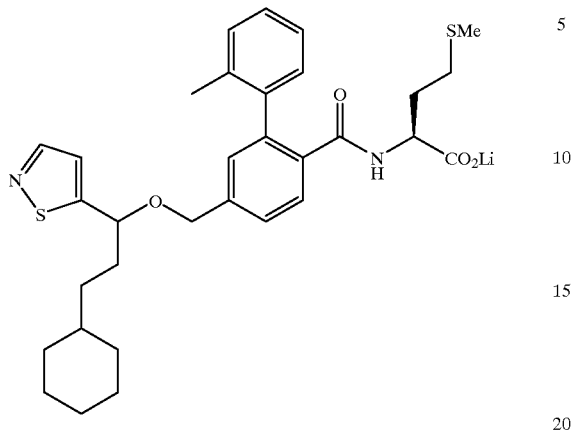

EXAMPLE 1223

N-[4-(1-(Isothiaz-5-yl)-3-cyclohexylpropan-1-yloxymethyl)-2-(2-methylphenyl)benzoyl] methionine lithium salt

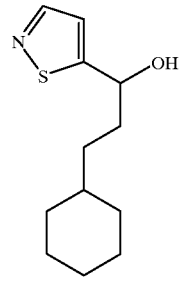

EXAMPLE 1223A 1-(Isothiaz-5-yl)-3-cyclohexylpropan-1-ol

Isothiazole was made from propynal (prepared using the procedure in Org. Syn., Coll. Vol. IV, 813) by the method in Can. J. Chem., 44, 1324 (1966), then converted to isothiazole-5-carboxaldehyde by the method in JCS, 446 (1964). That aldehyde was used to make the title compound by the method described in Example 1207B. MS (APCI) 226 $(M+H)^+$.

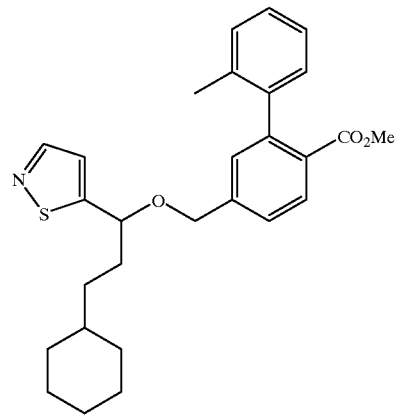

EXAMPLE 1223B 4-(1-(Isothiaz-5-yl)-3-cyclohexylpropan-1-yloxymethyl)-2-(2-methylphenyl)benzoic acid methyl ester The title compound was prepared from the compound described in Example 1223A and the bromide described in Example 1178D using the method of Example 1205B. MS (APCI) 464 $(M+H)^+$.

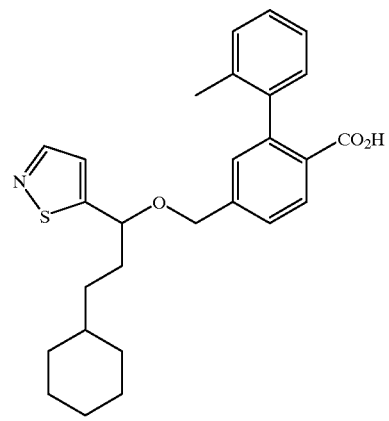

EXAMPLE 1223C 4-(1-(Isothiaz-5-yl)-3-cyclohexylpropan-1-yloxymethyl)-2-(2-methylphenyl)benzoic acid The title compound was prepared from the compound described in Example 1223B using the method of Example 1178H. MS (ESI) 450 $(M+H)^+$.

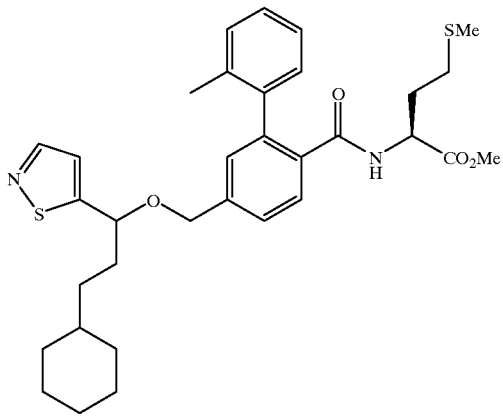

EXAMPLE 1223D

N-[4-(1-(Isothiaz-5-yl)-3-cyclohexylpropan-1-yloxymethyl)-2-(2-methylphenyl)benzoyl] methionine methyl ester The title compound was prepared from the compound described in Example 1223C using the method of Example 1205D. MS (APCI) 595 (M+H)+.

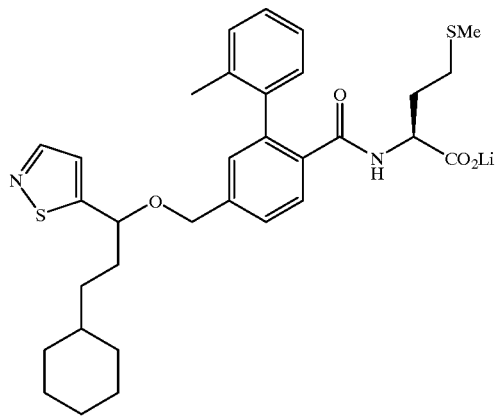

EXAMPLE 1223E

N-[4-(1-(Isothiaz-5-yl)-3-cyclohexylpropan-1-yloxymethyl)-2-(2-methylphenyl)benzoyl] methionine lithium salt The above compound was prepared from the compound described in Example 1223D according to the method of Example 1178J. $^1$H NMR (DMSO-$d_6$) δ8.50 (m, 1H), 7.54 (d, 1H), 7.37 (d, 1H), 7.33 (m, 1H), 7.20, 7.00 (both m, total 6H), 4.90 (t, 1H), 4.56 (dd, 2H), 3.70 (m, 1H), 2.17, 2.00, 1.91, 1.80, 1.60 (all m, total 17H), 1.17 (m, 6H), 0.80 (m, 2H). MS (ESI)$^-$579 (M−H)$^-$. Anal calcd for $C_{32}H_{39}LiN_2O_4S_2 \cdot 1.00\ H_2O$: C, 63.56; H, 6.83; N, 4.63. Found: C, 63.41; H, 6.77; N, 4.54.

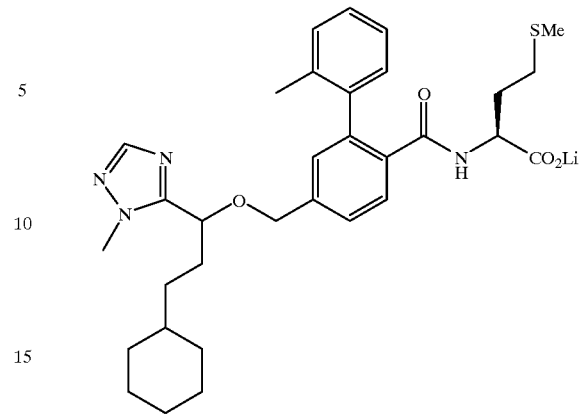

EXAMPLE 1224

N-[4-(1-(1-Methyl-1,2,4-triaz-5-yl)-3-cyclohexylpropan-1-yloxymethyl)-2-(2-methylphenyl)benzoyl]methionine lithium salt

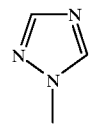

EXAMPLE 1224A

1-Methyl-1,2,4-triazole

Sodium (1.9 g, 83 mmol) was dissolved in MeOH (35 mL), allowed to cool to RT, then 1,2,4-triazole (5.7 g, 83 mmol) was added. The solution was cooled in an ice-water bath, then iodomethane (5.1 mL, 11.6 g, 82 mmol) was added dropwise. The reaction was allowed to warm to RT, stoppered, then heated at 38° C. overnight. The reaction was concentrated, then treated with hot benzene (25 mL) which resulted in the formation of white solids. Those solids were slurried in hot CHCl$_3$ (25 ML) and filtered off. The CHCl$_3$ slurry was repeated twice, the three filtrates combined, concentrated, and distlled (37–40° C./8 mm). Recovered 2.6 g (38%). $^1$H NMR (CDCl$_3$) δ8.05 (s, 1H), 7.93 (s, 1H), 3.96 (s, 3H).

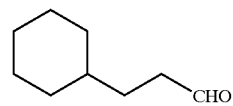

EXAMPLE 1224B

3-Cyclohexylpropanal

3-Cyclohexylpropan-1-ol was oxidized to the aldehyde using the method of Example 403G. $^1$H NMR (CDCl$_3$) δ9.77 (t, 1H), 2.42 (dt, 2H), 1.67 (m, 5H), 1.52 (m, 2H), 1.20 (m, 4H), 0.90 (m, 2H).

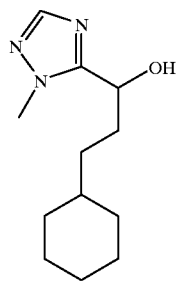

EXAMPLE 1224C 4-(1-(1-Methyl-1,2,4-triaz-5-yl)-3-cyclohexylpropan-1-ol

The compound described in Example 1224A (500 mg, 6.0 mmol) was dissolved in THF (25 mL), cooled to −77° C., then 2.5M BuLi in hexanes (2.5 mL) was added slowly, keeping the reaction temperature under −66° C. After stirring at −78° C. for 1 h the compound described in Example 1224B (0.86 g, 6.1 mmol) was added via syringe. The reaction was stirred cold for 30 min., then allowed to warm to RT, whereupon water was added, and the reaction was extracted with EtOAc. The organic layer washed with brine, dried over $Na_2SO_4$, then filtered and concentrated. Purification by chromatography using hex/EtOAc ⅓, then EtOAc gave 748 mg (56%). MS (DCI/$NH_3$) 224 $(M+H)^+$.

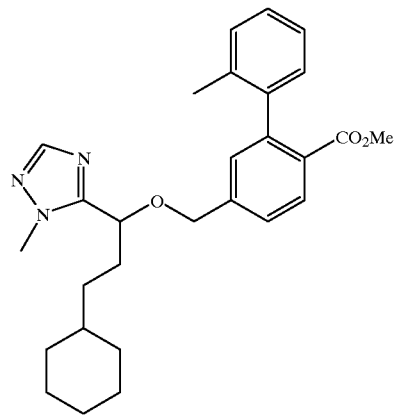

EXAMPLE 1224D 4-(1-(1-Methyl-1,2,4-triaz-5-yl)-3-cyclohexylpropan-1-yloxymethyl)-2-(2-methylphenyl)benzoic acid methyl ester The title compound was prepared from the compound described in Example 1224C and the bromide described in Example 1178D using the method of Example 1205B. MS (APCI) 462 $(M+H)^+$.

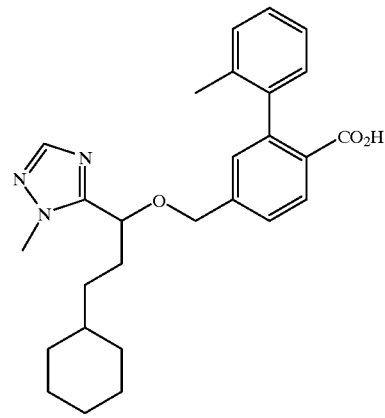

EXAMPLE 1224E 4-(1-(1-Methyl-1,2,4-triaz-5-yl)-3-cyclohexylpropan-1-yloxymethyl)-2-(2-methylphenyl)benzoic acid The title compound was prepared from the compound described in Example 1224D using the method of Example 1178H. MS (ESI) 448 $(M+H)^+$.

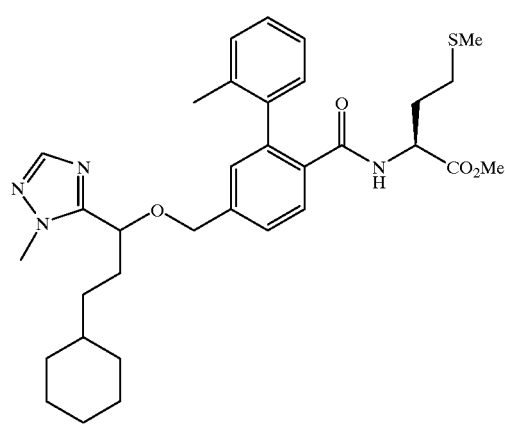

EXAMPLE 1224F

N-[4-(1-(1-Methyl-1,2,4-triaz-5-yl)-3-cyclohexylpropan-1-yloxymethyl)-2-(2-methylphenyl)benzoyl]methionine methyl ester The title compound was prepared from the compound described in Example 1224E using the method of Example 1205D. MS (APCI) 593 $(M+H)^+$.

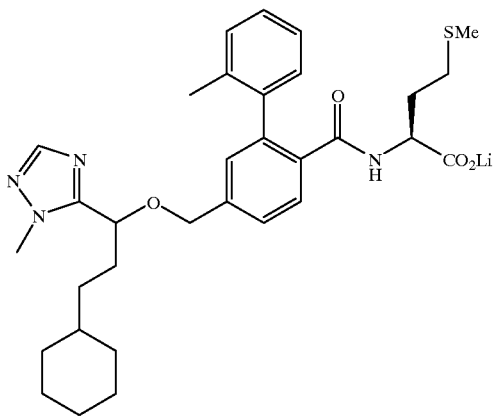

EXAMPLE 1224G

N-[4-(1-(1-Methyl-1,2,4-triaz-5-yl)-3-cyclohexylpropan-1-yloxymethyl)-2-(2-methylphenyl)benzoyl]methionine lithium salt The above compound was prepared from the compound described in Example 1224F according to the method of Example 1178J. $^1$H NMR (DMSO-d$_6$) δ7.70 (s, 1H), 7.51 (d, 1H), 7.33 (dd, 1H), 7.19, 7.08, 6.95 (all m, total 6H), 4.74 (t, 1H), 4.43 (dd, 2H), 3.86, 3.85 (both s, total 3H), 3.70 (m, 1H), 2.20–1.50 (envelope, 17H), 1.20 (m, 6H), 0.80 (m, 2H). MS (ESI) 577 (M–H)$^-$. Anal calcd for C$_{32}$H$_{41}$LiN$_4$O$_4$S.0.60 H$_2$O: C, 64.54; H, 7.14; N, 9.41. Found: C, 64.54; H, 7.33; N, 9.37.

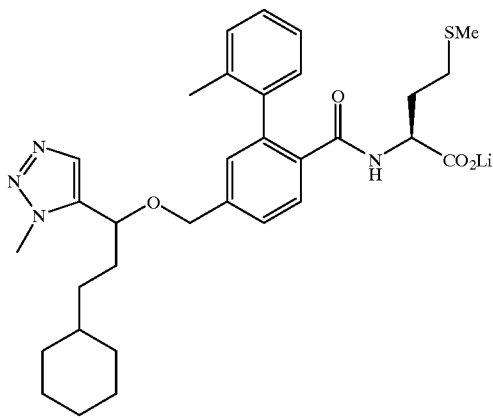

EXAMPLE 1225

N-[4-(1-(1-Methyl-1,2,3-triaz-5-yl)-3-cyclohexylpropan-1-yloxymethyl)-2-(2-methylphenyl)benzoyl]methionine lithium salt

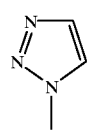

EXAMPLE 1225A

1-Methyl-1,2,3-triazole

Starting with 1,2,3-triazole the title compound was prepared by the method of Example 1224A, except the reaction was stirred at RT overnight. Dist. (88–90° C./n7 mm). $^1$H NMR (CDCl$_3$) δ7.73 (s, 1H), 7.37 (s, 1H), 4.15 (s, 3H).

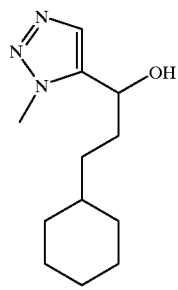

EXAMPLE 1225B 4-(1-(1-Methyl-1,2,3-triaz-5-yl)-3-cyclohexylpropan-1-ol

Starting with the compound described in Example 1225A, the title compound was prepared by the method of Example 1224C, except the reaction was 1.5 times more dilute, and was stirred at –55° C. instead of –78° C. (this lithium salt less soluble in THF than the one in Example 1224C). MS (DCI/NH$_3$) 224 (M+H)$^+$.

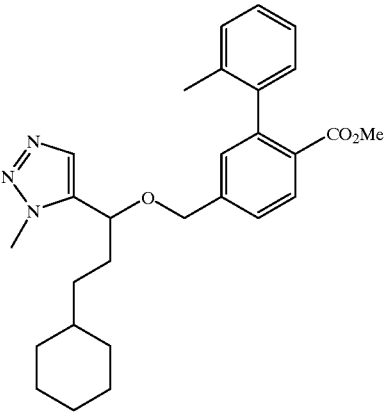

EXAMPLE 1225C 4-(1-(1-Methyl-1,2,3-triaz-5-yl)-3-cyclohexylpropan-1-yloxymethyl)-2-(2-methylphenyl)benzoic acid methyl ester The title compound was prepared from the compound described in Example 1225B and the bromide described in Example 1178D using the method of Example 1205B. MS (APCI) 462 (M+H)$^+$.

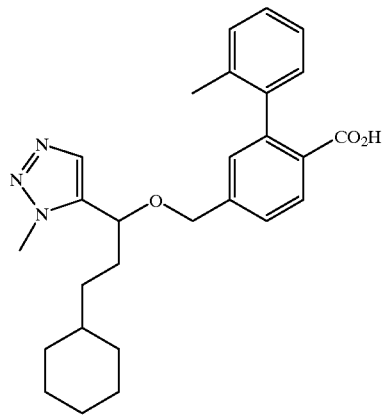

EXAMPLE 1225D 4-(1-(1-Methyl-1,2,3-triaz-5-yl)-3-cyclohexylpropan-1-yloxymethyl)-2-(2-methylphenyl)benzoic acid The title compound was prepared from the compound described in Example 1225C using the method of Example 1178H. MS (ESI) 448 (M+H)+.

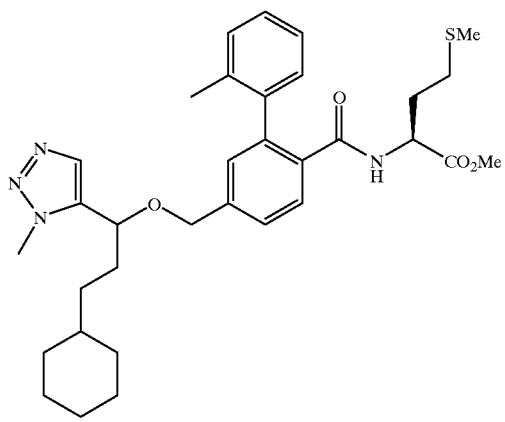

EXAMPLE 1225E

N-[4-(1-(1-Methyl-1,2,3-triaz-5-yl)-3-cyclohexylpropan-1-yloxymethyl)-2-(2-methylphenyl)benzoyl]methionine methyl ester The title compound was prepared from the compound described in Example 1225D using the method of Example 1205D. MS (APCI) 593 (M+H)+.

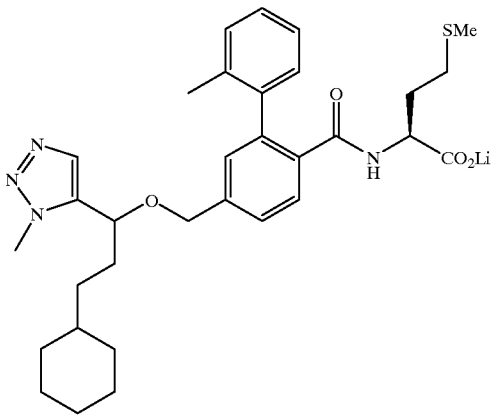

EXAMPLE 1225F

N-[4-(1-(1-Methyl-1,2,3-triaz-5-yl)-3-cyclohexylpropan-1-yloxymethyl)-2-(2-methylphenyl)benzoyl]methionine lithium salt The above compound was prepared from the compound described in Example 1225E according to the method of Example 1178J. $^1$H NMR (DMSO-$d_6$) δ7.68 (s, 1H), 7.51 (d, 1H), 7.33 (dd, 1H), 7.19, 7.08, 6.95 (all m, total 6H), 4.72 (t, 1H), 4.43 (dd, 2H), 3.97, 3.98 (both s, total 3H), 3.68 (m, 1H), 2.20–1.50 (envelope, 17H), 1.20 (m, 6H), 0.82 (m, 2H). MS (ESI) 577 (M−H)−. Anal calcd for $C_{32}H_{41}LiN_4O_4S \cdot 0.25$ $H_2O$: C, 65.23; H, 7.10; N, 9.51. Found: C, 65.02; H, 7.17; N, 9.21.

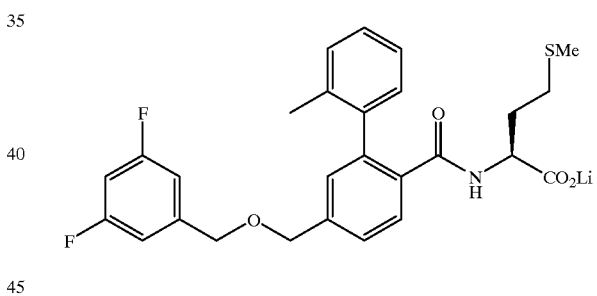

EXAMPLE 1226

N-[4-(3,5-trifluorobenzyloxymethyl)-2-(2-methylphenyl)benzoyl]methionine lithium salt

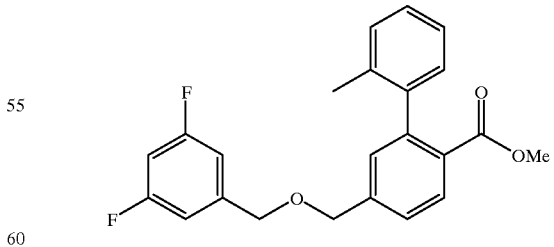

EXAMPLE 1226A

Prepared according to the procedure of example 1290D from the reaction between example 3,5-difluorobenzyl alcohol and 4-bormomethyl-2-(2-methylphenyl)benzoic acid methyl ester. NMR(CDCl$_3$) 7.95–8.00 (m, 1H); 7.42–7.48

(m, 1H); 7.10–7.30 (m, 4H); 7.05–7.10 (m, 2H); 6.73–6.80 (m, 1H); 4.65 (s, 2H); 4.55 (s, 2H); 3.60 (s, 3H); 2.06 (s, 3H). (DCI/NH$_3$)/MS: 383(M+H)$^+$; 400(M+NH$_4$)$^+$.

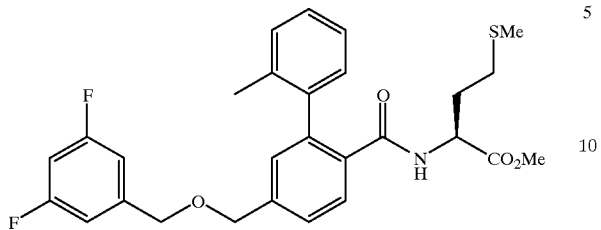

EXAMPLE 1226B

N-[4-(3,5-trifluorobenzyloxymethyl)-2-(2-methylphenyl)benzoyl]methionine, methyl ester Prepared according to the procedure of example 1258C from 1226A. NMR(CDCl$_3$) 7.82–8.02 (m, 1H); 7.40–7.50 (m, 1H); 7.18–7.40 (m, 5H); 6.80–6.92 (m, 1H); 6.68–6.80 (m, 1H); 5.90–5.96 (m, 1H); 4.65 (s, 2H); 4.56 (s, 2H); 3.65 (s, 3H); 2.00–2.20 (m, 8H); 1.70–2.00 (m, 1H); 1.50–1.70 (m, 1H). (DCI/NH$_3$)/MS: 514(M+H)$^+$; 531(M+NH$_4$)$^+$.

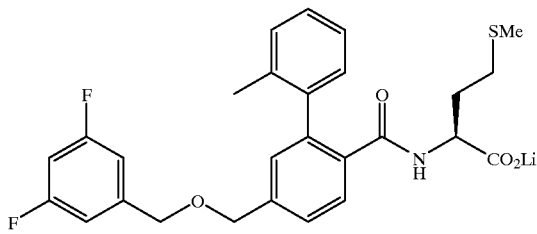

EXAMPLE 1226C

N-[4-(3,5-trifluorobenzyloxymethyl)-2-(2-methylphenyl)benzoyl]methionine lithium salt Prepared according to the procedure of example 1178J from 1226B. NMR $^1$H (d$_4$-MeOH): 7.67–7.77 (1H, m); 7.45–7.5 (1H, m); 7.1–7.35 (6H, m); 6.9–7.0 (2H, m); 6.8–6.9 (1H, m); 4.65 (2H, s); 4.6 (2H, s); 4.1 (1H, m) 2.2 (1H, s); 1.75–2.1 (8H, m); 1.6–1.75 (1H, m). ESI(–)/MS: 498 (M–Li).

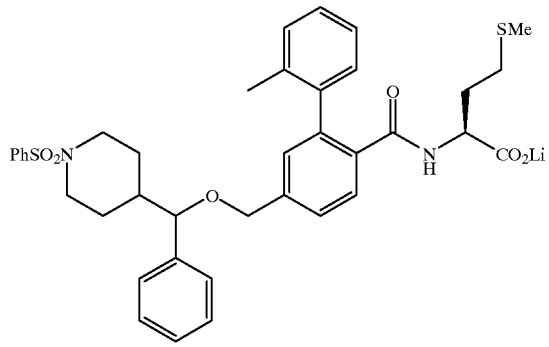

EXAMPLE 1252

N-[4-(1-(4-(N-phenylsulfonyl)piperidinyl)benzyloxymethyl-2-(2-methylphenyl)benzoyl] methionine lithium salt

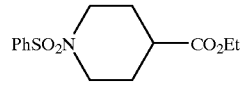

EXAMPLE 1252A

A mixture of ethyl 1-piperazinecarboxylate (3.14 g, 20 mmol), benzenesulfonyl chloride (3.53 g, 20 mmol), and triethylamine (4.05 g, 40 mmol) in methylene chloride was stirred for 12 hours. The reaction mixture was washed by 10% HCl, brine, and dried over anhydrous MgSO$_4$. Evaporation of methylene chloride afforded 5.8 g of the title compound (98%). NMR (CDCl$_3$) 7.75–7.8 (m, 2H); 7.4–7.6 (m, 3H); 4.3–4.1 (m, 2H); 3.5–3.6 (m, 2H); 2.6–2.7 (m, 2H); 2.2–2.3 (m, 1H); 1.9–2.1 (m, 2H); 1.7–1.9 (m, 2H); 1.01–1.1 (m, 3H). (DSI/NH$_3$)/MS: 298 (M+H)$^+$.

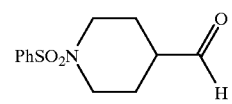

EXAMPLE 1252B 1252A (2.97 g, 10 mmol) in 20 ml of anhydrous toluene was treated with 1.0 M DiBAL toluene solution (10 ml, 10 mmol) at –78° C. The reaction mixture was stirred for 3 hours at –78° C. The reaction was quenched with 30 ml of 4 N NaOH solution. The organic layer was diluted with 20 ml of EtOAc, washed with brine, and dried over anhydrous MgSO$_4$. Flash chromatography of the residue eluting with 1:1EtOAc/Hexane afforded 2.01 g of the title compound. NMR(CDCl$_3$) 9.58 (s, 1H); 7.75–7.8 (m, 2H); 7.4–7.6 (m, 3H); 3.5–3.6 (m, 2H); 2.6–2.7 (m, 2H); 2.2–2.3 (m, 1H); 1.9–2.1 (m, 2H). (DSI/NH$_3$)/MS: 254 (M+H)$^+$; 271 (M+NH$_4$)$^+$.

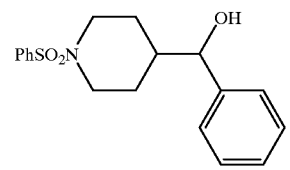

EXAMPLE 1252C 1252B (0.56 g, 2.2 mmol) in 15 ml of anhydrous THF was treated with 3.0 M phenylmagesium bromide solution (1.6 ml, 4.8 mmol) at 0° C. The reaction was stirred for 2 hours. The reaction was then quenched with saturated NH$_4$Cl solution. 10 ml of EtOAc was added to the solution, and the organic layer was washed with brine, dried over anhydrous MgSO$_4$. Flash chromatography of the residue eluting with 1:1/EtOAc/Hexane afforded 0.48 g of the title compound (65%). NMR(CDCl$_3$) 7.7–7.82 (m, 2H); 7.4–7.6 (m, 3H); 7.2–7.4 (m, 5H); 4.3–4.4 (m, 1H); 3.7–3.95 (m, 2H); 2.0–2.3 (m, 4H); 1.92 (m, 1); 1.2–1.6 (m, 4H). (DSI/NH$_3$)/MS: 332(M+H)$^+$; 349 (M+NH$_4$)$^+$.

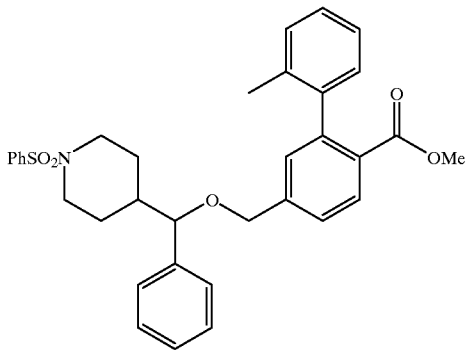

EXAMPLE 1252D

A mixture of 1252C (0.465. g, 1.40 mmol) and 4-bromomethyl-2-(2-methylphenyl)benzoic acid methyl ester (0.45 g, 1.40 mmol) in 1.4 ml of anhydrous DMF was treated with sodium hydride (0.102 g, 4.2 mmol) at 0° C. under $N_2$. The reaction mixture was stirred for another 2 hours. The reaction was quenched with 20 ml of water, extracted with EtOAc, washed with brine, and dried over $MgSO_4$. Flash chromatography of the residue eluting with 3:7/EtOAc/Hexane afforded 0.53 of the title compound (67%).

NMR(CDCl$_3$) 7,90–7.98 (m, 1H); 7.70–7.78 (m, 2H); 7.25–7.40 (m, 3H); 7.20–7.38 (m, 4H); 7.00–7.10 (m, 2H); 4.20–4.45 (m, 2H); 3.96–4.02 (m, 1H); 3.70 –3.90 (m, 2H); 3.60 (s, 3H); 2.10–2.20 (m, 2H); 2.08 (3H, m); 1.40–1.60 (m, 3H). (DSI/NH$_3$)/MS: 587(M+NH$_4$)$^+$.

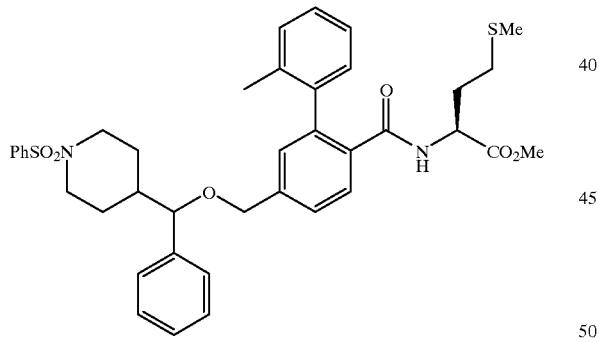

EXAMPLE 1252E

N-[4-(1-(4-(N-phenylsulfonyl)piperidinyl) benzyloxymethyl-2-(2-methylphenyl)benzoyl] methionine, methyl ester Prepared according to the procedure of example 1258C from 1252D. NMR(CDCl$_3$) 7.82–7.98 (m, 1H); 7.70–7.78 (m, 2H); 7.23–7.40 (m, 3H); 7.20–7.38 (m, 5H); 7.10 (s, 1H); 5.88–5.92 (m 2H); 4.55–4.70 (m, 1H); 4.20–4.45 (m, 2H); 3.96–4.02 (m, 1H); 3.70–3.90 (m, 2H); 3.60 (s, 3H); 2.00–2.20 (m, 10H); 1.80–2.00 (m, 1H); 1.40–1.70 (m, 4H). DSI/NH$_3$/MS: 701(M+H)$^+$; 718(M+NH$_4$)$^+$.

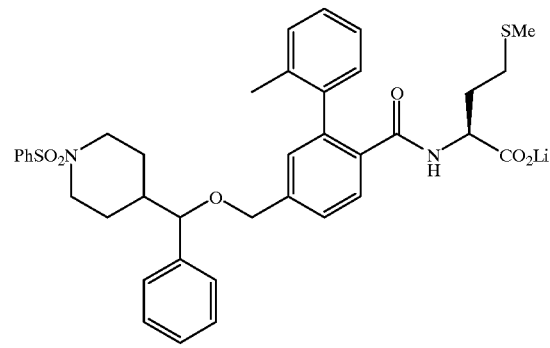

EXAMPLE 1252F

N-[4-(1-(4-(N-phenylsulfonyl)piperidinyl) benzyloxymethyl-2-(2-methylphenyl)benzoyl] methionine lithium salt

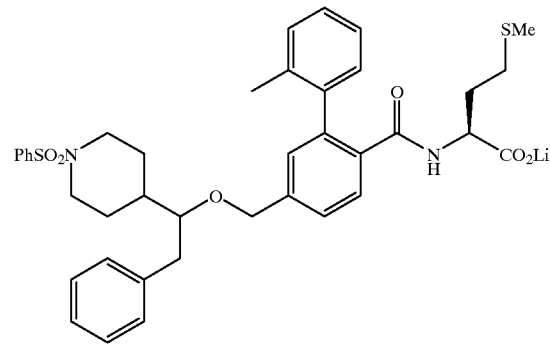

EXAMPLE 1253

N-[4-(2-phenyl-1-(4-(N-phenylsulfonyl)piperidinyl) ethyloxymethyl-2-(2-methylphenyl)benzoyl] methionine lithium salt

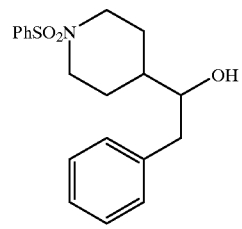

EXAMPLE 1253A

Prepared according to the procedure of example 1291C from the reaction between example 1252B and benzylmagesium bromide. NMR(CDCl$_3$) 7.75–7.62 (m, 2H); 7.50–7.66 (m, 3H); 7.15–735 (m, 5H); 3.93–3.98 (m, 2H); 3.50–3.70 (m, 1H); 2.80–2.90 (m, 1H); 2.50–2.60 (m, 1H); 2.20–2.30 (m, 2H); 1.90–2.00 (m, 1H); 1.70–1.84 (m, 1H); 1.30–170 (m, 3H). DSI/NH$_3$/MS: 345(M+H)$^+$; 363(M+NH$_4$)$^+$.

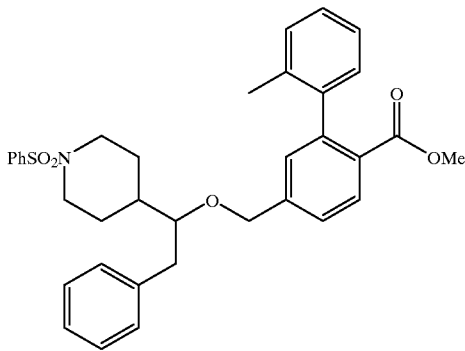

EXAMPLE 1253B

Prepared according to the procedure of example 1290D from the reaction between example 1253A and 4-bormomethyl-2-(2-methylphenyl)benzoic acid methyl ester.

NMR(CDCl$_3$) 7.85–7.90 (m, 2H); 7.70–7.80 (m, 3H); 7.05–7.45 (m, 9H); 6.94–7.05 (m, 2H); 4.30–4.40 (m, 2H); 3.80–3.95 (m, 2H); 3.60 (s, 3H); 3.50–3.70 (m, 1H); 2.70–2.90 (m, 2H); 2.11–2.23 (m, 2H); 2.05 (s, 3H); 1.80–1.95 (m, 1H); 1.70–1.84 (m, 1H); 1.30 –170 (m, 3H). DSI/NH$_3$)/MS: 601(M+NH$_4$)$^+$.

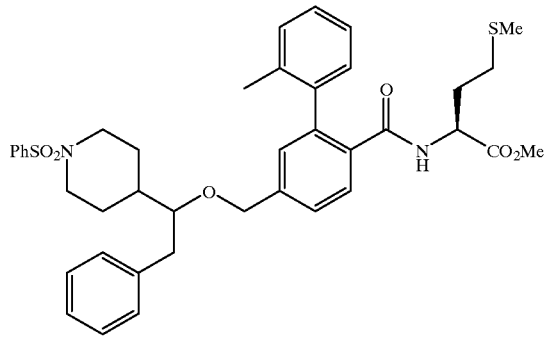

EXAMPLE 1253C

Prepared according to the procedure of example 1258C from 12953B.

NMR(CDCl$_3$) 7.82–7.95 (m, 1H); 7.70–7.80 (m, 2H); 7.50–7.65 (m, 3H); 7.10–7.40 (m, 10); 6.95 (m, 1H); 5.85–5.92 (m, 1H); 4.55–4.65 (m, 1H); 4.30–4.40 (m, 2H); 3.80–3.95 (m, 2H); 3.64 (s, 3H); 3.50–3.70 (m, 1H); 2.70–2.90 (m, 2H); 1.2–2.3 (m, 13H). (DSI/NH$_3$)/MS: 715 (M+NH$_4$)$^+$.

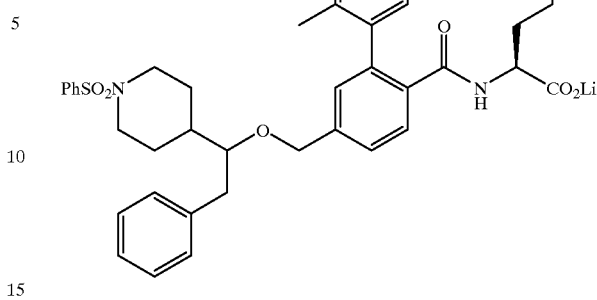

EXAMPLE 1253D

N-[4-(2-phenyl-1-(4-(N-phenylsulfonyl)piperidinyl) ethyloxymethyl-2-(2-methylphenyl)benzoyl] methionine lithium salt Prepared according to the procedure of example 1178J from 1252E. NMR $^1$H (d$_4$-MeOH): 7.4–7.8 (8H, m); 7.0–7.4 (10H, m); 4.1–4.55 (3H, s); 4.0 (1H, m) 3.6–3.8 (2H, s); 1.1–2.3 (17H, m). ESI(-)/MS: 685 (M–Li); 693 (M+H).

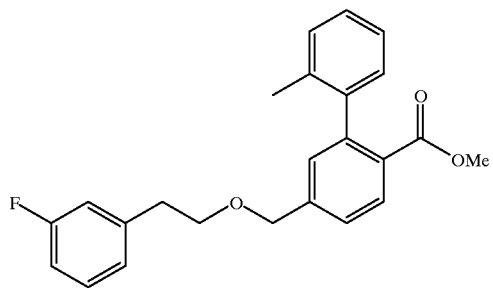

EXAMPLE 1274A

Prepared according to the procedure of example 1290D from the reaction between example 2-(3-fluorophenyl) ethanol and 4-bormomethyl-2-(2-methylphenyl)benzoic acid methyl ester. NMR(CDCl$_3$) 7.92–7.98 (m, 1H); 6.84–7.32 (m, 10H); 4.68 (s, 2H); 3.70–3.76 (t, 2H); 3.60 (s, 3H); 2.90–3.00 (t, 2H); 2.05 (s, 3H). (DCI/NH$_3$)/MS: 379 (M+H)$^+$; 396(M+NH$_4$)$^+$.

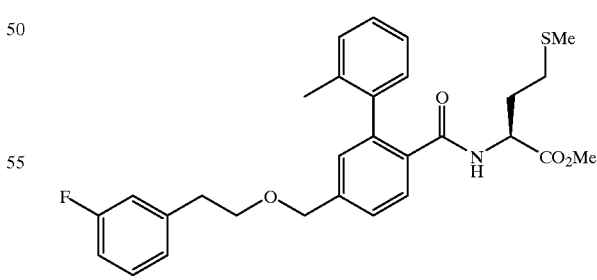

EXAMPLE 1274B

N-[4-(2-(3-fluorophenyl)ethyloxymethyl-2-(2-methylphenyl)benzoyl]methionine, methyl ester Prepared according to the procedure of example 1178J from 1274B. NMR(CDCl$_3$) 7.82–8.00 (m, 1H); 7.05–7.40

(m, 7H); 6.80–7.00 (m, 2H); 5.83–5.94 (m, 1H); 4.55–4.70 (m, 2H); 3.70–3.78 (t, 2H); 3.64 (s, 3H); 2.90–2.96 (t, 2H); 2.00–2.20 (m, 8H); 1.78–2.00 (m, 1H); 1.50–1.66 (m, 1H). DCI/NH$_3$/MS: 510(M+H)$^+$; 527(M+NH$_4$)$^+$.

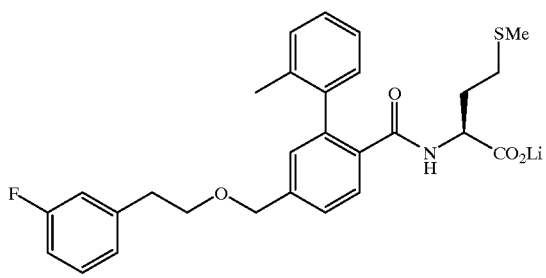

EXAMPLE 1274 (A-250000)

N-[4-(2-(3-fluorophenyl)ethyloxymethyl-2-(2-methylphenyl)benzoyl]methionine lithium salt Prepared according to the procedure of example 1 178J from 1274B. NMR $^1$H (d$_4$-MeOH): 7.6–7.7 (1H, m); 6.9–7.4 (10H, m); 6.7–6.8 (1H, m); 4.6 (2H, s); 4.1 (1H, m) 3.7–3.75 (2H, s); 2.9–2.95 (2H, s); 1.5–2.2 (10H, m). ESI(–)/MS: 494 (M–Li).

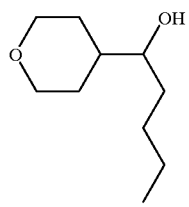

EXAMPLE 1282A

Prepared according to the procedure of example 1291C from the reaction between example 1279B andn-butylmagesium bromide. NMR(CDCl$_3$) 3.93–4.10 (m, 2H); 3.30–3.42 (m, 3H); 1.20–1.80 (m, 11H); 0.95–1.00 (t, 3H). (DCI/NH$_3$)/MS: 173(M+H)$^+$; 190(M+NH$_4$)$^+$.

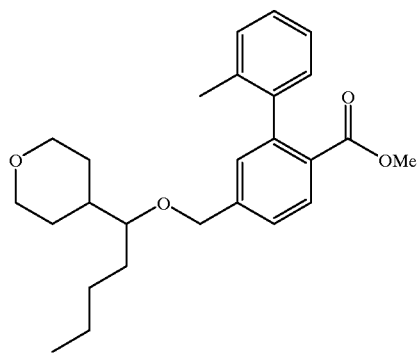

EXAMPLE 1282B

Prepared according to the procedure of example 1290D from the reaction between example 1282A and 4-bormomethyl-2-(2-methylphenyl)benzoic acid methyl ester.

NMR(CDCl$_3$) 7.93–7.98 (m 1H); 7.40–7.45 (m, 1H); 7.20–7.30 (m, 4H); 7.08–7.12 (m, 1H); 4.50–4.65 (m 2H); 3.95–4.05 (m, 2H); 3.60 (s, 3H); 3.30–3.45 (m, 3H); 3.12–3.30 (m, 2H); 2.06 (s, 3H); 1.30–1.80 (m, 11H); 0.92–0.96 (t, 3H). (DCI/NH$_3$)/MS: 411(M+H)$^+$; 428(M+NH$_4$)$^+$.

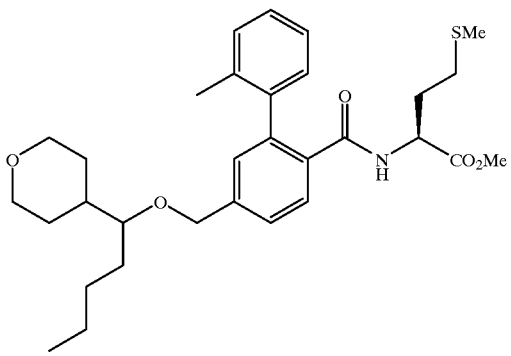

EXAMPLE 1282C

N-[4-(1-(4-tetrahydropyranyl)pentyloxymethyl-2-(2-methylphenyl)benzoyl]methionine, methyl ester Prepared according to the procedure of example 1258C from 1282B. NMR(CDCl$_3$) 7.82–8.00 (m, 1H); 7.38–7.42 (m, 1H); 7.15–7.36 (m, 5H); 5.83–5.92 (m, 1H); 4.50–4.65 (m, 2H); 4.50–4.68 (m, 3H); 3.94–4.02 (m, 2H); 3.65 (s, 3H); 3.25–3.42 (m, 2H); 3.10–3.20 (m, 1H); 1.22–2.00 (m, 18H); 0.88–0.92 (t, 3H). (DCI/NH$_3$)/MS: 542(M+H)$^+$; 559 (M+NH$_4$)$^+$.

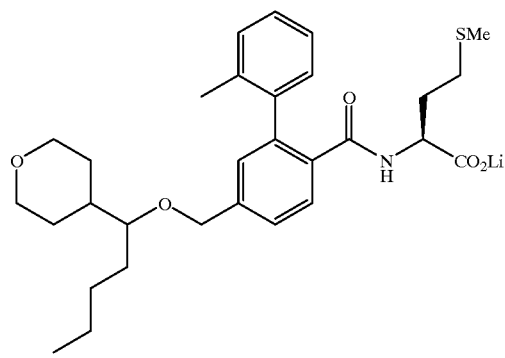

EXAMPLE 1282 (A-241617)

N-[4-(1-(4-tetrahydropyranyl)pentyloxymethyl-2-(2-methylphenyl)benzoyl]methionine lithium salt Prepared according to the procedure of example 1178J from 1282C. NMR $^1$H (d$_4$-MeOH): 7.6–7.7 (1H, m); 7.4–7.5 (1H, m); 7.05–7.4 (6H, m); 4.5–4.7 (2H, m); 4.25 (1H, m) 3.9–4.0 (2H, m); 3.2–3.4 (3H, m); (3H, s); 2.25 (1H, s); 1.3–2.2 (20H, m); 0.85–0.95 (3H, m). ESI(–)/MS: 526 (M–Li).

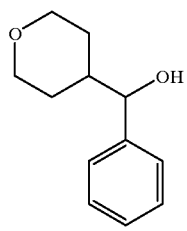

EXAMPLE 1283A

Prepared according to the procedure of example 1291C from the reaction between example 1279B and phenylmagesium bromide. NMR(CDCl$_3$) 7.20–7.30 (m, 5H); 4.36–4.41 (m, 1H); 3.83–4.08 (m, 2H); 3.22–3.42 (m, 2H); 1.05–2.00 (m, 5H).

(DCI/NH$_3$)/MS: 193(M+H)$^+$; 210(M+NH$_4$)$^+$.

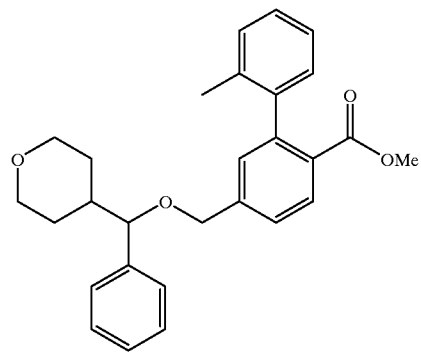

EXAMPLE 1283B

Prepared according to the procedure of example 1290D from the reaction between example 1283A and 4-bormomethyl-2-(2-methylphenyl)benzoic acid methyl ester.

NMR(CDCl$_3$) 7.20–7.30 (m, 5H); 4.36–4.41 (m, 1H); 3.83–4.08 (m, 2H); 3.22–3.42 (m, 2H); 1.05–2.00 (m, 5H). (DCI/NH$_3$)/MS: 193(M+H)$^+$; 210(M+NH$_4$)$^+$.

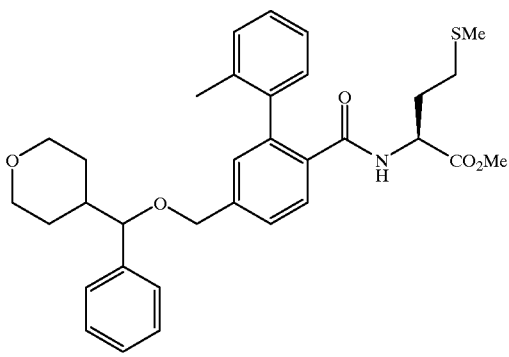

EXAMPLE 1283C

N-[4-(1-(4-tetrahydropyranyl)benzyloxymethyl-2-(2-methylphenyl)benzoyl]methionine lithium salt Prepared according to the procedure of example 1258C from 1283B. NMR(CDCl3) 7.92–7.92 (m, 1H); 7.13–7.41 (m, 10H); 7.12 (s, 1H); 5.88–5.96 (m, 1H); 4.53–4.70 (m, 1H); 4.22–4.50 (m, 2H); 3.80–4.02 (m, 3H); 3.65 (s, 3H); 3.20–3.42 (m, 2H); 1.02–2.20 (m 15H). (DCI/NH$_3$)/MS: 562(M+H)$^+$; 579(M+NH$_4$)$^+$.

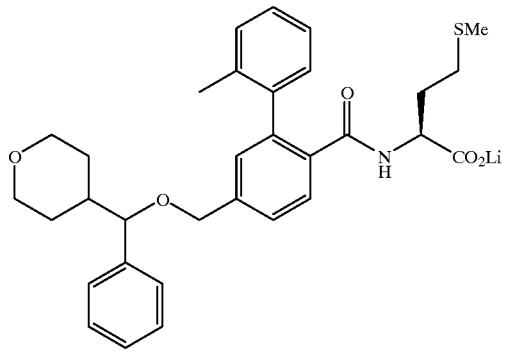

EXAMPLE 1283 (A-241616)

N-[4-(1-(4-tetrahydropyranyl)benzyloxymethyl-2-(2-methylphenyl)benzoyl]methionine lithium salt Prepared according to the procedure of example 1178J from 1282C. NMR $^1$H (d$_4$-MeOH): 7.6–7.7 (1H, m); 7.1–7.4 (12H, m); 4.3–4.5 (2H, dd); 4.2–4.3 (1H, m); 4.1 (1H, m); 3.8–4.0 (2H, dd); 3.3–3.4 (2H, s); 2.15 (1H, s); 1.75–2.1 (9H, m); 1.6–1.65 (1H, m); 1.2–1.65 (2H, m); 1.1–1.2 (1H, m). ESI(–)/MS: 546 (M–Li).

EXAMPLE 1288A

N-[4-(1-(4-piperidinyl)pentyloxymethyl-2-(2-methylphenyl)benzoyl]methionine, methyl ester A solution of 1289E (0.40 g, 0.625 mmol) 100 ml of methanol was saturated with anhydrous hydrochloride gas. The resulted solution was stirred for 10 hours at room temperature. After methanol was removed under vacuum, the residue was treated with saturated NaHCO$_3$, then extracted with EtOAc, washed with brine, and dried over MgSO$_4$. Evaporation of the solvent afforded 0.32 g of the title compound (95%). NMR(CDCl$_3$) 7.82–8.00 (m, 1H); 7.38–7.42 (m, 1H); 7.18–7.24 (m, 4H); 7.18 (s, 1H); 5.83–5.93 (m, 1H); 4.50–4.70 (m, 3H); 4.10–4.20 (m, 2H); 3.65 (s, 3H); 3.18–3.22(m, 1H); 2.57–2.70 (m, 2H); 1.20–2.20 (m, 21H); 0.88–0.94 (t, 3H). (DSI/NH$_3$)/MS: 541(M+H)$^+$.

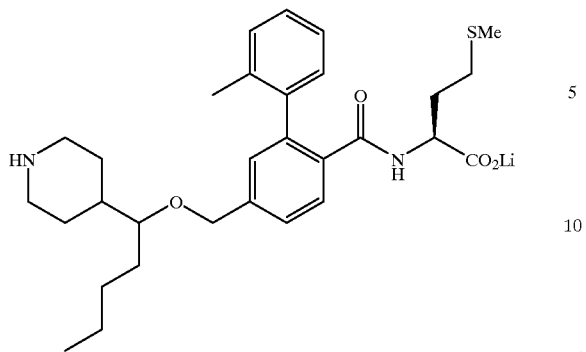

EXAMPLE 1288 (A-245500)

N-[4-(1-(4-piperidinyl)pentyloxymethyl-2-(2-methylphenyl)benzoyl]methionine lithium salt Prepared according to the procedure of example 1178J from 1288E. NMR $^1$H (d$_4$-MeOH): 7.6–7.7 (1H, m); 7.4–7.5 (1H, m); 7.1–7.3 (6H, m); 4.84 (2H, s); 4.2–4.3 (1H, m) 3.3 (1H, m); 3.1–3.2 (2H, m); 3.55–3.7 (2H, m); 2.15 (1H, s); 1.5–2.1 (16H, m); 1.3–1.5 (5H, m); 0.9–0.95 (3H, m). ESI(−)/MS: 587 (M+H) 533.

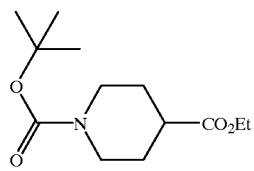

EXAMPLE 1289A

A mixture of ethyl 1-piperazinecarboxylate (7.85 g, 50 mmol), di-tert-butyl-dicarbonate (13.1 g, 60 mmol) in 60 ml of THF was treated by sodium hydroxide (2.4 g, 60 mmol) in 15 ml of water. After 30 min, TLC indicated that there was no any ethyl 1-piperazinecarboxylate left. The reaction mixture was diluted with 100 ml of ethyl ether, washed by NaHCO$_3$ solution, and then dried over anhydrous MgSO$_4$. Vacuum distillation of the residue afforded 10.2 g of the title product (80%). NMR(CDCl$_3$) 4.10–4.20 (q, 2H); 3.94–4.10 (m, 2H); 2.78–2.90 (m, 2H)1 2.38–2.50 (M, 1H); 1.80–1.94 (m, 2H); 1.50–1.70 (m, 1H); 1.45 (s, 9H); 1.20–1.28 (t, 3H). (DSI/NH$_3$)/MS: 258(M+H)$^+$; 275(M+NH$_4$)$^+$.

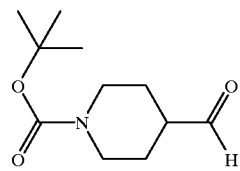

EXAMPLE 1289B

Prepared according to the procedure of example 129 1B from example 1291A.

NMR(CDCl$_3$) 9.84 (s, 1H); 3.92–4.10 (m, 2H); 2.82–3.00 (m, 2H); 2.18 (m, 2.48 (m, 1H); 1.93 (m, 2H); 1.50 1.70 (m, 2H); 1.45 (s, 9H). (DSI/NH$_3$)/MS: 214(M+H)$^+$; 231 (M+NH$_4$)$^+$.

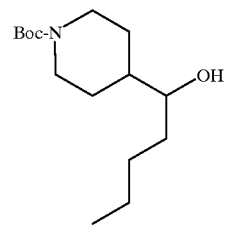

EXAMPLE 1289C

Prepared according to the procedure of example 1291C from the reaction between example 1289B and butylmagesium bromide. NMR(CDCl$_3$) 4.10–4.28 (m, 2H); 3.34–3.44(m, 1H); 2.60–2.70 (m, 2H); 1.15–1.80 (m, 20H); 0.88–0.94 (t, 3H). (DSI/NH$_3$)/MS: 272(M+H)$^+$; 287(M+NH$_4$)$^+$.

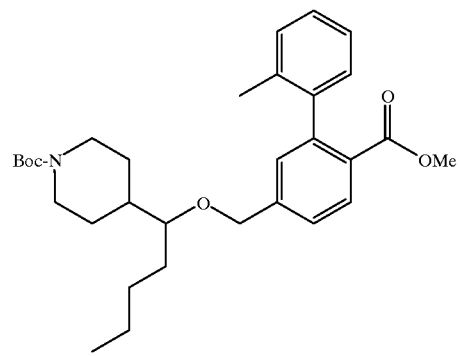

EXAMPLE 1289D

Prepared according to the procedure of example 1290D from the reaction between example 1289C and 4-bormomethyl-2-(2-methylphenyl)benzoic acid methyl ester.

NMR(CDCl$_3$) 7.94–8.00 (m, 1H); 7.38–7.42 (m, 1H); 7.18–7.24 (m, 4H); 7.05–7.10 (m, 1H); 4.50–4.68 (m, 2H); 4.10–4.20 (m, 2H); 3.60 (s, 3H); 3.18–3.22(m, 1H); 2.57–2.70 (m, 2H); 2.04 (s, 3H). 1.15–1.80 (m, 20H); 0.88–0.94 (t, 3H). (DSI/NH$_3$)/MS: 510(M+H)$^+$; 527(M+NH$_4$)$^+$.

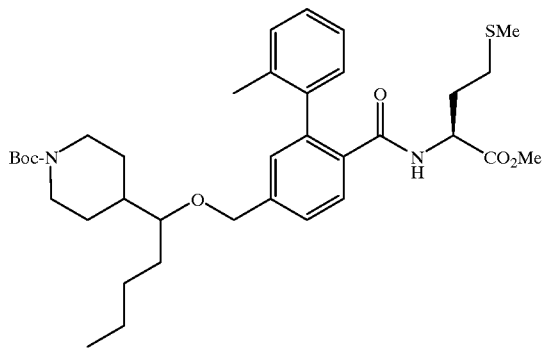

EXAMPLE 1289E

N-[4-(1-(4-(N-t-butoxycarbonyl)piperidinyl)pentyloxymethyl-2-(2-methylphenyl)benzoyl]methionine, methyl ester Prepared according to the procedure of example 1258C from 1289D. NMR(CDCl$_3$) 7.82–8.00 (m, 1H); 7.38–7.42

(m, 1H); 7.18–7.24 (m, 4H); 7.18 (s, 1H); 5.8–5.93 (m, 1H); 4.50–4.70 (m, 3H); 4.10–4.20 (m, 2H); 3.65 (s, 3H); 3.18–3.22(m, 1H); 2.57–2.70 (m, 2H); 1.20–2.20 (m, 30H); 0.88–0.94 (t, 3H). (DSI/NH$_3$)/MS: 640(M+H)$^+$; 657(M+NH$_4$)$^+$.

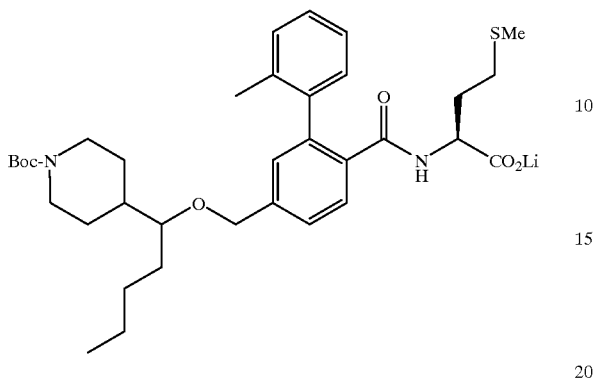

EXAMPLE 1289 (A-245499)

N-[4-(1-(4-(N-t-butoxycarbonyl)piperidinyl)pentyloxymethyl-2-(2-methylphenyl)benzoyl]methionine lithium salt Prepared according to the procedure of example 1178J from 1289E. NMR $^1$H (d$_4$-MeOH): 7.6–7.7 (1H, m); 7.4–7.5 (1H, m); 7.1–7.3 (6H, m); 4.84 (2H, m); 4.2–4.3 (1H, m); 4.1–4.2 (2H, m); 3.2 (1H, m); 2.6–2.8 (2H, m); 2.15 (1H, s); 1.2–2.1 (30H, m); 0.9–0.95 (3H, m). ESI(-)/MS: 633 (M+H).

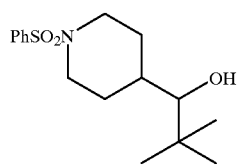

EXAMPLE 1290A

Prepared according to the procedure of example 1291C from the reaction between example 1291B and t-butylmagesium bromide. NMR(CDCl$_3$) 7.78–7.82 (m, 2H); 7.10–7.30 (m, 3H); 3.88–3.90 (m, 2H); 3.05–3.10)m, 1H); 2.20–2.35 (m, 2H); 1.60–1.85 (m, 8H); 0.90 (s, 9H). DSI/NH$_3$/MS: 312(M+H)$^+$; 329(M+NH$_4$)$^+$.

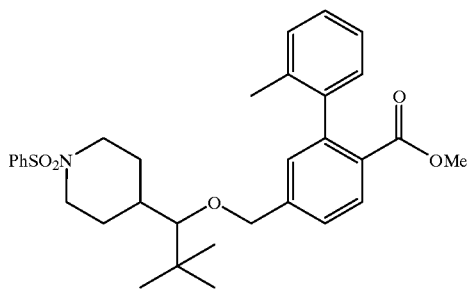

EXAMPLE 1290B

Prepared according to the procedure of example 1290D from the reaction between example 1290A and 4-bormomethyl-2-(2-methylphenyl)benzoic acid methyl ester.

NMR(CDCl$_3$) 7.92–7.99 (m, 1H); 7.72–7.80 (m, 2H); 7.45–7.62 (m, 3H); 7.38–7.42 (m, 1H); 7.10–7.28 (m, 6H); 4,50–4.70 (m, 2H); 3.88–3.90 (m, 2H); 3.60 (s, 3H); 2.80–2.84 (m, 1H); 2.10–2.30 (m, 2H); 2.05 (s, 3H); 1.60–1.85 (m, 8H); 0.90 (s, 9H).

DSI/NH$_3$)/MS: 567(M+NH$_4$)$^+$.

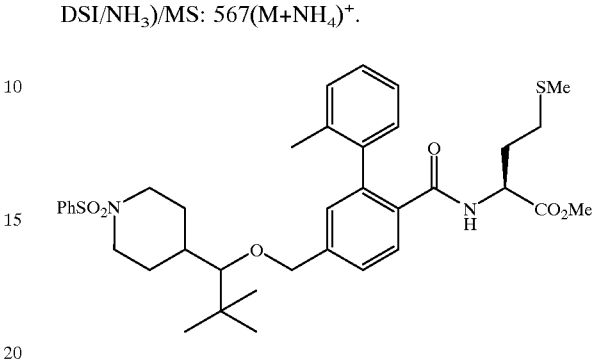

EXAMPLE 1290C

N-[4-(2,2-dimethyl-1-(4-(N-phenylsulfonyl)piperidinyl)propyloxymethyl-2-(2-methylphenyl)benzoyl]methionine, methyl ester Prepared according to the procedure of example 1258C from 1290B. NMR(CDCl$_3$) 7.92–7.99 (m, 1H); 7.72–7.80 (m, 2H); 7.45–7.62 (m, 3H); 7.38–7.42 (m, 1H); 7.10–7.28 (m, 6H); 5.90–5.95 (m, 1H); 4.50–4.72 (m, 3H); 3.78–3.90 (m, 2H); 3.65 (s, 3H); 2.80–2.84 (m, 1H); 2.00–2.30 (m, 10H); 1.7–2.0 (m, 2H); 1.60–1.85 (m, 4H); 0.90 (s, 9H).

DSI/NH$_3$)/MS: 681(M+H)$^+$; 698(M+NH$_4$)$^+$.

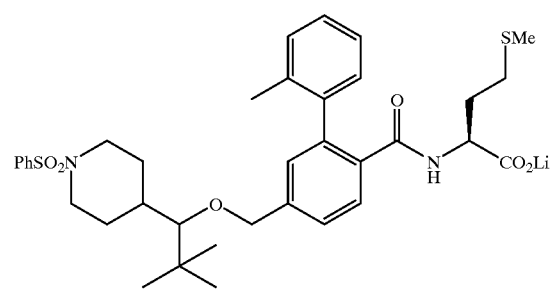

EXAMPLE 1290 (A-241624)

N-[4-(2,2-dimethyl-1-(4-(N-phenylsulfonyl)piperidinyl)propyloxymethyl-2-(2-methylphenyl)benzoyl]methionine lithium salt Prepared according to the procedure of example 1178J from 1290E. NMR $^1$H (d$_4$-MeOH): 7.7–7.8 (2H, m); 7.5–7.7 (4H, m); 7.2–7.4 (7H, m); 4.84 (2H, m); 4.2–4.3 (1H, m); 3.8 (2H, s); 2.9 (1H, s); 1.6–2.3 (18H, m); 0.9 (9H, s). ESI(-)/MS: 665 (M-Li).

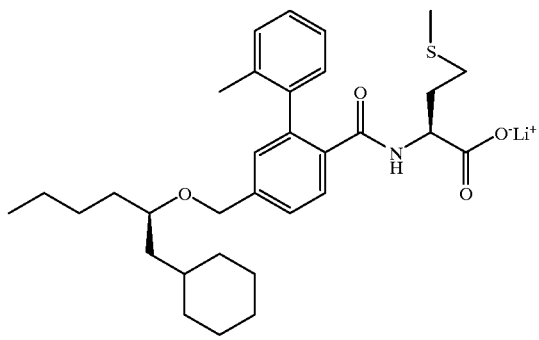

EXAMPLE 1303 (A-229042)

N-[4-(1-Cyclohexyl-2-hexyloxymethyl)-2-(2-methylphenyl)benzoyl]methionine Lithium Salt

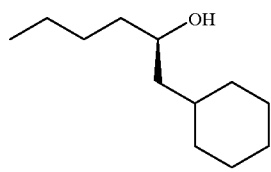

EXAMPLE 1303A

1-Cyclohexylhexan-2-ol

A solution of 2.0M propylmagnesium chloride in Et$_2$O (2.0 mL, 4.0 mmol) was added to a solution of the product from Example 1308C (463 mg, 3.3 mmol), copper(I) chloride (33 mg, 0.3 mmol) and chlorotrimethylsilane (460 µL, 3.6 mmol) in THF (11 mL) at 0° C. After 15 min of stirring, a solution of 2N HCl was added to the reaction vessel and the mixture was extracted with EtOAc (2×). The organic phases were combined, dried (MgSO4) and concentrated. The residue was chromatographed (silica gel; hexanes/EtOAc, 1:20) to afford the title compound as a clear oil. MS (CI/NH$_3$) m/z: (M+NH$_4$)$^+$ 202.

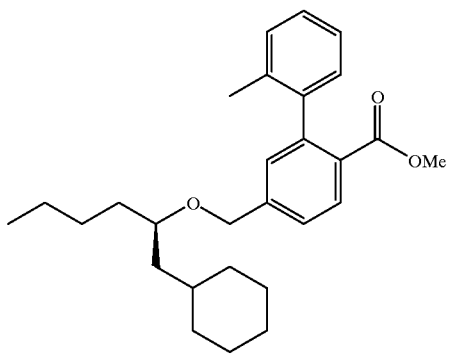

EXAMPLE 1303B

N-[4-(1-Cyclohexyl-2-hexyloxymethyl)-2-(2-methylphenyl)benzoyl]methionine methyl ester The product from Example 1303A (355 mg, 1.9 mmol) in DMF (250 µL), the product from Example 1308E (845 mg, 2.3 mmol) in DMF (500 µL), and NaH, 60% dispersion in mineral oil, (85 mg, 2.1 mmol) in DMF (250 µL) were allowed to react in a manner similar to that described in Example 1308F. The crude residue was chromatographed (silica gel; EtOAc/hexanes, 1:40) to afford the title compound as a clear oil (170 mg, 21%). MS (CI/NH$_3$) m/z: (M+H)$^+$ 423.

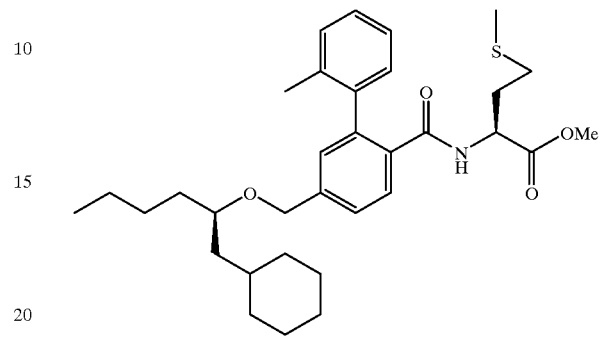

EXAMPLE 1303C

N-[4-(1-Cyclohexyl-2-hexyloxymethyl)-2-(2-methylphenyl)benzoyl]methionine methyl ester The product from Example 1303B (170 mg, 0.4 mmol) was saponified in a similar manner as that described in Example 608C. The crude acid was then allowed to react with EDCI (95 mg, 0.5 mmol), Hobt (55 mg, 0.4 mmol), (L)-methionine methyl ester hydrochloride (83 mg, 0.4 mmol) and NMM (70 µL, 0.6 mmol) in DMF (1.5 mL) in a manner similar to that described in Example 608D. The crude residue was chromatographed (silica gel; EtOAc/hexanes, 1:5) to afford the title compound as a clear oil (96 mg, 43%). MS (CI/NH$_3$) m/z: (M+H)$^+$ 554.

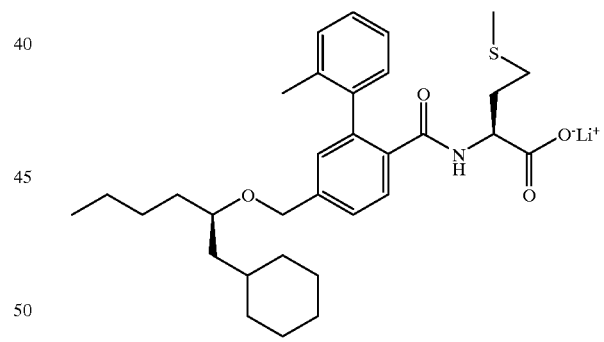

EXAMPLE 1303D

N-[4-(1-Cyclohexyl-2-hexyloxymethyl)-2-(2-methylphenyl)benzoyl]methionine Lithium Salt The product from Example 1303C (91 mg, 0.16 mmol) was allowed to react with lithium hydroxide monohydrate (7 mg, 0.17 mmol) in a manner similar to that described in Example 608E to afford the title compound. $^1$H NMR (DMSO-d$_6$, 300 MHz) δ0.81–0.90 (m, 5H), 1.05–1.70 (m, 21H), 1.91–2.03 (m, 5H), 2.16 (m, 1H), 3.41 (m, partially buried under water peak 1H), 3.63 (m, 1H), 4.47 (d, J=12.5 Hz 1H), 4.57 (d, J=12.5 Hz 1H), 6.95 (m, 1H), 7.08–7.25 (m, 4H), 7.36 (d, J=8.5 Hz 1H), 7.51 (d, J=8 Hz, 1H); MS (APCI(−)) m/z: (M−H)$^-$ 538; Anal. Calcd for $C_{32}H_{44}LiNO_4S \cdot 1.50\ H_2O$: C, 67.11; H, 8.27; N, 2.45. Found: C, 67.13; H, 7.84; N, 2.22.

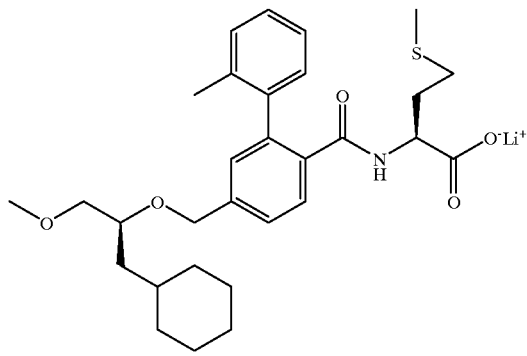

EXAMPLE 1304 (A-260016)

N-[4-(3-Cyclohexyl-1-methoxyprop-2-yloxymethyl)-2-(2-methylphenyl)benzoyl] methionine Lithium Salt

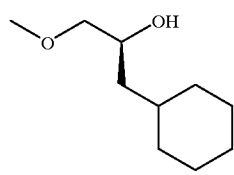

EXAMPLE 1304A

3-Cyclohexylpropan-2-ol

The product from Example 1308C (600 mg, 4.3 mmol) in DMF (4.0 mL) was added to a solution of DMF (4.5 mL) and 1.0M lithium methoxide in MeOH (4.5 mL, 4.5 mmol) at ambient temperature. The mixture was heated at 65° C. for 18 hours and then allowed to cool to ambient temperature. A solution of 2N HCl was added to the mixture followed by extration with EtOAc (2×). The organic phases were combined, dried ($MgSO_4$) and concentrated. The residue was chromatographed (silica gel; EtOAc/hexanes, 1:10) to afford a clear oil (505 mg, 68%). $^1$H NMR ($CDCl_3$, 300 MHz) δ 0.77–1.00 (m, 2H), 1.11–1.84 (m, 8H), 3.20 (dd, J=8. 9.5 Hz, 1H), 3.38 (dd, J=3, 9.5 Hz, 1H), 3.39 (s, 3H), 3.90 (m, 1H).

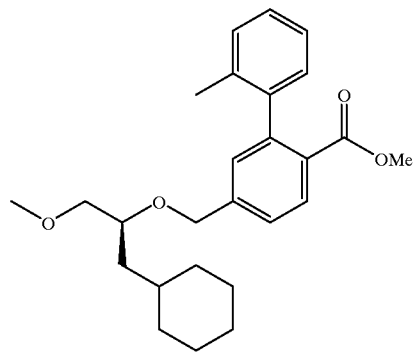

EXAMPLE 1304B

N-[4-(3-Cyclohexyl-1-methoxyprop-2-yloxymethyl)-2-(2-methylphenyl)benzoyl] methionine methyl ester The product from Example 1304A (250 mg, 1.4 mmol) in DMF (1.4 mL), the product from Example 1308E (622 mg, 1.4 mmol) in DMF (1.5 mL), and NaH, 60% dispersion in mineral oil, (70 mg, 1.7 mmol) in DMF (4 mL) were allowed to react in a manner similar to that described in Example 1308F. The crude residue was chromatographed (silica gel; EtOAc/hexanes, 1:20) to afford the title compound as a clear oil (201 mg, 34%). MS ($CI/NH_3$) m/z: $(M+H)^+$ 411.

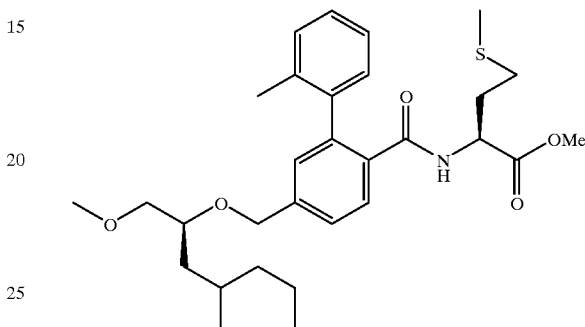

EXAMPLE 1304C

N-[4-(3-Cyclohexyl-1-methoxyprop-2-yloxymethyl)-2-(2-methylphenyl)benzoyl] methionine methyl ester The product from Example 1304B (193 mg, 0.47 mmol) was saponified in a similar manner as that described in Example 608C. The crude acid was then allowed to react with EDCI (126 mg, 0.66 mmol), Hobt (70 mg, 0.52 mmol), (L)-methionine methyl ester hydrochloride (113 mg, 0.56 mmol) and NMM (95 μL, 0.85 mmol) in DMF (2.0 mL) in a manner similar to that described in Example 608D. The crude residue was chromatographed (silica gel; EtOAc/hexanes, 1:3) to afford the title compound as a clear oil (204 mg, 80%). MS ($CI/NH_3$) m/z: $(M+H)^+$ 542.

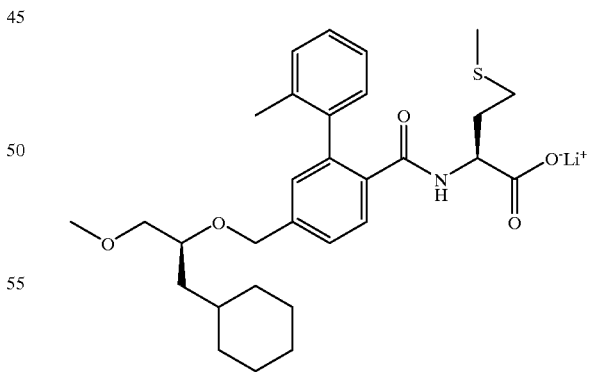

EXAMPLE 1304D

N-[4-(3-Cyclohexyl-1-methoxyprop-2-yloxymethyl)-2-(2-methylphenyl)benzoyl] methionine Lithium Salt The product from Example 1304C (195 mg, 0.36 mmol) was allowed to react with lithium hydroxide monohydrate (16 mg, 0.38 mmol) in a manner similar to that described in Example 608E to afford the title compound. $^1$H NMR (DMSO-$d_6$, 300 MHz) δ0.72–1.41 (m, 9H), 1.50–1.77 (m, 9H), 1.80–2.03 (m, 6H), 2.15 (m, 1H), 3.24 (s, 3H), 3.55–3.75 (m, 2H), 4.53 (d, J=12.5 Hz 1H), 4.68 (d, J=12.5 Hz 1H), 6.96 (m, 1H), 7.10–7.27 (m, 4H), 7.36 (d, J=8 Hz 1H), 7.52 (d, J=8 Hz, 1H); MS (APCI(−)) m/z: (M−H)$^-$ 526; Anal. Calcd for $C_{30}H_{40}LiNO_5S \cdot 0.90$ $H_2O$: C, 65.53; H, 7.66; N, 2.55. Found: C, 65.49; H, 7.43; N, 2.46.

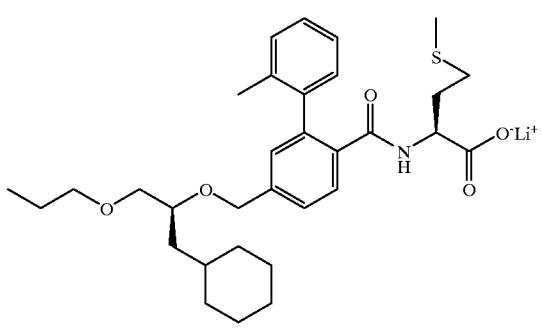

EXAMPLE 1305 (A-257321)

N-[4-(3-Cyclohexyl-1-propoxyprop-2-yloxymethyl)-2-(2-methylphenyl)benzoyl]methionine Lithium Salt

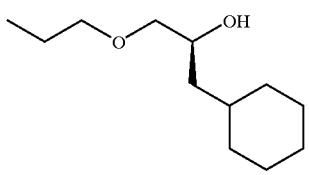

EXAMPLE 1305A

3-Cyclohexyl-1-propoxypropan-2-ol

The product from Example 1308C (600 mg, 4.3 mmol) in DMF (4.5 mL), n-propanol (336 μL, 4.5 mmol) in DMF (4.5 mL) and NaH, 60% dispersion in mineral oil, (200 mg, 5.0 mmol) in DMF (10 mL) were allowed to react in a manner similar to that described in Example 1308D. The residue was chromatographed (silica gel; EtOAc/hexanes, 1:10) to afford a light yellow oil (581 mg, 67%). MS (CI/NH$_3$) m/z: (M+NH$_4$)$^+$ 218.

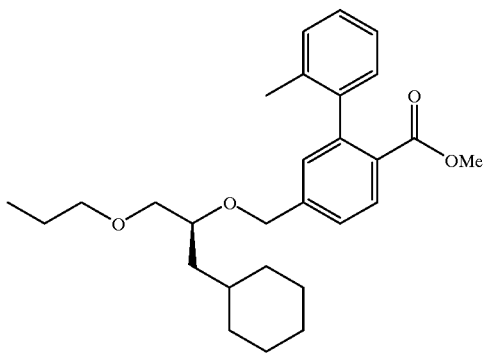

EXAMPLE 1305B

N-[4-(3-Cyclohexyl-1-propoxyprop-2-yloxymethyl)-2-(2-methylphenyl)benzoyl]methionine methyl ester The product from Example 1305A (300 mg, 1.5 mmol) in DMF (1.5 mL), the product from Example 1308E (650 mg, 1.8 mmol) in DMF (2.5 mL), and NaH, 60% dispersion in mineral oil, (75 mg, 1.8 mmol) in DMF (4 mL) were allowed to react in a manner similar to that described in Example 1308F. The crude residue was chromatographed (silica gel; EtOAc/hexanes, 1:20) to afford the title compound as a clear oil (344 mg, 52%). MS (CI/NH$_3$) m/z: (M+NH$_4$)$^+$ 456.

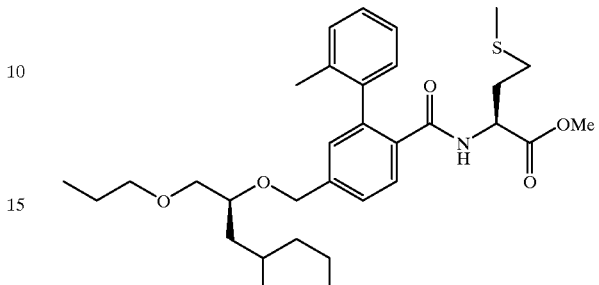

EXAMPLE 1305C

N-[4-(3-Cyclohexyl-1-propoxyprop-2-yloxymethyl)-2-(2-methylphenyl)benzoyl]methionine methyl ester The product from Example 1306B (334 mg, 0.8 mmol) was saponified in a similar manner as that described in Example 608C. The crude acid was then allowed to react with EDCI (215 mg, 1.1 mmol), Hobt (120 mg, 0.9 mmol), (L)-methionine methyl ester hydrochloride (192 mg, 1.0 mmol) and NMM (160 μL, 1.4 mmol) in DMF (3.0 mL) in a manner similar to that described in Example 608D. The crude residue was chromatographed (silica gel; EtOAc/hexanes, 1:4) to afford the title compound as a clear oil (223 mg, 49%). MS (CI/NH$_3$) m/z: (M+H)$^+$570.

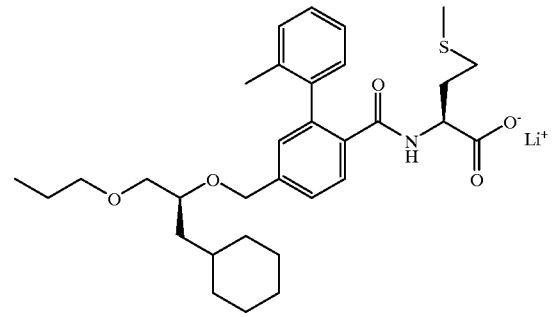

EXAMPLE 1305D

N-[4-(3-Cyclohexyl-1-propoxyprop-2-yloxymethyl)-2-(2-methylphenyl)benzoyl]methionine Lithium Salt The product from Example 1305C (218 mg, 0.38 mmol) was allowed to react with lithium hydroxide monohydrate (18 mg, 0.40 mmol) in a manner similar to that described in Example 608E to afford the title compound. $^1$H NMR (DMSO-$d_6$, 300 MHz) δ0.74–0.92 (m, 5H), 1.00–1.74 (m, 16H), 1.78–2.03 (m, 6H), 2.15 (m, 1H), 3.29–3.45 (m, 4H), 3.55–3.70 (m, 2H), 4.55 (d, J=12.5 Hz 1H), 4.69 (d, J=12.5 Hz 1H), 6.95 (m, 1H), 7.10–7.25 (m, 4H), 7.35 (d, J=7.5 Hz 1H), 7.52 (d, J=8 Hz, 1H); MS (APCI(−)) m/z: (M−H)$^-$ 554; Anal. Calcd for $C_{32}H_{44}LiNO_5S \cdot 1.25$ $H_2O$: C, 65.79; H, 8.02; N, 2.40 Found: C, 65.79; H, 7.72; N, 2.30.

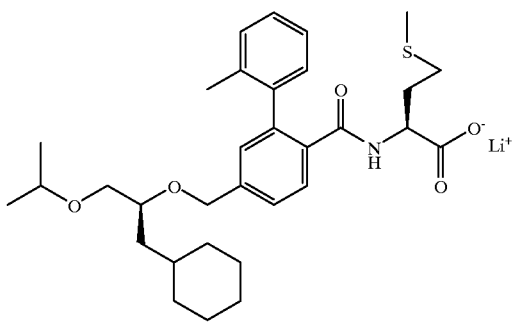

EXAMPLE 1306 (A-257311)

N-[4-[(S)-3-Cyclohexyl-1-(1-methylethoxy)prop-2-yloxymethyl]-2-(2-methylphenyl)benzoyl] methionine Lithium Salt

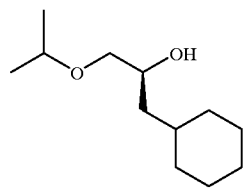

EXAMPLE 1306A (S)-3-Cyclohexyl-1-(1-methylethoxy)propan-2-ol

The product from Example 1308C (600 mg, 4.3 mmol) in DMF (4.5 mL), 2-propanol (348 μL, 4.5 mmol) in DMF (4.5 mL) and NaH, 60% dispersion in mineral oil, (200 mg, 5.0 mmol) in DMF (10 mL) were allowed to react in a manner similar to that described in Example 1308D. The residue was chromatographed (silica gel; EtOAc/hexanes, 1:12) to afford a clear oil (312 mg, 34%). MS (CI/NH$_3$) m/z: (M+NH$_4$)+218.

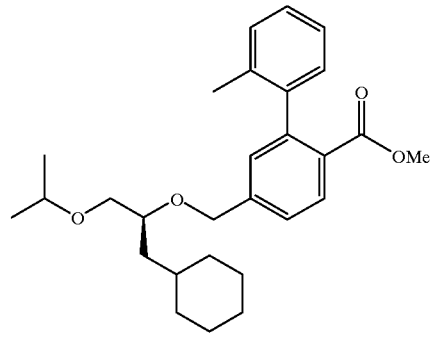

EXAMPLE 1306B

4-[(S)-3-Cyclohexyl-1-(1-methylethoxy)prop-2-yloxymethyl]-2-(2-methylphenyl)benzoic acid, methyl ester The product from Example 1306A (300 mg, 1.5 mmol) in DMF (4.5 mL), the product from Example 1308E (659 mg, 1.8 mmol) in DMF (4.5 mL), and NaH, 60% dispersion in mineral oil, (72 mg, 1.8 mmol) in DMF (3 mL) were allowed to react in a manner similar to that described in Example 1308F. The crude residue was chromatographed (silica gel; EtOAc/hexanes, 1:20) to afford the title compound as a clear oil (356 mg, 54%). MS (CI/NH$_3$) m/z: (M+H)$^+$ 439.

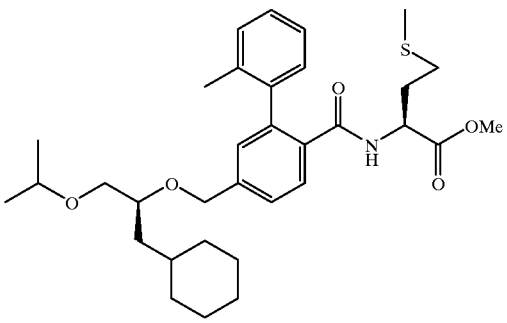

EXAMPLE 1306C

N-[4-[(S)-3-Cyclohexyl-1-(1-methylethoxy)prop-2-yloxymethyl]-2-(2-methylphenyl)benzoyl] methionine methyl ester The product from Example 1306B (350 mg, 0.8 mmol) was saponified in a similar manner as that described in Example 608C. The crude acid was then allowed to react with EDCI (215 mg, 1.1 mmol), Hobt (120 mg, 0.9 mmol), (L)-methionine methyl ester hydrochloride (192 mg, 1.0 mmol) and NMM (160 μL, 1.4 mmol) in DMF (2.5 mL) in a manner similar to that described in Example 608D. The crude residue was chromatographed (silica gel; EtOAc/hexanes, 1:4) to afford the title compound as a clear oil (176 mg, 38%). MS (CI/NH$_3$) m/z: (M+H)$^+$ 570.

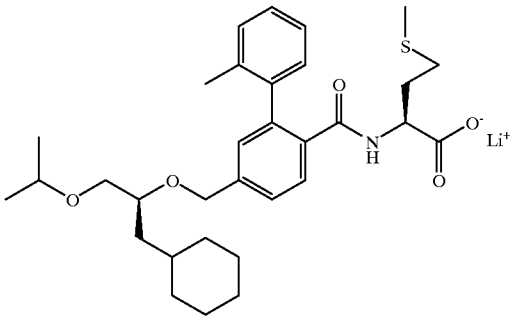

EXAMPLE 1306D

N-[4-[(S)-3-Cyclohexyl-1-(1-methylethoxy)prop-2-yloxymethyl]-2-(2-methylphenyl)benzoyl] methionine Lithium Salt The product from Example 1306C (166 mg, 0.29 mmol) was allowed to react with lithium hydroxide monohydrate (13 mg, 0.31 mmol) in a manner similar to that described in Example 608E to afford the title compound. $^1$H NMR (DMSO-d$_6$, 300 MHz) δ0.73–1.44 (m, 16H), 1.50–1.74 (m, 6H), 1.78–2.03 (m, 6H), 2.15 (m, 1H), 3.30–3.59 (m, 4H), 3.67 (m, 1H), 4.55 (d, J=12.5 Hz 1H), 4.69 (d, J=12.5 Hz 1H), 6.95 (m, 1H), 7.10–7.25 (m, 4H), 7.35 (d, J=7 Hz 1H), 7.52 (d, J=8 Hz, 1H); MS (APCI(–)) m/z: (M–H)$^-$ 554; Anal.

Calcd for C$_{32}$H$_{44}$LiNO$_5$S.0.70 H$_2$O: C, 66.92; H, 7.97; N, 2.44. Found: C, 66.97; H, 7.76; N, 2.31.

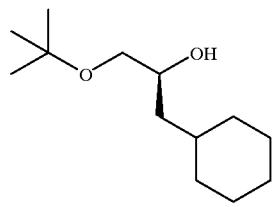

EXAMPLE 1307A (S)-1-(tert-Butoxy)-3-cyclohexyl-propan-2-ol (S)-1-(tert-Butoxy)-3-cyclohexyl-propan-2-ol was prepared according to the procedure described by Alan Armstrong et al., Tetrahedron Letters 1988, 29: 2483–2486. Three drops of boron trifuoride etherate were added to a solution of (S)-3-cylcolhexyl 1,2-propanediol (540 mg, 3.4 mmol) and tert-butyl 2,2,2-trichloroacetamide (670 µL, 3.8 mmol) in cyclohexane (7 mL) at ambient temperature. After stirring for 21 hours, a saturated solution of NaHCO$_3$ was added to the reaction mixture and the mixture was extracted with EtOAc (2×). The EtOAc phases were combined, dried (MgSO$_4$) and concentrated. The residue was chromatographed (silica gel; EtOAc/hexanes, 1:10) to afford a clear oil (235 mg, 32%). $^1$H NMR (CDCl$_3$, 300 MHz) δ0.79–1.01 (m, 2H), 1.12–1.53 (m, 6H), 1.20 (s, 9H) 1.58–1.84 (m, 5H), 3.12 (dd, J=9, 9 Hz, 1H), 3.35 (dd, J=3, 9 Hz, 1H), 3.81 (m, 1H); MS (CI/NH$_3$) m/z: (M+H)$^+$ 215.

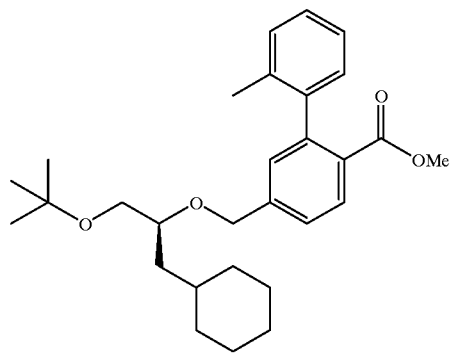

EXAMPLE 1307B

4-[(S)-1-tert-Butoxy-3-cyclohexylprop-2-yloxymethyl]-2-(2-methylphenyl)benzoic acid, methyl ester The product from Example 1307A (226 mg, 1.0 mmol) in DMF (1.0 mL), the product from Example 1308E (460 mg, 1.3 mmol) in DMF (3.0 niL), and NaH, 60% dispersion in mineral oil, (51 mg, 1.3 mmol) in DMF (3 mL) were allowed to react in a manner similar to that described in Example 1308F. The crude residue was chromatographed (silica gel; EtOAc/hexanes, 1:15) to afford the title compound as a clear oil (185 mg, 39%). MS (CI/NH$_3$) m/z: (M+H)$^+$ 470.

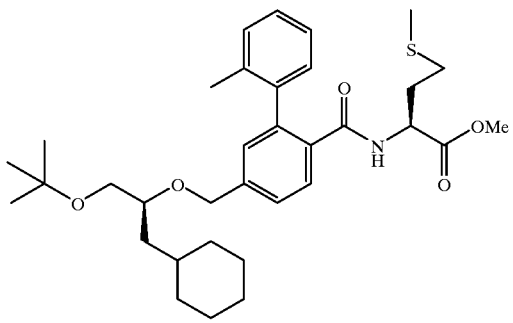

EXAMPLE 1307C

N-[4-[(S)-1-tert-Butoxy-3-cyclohexylprop-2-yloxymethyl]-2-(2-methylphenyl)benzoyl] methionine methyl ester The product from Example 1307B (180 mg, 0.40 mmol) was saponified in a similar manner as that described in Example 608C. The crude acid was then allowed to react with EDCI (110 mg, 0.56 mmol), Hobt (60 mg, 0.44 mmol), (L)-methionine methyl ester hydrochloride (100 mg, 0.48 mmol) and NMM (80 µL, 0.72 mmol) in DMF (2.0 mL) in a manner similar to that described in Example 608D. The crude residue was chromatographed (silica gel; EtOAc/hexanes, 1:6) to afford the title compound as a clear oil (84 mg, 36%). MS (CI/NH$_3$) m/z: (M+H)$^+$ 584.

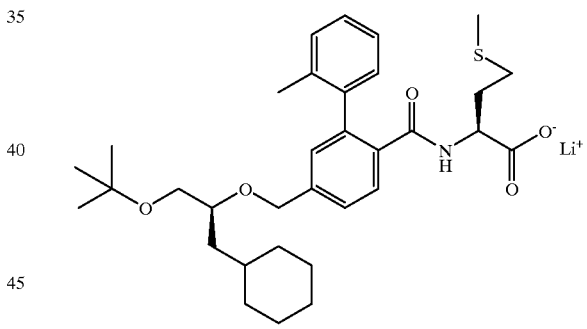

EXAMPLE 1307D

N-[4-[(S-1-tert-Butoxy-3-cyclohexylprop-2-yloxymethyl]-2-(2-methylphenyl)benzoyl] methionine Lithium Salt The product from Example 1307C (77 mg, 0.13 mmol) was allowed to react with lithium hydroxide monohydrate (6 mg, 0.14 mmol) in a manner similar to that described in Example 608E to afford the title compound. $^1$H NMR (DMSO-d$_6$, 300 MHz) δ0.75–1.20 (m, 19H), 1.57–1.74 (m, 6H), 1.80–2.03 (m, 6H), 2.15 (m, 1H), 3.26–3.41 (m, 2H), 3.50 (m, 1H), 3.67 (m, 1H), 4.55 (d, J=13 Hz 1H), 4.70 (d, J=13 Hz 1H), 6.95 (m, 1H), 7.12–7.25 (m, 4H), 7.35 (m, 1H), 7.52 (d, J=8 Hz, 1H); MS (APCI (–)) m/z: (M–H)$^-$ 568; Anal. Calcd for C$_{33}$H$_{46}$LiNO$_5$S.1.80 H$_2$O: C, 65.17; H, 8.22; N, 2.30. Found: C, 65.12; H, 7.77; N, 2.34.

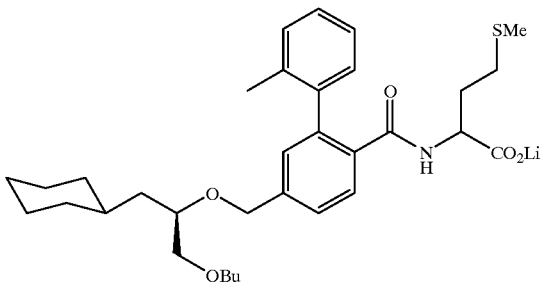

EXAMPLE 1308 (A-260015)

N-[4-(3-Cyclohexyl-1-butoxyprop-2-yloxymethyl)-2-(2-methylphenyl)benzoyl]methionine Lithium Salt

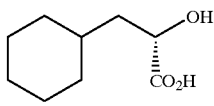

EXAMPLE 1308A (S)-3-Cyclohexyllactic acid

To a solution of (S)-3-phenyllactic acid (20g) in ethanol (250mL) was added 5% rhodium on alumina (2.5 g), and the reaction was shaken under 4atm $H_2$ for 24 h. The reaction was filtered, and concentrated to give product as a white solid (≈20 g). $^1$H NMR (300 MHz, $CDCl_3$) δ0.86–1.07 (m, 2H), 1.08–1.39 (m, 3H), 1.54–1.91 (m, 9H), 4.33 (dd, J=9.3, 3.6 Hz, 1H). MS(CI/$NH_3$) m/e: $(M+NH_4)^+$ 190.

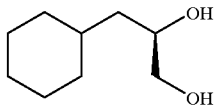

EXAMPLE 1308B (S)-3-Cyclohexyl-1,2-propanediol

To a solution of (S)-3-cyclohexyllactic acid (15 g) in THF (100 mL) at 0° C. was added 1M $BH_3$-THF (130 mL), and the reaction was warmed to ambient temperature. After 5 h, the reaction was quenched cautiously with aqueous THF (1:1, 100 mL), then with 1M KOH (100 mL). The reaction was concentrated, diluted with water (200 mL), and washed with EtOAc (3×150 mL). The organic extracts were washed with brine (100 mL), dried ($MgSO_4$), filtered and concentrated to give a colorless oil (14 g). $^1$H NMR (300 MHz, $CDCl_3$) δ0.80–1.04 (m, 2H), 1.05–2.00 (m, 13H), 3.41 (dd, J=10.8, 7.5 Hz, 1H), 3.64 (dd, J=10.8, 2.7 Hz, 1H), 3.84 (m, 1H). MS(CI/$NH_3$) m/e: $(M+NH_4)^+$ 176.

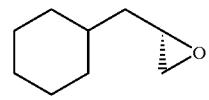

EXAMPLE 1308C (S)-Cyclohexylmethyloxirane

To a solution of (S)-3-cyclohexyl-1,2-propanediol in $CH_2Cl_2$ was added triethylamine (6.6 mL), 2,4,6-triisopropylbenzenesulfonyl chloride (11.5 g), and DMAP (0.386 g). After 14 h, the reaction was diluted with ether, chilled to 0° C., filtered through celite and concentrated. The residue was dissolved in ethanol (100 mL), and 1M NaOH was added (32 mL). After 30 min, the reaction was carefully concentrated, diluted with water (100 mL) and extracted into ether (3×50 mL). The organic extracts were washed with brine (20 mL), dried ($MgSO_4$), filtered and concentrated to give a colorless aromatic oil which was purified first by passage through a plug of silica gel eluting with 5%EtOAc/hexane, then by bulb-to-bulb distillation under reduced pressure to give a colorless aromatic oil (3.3 g, 75%). $^1$H NMR (300 MHz, $CDCl_3$) δ0.90–1.09 (m, 2H), 1.10–1.85 (m, 11H), 2.43 (dd, J=5.1, 2.7 Hz, 1H), 2.75 (dd, J=5.1, 4.5 Hz, 1H), 2.94 (m, 1H).

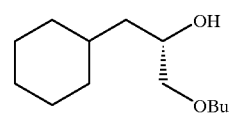

EXAMPLE 1308D (S)-3-Cyclohexyl-1-butoxy-2-propanol n-Butanol (2.2 mL) was dissolved in DMF (50 mL) followed by addition of NaH (0.49 g of a 60% oil dispersion). After gas evolution ceased, (S)-cyclohexylmethyloxirane (example 1308C, 0.86 g) was added, and the reaction was stirred at ambient temperature overnight. The reaction was warmed to 60° C. for one hour, then cooled and quenched by pouring into water (500 mL). The mixture was washed with ether/hexane (1:1, 3×150 mL), and the organic extracts were washed with brine (100 mL), dried ($MgSO_4$), filtered and concentrated. The residue was purified by silica gel chromatography eluting with 7.5% EtOAc/hexane to afford a colorless oil (1.07 g, 81%). $^1$H NMR (300 MHz, $CDCl_3$) δ0.80–1.02 (m, 2H), 0.92 (t, J=7.5 Hz, 3H), 1.06–1.83 (m, 16H), 2.27 (brd, J=2.4 Hz, 1H), 3.20 (dd, J=9.6, 8.1 Hz, 1H), 3.38–3.53 (m, 3H), 3.82–3.92 (m, 1H). MS(CI/$NH_3$) m/e: $(M+NH_3)^+$ 232.

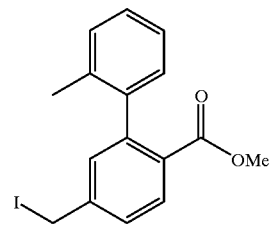

EXAMPLE 1308E

4-Iodomethyl-2-(2-methylphenyl)benzoic acid, methyl ester

Triphenylphosphine (5.16 g), and imidazole (1.34 g) were dissolved in 3:1 ether:acetonitrile (80 mL), and the reaction was cooled to 0° C. Iodine (5.0 g) was added with vigorous stirring, and the reaction was warmed to ambient temperature. After 1 h, the reaction was recooled to 0° C. and 4-hydroxymethyl-2-(2-methylphenyl)benzoic acid, methyl ester (example 1178C, 4.6 g) was added as a solution in ether (20 mL). After 4 h at ambient temperature, the reaction was diluted with hexane/ether (1:1, 200 mL) and filtered. The filtrate was washed with a dilute solution of $Na_2SO_3$ until colorless, then with water (2×50 mL). The organic extracts were washed with brine (20 mL), dried (MgSO$_4$), filtered and concentrated. The residue was purified by silica gel chromatography eluting with 10% EtOAc/hexane to give a light yellow oil (4.7 g) which slowly crystalizes in the freezer. $^1$H NMR (300 MHz, CDCl$_3$) δ2.06 (s, 3H), 3.60 (s, 3H), 4.45 (AB$_q$, J$_{AB}$=9.7 Hz, Δv$_{AB}$=6.7 Hz, 2H), 7.03 (brd, J=6.6 Hz, 1H), 7.17–7.29 (m, 4H), 7.41 (dd, J=8.1, 1.6 Hz, 1H), 7.90 (d, J=8.1 Hz, 1H)). MS(CI/NH$_3$) m/e: (M+NH$_4$)$^+$ 384.

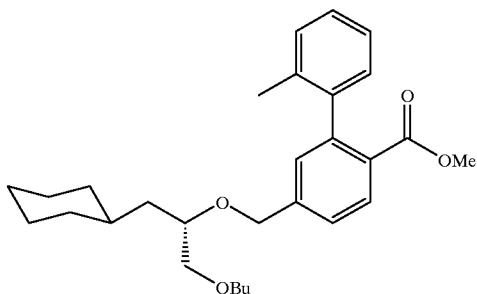

EXAMPLE 1308F 4-(3-Cyclohexyl-1-butoxyprop-2-yloxymethyl)-2-(2-methylphenyl)benzoic acid, methyl ester To a solution of (S)-3-cyclohexyl-1-butoxy-2-propanol (example 1308D, 1.0 g) in DMF (15 mL) was added NaH (0.184 g of a 60% oil dispersion). After 15 min, the reaction was chilled to 0° C., and 4-iodomethyl-2-(2-methylphenyl) benzoic acid, methyl ester (example 1308E, 1.54 g) was added. After 45 min, the reaction was poured into water (150 mL), and extracted with EtOAc (2×75 mL). The organic extracts were washed with brine (20 mL), dried (MgSO$_4$), filtered and concentrated. The residue was purified by silica gel chromatography eluting with 5% EtOAc/hexane to give a colorless oil (1.18 g, 62%).

$^1$H NMR (300 MHz, CDCl$_3$) δ0.80–0.95 (m, 2H), 0.90 (t, J=7.5 Hz, 3H), 1.06–1.71 (m, 15H), 2.06 (s, 3H), 3.38–3.49 (m, 4H), 3.61 (s, 3H), 3.67 (m, 1H), 4.62 (d, J=12.6 Hz, 1H), 4.79 (dd, J=12.6, 1.6 Hz, 1H), 7.07 (dt, J=7.2, 0.9 Hz, 1H), 7.16–7.28 (m, 4H), 7.42 (dd, J=7.8, 1.5 Hz, 1H), 7.94 (d, J=7.8 Hz, 1H). MS(CI/NH$_3$) m/e: (M+NH$_4$)$^+$ 470.

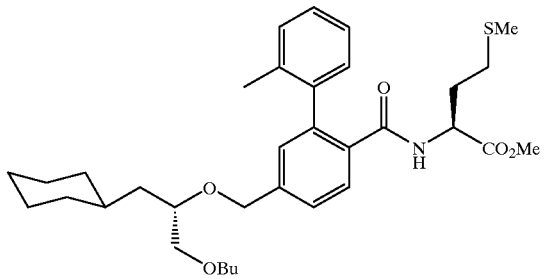

EXAMPLE 1308G

N-[4-(3-Cyclohexyl-1-butoxyprop-2-yloxymethyl)-2-(2-methylphenyl)benzoyl]methionine methyl ester 4-(3-Cyclohexyl-1-butoxyprop-2-yloxymethyl)-2-(2-methylphenyl)benzoic acid, methyl ester (1.1 g) was converted into the title compound by the procedure in examples 608C and D. Product was isolated as a colorless oil (1.06 g). $^1$H NMR (300 MHz, CDCl$_3$) δ0.80–0.95 (m, 2H), 0.90 (t, J=7.2 Hz, 3H), 1.07–1.72 (m, 15H), 1.80–1.93 (m, 2H), 2.00–2.20 (m, 8H), 3.37–3.52 (m, 4H), 3.65 (s, 3H), 3.65–3.71 (m, 1H), 4.56–4.68 (m, 1H), 4.62 (d, J=12.6 Hz, 1H), 4.78 (d, J=12.6 Hz, 1H), 5.89 (brd, J=6.3 Hz, 1H), 7.16–7.47 (m, 5H), 7.44 (brd, J=6.9 Hz, 1H), 7.94 ("dd", J=15.6, 7.8 Hz, 1H). MS(APCI(+)) m/e: (M+H)$^+$ 584, MS(APCI(-)) m/e: (M-H)$^-$ 582.

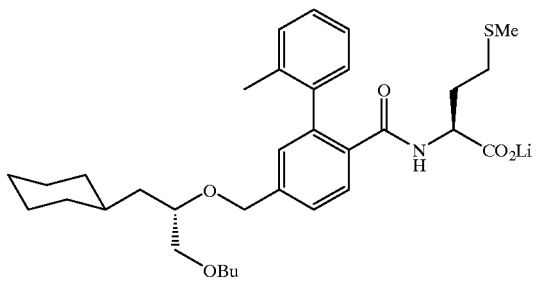

EXAMPLE 1308I

N-[4-(3-Cyclohexyl-1-butoxyprop-2-yloxymethyl)-2-(2-methylphenyl)benzoyl]methionine Lithium Salt N-[4-(3-Cyclohexyl-1-butoxyprop-2-yloxymethyl)-2-(2-methylphenyl)benzoyl]methionine methyl ester (1.05 g) was converted to the title compound by the procedure in example 608E. Product was isolated as a white powder (1.02 g). $^1$H NMR (DMSO-d$_6$, 300 MHz) δ7.52 (d, J=8 Hz, 1H), 7.35 (d, J=8 Hz,1H), 7.25–7.10 (m, 4H), 6.95 (m, 1H), 4.69 (d, J=13 Hz 1H), 4.55 (d, J=13 Hz 1H), 3.71–3.53 (m, 2H), 3.45–3.31 (m, 4H), 2.15 (m, 1H), 2.04–1.52 (m, 14H), 1.49–1.00 (m, 10H), 0.95–0.75 (m, 2H), 0.84 (t, J=7 Hz, 3H); MS (CI/NH$_3$) m/z: (M-H)$^-$ 568; Anal. Calcd for C$_{33}$H$_{46}$LiNO$_5$S.1.15 H$_2$O: C, 66.45; H, 8.16; N, 2.35. Found: C, 66.43; H, 7.90; N, 2.19.

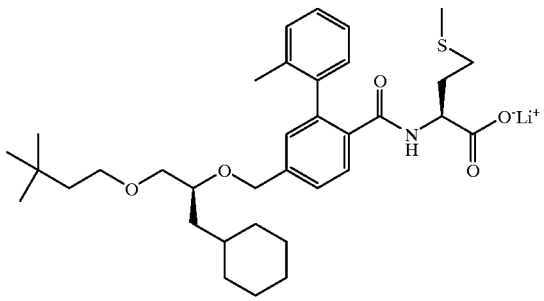

EXAMPLE 1309 (A-237810)

N-[4-(3-Cyclohexyl-1-(3,3-dimethylbut-1-yloxy)prop-2-yloxymethyl)-2-(2-methylphenyl)benzoyl]methionine Lithium Salt

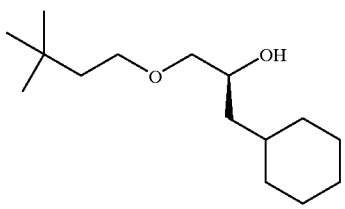

EXAMPLE 1309A (S)-3-Cyclohexyl-1-(3,3-dimethylbut-1-yloxy)propan-2-ol

The product from Example 1308C (435 mg, 3.1 mmol) in DMF (2.0 mL), 3,3-dimethylbutanol (400 μL, 3.3 mmol) in DMF (3.0 mL) and NaH, 60% dispersion in mineral oil, (145 mg, 3.6 mmol) in DMF (7.0 mL) were allowed to react in a manner similar to that described in Example 1308D. The residue was chromatographed (silica gel; EtOAc/hexanes, 1:20) to afford a light yellow oil (458 mg, 57%). $^1$H NMR (CDCl$_{13}$, 300 MHz) δ0.78–1.01 (m, 2H), 0.92 (s, 9H), 1.11–1.57 (m, 8H), 1.62–1.85 (m, 5H), 3.21 (dd, J=8, 9 Hz, 1H), 3.40–3.66 (m, 3H), 3.89 (m, 1H); MS (CI/NH$_3$) m/z: (M+NH$_4$)$^+$ 260.

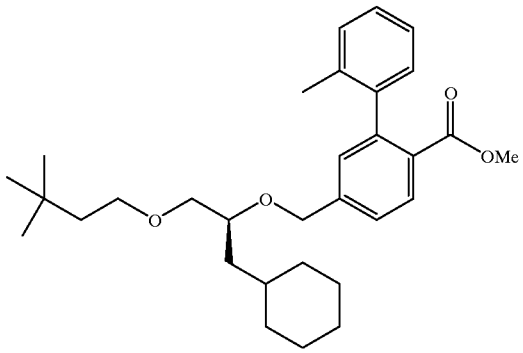

EXAMPLE 1309B

4-[(S)-3-Cyclohexyl-1-(3,3-dimethylbut-1-yloxy)prop-2-yloxymethyl]-2-(2-methylphenyl)benzoic acid, methyl ester The product from Example 1309A (450 mg, 1.9 mmol) in DMF (2.0 mL), the product from Example 1308E (817 mg, 2.2 mmol) in DMF (5.0 mL), and NaH, 60% dispersion in mineral oil, (90 mg, 2.2 mmol) in DMF (5 mL) were allowed to react in a manner similar to that described in Example 1308F. The crude residue was chromatographed (silica gel; EtOAc/hexanes, 1:15) to afford the title compound as an amber oil (563 mg, 63%). $^1$H NMR (CDCl$_{13}$, 300 MHz) δ0.80–0.95 (m, 2H), 0.90 (s, 9H), 1.08–1.72 (m, 13H), 2.06 (s, 3H), 3.35–3.50 (m, 4H), 3.61 (s, 3H), 3.65 (m, 1H) 4.62 (d, J=13 Hz, 1H), 4.78 (d, J=13 Hz, 1H), 7.05 (d, J=7 Hz, 1H), 7.16–7.27 (m, 4H), 7.43 (dd, J=1, 8 Hz, 1H), 7.95 (d, J=8 Hz, 1H); MS (CI/NH$_3$) m/z: (M+H)$^+$ 481.

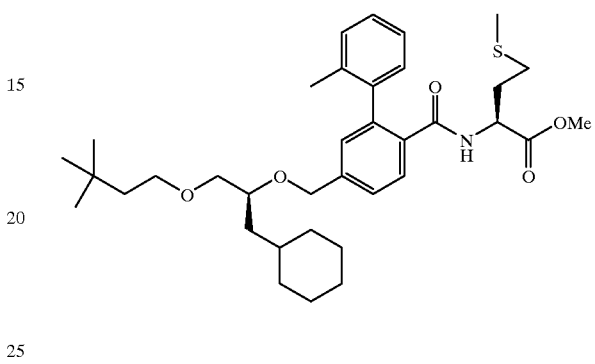

EXAMPLE 1309C

N-[4-(3-Cyclohexyl-1-(3,3-dimethylbut-1-yloxy)prop-2-yloxymethyl)-2-(2-methylphenyl)benzoyl]methionine methyl ester The product from Example 1309B (555 mg, 1.1 mmol) was saponified in a similar manner as that described in Example 608C. The crude acid was then allowed to react with EDCI (310 mg, 1.6 mmol), Hobt (170 mg, 1.3 mmol), (L)-methionine methyl ester hydrochloride (275 mg, 1.4 mmol) and NMM (230 μL, 2.1 mmol) in DMF (5.0 mL) in a manner similar to that described in Example 608D. The crude residue was chromatographed (silica gel; EtOAc/hexanes, 1:8) to afford the title compound as a clear oil (184 mg, 26%). $^1$H NMR (CDCl$_3$, 300 MHz) δ0.80–0.95 (m, 2H), 0.89 (s, 9H), 1.07–1.72 (m, 16H), 1.85 (m, 1H), 1.98–2.10 (m, 6H), 3.37–3.50 (m, 4H), 3.65 (s, 3H), 3.66 (m, 1H) 4.61 (m, 1H), 4.62 (d, J=12.5 Hz, 1H), 4.78 (d, J=12.5 Hz, 1H), 5.89 (d, J=8 Hz, 1H), 7.19 (d, J=2 Hz, 1H), 7.24–7.33 (m, 31H), 7.44 (dd, J=8 Hz, 1H), 7.94 (dd, J=8, 16 Hz, 1H); MS (CI/NH3) n/z: (M+H)$^+$ 612.

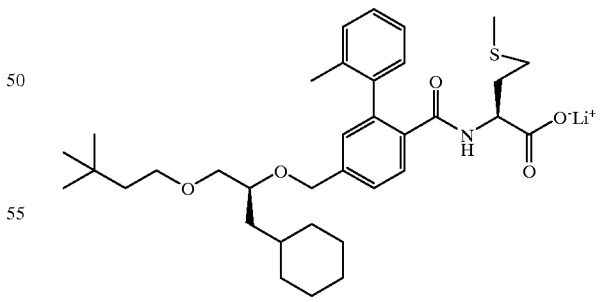

EXAMPLE 1309D

N-[4-(3-Cyclohexyl-1-(3,3-dimethylbut-1-yloxy)prop-2-yloxymethyl)-2-(2-methylphenyl)benzoyl]methionine Lithium Salt The product from Example 1309C (172 mg, 0.28 mmol) was allowed to react with lithium hydroxide monohydrate (12 mg, 0.29 mmol) in a manner similar to that described in Example 608E to afford the title compound. $^1$H NMR (DMSO-d$_6$, 300 MHz) δ0.75–0.94 (m, 2H) 0.85 (s, 9H), 1.05–1.44 (m, 8H), 1.50–1.70 (m, 8H), 1.77–2.04 (m, 6H), 2.15 (m, 1H), 3.35–3.45 (m, 4H), 3.53–3.71 (m, 2H), 4.55 (d, J=12.5 Hz 1H), 4.68 (d, J=12.5 Hz 1H), 6.95 (m, 1H), 7.10–7.25 (m, 4H), 7.35 (d, J=8 Hz,1H), 7.51 (d, J=8 Hz, 1H); MS (APCI (-)) m/z: (M–H)⁻596; Anal. Calcd for C$_{35}$H$_{50}$LiNO$_5$S.1.05 H$_2$O: C, 67.51; H, 8.43; N, 2.25. Found: C, 67.53; H, 8.38; N, 2.04.

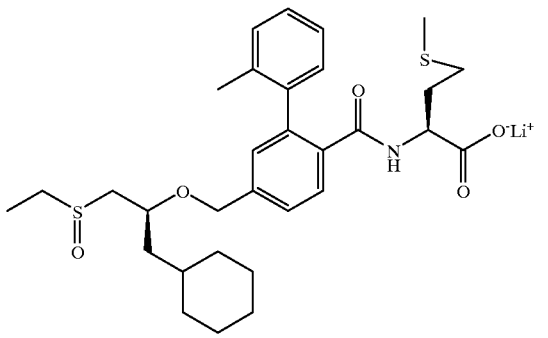

EXAMPLE 1310 (A-240191)

N-[4-(3-Cyclohexyl-1-ethylsulfenylprop-2-yloxymethyl)-2-(2-methylphenyl)benzoyl] methionine Lithium Salt

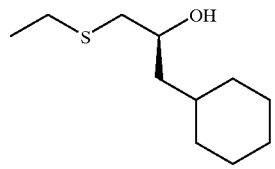

EXAMPLE 1310A (S)-3-Cyclohexyl-1-ethylthiopropan-2-ol

Ethanethiol (317 μL, 4.3 mmol) was added to a 60% dispersion in mineral oil NaH (180 mg, 4.5 mmol) slurry in DMF (26 mL) at ambient temperature. After stirring for 15 min, the product from Example 1308C (300 mg, 2.1 mmol) in DMF (2.0 mL) was added to the reaction vessel. After stirring for 30 min, a solution of saturated NH$_4$Cl was added to the mixture followed by extraction with EtOAc (2×). The organics were combined, dried (MgSO$_4$) and concentrated. The residue was chromatographed (silica gel; EtOAc/hexanes 1:20) to afford a light yellow oil (347 mg, 80%). $^1$H NMR (CDCl$_3$, 300 MHz) δ0.80–1.00 (m, 2H), 1.12–1.32 (m, 7H), 1.39–1.75 (m, 6H), 1.81 (m, 1H), 2.42 (dd, J=9, 14 Hz, 1H), 2.56 (q, J=7.5 Hz, 2H), 2.74 (dd, J=3, 14 Hz, 1H), 3.76 (m, 1H); MS (CI/NH$_3$) m/z: 203 (M+H)⁺.

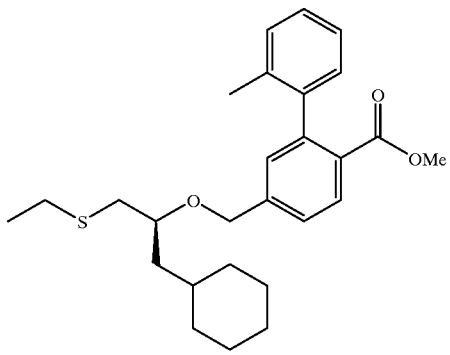

EXAMPLE 1310B

4-[(S)-3-Cyclohexyl-1-ethylthioprop-2-yloxymethyl]-2-(2-methylphenyl)benzoic acid, methyl ester The product from Example 1310A (347 mg, 1.7 mmol) in DMF (0.85 mL), the product from Example 1308E (685 mg, 1.9 mmol) in DMF (1.0 mL), and NaH, 60% dispersion in mineral oil, (85 mg, 2.1 mmol) in DMF (4 mL) were allowed to react in a manner similar to that described in Example 1308F. The crude residue was chromatographed (silica gel; EtOAc/hexanes, 1:30) to afford the title compound as an amber oil (290 mg, 39%). $^1$H NMR (CDCl$_3$, 300 MHz) δ0.80–1.02 (m, 2H), 1.10–1.30 (m, 6H), 1.42–1.93 (m, 8H), 2.06 (s, 3H), 2.56 (q, J=7 Hz, 2H), 2.64 (dd, J=6,13 Hz, 1H), 2.75 (dd, J=5, 13 Hz, 1H), 3.61 (s, 3H), 3.65 (m, 1H) 4.56 (d, J=12 Hz, 1H), 4.71 (d, J=12 Hz, 1H), 7.05 (d, J=7 Hz, 1H), 7.16–7.27 (m, 4H), 7.43 (dd, J=1.5, 8 Hz, 1H), 7.96 (d, J=8 Hz, 1H); MS (CI/NH$_3$) m/z: (M+NH$_4$)⁺ 458.

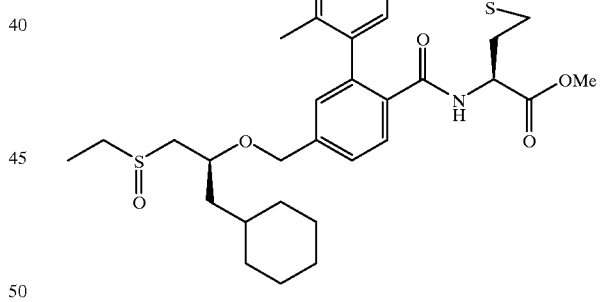

EXAMPLE 1310C

N-[4-(3-Cyclohexyl-1-ethylsulfenylprop-2-yloxymethyl)-2-(2-methylphenyl)benzoyl] methionine methyl ester The product from Example 1310B (220 mg, 0.5 mmol) in MeOH (4 mL) was combined with a saturated solution of LiOH (2 mL) and heated at reflux for 90 min. The reaction mixture was allowed to cool to ambient temperature and concentrated HCl was added to the reaction vessel. The mixture was extracted with EtOAc. The organic phase was dried (MgSO$_4$) and concentrated to give the crude acid.

The crude acid was immersed in THF (2 mL) at ambient temperature and a solution of 30% hydrogen peroxide (51 μL) was added to the reaction vessel. After stirring for 72 hours, a solution of 10% sodium thiosulfate (2 mL) was added to the reaction mixture followed by concentrated HCl. The mixture was extracted with CH₂Cl₂ (2×). The organic phases were combined, dried (MgSO₄) and conctrated to dryness to afford the crude sulfoxide.

The crude sulfoxide was then allowed to react with EDCI (135 mg, 0.7 mmol), Hobt (75 mg, 0.55 mmol), (L)-methionine methyl ester hydrochloride (120 mg, 0.6 mmol) and NMM (100 μL, 0.9 mmol) in DMF (2.0 mL) in a manner similar to that described in Example 608 D. The crude residue was chromatographed (silica gel; EtOAc) to afford the title compound as a clear oil (92 mg, 31%). MS (CI/NH₃) m/z: (M+H)⁺ 588.

EXAMPLE 1310D

N-[4-(3-Cyclohexyl-1-ethylsulfenylprop-2-yloxymethyl)-2-(2-methylphenyl)benzoyl] methionine Lithium Salt The product from Example 1310A (80 mg, 0.14 mmol) was allowed to react with lithium hydroxide monohydrate (6 mg, 0.14 mmol) in a manner similar to that described in Example 608E to afford the title compound. ¹H NMR (DMSO-d₆, 300 MHz) δ0.73–0.95 (m, 2H), 1.05–1.25 (m, 6H), 1.32–1.75 (m, 12H), 1.80–2.18 (m, 7H), 1.60–2.85 (m, 2H), 2.95 (m, 1H), 3.68 (m, 1H), 3.92 (m, 1H), 4.49 (d, J=12.5 Hz 1H), 4.64 (d, J=12.5 Hz 1H), 6.95 (m, 1H), 7.10–7.25 (m, 4H), 7.38 (d, J=8 Hz,1H), 7.53 (d, J=8 Hz, 1H); MS (APCI(−)) m/z: (M−H)⁻ 572; Anal. Calcd for C₃₁H₄₂LiNO₅S₂·3.45 H₂O: C, 58.01; H, 7.68; N, 2.18. Found: C, 58.02; H, 7.19; N, 1.96.

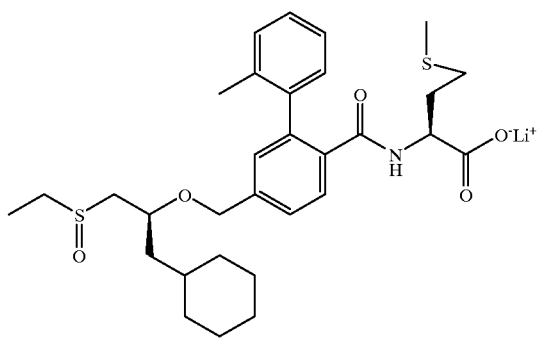

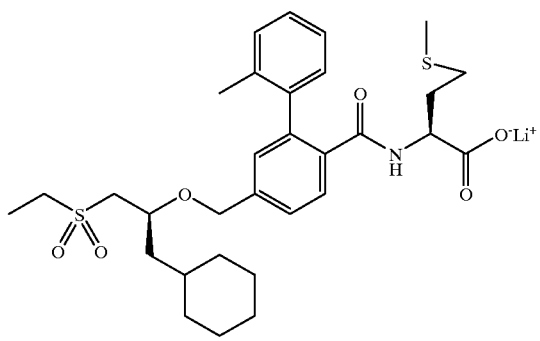

EXAMPLE 1311 (A-228419)

N-[4-(3-Cyclohexyl-1-ethylsulfonylprop-2-yloxymethyl)-2-(2-methylphenyl)benzoyl] methionine Lithium Salt

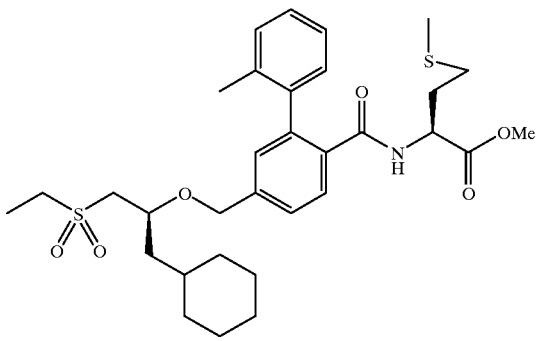

EXAMPLE 1311A

N-[4-(3-Cyclohexyl-1-ethylsulfonylprop-2-yloxymethyl)-2-(2-methylphenyl)benzoyl] methionine Lithium Salt The product from Example 1310B (285 mg, 0.65 mmol) in MeOH (2.5 mL) was combined with a solution of saturated LiOH (0.75 mL) and heated at reflux for 2 hours. The mixture was allowed to cool to ambient temperature and concentrated HCl was added to the reaction vessel. The mixture was extracted with CH₂Cl₂ (2×). The organic phases were combined, dried (MgSO₄) and concentrated. MS (CI/NH₃) m/z: 444 (M+NH₄).

The crude acid and 3-chloroperoxybenzoic acid (460 mg, 2.6 mmol) were immersed in CH₂Cl₂:EtOH (3.0 mL:1.0 mL) at ambient temperature and allowed to stir for 24 hours. A solution of 10% sodium thiosulfate was added to the reaction vessel followed by concentrated HCl. The organic phase was separated, dried (MgSO₄) and concentrated.

The crude sulfone was then allowed to react with EDCI (180 mg, 0.9 mmol), Hobt (100 mg, 0.7 mmol), (L)-methionine methyl ester hydrochloride (160 mg, 0.8 mmol) and NMM (130 μL, 1.2 mmol) in DMF (2.5 mL) in a manner similar to that described in Example 608 D. The crude residue was chromatographed (silica gel; EtOAc/hexanes, 1:2) to afford the title compound as an oil (178 mg, 44%). ¹H NMR (CDCl₃, 300 MHz) δ0.85–1.03 (m, 2H), 1.06–1.94 (m, 17H), 1.98–2.10 (m, 7H), 2.96–3.08 (m, 3H), 3.26 (dd, J=9, 15 Hz, 1H), 3.66 (s, 3H), 4.16 (m, 1H), 4.57–4.69 (m, 3H), 5.90 (d, J=8 Hz, 1H), 7.16 (s, 1H), 7.25–7.38 (m, 3H), 7.43 (dd, J=1, 8 Hz, 1H), 7.95 (dd, J=8, 16.5 Hz, 1H).

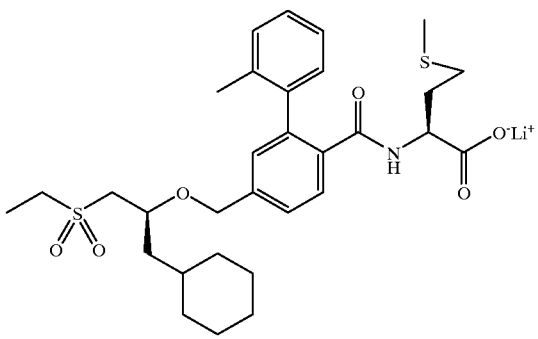

EXAMPLE 1311B

N-[4-(3-Cyclohexyl-1-ethylsulfonylprop-2-yloxymethyl)-2-(2-methylphenyl)benzoyl] methionine Lithium Salt The product from Example 1311A (169 mg, 0.28 mmol) was allowed to react with lithium hydroxide monohydrate (13 mg, 0.29 mmol) in a manner similar to that described in Example 608E to afford the title compound. $^1$H NMR (DMSO-d$_6$, 300 MHz) δ0.82–0.97 (m, 2H), 1.03–1.30 (m, 8H), 1.37–2.04 (m, 16H), 2.16 (t, J=7 Hz, 2H), 3.05 (q, J=7 Hz, 2H), 3.67 (m, 1H), 4.55 (s, 2H), 5.30 (m, 1H), 6.95 (m, 1H), 7.10–7.25 (m, 4H), 7.36 (d, J=8 Hz,1H), 7.51 (d, J=8 Hz, 1H); MS (APCI(–)) m/z: (M–H)$^-$ 588; Anal. Calcd for C$_{31}$H$_{42}$LiNO$_6$S$_2$.1.80 H$_2$O: C, 59.27; H, 7.32; N, 2.23. Found: C, 59.25; H, 7.02; N, 2.17.

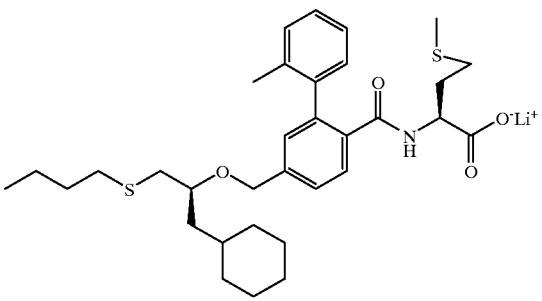

EXAMPLE 1312 (A-264870)

N-[4-(1-Butylthio-3-cyclohexylprop-2-yloxymethyl)-2-(2-methylphenyl)benzoyl] methionine Lithium Salt

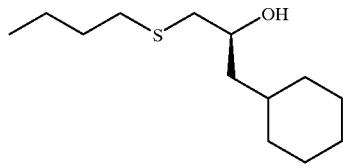

EXAMPLE 1312A (S)-1-Butylthio-3-cyclohexylpropan-2-ol

Butanethiol (765 μL, 7.1 mmol), the product from Example 1308C (500 mg, 3.6 mmol) in DMF (3.0 mL), and NaH, 60% dispersion in mineral oil, (305 mg, 7.6 mmol) in DMF (40 mL) were allowed to react in a manner similar to that described in Example 1310A. The residue was chromatographed (silica gel; EtOAc/hexanes 1:40) to afford a clear oil (641 mg, 77%). $^1$H NMR (CDCl$_3$, 300 MHz) δ0.80–1.00 (m, 2H), 0.92 (t, J=7 Hz, 3H), 1.08–1.34 (m, 4H), 1.37–1.75 (m, 10H), 1.81 (m, 1H), 2.42 (dd, J=9, 13.5 Hz, 1H), 2.53 (t, J=7 Hz, 2H), 2.72 (dd, J=3, 13.5 Hz, 1H), 3.76 (m, 1H); MS (CI/NH$_3$) m/z: 231 (M+H)$^+$.

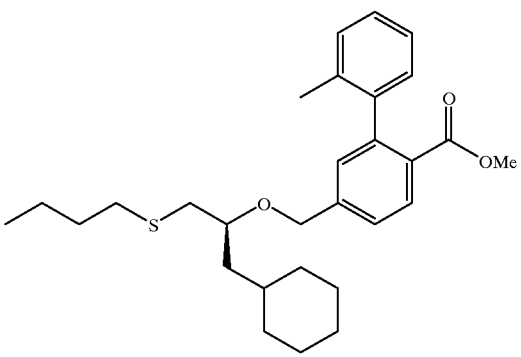

EXAMPLE 1312B

4-[(S)-1-Butylthio-3-cyclohexylprop-2-yloxymethyl]-2-(2-methylphenyl)benzoic acid, methyl ester The product from Example 1312A (308 mg, 1.3 mmol) in DMF (1.5 mL), the product from Example 1308E (588 mg, 1.6 mmol) in DMF (2.5 mL), and NaH, 60% dispersion in mineral oil, (65 mg, 1.6 mmol) in DMF (2.5 mL) were allowed to react in a manner similar to that described in Example 1308F. The crude residue was chromatographed (silica gel; EtOAc/hexanes, 1:30) to afford the title compound as an amber oil (361 mg, 59%). MS (CI/NH$_3$) m/z: (M+NH$_4$)$^+$ 486.

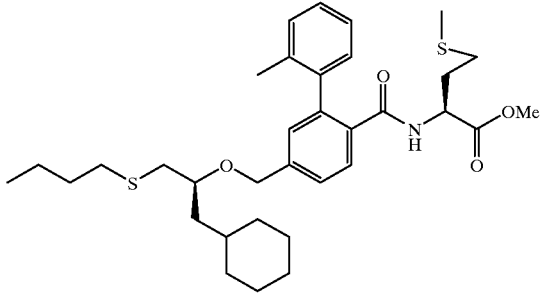

EXAMPLE 1312C

N-[4-(1-Butylthio-3-cyclohexylprop-2-yloxymethyl)-2-(2-methylphenyl)benzoyl] methionine methyl ester The product from Example 1312B (350 mg, 0.75 mmol) was saponified in a similar manner as that described in Example 608C. The crude acid was then allowed to react with EDCI (201 mg, 1.0 mmol), Hobt (111 mg, 0.8 mmol), (L)-methionine methyl ester hydrochloride (180 mg, 0.9 mmol) and NMM (150 μL, 1.4 mmol) in DMF (3.0 mL) in a manner similar to that described in Example 608 D. The crude residue was chromatographed (silica gel; EtOAc/ hexanes, 1:6) to afford the title compound as a clear oil (252 mg, 56%). ¹H NMR (CDCl₃, 300 MHz) δ0.82–0.97 (m, 2H), 0.89 (t, J=7 Hz, 3H), 1.08–1.72 (m, 17H), 1.85 (m, 1H), 1.98–2.10 (m, 7H), 2.53 (t, J=7 Hz, 2H), 2.63 (dd, J=6, 13 Hz, 1H), 2.73 (dd, J=5, 13 Hz, 1H), 3.64 (m, 1H), 3.66 (s, 3H), 4.55 (d, J=12 Hz, 1H), 4.62 (m, 1H), 4.71 (d, J=12 Hz, 1H), 5.90 (d, J=7.5 Hz, 1H), 7.19 (s, 1H), 7.26–7.34 (m, 3H), 7.44 (dd, J=2, 8 Hz, 1H), 7.95 (dd, J=8, 16 Hz, 1H).

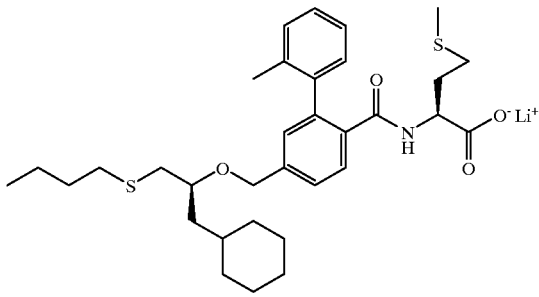

EXAMPLE 1312D

N-[4-(1-Butylthio-3-cyclohexylprop-2-yloxymethyl)-2-(2-methylphenyl)benzoyl]methionine Lithium Salt The product from Example 1312C (242 mg, 0.4 mmol) was allowed to react with lithium hydroxide monohydrate (18 mg, 0.42 mmol) in a manner similar to that described in Example 608E to afford the title compound. ¹H NMR (DMSO-d₆, 300 MHz) δ0.73–0.93 (m, 2H), 0.82 (t, J=7 Hz, 3H), 1.02–1.74 (m, 20H), 1.77–2.02 (m, 6H), 2.15 (m, 1H), 2.59 (dd, J=6.5, 13 Hz, 1H), 2.72 (dd, J=4.5, 13 Hz, 1H), 3.55–3.73 (m, 2H), 4.51 (d, J=12.5 Hz, 1H), 4.65 (d, J=12.5 Hz, 1H), 6.95 (m, 1H), 7.10–7.25 (m, 4H), 7.37 (d, J=7.5 Hz, 1H), 7.53 (d, J=8 Hz, 1H); MS (APCI(-)) m/z: (M-H)⁻ 584; Anal. Calcd for C₃₃H₄₆LiNO₄S₂·0.85 H₂O: C, 65.29; H, 7.92; N, 2.31. Found: C, 65.29; H, 7.45; N, 2.15.

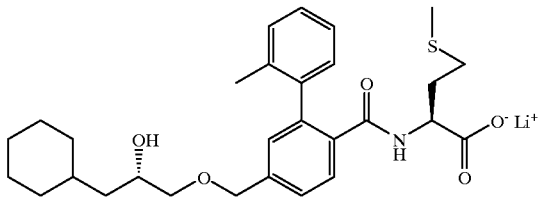

EXAMPLE 1314 (A-265088)

N-[4-(3-Cyclohexyl-2-hydroxyprop-1-yloxymethyl)-2-(2-methylphenyl)benzoyl]methionine Lithium Salt

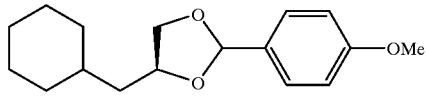

EXAMPLE 1314A (3S)-3-Cyclohexyl-2-(4-methoxyphenyl)-1,3-dioxolane

To a solution of (S)-3-cyclohexyl-1,2-propanediol (example 1308B, 5.0 g) in toluene (60 mL) was added p-anisaldehyde (4.6 mL), magnesium sulfate (7.6 g), and p-toluenesulfonic acid hydrate (600 mg). After stirring 16 h at ambient temperature, the reaction was diluted with diethyl ether (100 mL), filtered through infusorial earth, and concentrated. The residue was purified by silica gel chromatography eluting with 5% EtOAc/hexane to give the title compound (an inseparable mixture of diastereomers at the acetal center) as a colorless oil (6.5 g, 85%). ¹H NMR (300 MHz, CDCl₃) δ0.85–1.08 (m, 2H), 1.10–1.84 (m, 11H), 3.56 (t, J=7.3 Hz, 0.4H), 3.61 (t, J=7.2 Hz, 0.6H), 3.81 (s, 3H), 4.23–4.38 (m, 2H), 5.75 (s, 0.6H), 5.86 (s, 0.4H), 6.90 (d, J=8.4 Hz, 2H), 7.38–7.43 (m, 2H). MS (DCI/NH₃) m/e 277 (M+H)⁺.

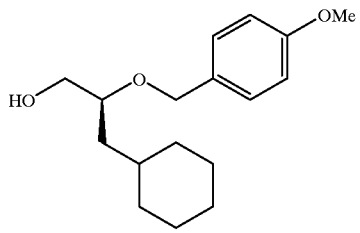

EXAMPLE 1314B

3-Cyclohexyl-2-(4-methoxybenzyloxy)propan-1-ol

The product from Example 1314A (1.9 g, 7.0 mmol) and a solution of 1.0M borane THF complex (7.7 mL, 7.7 mmol) were combined in THF (20 mL) and heated at reflux for 2 hours. The reaction mixture was allowed to cool to ambient temperature and a solution of saturated NaHCO₃ was added to the reaction vessel. After stirring for 2 hours the mixture was extracted with EtOAc (2×). The organic phases were combined, dried (MgSO₄) and concentrated. The residue was chromatographed (silica gel; EtOAc/hexanes, 1:4) to afford a clear oil (1.1 g, 56%). ¹H NMR (CDCl₃, 300 MHz) δ0.80–0.97 (m, 2H), 1.10–1.92 (m, 5H), 1.52–1.90 (m, 6H), 3.47 (dd, J=6, 11 Hz, 1H), 3.58 (m, 1H), 3.70 (dd, J=3, 11 Hz, 1H), 3.81 (s, 3H), 4.48 (d, J=11 Hz, 1H), 4.54 (d, J=11 Hz, 1H), 6.89 (d, J=9 Hz, 2H), 7.27 (d, J=9 Hz, 2H); MS (CI/NH₃) m/z: 296 (M+NH₄)⁺.

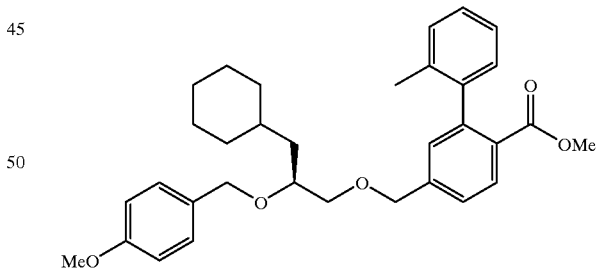

EXAMPLE 1314C

4-[(S)-3-Cyclohexyl-2-(4-methoxybenzyloxy)prop-1-yloxymethyl]-2-(2-methylphenyl)benzoic acid, methyl ester The product from Example 1314B (717 mg, 2.6 mmol) in DMF (2.5 mL) was added to NaH, 60% dispersion in mineral oil, (110 mg, 2.7 mmol) in DMF (4 mL) at ambient temperature. After stirring for 20 min, the mixture was cooled to 0° C. and the product from Example 1308E (900 mg, 2.5 mmol) in DMF (3.0 mL) was added to the reaction vessel. After 2.5 hours, water was added to the reaction mixture the mixture was extracted with EtOAc (2×). The organic phases were combined, washed with brine, dried (MgSO$_4$) and concentrated. The crude residue was chromatographed (silica gel; EtOAc/hexanes, 1:20) to afford the title compound as a light yellow oil (584 mg, 46%). MS (CI/NH$_3$) m/z: 534 (M+NH$_4$)$^+$.

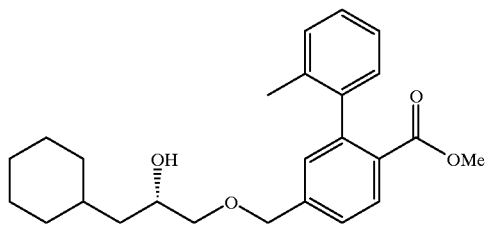

EXAMPLE 1314D

4-[(S)-3-Cyclohexyl-2-hydroxyprop-1-yloxymethyl]-2-(2-methylphenyl)benzoic acid, methyl ester 2,3-Dichloro-5,6-dicyano-1,4-benzoquinone (182 mg, 0.8 mmol) was added to a solution of the product from Example 1314C (343 mg, 0.7 mmol) in CH$_2$Cl$_2$ (2.5 mL) at ambient temperature. After stirring for 2.5 hours, a solution of EtOAc:hexanes (1:1) (20 mL) was added to the reaction vessel. The reaction mixture was filtered through celite and the filtrate concentrated. The residue was chronmatographed (silica gel; EtOAc/hexanes, 1:4) to afford a yellow oil (197 mg, 75%). MS (CI/NH$_3$) m/z: 397 (M+H)$^+$.

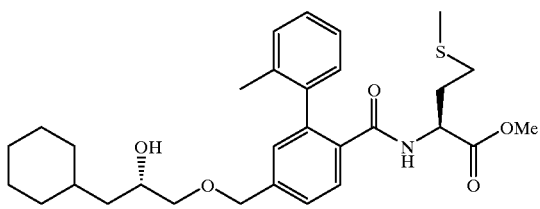

EXAMPLE 1314E

N-[4-(3-Cyclohexyl-2-hydroxyprop-1-yloxymethyl)-2-(2-methylphenyl)benzoyl]methionine methyl ester The product from Example 1314D (191 mg, 0.5 mmol) was saponified in a manner similar to that described in Example 608C. The crude acid was then allowed to react with EDCI (130 mg, 0.7 mmol), Hobt (70 mg, 0.5 mmol), (L)-methionine methyl ester hydrochloride (115 mg, 0.6 mmol) and NMM (95 μL, 0.9 mmol) in DMF (2.0 mL) in a manner similar to that described in Example 608 D. The crude residue was chromatographed (silica gel; EtOAc/hexanes, 1:2) to afford the title compound as a clear oil (173 mg, 68%). MS (CI/NH$_3$) m/z: (M+H)$^+$ 528.

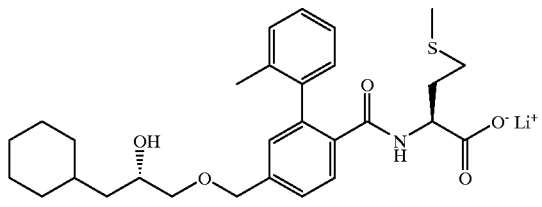

EXAMPLE 1314F

N-[4-(3-Cyclohexyl-2-hydroxyprop-1-yloxymethyl)-2-(2-methylphenyl)benzoyl]methionine Lithium Salt The product from Example 1314E (161 mg, 0.31 mmol) was allowed to react with lithium hydroxide monohydrate (13.5 mg, 0.32 mmol) in a manner similar to that described in Example 608E to afford the title compound. $^1$H NMR (DMSO-d$_6$, 300 MHz) δ0.70–0.94 (m, 2H), 1.06–1.28 (m, 5H), 1.36–2.00 (m, 15H), 2.15 (m, 1H), 3.25–3.36 (m, 2H), 3.63–3.76 (m, 2H), 4.54 (s, 2H), 6.95 (m, 1H), 7.10–7.25 (m, 4H), 7.38 (dd, J=8, 1 Hz,1H), 7.52 (d, J=8 Hz, 1H); MS (APCI(-)) m/z: (M-H)$^-$ 512; Anal. Calcd for C$_{29}$H$_{38}$LiNO$_5$S.1.40 H$_2$O: C, 63.93; H, 7.55; N, 2.57. Found: C, 63.95; H, 7.31; N, 2.47.

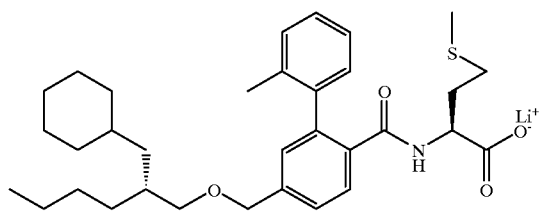

EXAMPLE 1315 (A-237785)

N-[4-(2-Cyclohexylmethylhex-1-yloxymethyl)-2-(2-methylphenyl)benzoyl]methionine Lithium Salt

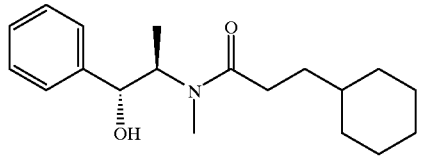

EXAMPLE 1315A

N-(1-Hydroxy-1-phenylprop-2-yl)-N-methyl-3-cyclohexylpropionamide

Thionyl chloride (3.5 mL, 48 mmol) was added to a solution of cyclohexanepropionic acid (5.5 mL, 32 mmol) in CH$_2$Cl$_2$ (60 mL). The mixture was heated at reflux for 60 min and then allowed to cool to ambient temperature and the solvent removed. The residue was redissolved in THF (50 mL) and (1R,2R) pseudoephedrine (4.8 g, 29 mmol) in THF (60 mL) was added to the reaction mixture at 0° C. After stirring for 30 min, a solution of saturated NaHCO$_3$ was added to the mixture which was then extracted with EtOAc. The organic phase was dried (MgSO$_4$) and concentrated. The residue was chromatographed (silica gel; EtOAc/hexanes 1:1) to afford an oil which solidified when placed in the refrigerator over night (8.2 g, 94%). MS (CI/NH$_3$) m/z: 304 (M+H)$^+$.

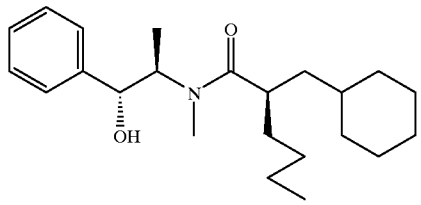

EXAMPLE 1315B

N-(1-Hydroxy-1-phenylprop-2-yl)-N-methyl-2-butyl-3-cyclohexylpropionamide

A solution of 2.5M nBuLi in hexanes (5.8 mL, 14.5 mmol), diisopropylamine (2.0 mL, 14.5 mmol), lithium chloride (1.6 g, 39 mmol), iodobutane (130 µL, 6.4 mmol) and the product from Example 1315A (2.0 g, 6.4 mmol) were allowed to react in a manner similar to that described by A. G. Myers et al., Journal of the American Chemical Society 1994, 116: 9361–9362. The crude residue was chromatographed (silica gel; EtOAc/hexanes, 1:4) to afford the title compound as a yellow oil (1.2 g, 53%). MS (CI/NH$_3$) m/z: 360 (M+H)$^+$.

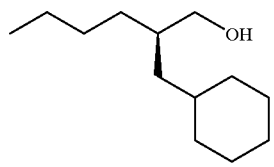

EXAMPLE 1315C

2-Cyclohexylmethylhexan-1-ol

A solution of 1.6M nBuLi (8.5 mL, 13.6 mmol), lithium amidotrihydroborane (470 mg, 13.6 mmol) and the product from Example 1315B (1.2 g, 3.4 mmol) were allowed to react in a manner similar to that described by A. G. Myers et al., Tetrahedron Letters 1996, 37: 3623–3626. The residue was chromatographed (silica gel; EtOAc/hexanes, 1:8) to afford the title compound as a clear oil (595 mg, 89%).

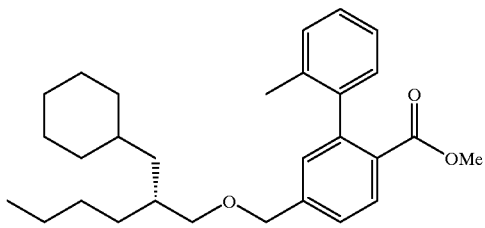

EXAMPLE 1315D (R) 4-(2-Cyclohexylmethylhex-1-yloxymethyl)-2-(2-methylphenylbenzoic acid, methyl ester The product from Example 1315C (185 mg, 0.9 mmol) in DMF (1.0 mL), the product from Example 1308E (380 mg, 1.0 mmol) in DMF (1.0 mL), and NaH, 60% dispersion in mineral oil, (45 mg, 1.1 mmol) in DMF (2 mL) were allowed to react in a manner similar to that described in Example 1308F. The crude residue was chromatographed (silica gel; EtOAc/hexanes, 1:50) to afford the title compound as a clear oil (82 mg, 20%). MS (CI/NH$_3$) m/z: (M+H)$^{30}$ 437.

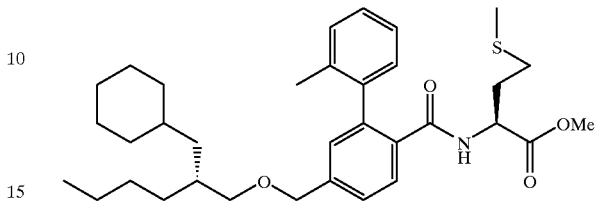

EXAMPLE 1315E

N-[(R) 4-(2-Cyclohexylmethylhex-1-yloxymethyl-2-(2-methylphenyl)benzoyl]methionine methyl ester The product from Example 1315D (77 mg, 0.2 mmol) was saponified in a similar manner as that described in Example 608C. The crude acid was then allowed to react with EDCI (75 mg, 0.4 mmol), Hobt (40 mg, 0.3 mmol), (L)-methionine methyl ester hydrochloride (65 mg, 0.3 mmol) and NMM (55 µL, 0.5 mmol) in DMF (1.0 mL) in a manner similar to that described in Example 608 D. The crude residue was chromatographed (silica gel; EtOAc/hexanes, 1:6) to afford the title compound as a clear oil (56 mg, 36%). MS (CI/NH$_3$) m/z: (M+H)$^+$ 568.

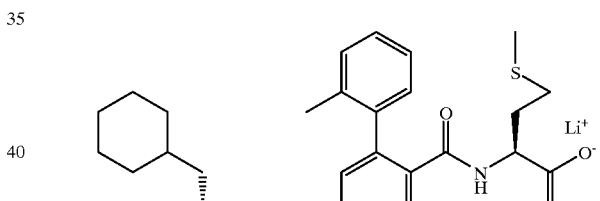

EXAMPLE 1315F

N-[4-(2-Cyclohexylmethylhex-1-yloxymethyl)-2-(2-methylphenyl)benzoyl]methionine Lithium Salt The product from Example 1315E (48 mg, 0.08 mmol) was allowed to react with lithium hydroxide monohydrate (4 mg, 0.09 mmol) in a manner similar to that described in Example 608E to afford the title compound. MS (APCI(–)) m/z: (M–H)$^-$ 552; $^1$H NMR (DMSO-d$_6$, 300 MHz) δ0.74–0.86 (m, 5H), 1.00–1.34 (m, 12H), 1.54–2.02 (m, 15H), 2.15 (m, 1H), 3.26–3.32 (m, 2H), 3.65 (m, 1H), 4.50 (s, 2H), 6.95 (m, 1H), 7.10–7.25 (m, 4H), 7.34 (d, J=8, Hz,1H), 7.52 (d, J=8 Hz, 1H); MS (APCI(–)) m/z: (M–H)$^-$ 552; Anal. Calcd for C$_{33}$H$_{46}$LiNO$_4$S.1.30 H$_2$O: C, 67.97; H, 8.40; N, 2.40. Found: C, 67.92; H, 8.06; N, 2.35.

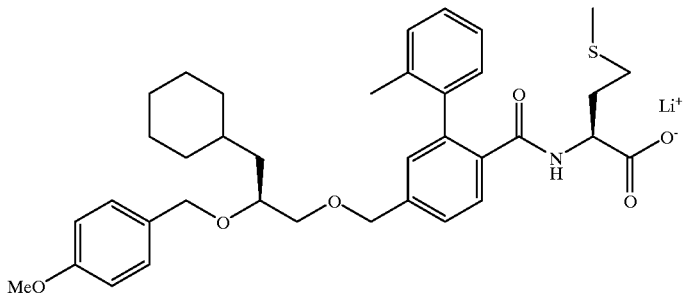

EXAMPLE 1316 (A-264976)

N-[4-(3-Cyclohexyl-2-(4-methoxybenzyloxy)prop-1-yloxymethyl)-2-(2-methylphenyl)benzoyl] methionine Lithium Salt

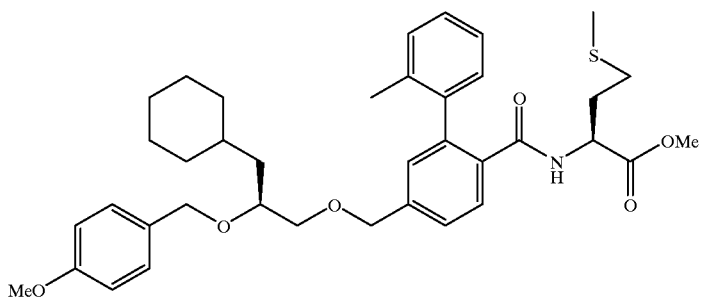

EXAMPLE 1316A

N-[4-(3-Cyclohexyl-2-(4-methoxybenzyloxy)prop-1-yloxymethyl)-2-(2-methylphenyl)benzoyl] methionine methyl ester The product from Example 1314C (188 mg, 0.4 mmol) was saponified in a manner similar to that described in Example 608C. The crude acid was then allowed to react with EDCI (97 mg, 0.5 mmol), Hobt (55 mg, 0.4 mmol), (L)-methionine methyl ester hydrochloride (86 mg, 0.4 mmol) and NMM (75 μL, 0.6 mmol) in DMF (1.5 mL) in a manner similar to that described in Example 608 D. The crude residue was chromatographed (silica gel; EtOAc/hexanes, 1:4) to afford the title compound as a clear oil (120.5 mg, 52%). MS (CI/NH$_3$) m/z: (M+H)$^+$ 648.

EXAMPLE 1316B

N-[4-(3-cyclohexyl-2-(4-methoxybenzyloxy)prop-1-yloxymethyl)-2-(2-methylphenyl)benzoyl] methionine Lithium Salt The product from Example 1316A (107 mg, 0.26 mmol) was allowed to react with lithium hydroxide monohydrate (7 mg, 0.17 mmol) in a manner similar to that described in Example 608E to afford the title compound. $^1$H NMR (DMSO-d$_6$, 300 MHz) δ0.66–0.91 (m, 2H), 1.02–1.40 (m, 6H), 1.48–2.16 (m, 15H), 3.43–3.71 (m, 4H), 3.72 (s, 3H), 4.38 (d, J=11.5 Hz, 1H), 4.53 (d, J=11.5 Hz, 1H), 4.57 (s, 2H), 6.85 (d, J=8.5 Hz, 2H), 6.95 (m, 1H), 7.10–7.25 (m, 6H), 7.37 (d, J=8, Hz, 1H), 7.53 (d, J=8 Hz, 1H); MS (APCI(−)) m/z: (M−H)$^−$ 632; Anal. Calcd for

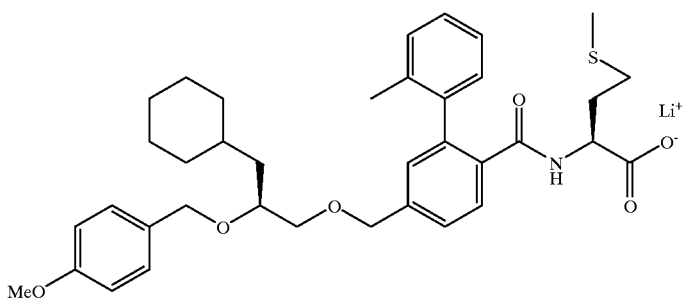

$C_{37}H_{46}LiNO_6S \cdot 1.25 \ H_2O$: C, 67.10; H, 7.38; N, 2.11. Found: C, 67.09; H, 6.95; N, 1.92.

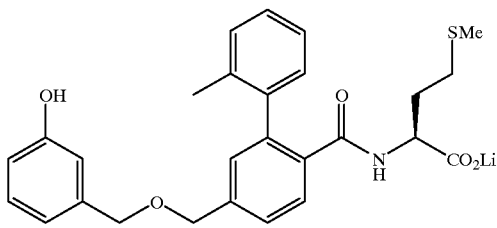

EXAMPLE 1343

N-[4-(3-hydroxybenzyloxymethyl)-2-(2-methylphenyl)benzoyl]methionine, Lithium Salt

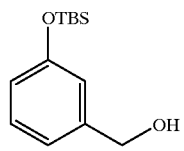

EXAMPLE 1343A

4-Hydroxymethyl-tert-butyldimethylsiloxybenzene

The title compound was prepared according to the procedure in example 1042A, replacing methyl salycilate with methyl 3-hydroxybenzoate, and was isolated as a colorless oil. $^1$H NMR (300 MHz, CDCl$_3$) δ0.20 (s, 6H), 0.99 (s, 9H), 4.64 (brs, 2H), 6.76 (ddd, J=8.3, 2.4, 0.9 Hz, 1H), 6.86 (t, J=1.5 Hz, 1H), 6.94 (dm, J=7.2 Hz, 1H), 7.21 (t, J=7.8 Hz, 1H).

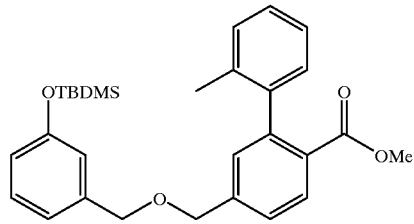

EXAMPLE 1343B 4-(3-tert-Butyldimethylsiloxybenzyloxymethyl)-2-(2-methylphenyl)benzoic acid, Methyl Ester The title compound was prepared from 4-hydroxymethyl-tert-butyldimethylsiloxybenzene according to the procedure described in example 1308F, and was isolated as a colorless oil. MS(APCI(+)) m/e 494 (M+NH$_4$)$^+$. MS (APCI(−)) m/e 475 (M−H)$^-$.

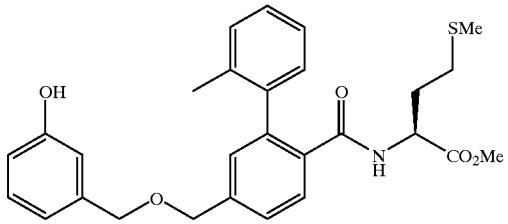

EXAMPLE 1343C

N-[4-(3-Hydroxybenzyloxymethyl)-2-(2-methylphenyl)benzoyl]methionine, Methyl Ester The title compound was prepared from 4-(3-tert-butyldimethylsiloxybenzyloxymethyl)-2-(2-methylphenyl) benzoic acid methyl ester according to the procedure in example 1308G. MS (APCI(+) m/e (M+H)$^+$ 494, MS (APCI (−) m/e (M−H)$^-$ 492.

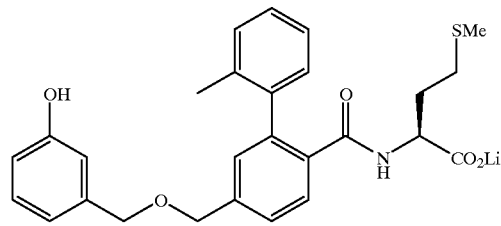

EXAMPLE 1343D

N-[4-(3-hydroxybenzyloxymethyl)-2-(2-methylphenyl)benzoyl]methionine, Lithium Salt N-[4-(3-hydroxybenzyloxymethyl)-2-(2-methylphenyl)benzoyl]methionine methyl ester was converted to the title compound by the procedure in example 1308H. The product was isolated as a white powder. $^1$H NMR (300 MHz, DMSO) δ1.49–1.75 (m, 4H), 1.90 (s, 3H), 1.95–2.15 (m, 3H), 3.60–3.72 (m, 1H), 4.44 (d, J=5 Hz, 2H), 5.13–5.19 (m, 3H), 6.82–6.90 (m, 2H), 6.94–6.98 (m, 2H), 7.10–7.25 (m, 6H), 7.47 (d, J=8.1 Hz, 1H), 7.55 (d, J=8.1 Hz, 1H). MS (APCI(−)) m/e 478 (M−H); Analysis calc'd for $C_{27}H_{28}LiNO_5S \cdot 1.20H20$: C, 63.95; H, 6.04; N, 2.78; found: C, 63.97; H, 5.90; N, 2.66.

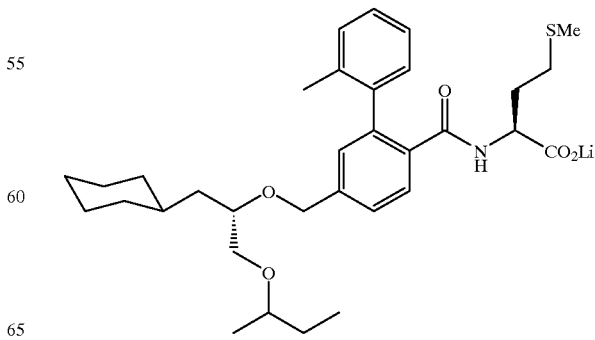

(270171) EXAMPLE 1344

N-[4-(-1-sec-Butoxy-3-cyclohexylprop-2-yloxymethyl)-2-(2-methylphenyl)benzoyl] methionine Lithium Salt

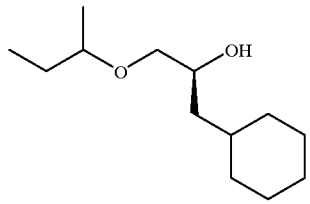

EXAMPLE 1344A 1-sec-Butoxy-3-cyclohexylpropan-2-ol

The product from Example 1308C (420 mg, 3.0 mmol) in DMF (3.0 mL), 2-butanol (1.1 mL, 12.0 mmol) in DMF (6.0 mL) and NaH, 60% dispersion in mineral oil, (240 mg, 6.0 mmol) in DMF (12 mL) were allowed to react in a manner similar to that described in Example 1308D. The residue was chromatographed (silica gel; EtOAc/hexanes, 1:12) to afford a clear oil (355 mg, 55%). MS (CI/NH$_3$) m/z: (M+NH$_4$)$^+$ 232.

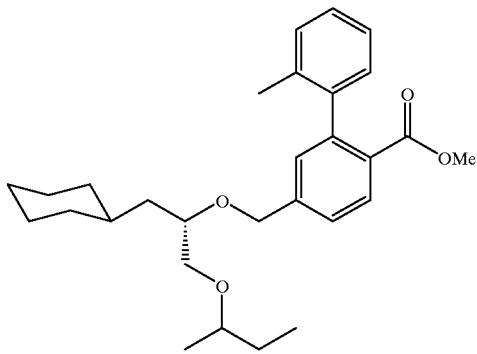

EXAMPLE 1344B

N-[4-(1-sec-Butoxy-3-cyclohexylprop-2-yloxymethyl)-2-(2-methylphenyl)benzoyl] methionine methyl ester The product from Example 1344A (345 mg, 1.6 mmol) in DMF (1.6 mL), the product from Example 1308E (560 mg, 1.5 mmol) in DMF (1.5 mL), and NaH, 60% dispersion in mineral oil, (68 mg, 1.7 mmol) in DMF (3.2 mL) were allowed to react in a manner similar to that described in Example 1308F. The crude residue was chromatographed (silica gel; EtOAc/hexanes, 1:30) to afford the title compound as a clear oil (289 mg, 42%). MS (CI/NH$_3$) m/z: (M+H)$^+$ 453.

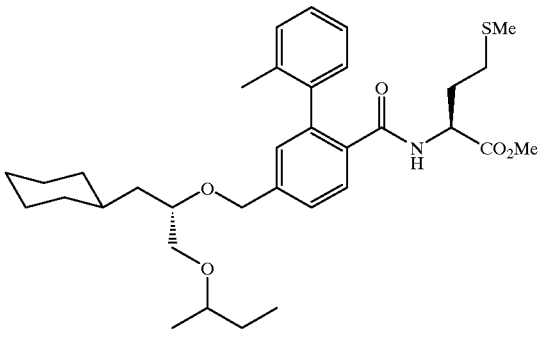

EXAMPLE 1344C

N-[4-(1-sec-Butoxy-3-Cyclohexylprop-2-yloxymethyl)-2-(2-methylphenyl)benzoyl] methionine methyl ester The product from Example 1344B (280 mg, 0.62 mmol) was saponified in a manner similar to that described in Example 1308G. The crude acid was then allowed to react with EDCI (166 mg, 0.88 mmol), Hobt (92 mg, 0.68 mmol), (L)-methionine methyl ester hydrochloride (150 mg, 0.74 mmol) and NMM (125 µL, 1.1 mmol) in DMF (1.5 mL) in a manner similar to that described in Example 1308G. The crude residue was chromatographed (silica gel; EtOAc/hexanes, 1:6) to afford the title compound as a clear oil (168 mg, 46%). MS (CI/NH$_3$) m/z: (M+H)$^+$ 584.

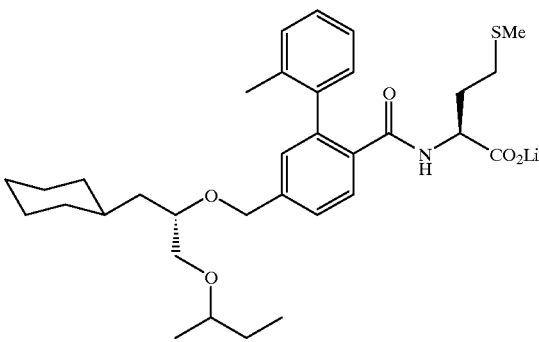

EXAMPLE 1344D

N-[4-(1-sec-Butoxy-3-cyclohexylprop-2-yloxymethyl)-2-(2-methylphenyl)benzoyl] methionine Lithium Salt The product from Example 1344C (153 mg, 0.26 mmol) was allowed to react with lithium hydroxide monohydrate (12 mg, 0.27 mmol) in a manner similar to that described in Example 1308H to afford the title compound. $^1$H NMR (DMSO-d$_6$, 300 MHz) δ0.75–1.68 (m, 25H), 1.78–2.02 (m, 5H), 2.15 (m, 1H), 3.25–3.58 (m, 4H), 3.65 (m, 1H), 4.55 (d, J=12.5 Hz 1H), 4.69 (d, J=12.5 Hz 1H), 6.95 (m, 1H), 7.10–7.24 (m, 4H), 7.36 (d, J=7 Hz 1H), 7.52 (d, J=8 Hz, 1H); MS (APCI(−)) m/z: (M−H)$^−$ 568; Anal. Calcd for C$^{33}$H$_{46}$LiNO$_5$S.0.70 H$_2$O: C, 67.37; H, 8.12; N, 2.38. Found: C, 67.33; H, 7.79; N, 2.13.

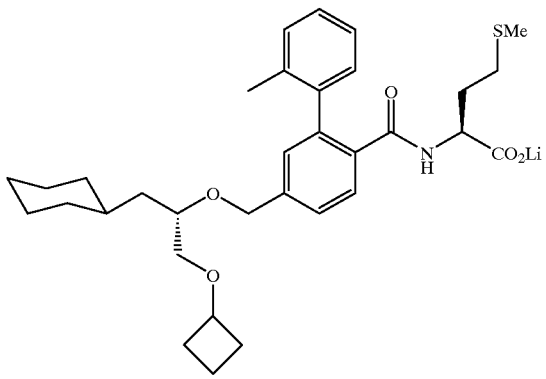

EXAMPLE 1345

N-[4-(3-Cyclohexyl-1-cyclobutoxyprop-2-yloxymethyl)-2-(2-methylphenylbenzoyl] methionine, Lithium Salt

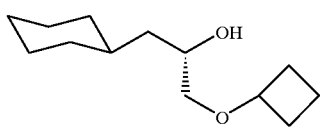

EXAMPLE 1345A (S)-3-Cyclohexyl-1-cyclobutoxy-2-propanol

The title compound was prepared according to example 1308D, replacing n-butanol with cyclobutanol. MS(CI/NH$_3$) m/e 230 (M+NH$_4$)$^+$.

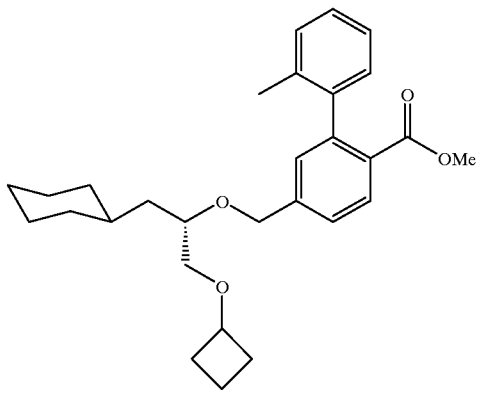

EXAMPLE 1345B

N-[4-(3-Cyclohexyl-1-(cyclobutoxyprop-2-yloxymethyl)-2-(2-methylphenyl)benzoic acid, Methyl Ester The title compound was prepared from (S)-3-cyclohexyl-1-cyclobutoxy-2-propanol according to example 1308F. MS(APCI(+)) m/e 451 (M+H)$^+$, 468 (M+NH$_4$)$^+$. MS(APCI(−)) m/e 449 (M−H)$^-$.

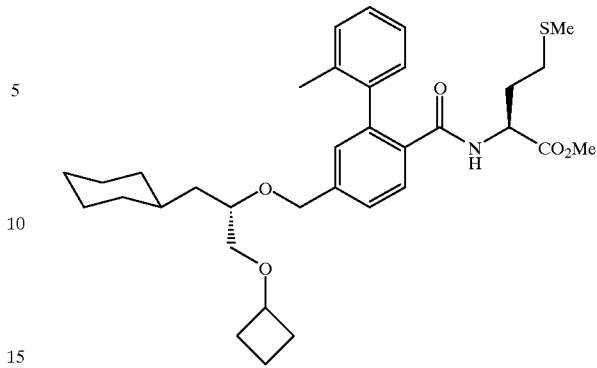

EXAMPLE 1345C

N-[4-(3-Cyclohexyl-1-cyclobutoxyprop-2-yloxymethyl)-2-(2-methylphenyl)benzoyl] methionine, Methyl Ester The title compound was prepared from N-[4-(3-cyclohexyl-1-cyclobutoxyprop-2-yloxymethyl)-2-(2-methylphenyl)benzoic acid methyl ester according to the procedure in example 1308G. MS(APCI(+)) m/e 582 (M+H)$^+$. MS(APCI(−)) m/e 580 (M−H)$^-$.

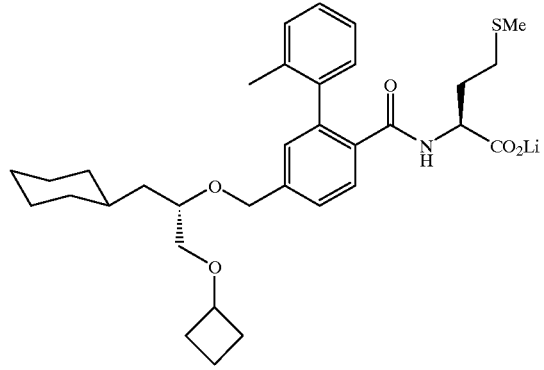

EXAMPLE 1345D

N-[4-(3-Cyclohexyl-1-cyclobutoxyprop-2-yloxymethyl)-2-(2-methylphenyl)benzoyl] methionine, Lithium Salt The title compound was prepared from N-[4-(3-cyclohexyl-1-cyclobutoxyprop-2-yloxymethyl)-2-(2-methylphenyl)benzoyl]methionine methyl ester according to the procedure in example 1308H, and was isolated as a white powder. $^1$H NMR (300 MHz, DMSO) δ 0.70–0.95 (m, 2H), 1.00–2.18 (m, 24H), 1.91 (s, 3H), 2.27–3.32 (m, 1H), 3.52–3.71 (m, 2H), 3.86 (quintet, J=7.2 Hz, 1H), 4.54 (d, J=12.6 Hz, 1H), 4.67 (d, J=12.6 Hz, 1H), 6.89–6.98 (m, 1H), 7.07–7.26 (m, 5H), 7.36 (d, J=8.1 Hz, 1H), 7.51 (d, J=7.8 Hz, 1H). MS (APCI(+)) m/e 586 (M+H)$^+$, MS (APCI(−)) 586 (M−H)$^-$; Analysis calc'd for C$_{33}$H$_{44}$LiNO$_5$S.0.30H$_2$O: C, 68.44; H, 7.76; N, 2.42; found: C, 68.44; H, 7.53; N, 2.35.

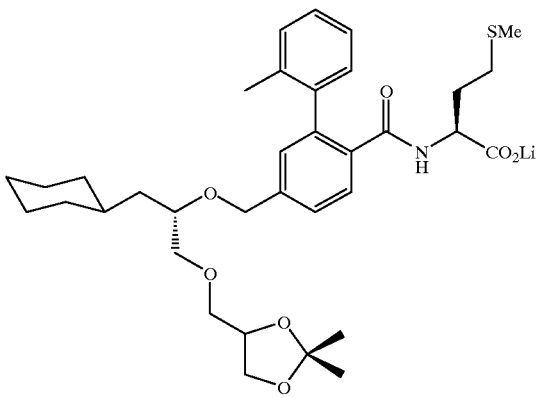

EXAMPLE 1346

N-[4-(3-Cyclohexyl-1-(2,2-dimethyl-1,3-dioxolan-4-methanoxy)prop-2-yloxymethyl)-2-(2-methylphenyl)benzoyl]methionine, Lithium Salt

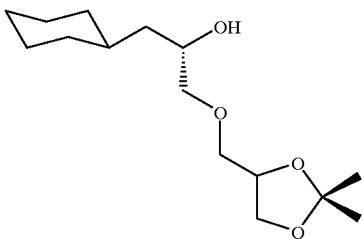

EXAMPLE 1346A

3-Cyclohexyl-1-(2,2-dimethyl-1,3-dioxolan-4-methanoxy)-2-propanol

The title compound was prepared according to example 1308D, replacing n-butanol with (±)-2,2-dimethyl-1,3-dioxolane-4-methanol. MS(CI/NH$_3$) m/e 290 (M+NH$_4$)$^+$.

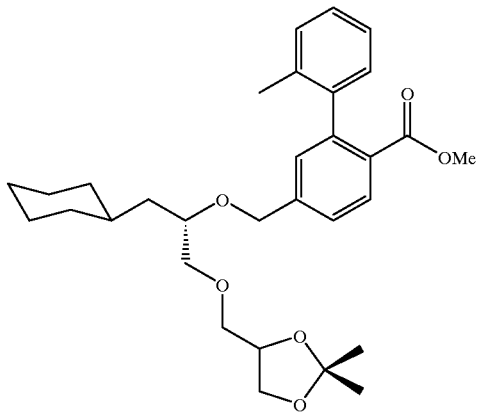

EXAMPLE 1346B

N-[4-(3-Cyclohexyl-1-(2,2-dimethyl-1,3-dioxolan-4-methanoxy)-prop-2-yloxymethyl)-2-(2-methylphenyl)benzoic acid, Methyl Ester The title compound was prepared from 3-cyclohexyl-1-(2,2-dimethyl-1,3-dioxolan-4-methanoxy)-2-propanol according to example 1308F. MS(APCI(+)) m/e 511 (M+H)$^+$, 528 (M+NH$_4$)$^+$.

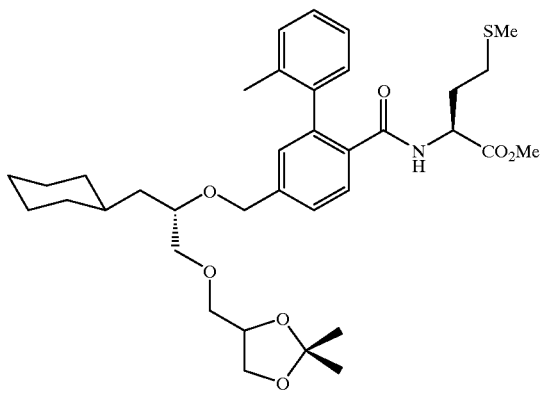

EXAMPLE 1346C

N-[4-(3-Cyclohexyl-1-(2,2-dimethyl-1,3-dioxolan-4-methanoxy)-prop-2-yloxymethyl)-2-(2-methylphenyl)benzoyl]methionine, Methyl Ester The title compound was prepared from N-[4-(3-cyclohexyl-1-(2,2-dimethyl-1,3-dioxolan-4-methanoxy)-prop-2-yloxymethyl)-2-(2-methylphenyl)benzoic acid methyl ester according to the procedure in example 1308G. MS(APCI(+)) m/e 642 (M+H)$^+$. MS(APCI(−)) m/e 640 (M−H)$^-$.

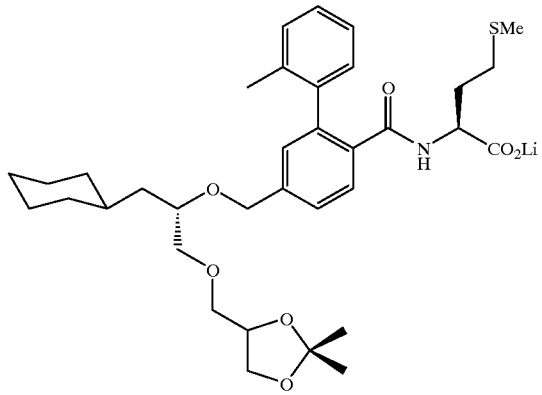

EXAMPLE 1346D

N-[4-(3-Cyclohexyl-1-(2,2-dimethyl-1,3-dioxolan-4-methanoxy)-prop-2-yloxymethyl)-2-(2-methylphenyl)benzoyl]methionine Lithium Salt The title compound was prepared from N-[4-(3-cyclohexyl-1-(2,2-dimethyl-1,3-dioxolan-4-methanoxy)-prop-2-yloxymethyl)-2-(2-methylphenyl)benzoyl]methionine methyl ester according to the procedure in example 1308H, and was isolated as a white powder. $^1$H NMR (300 MHz, DMSO) δ0.70–0.95 (m, 2H), 1.04–1.68 (m, 11H), 1.24 (s, 3H), 1.28 (s, 3H), 1.74–1.89 (m, 2H), 1.90–2.20 (m, 5H), 1.92 (s, 3H), 3.28–3.73 (m, 7H), 3.93 (t, J=7.5 Hz, 1H), 4.14 (quintet, J=6.0 Hz, 1H), 4.54 (d, J=12.6 Hz, 1H), 4.70 (d, J=12.6 Hz, 1H), 6.90–6.98 (m, 1H), 7.09–7.26 (m, 5H), 7.36 (d, J=8.1 Hz, 1H), 7.52 (d, J=8.1 Hz, 1H). MS (APCI(+)) m/e 628 (M+H)$^+$, MS (APCI(−)) 626 (M−H)$^-$; Analysis calc'd for C$_{35}$H$_{48}$LiNO$_7$S.0.65H$_2$O:

C, 65.13; H, 7.70; N, 2.17; found: C, 65.13; H, 7.44; N, 2.10.

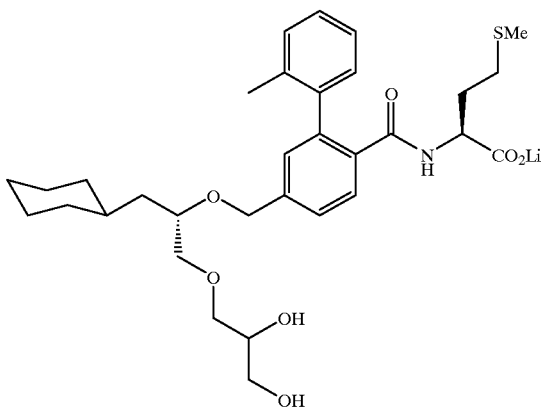

EXAMPLE 1347

N-[4-(3-Cyclohexyl-1-(2,3-dihydroxy-1-propoxy)-prop-2-yloxymethyl)-2-(2-methylphenyl)benzoyl]methionine, Lithium Salt

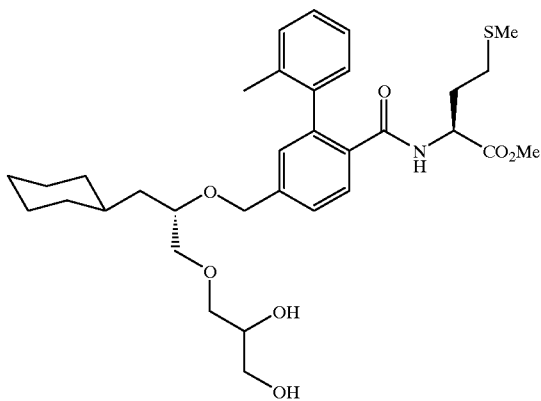

EXAMPLE 1347A

N-[4-(3-Cyclohexyl-1-(2,3-dihydroxy-1-propoxy)-prop-2-yloxymethyl)-2-(2-methylphenyl)benzoyl]methionine, Methyl Ester To a solution of N-[4-(3-cyclohexyl-1-(2,2-dimethyl-1,3-dioxolan-4-methanoxy)-prop-2-yloxymethyl)-2-(2-methylphenyl)benzoyl]methionine methyl ester (example 1346C, 330 mg) in methanol (2 mL) was added p-toluenesulfonic acid hydrate (10 mg). After 3 h, the solvent was removed under a stream of dry nitrogen, and the residue was purified by silica gel chromatography eluting with 50%–100% EtOAc/hexane to give the title compound (230 mg, 75%) as a colorless oil. MS(APCI(+)) m/e 602 (M+H)$^+$. MS(APCI(−)) m/e 600 (M−H)$^-$.

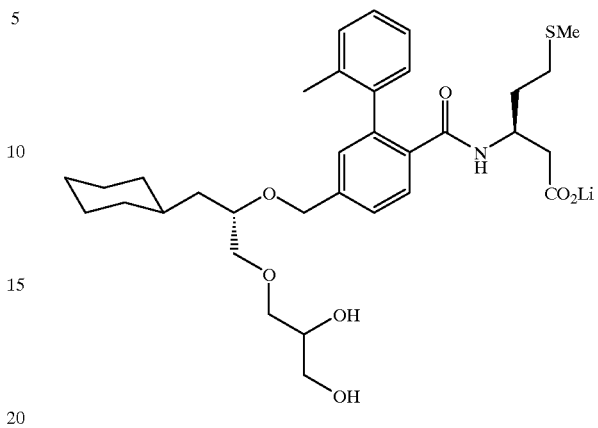

EXAMPLE 1347B

N-[4-(3-Cyclohexyl-1-(2,3-dihydroxy-1-propoxy)-prop-2-yloxymethyl)-2-(2-methylphenyl)benzoyl]methionine, Lithium Salt The title compound was prepared from N-[4-(3-cyclohexyl-1-(2,3-dihydroxy-1-propoxy)-prop-2-yloxymethyl)-2-(2-methylphenyl)benzoyl]methionine methyl ester according to the procedure in example 1308H, and was isolated as a white powder. $^1$H NMR (300 MHz, DMSO) δ 0.70–0.94 (m, 2H), 1.02–1.74 (m, 11H), 1.74–2.18 (m, 7H), 1.91 (s, 3H), 3.23–3.68 (m, 9H), 4.49–4.55 (m, 1H), 4.54 (d, J=12.6 Hz, 1H), 4.65 (dd, J=4.8, 3.3 Hz, 1H), 4.70 (d, J=12.3 Hz, 1H), 6.89–6.97 (m, 1H), 7.06–7.23 (m, 5H), 7.37 (d, J=8.1 Hz, 1H), 7.51 (d, J=8.1 Hz, 1H). MS (APCI(+)) m/e 588 (M+H)$^+$, (APCI(+)) 586 (M−H)$^-$; Analysis calc'd for $C_{32}H_{44}LiNO_7S \cdot H_2O$: C, 63.49; H, 7.54; N, 2.31; found: C, 63.48; H, 7.24; N, 2.24.

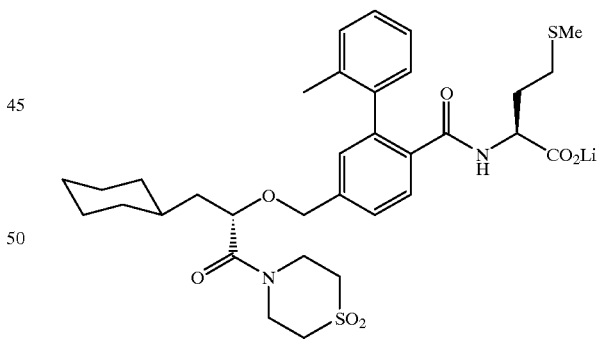

EXAMPLE 1348

N-[4-(3-cyclohexyl-N-thiomorpholin-S,S-dioxide-4-ylpropion-2-yloxymethyl)-2-(2-methylphenyl)benzoyl]methionine, Lithium Salt

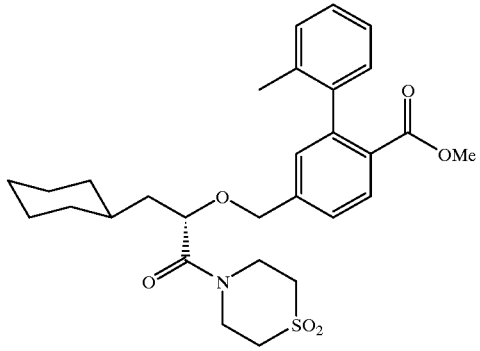

EXAMPLE 1348A 4-(3-Cyclohexyl-N-thiomorpholin-S,S-dioxide-4-ylpropion-2-yloxymethyl)-2-(2-methylphenyl)benzoic acid, Methyl Ester To a solution of 4-(3-cyclohexyl-N-thiomorpholin-4-ylpropion-2-yloxymethyl)-2-(2-methylphenyl)benzoic acid methyl ester (example 1054B, 170 mg) in dichloromethane (2.0 mL) at ambient temperature was added m-chloroperbenzoic acid (207 mg, 55% pure). After 15 min, the reaction was quenched by the addition of dilute aqueous sodium sulfite. The reaction was diluted with ether (50 mL), and washed with 1M NaOH (2×5 mL), and brine (2×5 mL). The organic solution was dried (MgSO$_4$), filtered and concentrated to afford a light yellow oil which was purified by silica gel chromatography eluting with 30%–50% EtOAc/hexane to give a colorless oil (150 mg, 84%). MS(APCI(+)) m/e 528 (M+H)$^+$.

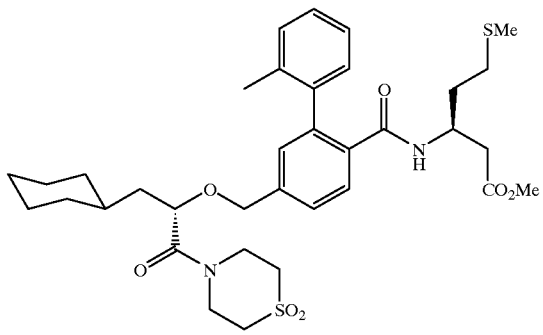

EXAMPLE 1348B

N-[4-(3-Cyclohexyl-N-thiomorpholin-S,S-dioxide-4-ylpropion-2-yloxymethyl)-2-(2-methylphenyl)benzoyl]methionine, Methyl Ester The title compound was prepared from 4-(3-cyclohexyl-N-thiomorpholin-S,S-dioxide-4-ylpropion-2-yloxymethyl)-2-(2-methylphenyl)benzoic acid methyl ester according to the procedure in example 1308G. MS(APCI(+)) m/e 659 (M+H)$^+$. MS(APCI(-)) m/e 657 (M-H)$^-$.

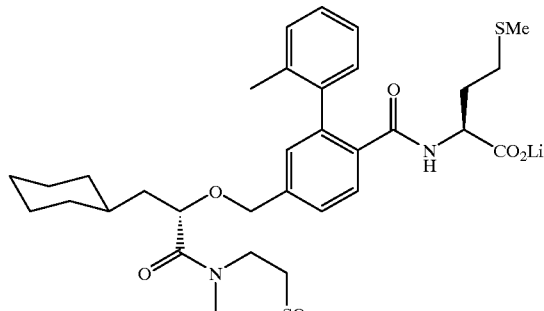

EXAMPLE 1348C

N-[4-(3-Cyclohexyl-N-thiomorpholin-S,S-dioxide-4-ylpropion-2-yloxymethyl)-2-(2-methylphenyl)benzoyl]methionine, Lithium Salt N-[4-(3-Cyclohexyl-N-thiomorpholin-S,S-dioxide-4-ylpropion-2-yloxymethyl)-2-(2-methylphenyl)benzoyl]methionine methyl ester was converted into the title compound according to the procedure in example 1308H, and was isolated as a white powder. $^1$H NMR (300 MHz, DMSO) δ0.76–0.99 (m, 2H), 1.02–1.22 (m, 3H), 1.36–1.75 (m, 8H), 1.75–2.29 (m, 7H), 1.92 (s, 3H), 3.11–3.22 (m, 4H), 3.61–3.73 (m, 1H), 3.74–3.86 (m, 2H), 3.90–4.02 (m, 3H), 4.34–4.37 (m, 1H), 4.41 (d, J=12.3 Hz, 1H), 4.62 (d, J=12.3 Hz, 1H), 6.96 (brs, 1H), 7.12–7.27 (m, 5H), 7.38 (d, J=7.8 Hz, 1H), 7.53 (d, J=7.8 Hz, 1H). MS (APCI(-)) m/e 643 (M-H); Analysis calc'd for C$_{33}$H$_{43}$LiN$_2$O$_7$S$_2$.1.9H$_2$O: C, 57.86; H, 6.89; N, 4.09; found: C, 57.90; H, 6.89; N, 4.07.

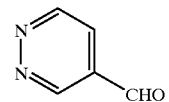

EXAMPLE 1349-A

Pyridazine-4-carboxaldehyde

Starting with the compound described in Example 1221C, the title compound was prepared by a Swern oxidation as outlined in Example 1224B, except after warming to RT and diluting with Et$_2$O, there was no aqueous work-up. Instead, the Et$_2$O slurry was filtered through celite, the filtrate concentrated, and the material purified by chromatography using EtOAc. MS (DCI/NH$_3$) 109 (M+H)$^+$ and 126 (M+H+NH$_3$)$^+$.

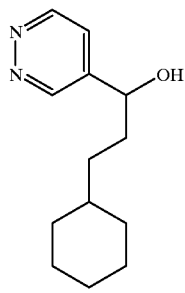

EXAMPLE 1349-B 1-(Pyridazin-4-yl)-3-cyclohexylpropan-1-ol

The bromide described in Example 1207A was converted to the Grignard reagent, resulting in a THF solution ca. 0.8M. That solution (3.5 mL, 2.8 mmol) was added to a mechanically stirred solution of the compound described in Example 1349-A (300 mg, 2.8 mmol) in THF (30 mL) at −44° C. (dry ice-CH$_3$CN bath). The reaction was stirred at −44° C. for 50 min., then water was added and the reaction allowed to warm to RT. Used 2N HCl to adjust to pH 3, then extracted with EtOAc. The EtOAc solution was dried over Na$_2$SO$_4$, filtered, concentrated, and the residue purified by chromatography using EtOAc/EtOH 98/2. Recovered 74 mg (12%). MS (DCI/NH$_3$) 221 (M+H)$^+$ and 238 (M+H+NH$_3$)$^+$.

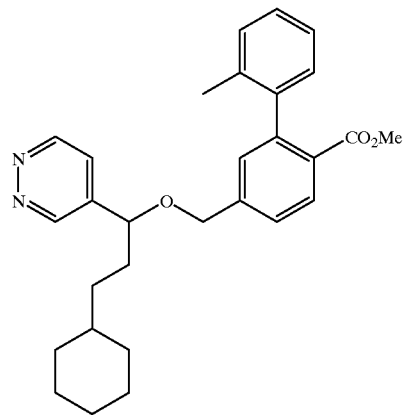

EXAMPLE 1349C 4-(1-(Pyridazin-4-yl)-3-cyclohexylpropan-1-yloxymethyl)-2-(2-methylphenyl)benzoic acid methyl ester The bromide described in Example 1132D and the alcohol described in Example 1349-B were reacted to give the title compound using the method of Example 1221D. MS (APCI) 459 (M+H)$^+$.

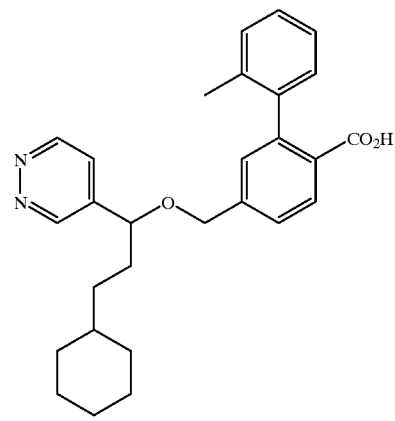

EXAMPLE 1349D 4-(1-(Pyridazin-4-yl)-3-cyclohexylpropan-1-yloxymethyl)-2-(2-methylphenyl)benzoic acid Starting with the compound described in Example 1349-C, the title compound was prepared by the method of Example 1205C, except that during the work-up, the aqueous layer was water and enough 2N HCl to get pH 3–4. MS (ESI) 443 (M−H)$^−$.

EXAMPLE 1349E

N-[4-(1-(Pyridazin-4-yl)-3-cyclohexylpropan-1-yloxymethyl)-2-(2-methylphenyl)benzoyl] methionine methyl ester Starting with the compound described in Example 1349-D, the title compound was prepared by the method of Example 1205D, except that during the work-up, the 2N HCl wash was eliminated, and the chromatography used hex/EtOAc 3/7. MS (APCI) 590 (M+H)$^+$.

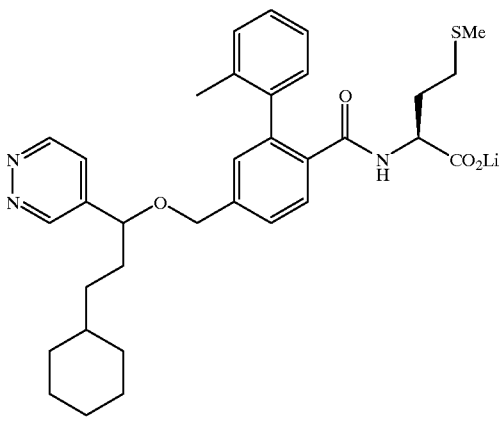

EXAMPLE 1349F

N-[4-(1-(Pyridazin-4-yl)-3-cyclohexylpropan-1-yloxymethyl)-2-(2-methylphenyl)benzoyl] methionine lithium salt Starting with the compound described in Example 1349-E, the title compound was prepared by the method of Example 1132H. $^1$H NMR (DMSO-$d_6$) δ 9.22 (s, 1H), 9.18 (d, 1H), 7.63 (m, 1H), 7.51 (d, 1H), 7.36 (m, 1H), 7.20, 7.12, 6.94 (all m, total 6H), 4.50, 4.40 (both m, total 3H), 3.68, (m, 1H), 2.20–1.50 (envelope 17H), 1.10 (m, 6H), 0.79 (m, 2H). MS (ESI) 574 (M−H)$^−$. Anal calcd for $C_{33}H_{40}LiN_3O_4S \cdot 0.80\, H_2O$: C, 66.49; H, 7.03; N, 7.05. Found: C, 66.47; H, 7.02; N, 6.94.

What is claimed is:

1. A compound having Formula I

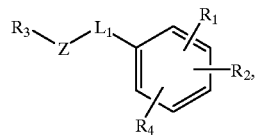

or a pharmaceutically acceptable salt thereof, wherein
$R_1$ is phenyl, wherein the phenyl is unsubstituted or substituted with loweralkyl;
$R_2$ is selected from the group consisting of —$L_{11}$—C($R_{14}$)($R_\nu$)—C(O)O$R_{15}$ and —C(O)NH—CH($R_{14}$)—C(O)NHSO$_2R_{16}$; wherein
$L_{11}$ is —C(O)—;
$R_\nu$ is hydrogen;
$R_{14}$ is selected from the group consisting of alkylsulfonylalkyl and thioalkoxyalkyl;
$R_{15}$ is selected from the group consisting of hydrogen and loweralkyl;
$R_{16}$ is aryl, wherein the aryl is unsubstituted or substituted with a substituent selected from the group consisting of loweralkyl and halogen;
$L_1$ is —$L_4$—O—$L_5$—, wherein
$L_4$ is absent or selected from the group consisting of $C_1$-to-$C_{10}$-alkylene and $C_2$-to-$C_{16}$-alkenylene, wherein the alkylene and alkenylene groups are unsubstituted or substituted with 1, 2 or 3 substitutents independently selected from the group consisting of alkoxyalkyl, alkyl[S(O)$_q$]alkyl, arylalkyl, hydroxyl, cycloalkoxyalkyl, cycloalkylalkyl, oxo, and arylalkoxyalkyl, wherein the arylalkoxyalkyl is unsubstituted or substituted with alkoxy;
q is zero, one or two;
$L_5$ is absent or selected from the group consisting of $C_1$-to-$C_{10}$-alkylene and $C_2$-to-$C_{16}$-alkenylene wherein the alkylene and alkenylene is unsubstituted or substituted as defined previously;
with the proviso that at least one of $L_4$ and $L_5$ is not absent;
Z is a covalent bond;
$R_3$ is selected from the group consisting of aryl, cycloalkyl, and cycloalkenyl, wherein the aryl is unsubstituted or substituted with a substituent selected from the group consisting of alkanoyl, alkoxyalkyl, alkoxycarbonyl, arylalkyl, aryl, aryloxy, (aryl)oyl, carboxaldehyde, carboxy, carboxyalkyl, cyano, cyanoalkyl, cycloalkyl, cycloalkylalkyl, cycloalkoxyalkyl, halogen, haloalkyl, hydroxyl, hydroxyalkyl, loweralkyl, nitro, —NRR', thioalkoxy, and alkoxy, wherein the alkoxy is unsubstituted or substituted with cycloalkyl; wherein
R and R' are independently selected from the group consisting of hydrogen and loweralkyl; and
$R_4$ is selected from the group consisting of hydrogen and arylalkyl.

2. A compound according to claim 1, wherein $R_3$ is aryl, and the aryl is substituted or unsubstituted.

3. A compound according to claim 2 selected from the group consisting of N-[4-(1,3-diphenylpropan-2-yl)oxymethyl-2-(2-methylphenyl)benzoyl]methionine, N-[4-(3-phenyl)prop-2-en-1-yloxy-2-(2-methylphenyl)benzoyl]methionine, N-[4-(benzyloxymethyl)-2-(2-methylphenyl)benzoyl]methionine, N-[4-(naphth-2-yloxymethyl)-2-(2-methylphenyl)benzoyl]methionine, N-[4-(naphth-1-yloxymethyl)-2-(2-methylphenyl)benzoyl]methionine, N-[4-(benzyloxymethyl)-2-phenylbenzoyl]methionine, N-2-[4-(benzyloxymethyl)-2-(2-methylphenyl)benzoyl]amino-4-methanesulfonylbutanoic acid, N-[4-(2-methylbenzyloxymethyl)-2-(2-methylphenyl)benzoyl]methionine, N-[4-(3-methylbenzyloxymethyl)-2-(2-methylphenyl)benzoyl]methionine, N-[4-(4-methylbenzyloxymethyl)-2-(2-methylphenyl)benzoyl]methionine, benzenesulfonyl N-2-[4-(benzyloxymethyl)-2-(2-methylphenyl)benzoyl]amino-4-methylthiobutanamide, 4-chlorobenzenesulfonyl N-2-[4-(benzyloxymethyl)-2-(2-methylphenyl)benzoyl]amino-4-methylthiobutanamide 4-methylbenzenesulfonyl N-2-[4-(benzyloxymethyl)-2-(2-methylphenyl)benzoyl]amino-4-methylthiobutanamide, N-[4-(naphth-2-ylmethoxymethyl)-2-(2-methylphenyl)benzoyl]methionine, N-[4-(naphth-1-ylmethoxymethyl)-2-(2-methylphenyl)benzoyl]methionine, N-[4-(2-phenylethoxymethyl)-2-(2-methylphenyl)benzoyl]methionine, N-[4-(2-(2-chlorophenyl)ethoxymethyl)-2-(2-methylphenyl)benzoyl]methionine, N-[4-(2-(2-methoxyphenyl)ethoxymethyl)-2-(2-methylphenyl)benzoyl]methionine, N-[4-(2-(4-chlorophenyl)ethoxymethyl)-2-(2-methylphenyl)benzoyl]methionine, N-[4-(2-(2,4-dichlorophenyl)ethoxymethyl)-2-(2-methylphenyl)benzoyl]methionine, N-[4-(2-naphth-1-ylethoxymethyl)-2-(2-methylphenyl)
benzoyl]methionine,
N-[4-(2-naphth-2-ylethoxymethyl)-2-(2-methylphenyl)
benzoyl]methionine,
N-[4-(3-phenylpropoxymethyl)-2-(2-methylphenyl)
benzoyl]methionine,
N-[4-(4-phenylbutoxymethyl)-2-(2-methylphenyl)benzoyl]-
N-methylmethionine,
N-[4-(4-phenoxyphenoxymethyl)-2-(2-methylphenyl)
benzoyl]methionine,
N-[5-benzyl-4-(2-phenylethoxymethyl)-2-(2-methylphenyl)
benzoyl]methionine,
N-[4-(2-chlorobenzyloxymethyl)-2-(2-methylphenyl)
benzoyl]methionine,
N-[4-(2-methoxybenzyloxymethyl)-2-(2-methylphenyl)
benzoyl]methionine,
N-[4-(3-methoxybenzyloxymethyl)-2-(2-methylphenyl)
benzoyl]methionine,
N-[4-(4-chlorobenzyloxymethyl)-2-(2-methylphenyl)
benzoyl]methionine,
N-[4-(3-chlorobenzyloxymethyl)-2-(2-methylphenyl)
benzoyl]methionine,
N-[4-(4-methoxybenzyloxymethyl)-2-(2-methylphenyl)
benzoyl]methionine,
N-[4-(2-(4-methoxyphenyl)ethoxymethyl)-2-(2-
methylphenyl)benzoyl]methionine,
N-[4-(2-isopropylbenzyloxymethyl)-2-(2-methylphenyl)
benzoyl]methionine,
N-[4-(3-isopropylbenzyloxymethyl)-2-(2-methylphenyl)
benzoyl]methionine,
N-[4-(4-isopropylbenzyloxymethyl)-2-(2-methylphenyl)
benzoyl]methionine,
N-[4-(3-N,N-dimethylaminobenzyloxymethyl)-2-(2-
methylphenyl)benzoyl]methionine,
N-[4-(1-(2-chlorophenyl)hexan-2-yloxymethyl)-2-(2-
methylphenyl)benzoyl]methionine,
N-[4-(2-hydroxymethylphenoxymethyl)-2-(2-
methylphenyl)benzoyl]methionine,
N-[4-(2-hydroxymethylbenzyloxymethyl)-2-(2-
methylphenyl)benzoyl]methionine,
N-[4-(3-hydroxymethylbenzyloxymethyl)-2-(2-
methylphenyl)benzoyl]methionine,
N-[4-(4-hydroxymethylbenzyloxymethyl)-2-(2-
methylphenyl)benzoyl]methionine,
N-[4-(4-hydroxybenzyloxymethyl)-2-(2-methylphenyl)
benzoyl]methionine,
N-[4-(3-cyclohexyl-1-hydroxyprop-2-yloxymethyl)-2-(2-
methylphenyl)benzoyl]methionine,
N-[4-(2-(2-chlorophenyl)hexan-1-yloxymethyl)-2-(2-
methylphenyl)benzoyl]methionine,
N-[4-(1-(3-chlorophenyl)pentan-1-yloxymethyl)-2-(2-
methylphenyl)benzoyl]methionine,
N-[4-(1-(3-chlorophenyl)-3-cyclohexylpropan-1-
yloxymethyl)-2-(2-methylphenyl)benzoyl]methionine,
N-[4-(1-(3-methoxyphenyl)pentan-1-yloxymethyl)-2-(2-
methylphenyl)benzoyl]methionine,
N-[4-(3-(1-propoxy)benzyloxymethyl)-2-(2-methylphenyl)
benzoyl]methionine,
N-[4-(3-cyclohexylmethyloxybenzyloxymethyl)-2-(2-
methylphenyl)benzoyl]methionine,
N-[4-(3,5-trifluorobenzyloxymethyl)-2-(2-methylphenyl)
benzoyl]methionine,
N-[4-(2-(3-fluorophenyl)ethyloxymethyl-2-(2-
methylphenyl)benzoyl]methionine, and
N-[4-(3-hydroxybenzyloxymethyl)-2-(2-methylphenyl)
benzoyl]methionine.

4. A compound according to claim 2 which is N-[5-benzyl-4-benzyloxymethyl-2-(2-methylphenyl)benzoyl]
methionine.

5. A compound according to claim 1 wherein $R_3$ is cycloalkyl.

6. A compound according to claim 5 selected from the group consisting of

4-[2-(1-adamantane)ethoxy]methyl-2-(2-methylphenyl)
benzoylmethionine,
4-(3-cyclohexylpropoxy)methyl-2-(2-methylphenyl)
benzoylmethionine,
N-[4-(3-cyclohexyl-1-ethoxypropan-2-yl)oxymethyl-2-(2-
methylphenyl)benzoyl]methionine,
N-[4-(2-cyclohexylethoxy)-2-(2-methylphenyl)benzoyl]
methionine,
N-[4-(2-adamantan-1-ylpropoxy)-2-(2-methylphenyl)
benzoyl]methionine,
N-[4-(3-cyclohexylpropoxy)-2-(2-methylphenyl)benzoyl]
methionine,
N-[4-(4-cyclohexyl)butoxy-2-(2-methylphenyl)benzoyl]
methionine,
N-[4-(cyclohexylmethoxymethyl)-2-(2-methylphenyl)
benzoyl]methionine,
N-[4-(2-cyclohexylethoxymethyl)-2-(2-methylphenyl)
benzoyl]methionine,
N-[4-(3-cyclohexylpropoxymethyl)-2-(2-methylphenyl)
benzoyl]-N-methylmethionine,
N-[4-(3-adamant-1-ylpropoxymethyl)-2-(2-methylphenyl)
benzoyl]methionine,
N-[4-(4-cyclohexylbutoxymethyl)-2-(2-methylphenyl)
benzoyl]-N-methylmethionine,
N-[4-(3-phenylpropoxy)-2-(2-methylphenyl)benzoyl]
methionine,
N-[4-(3-cyclohexyl-2-cyclohexylmethylpropan-2-yl)
oxymethyl-2-(2-methylphenyl)benzoyl]methionine,
N-[4-(1,3-dicyclohexylpropan-2-yloxymethyl)-2-(2-
methylphenyl)benzoyl]methionine,
N-[4-(3-cyclohexyl-1-(4-methoxybenzyloxy)prop-2-
yloxymethyl)-2-(2-methylphenyl)benzoyl]methionine,
N-[4-(cyclohexyloxycarbonylethyl)-2-(2-methylphenyl)
benzoyl]methionine,
N-[4-(cyclohexylmethoxycarbonylethyl)-2-(2-
methylphenyl)benzoyl]methionine,
N-[4-(1-cyclohexylheptan-3-yloxymethyl-2-(2-
methylphenyl)benzoyl]methionine,
N-[4-(1-cyclohexyl-2-hexyloxymethyl)-2-(2-methylphenyl)
benzoyl]methionine,
N-[4-(3-cyclohexyl-1-methoxyprop-2-yloxymethyl)-2-(2-
methylphenyl)benzoyl]methionine,
N-[4-(3-cyclohexyl-1-propoxyprop-2-yloxymethyl)-2-(2-
methylphenyl)benzoyl]methionine,
N-[4-[(S)-3-cyclohexyl-1-(1-methylethoxy)prop-2-
yloxymethyl]-2-(2-methylphenyl)benzoyl]methionine,
N-[4-[(S)-1-tert-butoxy-3-cyclohexylprop-2-yloxymethyl]-
2-(2-methylphenyl)benzoyl]methionine,
N-[4-(3-cyclohexyl-1-butoxyprop-2-yloxymethyl)-2-(2-
methylphenyl)benzoyl]methionine,
N-[4-(3-cyclohexyl-1-(3,3-dimethylbut-1-yloxy)prop-2-
yloxymethyl)-2-(2-methylphenyl)benzoyl]methionine,
N-[4-(3-cyclohexyl-1-ethylsulfenylprop-2-yloxymethyl)-2-
(2-methylphenyl)benzoyl]methionine,
N-[4-(3-cyclohexyl-2-hydroxyprop-1-yloxymethyl)-2-(2-
methylphenyl)benzoyl]methionine,
N-[4-(2-cyclohexylmethylhex-1-yloxymethyl)-2-(2-
methylphenyl)benzoyl]methionine,
N-[4-(3-cyclohexyl-2-(4-methoxybenzyloxy)prop-1-
yloxymethyl)-2-(2-methylphenyl)benzoyl]methionine,
N-[4-(-1-sec-butoxy-3-cyclohexylprop-2-yloxymethyl)-2-
(2-methylphenyl)benzoyl]methionine, and
N-[4-(3-cyclohexyl-1-cyclobutoxyprop-2-yloxymethyl)-2-
(2-methylphenyl)benzoyl]methionine.

7. A compound according to claim 1 wherein $R_3$ is cycloalkenyl.

8. A method of inhibiting protein isoprenyl transferases in a mammal in need of, such treatment comprising administering to the mammal a therapeutically, effective amount of a compound of claim 1.

9. A composition for inhibiting protein isoprenyl transferases comprising a pharmaceutical carrier and a therapeutically effective amount of a compound of claim 1.

10. A method for inhibiting or treating cancer in a mammal, comprising administering to the mammal a therapeutically effective amount of a compound of claim 1 alone or in combination with another chemotherapeutic agent.

11. A composition for the treatment of cancer comprising a compound of claim 1 in combination with another chemotherapeutic agent and a pharmaceutically acceptable carrier.

12. A method for inhibiting post-translational modification of the oncogenic Ras protein by protein farnesyltransferase, protein geranylgeranyltransferase, or both in a mammal comprising administering to the mammal a therapeutically effective amount of a compound of claim 1.

13. A composition for inhibiting post-translational modification of the oncogenic Ras protein by protein farnesyltransferase, protein geranylgeranyltransferase, or both comprising a compound of claim 1 in combination with a pharmaceutical carrier.

14. A method for treating intimal hyperplasia associated with restenosis and atherosclerosis in a mammal comprising administering to the mammal a therapeutically effective amount of a compound of claim 1.

15. A composition for treating restenosis in a mammal comprising a compound of claim 1 in combination with a pharmaceutically acceptable carrier.

* * * * *